United States Patent
Jiang et al.

(10) Patent No.: US 12,280,114 B2
(45) Date of Patent: Apr. 22, 2025

(54) EXTRACTION OF PLANT SOURCE "MEDICINAL SOUP" AND MANUAL PREPARATION OF "HERBAL MEDICINE" AND RELATED PRODUCTS

(71) Applicant: BEIJING BAISHIHEKANG PHARMACEUTICAL TECHNOLOGY (BSJPHARMA) CO., LTD, Beijing (CN)

(72) Inventors: Chengyu Jiang, Beijing (CN); Xiaoyun Li, Beijing (CN); Jianchao Du, Beijing (CN); Zhu Liang, Beijing (CN); Zhiqing Wang, Beijing (CN); Chenxuan Wang, Beijing (CN)

(73) Assignee: INSTITUTE OF BASIC MEDICAL SCIENCES, Beijing (CN)

( * ) Notice: Subject to any disclaimer, the term of this patent is extended or adjusted under 35 U.S.C. 154(b) by 0 days.

(21) Appl. No.: 17/042,924

(22) PCT Filed: Mar. 5, 2019

(86) PCT No.: PCT/CN2019/077004
§ 371 (c)(1),
(2) Date: Sep. 29, 2020

(87) PCT Pub. No.: WO2019/184663
PCT Pub. Date: Oct. 3, 2019

(65) Prior Publication Data
US 2021/0113641 A1    Apr. 22, 2021

(30) Foreign Application Priority Data

Mar. 29, 2018 (WO) ............... PCT/CN2018/081155

(51) Int. Cl.
| | | |
|---|---|---|
| A61K 47/14 | (2017.01) |
| A61K 36/288 | (2006.01) |
| A61K 36/41 | (2006.01) |
| A61K 45/06 | (2006.01) |
| B82Y 5/00 | (2011.01) |
| B82Y 40/00 | (2011.01) |
| C12N 15/113 | (2010.01) |

(52) U.S. Cl.
CPC ............ *A61K 47/14* (2013.01); *A61K 36/288* (2013.01); *A61K 36/41* (2013.01); *A61K 45/06* (2013.01); *C12N 15/113* (2013.01); *A61K 2236/331* (2013.01); *A61K 2236/333* (2013.01); *A61K 2236/37* (2013.01); *A61K 2236/51* (2013.01); *A61K 2236/53* (2013.01); *B82Y 5/00* (2013.01); *B82Y 40/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

2013/0315937 A1    11/2013    Lee et al.

FOREIGN PATENT DOCUMENTS

| AU | 2012209339 A1 | * | 9/2013 | ......... A61K 38/4893 |
|---|---|---|---|---|
| CN | 1897918 A | | 1/2007 | |
| CN | 105534908 A | | 5/2016 | |
| CN | 107530399 A | | 1/2018 | |
| EP | 2675918 B1 | * | 11/2017 | ......... A61K 47/6913 |
| JP | 20182727 A | * | 1/2018 | |
| WO | 2012/112730 A2 | | 8/2012 | |
| WO | 2016/004318 A1 | | 1/2016 | |
| WO | WO-2016153012 A1 | * | 9/2016 | ......... A61K 31/7088 |
| WO | 2018177383 A1 | | 10/2018 | |

OTHER PUBLICATIONS

Li (Polyubiquitin chains: functions, structures, and mechanisms, Cell Mol Life Sci. Aug. 2008, 65(15): 2397-2406). (Year: 2008).*
JP20182727A translated doc (Year: 2018).*
WO-2016153012-A1 translated doc (Year: 2016).*
Saraf (Sphingosomes a Novel Approach to Vesicular Drug Delivery, Journal of Pharmacy and Technology, Apr. 5, 2011), (Year: 2011).*
Allegood (Application of Liquid Chromatography Tandem Mass Spectrometry for the Separation and Quantitative Analysis of Sphingolpids, Georgia Institute of Technology, Dec. 2011) (Year: 2011).*
Zhou (miR-625 suppresses tumor migration and invasion by targeting IGF2BP1 in hepatocellular carcinoma, Oncogene (2015) 345, 965-977). (Year: 2015).*
Du Jianchao et al: "Plant-derived phosphocholine facilitates cellular uptake of anti-pulmonary fibrotic HJT-sRNA-m7", Science China Life Sciences, Zhongguo Kexue Zazhishe, China, vol. 62, No. 3, Mar. 31, 2017 (Mar. 31, 2017), pp. 309-320, XP009531166, ISSN: 1674-7305, DOI: 10.1007/S11427-017-9026-7 *the whole document*.
Yang Chunhua et al: "Advances in plant-derived edible nanoparticle-based lipid nano-drug delivery systems as therapeutic nanomedicines", Journal of Materials Chemistry. B, vol. 6, No. 9, Jan. 29, 2018 (Jan. 29, 2018), pp. 1312-1321, XP055899825, GB ISSN: 2050-750X, DOI: 10.1039/C7TB03207B *the whole document*.

(Continued)

*Primary Examiner* — Aaron J Kosar
*Assistant Examiner* — Jacob A Boeckelman
(74) *Attorney, Agent, or Firm* — Jun He Law Offices P.C; Zhaohui Wang

(57) ABSTRACT

Provided is a method for preparing bencaosome comprising the steps of: mixing one or more lipid components with any one or more of the following: nucleic acid, compound and macromolecules, and treating the obtained mixture by heating. Also provided is a method for extracting decoctosome from plants comprising the steps of: preparing an extract of the plant with a solvent; performing differential centrifugation to the extract; resuspending the precipitates with an aqueous solution to provide the decoctosome.

6 Claims, 131 Drawing Sheets

Figure 1:
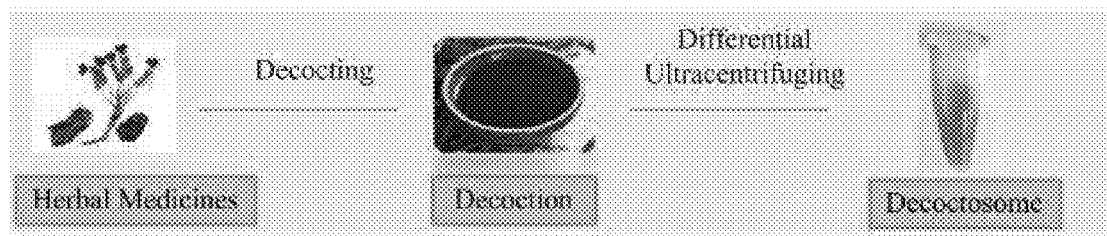

Specification includes a Sequence Listing.

(56) References Cited

OTHER PUBLICATIONS

Zhang Mingzhen et al: "Oral administration of ginger-derived nanolipids loaded with siRNA as a novel approach for efficient siRNA drug delivery to treat ulcerative colitis", Nanomedicine, vol. 12, No. 16, Aug. 1, 2017 (Aug. 1, 2017), pp. 1927-1943, XP055858846, GB ISSN: 1743-5889, DOI: 10.2217/nnm-2017-0196 *the whole document*.
Zhen Zhou et al: "Honeysuckle-encoded atypical microRNA2911 directly targets influenza A viruses", Cell Research, vol. 25, No. 1, Jan. 1, 2015 (Jan. 1, 2015), pp. 39-49, XP055247995, Singapore ISSN : 1001-0602, DOI: 10.1038/cr.2014.130 *the whole document*.
Swarnlata Saraf Prof et al: "Sphingosomes a novel appoach to vesicular drug delivery", Jan. 1, 2011 (Jan. 1, 2011), XP05590-2930 *the abstract*.
Lukasik Anna et al: "Plant MicroRNAs-Novel Players in Natural Medicine?", International Journal of Molecular Sciences, vol. 18, No. 1, Dec. 22, 2016 (Dec. 22, 2016), p. 9, XP055901893, DOI: 10.3390/ijmsl8010009 *the whole document*.
Partial supplementary European search report (Rule 164 (1) EPC) of the corresponding EP 19777982.0, mailed on Apr. 4, 2022.

\* cited by examiner

*Rhodiola* Decoctosome

*Taraxacum Mongolicum* Decoctosome
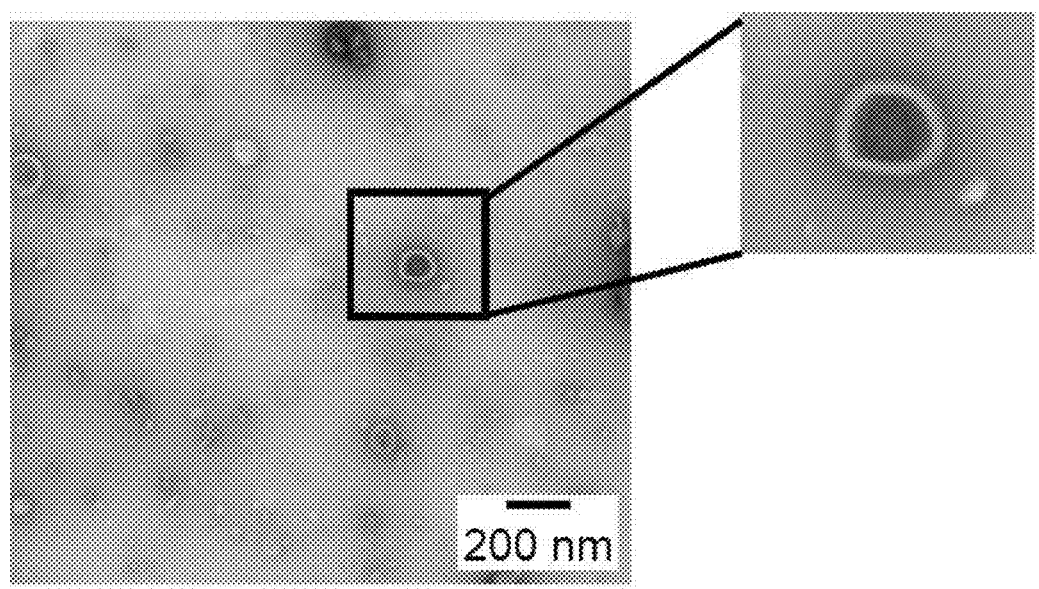
Fig. 3
Particle Size Distribution of *Rhodiola* Decoctosome
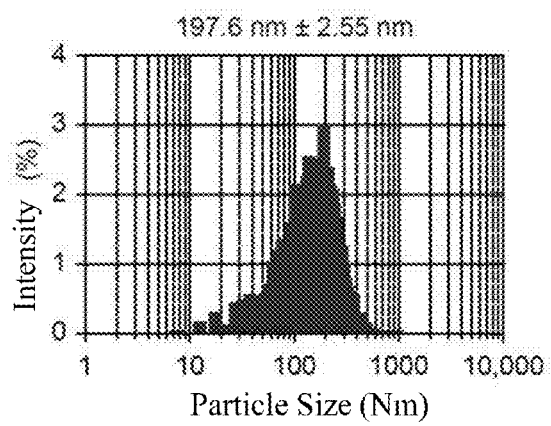
Zeta Potential of *Taraxacum Mongolicum* Decoctosome
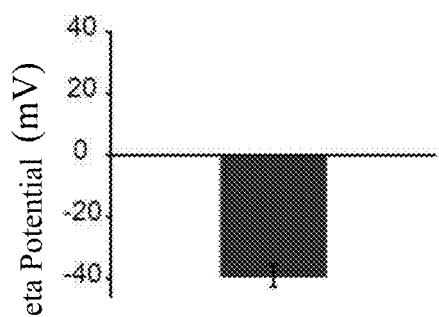
Fig. 4

*Rhodiola* Decoctosome Proteome (38)

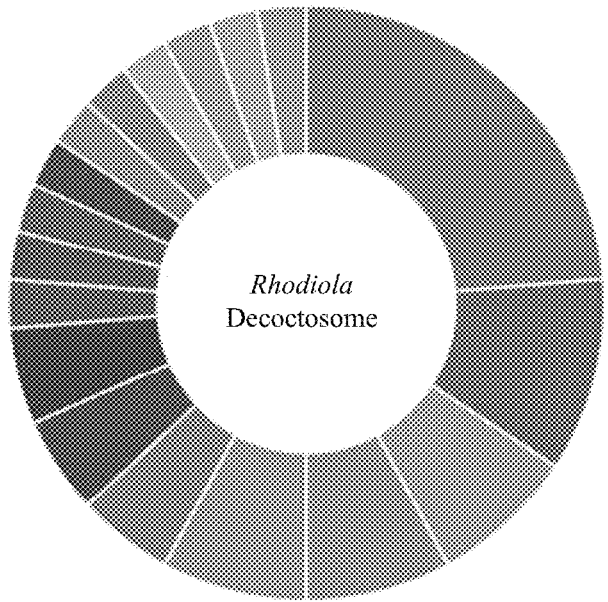

- Metabolic Processing (9)
- Protein Ubiquitination (4)
- Signal Transduction (3)
- Nucleic Acid Processing (3)
- Translation (3)
- Transcription (2)
- Protein Transportation (2)
- Defense Response (2)
- Cytokinesis (1)
- Mitochondrial RNA 3' End Processing (1)
- Plastid Differentiation (1)
- Nodulation (1)
- Histone Acetylation (1)
- Nutrition Library Activation (1)
- Mrna Processing (1)
- Protein Folding (1)
- Photosynthesis (1)
- Others (1)

Fig. 19

*Taraxacum Mongolicum* Decoctosome Proteome (140)

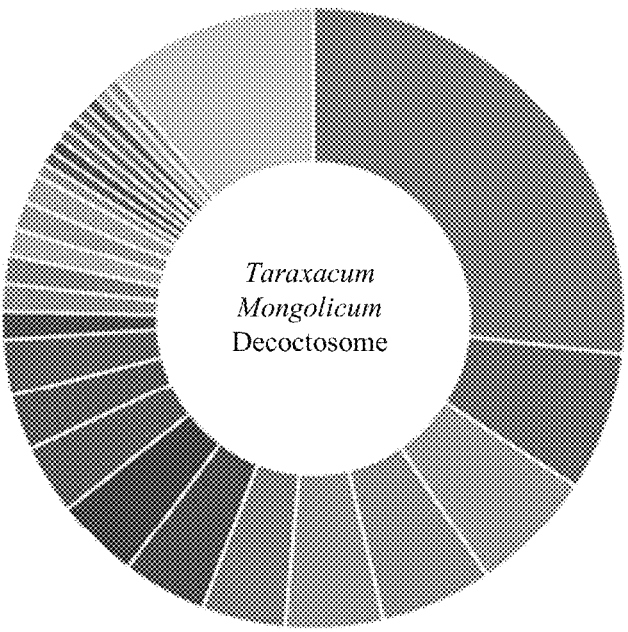

- Metabolic Processing (37)
- Transcription (11)
- Translation (9)
- Signal Transduction (8)
- Immune Response (7)
- Stress Response (6)
- Mrna Processing (6)
- Protein Folding (6)
- Photosynthesis (5)
- Protein Ubiquitination (4)
- Cytokinesis (4)
- Cell Division (3)
- Photosynthetic Respiration (2)
- ATP Biosynthetic Processing (2)
- Cell Wall Modification (2)
- DNA Replication (2)
- Gene Silencing (2)
- Nucleic Acid Modification (1)
- Protein Transcription (1)
- Methylthioadenosine Methionine (1)
- Endonuclease Cleavage (1)
- Electron Transfer (1)
- Nucleosome Assembly (1)
- Stomatal Movement (1)
- Embryonic Development (1)
- Ribosomal Biosynthesis (1)
- Others (15)

Fig. 20

Small RNA Length Distribution of *Rhodiola* Decoctosome

Small RNA Length Distribution of *Taraxacum Mongolicum* Decoctosome

PBMC poly I:C (1μg/ml)

1 Structure of reagent for testing the CMC property (critical micelle concentration) 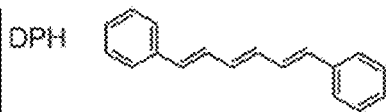
2 CMC value of small RNA alone
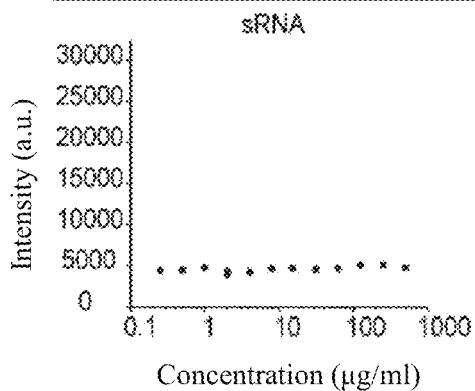
3 CMC value of Sphinganine alone
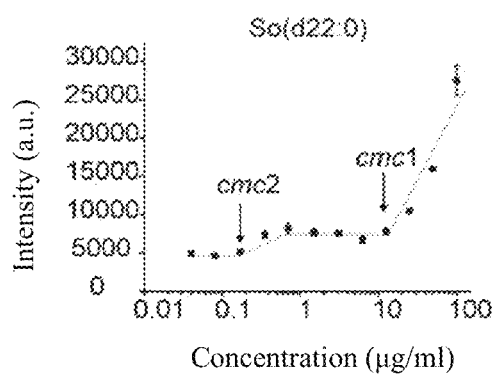
Fig. 43

30 ug/mL So(d22:0)

30 ug/mL So(d22:0)+600 nM sRNA

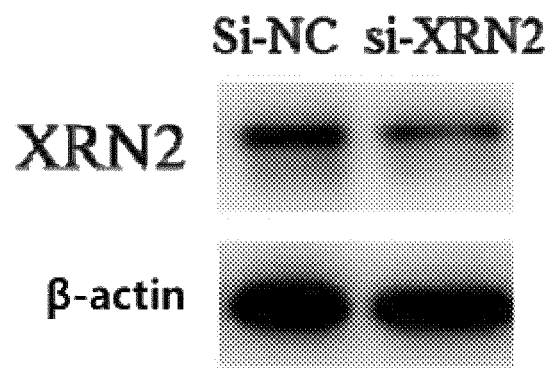
Fig. 95
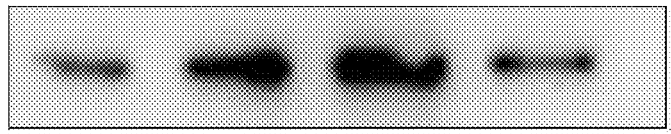
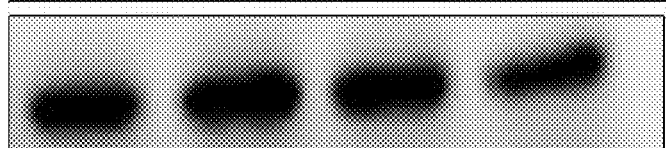
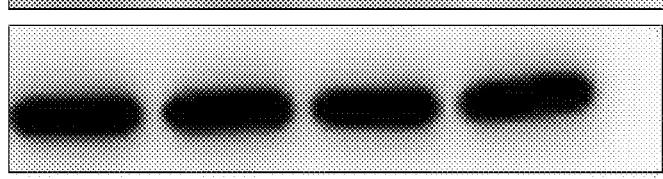
Fig. 96

No1:8:12:4:31:29:16(2:1:2:2:3:1:3)
Boiling Method

Naïve　si-NC　si-XRN2

XRN2

β-actin

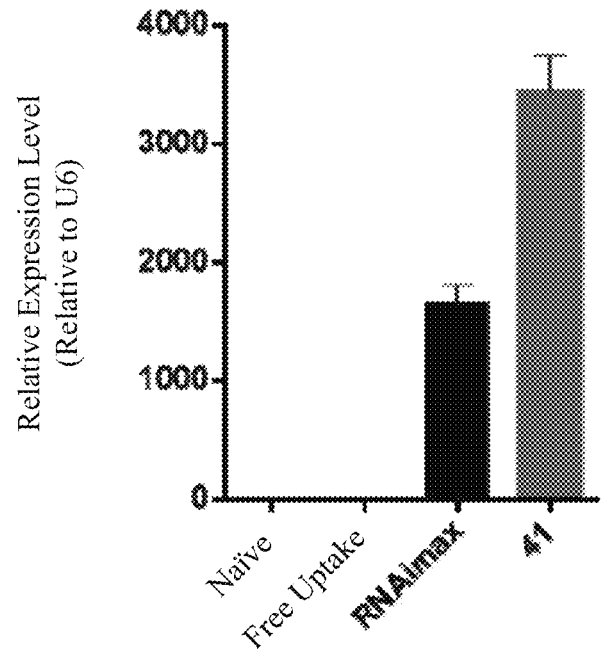
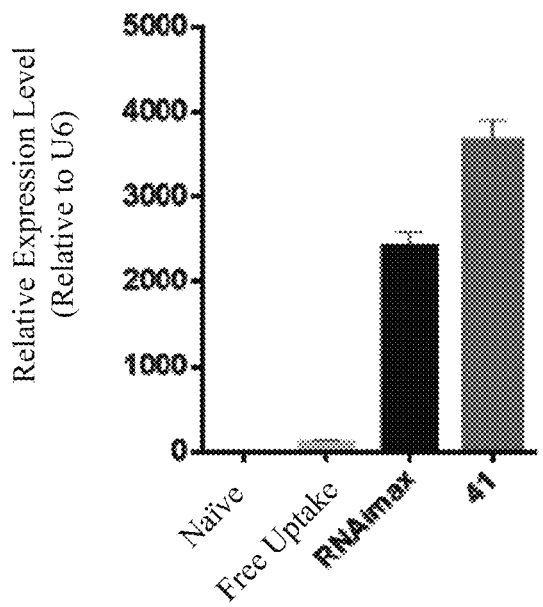
Fig. 108

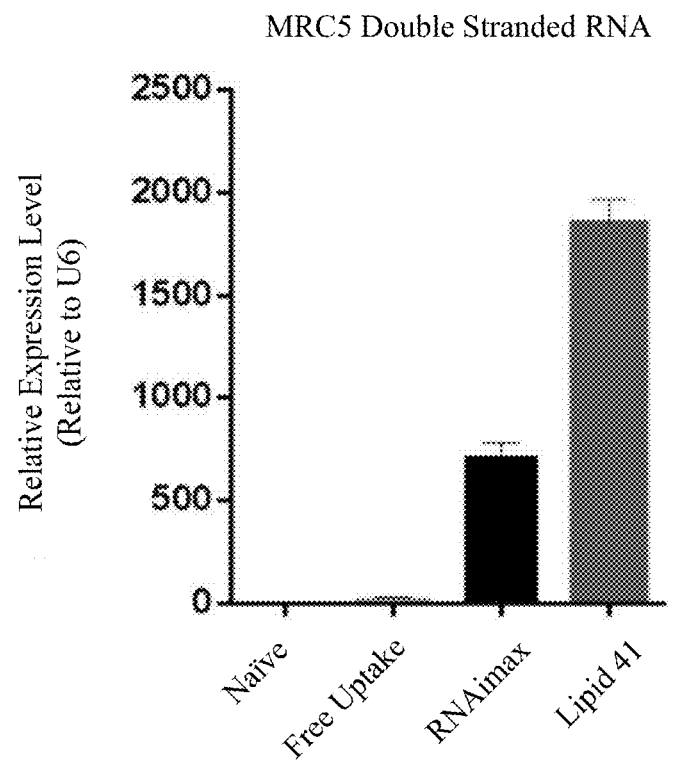
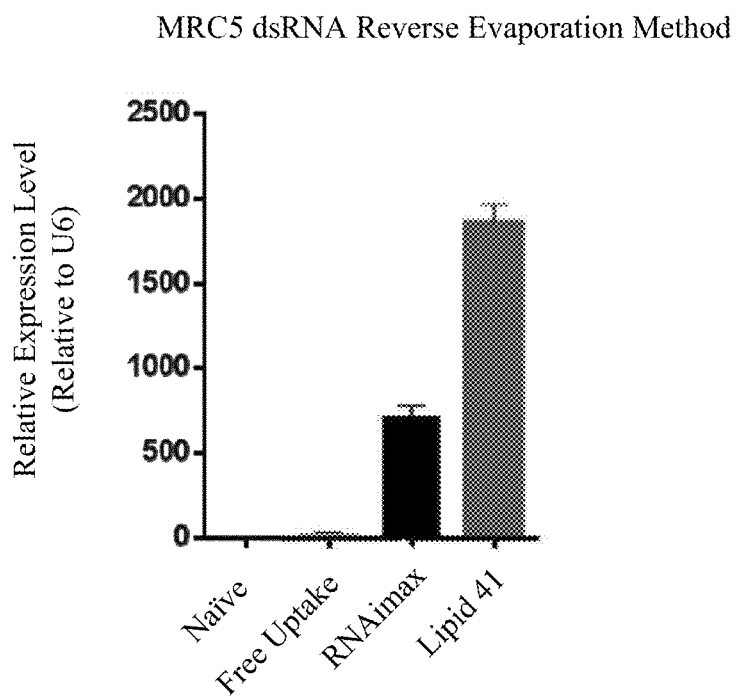
Fig. 109

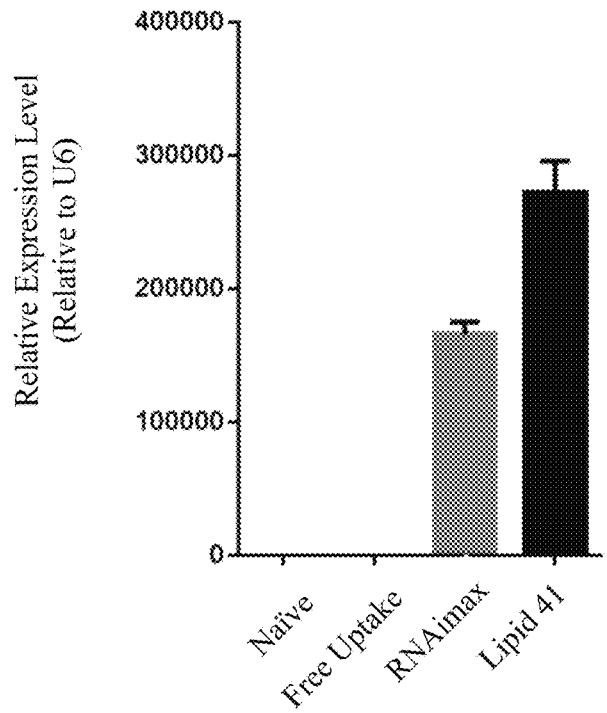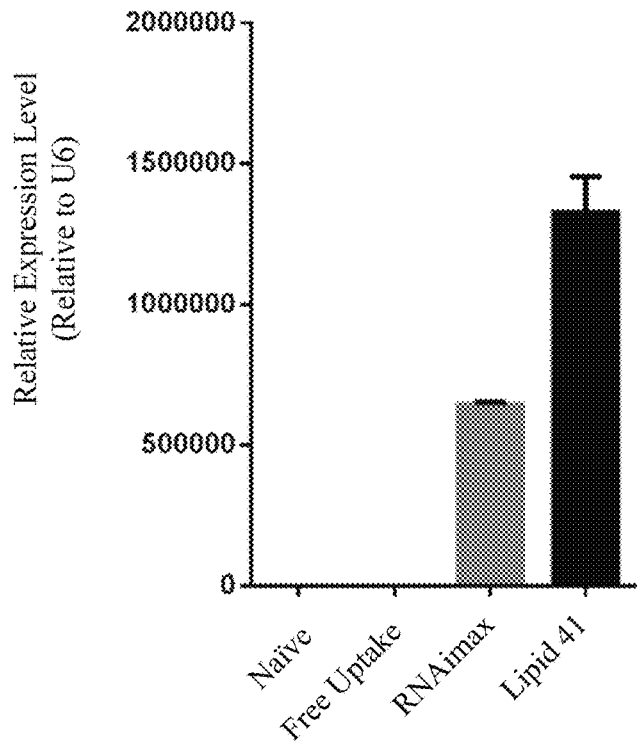
Fig. 110

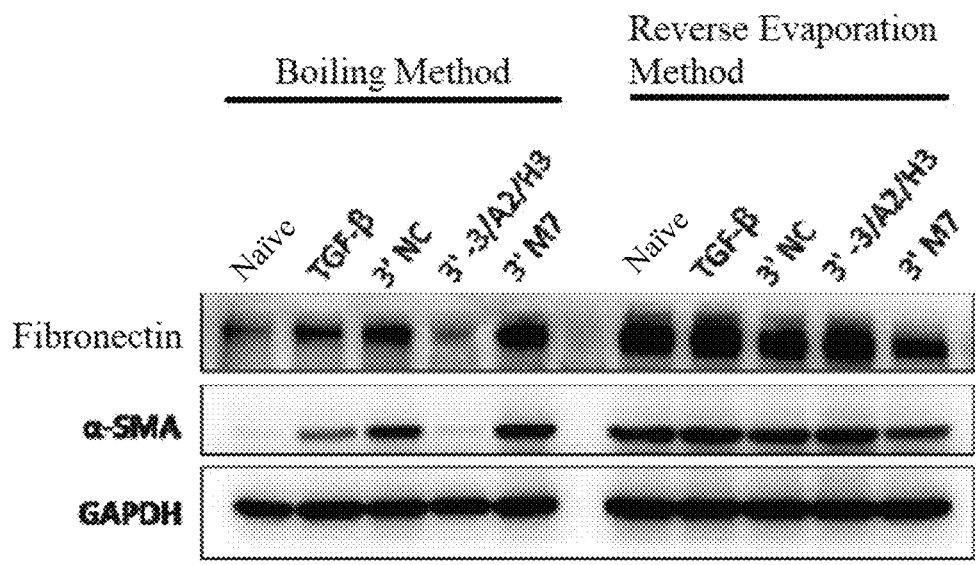
40(PE)+12(PC)+41(So)=2:4:3
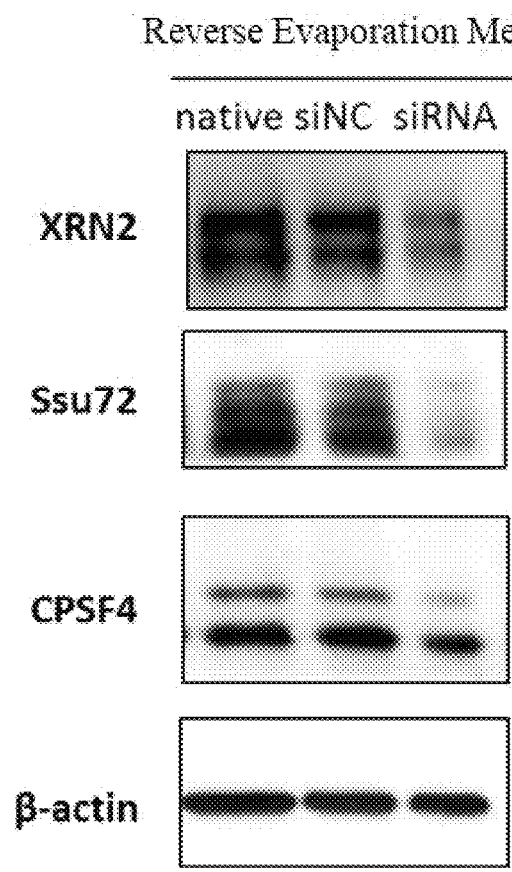
Fig. 119

12(PC)+41(So)=1:6
Reverse Evaporation Method
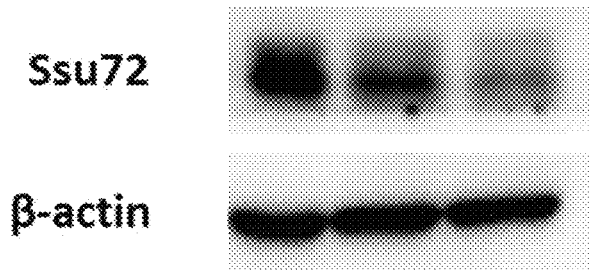
12(PC)+41(So)=1:1
Reverse Evaporation Method
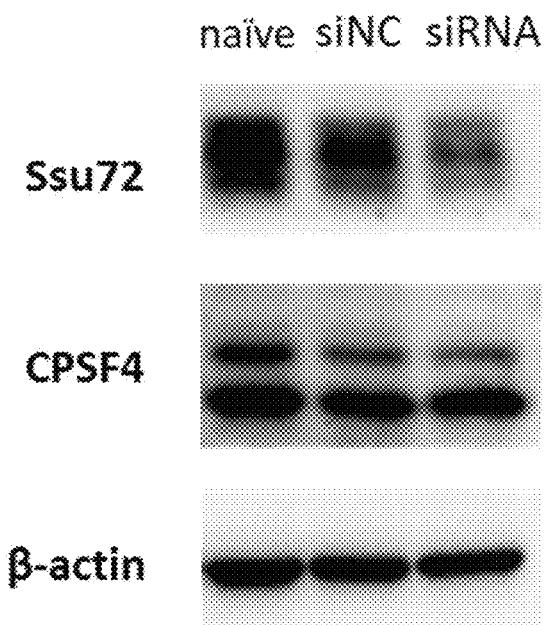
Fig. 120

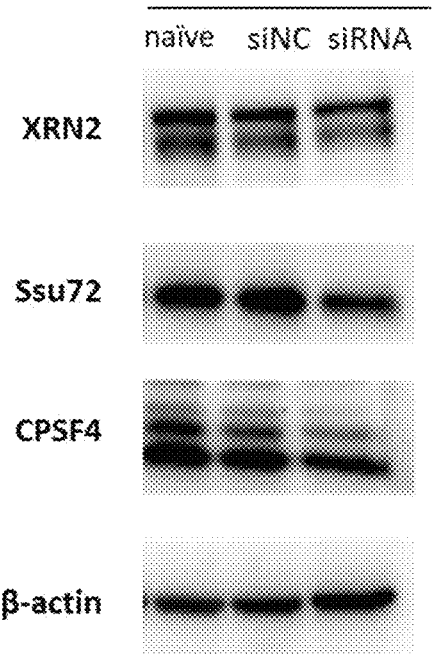
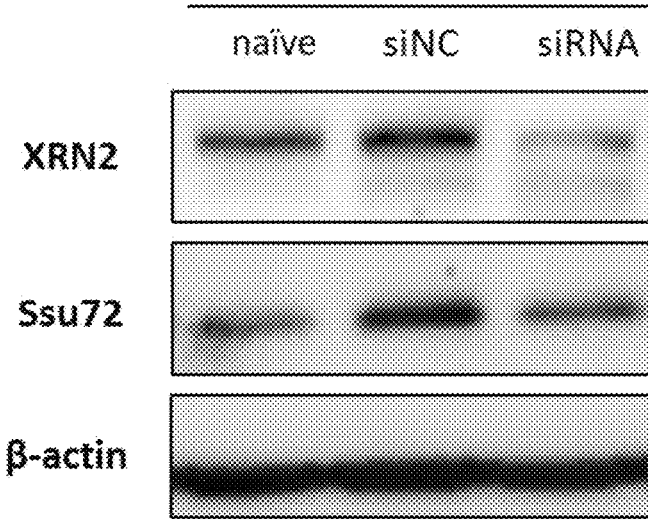
Fig. 121

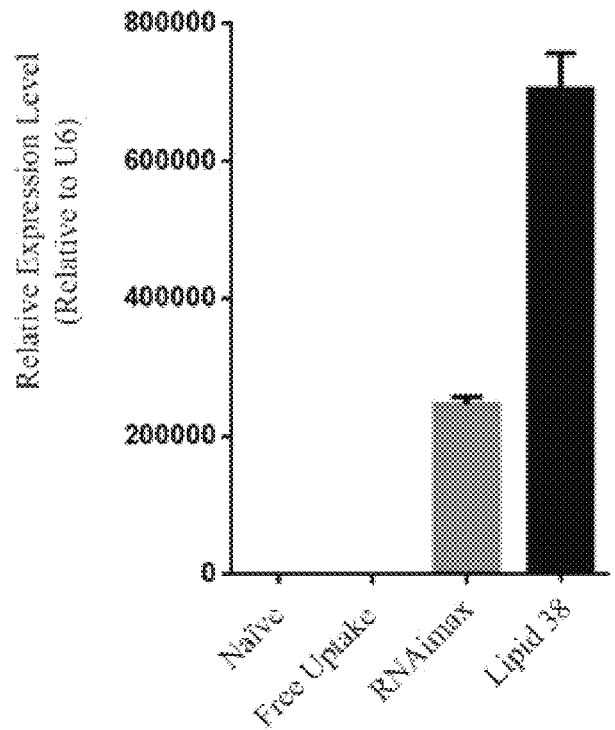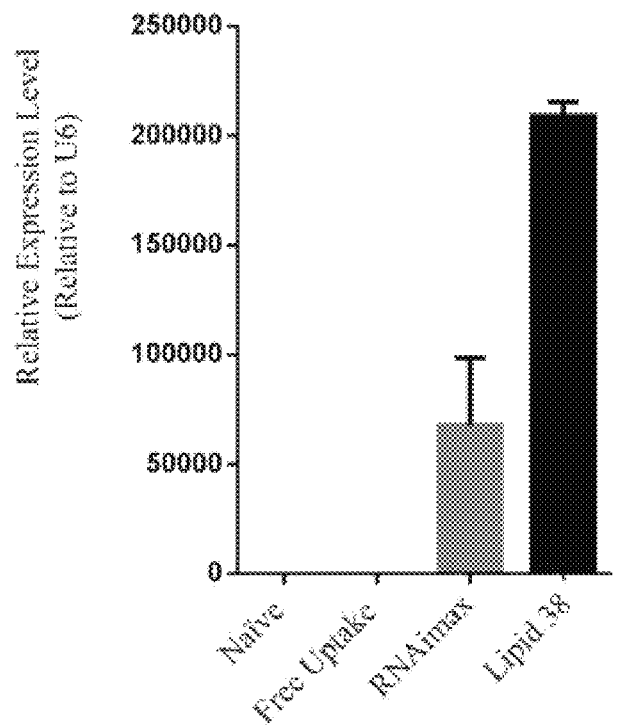
Fig. 124

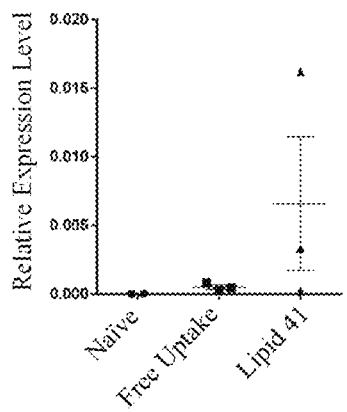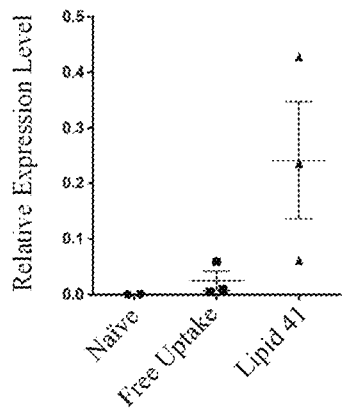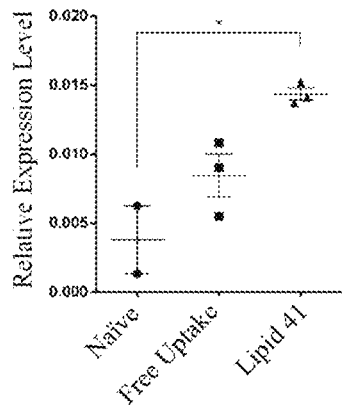
Fig. 142

GFP 3.6%

10ug/mL GFP 23.4%

GFP 3.6%

10ug/mL 5.5%

EXTRACTION OF PLANT SOURCE "MEDICINAL SOUP" AND MANUAL PREPARATION OF "HERBAL MEDICINE" AND RELATED PRODUCTS

SEQUENCE LISTING

A copy of the Sequence Listing is submitted with the specification electronically via EFS-Web as an ASCII formatted sequence listing with a file name of "074844-8005US01-SL-20201208_ST25", a creation date of Dec. 8, 2020, and a size of 21,468 bytes. The sequence listing contained in this ASCII formatted document is part of the specification and is herein incorporated by reference in its entirety.

CROSS-REFERENCE TO RELATED APPLICATIONS

The present application claims the priority of PCT application No. PCT/CN2018/081155 entitled "Application of compound or traditional Chinese medicine extract in the preparation of a nucleic delivery reagent and related products thereof", filed on Mar. 29, 2018, the entirety of which is hereby incorporated by reference.

TECHNICAL FIELD

The present application relates to the method of extracting an active substance decoctosome and the artificial method of preparing a bencaosome, specially relates to the method of extracting an active substance from the herbal medicine and the artificial method of preparing a bencaosome.

BACKGROUND

In the traditional Chinese medical research, the Chinese medicine decoction pieces are soaked in water and then decocted to produce decoctions having the effect of treating diseases. Most previous studies on herbal medicines have focused on the investigation of the function of the main chemical components of herbal medicines. Few studies have focused on the nucleic acid molecules in herbal medicines.

Our previous studies show that, there are millions of small RNAs present in Chinese herbal medicines, and thousands of small RNAs of herbal medicines are found in human organs and tissues after drinking decoction (Huang et al., 2018). Our research results show that small RNA may be the functional ingredient of herbal medicine, and the delivery mechanism of small RNA in herbal medicines can help overcome current clinical challenges of therapeutic RNAi delivery. Since the 1980s, nucleic acid delivery drugs targeting human genes have a potential market of trillions of dollars. Since last century, the FDA has approved six small RNA drugs, including Vitravene, Macugen, Kynamro, Exondys 51, Defitelio, Spinraza, and Patisiran. However, their delivery effects are not very good, which hinder the development of nucleic acid. Most small RNA drugs are delivered in the form of nanoparticles by intravenous injection.

According to the theory of Chinese medicine, the functional components of different medicinal materials enter different human organs and tissues to target different diseases. The human genome is composed of approximately 20,000 genes. In theory, plentiful small RNAs of herbal medicines can regulate all these genes. Our previous article proved that HJT-sRNA-m7 can simultaneously down-regulate at least three fibrosis genes (Du et al., 2017). At the same time, our laboratory provides experimental methods and programs for screening and identifying effective therapeutic small RNAs. We believe that one or more small RNAs of herbal medicines can be identified for each gene, and the expression of human genes can be regulated through small RNAs of herbal medicines. Since many diseases involve unbalanced gene expression, the combination of small RNAs of herbal medicines may precisely target unbalanced genes in the disease and provide potential healing effects.

Prior studies on entry of small RNA of herbal medicines into the human body have not investigated the detailed entry mechanism, and the decoction of herbal medicines have not been investigated either.

There remains needs for new methods for separating active compositions, i.e., exosome-like nanoparticles, from herbal medicines, and for preparing the active compositions.

SUMMARY OF INVENTION

The present application is partly based on the findings of the inventors: the active composition of herbal medicines can be obtained by preparing the herbal medicine extract using a solvent followed by differential centrifugation. The active composition is a nanoparticulate substance with a membrane structure after being dissolved in a solvent, preferably a nanoparticulate substance with a double-layer membrane structure, and can be orally administered to reduce a series of inflammatory factors and treat related diseases. In addition, the present application is also partly based on the findings of the inventors: heating nucleic acids, especially small RNAs and lipids, can promote the insertion of nucleic acids into the lipid layer and increase the stability of the process of embedding of nucleic acids in the lipid membrane. The present application provides a new extraction and preparation method of plant active composition and a method for preparing a bencaosome, comprising mixing one or more lipid components or/and any one or more of the following: one or more synthetic or purified nucleic acids, one or more synthetic or purified compounds, one or more synthetic or purified macromolecules, and treating the mixture by heating. The invention also provides the use of decoctosome or bencaosome as an effective method for treating diseases.

In each embodiment, the decoctosome, bencaosome, medicament or composition provided herein can be administered orally or intravenously, such as via bolus injection or continuous infusion for a period of time, or administered subcutaneously, intramuscularly, intraarterially, intraperitoneally, intrapulmonarily, intracerebrospinally, intraarticularly, intrasynovially, intrathecally, intralesionally, or administered via inhalation routes such as intranasal, typically administered intravenously or subcutaneously.

In each embodiment, the decoctosome or bencaosome provided herein can be used in (1) lowering the expression of fibronectin and/or alpha-SMA, preferable the protein expression of fibronectin in MRC-5 cells fibrosis model induced by TGF-beta1; (2) reducing hydroxyproline, preferably the hydroxyproline in pulmonary fibrosis model, preferably the hydroxyproline in pulmonary fibrosis model of mice; (3) preventing or treating fibrosis, preferably pulmonary fibrosis, preferably in the fibrosis model of MRC-5 cells induced by TGF-beta1 or the fibrosis model of mice induced by Bleomycin; (4) lowering IL-1beta, IL-6 and/or TNF-alpha, preferably the IL-1beta, IL-6 and/or TNF-alpha in A549 cells model induced by poly(I:C); (5) lowing the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse; (6) treating IL-1beta, IL-6 and/or TNF-alpha-associated diseases, or for anti-inflammation, and (7) enabling small RNA to enter cells efficiently; and/or (8) lowering the expression of RELA genes; can be used for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy Rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout.

In each embodiment, the nucleic acid is synthesized or purified and is selected from RNA and DNA, such as selected from single stranded or double stranded or partially double-stranded RNA and DNA.

In each embodiment, the RNA is selected from the group consisting of messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, Transfer-messenger RNA (tmRNA), telomerase RNA and antisense RNA, preferably small RNA, preferably one or more small RNAs shown in Table 8, 9 or 13.

In each embodiment, the DNA is selected from the group consisting of complementary DNA (cDNA), chloroplast DNA, multicopy single-stranded DNA (msDNA), mitochondrial DNA (mtDNA) and ribosomal DNA (rDNA).

In each embodiment, the compound is synthesized or purified and includes small molecule drugs and/or one or more compounds shown in Tables 2-5.

In each embodiment, macromolecule is synthesized or purified and is selected from proteins or polysaccharide drugs, and/or one or more macromolecules shown in Table 6 or 7.

In each embodiment, the protein is selected from the group consisting of antibody, β-lactoglobulin, albumin, erythropoietin (EPO), interferon, colony stimulating factor, tissue plasminogen activator and various labeled proteins, such as green fluorescent protein, red fluorescent protein, phycoerythrin, etc.

In each embodiment, the antibody is selected from IgG, IgA, IgM, IgD or IgE antibodies.

DESCRIPTIONS OF THE DRAWINGS

FIG. 1: A schematic diagram of the preparation process of the decoctosome of herbal medicines.

Figure 2:
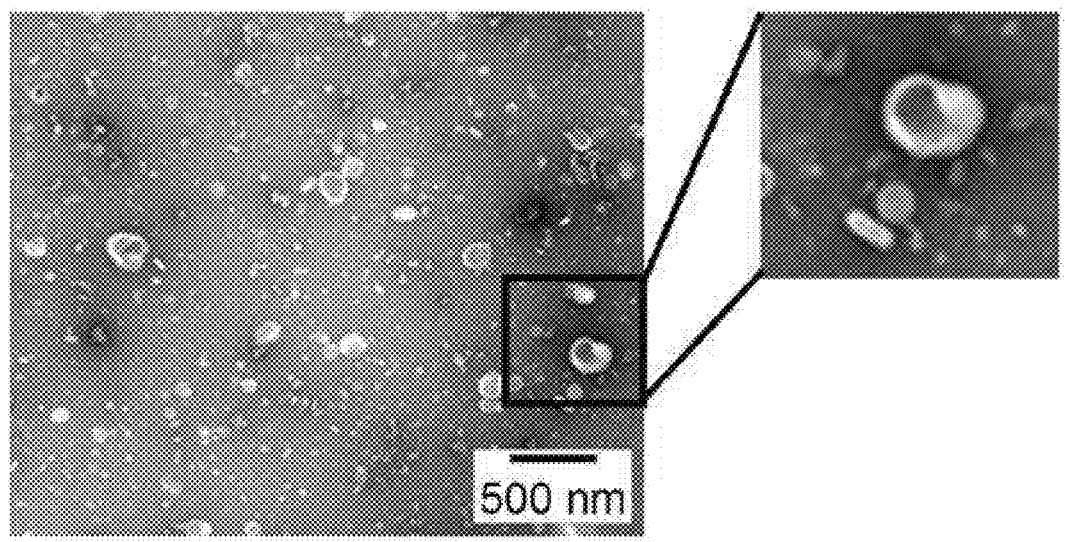

FIG. 2: Transmission electron microscopy results of HJT decoctosome.

FIG. 3: Transmission electron microscopy results of PGY decoctosome.

FIG. 4: Results of particle size and Zeta potential of HJT decoctosome.

Figure 5:
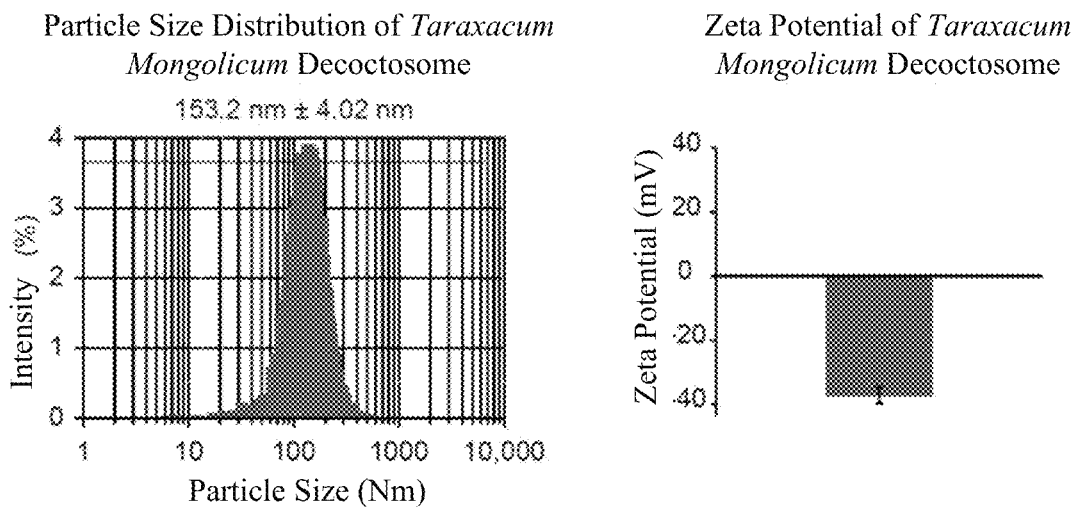

FIG. 5: Results of particle size and Zeta potential of PGY decoctosome.

Figure 6:
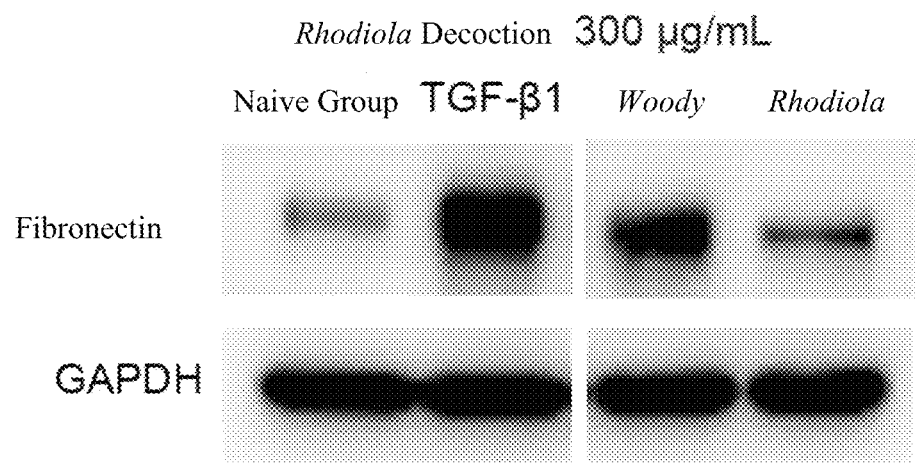

FIG. 6: HJT decoction can reduce the protein expression of fibronectin in the fibrosis model of MRC-5 cells induced by TGF-β1.

Figure 7:
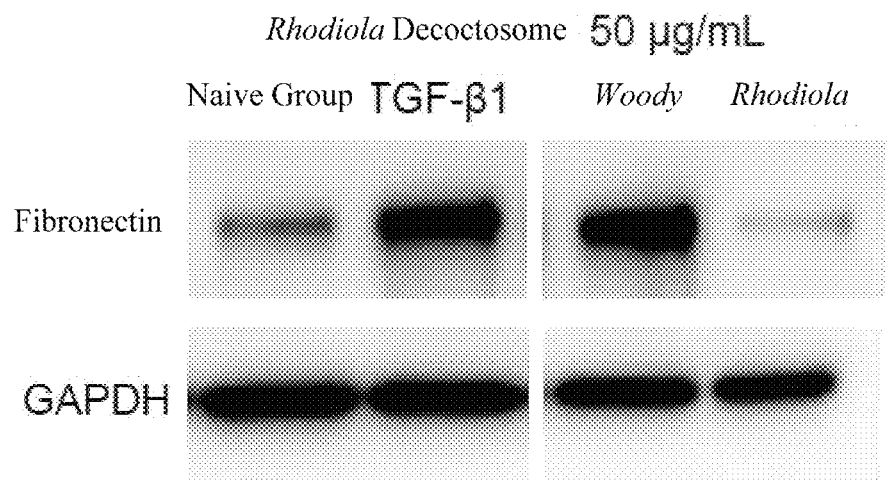

FIG. 7: HJT decoctosome can reduce the protein expression of fibronectin in the fibrosis model of MRC-5 cells induced by TGF-β1.

Figure 8A:
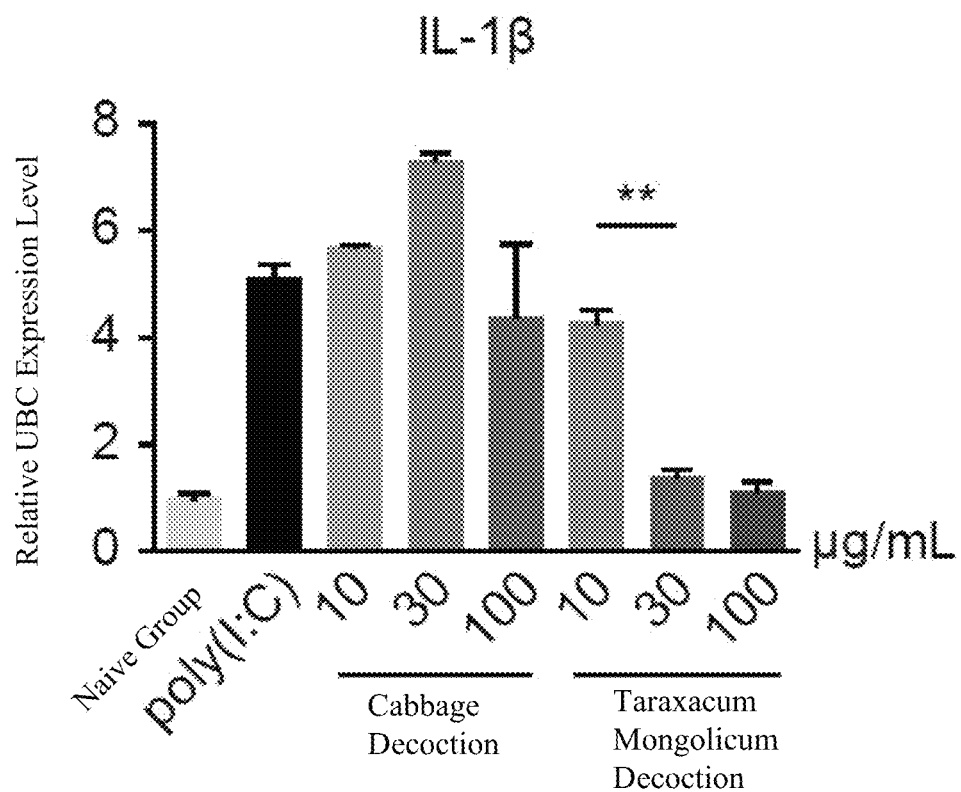
Figure 8B:
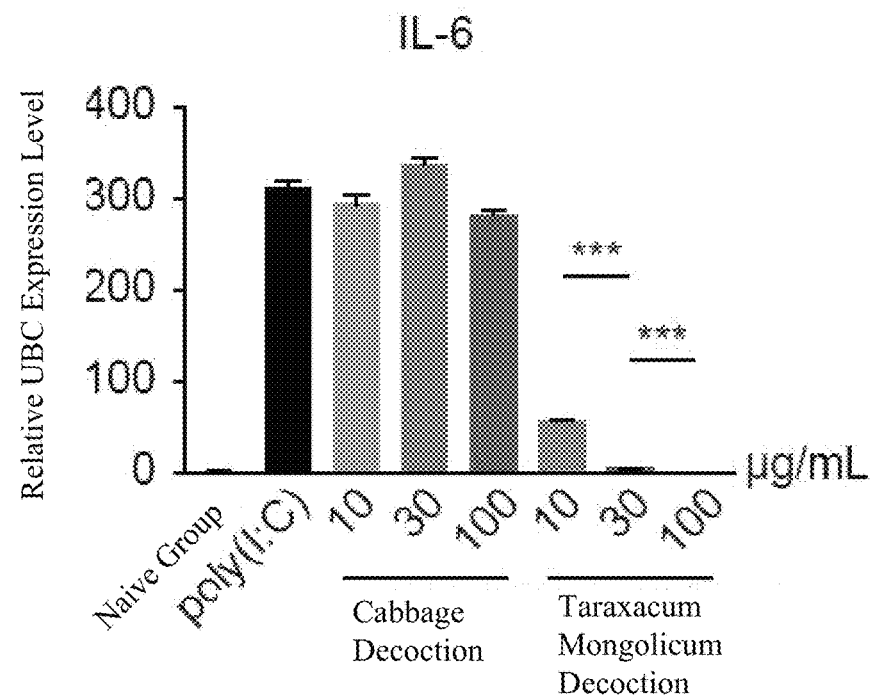
Figure 8C:
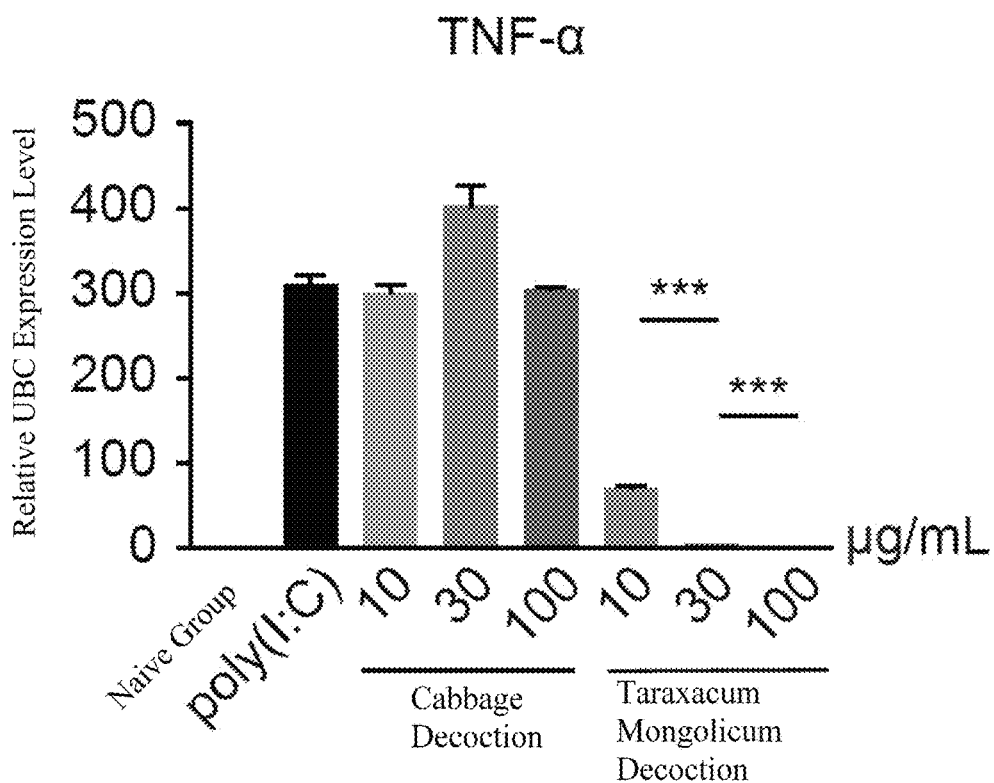

FIG. 8A-C: PGY decoction can reduce the relative expression of IL-1β/IL-6/TNF-α mRNA in the A549 cell inflammation model induced by poly(I:C).

Figure 9A:
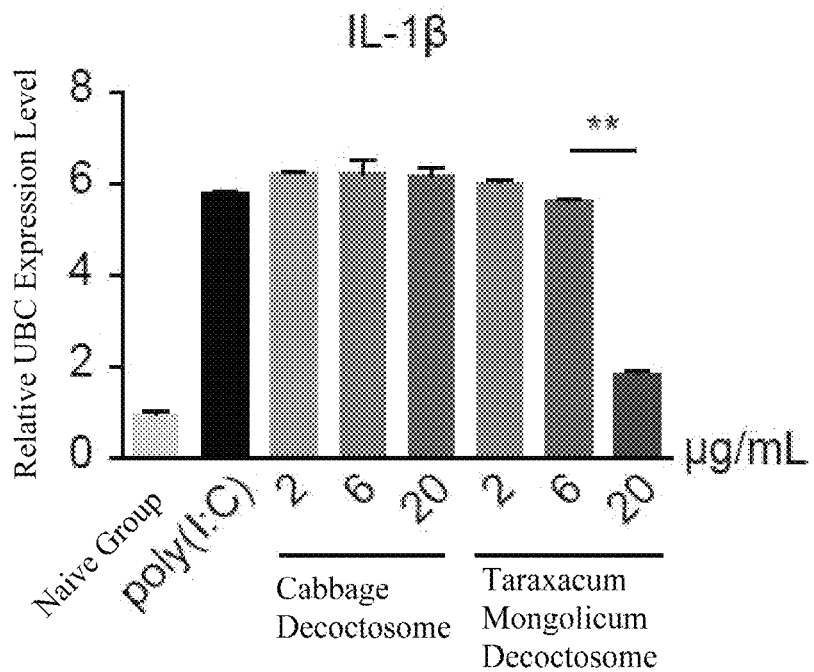
Figure 9B:
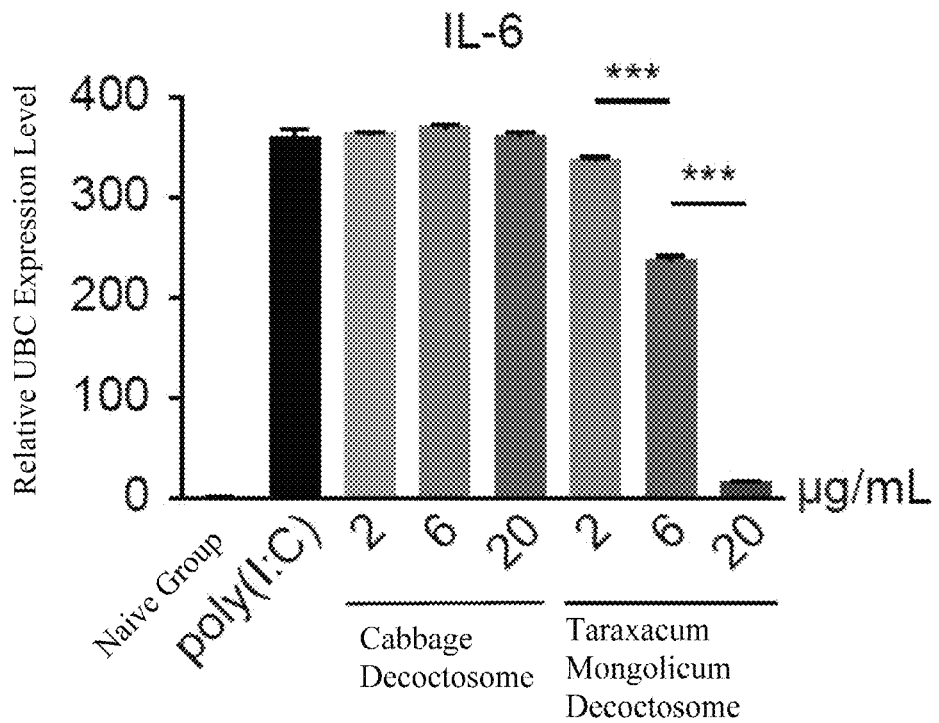
Figure 9C:
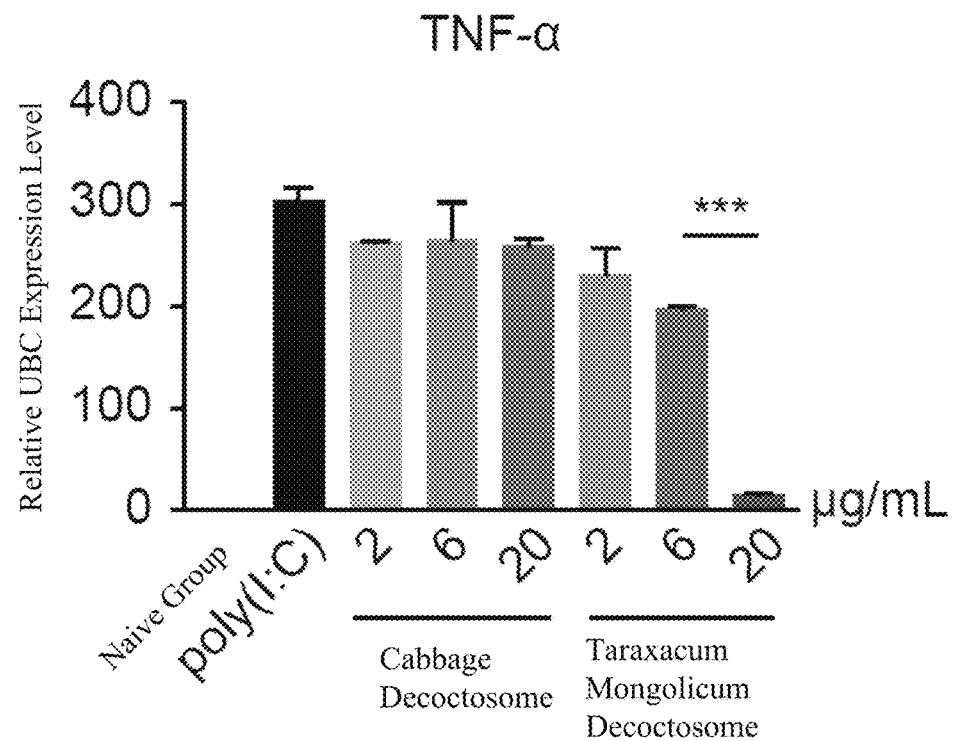

FIG. 9A-C: PGY decoctosome can reduce the relative expression of IL-1β/IL-6/TNF-α mRNA in the A549 cell inflammation model induced by poly(I:C).

Figure 9D:
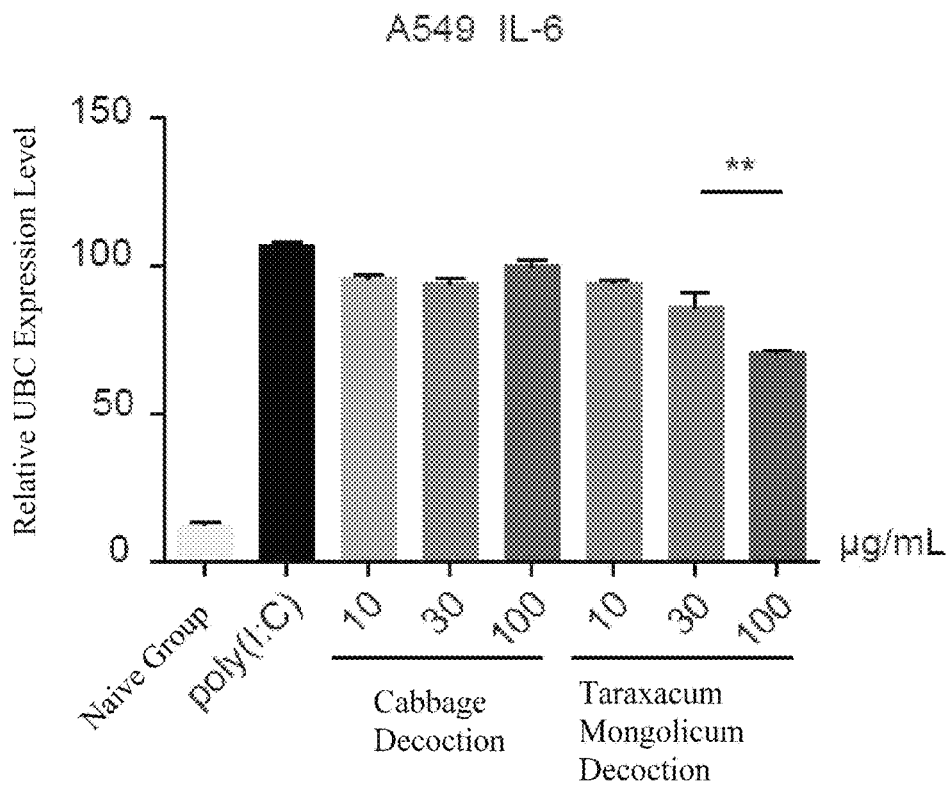
Figure 9E:
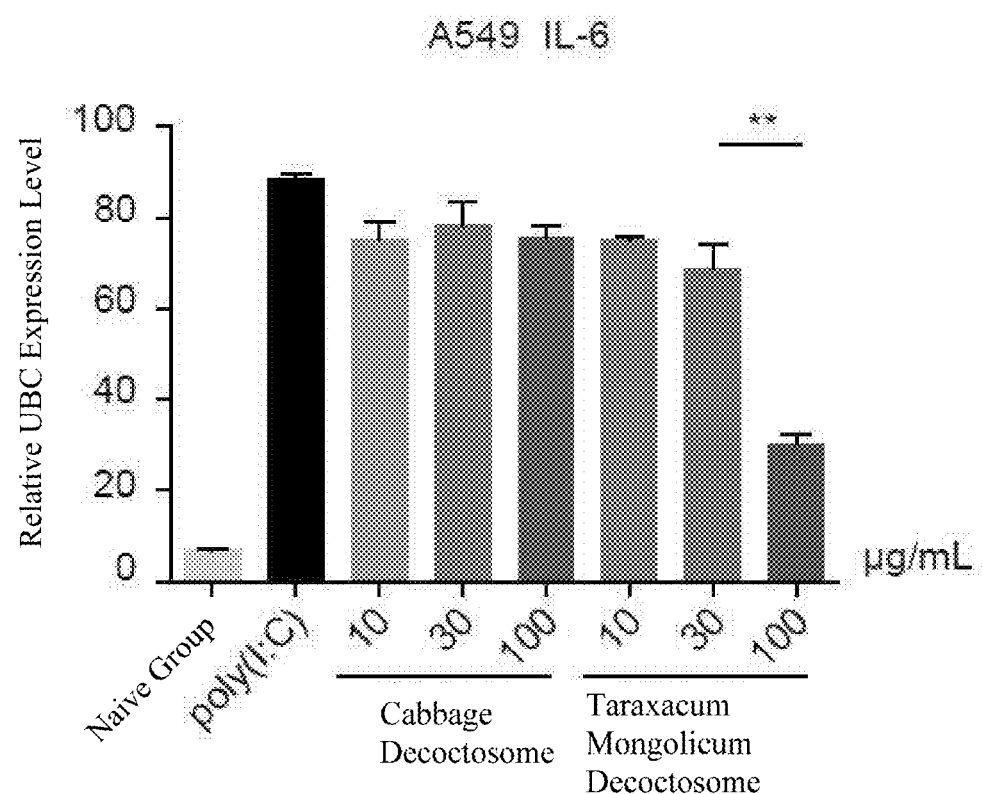

FIG. 9D-E: PGY decoction and decoctosome can reduce the protein expression level of IL-6 in the inflammation model of A549 cells.

Figure 9F:
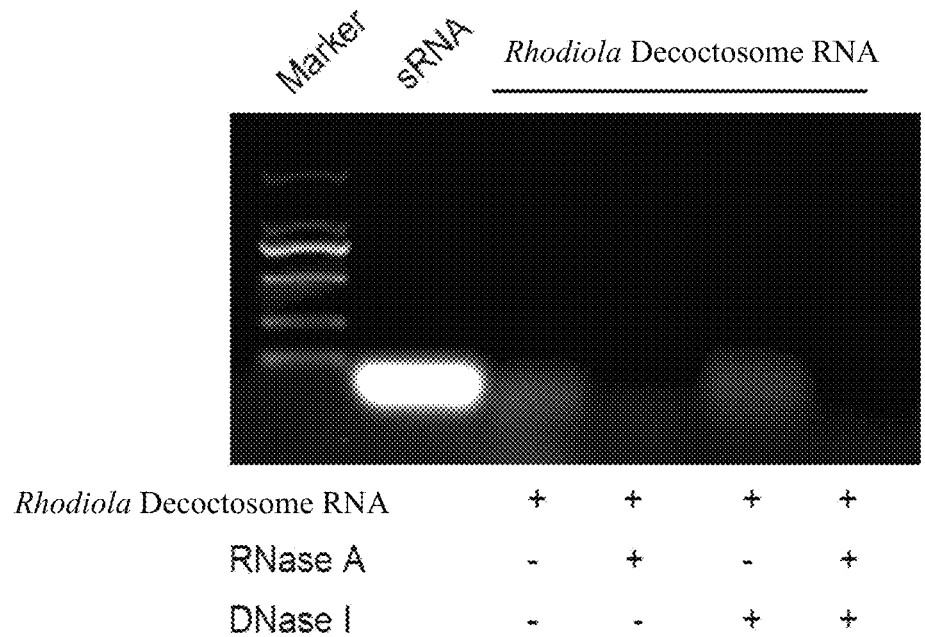

FIG. 9F: The results of cleavage with RNase A and DNase I of RNA in HJT decoctosome.

Figure 9G:
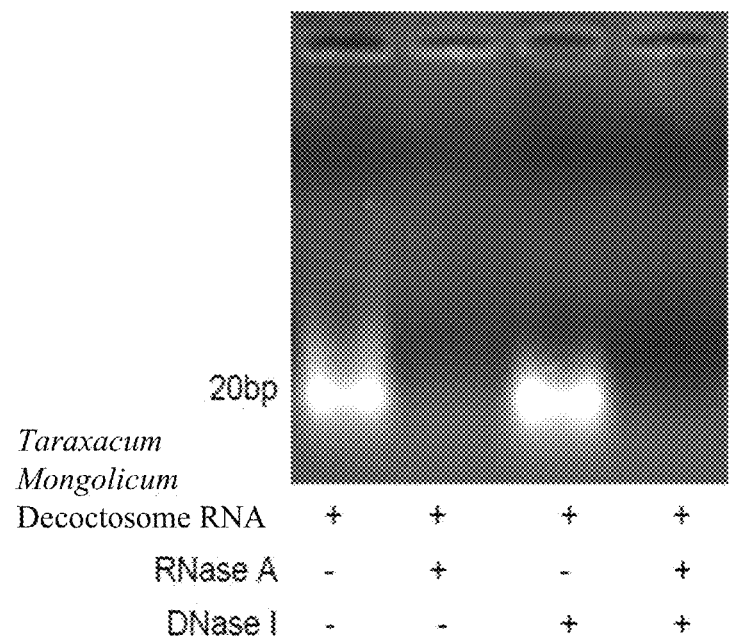

FIG. 9G: The results of cleavage with RNase A and DNase I of RNA in PGY decoctosome.

Figure 10:
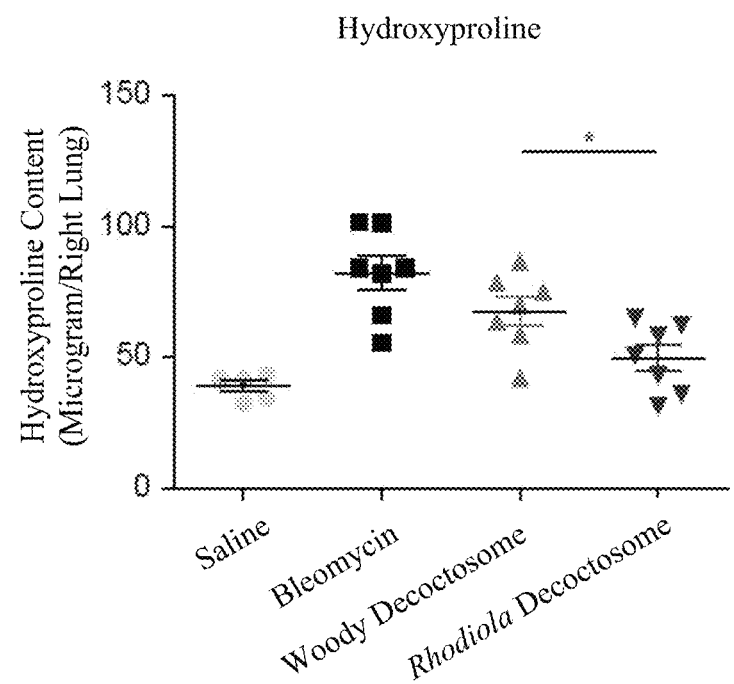

FIG. 10: The test results of reducing the expression of hydroxyproline in a pulmonary fibrosis model of mice for the control MX and HJT decoctosome.

Figure 11:
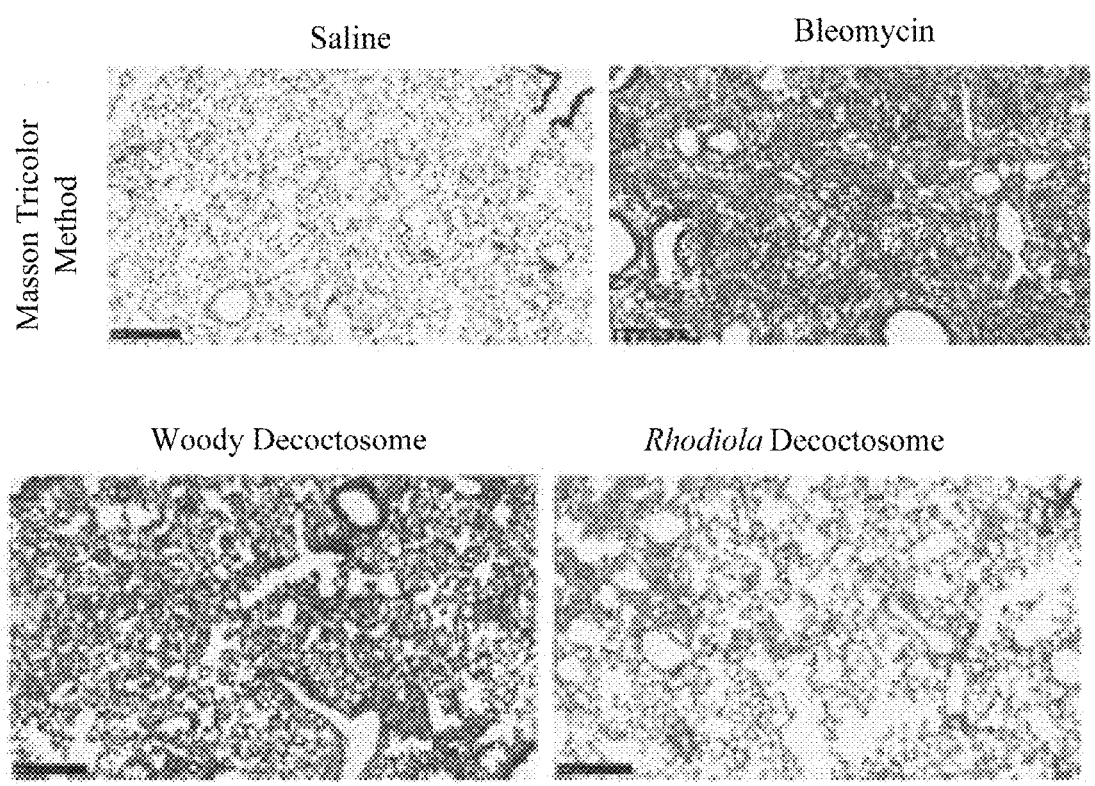

FIG. 11: The results of Masson staining in a pulmonary fibrosis model of mice alleviated by the control MX and HJT decoctosome.

Figure 12:
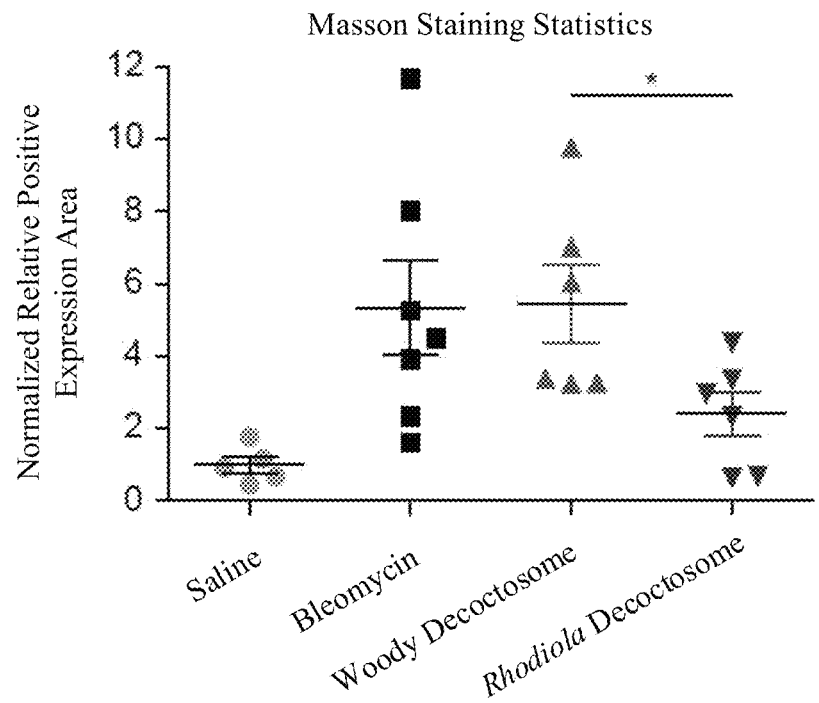

FIG. 12: The statistical results of Masson staining in a pulmonary fibrosis model of mice alleviated by the control MX and HJT decoctosome.

Figure 13:
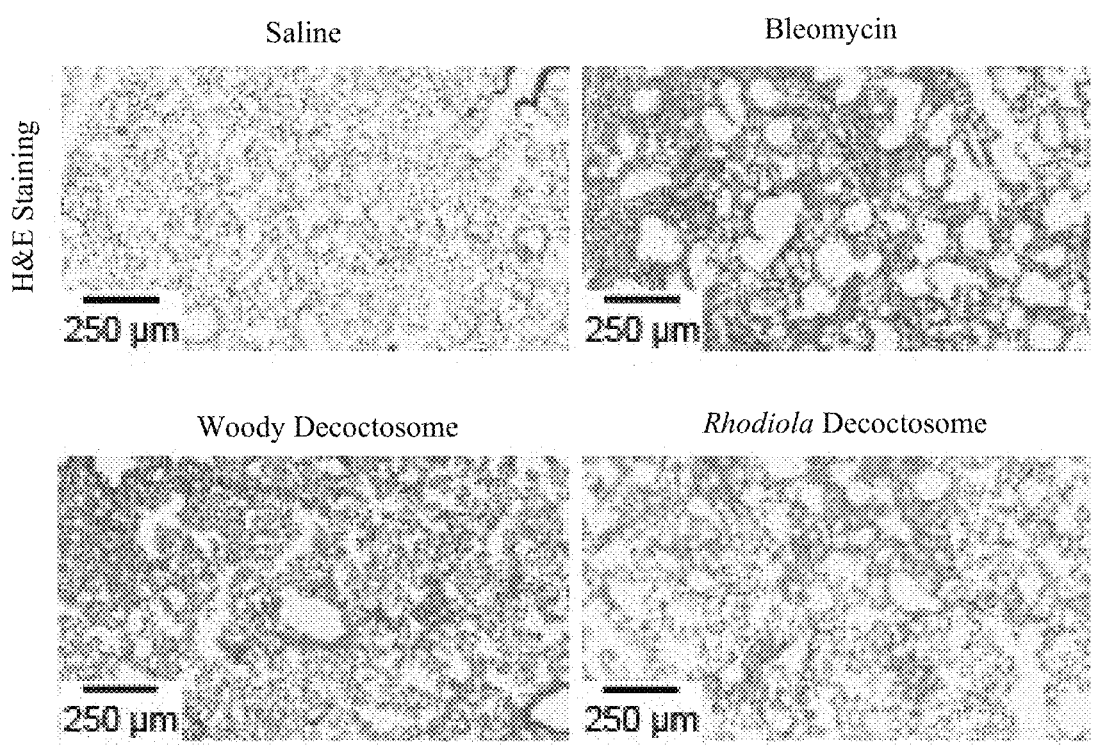

FIG. 13: The pathological test results in a pulmonary fibrosis model of mice alleviated by the control MX and HJT decoctosome.

Figure 14A:
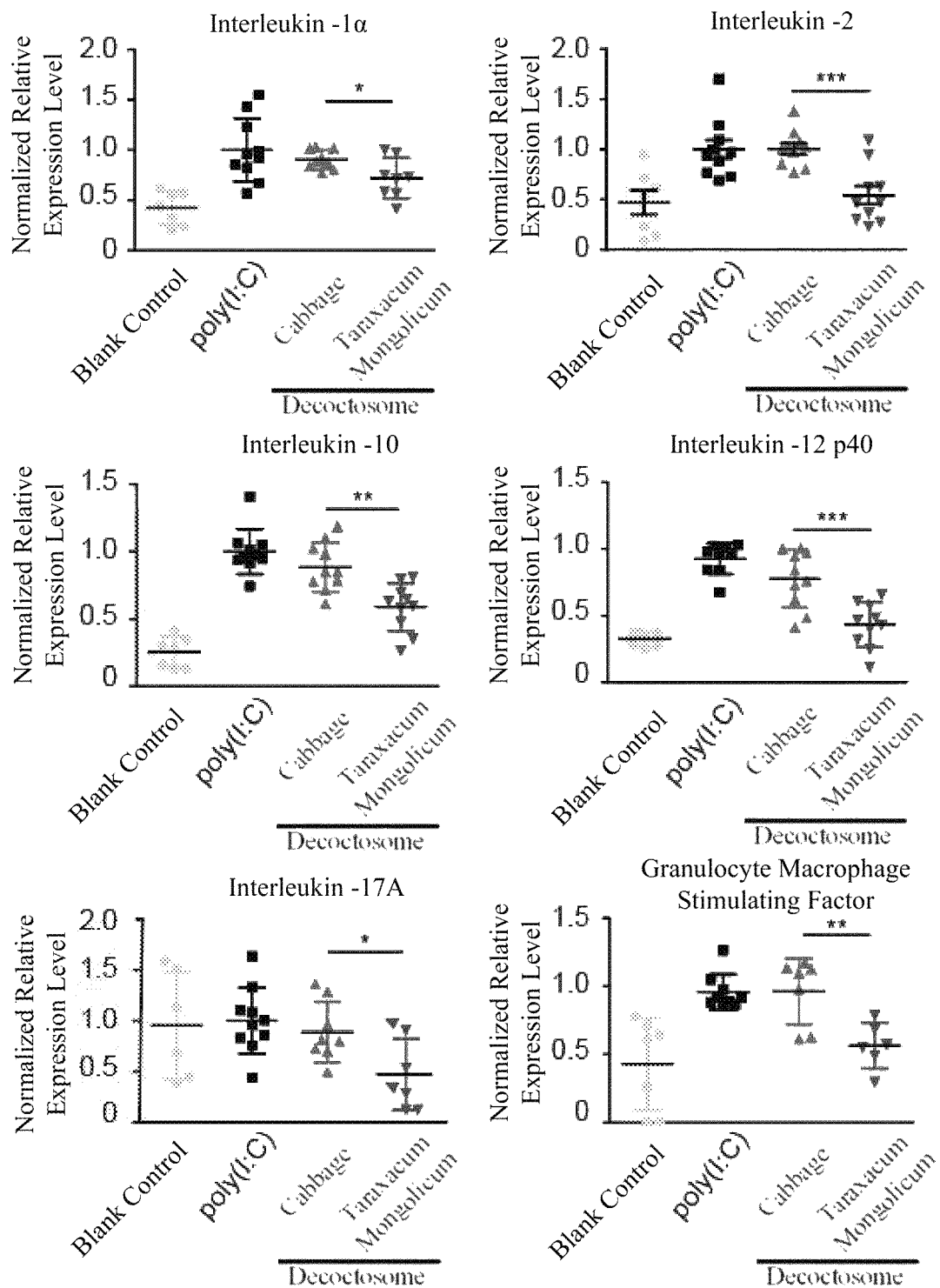
Figure 14B:
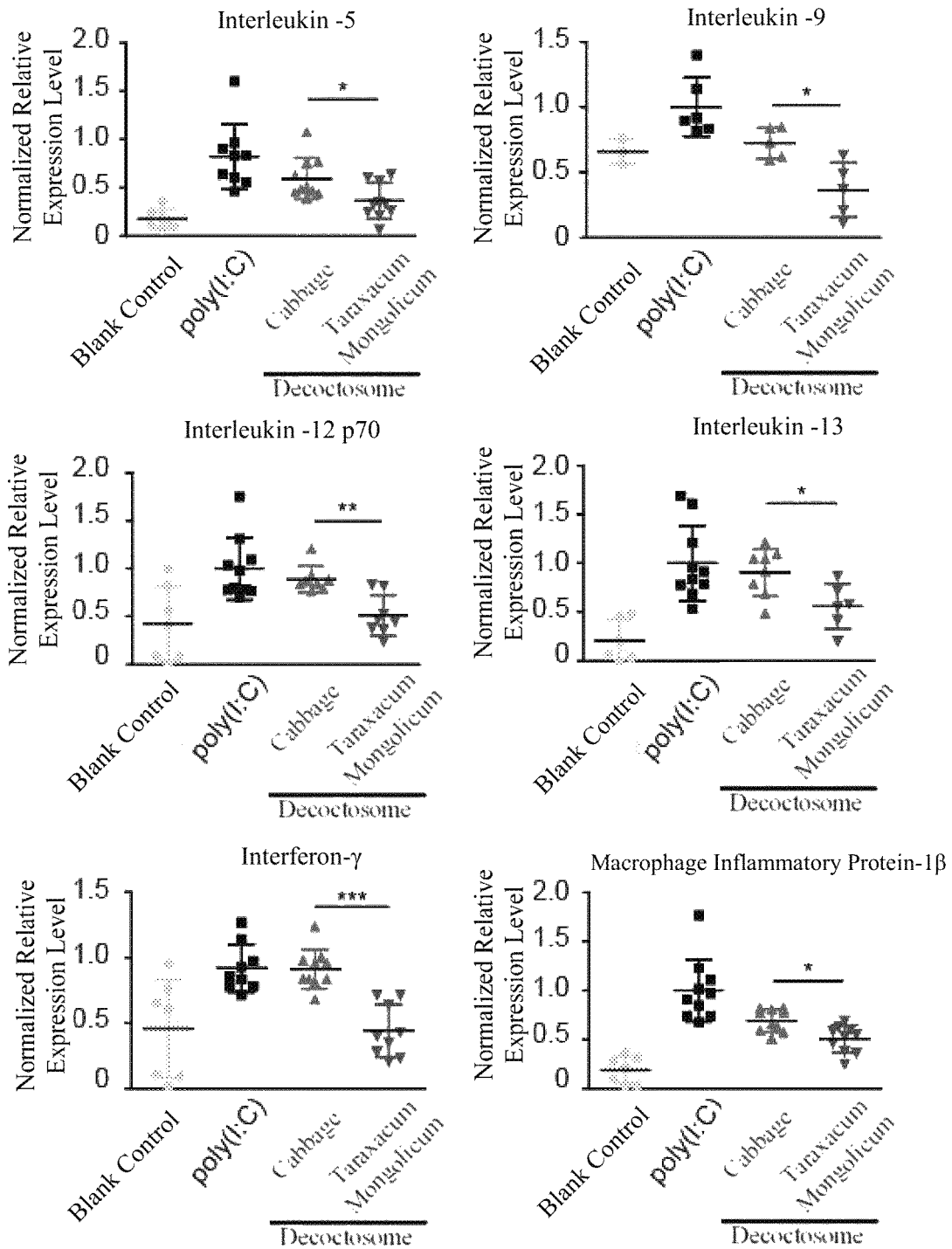

FIG. 14A-B: The test results of reducing the cytokine expression in plasma in an inflammation model of mice for the control cabbage and PGY decoctosome.

Figure 15:
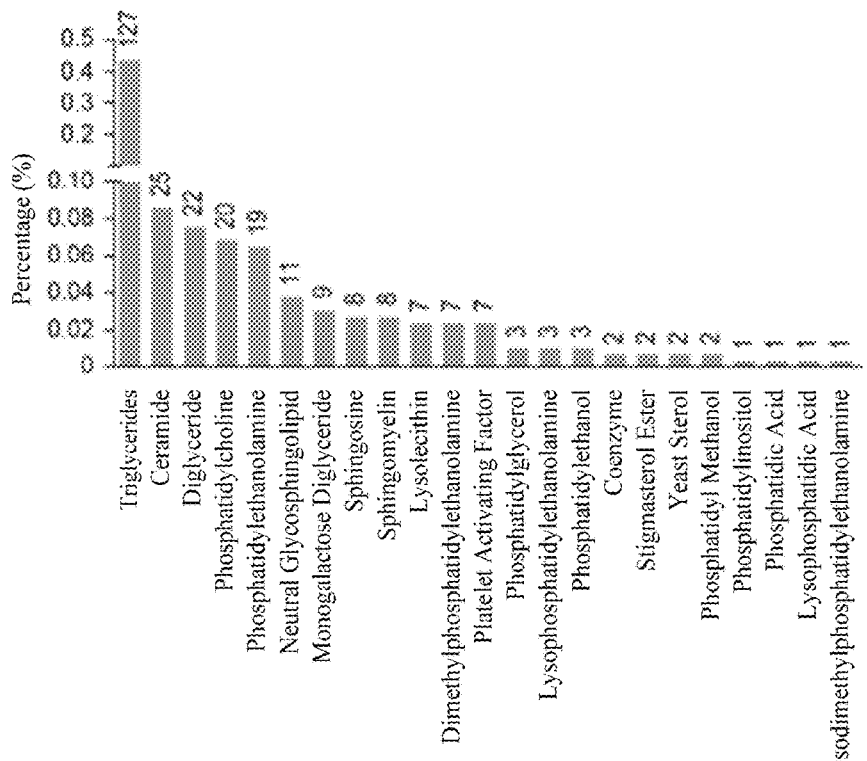

FIG. 15: Identification results of lipids in HJT decoctosome.

Figure 16:
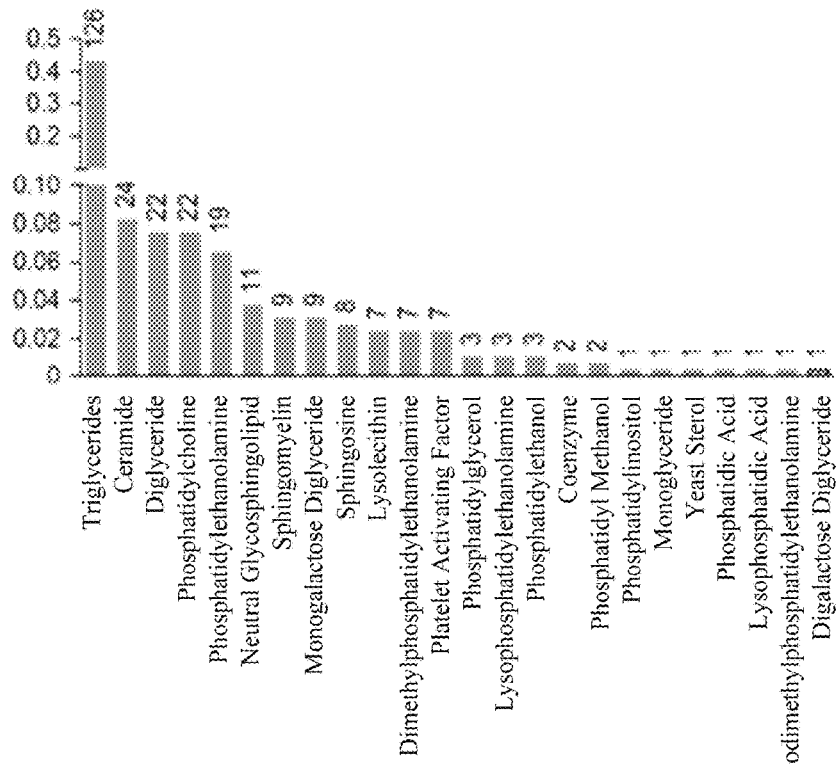

FIG. 16: Identification results of lipids in PGY decoctosome.

Figure 17:
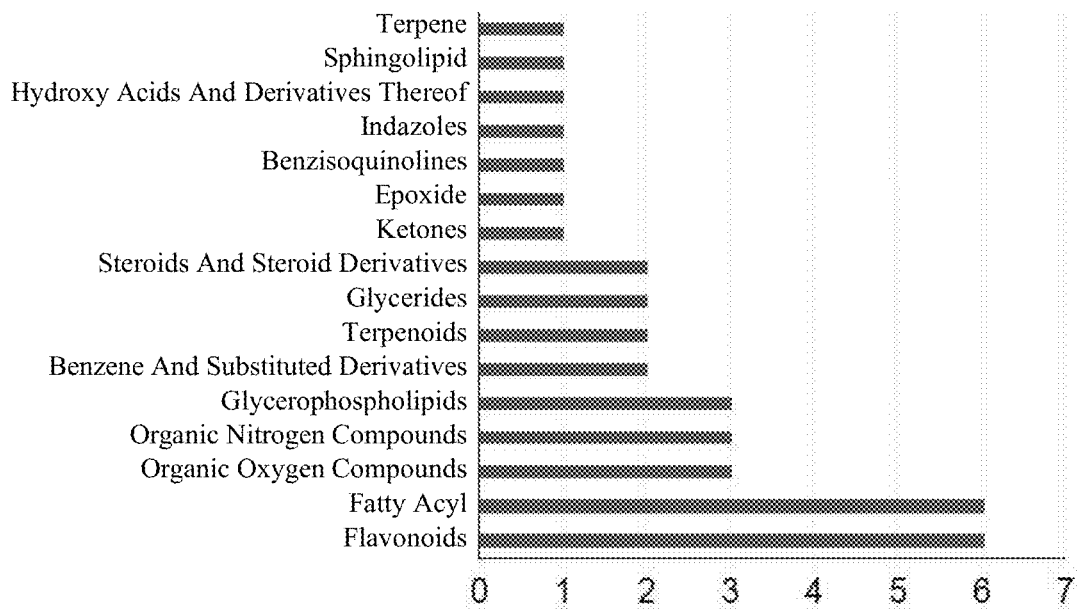

FIG. 17: Identification results of small molecules in HJT decoctosome.

Figure 18:
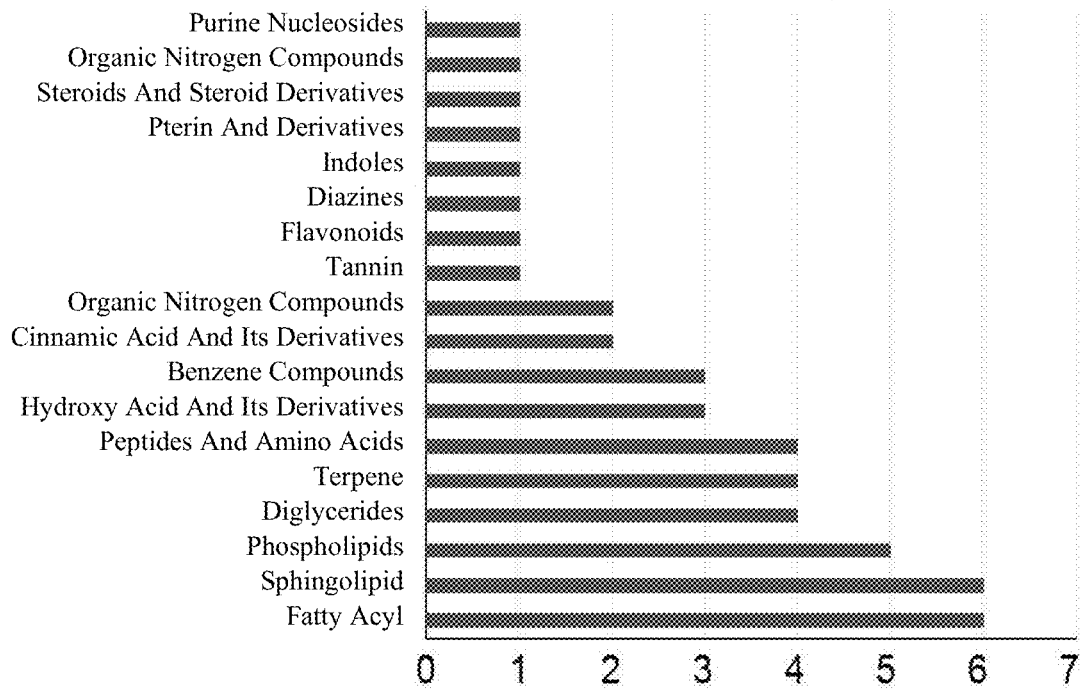

FIG. 18: Identification results of small molecules in PGY decoctosome.

FIG. 19: Identification results of proteins in HJT decoctosome.

FIG. 20: Identification results of proteins in PGY decoctosome.

Figure 21:
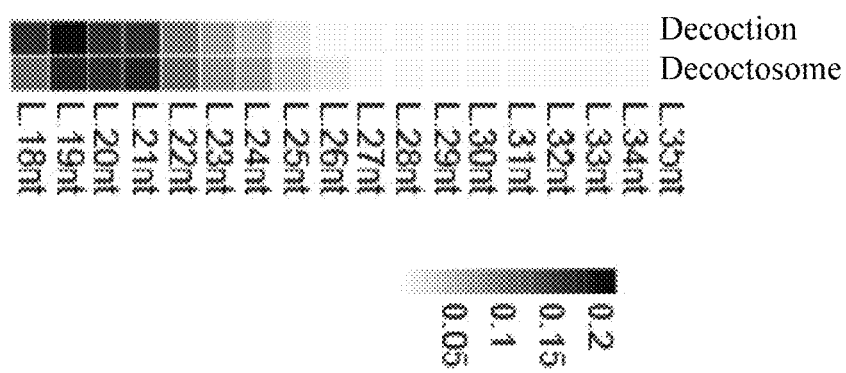

FIG. 21: Length distribution of small RNAs in HJT decoctosome.

Figure 22:
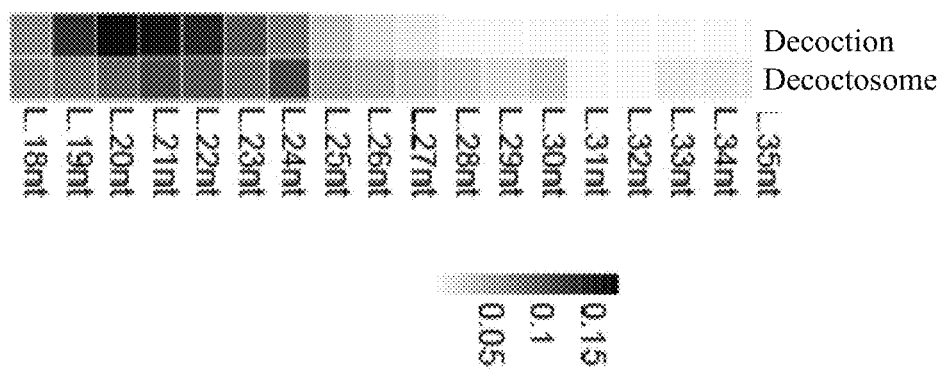

FIG. 22: Length distribution of small RNAs in PGY decoctosome.

Figure 23:
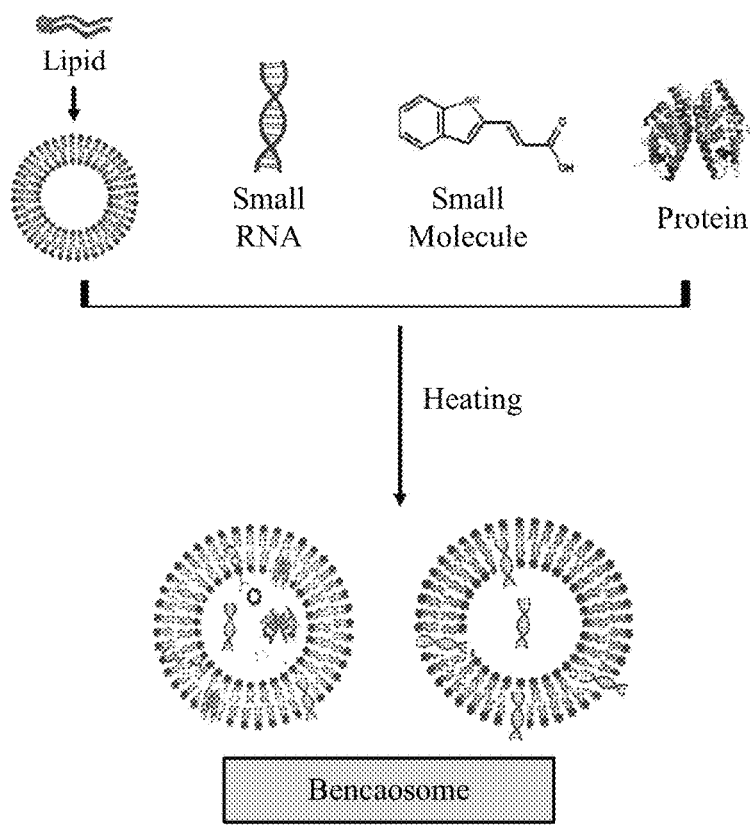

FIG. 23: A schematic diagram of the preparation process of the bencaosome.

Figure 24:
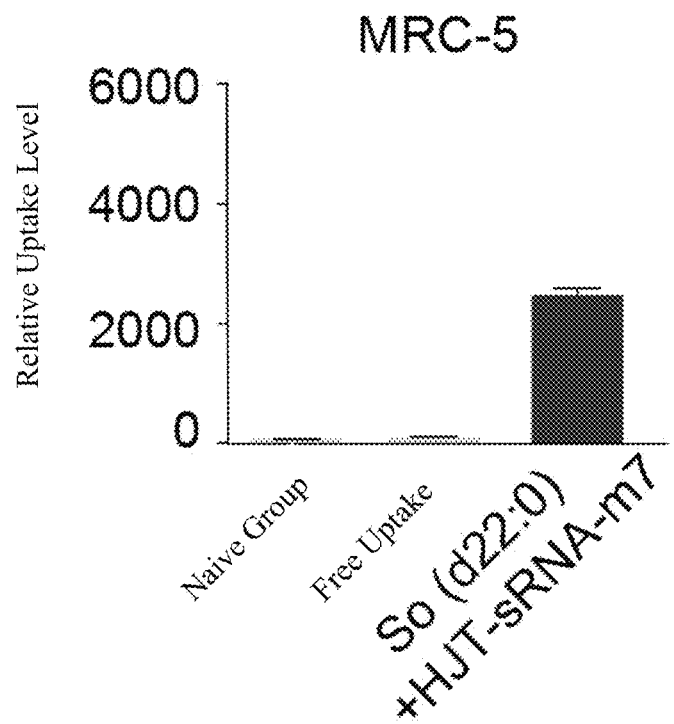

FIG. 24: The relative expression of HJT-sRNA-m7 as determined by RT-PCR.

Figure 25:
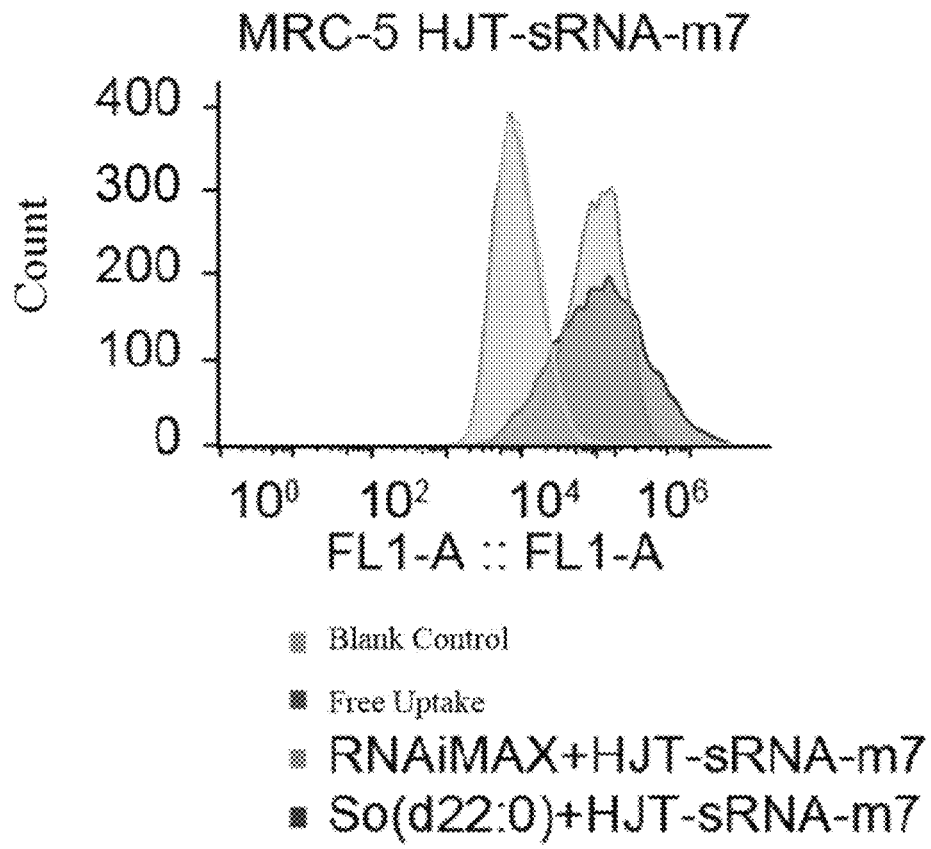

FIG. 25: The entry of HJT-sRNA-m7 as determined by flow cytometry.

Figure 26:
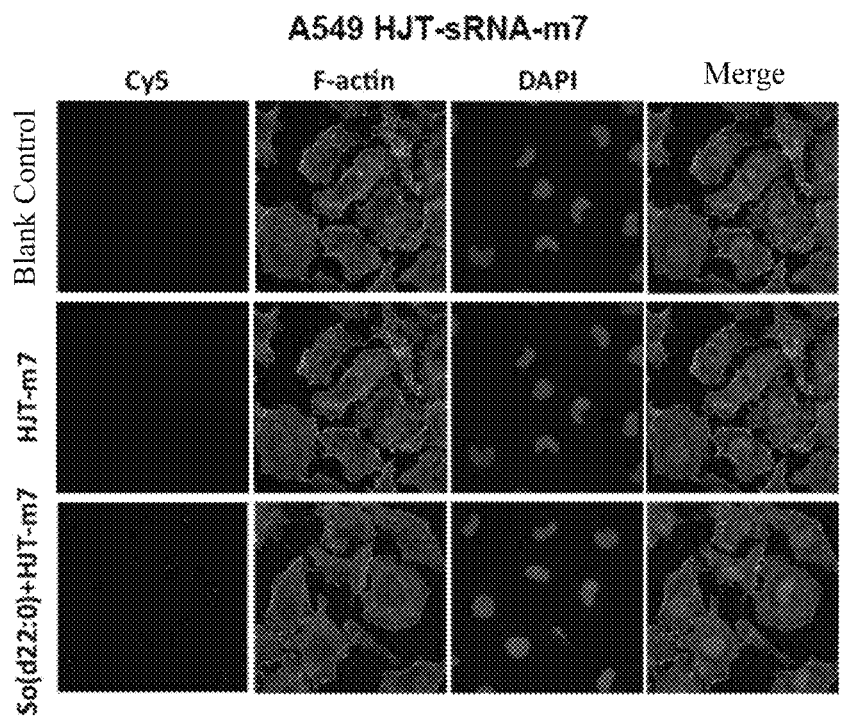

FIG. 26: The entry of Cy5 labeled HJT-sRNA-m7 as determined by cell confocal test FIG. 27: Addition of Sphinganine-HJT-sRNA-m7 reduces the expression of cell fibrosis-related proteins fibronectin and α-matrix protein (α-SMA), as determined by Western blotting test.

Figure 28:
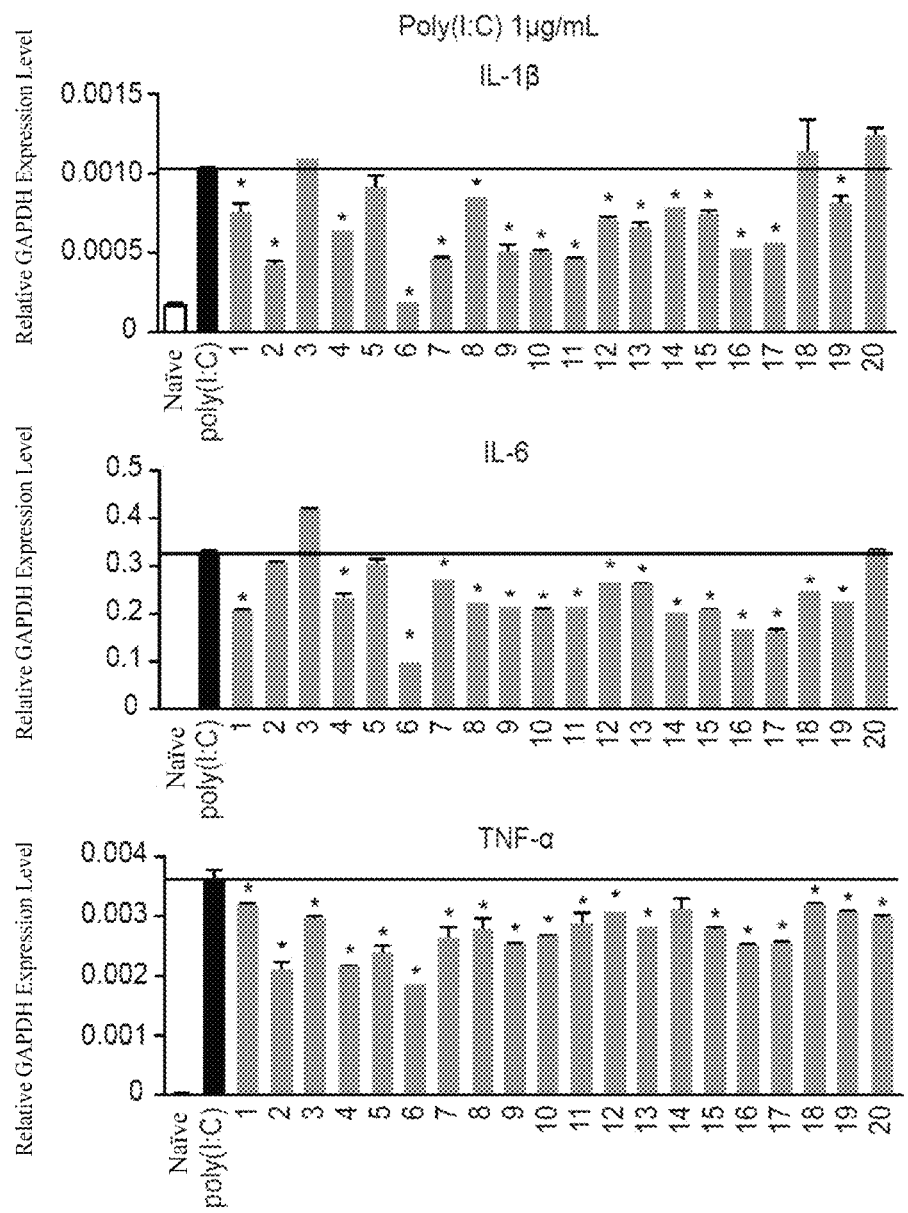

FIG. 28: Different small RNAs in PGY reduce the relative expression of IL-1β/IL-6/TNF-α in A549 cells inflammation models, as determined by RT-PCR test.

Figure 29A:
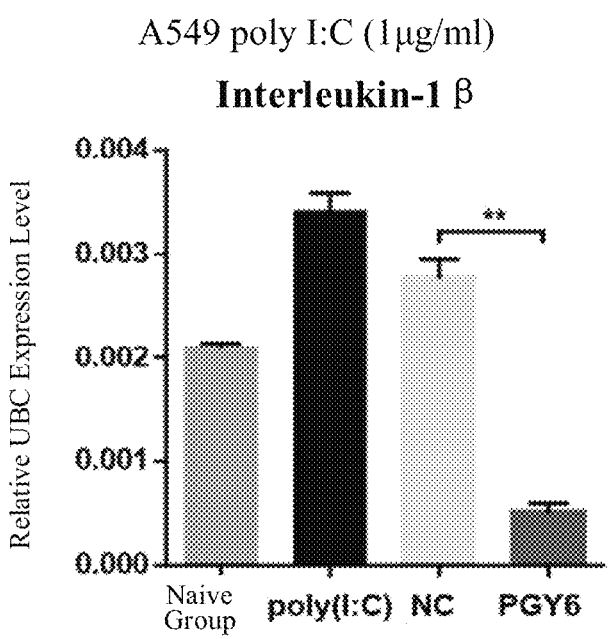
Figure 29B:
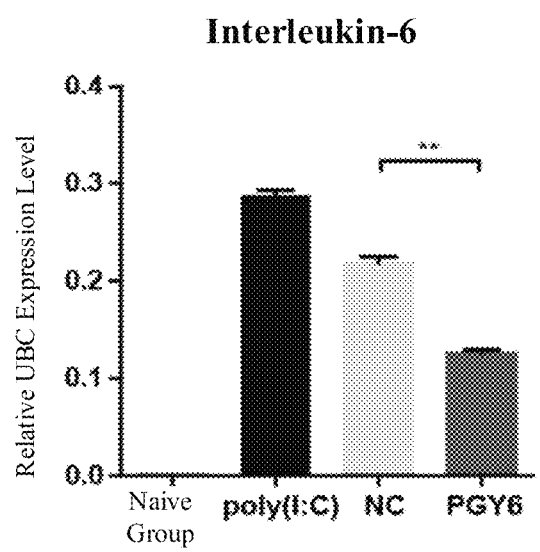
Figure 29C:
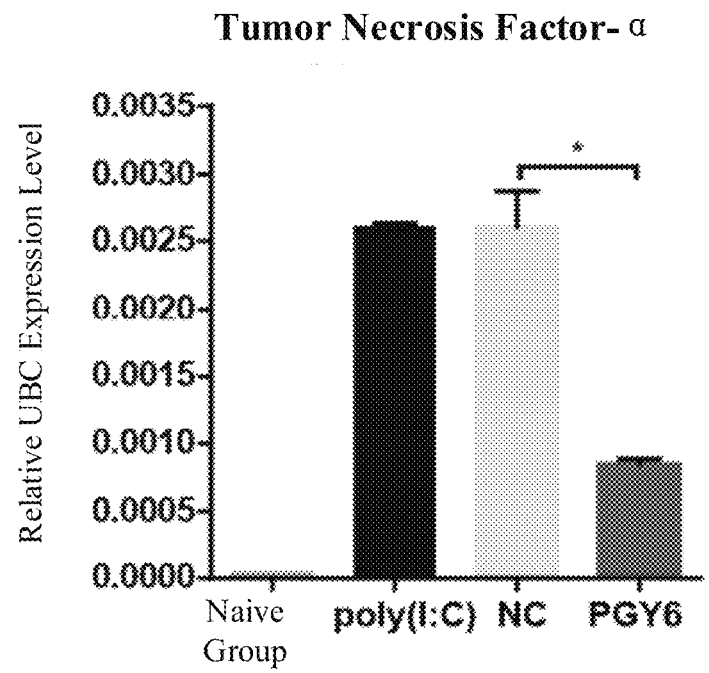

FIG. 29A-C: Transfection of PGY-sRNA-6 reduces the relative expression of IL-1β/IL-6/TNF-α after poly(I:C) stimulates A549 cells, as determined by RT-PCR test.

Figure 30A:
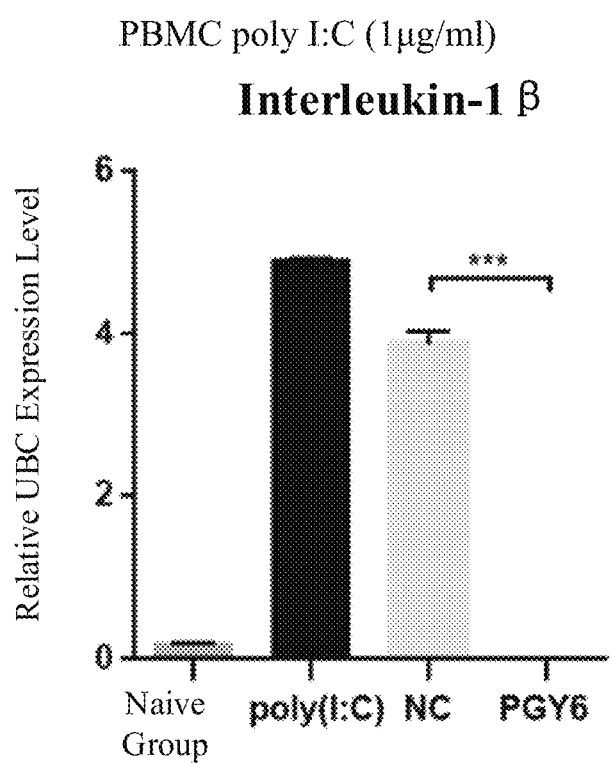
Figure 30B:
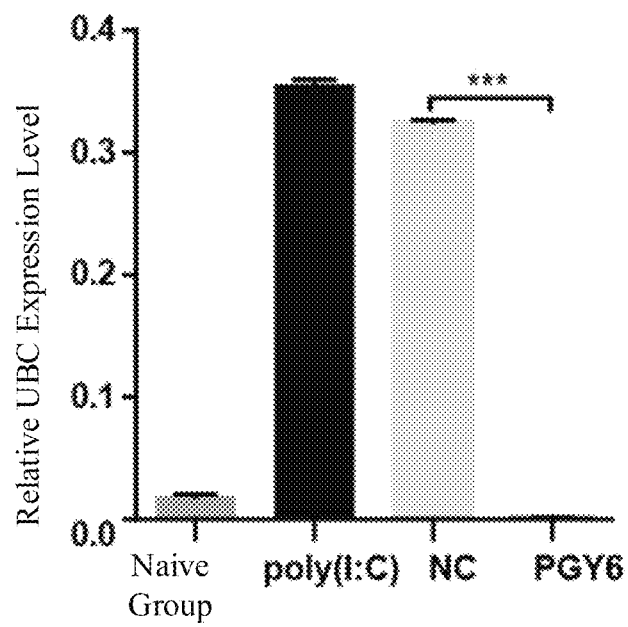
Figure 30C:
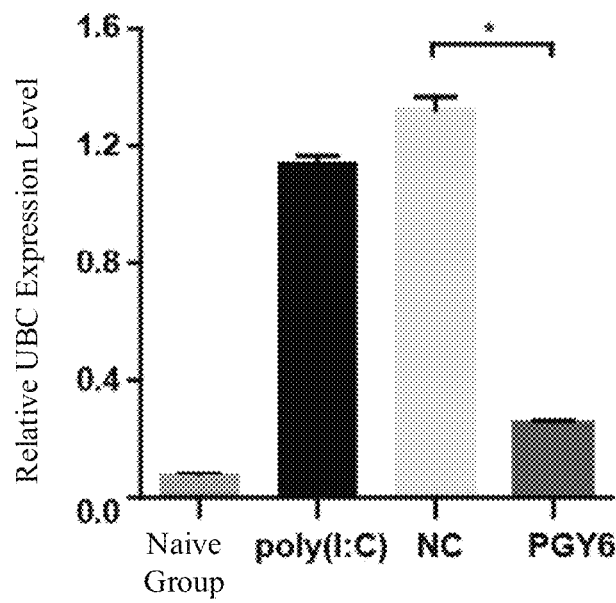

FIG. 30A-C: Transfection of PGY-sRNA-6 reduces the relative expression of IL-1β/IL-6/TNF-α after poly(I:C) stimulates PBMC cells, as determined by RT-PCR test.

Figure 31:
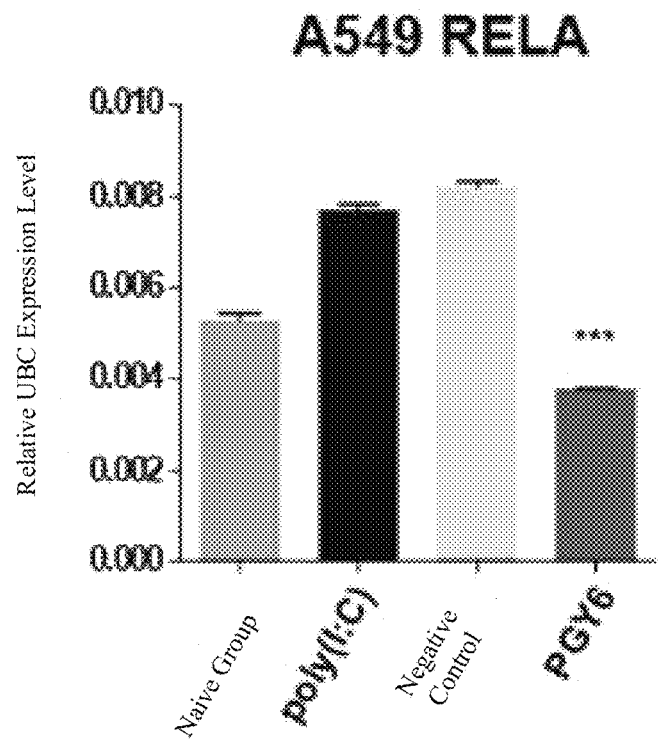

FIG. 31: Transfection of PGY-sRNA-6 reduces the relative expression of RELA genes after poly(I:C) stimulates A549 cells, as determined by RT-PCR assay.

Figure 32:
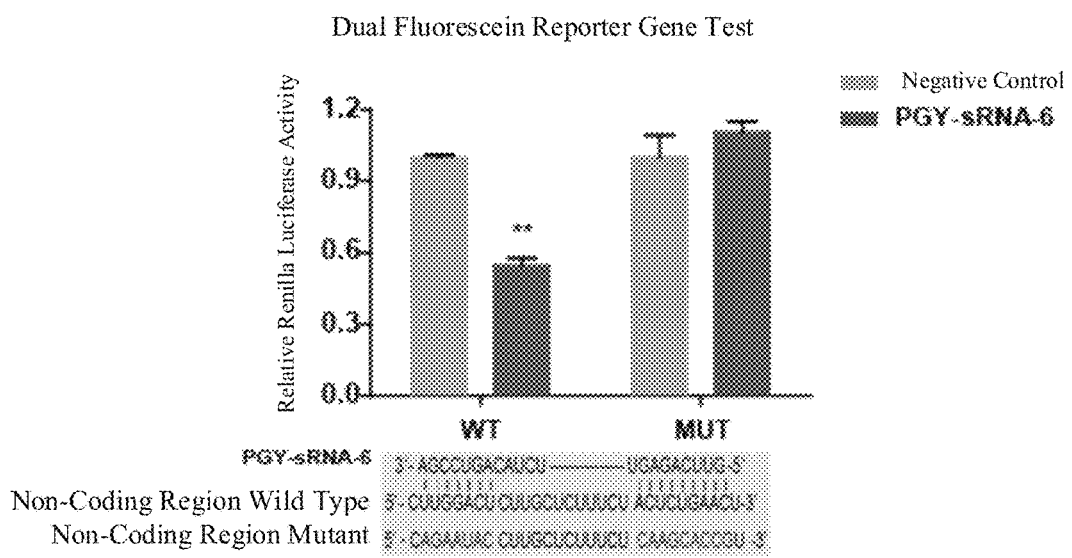

FIG. 32: RELA is the target gene of PGY-sRNA-6 as determined by double fluorescent reporter gene test.

Figure 33:
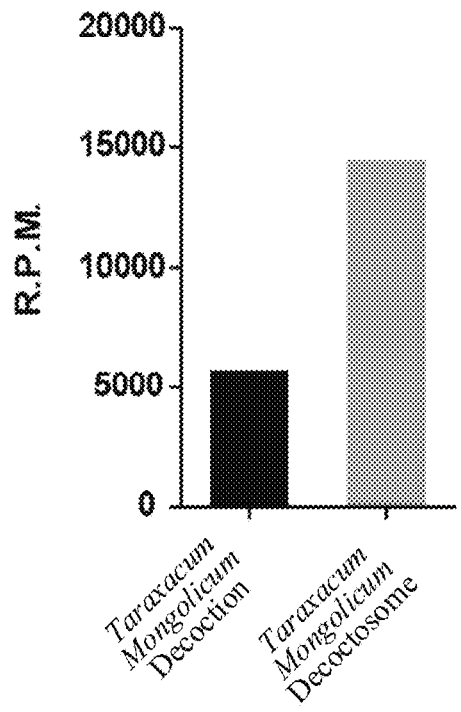

FIG. 33: The analysis of kurtosis of PGY-sRNA-6 in PGY decoction and PGY decoctosome.

Figure 34:
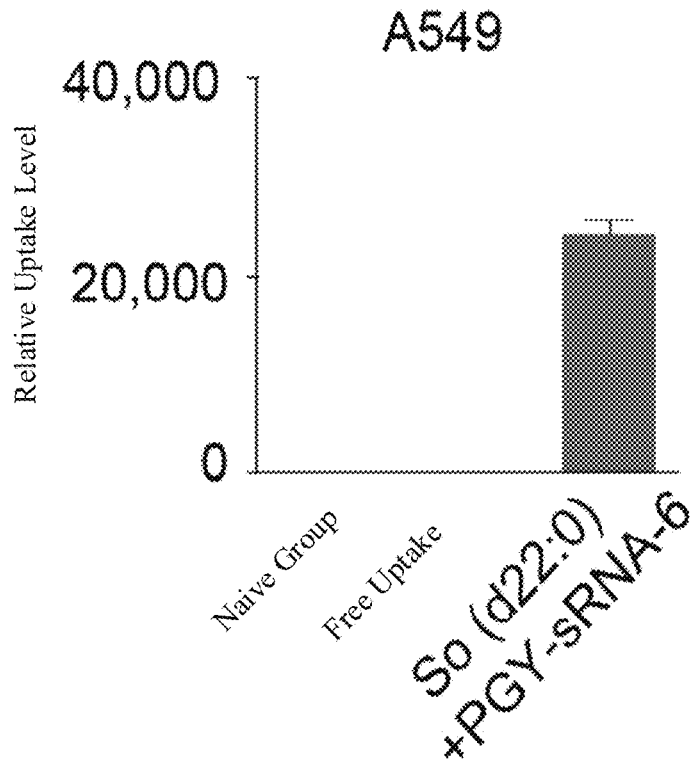

FIG. 34: The relative uptake of PGY-sRNA-6 as determined by RT-PCR.

Figure 35:
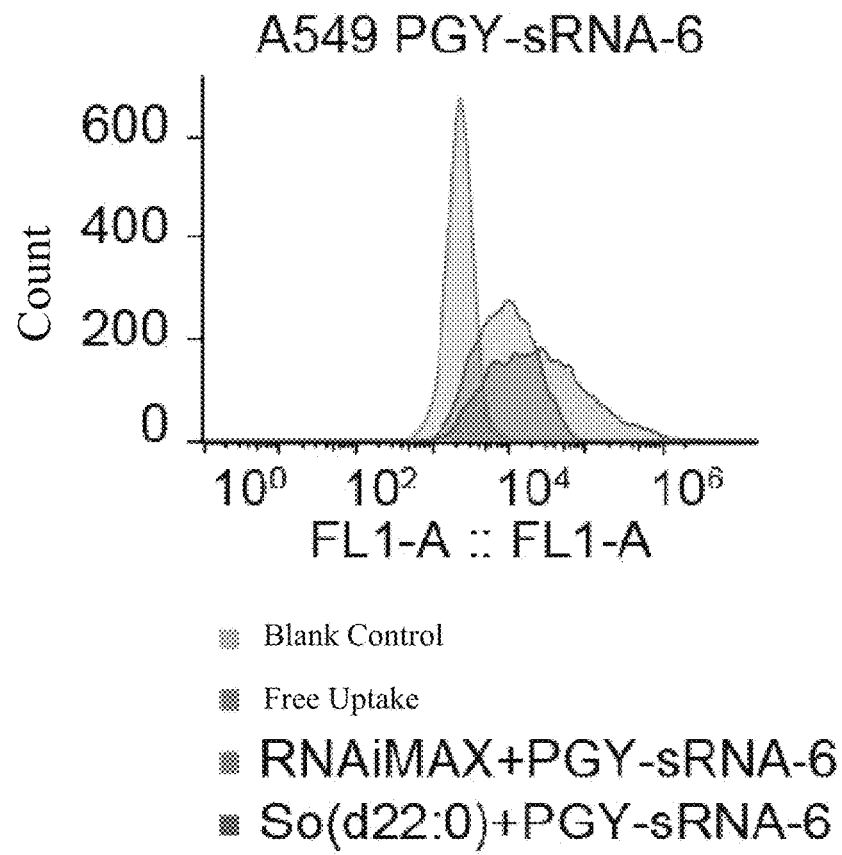

FIG. 35: The entry of PGY-sRNA-6 as detected by flow cytometry.

Figure 36:
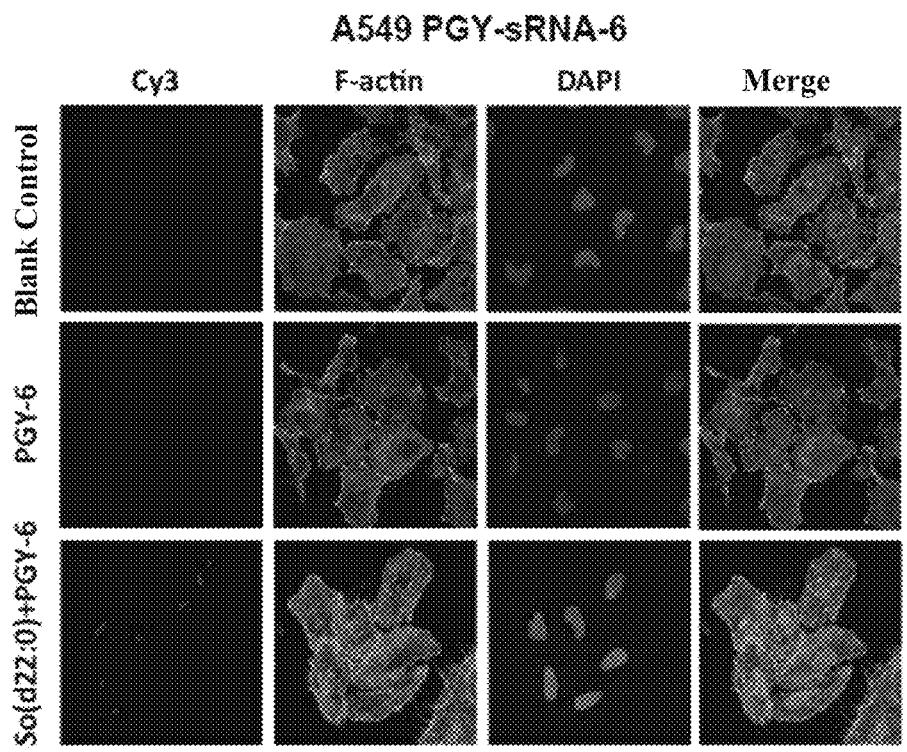

FIG. 36: The entry of Cy3 labeled PGY-sRNA-6 as detected by cell confocal test.

Figure 37A:
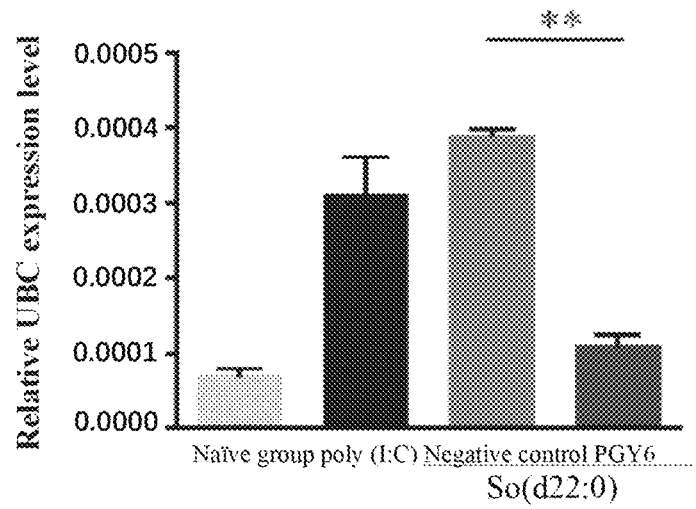
Figure 37B:
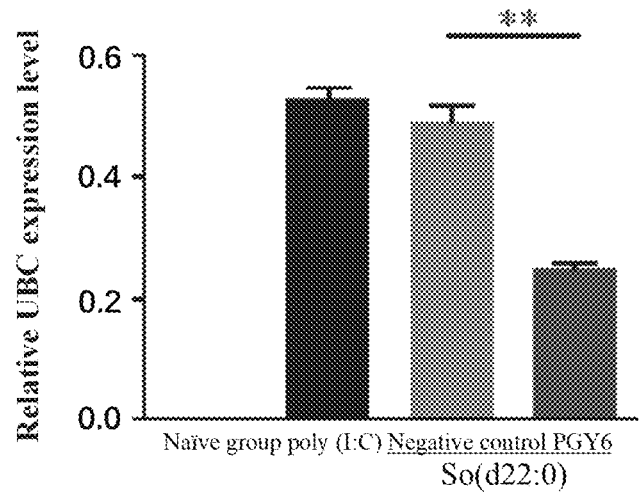
Figure 37C:
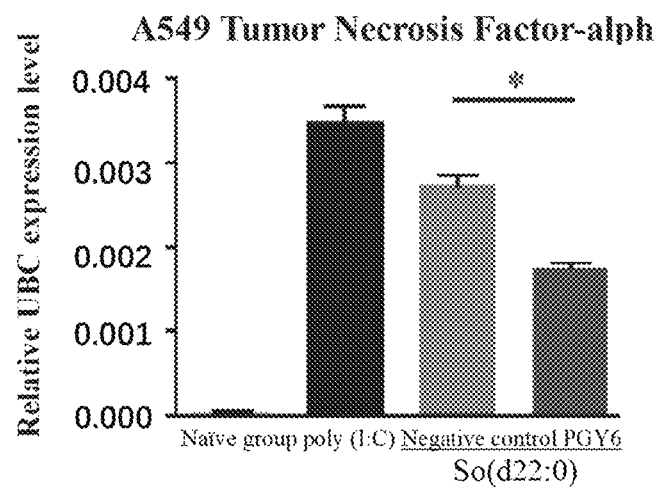

FIG. 37A-C: Sphinganine-PGY-sRNA-6 reduces the relative expression of IL-1β/IL-6/TNF-α mRNA in A549 cells stimulated by poly(I:C), as determined by RT-PCR.

Figure 38:
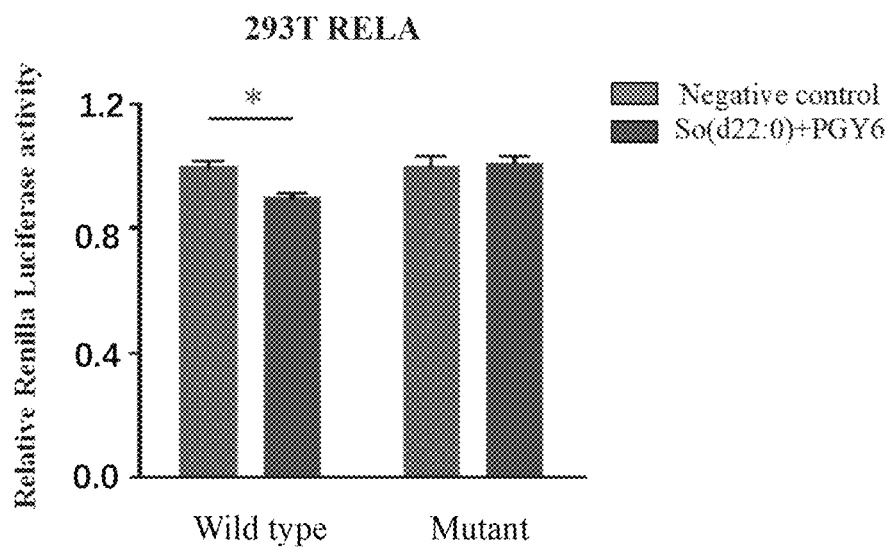

FIG. 38: The relative fluorescent intensity after adding Sphinganine-PGY-sRNA-6 as determined by double fluorescent reporter gene test.

Figure 39:
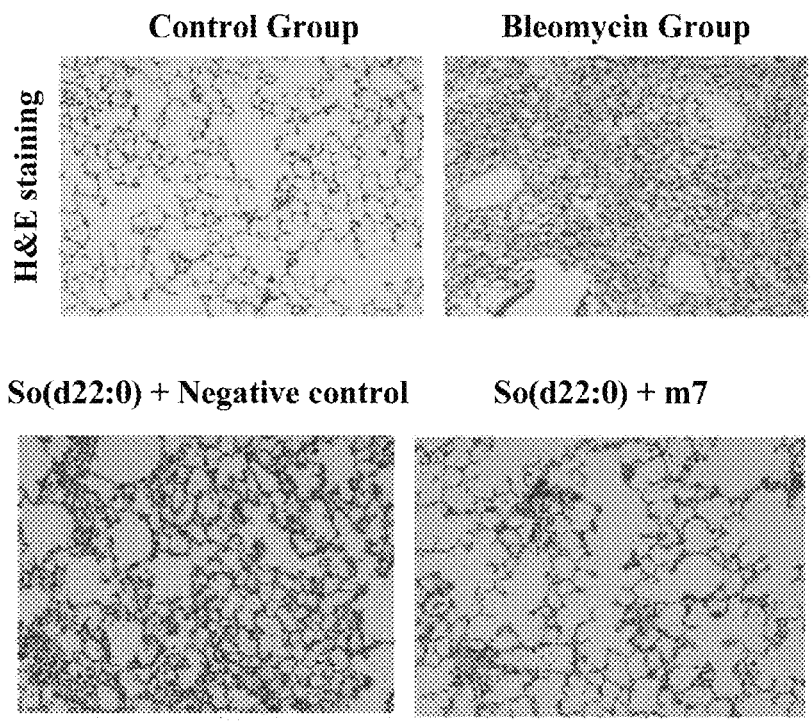

FIG. 39: The pathological test results in a pulmonary fibrosis model of mice alleviated by Sphinganine-HJT-sRNA-m7.

Figure 40:
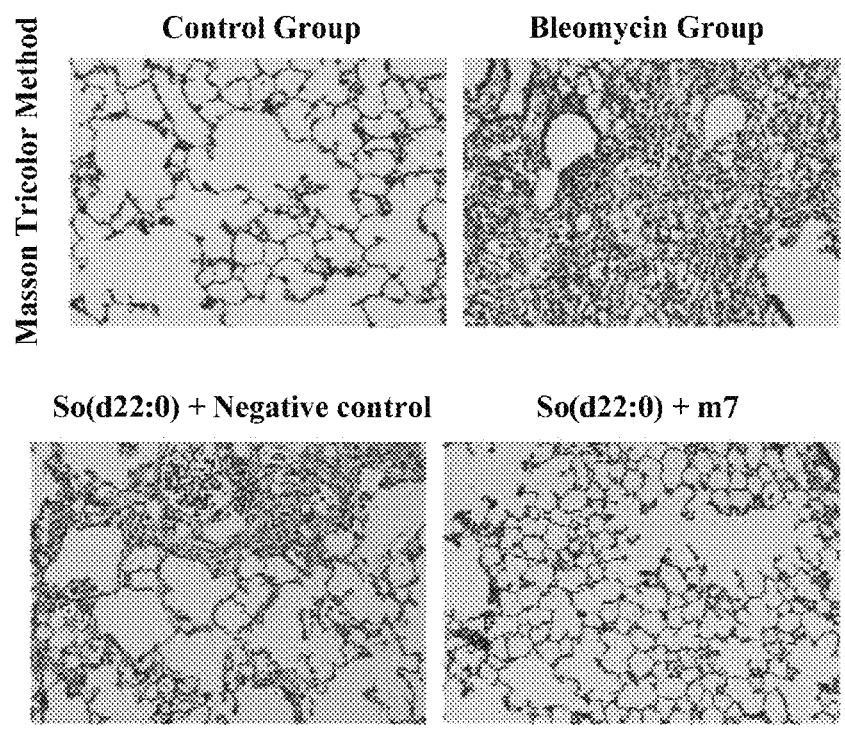

FIG. 40: The results of Masson staining in a pulmonary fibrosis model of mice alleviated by Sphinganine-HJT-sRNA-m7.

Figure 41:
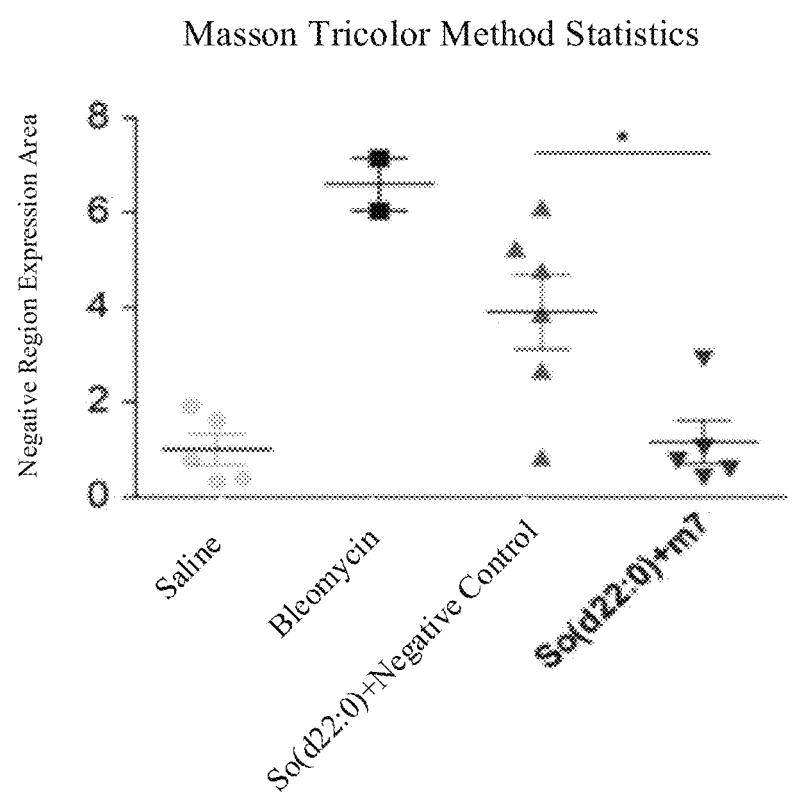
Figure 42A:
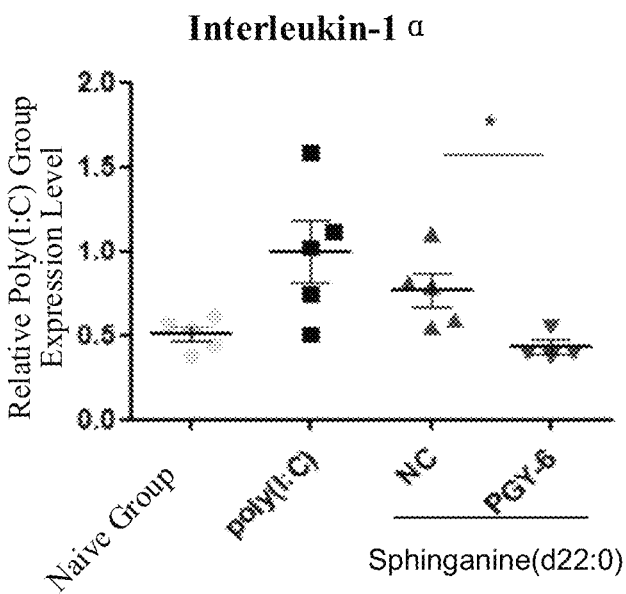
Figure 42B:
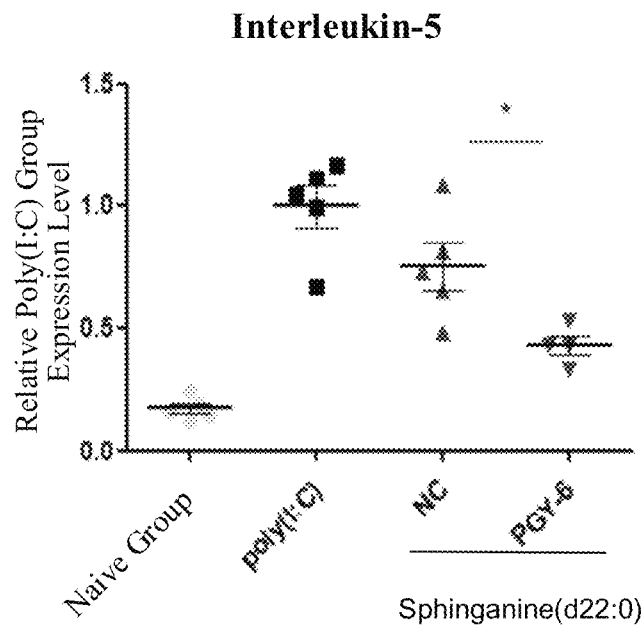
Figure 42C:
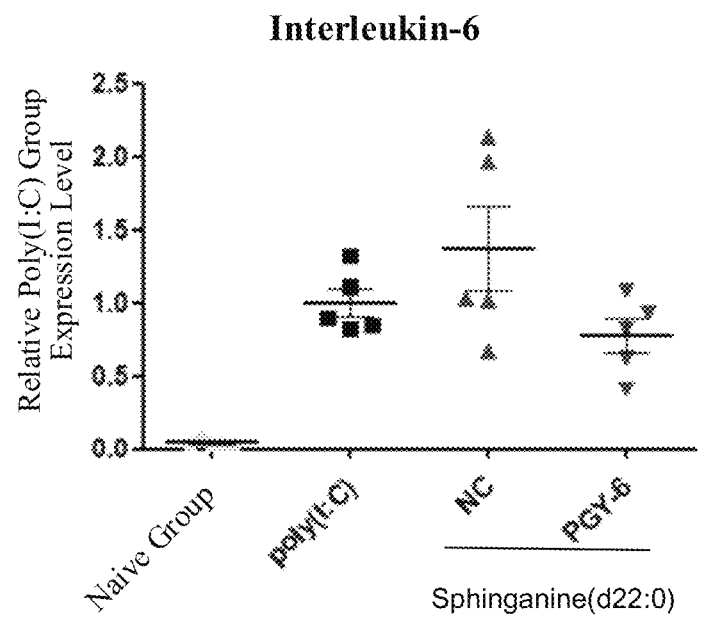
Figure 42D:
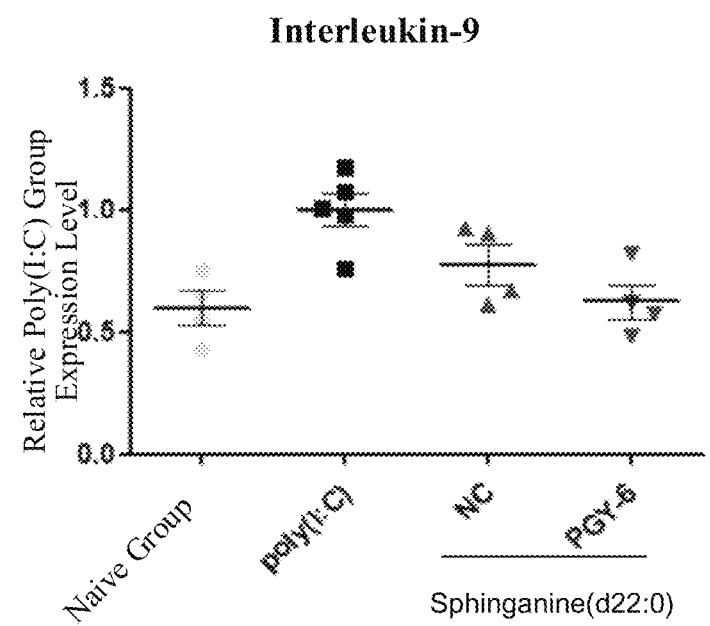
Figure 42E:
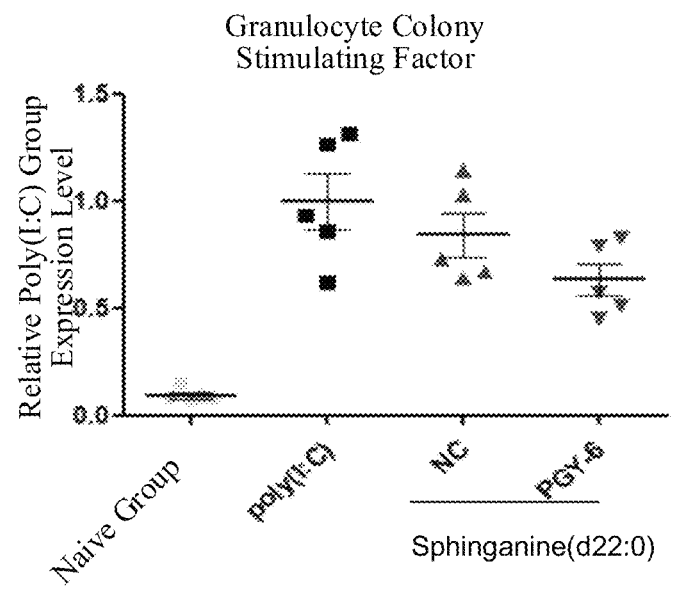
Figure 42F:
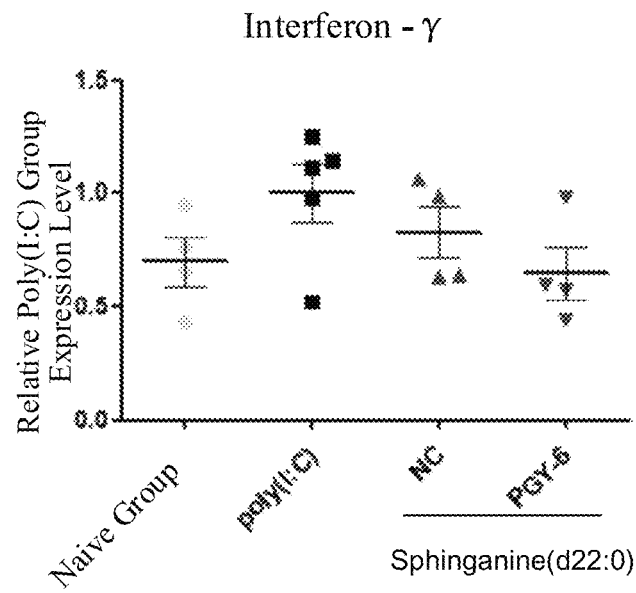
Figure 42G:
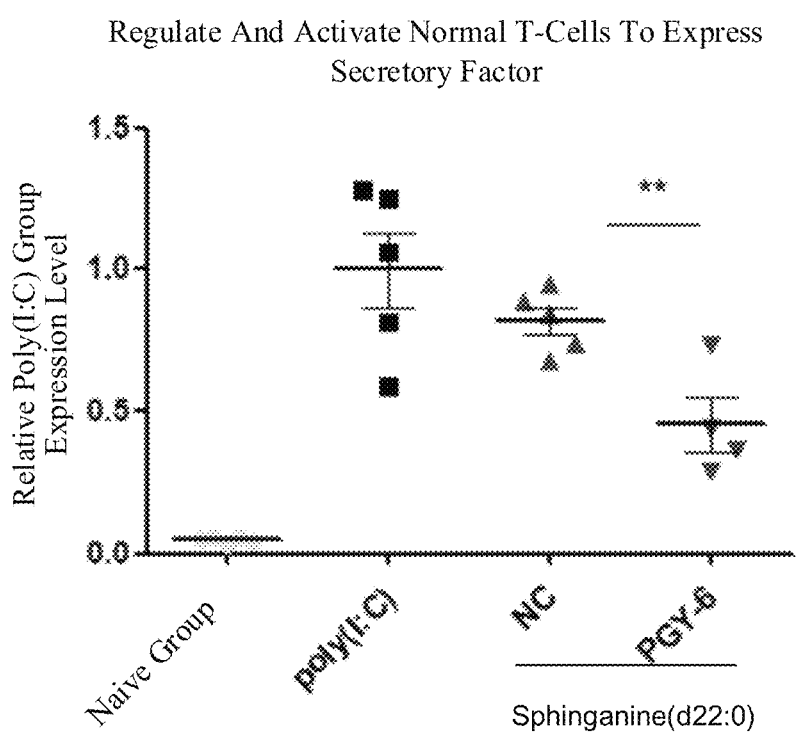
Figure 44A:
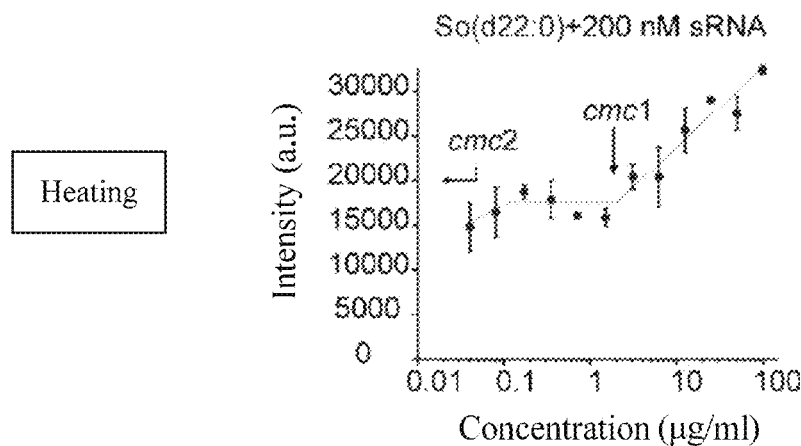
Figure 44B:
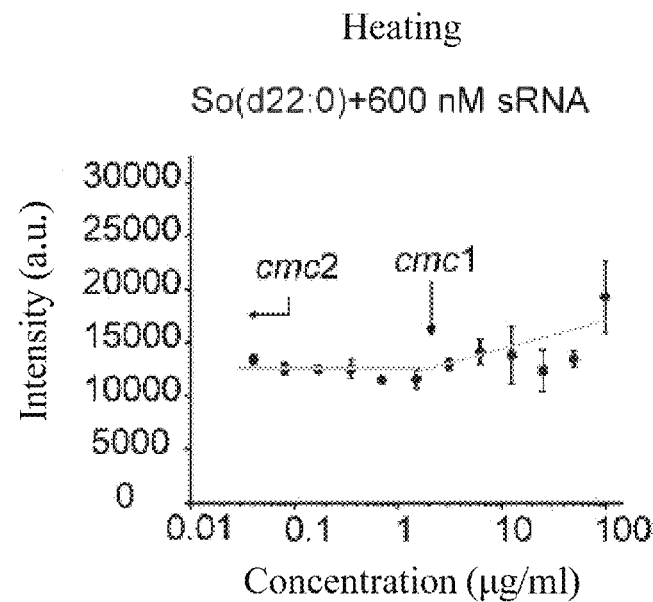
Figure 44C:
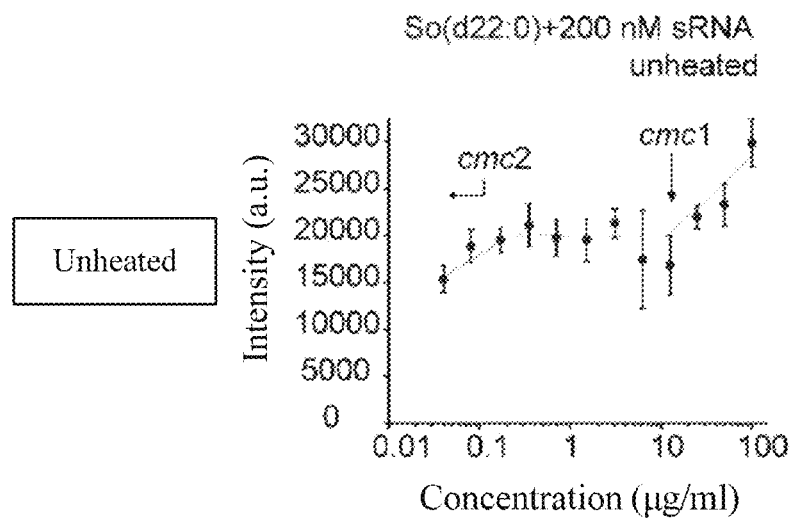
Figure 44D:
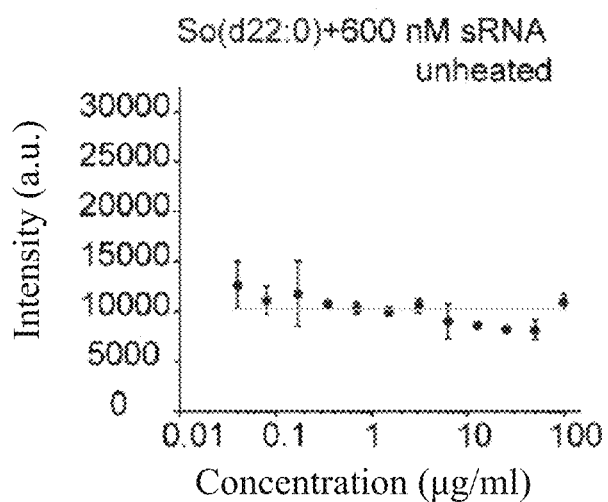

FIG. 41: The statistical results of Masson staining in a pulmonary fibrosis model of mice alleviated by Sphinganine-HJT-sRNA-m7.

FIG. 42A-G: The test results of the cytokine expression level in plasma of mouse inflammation model reduced by Sphinganine-PGY-sRNA-6.

FIG. 43: By measuring the dependency of the fluorescence emission intensity of 1,6-diphenyl-1,3,5-hexatriene (DPH) on the concentration of surfactants, the critical micelle concentration (cmc) values of only small RNA and only Sphinganine are shown.

FIG. 44A-D: The CMC properties of bencaosome sphinganine (So(d22:0))+200 nM or 600 nM sRNA with and without heat treatment.

Figure 45:
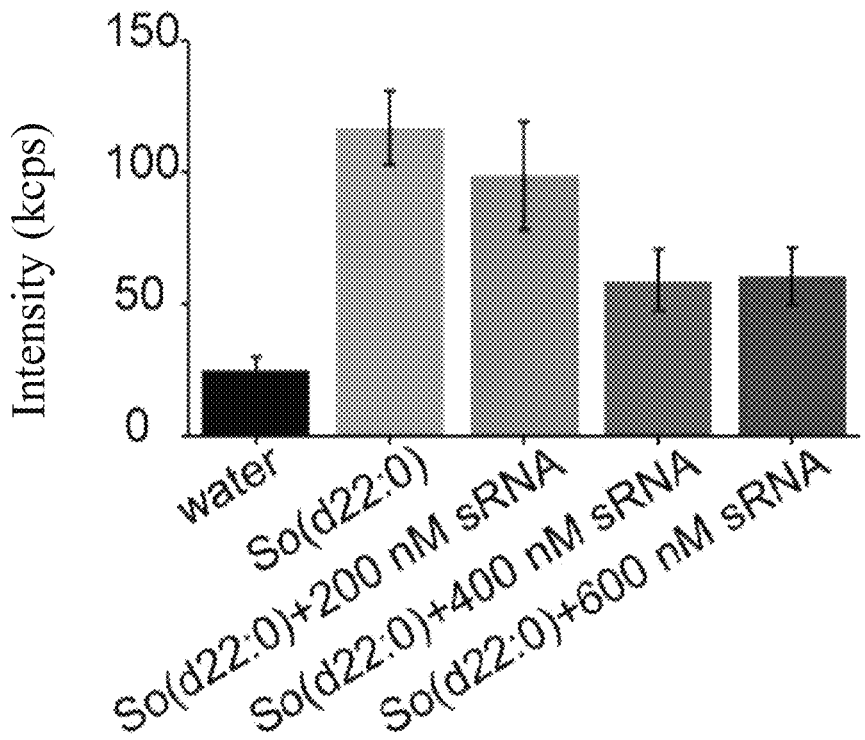

FIG. 45: Comparison of the static light scattering intensity of water, So(d22:0), So(d22:0)+200 nM, 400 nM or 600 nM sRNA.

Figure 46:
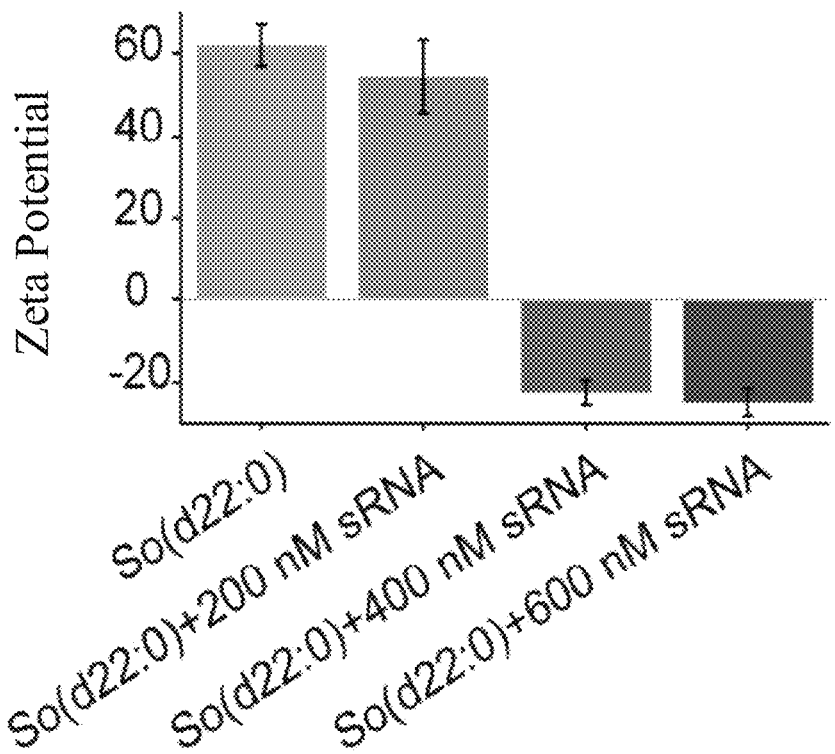

FIG. 46: Comparison of the Zeta potential of So(d22:0), So(d22:0)+200 nM, 400 nM or 600 nM sRNA.

Figure 47A:
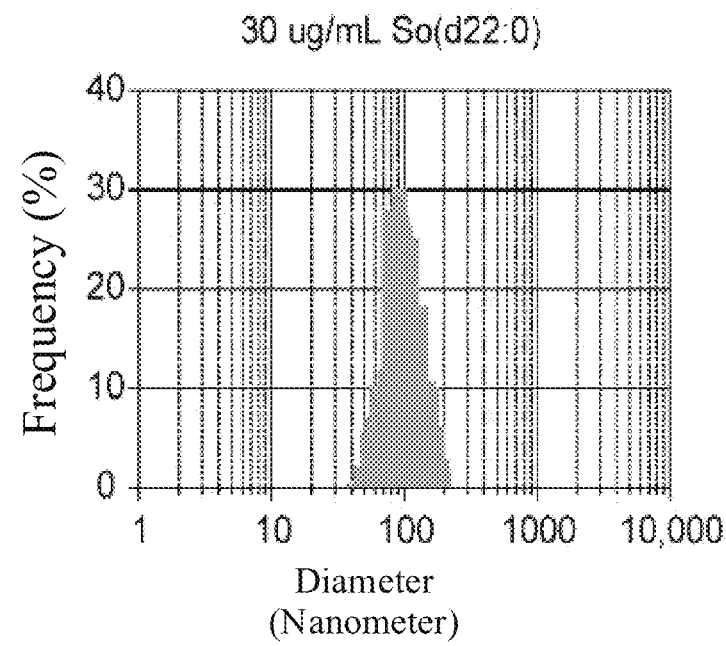
Figure 47B:
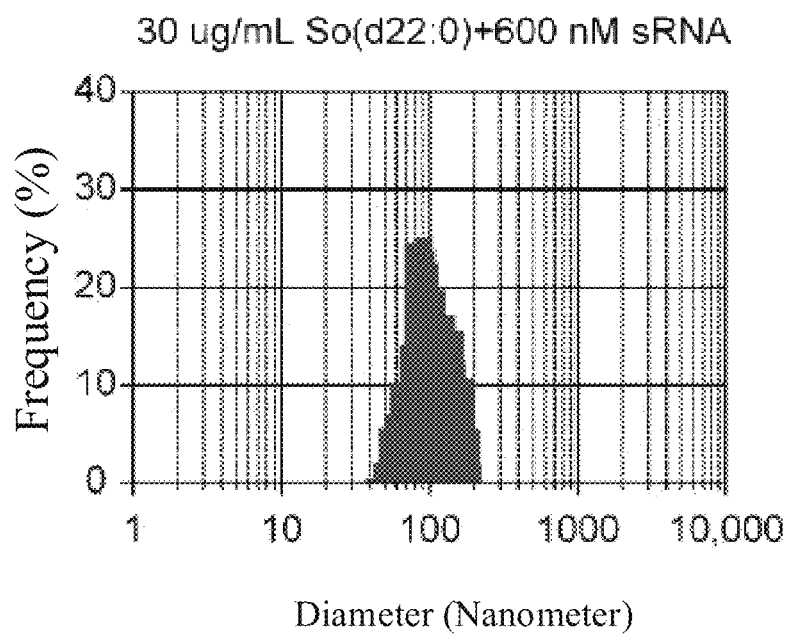

FIG. 47A-B: Particle size distribution of So(d22:0) and So(d22:0)+600 nM sRNA.

Figure 47C:
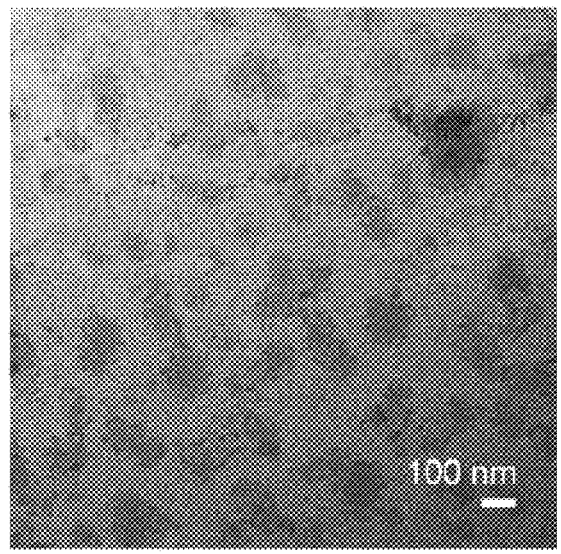
Figure 47D:
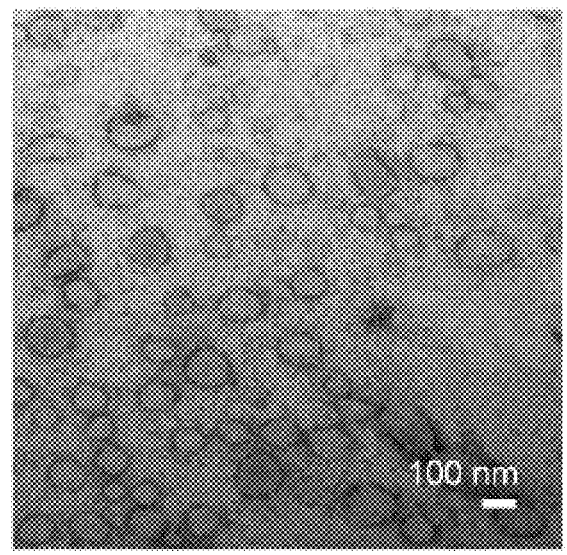

FIG. 47C-D: Transmission electron microscopy of So(d22:0) and So(d22:0)+600 nM sRNA.

Figure 48:
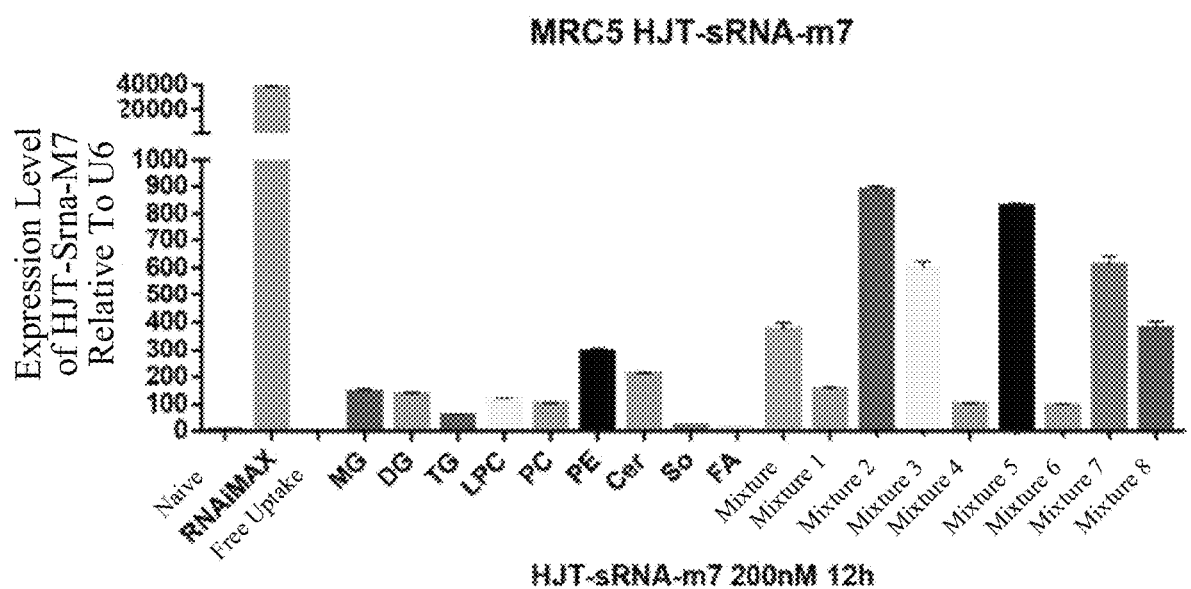

FIG. 48: Different types of lipid combinations deliver single-stranded nucleic acid into MRC-5.

Figure 49A:
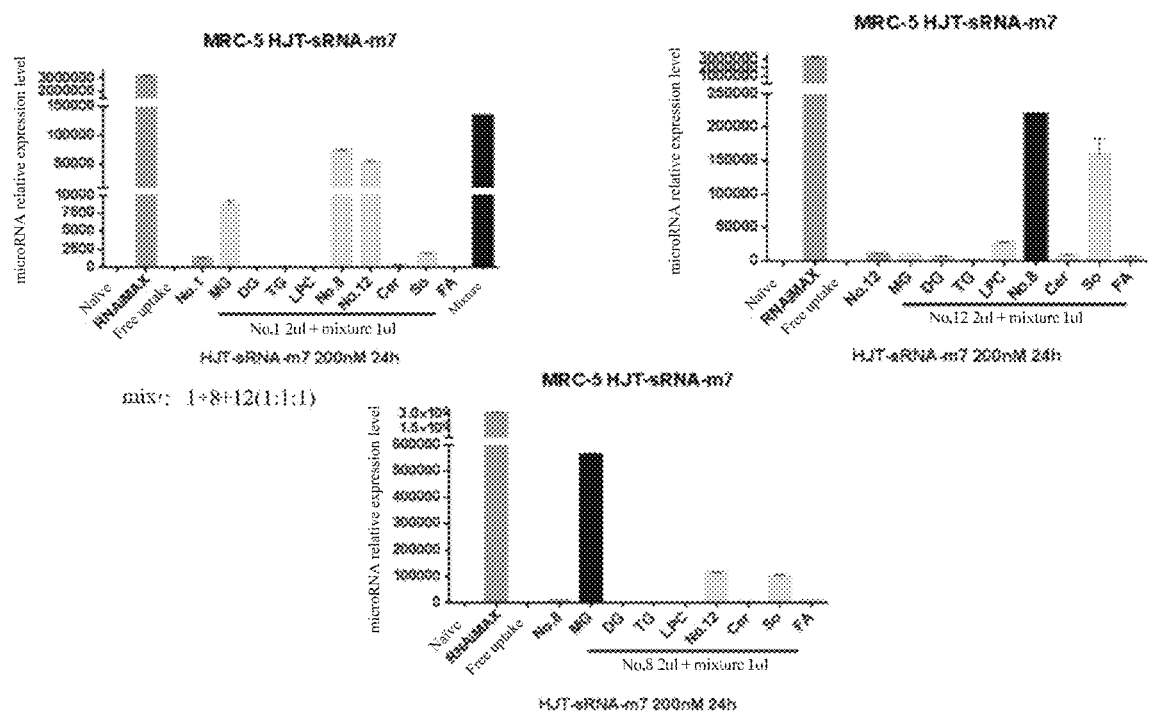
Figure 49B:
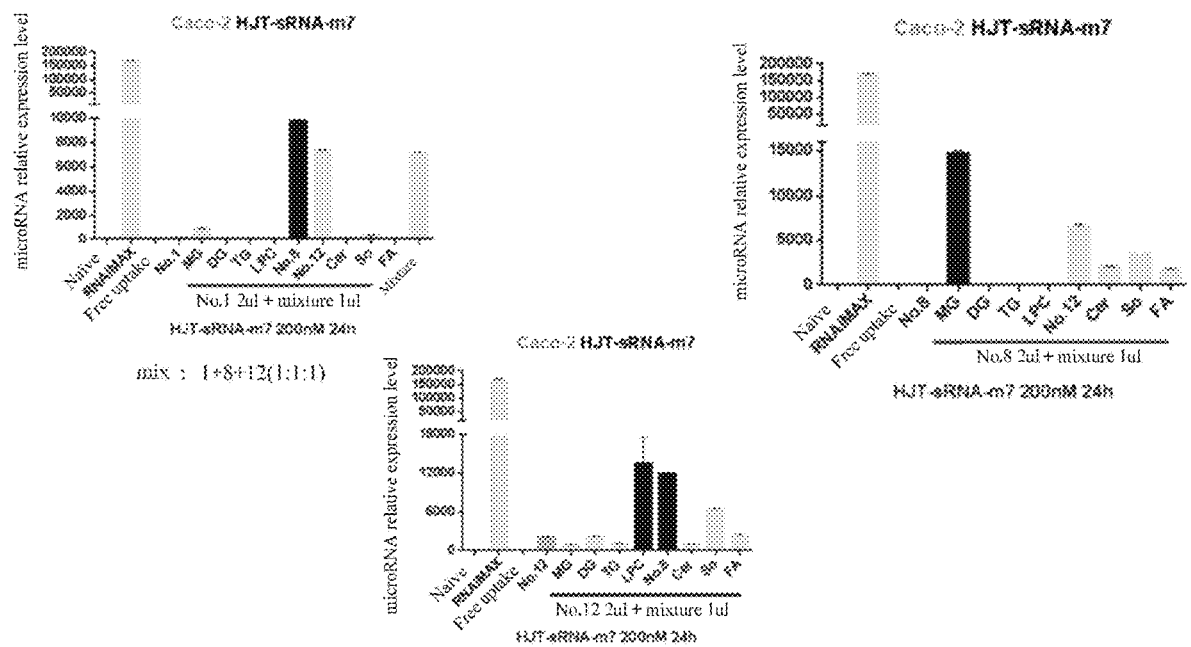

FIG. 49A-B: Lipid combination delivers single-stranded nucleic acid into MRC-5 or Caco-2 cells.

Figure 50:
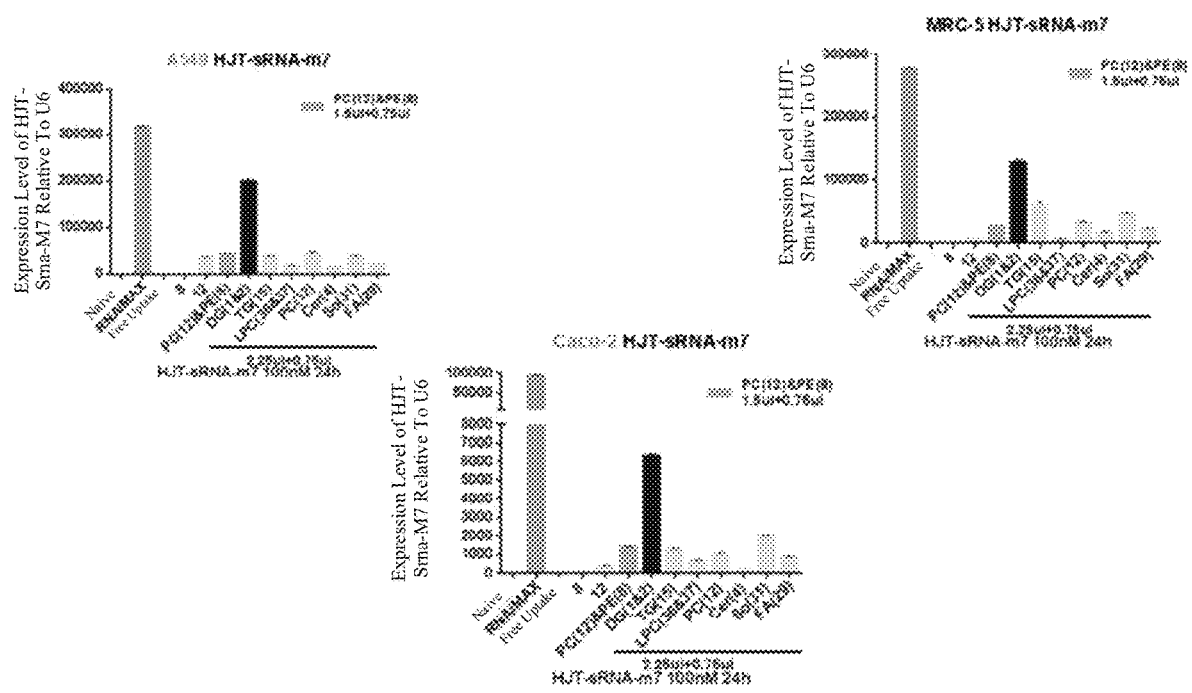

FIG. 50: Lipid combination delivers single-stranded nucleic acid into cells.

Figure 51:
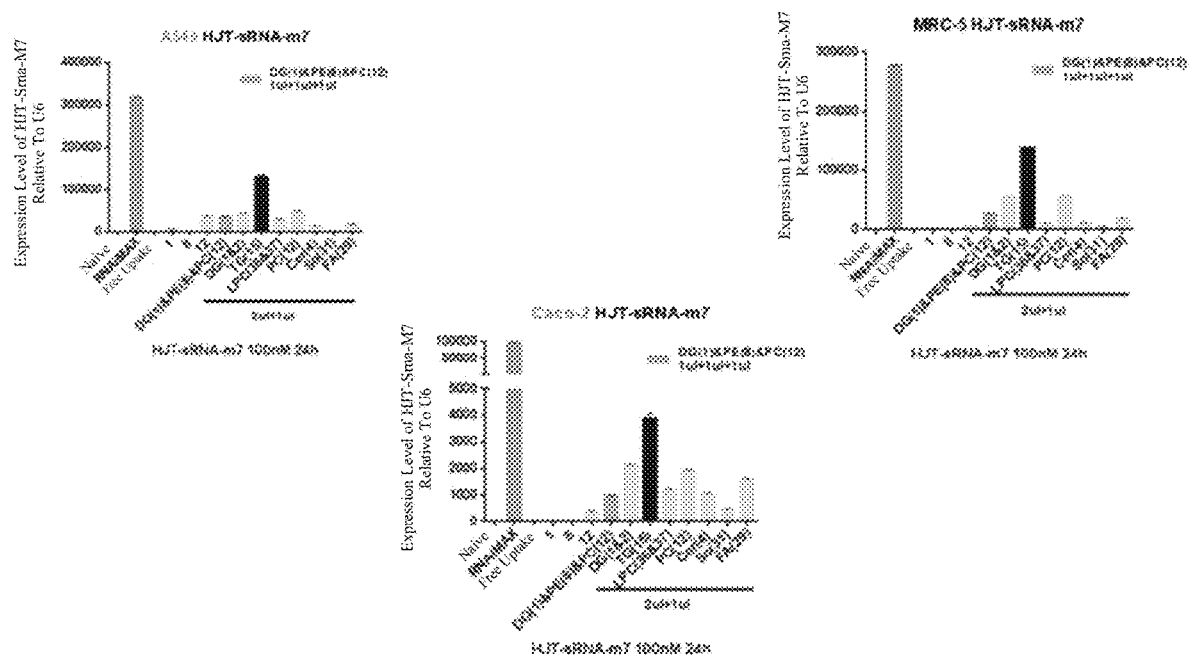

FIG. 51: Lipid combination delivers single-stranded nucleic acid into cells.

Figure 52:
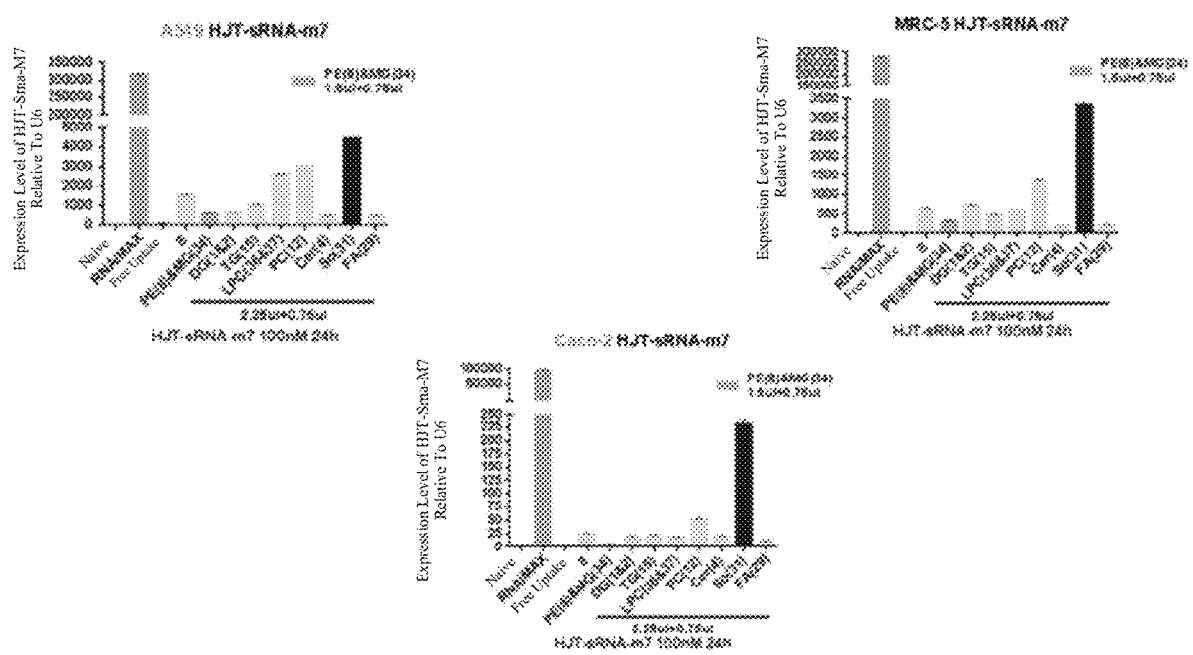

FIG. 52: Lipid combination delivers single-stranded nucleic acid into cells.

Figure 53:
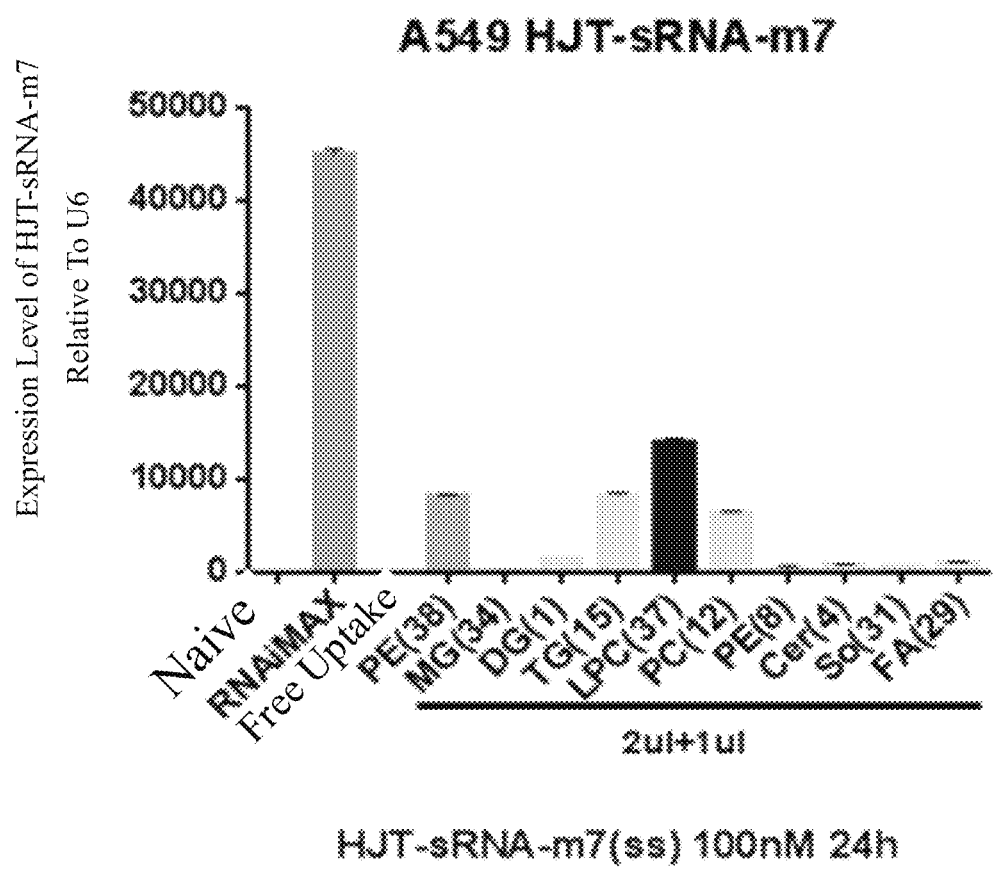

FIG. 53: Lipid combination delivers single-stranded nucleic acid into A549 cells.

Figure 54:
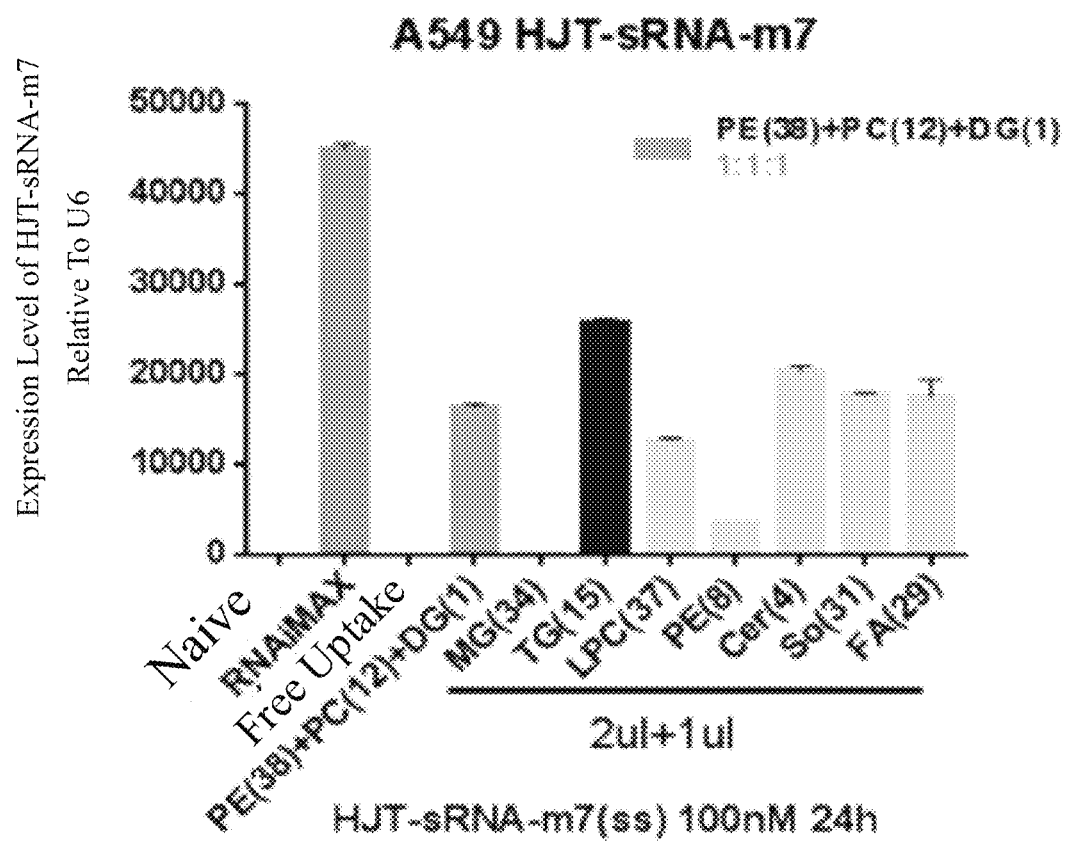

FIG. 54: Lipid combination delivers single-stranded nucleic acid into A549 cells.

Figure 55:
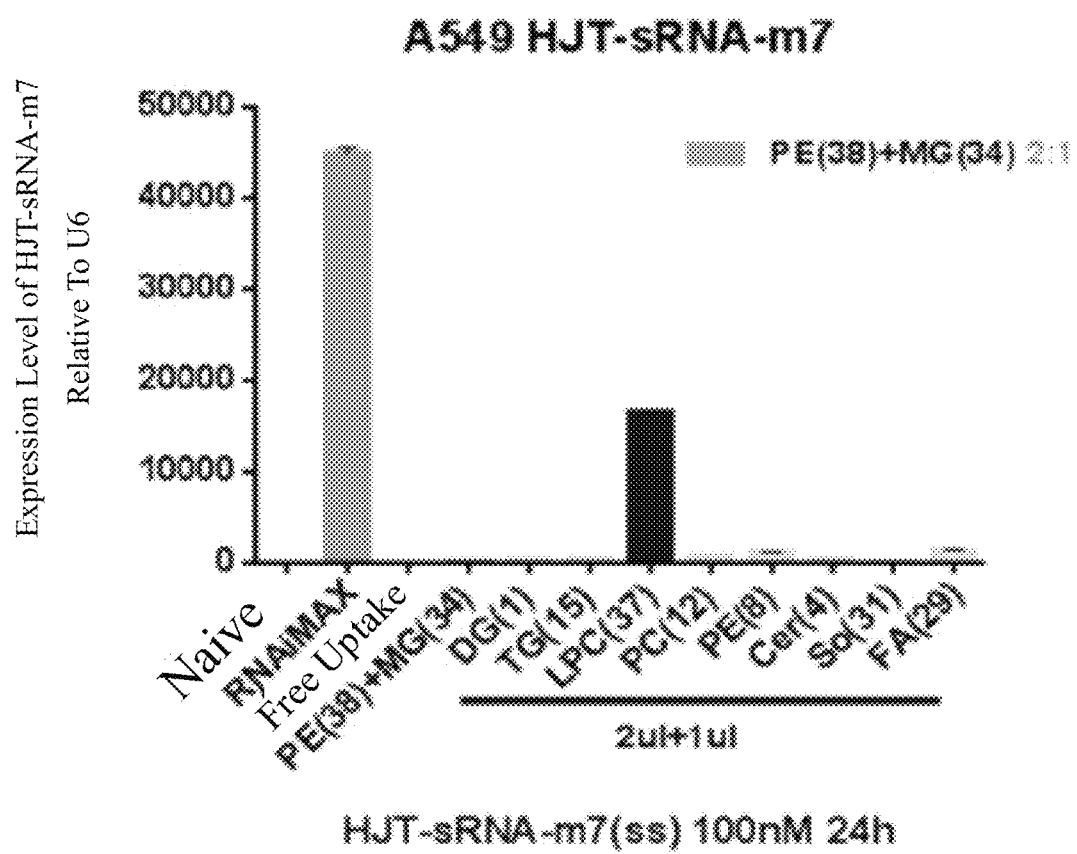

FIG. 55: Lipid combination delivers single-stranded nucleic acid into A549 cells.

Figure 56:
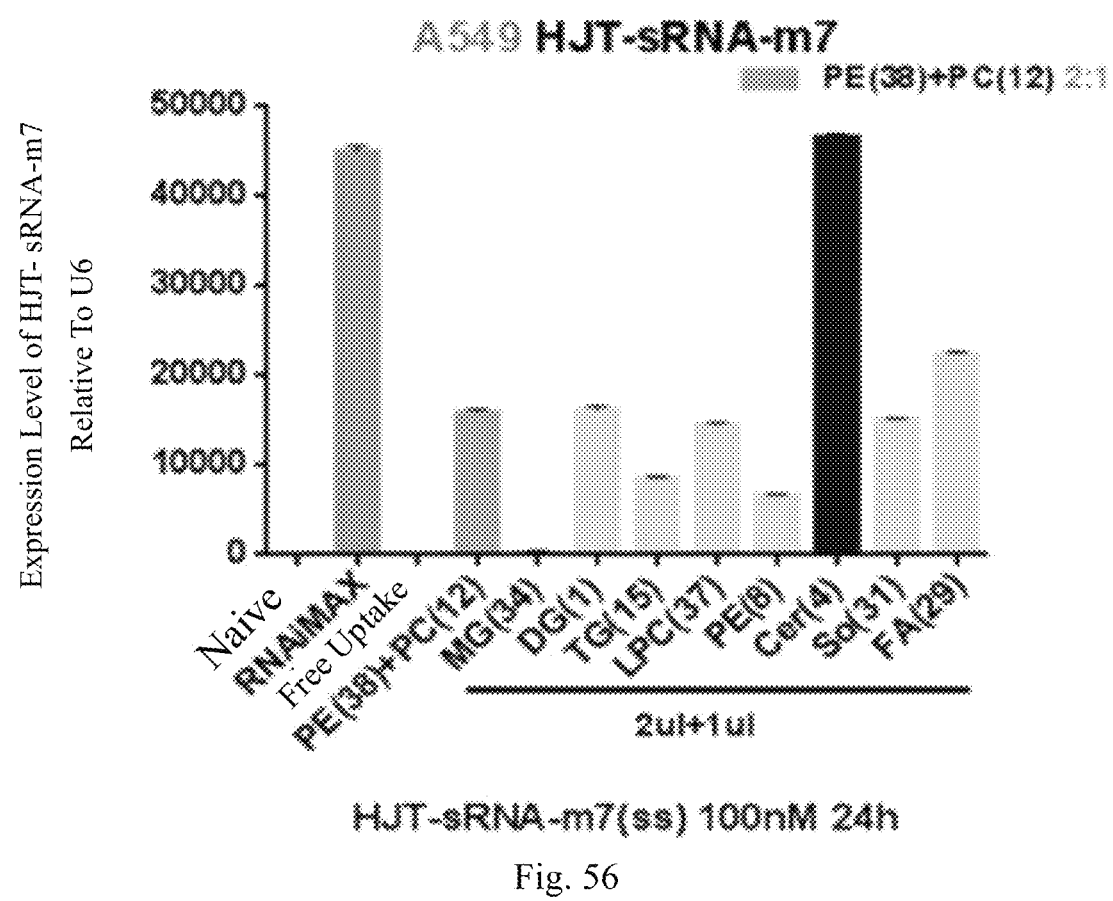

FIG. 56: Lipid combination delivers single-stranded nucleic acid into A549 cells.

Figure 57:
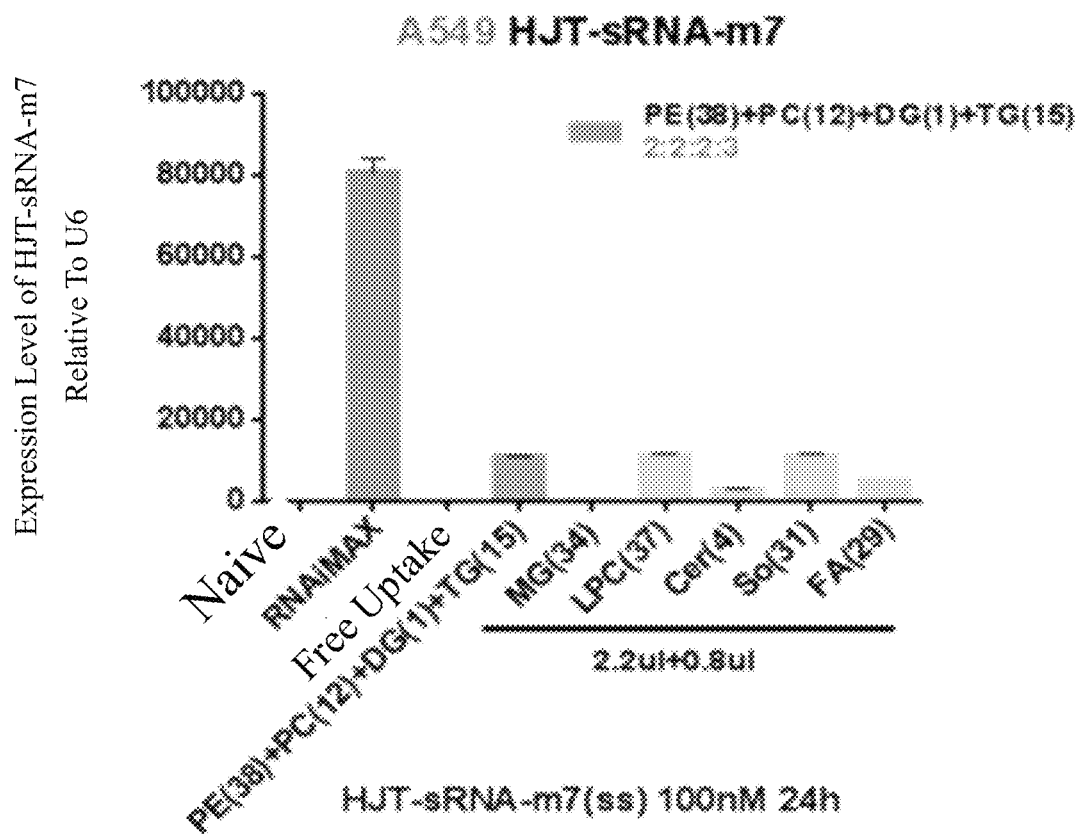

FIG. 57: Lipid combination delivers single-stranded nucleic acid into A549 cells.

Figure 58:
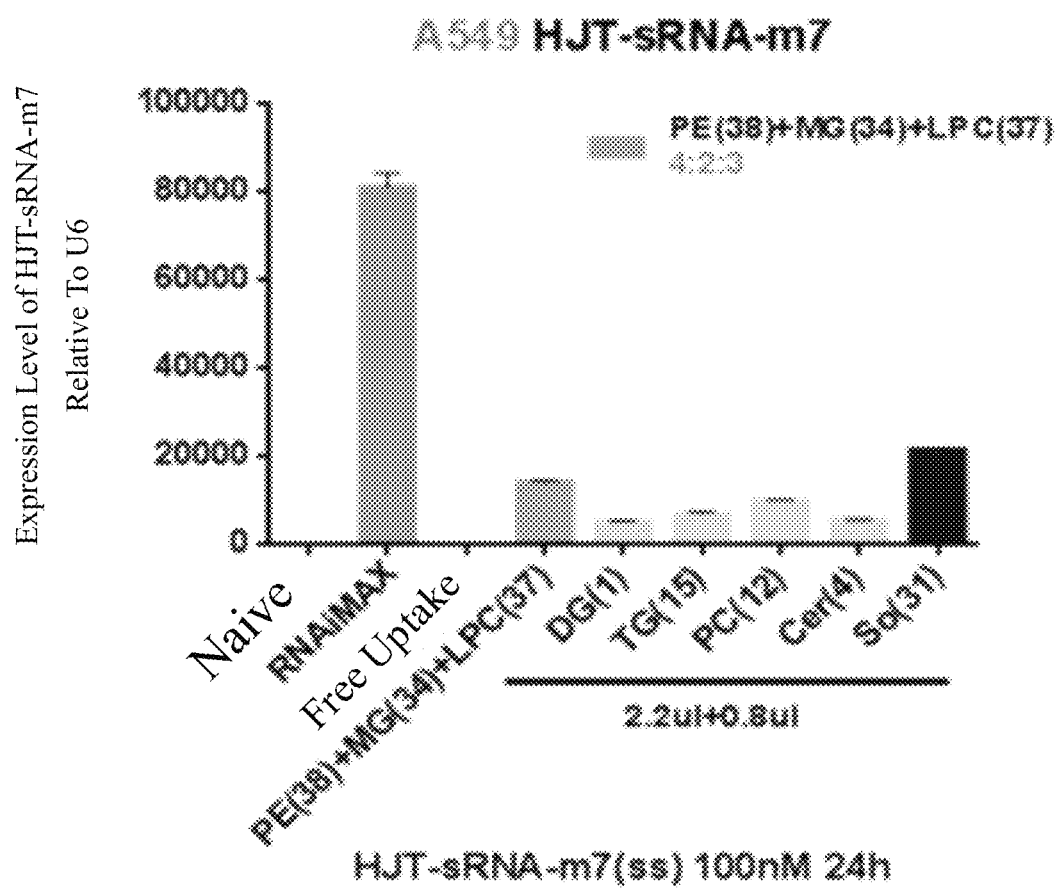

FIG. 58: Lipid combination delivers single-stranded nucleic acid into A549 cells.

Figure 59:
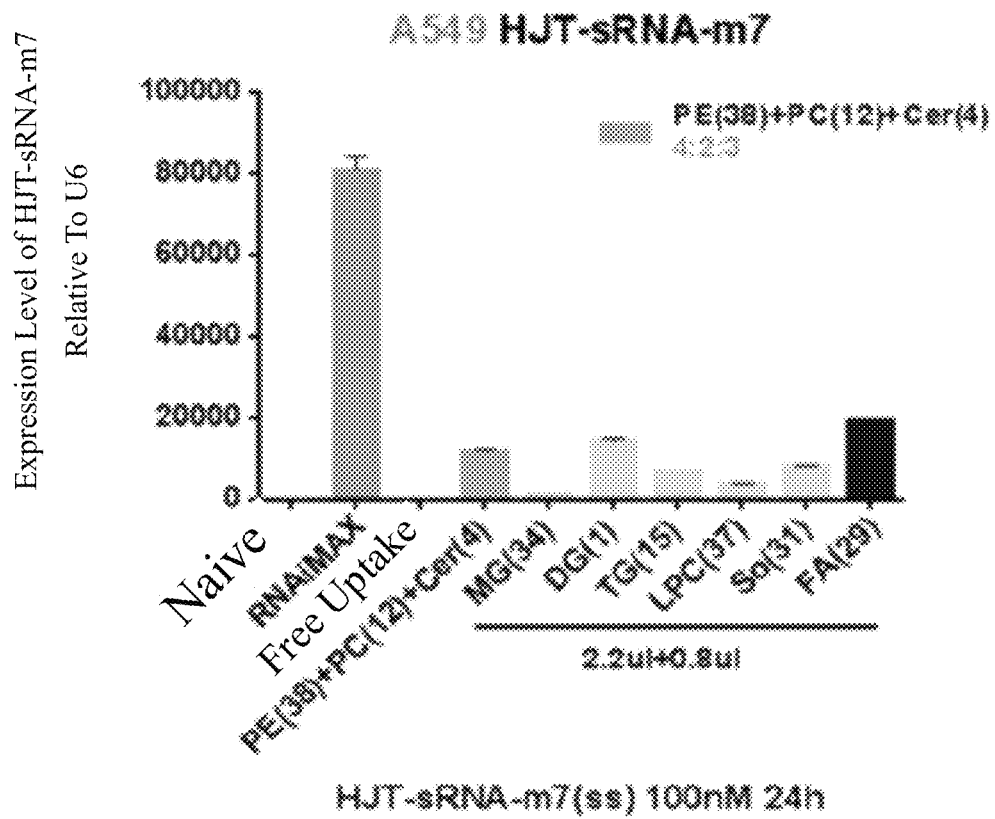

FIG. 59: Lipid combination delivers single-stranded nucleic acid into A549 cells.

Figure 60:
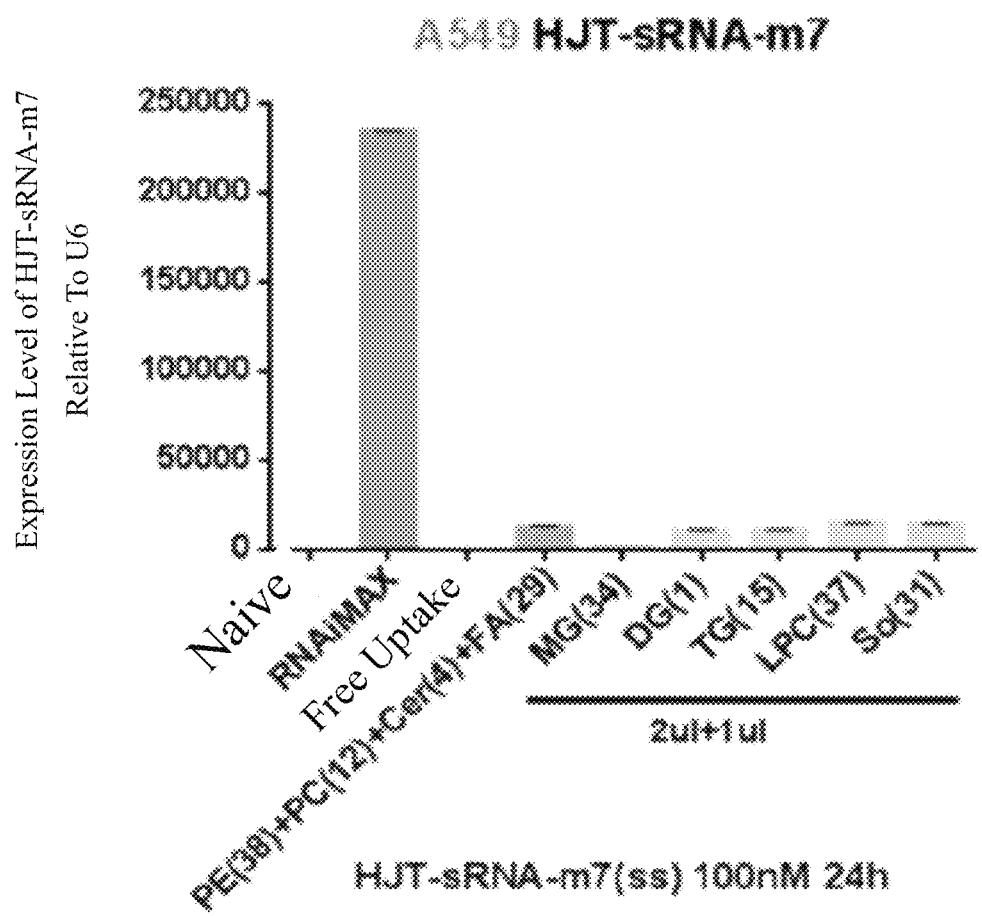

FIG. 60: Lipid combination delivers single-stranded nucleic acid into A549 cells.

Figure 61:
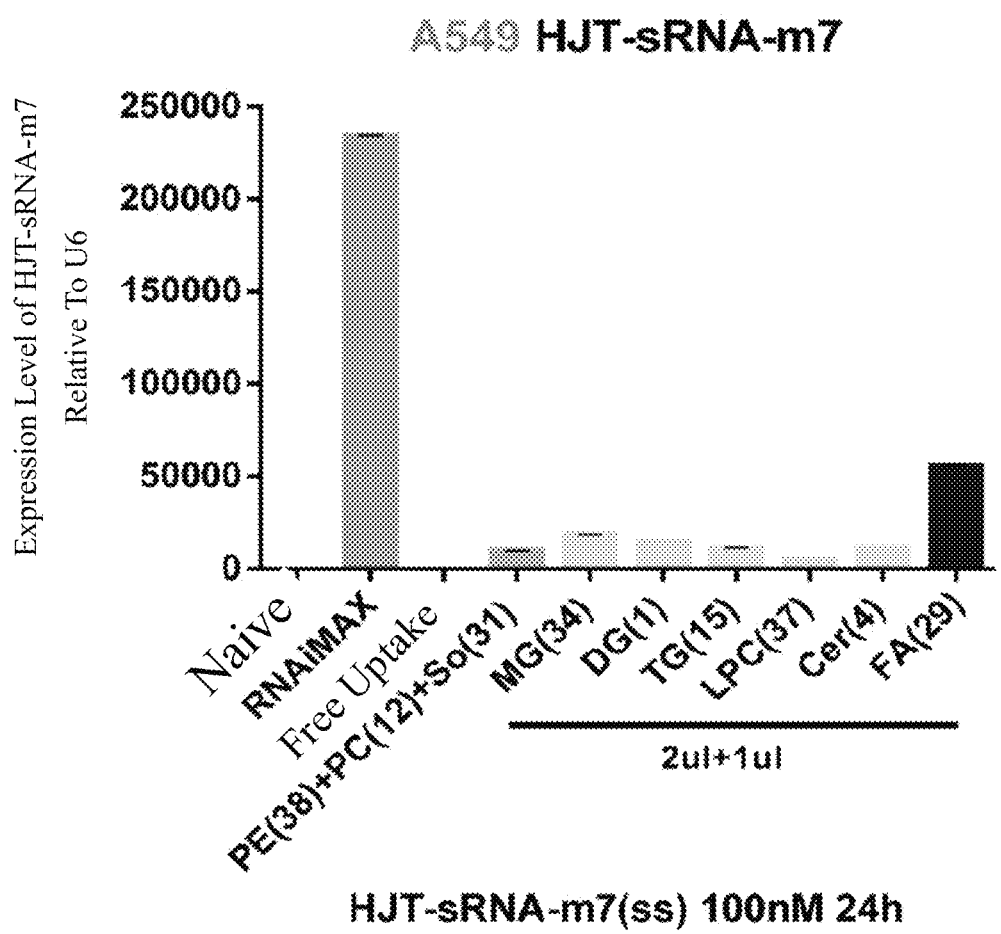

FIG. 61: Lipid combination delivers single-stranded nucleic acid into A549 cells.

Figure 62:
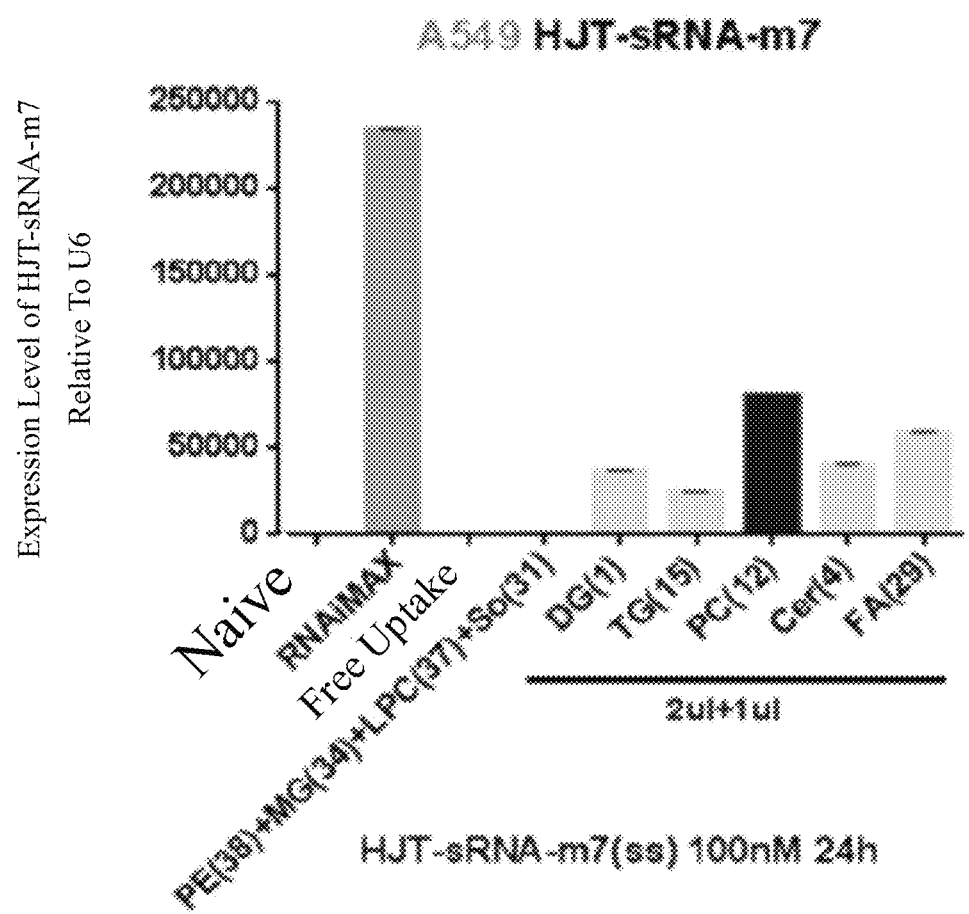

FIG. 62: Lipid combination delivers single-stranded nucleic acid into A549 cells.

Figure 63:
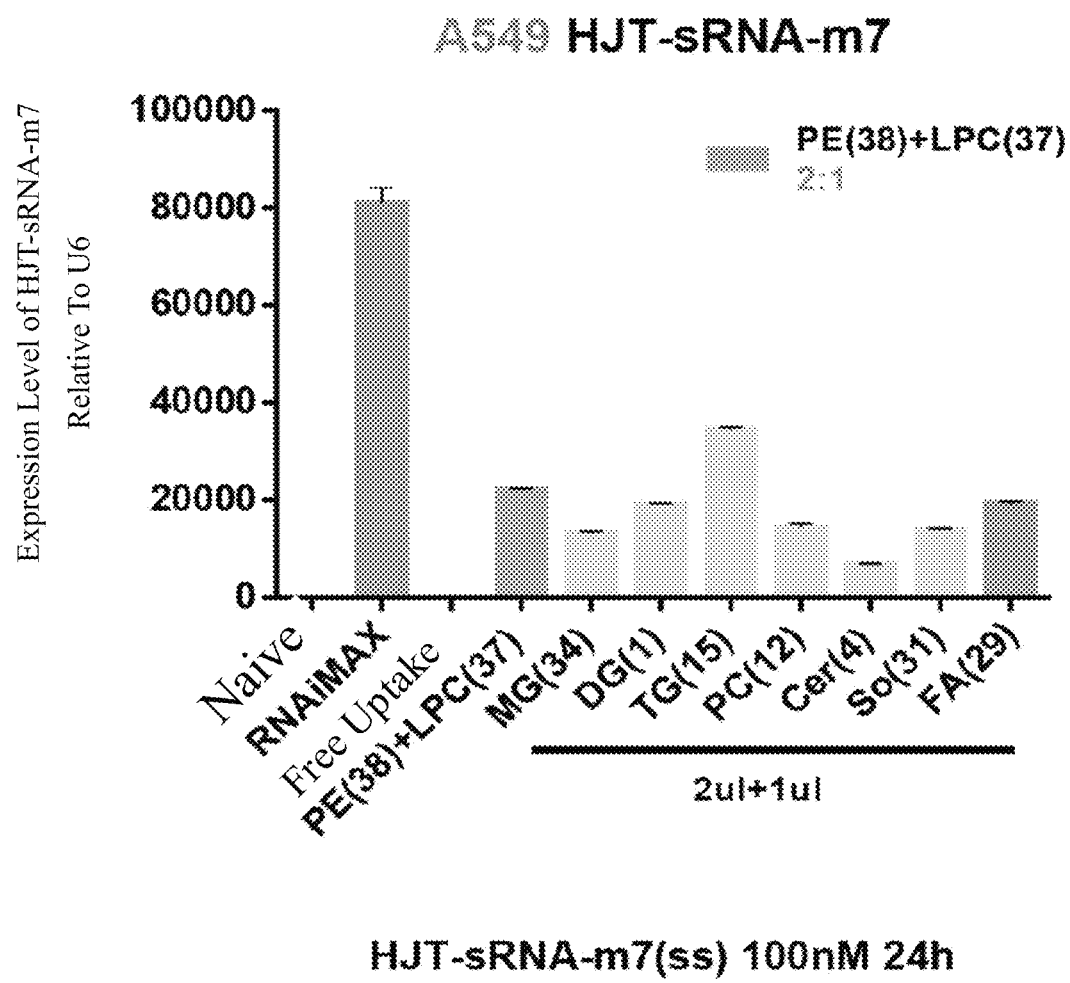

FIG. 63: Lipid combination delivers single-stranded nucleic acid into A549 cells.

Figure 64:
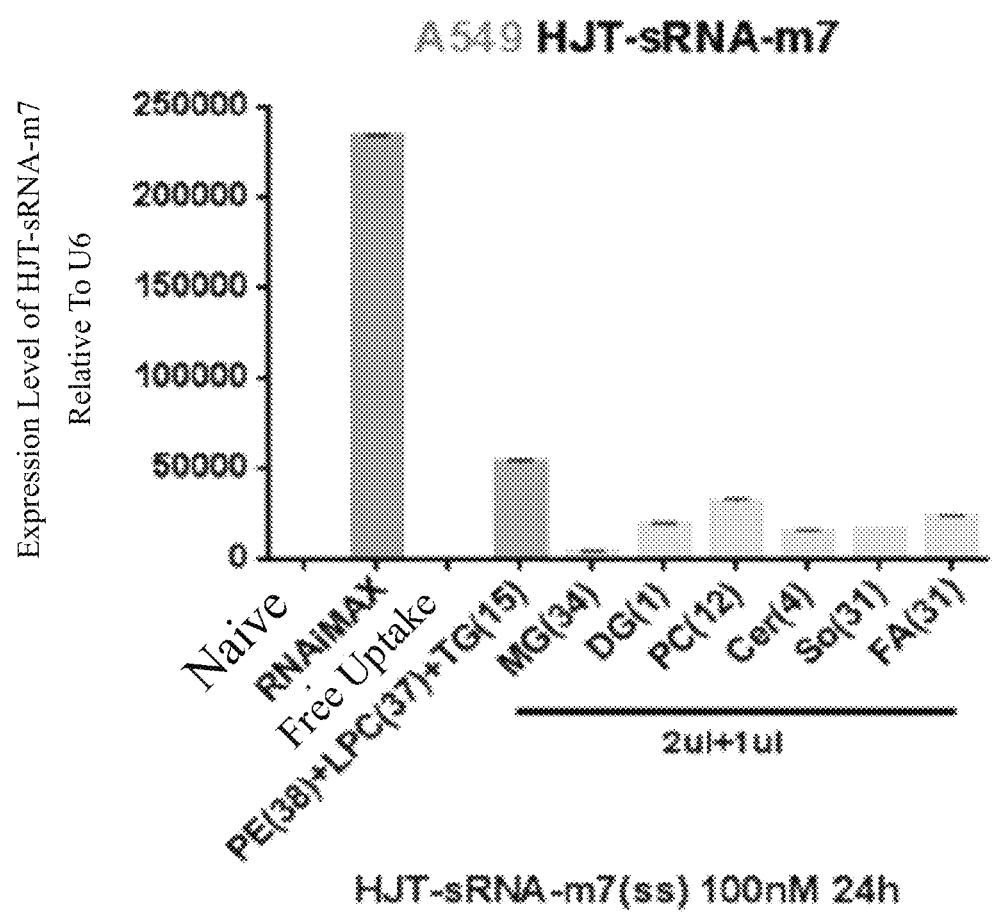

FIG. 64: Lipid combination delivers single-stranded nucleic acid into A549 cells.

Figure 65:
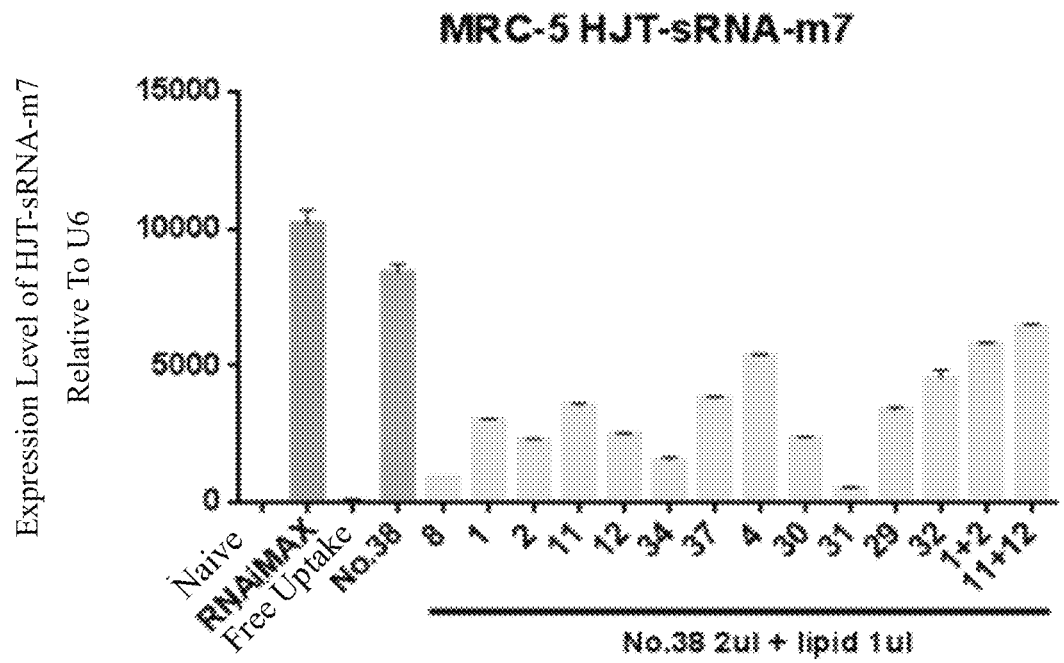

FIG. 65: Lipid combination delivers double-stranded nucleic acid into MRC-5 cells.

Figure 66:
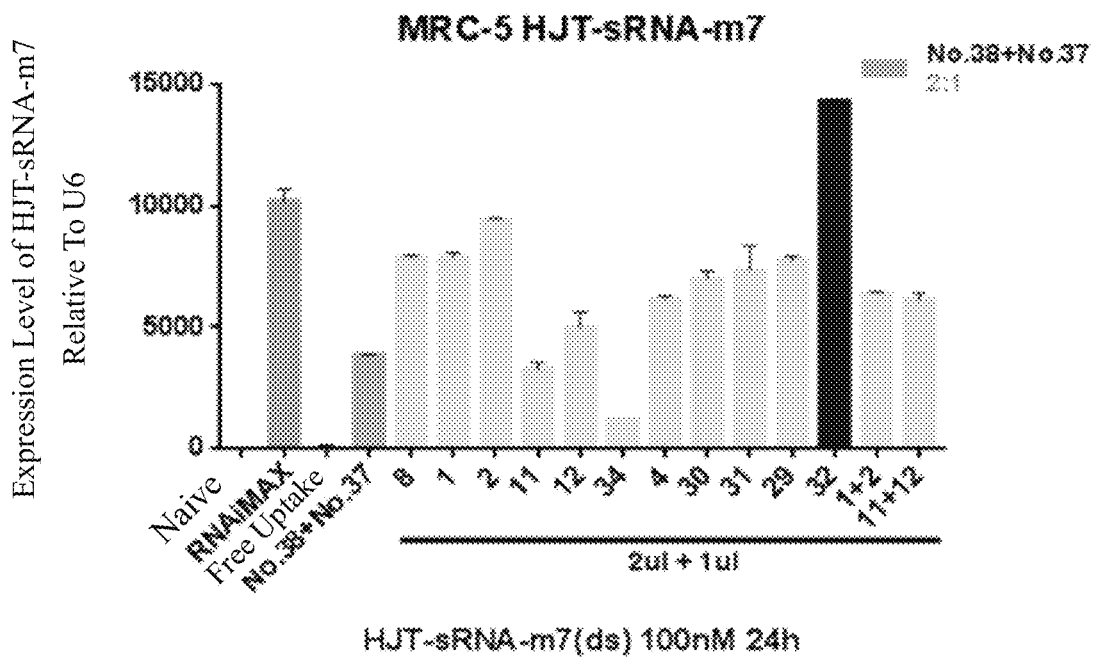

FIG. 66: Lipid combination delivers double-stranded nucleic acid into MRC-5 cells.

Figure 67:
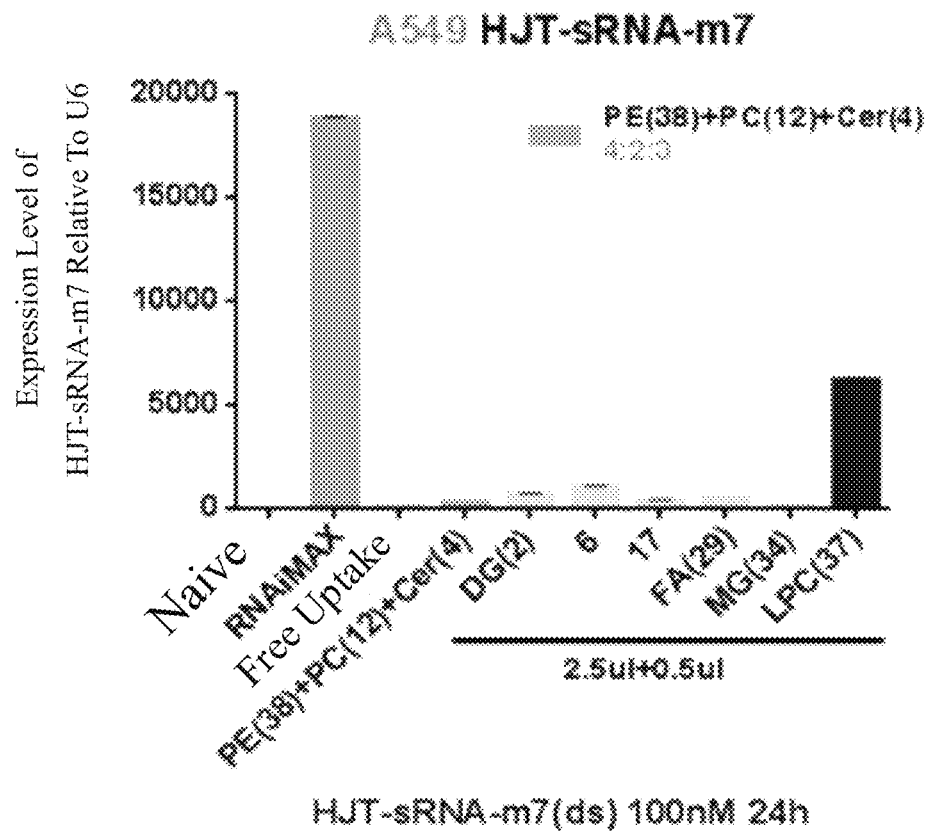

FIG. 67: Lipid combination delivers double-stranded nucleic acid into A549 cells.

Figure 68:
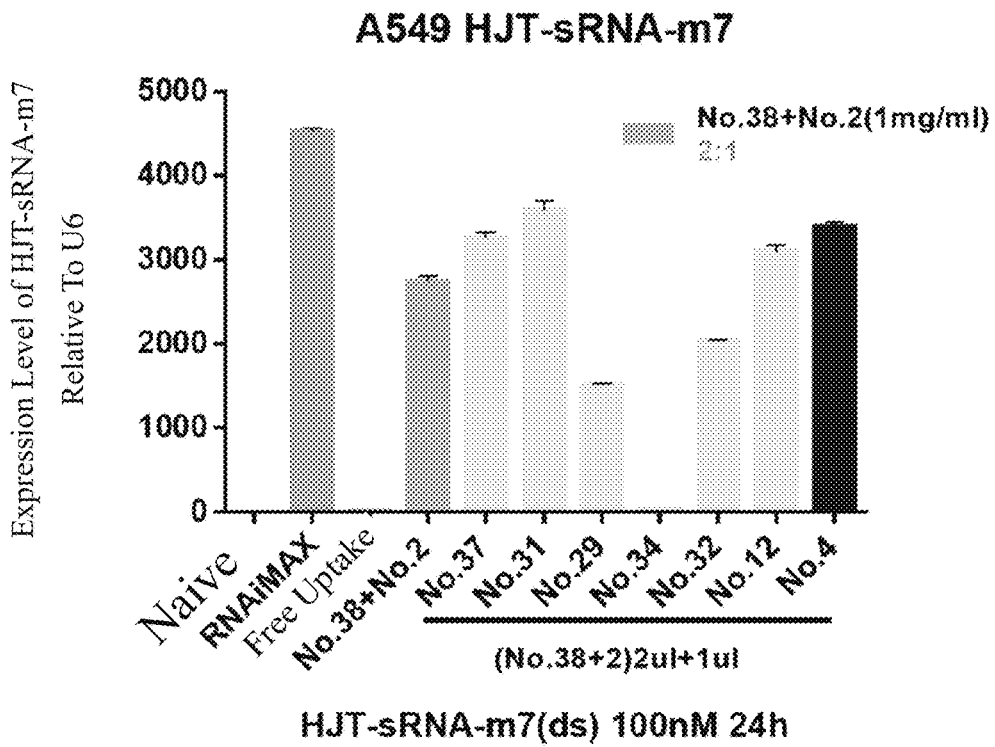

FIG. 68: Lipid combination delivers double-stranded nucleic acid into A549 cells.

Figure 69:
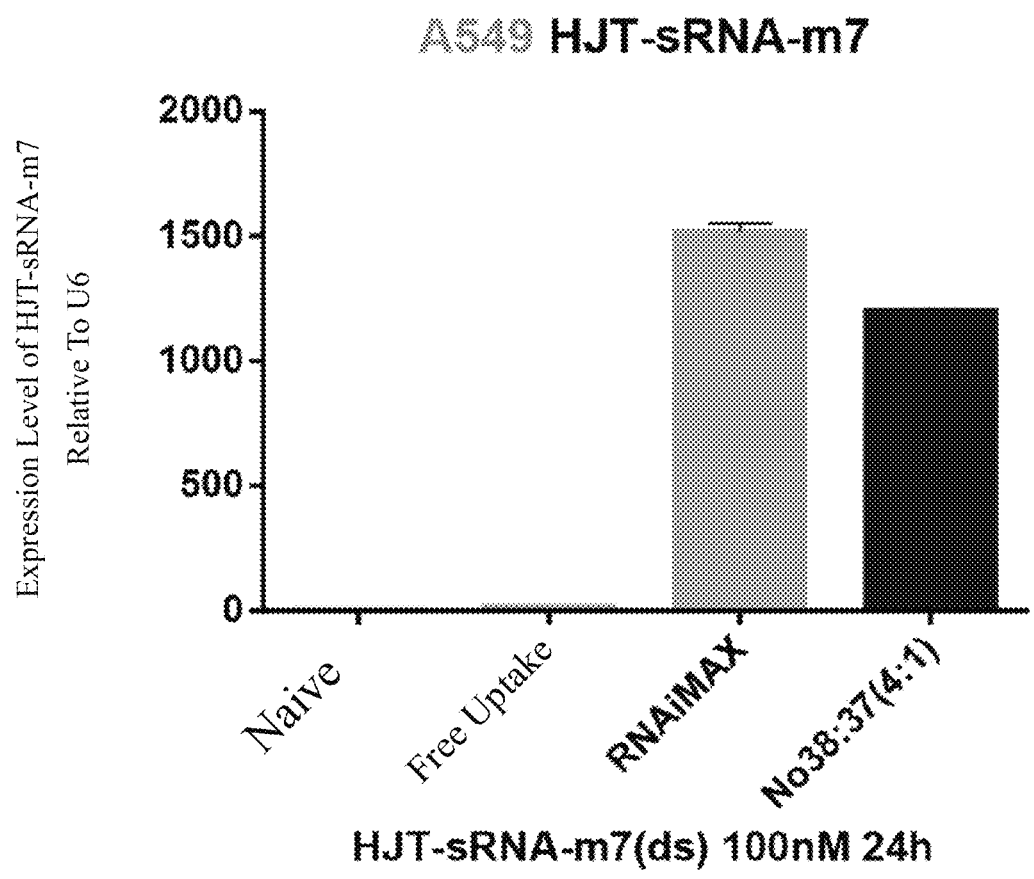

FIG. 69: Lipid combination delivers double-stranded nucleic acid into A549 cells.

Figure 70:
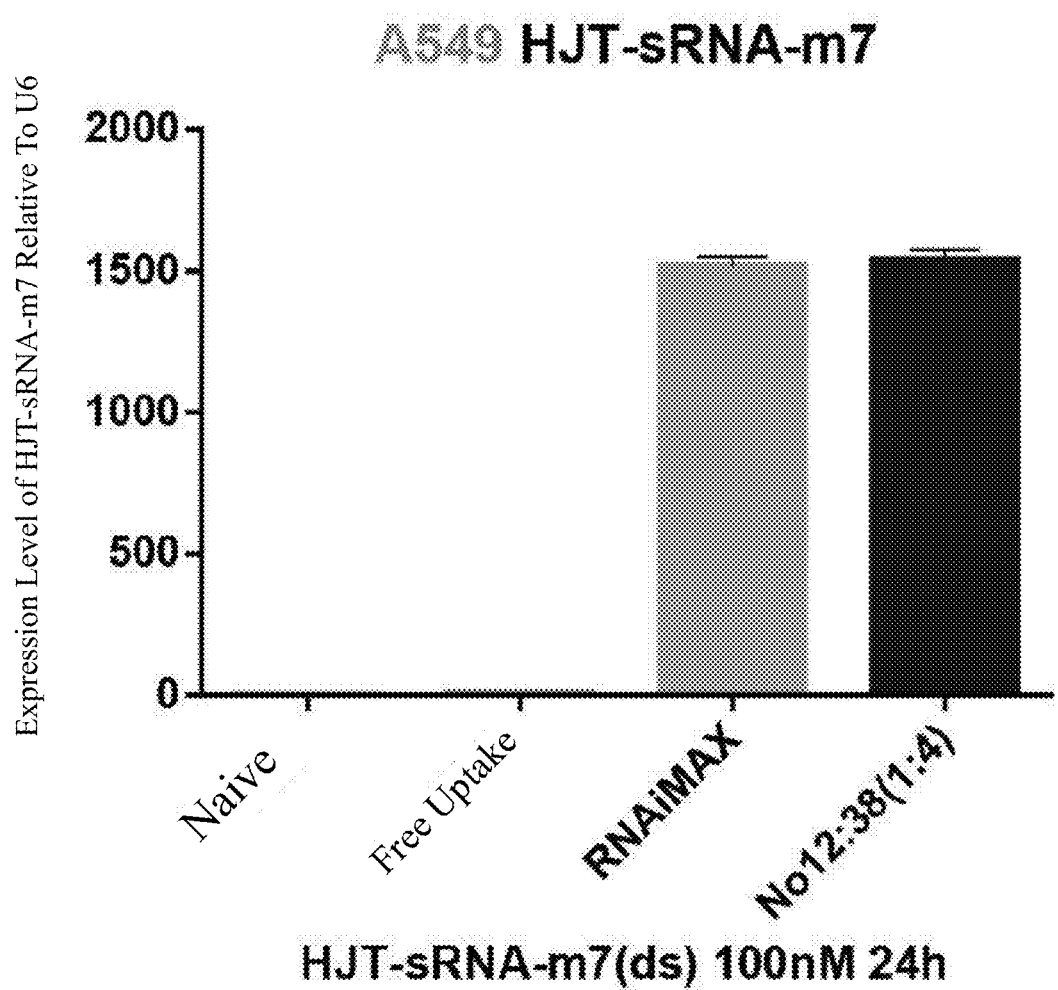

FIG. 70: Lipid combination delivers double-stranded nucleic acid into A549 cells.

Figure 71:
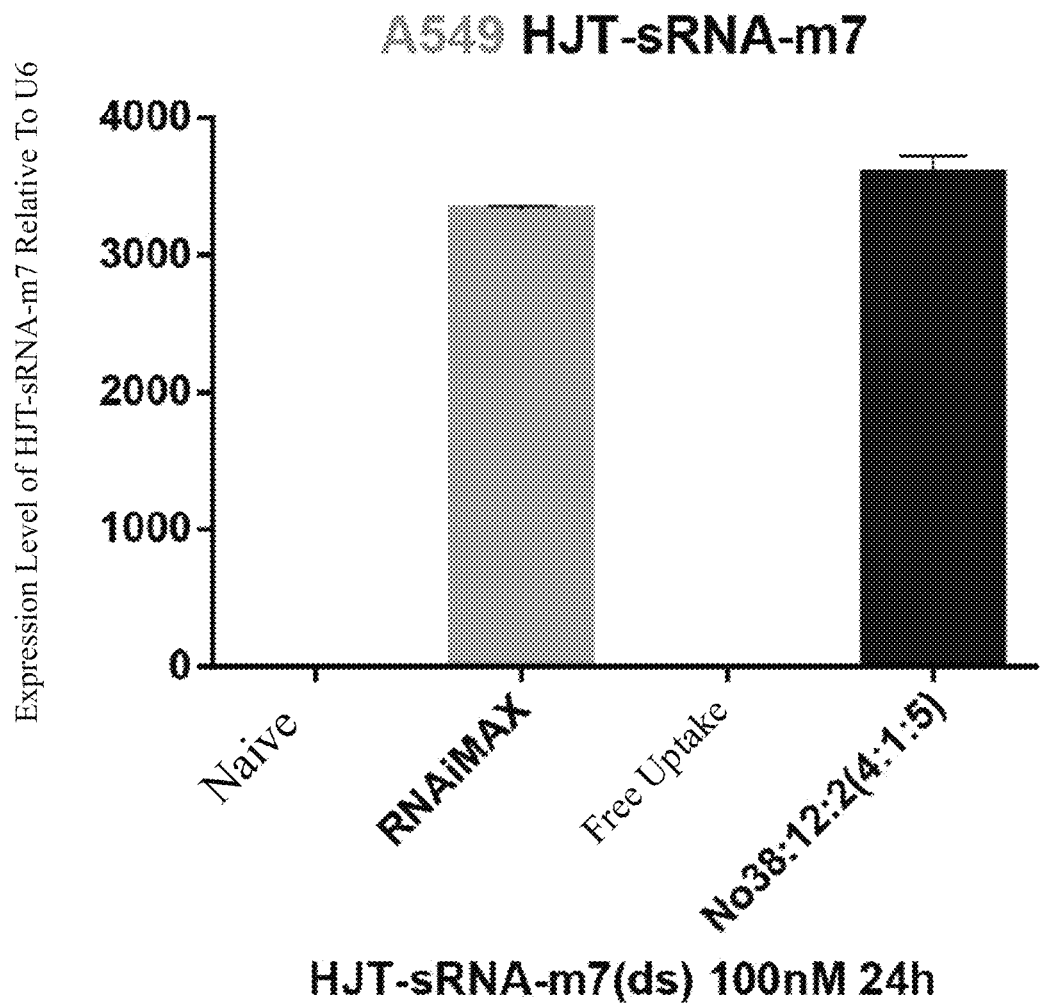

FIG. 71: Lipid combination delivers double-stranded nucleic acid into A549 cells.

Figure 72:
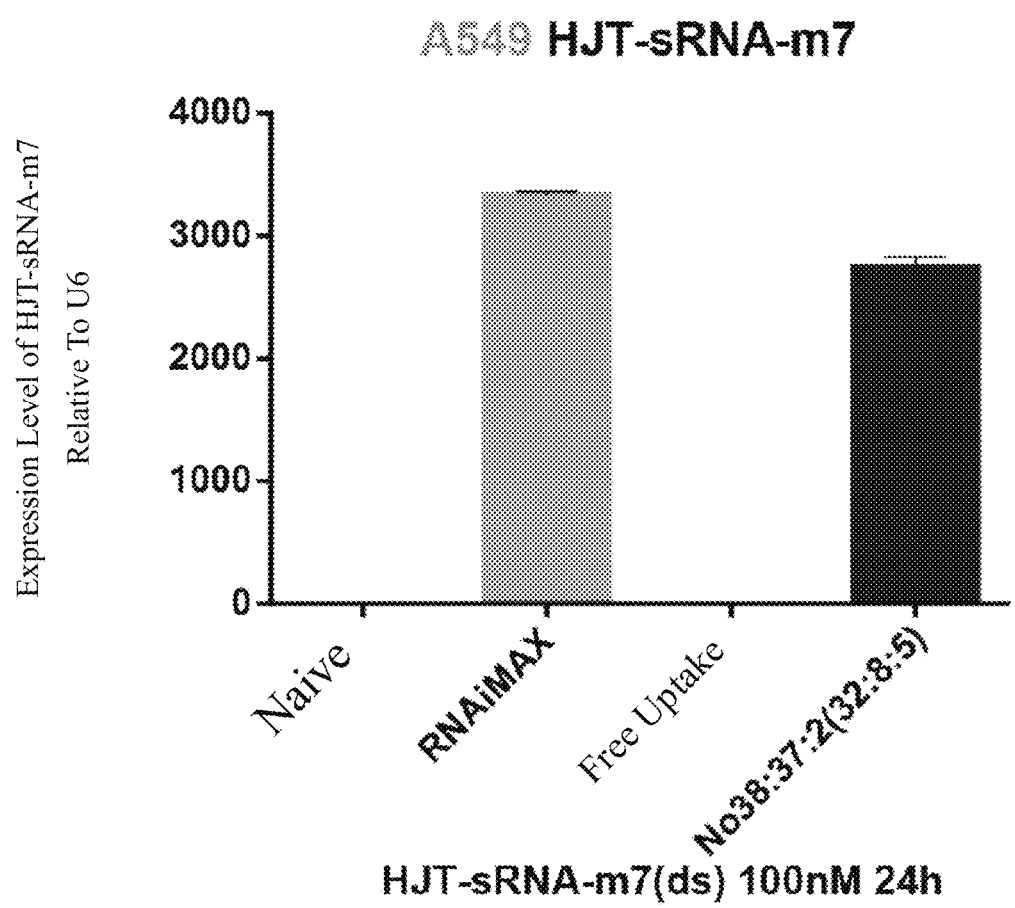

FIG. 72: Lipid combination delivers double-stranded nucleic acid into A549 cells.

Figure 73:
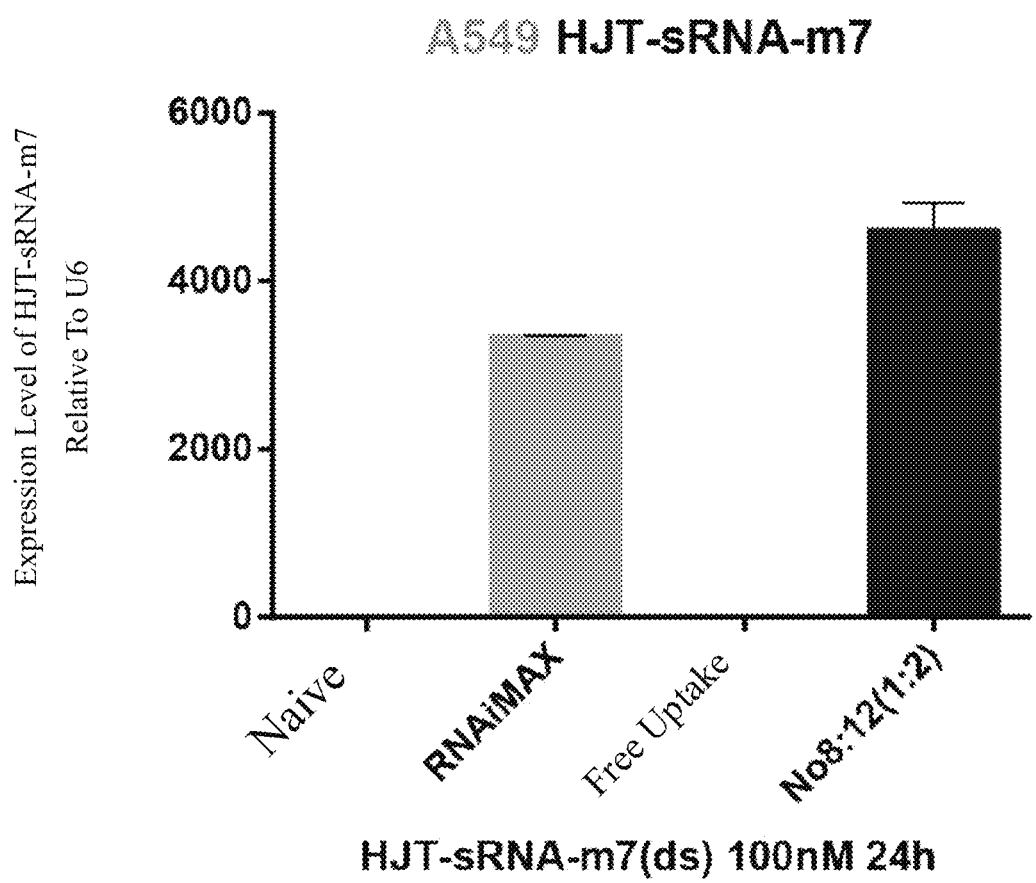

FIG. 73: Lipid combination delivers double-stranded nucleic acid into A549 cells.

Figure 74:
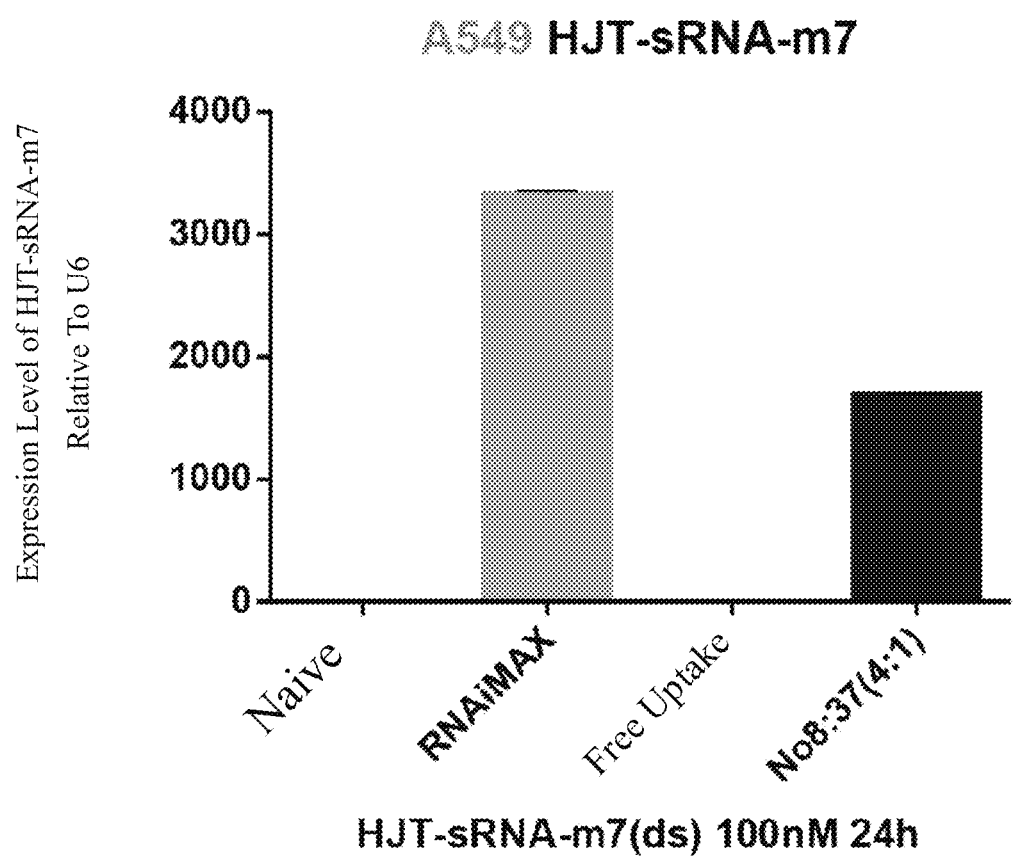
Figure 75:
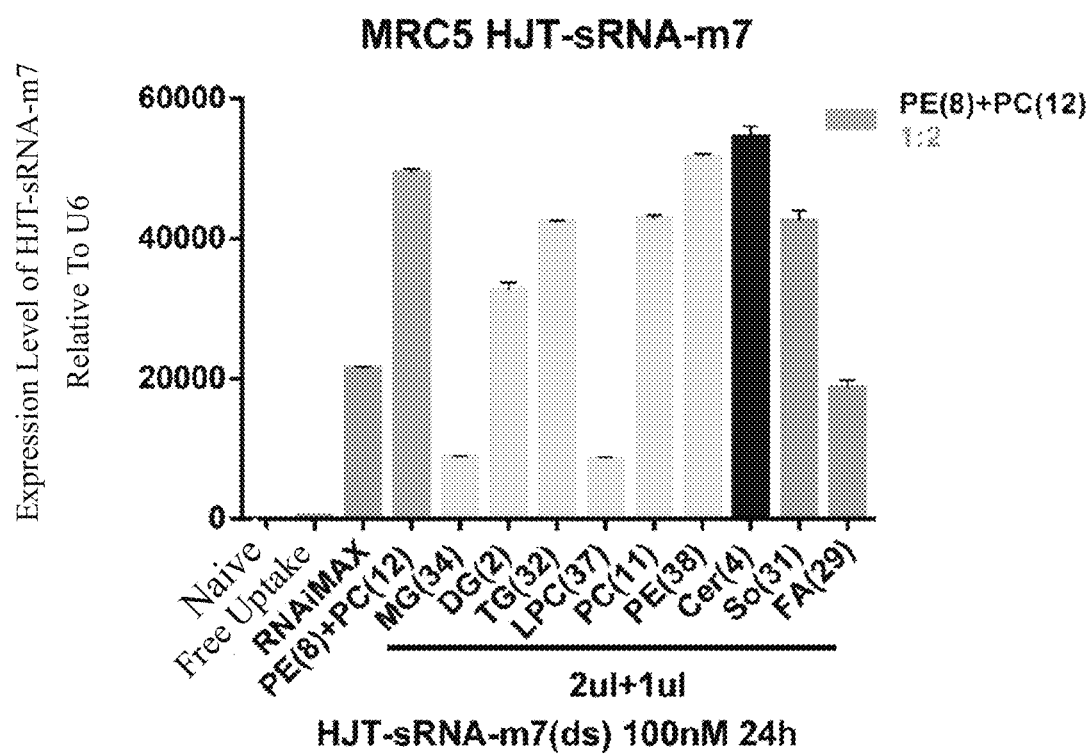

FIG. 74: Lipid combination delivers double-stranded nucleic acid into A549 cells FIG. 75: Lipid combination delivers double-stranded nucleic acid into MRC-5 cells.

Figure 76:
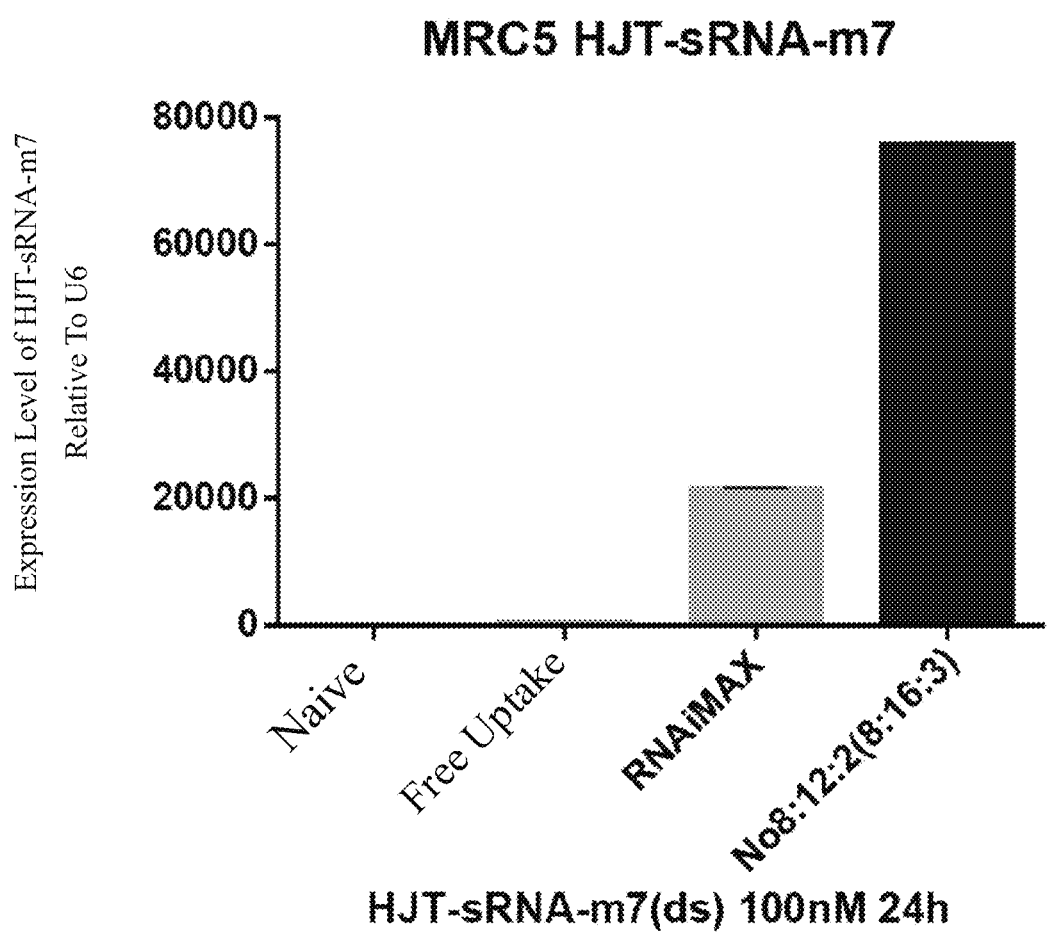

FIG. 76: Lipid combination delivers double-stranded nucleic acid into MRC-5 cells.

Figure 77:
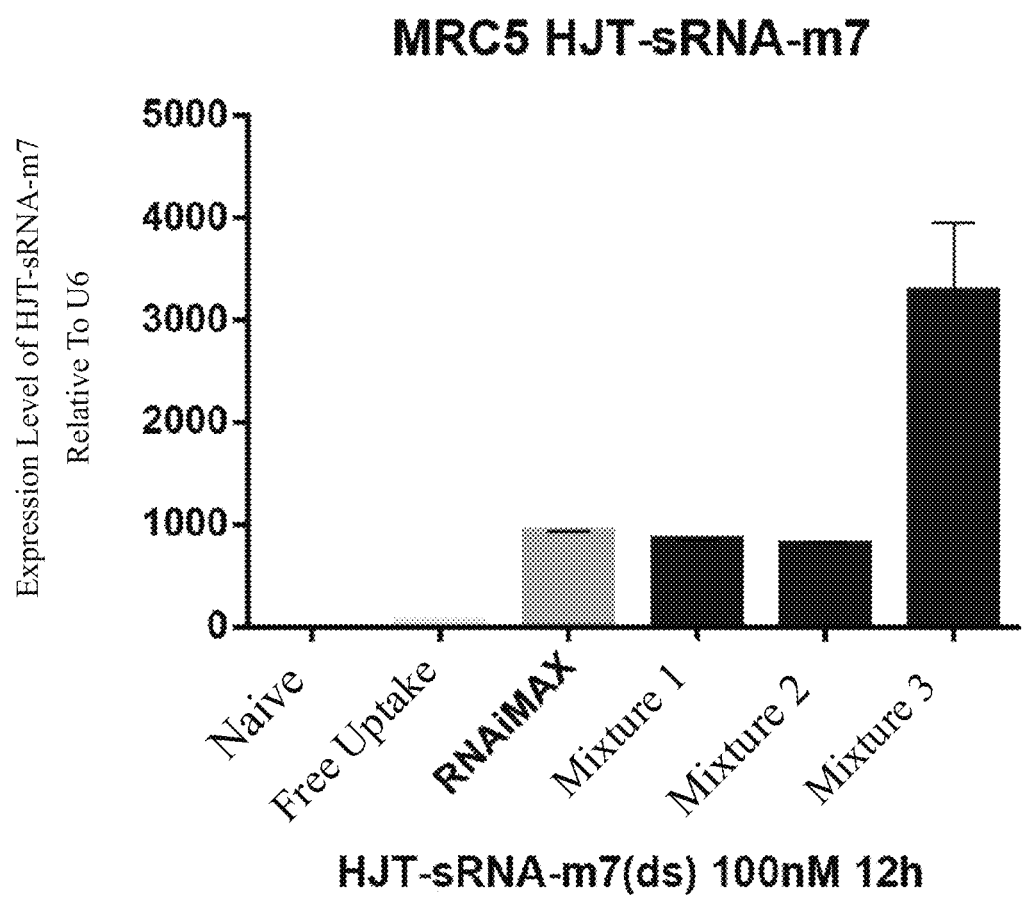

FIG. 77: Lipid combination delivers double-stranded nucleic acid into MRC-5 cells.

Figure 78:
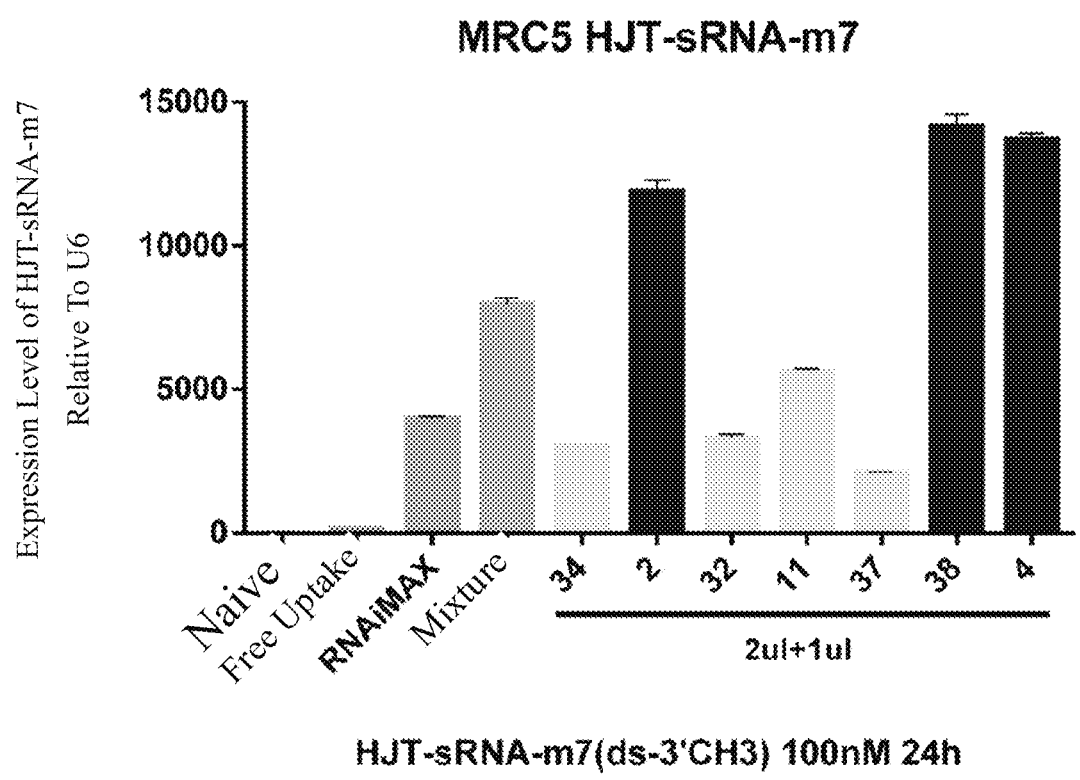

FIG. 78: Lipid combination delivers double-stranded nucleic acid into MRC-5 cells.

Figure 79:
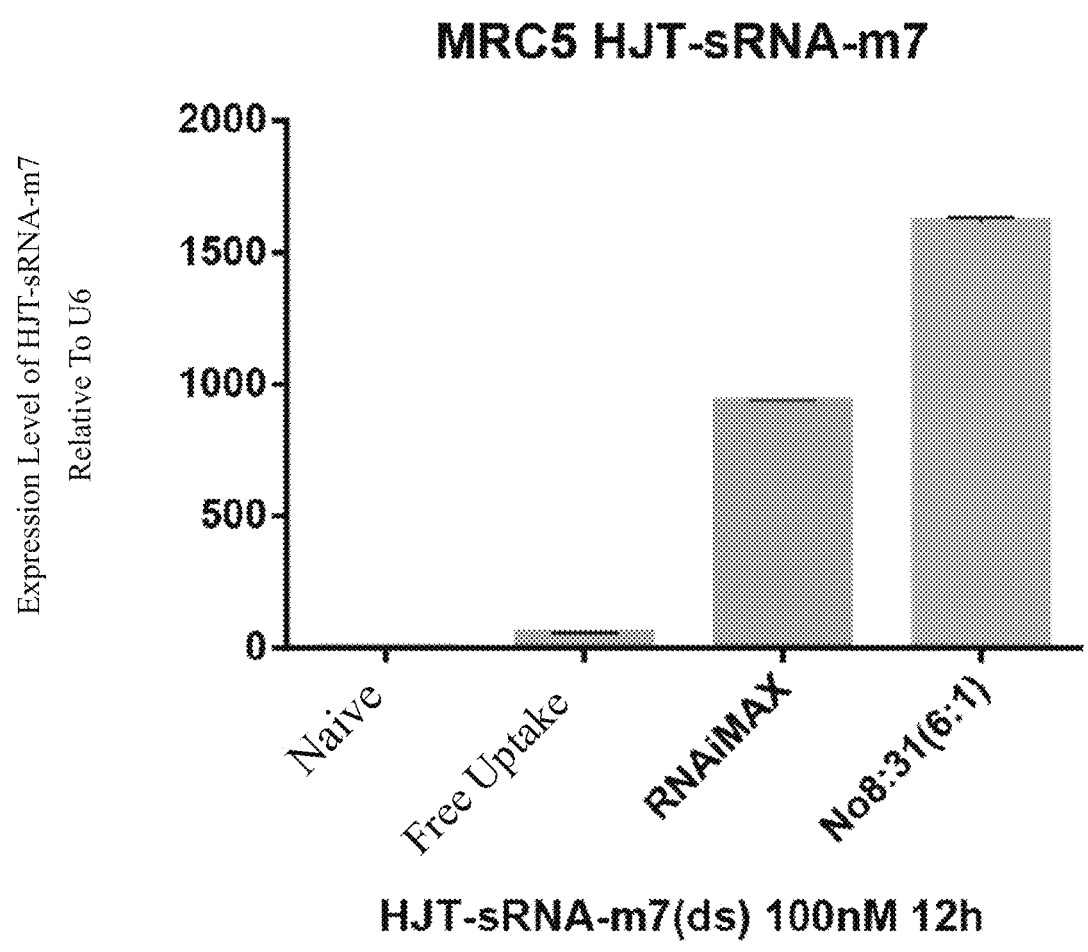

FIG. 79: Lipid combination delivers double-stranded nucleic acid into MRC-5 cells.

Figure 80:
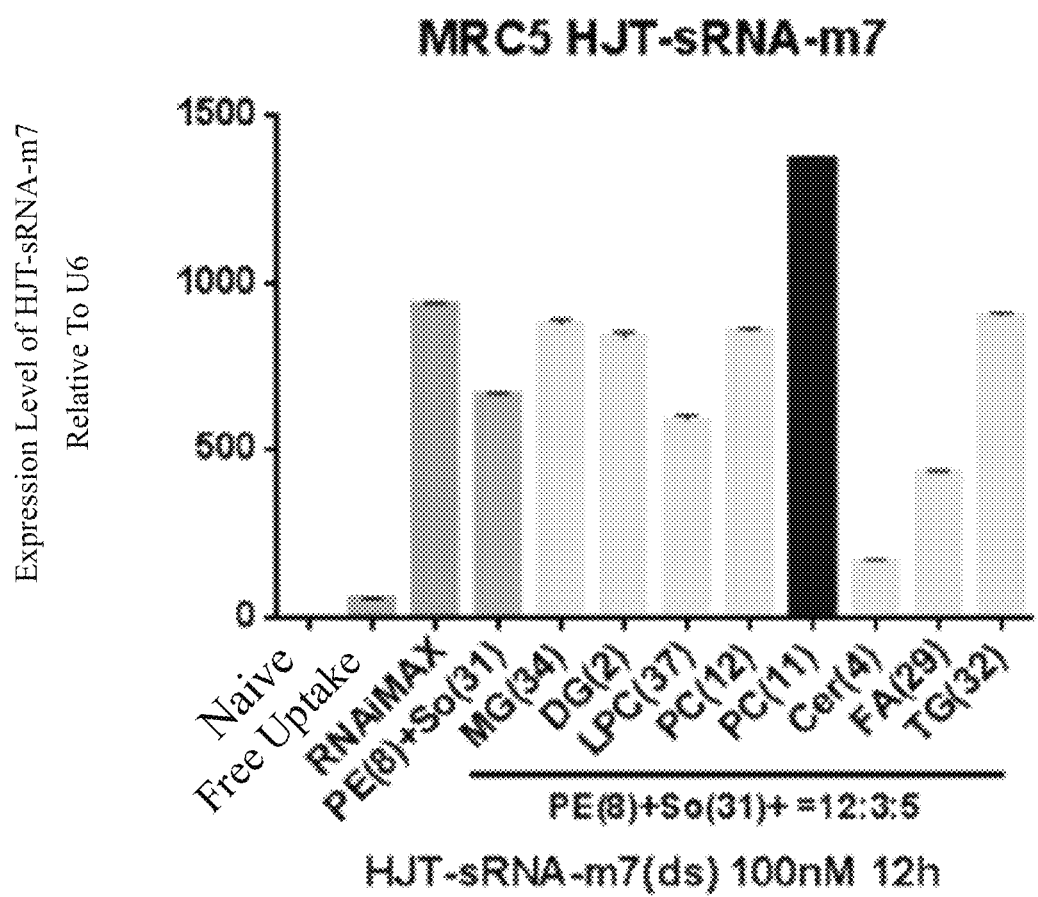

FIG. 80: Lipid combination delivers double-stranded nucleic acid into MRC-5 cells.

Figure 81:
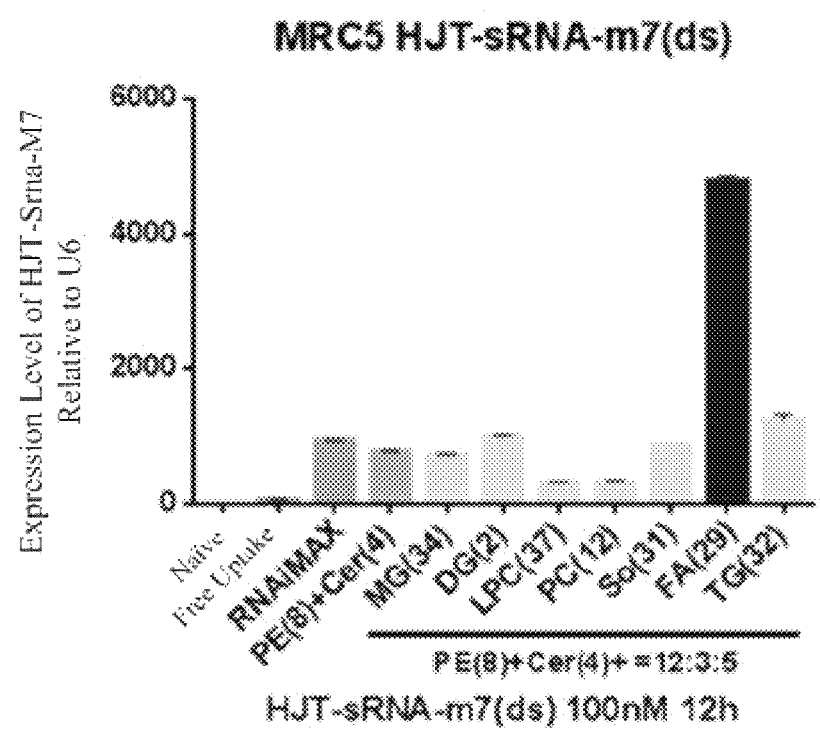

FIG. 81: Lipid combination delivers double-stranded nucleic acid into MRC-5 cells.

Figure 82:
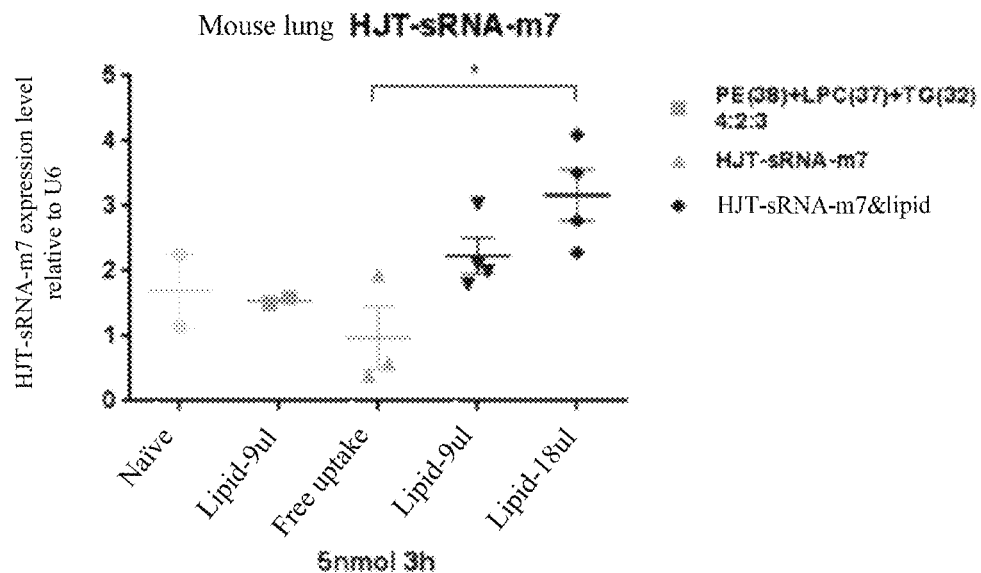

FIG. 82: Lipid composition facilitates nucleic acids to enter lung through the digestive tract.

Figure 83:
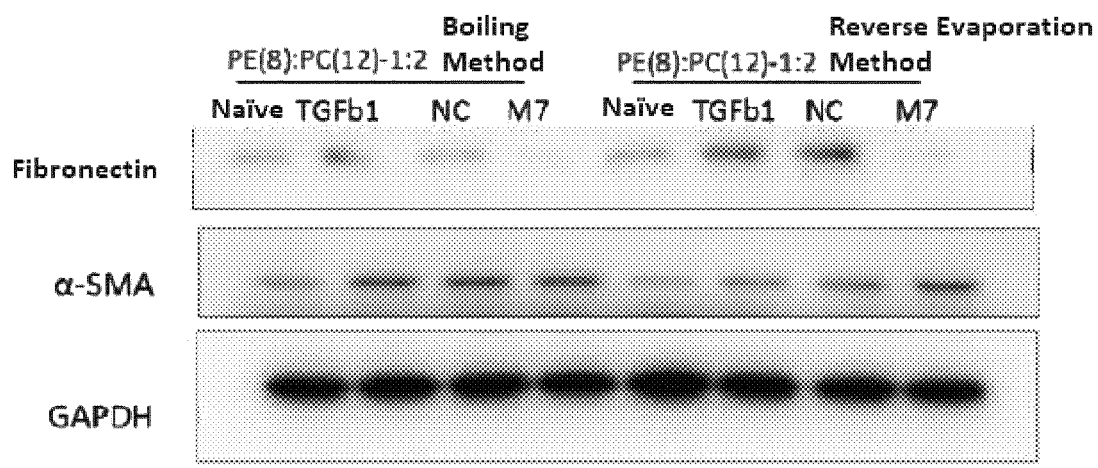

FIG. 83: No. 8 (PE): No. 12 (PC) (v:v=1:2) mediates the entry of anti-fibrotic HJT-sRNA-m7 into MRC-5 cells to reduce the expression of fibronectin.

Figure 84:
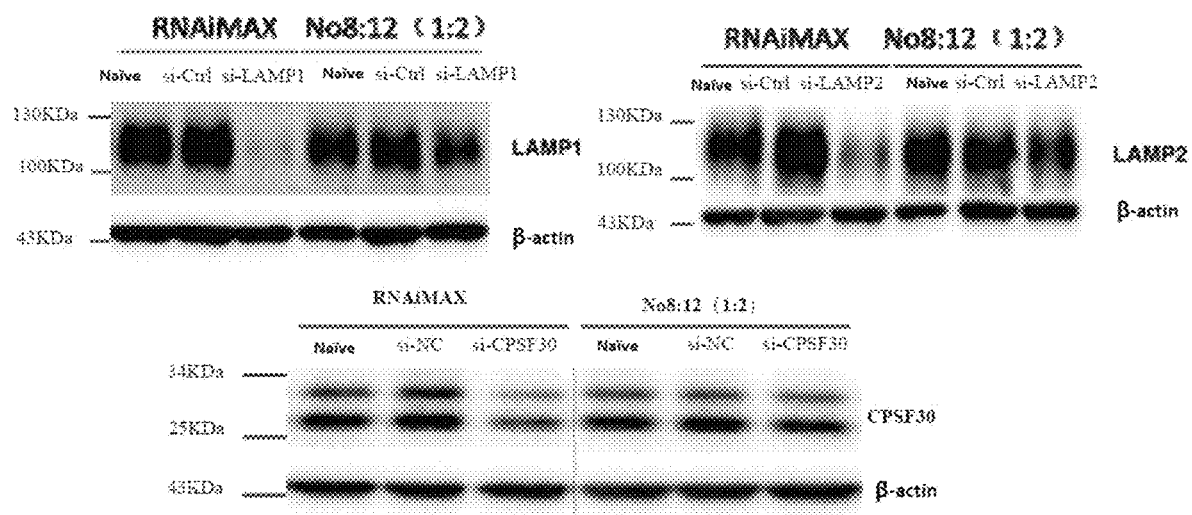

FIG. 84: No. 8 (PE): No. 12 (PC) (v:v=1:2) mediates the entry of siRNA into A549 cells to inhibit the expression of corresponding proteins.

Figure 85:
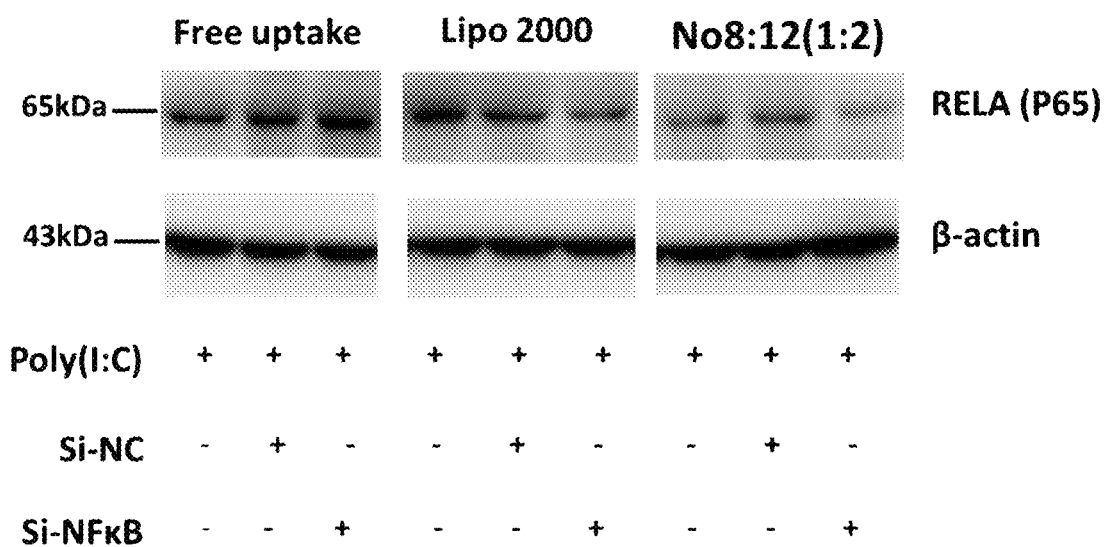

FIG. 85: No. 8 (PE): No. 12 (PC) (v:v=1:2) mediates the entry of siRNA into A549 cells to inhibit the expression of corresponding proteins.

Figure 86:
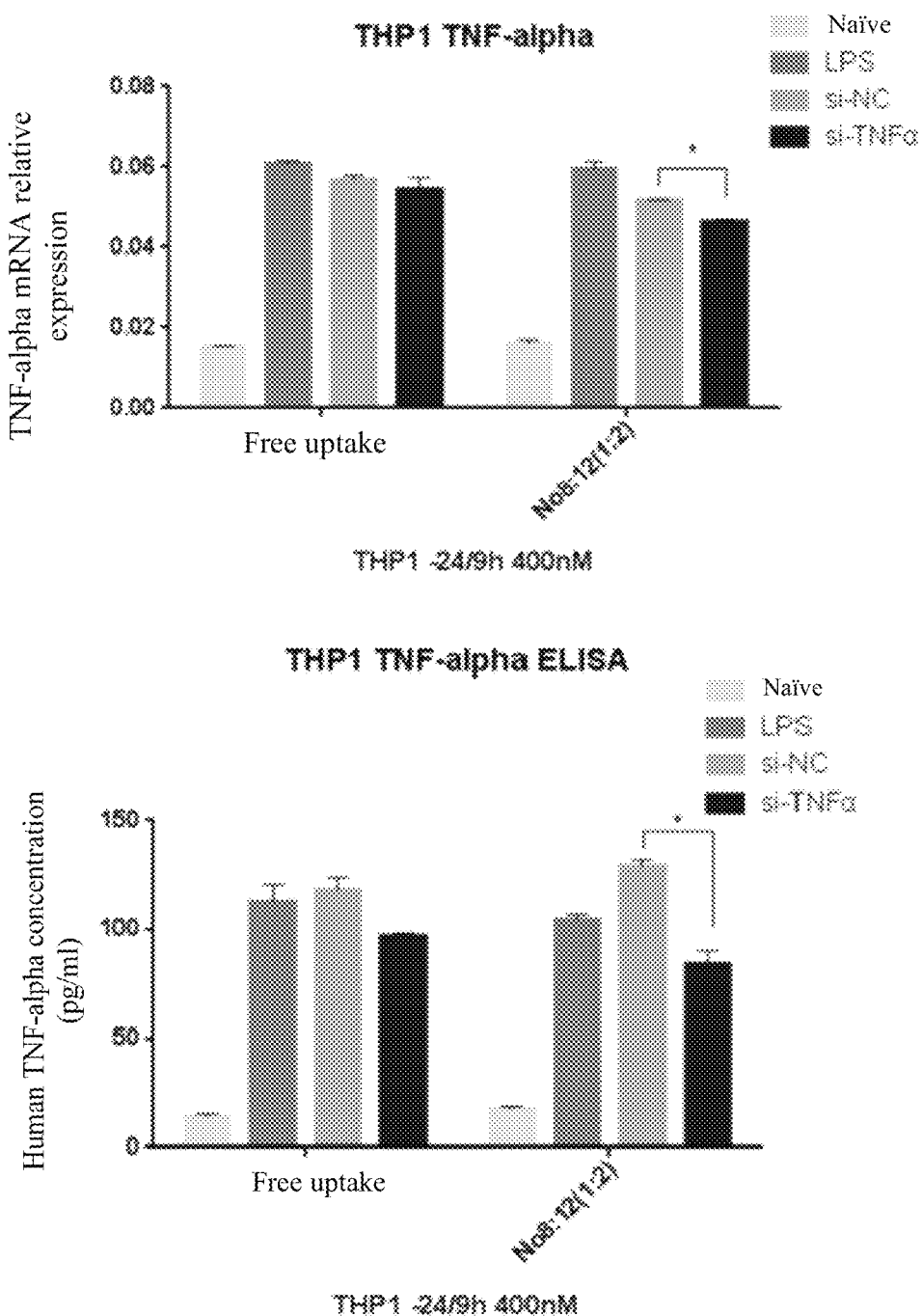

FIG. 86: No. 8 (PE): No. 12 (PC) (v:v=1:2) mediates the entry of siRNA into THP-1 cells to inhibit the expression of corresponding proteins.

Figure 87:
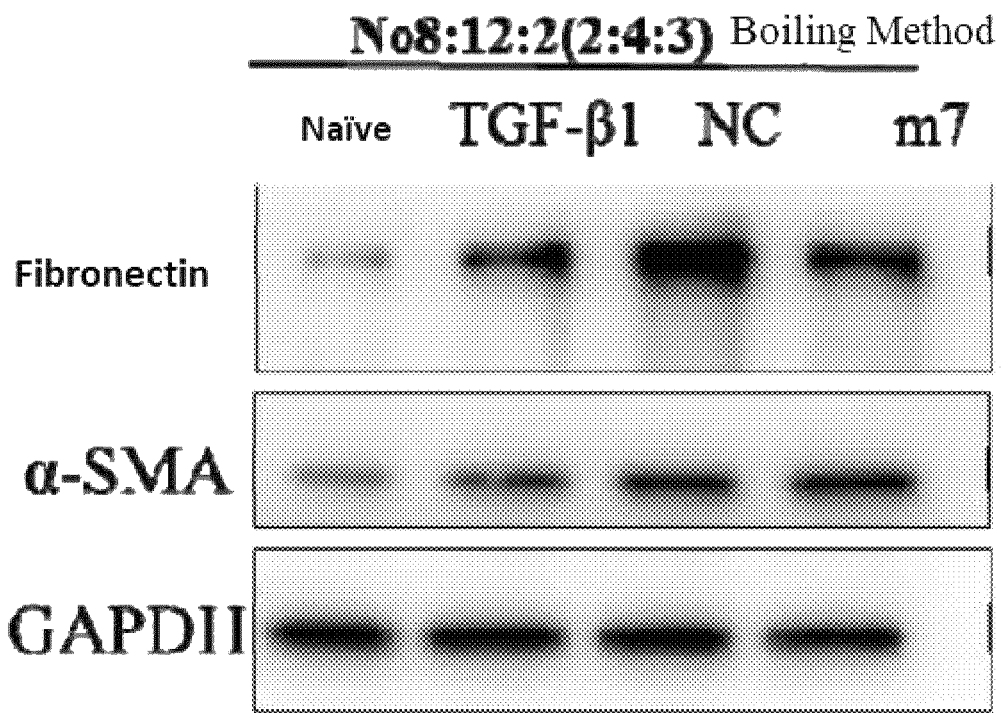

FIG. 87: No. 8 (PE): No. 12 (PC): No. 2 (DG) (v:v:v=2:4:3) mediates the entry of anti-fibrotic HJT-sRNA-m7 into MRC-5 cells to reduce the expression of fibronectin.

Figure 88:
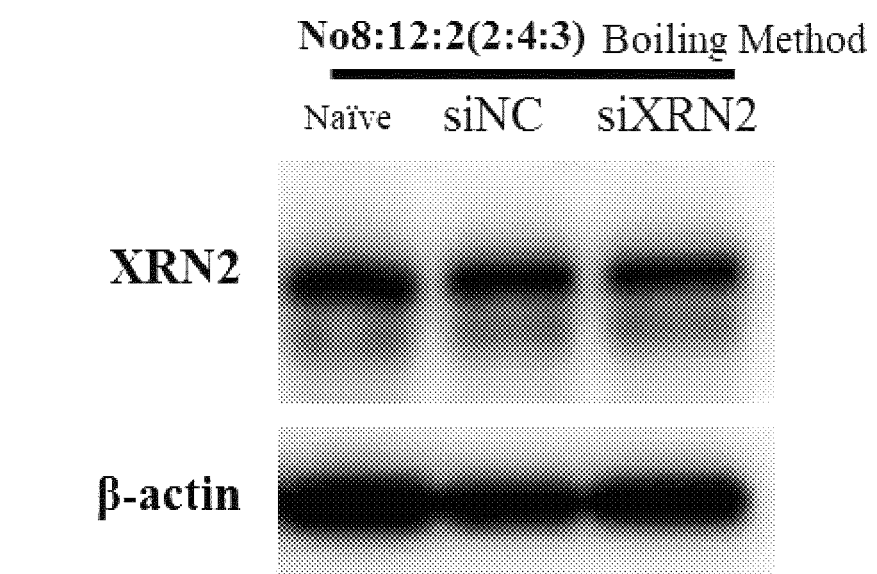

FIG. 88: No. 8 (PE): No. 12 (PC): No. 2 (DG) (v:v:v=2:4:3) lipid combination mediates the entry of XRN2 siRNA into A549 cells to inhibit gene expression (boiling method).

Figure 89:
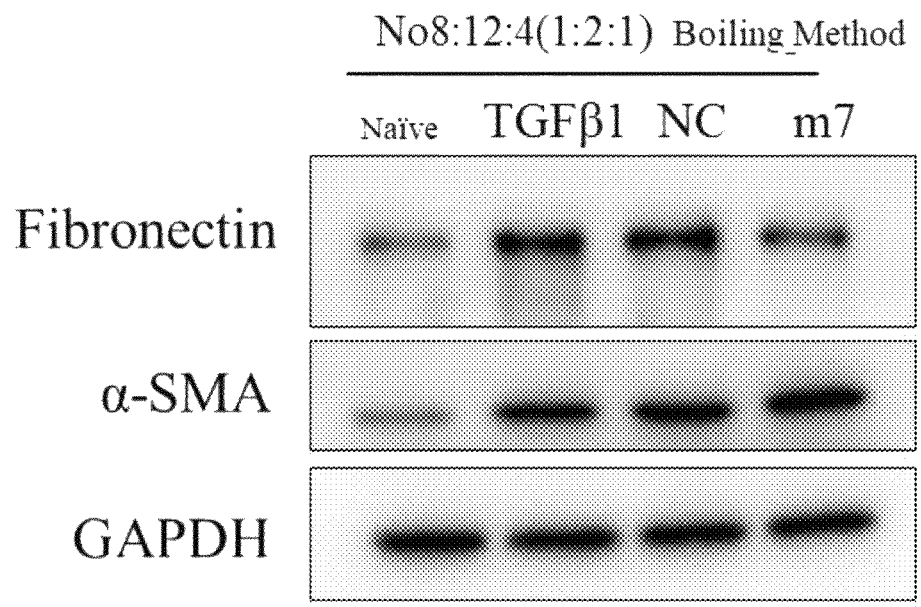

FIG. 89: No. 8 (PE): No. 12 (PC): No. 4 (Cer) (v:v:v=1:2:1) lipid combination mediates the entry of anti-fibrotic HJT-sRNA-m7 into MRC-5 cells (boiling method).

Figure 90:
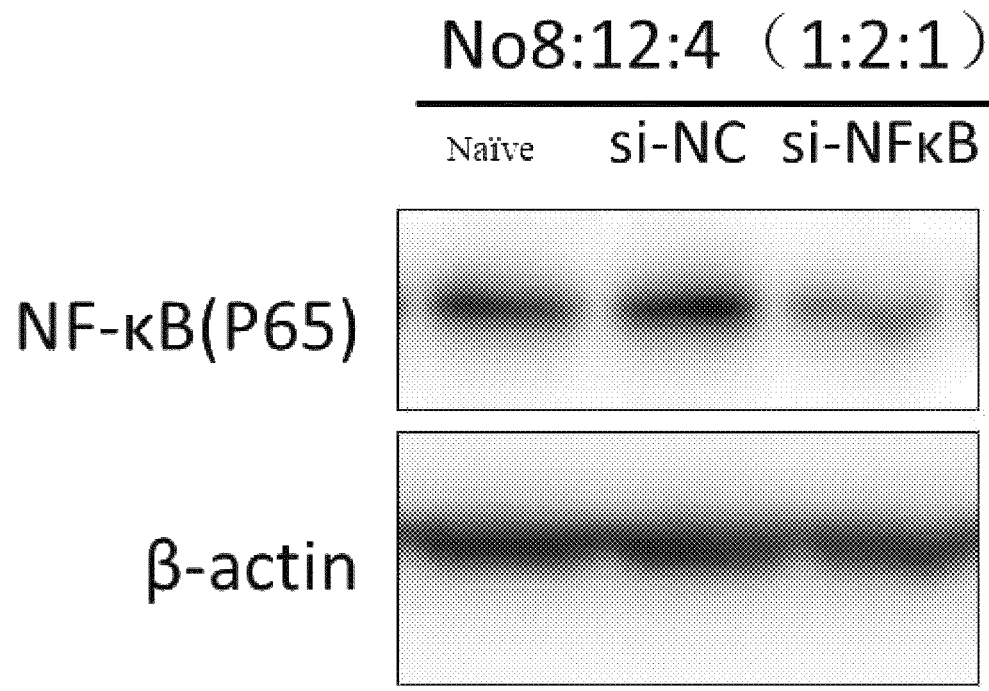

FIG. 90: No. 8 (PE): No. 12 (PC): No. 4 (Cer) (v:v:v=1:2:1) lipid combination mediates the entry of NFκB siRNA into THP-1 cells to inhibit gene expression (boiling method).

Figure 91:
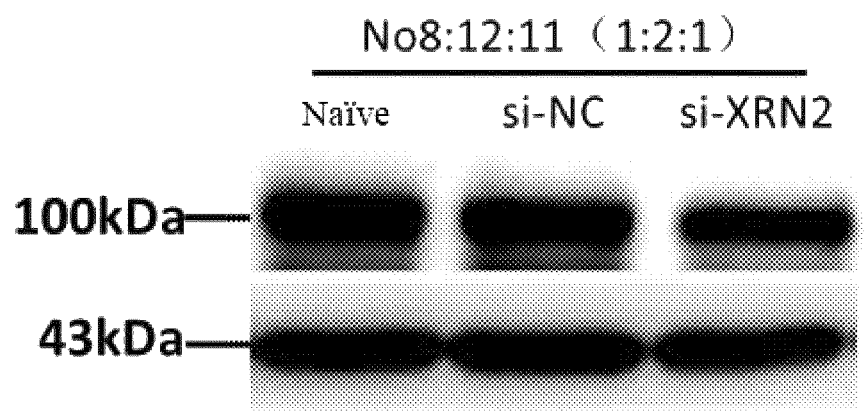

FIG. 91: No. 8 (PE): No. 12 (PC): No. PC(11) (v:v:v=1:2:1) lipid combination mediates the entry of XRN2 siRNA into A549 cells to inhibit gene expression.

Figure 92:
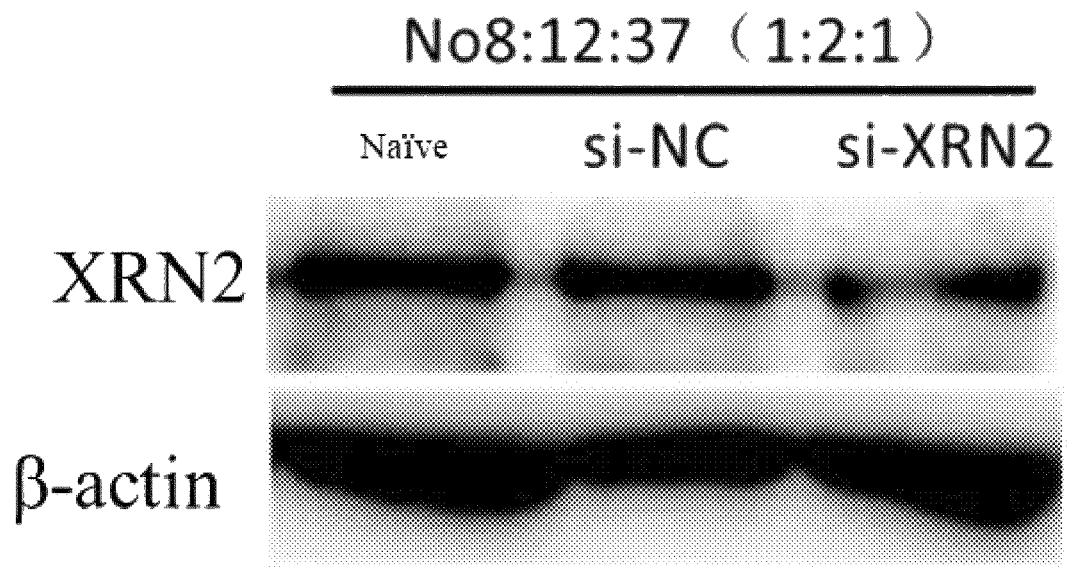

FIG. 92: No. 8 (PE): No. 12 (PC): No. LPC(37) (v:v:v=1:2:1) lipid combination mediates the entry of XRN2 siRNA into A549 cells to inhibit gene expression.

Figure 93:
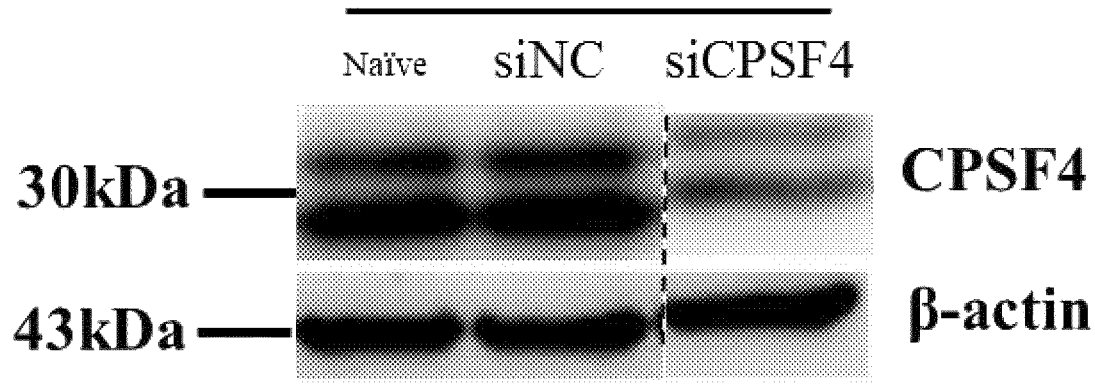

FIG. 93: No. 8 (PE): No. 12 (PC): No. MG (34) (v:v:v=2:3:1) lipid combination mediates the entry of CPSF4 siRNA into A549 cells to inhibit gene expression.

Figure 94:
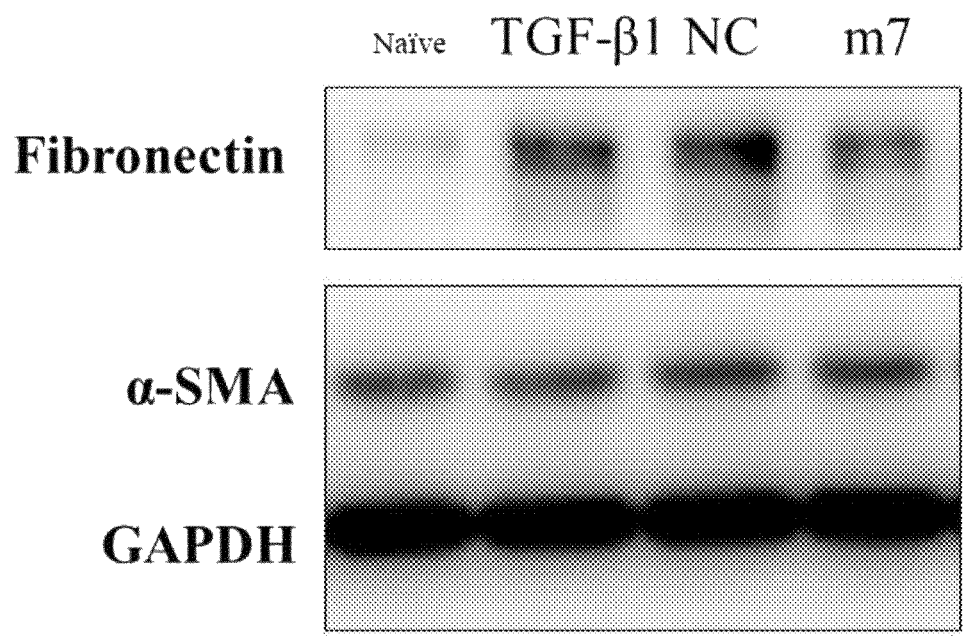

FIG. 94: No. 38 (PE): No. 37 (LPC): No. 32 (TG) (v:v:v=32:8:5) lipid combination mediates the entry of anti-fibrotic HJT-sRNA-m7 into MRC-5 cells (boiling method).

FIG. 95: No. 38 (PE): No. 37 (LPC): No. 32 (TG) (v:v:v=32:8:5) lipid combination mediates the entry of XRN2 siRNA into A549 cells to inhibit gene expression.

FIG. 96: No. 1 (DG), No. 8 (PE), No. 12 (PC), No. 4 (Cer), No. 31 (So), No. 29 (FA), No. 16 (TG) (v:v:v:v:v:v:v=2:1:2:2:3:1:3) mediates the entry of anti-fibrotic HJT-sRNA-m7 into MRC-5 cells (boiling method) to reduce the expression of fibronectin.

Figures 97, 98:
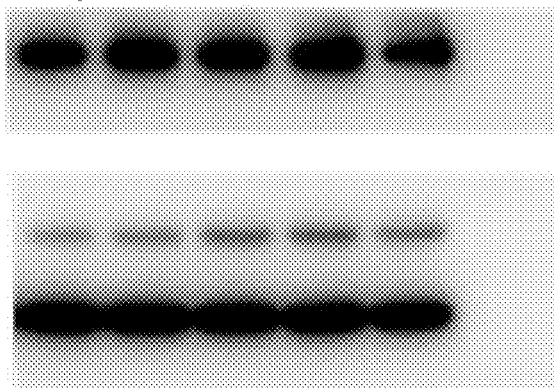

FIG. 97: No. 1 (DG), No. 8 (PE), No. 12 (PC), No. 4 (Cer), No. 31 (So), No. 29 (FA), No. 16 (TG) (v:v:v:v:v:v:v=2:1:2:2:3:1:3) lipid combination mediates the entry of XRN2 siRNA into A549 cells to inhibit gene expression.

FIG. 98: No. 8 (PE): No. 12 (PC): No. 31 (So): No. 29 (FA): No. 4 (Cer) (v:v:v:v:v=2:4:2:2:2.5) mediates the entry of anti-fibrotic HJT small RNA HJT-sRNA-3, HJT-sRNA-a2, HJT-sRNA-h3, HJT-sRNA-m7 into MRC-5 cells (boiling method) to reduce the expression of fibronectin.

Figure 99:
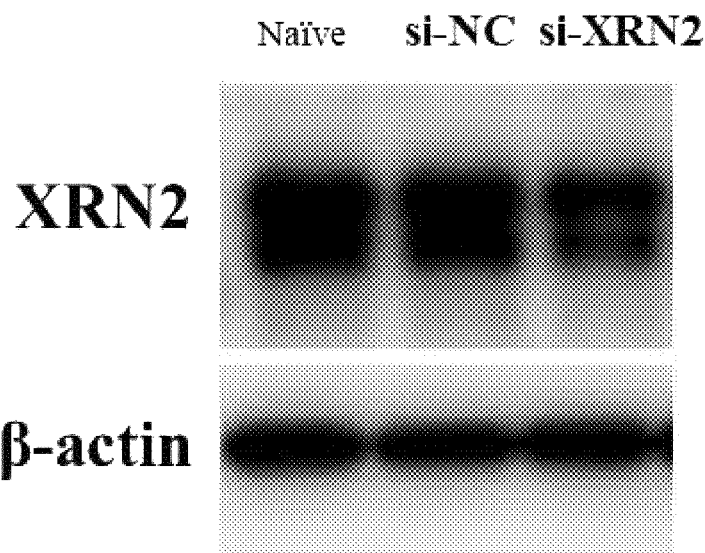

FIG. 99: No. 8 (PE): No. 12 (PC): No. 31 (So): No. 29 (FA): No. 4 (Cer) (v:v:v:v:v=2:4:2:2:2.5) lipid combination can effectively deliver nucleic acid into cells to function.

Figure 100:
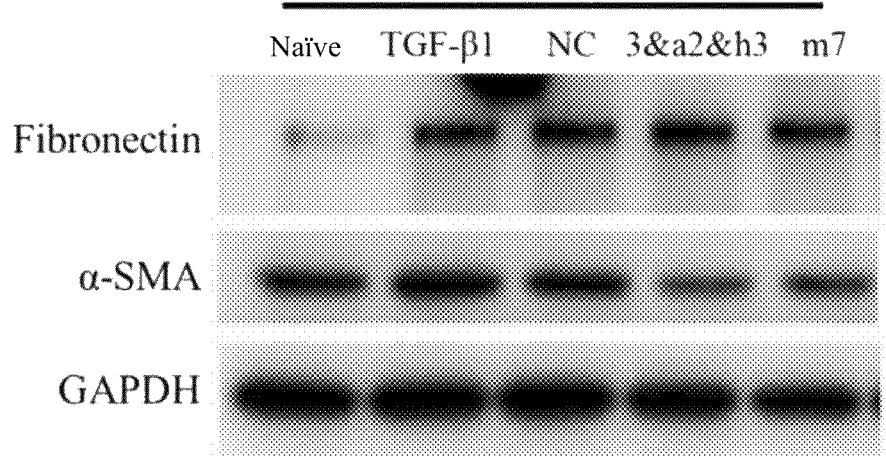

FIG. 100: No. 38 (PE): No. 37 (LPC) (v:v=4:1) mediates the entry of anti-fibrotic HJT small RNA HJT-sRNA-3, HJT-sRNA-a2, HJT-sRNA-h3, HJT-sRNA-m7 into MRC-5 cells (boiling method) to reduce the expression of fibronectin and alpha-matrix protein.

FIG. 101: No. 38 (PE): No. 37 (LPC) (v:v=4:1) lipid combination mediates the entry of XRN2 siRNA into A549 cells to inhibit gene expression (boiling method).

FIG. 102: No. 38 (PE): No. 12 (PC): No. 2 (DG) (v:v:v=4:1:3) lipid combination mediates the entry of XRN2 siRNA into A549 cells to inhibit gene expression.

FIG. 103: No. 38 (PE): No. 37 (LPC): No. 12 (PC) (v:v:v=4:1:1) lipid combination mediates the entry of XRN2 siRNA into A549 cells to inhibit gene expression (reverse evaporation method).

FIG. 104: No. 4 (Cer): No. 12 (PC): No. 38 (PE): No. 37 (LPC) (v:v:v:v=5:2:8:3) lipid combination mediates the entry of anti-fibrotic HJT small RNA HJT-sRNA-3, HJT-sRNA-a2, HJT-sRNA-h3, HJT-sRNA-m7 into MRC-5 cells (boiling method).

FIG. 105: No. 4 (Cer): No. 12 (PC): No. 38 (PE): No. 37 (LPC) (v:v:v:v=5:2:8:3) lipid combination mediates the entry of XRN2 siRNA into A549 cells to inhibit gene expression (boiling method).

FIG. 106: No. 38 (PE): No. 2 (DG): No. 31 (So) (v:v:v=4:2:3) lipid combination mediates the entry of anti-fibrotic HJT small RNA HJT-sRNA-3, HJT-sRNA-a2, HJT-sRNA-h3, HJT-sRNA-m7 into MRC-5 cells (boiling method).

FIG. 107: No. 38 (PE): No. 2 (DG): No. 31 (So) (v:v:v=4:2:3) lipid combination mediates the entry of XRN2 siRNA into A549 cells to inhibit gene expression (boiling method).

FIG. 108: Lipid No. 41 delivers double-stranded DNA into A549 cells by different preparation methods (boiling method or reverse evaporation method).

FIG. 109: Lipid No. 41 delivers double-stranded RNA into MRC-5 cells by different preparation methods (boiling method or reverse evaporation method).

FIG. 110: Lipid No. 41 delivers single-stranded RNA into A549 and MRC-5 cells by boiling method.

FIG. 111: The efficiency of lipid delivery of nucleic acid determined by digital PCR (ddPCR) technique.

FIG. 112: The efficiency of lipid delivery of nucleic acid determined by flow cytometry.

FIG. 113: The locations of lipid-delivered nucleic acid in cells observed using confocal fluorescence microscope.

FIG. 114: The efficiency of lipid delivery of nucleic acid determine by Western Blotting test.

FIG. 115: Lipid monomer No. 41 mediates the entry of anti-fibrotic HJT-sRNA-m7 into MRC-5 cells (boiling method).

FIG. 116: The use of lipid combination 1 (No. 8+No. 41=6:1) and lipid combination 2 (No. 38+No. 41=6:1) in the delivery of nucleic acids.

FIG. 117: The use of lipid combination 3 (No. 39+No. 41=6:1) and lipid combination 4 (No. 40+No. 41=6:1) in the delivery of nucleic acids.

FIG. 118: The use of lipid combination 5 (38+12+41+29=1:2:1:1) in the delivery of nucleic acids.

FIG. 119: The use of lipid combination 6 (40(PE)+12(PC)+41(So)=2:4:3) in the delivery of nucleic acids.

FIG. 120: The use of lipid combination 7 (12(PC)+41(So)=1:6) and lipid combination 8 (12(PC)+41(So)=1:1) in the delivery of nucleic acids.

FIG. 121: The use of lipid combination 9 (12(PC)+41(So)=6:1) and lipid combination 10 (40(PE)+12(PC)+41(So)=2:2:2) in the delivery of nucleic acids.

FIG. 122: The use of lipid combination 11 (4(Cer)+12(PC)+41(So)=1:1:1) in the delivery of nucleic acids.

FIG. 123: Lipid No. 38 delivers double-stranded RNA into A549 and MRC-5 cells by boiling method.

FIG. 124: Lipid No. 38 delivers single-stranded RNA into A549 and MRC-5 cells by boiling method.

FIG. 125: The efficiency of lipid delivery of nucleic acid determined by Digital PCR (ddPCR) technique.

FIG. 126: The efficiency of lipid delivery of nucleic acid determined by flow cytometry.

FIG. 127: The locations of lipid-delivered nucleic acid in cells observed using confocal fluorescence microscope.

FIG. 128: Lipid No. 64 delivers double-stranded RNA into A549 cells by different preparation methods (boiling method or reverse evaporation method).

FIG. 129: The efficiency of lipid delivery of nucleic acid determined by flow cytometry.

FIG. 130: The locations of lipid-delivered nucleic acid in cells observed using confocal fluorescence microscope.

FIG. 131: The delivery effects of lipid No. 40 in boiling method and reverse evaporation method.

FIG. 132: The efficiency of lipid delivery of nucleic acid determined by Digital PCR (ddPCR) technique.

FIG. 133: The locations of lipid-delivered nucleic acid in cells observed using confocal fluorescence microscope.

FIG. 134: The efficiency of lipid delivery of nucleic acid determined by Western Blotting test.

Figure 135:
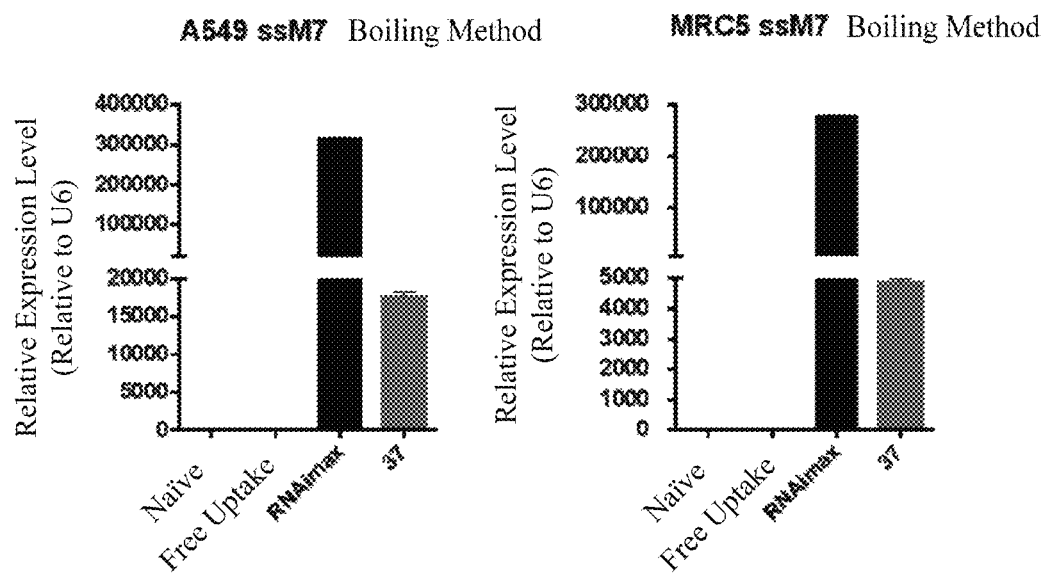

FIG. 135: Lipid No. 37 delivers single-stranded RNA into A549 cells and MRC-5 cells by boiling method.

Figure 136:
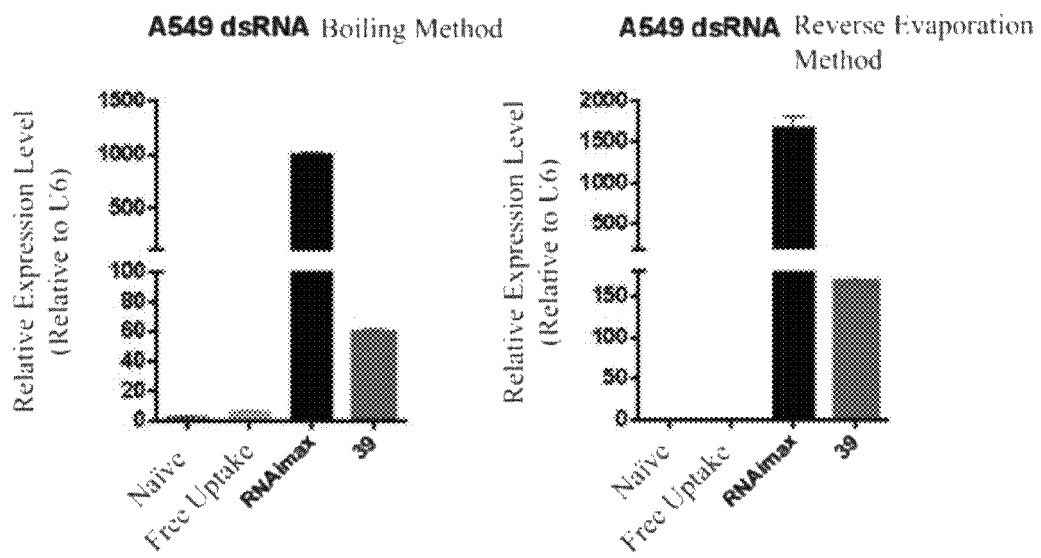

FIG. 136: Lipid No. 39 delivers double-stranded RNA into A549 cells by different preparation methods (boiling method or reverse evaporation method).

Figure 137:
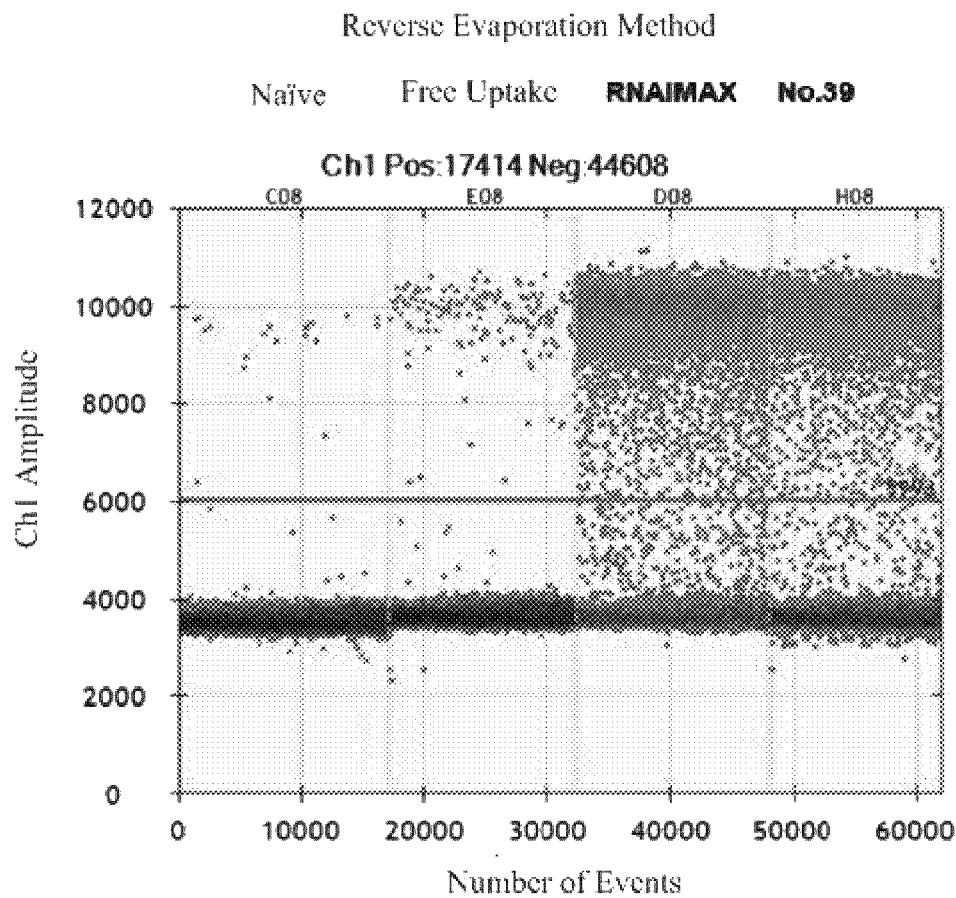

FIG. 137: The efficiency of lipid delivery of nucleic acid determined by Digital PCR (ddPCR) technique.

Figure 138:
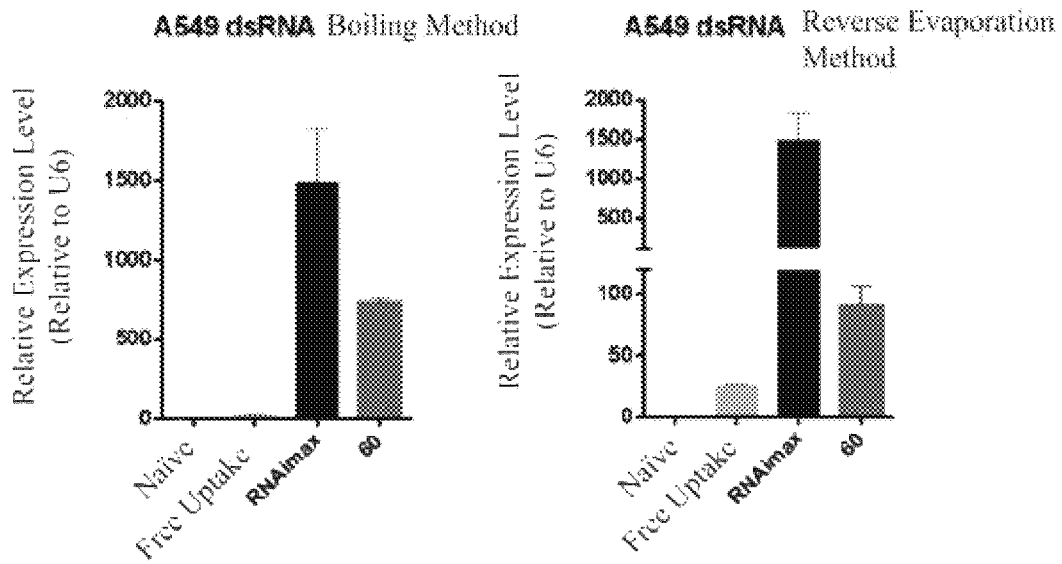

FIG. 138: Lipid No. 60 delivers double-stranded RNA into A549 cells by different preparation methods (boiling method or reverse evaporation method).

Figure 139:
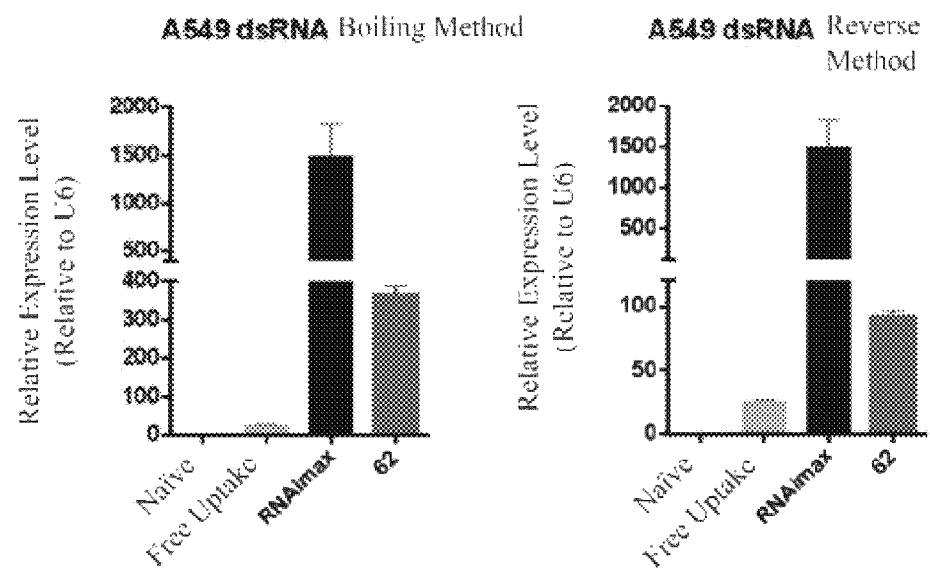

FIG. 139: Lipid No. 62 delivers double-stranded RNA into A549 cells by different preparation methods (boiling method or reverse evaporation method).

Figure 140:
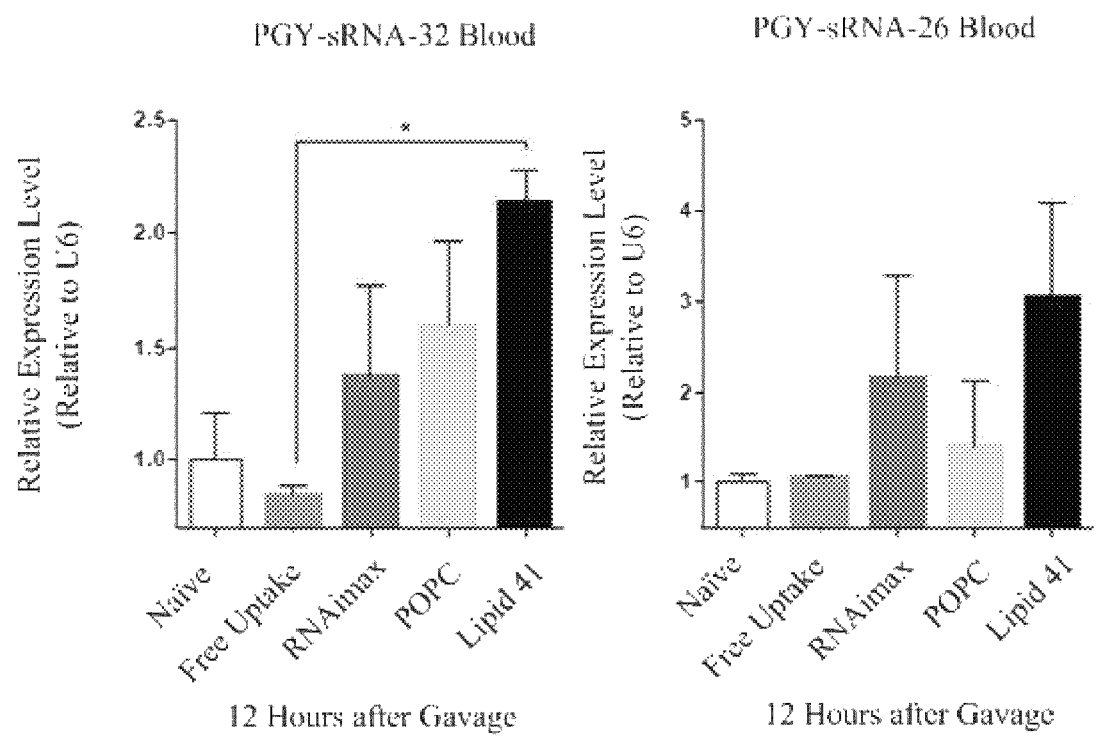

FIG. 140: Lipid No. 41 can promote the entry of small RNA into blood and protect it from degradation in the blood.

Figure 141:
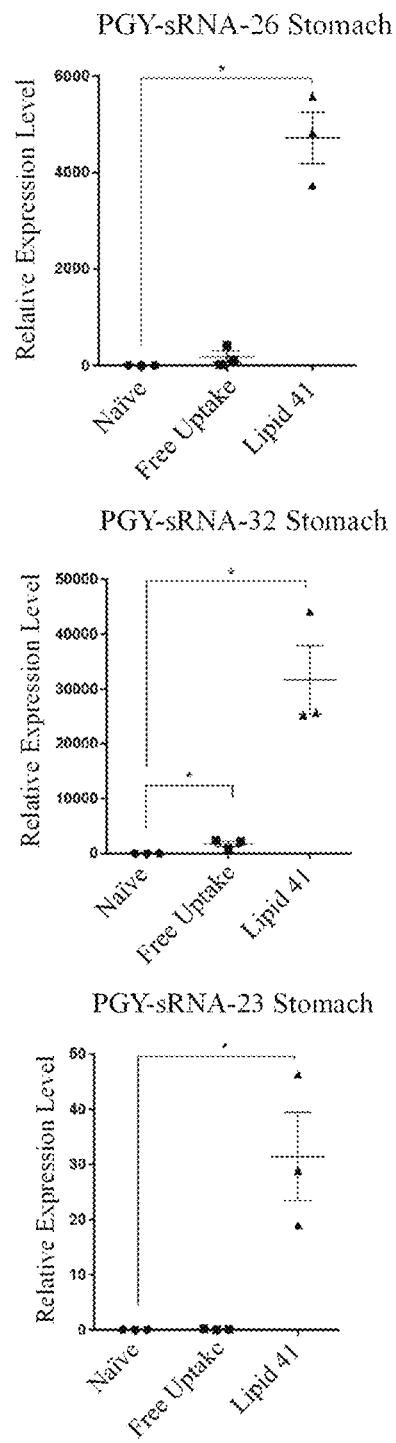

FIG. 141: Lipid No. 41 can promote the entry of small RNA into gastric cells and protect it from degradation in the stomach.

FIG. 142: Lipid No. 41 can promote the entry of small RNA into small intestinal cells and protect it from degradation in the small intestine.

Figure 143:
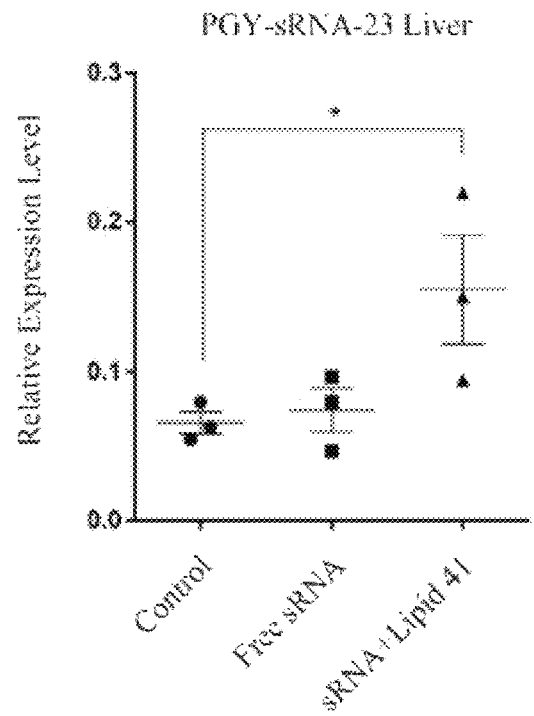

FIG. 143: Lipid No. 41 can promote the entry of small RNA into liver and protect it from degradation in the liver.

Figure 144:
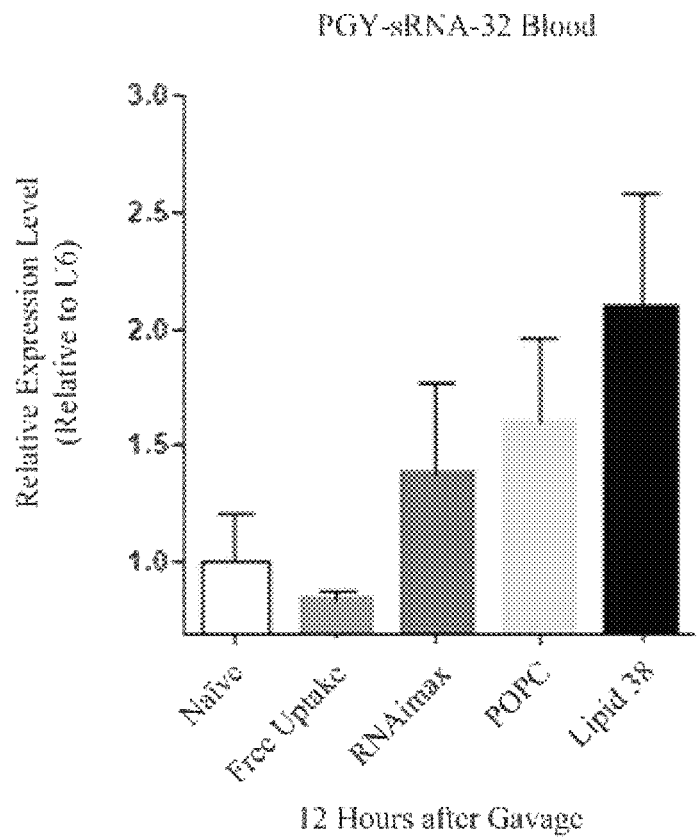

FIG. 144: PE monomer (No. 38) can effectively deliver sRNA single-stranded nucleic acid into the blood of mice by oral administration.

Figure 145:
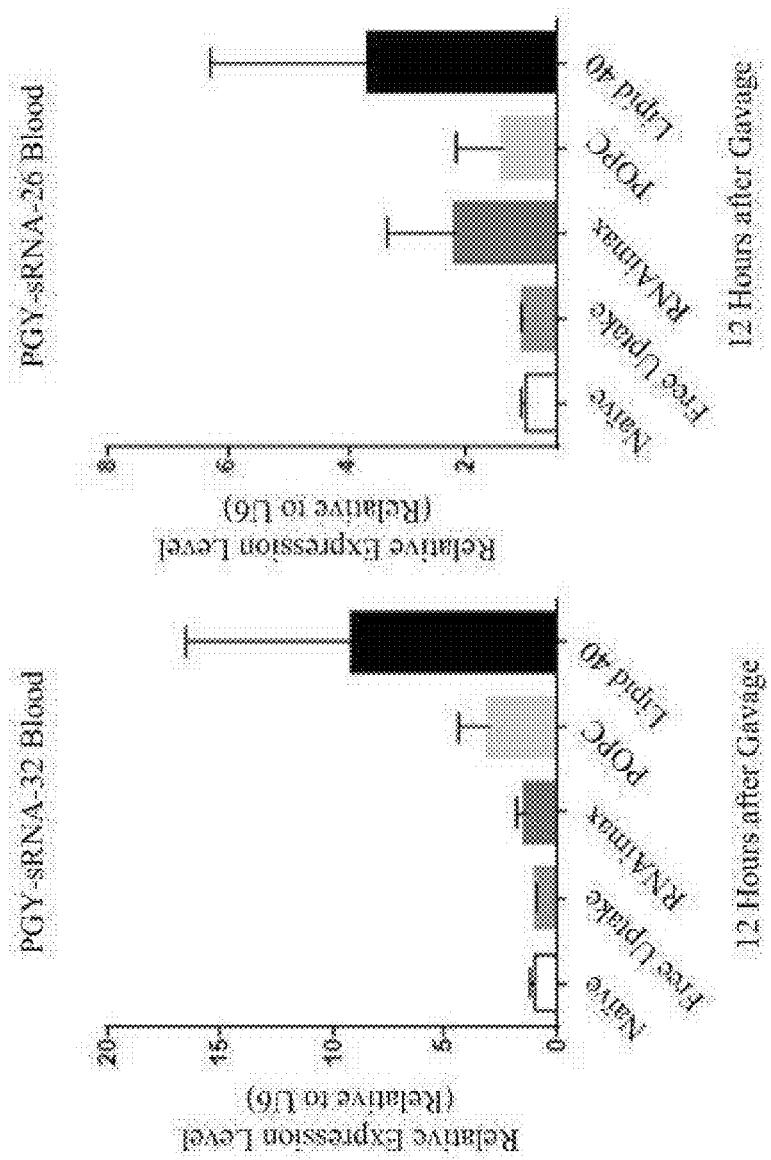

FIG. 145: PE monomer (No. 40) can effectively deliver sRNA single-stranded nucleic acid into the blood of mice by oral administration.

Figure 146:
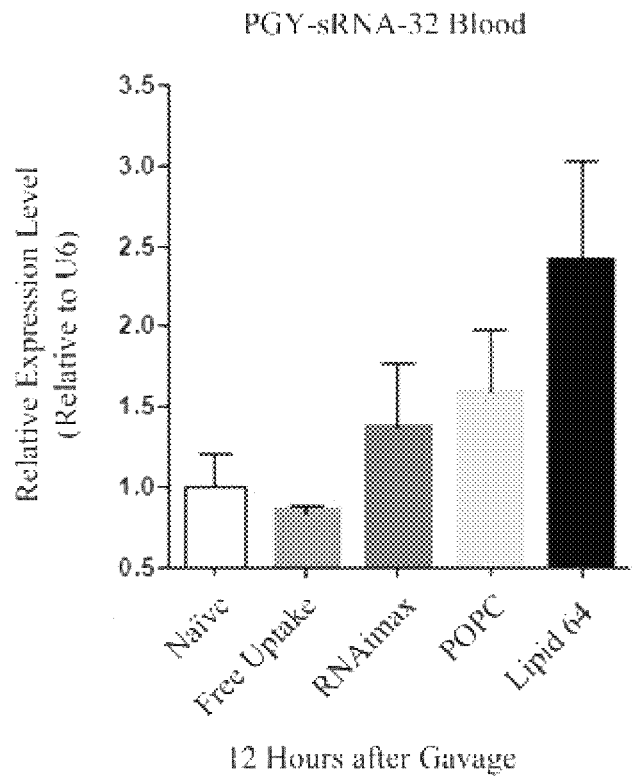

FIG. 146: PE monomer (No. 64) can effectively deliver sRNA single-stranded nucleic acid into the blood of mice by oral administration.

Figure 147:
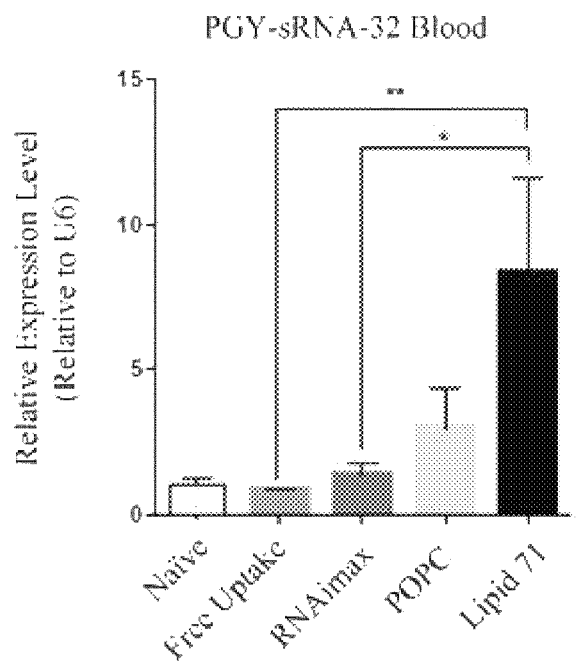

FIG. 147: PE monomer (No. 71) can effectively deliver sRNA single-stranded nucleic acid into the blood of mice by oral administration.

Figure 148:
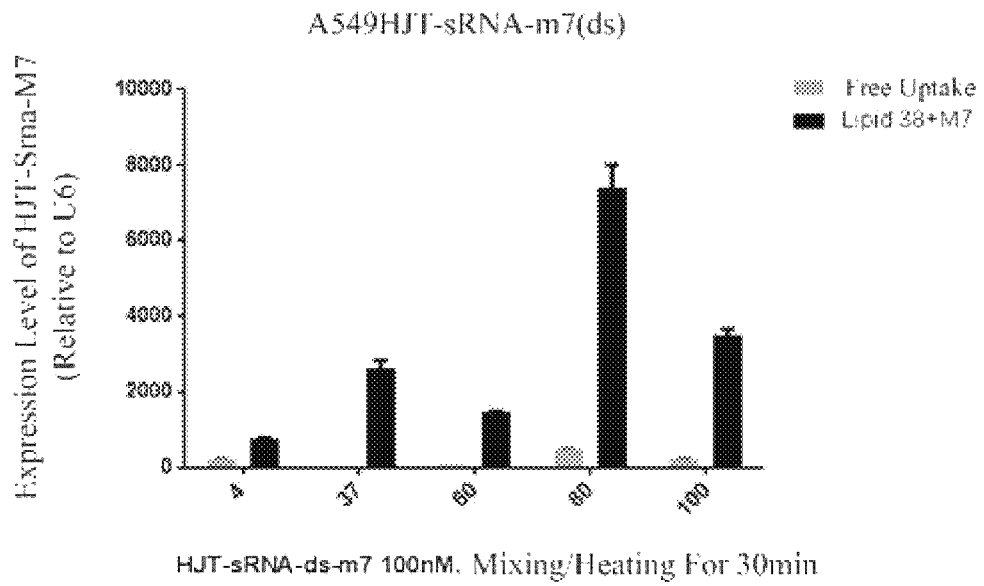
Figure 149A:
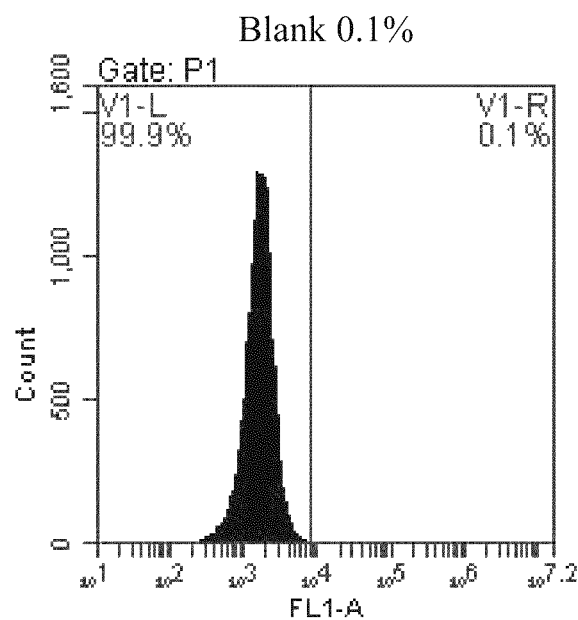
Figure 149B:
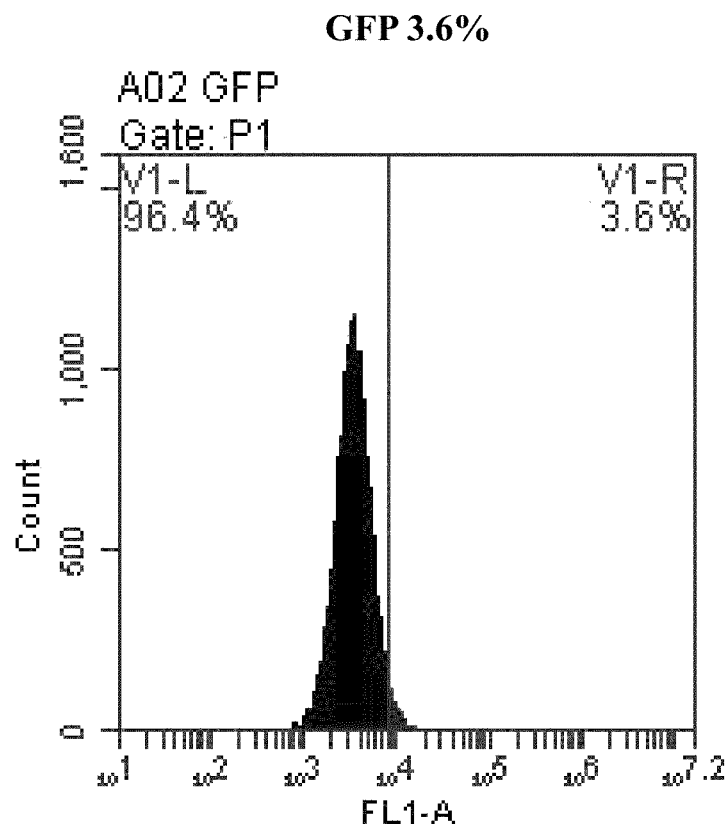
Figure 149C:
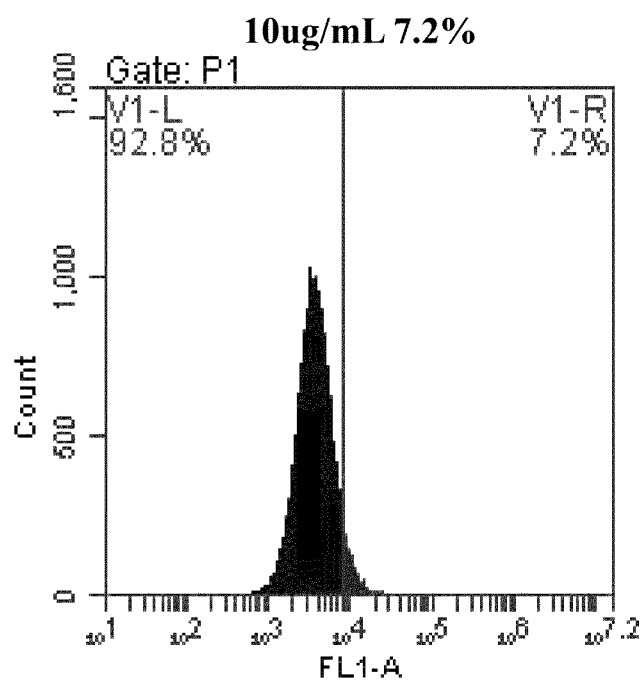
Figure 149D:
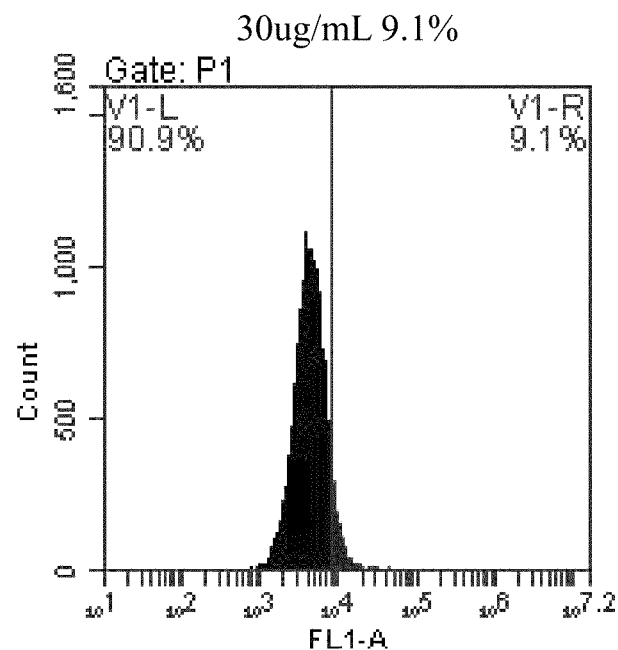
Figure 150A:
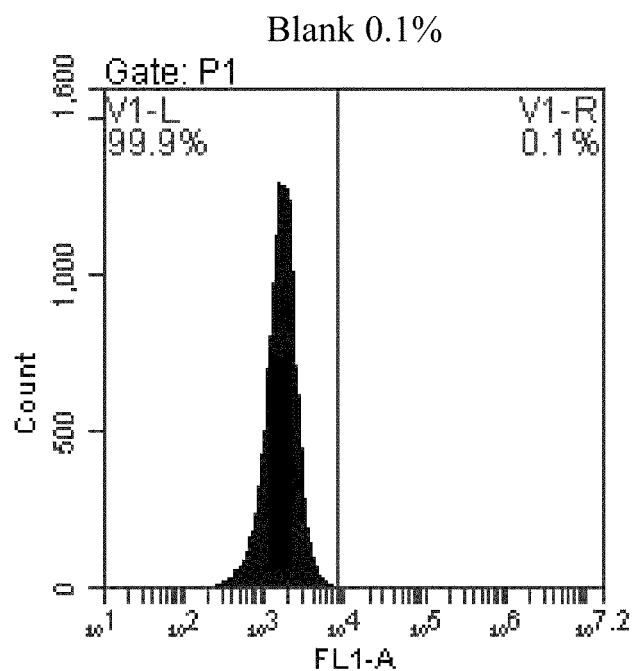
Figure 150B:
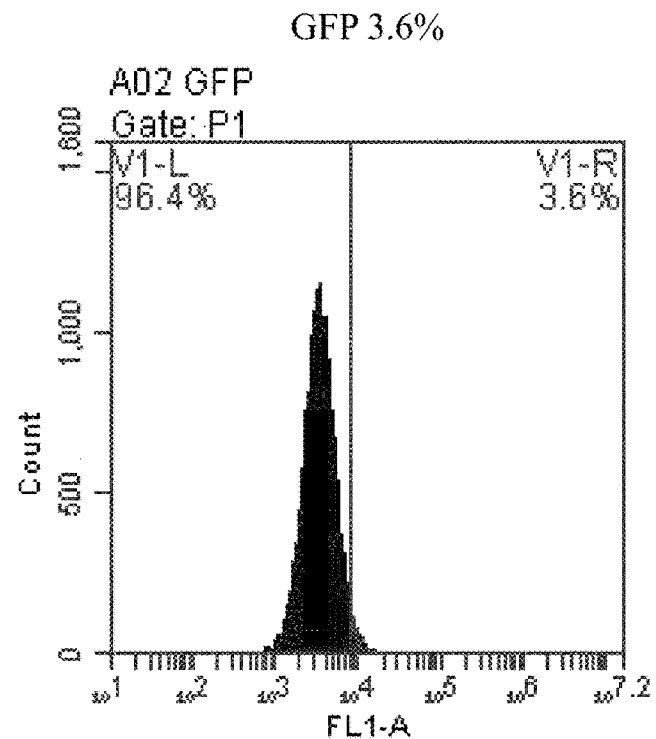
Figure 150C:
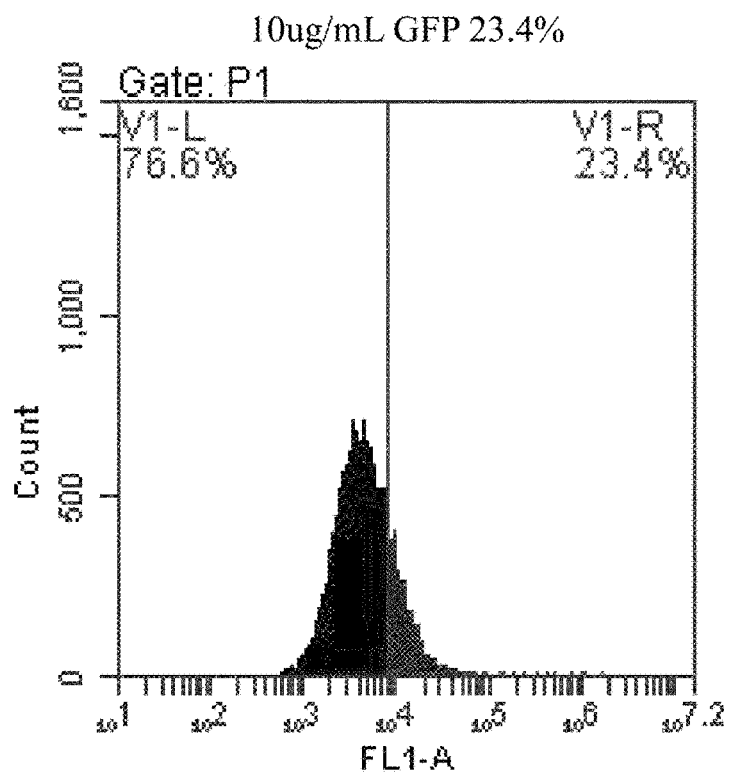
Figure 150D:
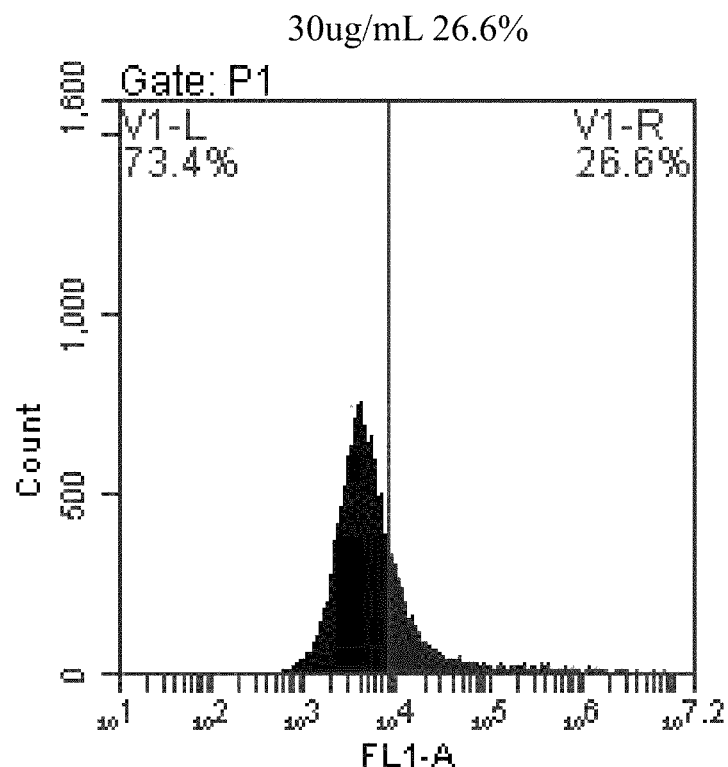
Figure 150E:
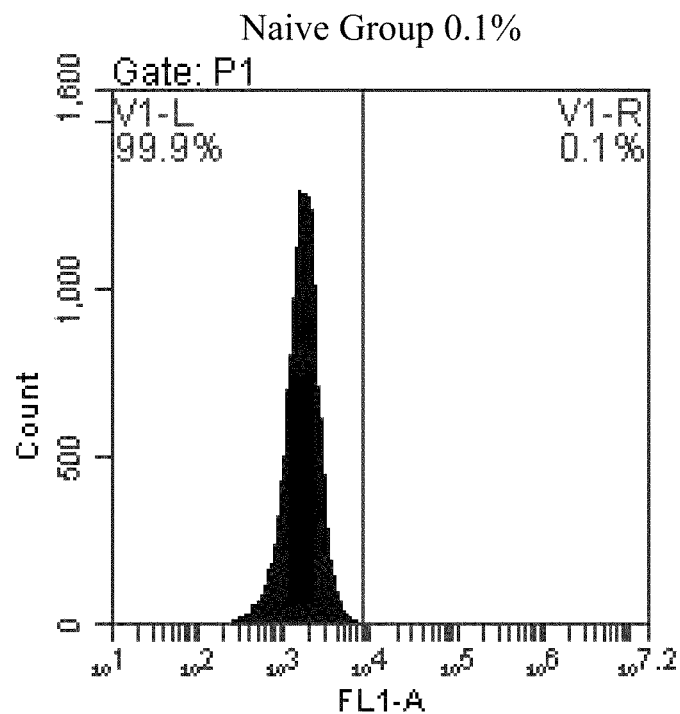
Figure 150F:
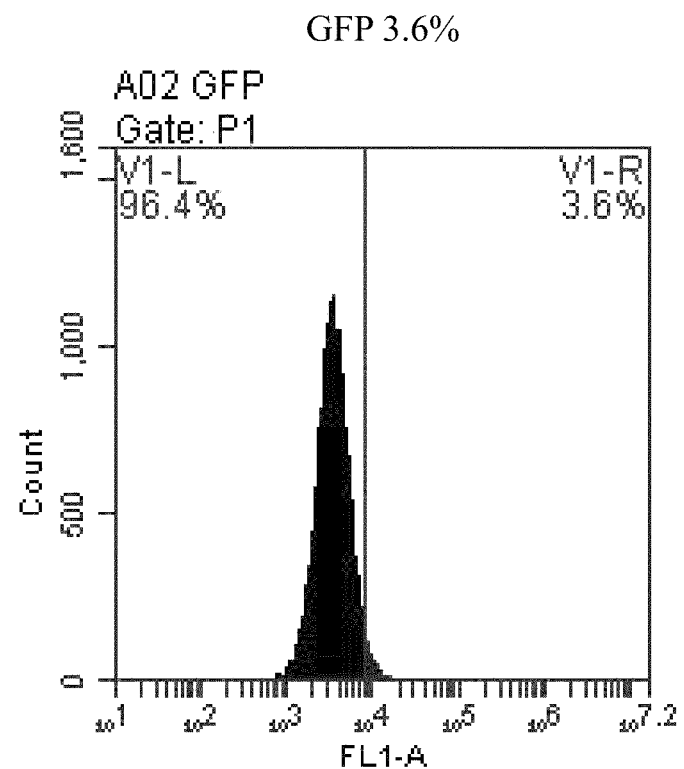
Figure 150G:
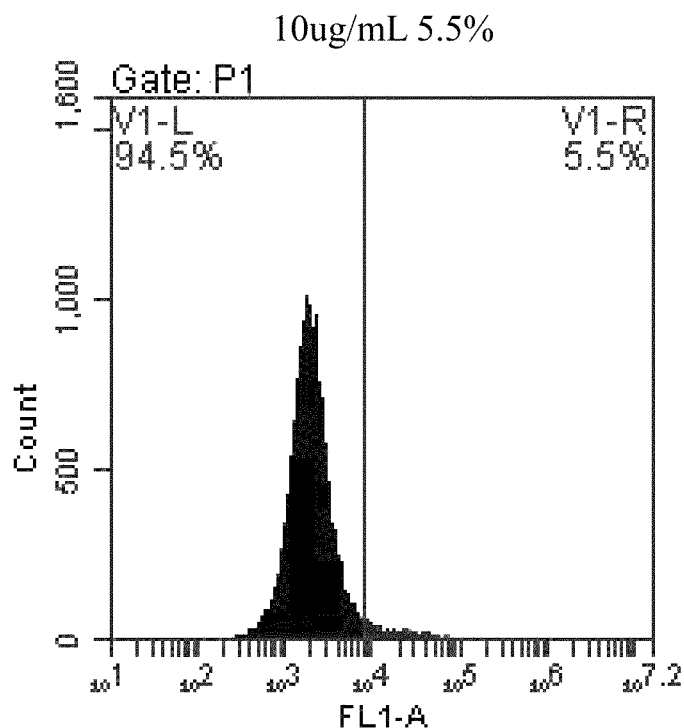
Figure 150H:
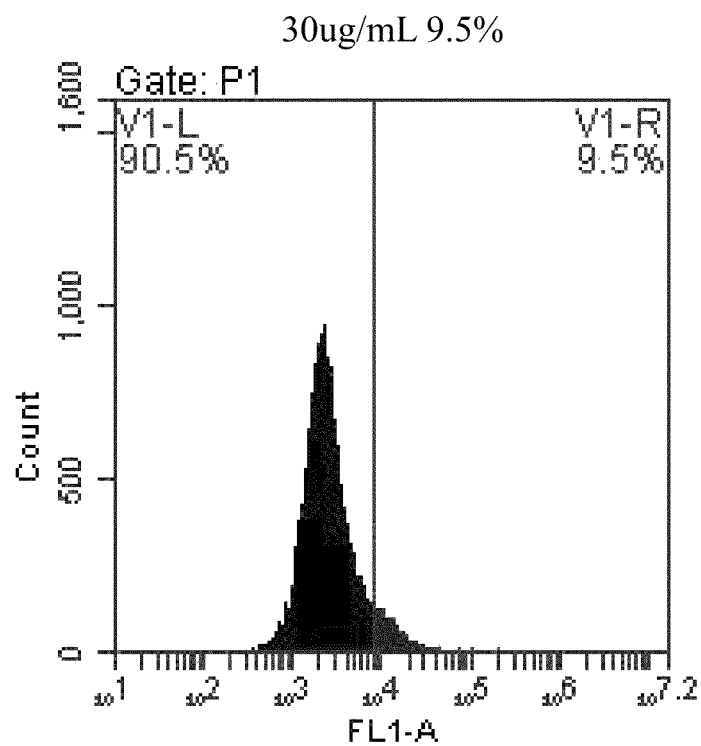
Figure 151A:
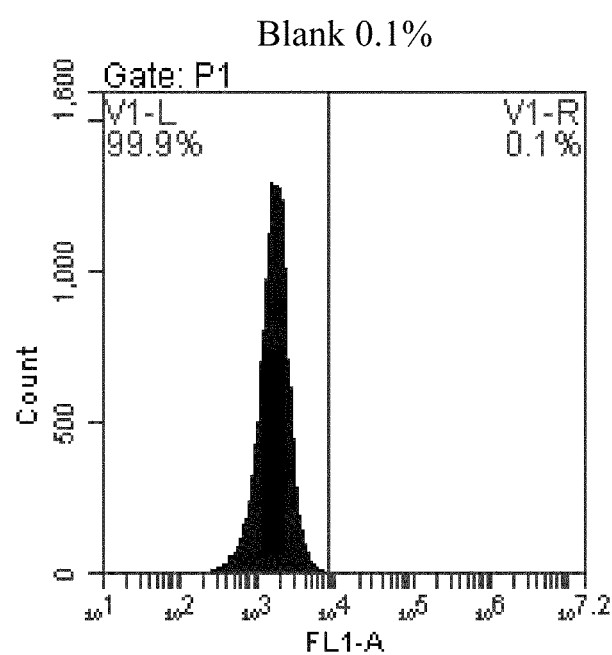
Figure 151B:
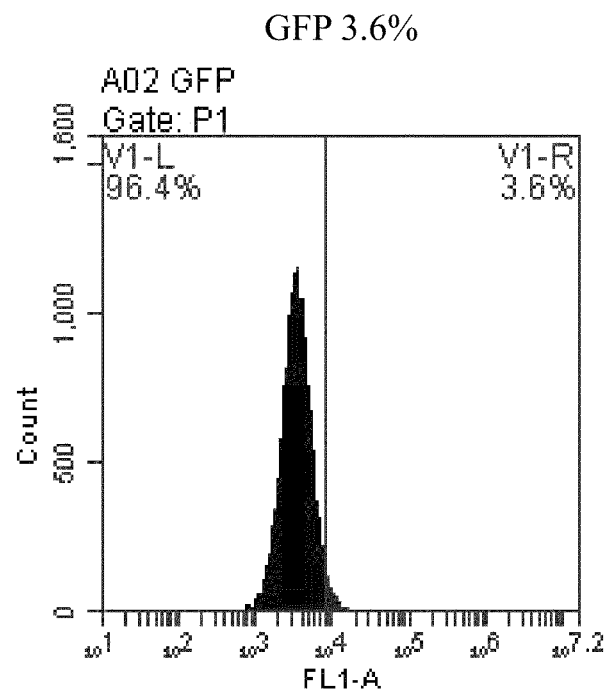
Figure 151C:
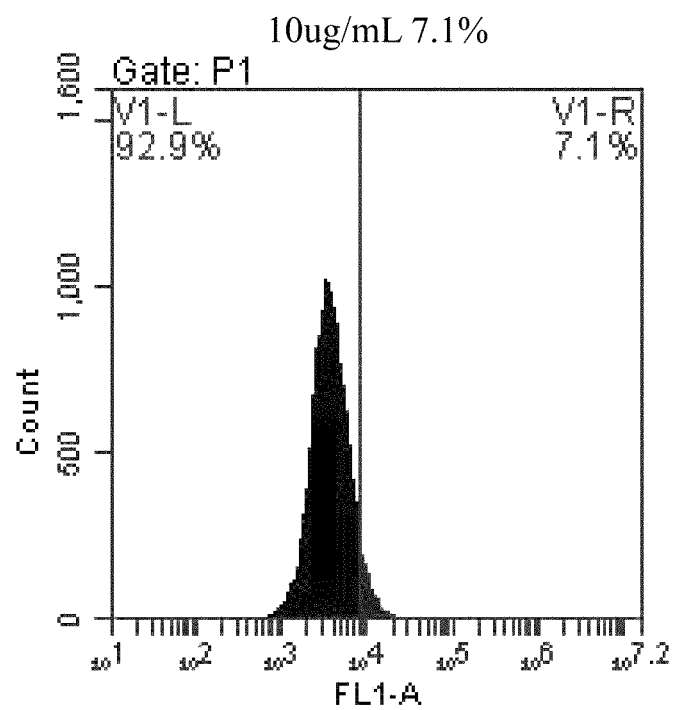
Figure 151D:
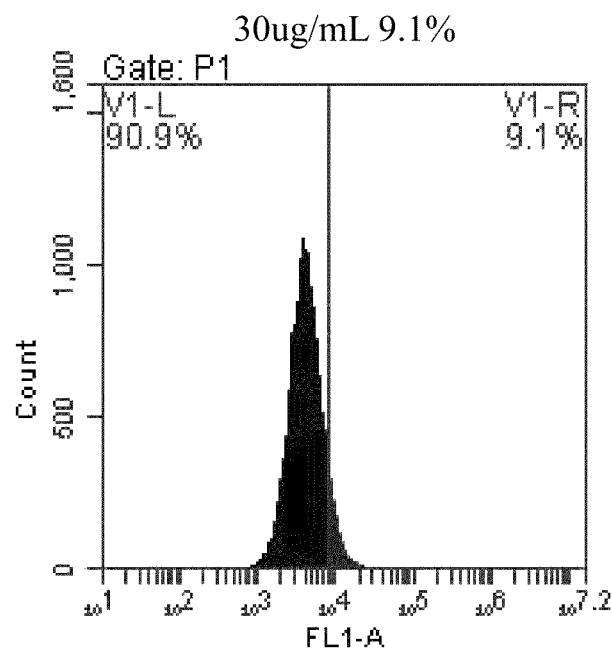

FIG. 148: Lipids effectively deliver single-stranded nucleic acids into MRC5 cells under different temperature gradients.

FIG. 149A-D: The entry of GFP protein of PE(16:0/22:1)-GFP (reverse evaporation method) into A549 cells as determined by flow cytometry.

FIG. 150A-H: The entry of GFP protein of sphinganine (d22:0)-GFP (reverse evaporation method and boiling method) in A549 cells as determined by flow cytometry.

FIG. 151A-D: The entry of GFP protein of PE(16:0/16:0)-GFP (reverse evaporation method) in A549 cells as determined by flow cytometry.

Figure 152:
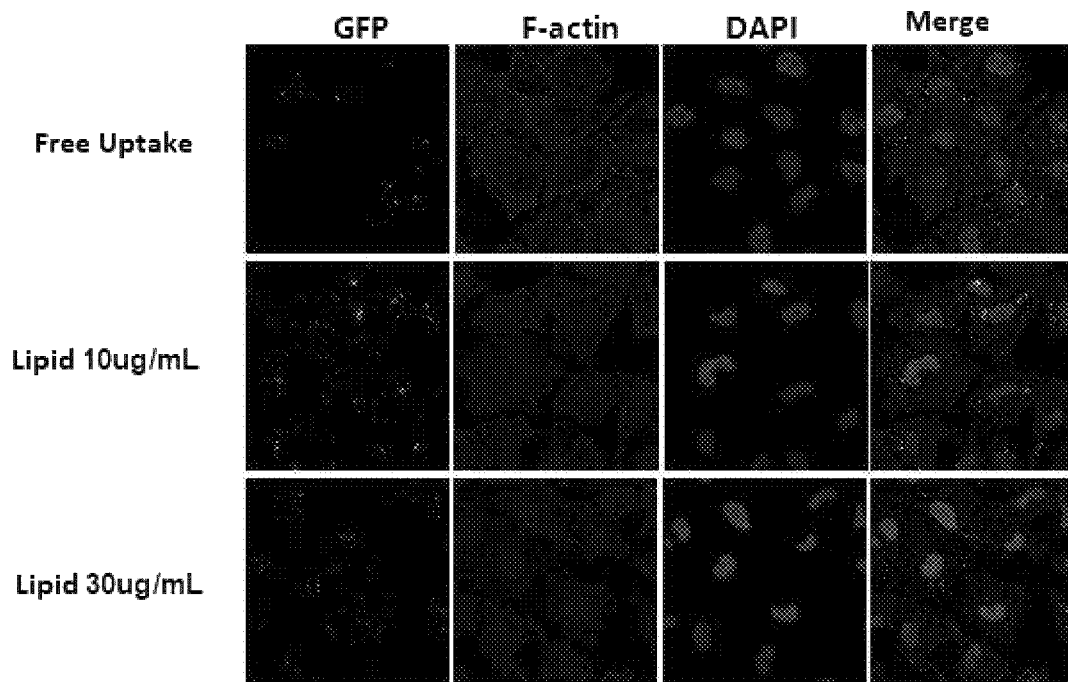

FIG. 152: The entry of GFP protein of PE(16:0/22:1)-GFP (reverse evaporation method) in A549 cells as determined by flow cytometry.

Figure 153:
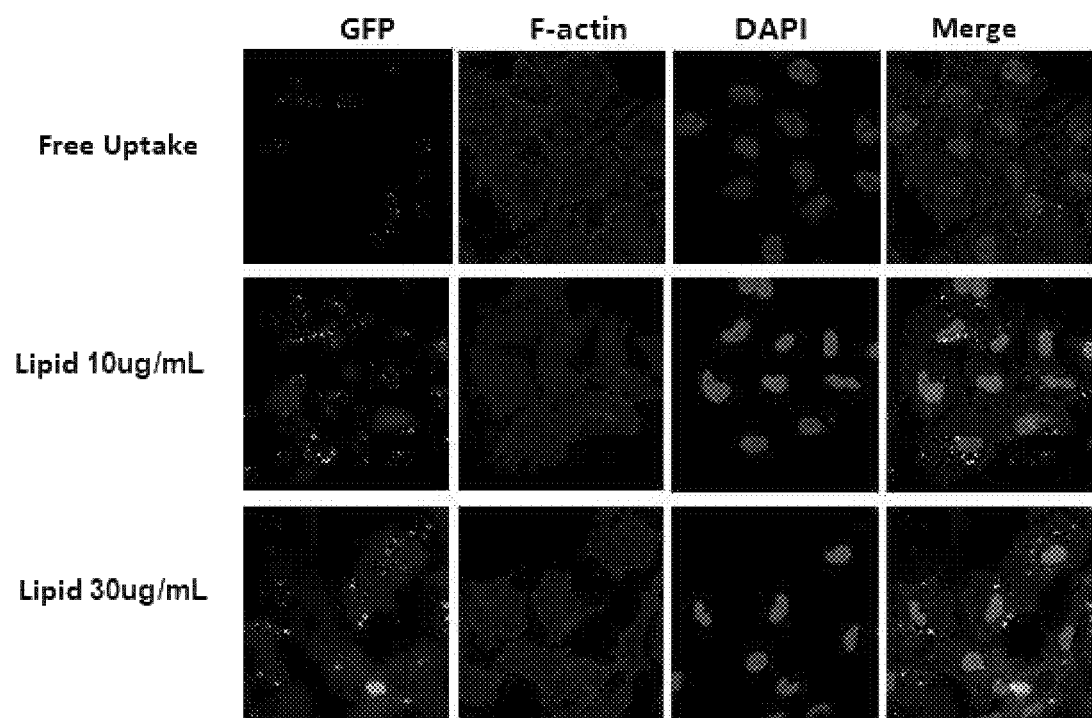

FIG. 153: The entry of GFP protein of sphinganine (d22:0)-GFP (reverse evaporation method) in A549 cells as determined by confocal fluorescence microscope.

Figure 154:
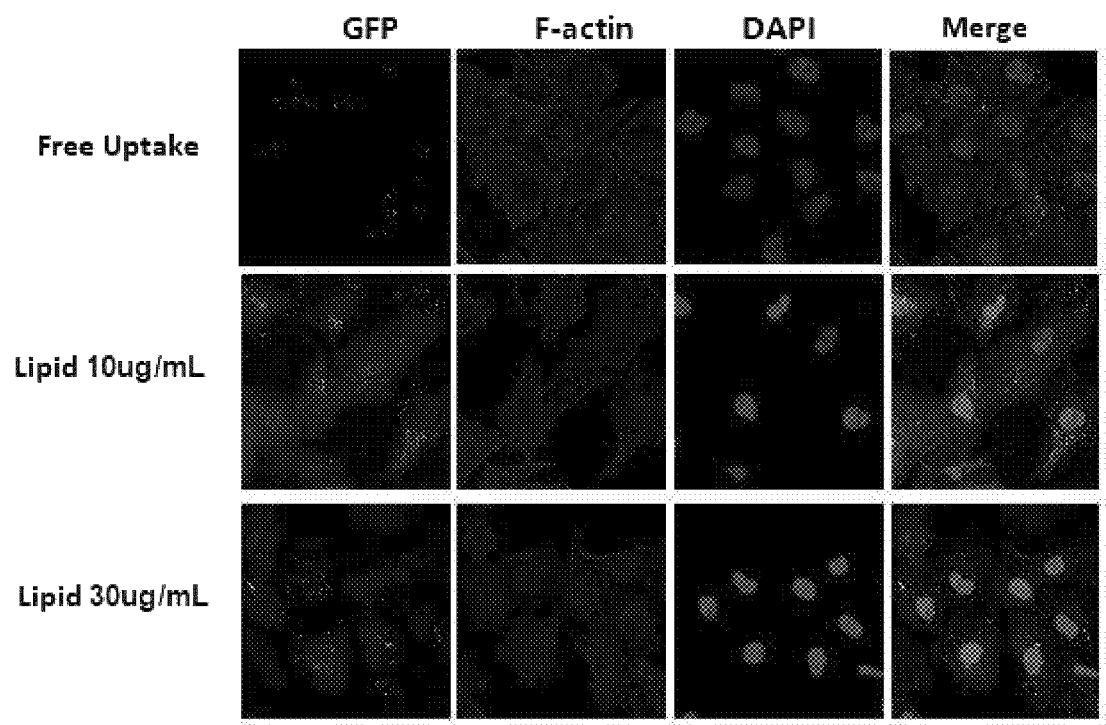

FIG. 154: The entry of GFP protein of PE(16:0/16:0)-GFP (reverse evaporation method) in A549 cells as determined by confocal fluorescence microscope.

DETAILED DESCRIPTION

A decoction is thermally processed and its main functional components must be thermally stable. Our research proved that small RNA is a new type of functional component in decoction for the first time. We extracted thermally stable "decoctosome" from the decoction and identified its ingredients. We found that the "decoctosome" comprises a large amount of lipids, compounds, proteins and nucleic acids. Our lab proved that "decoctosome" has better disease treatment effect than decoction by comparison. The "decoctosome" was confirmed by us for the first time as a new type of drug. We also found that a single compound, sphingosine, can deliver herbal medicine small RNAs in mice by oral administration, thereby improving disease symptoms. We mixed the single compound sphingosine with small RNA and conducted heating treatment to form a "bencaosome". We also revealed the method for preparing "bencaosome" for the first time. This may be a combination drug in precision medicine, and also provides an effective oral delivery route for nucleic acid therapy.

Through a lot of experiments, the inventor surprisingly discovered that there were some lipid components in some herbal medicines (including *Rhodiola crenulata, Taraxacum mongolicum, Andrographis paniculata* and *Lonicera japonica*). These lipids derived from herbal medicines can promote the absorption/entry of nucleic acids such as small RNAs into cells and/or target sites in a subject in need thereof. In the present application, the lipid component is synthetic.

The inventor has surprisingly found that various lipids can form lipid-nucleic acid mixture that effectively promote the absorption and entry of nucleic acid into cells, which has the potential to increase the efficiency of clinical delivery of the nucleic acid drug. Further studies have shown that the lipid nucleic acid mixture of the present application promotes the efficiency of nucleic acid absorption and entry into cells in different cell lines, but differences were observed in different cell lines, which provides the possibility of targeted drug delivery. Moreover, such lipid nucleic acid mixtures show no sequence selectivity in nucleic acid delivery, and could deliver nucleic acid fragments having different sequences and sizes corresponding to small RNA (e.g. about 20 bp). In addition, confocal laser-scanning microscopy confirmed that the lipid nucleic acid mixture formed by artificially synthetic lipids can effectively promote the entry of exogenous nucleic acids into cytoplasm. The inventor has unexpectedly discovered that lipid nucleic acid mixtures prepared by boiling method or reverse evaporation method can facilitate entry of nucleic acids, such as RNA, into blood circulation and target tissues via non-invasive routes (e.g. via digestive tract, respiratory tract and topical administration). The inventor has also surprisingly discovered that lipids of the present application are capable of promoting entry of nucleic acids, such as RNA, into cells and modulating (e.g., inhibiting) the expression of their target sequences, while not exhibiting such modulating effects on non-target sequences, suggesting a target-specific modulating effect, which can be used as a mean for the delivery of nucleic acid drug.

TABLE 1

Lipids in HJT decoctosome and PGY decoctosome.

| No. | Lipid in ionic form | Molecular weight | Molecular formula | HJT decoctosome | PGY decoctosome |
|---|---|---|---|---|---|
| 1 | So(d20:0) + H | 330.3366555 | C20 H44 O2 N1 | 390326.091 | 1 |
| 2 | So(d22:2) + H | 354.3366555 | C22 H44 O2 N1 | 1379473.756 | 1 |
| 3 | So(d22:1) + H | 356.3523555 | C22 H46 O2 N1 | 3097636.171 | 1 |
| 4 | So(d22:0) + H | 358.3679555 | C22 H48 O2 N1 | 4320212.925 | 1 |
| 5 | LPC(16:0e) + H | 482.3605035 | C24 H53 O6 N1 P1 | 4320212.925 | 1 |
| 6 | Cer(d14:1/16:0) + H | 484.4724205 | C30 H62 O3 N1 | 4586722.432 | 1 |
| 7 | LPC(16:0) + H | 496.3397685 | C24 H51 O7 N1 P1 | 8208508.397 | 1 |
| 8 | DG(6:0/22:5) + H | 503.3731015 | C31 H51 O5 | 4.72E+07 | 1 |
| 9 | DG(16:1p/13:0) + H | 509.4564365 | C32 H61 O4 | 5.42E+07 | 1 |
| 10 | LPC(18:0e) + H | 510.3918035 | C26 H57 O6 N1 P1 | 5.42E+07 | 1 |
| 11 | Cer(d16:0/16:0) + H | 512.5037205 | C32 H66 O3 N1 | 2.34E+08 | 1 |
| 12 | LPC(18:3) + H | 518.3241185 | C26 H49 O7 N1 P1 | 316425.605 | 4.07E+02 |
| 13 | LPC(18:2) + H | 520.3397685 | C26 H51 O7 N1 P1 | 5807248.56 | 1075.766 |
| 14 | LPC(18:1) + H | 522.3554185 | C26 H53 O7 N1 P1 | 5078868.945 | 6711.751 |
| 15 | LPC(18:0) + H | 524.3710685 | C26 H55 O7 N1 P1 | 1.07E+05 | 6.72E+03 |
| 16 | Cer(d18:2/16:1) + H | 534.4880705 | C34 H64 O3 N1 | 2.97E+07 | 7810.991 |
| 17 | Cer(d18:1/16:1) + H | 536.5037205 | C34 H66 O3 N1 | 340747.965 | 14732.878 |
| 18 | Cer(d18:1/16:0) + H | 538.5193705 | C34 H68 O3 N1 | 1.00E+00 | 3.72E+04 |
| 19 | Cer(d16:0/18:0) + H | 540.5350205 | C34 H70 O3 N1 | 4.54E+06 | 4.05E+04 |
| 20 | DG(161p/16:1) + H | 549.4877365 | C35 H67 O4 | 2373784.858 | 5.96E+04 |
| 21 | DG(16:1p/16:0) + H | 551.5033865 | C35 H67 O4 | 3785087.325 | 59743.287 |
| 22 | Cer(d18:2/16:0 + O) + H | 552.4986355 | C34 H66 O4 N1 | 328656.286 | 6.47E+04 |
| 23 | Cer(d18:1/16:0 + O) + H | 554.5142855 | C34 H68 O4 N1 | 1709530.119 | 6.57E+04 |
| 24 | Cer(d18:0/16:0 + O) + H | 556.5299355 | C34 H70 O4 N1 | 69546.865 | 77640.353 |
| 25 | Cer(d18:0/18:3) + H | 562.5193705 | C36 H68 O3 N1 | 8092209.236 | 78841.083 |
| 26 | Cer(d18:0/18:0) + H | 568.5663205 | C36 H74 O3 N1 | 6263411.658 | 80672.649 |
| 27 | DG(16:1p/18:3) + H | 573.4877365 | C37 H65 O4 | 3183225.696 | 95450.14 |
| 28 | DG(16:1p/18:2) + H | 575.5033865 | C37 H67 O4 | 8060692.43 | 100225.291 |
| 29 | DG(16:1p/18:1) + H | 577.5190365 | C37 H69 O4 | 3008362.348 | 109555.742 |
| 30 | Cer(d18:2/18:1 + O) + H | 578.5142855 | C36 H68 O4 N1 | 154813.142 | 117172.14 |
| 31 | MG(33:4) + NH4 | 578.5142855 | C36 H68 O4 N1 | 198407.509 | 134402.957 |
| 32 | Cer(d18:1/18:1 + O) + H | 580.5299355 | C36 H70 O4 N1 | 9278565.831 | 139454.808 |
| 33 | Cer(d18:1/18:0 + O) + H | 582.5455855 | C36 H72 O4 N1 | 922911.966 | 140010.676 |
| 34 | DG(18:4/16:0) + H | 589.4826515 | C37 H65 O5 | 414144.075 | 146303.475 |
| 35 | DG(16:0/16:0) + Na | 591.4958965 | C35 H68 O5 Na1 | 810363.971 | 159657.752 |
| 36 | DG(16:0/18:3) + H | 591.4983015 | C37 H67 O5 | 1237322.198 | 161541.242 |
| 37 | Cer(d20:0/18:0) + H | 596.5976205 | C38 H78 O3 N1 | 535487.515 | 162548.741 |
| 38 | DG(18:2p/18:3) + H | 599.5033865 | C39 H67 O4 | 2100112.341 | 214838.29 |
| 39 | DG(16:0e/18:2) + Na | 601.5166315 | C37 H70 O4 Na1 | 5987013.807 | 215132.574 |
| 40 | DG(18:2p/18:2) + H | 601.5190365 | C39 H69 O4 | 5992262.247 | 215132.574 |
| 41 | DG(16:0e/18:1) + Na | 603.5322815 | C37 H72 O4 Na1 | 911489.165 | 264655.886 |
| 42 | DG(18:2p/18:1) + H | 603.5346865 | C39 H71 O4 | 293514.636 | 281788.08 |
| 43 | DG(18: p/18:0) + H | 607.5659865 | C39 H75 O4 | 125637.415 | 295480.566 |
| 44 | Cer(d18:2/20:0 + O) + H | 608.5612355 | C38 H74 O4 N1 | 1318843.199 | 312661.769 |
| 45 | DG(16:0/18:2) + NH4 | 610.5405005 | C39 H72 O5 N1 | 611494.546 | 340900.922 |
| 46 | Cer(d18:1/20:0 + O) + H | 610.5768855 | C38 H76 O4 N1 | 2.33E+07 | 380924.111 |
| 47 | DG(18:4/18:3) + H | 611.4670015 | C39 H63 O5 | 1.63E+07 | 390486.593 |
| 48 | DG(18:3/18:3) + H | 613.4826515 | C39 H65 O5 | 2984204.99 | 413899.239 |
| 49 | DG(18:3/18:2) + H | 615.4983015 | C39 H67 O5 | 285681.918 | 414960.383 |
| 50 | DG(18:1/18:3) + H | 617.5139515 | C39 H69 O5 | 2292951.254 | 421434.548 |
| 51 | Cer(d18:2/22:0) + H | 620.5976205 | C40 H78 O3 N1 | 3293287.666 | 422725.598 |
| 52 | TG(4:0/14:0/16:2) + NH4 | 624.5197655 | C37 H70 O6 N1 | 547860.816 | 427994.277 |
| 53 | Cer(d22:0/18:0) + H | 624.6289205 | C40 H82 O3 N1 | 547860.816 | 427994.277 |
| 54 | Cer(d18:2/24:1) + H | 646.6132705 | C42 H80 O3 N1 | 4570947.798 | 463579.332 |
| 55 | Cer(d18:2/24:0) + H | 648.6289205 | C42 H82 O3 N1 | 927304.311 | 467709.326 |
| 56 | Cer(d18:1/24:0) + H | 650.6445705 | C42 H84 O3 N1 | 2.26E+05 | 4.88E+05 |
| 57 | Cer(d18:0/24:0) + H | 652.6602205 | C42 H86 O3 N1 | 191262.664 | 493993.59 |
| 58 | DG(17:1/22:5) + H | 655.5296015 | C42 H71 O5 | 226398.328 | 493993.59 |
| 59 | PE(15:0/15:0) + H | 664.4911835 | C35 H71 O8 N1 P1 | 9690748.232 | 505250.994 |
| 60 | Cer(d18:2/26:1) + H | 674.6445705 | C44 H84 O3 N1 | 1061171.306 | 5.24E+05 |
| 61 | SM(d16:0/16:1) + H | 675.5435525 | C37 H76 O6 N2 P1 | 5.81E+05 | 5.24E+05 |
| 62 | PE(16:1/15:0) + H | 676.4911835 | C36 H71 O8 N1 P1 | 1212434.548 | 527966.642 |
| 63 | TG(8:0e/13:0/18:2) + NH4 | 680.6187505 | C42 H82 O5 N1 | 2.10E+07 | 586734.726 |
| 64 | TG(8:0p/15:1/18:2) + H | 687.5922015 | C44 H79 O5 | 2016850.917 | 591047.503 |
| 65 | PE(16:1/16:1) + H | 688.4911835 | C37 H71 O8 N1 P1 | 2016850.917 | 591047.503 |
| 66 | PE(16:0/16:1) + H | 690.5068335 | C37 H73 O8 N1 P1 | 2044649.034 | 591047.503 |
| 67 | PE(16:0/16:0) + H | 692.5224835 | C37 H75 O8 N1 P1 | 1 | 596452.251 |
| 68 | PA(16:0/18:2) + Na | 695.4622295 | C37 H69 O8 N0 P1 Na1 | 1583729.741 | 604589.292 |
| 69 | CerG1(d18:2/16:1) + H | 696.5408955 | C40 H74 O8 N1 | 2.94E+07 | 607151.481 |
| 70 | CerG1(d18:2/16:0) + H | 698.5565455 | C40 H76 O8 N1 | 1001209.029 | 612230.949 |
| 71 | CerG1(d18:1/16:0)+H | 700.5721955 | C40 H78 O8 N1 | 1001209.029 | 612230.949 |
| 72 | SM(d16:0/18:2) + H | 701.5592025 | C39 H78 O6 N2 P1 | 1 | 615958.136 |
| 73 | SM(d16:0/18:1) + H | 703.5748525 | C39 H80 O6 N2 P1 | 9689636.668 | 620573.75 |
| 74 | PE(16:0/17:1) + H | 704.5224835 | C38 H75 O8 N1 P1 | 1119078.425 | 626407.441 |
| 75 | PE(16:1/18:3) + H | 712.4911835 | C39 H71 O8 N1 P1 | 4712407.932 | 641633.829 |

TABLE 1-continued

Lipids in HJT decoctosome and PGY decoctosome.

| No. | Lipid in ionic form | Molecular weight | Molecular formula | HJT decoctosome | PGY decoctosome |
|---|---|---|---|---|---|
| 76 | PE(16:0/18:3) + H | 714.5068335 | C39 H73 O8 N1 P1 | 4712407.932 | 641633.829 |
| 77 | CerG1(d18:2/16:0 + O) + H | 714.5514605 | C40 H76 O9 N1 | 5374247.838 | 655355.366 |
| 78 | PE(16:0/18:2) + H | 716.5224835 | C39 H75 O8 N1 P1 | 77238.228 | 657638.592 |
| 79 | CerG1(d16:0/18:1 + O) + H | 716.5671105 | C40 H78 O9 N1 | 163980.93 | 737837.362 |
| 80 | PE(16:0/18:1) + H | 718.5381335 | C39 H77 O8 N1 P1 | 1894363.216 | 808505.904 |
| 81 | PC(16:0e/16:1) + H | 718.5745185 | C40 H81 O7 N1 P1 | 1894363.216 | 808505.904 |
| 82 | CerG1(d18:2/18:2) + H | 722.5565455 | C42 H76 O8 N1 | 6.74E+07 | 816985.595 |
| 83 | PE(17:1/18:1) + H | 730.5381335 | C40 H77 O8 N1 P1 | 9583122.002 | 833575.452 |
| 84 | SM(d16:0/20:1) + H | 731.6061525 | C41 H84 O6 N2 P1 | 2523788.556 | 835252.778 |
| 85 | PE(16:0/19:1) + H | 732.5537835 | C40 H79 O8 N1 P1 | 936107.02 | 864415.827 |
| 86 | PC(16:0/16:1) + H | 732.5537835 | C40 H79 O8 N1 P1 | 936107.02 | 864415.827 |
| 87 | PC(16:0/16:0) + H | 734.5694355 | C40 H81 O8 N1 P1 | 1407657.532 | 879913.51 |
| 88 | PE(18:3/18:2) + H | 738.5068335 | C41 H73 O8 N1 P1 | 9925101.043 | 985477.837 |
| 89 | PE(18:2/18:2) + H | 740.5224835 | C41 H75 O8 N1 P1 | 3302104.175 | 1077270.174 |
| 90 | TG(8:0/14:0/20:0) + NH4 | 740.6762655 | C45 H90 O6 N1 | 2264998.498 | 1094998.386 |
| 91 | PE(18:1/18:2) + H | 742.5381335 | C41 H77 O8 N1 P1 | 1150383.999 | 1109902.361 |
| 92 | PC(15:0/18:2) + H | 744.5537835 | C41 H79 O8 N1 P1 | 1150383.999 | 1109902.361 |
| 93 | PE(18:1/18:1) + H | 744.5537835 | C41 H79 O8 N1 P1 | 1150383.999 | 1109902.361 |
| 94 | PC(16:0e/18:1) + H | 746.6058185 | C42 H85 O7 N1 P1 | 1229361.511 | 1129970.461 |
| 95 | StE(22:1) + NH4 | 750.7122555 | C51 H92 O2 N1 | 2745523.195 | 1129999.635 |
| 96 | Cer(d18:2/32:4) + H | 752.6915205 | C50 H90 O3 N1 | 2745523.195 | 1129999.635 |
| 97 | MGDG(16:0/18:3) + H | 753.5511265 | C43 H77 O10 | 2832053.494 | 1144067.874 |
| 98 | TG(16:0/13:0/14:0) + NH4 | 754.6919155 | C46 H92 O6 N1 | 4167371.876 | 1156642.369 |
| 99 | PC(16:1/18:2) + H | 756.5537835 | C42 H79 O8 N1 P1 | 2.92E+07 | 1187856.898 |
| 100 | PC(16:0/18:2) + H | 758.5694335 | C42 H81 O8 N1 P1 | 573145.979 | 1202535.92 |
| 101 | SM(d16:0/22:1) + H | 759.6374525 | C43 H88 O6 N2 P1 | 1811041.154 | 1279973.45 |
| 102 | PC(16:0/18:1) + H | 760.5850835 | C42 H83 O8 N1 P1 | 1811041.154 | 1279973.45 |
| 103 | PC(18:0/16:0) + H | 762.6007335 | C42 H85 O8 N1 P1 | 1811041.154 | 1279973.45 |
| 104 | TG(10:0/16:0/18:2) + NH4 | 764.6762655 | C47 H90 O6 N1 | 1479856.98 | 1297842.776 |
| 105 | TG(16:1/14:0/14:0) + NH4 | 766.6919155 | C47 H92 O6 N1 | 1571400.019 | 1312345.569 |
| 106 | PC(16:0e/20:4) + H | 768.5901685 | C44 H83 O7 N1 P1 | 51584.528 | 1330852.698 |
| 107 | TG(16:0/14:0/14:0) + NH4 | 768.7075655 | C47 H94 O6 N1 | 1699184.802 | 1335516.265 |
| 108 | PC(18:0e/18:2) + H | 772.6214685 | C44 H87 O7 N1 P1 | 1699184.802 | 1335516.265 |
| 109 | ZyE(26:4) + NH4 | 772.6966055 | C53 H90 O2 N1 | 3061880.829 | 1337721.591 |
| 110 | StE(24:3) + NH4 | 774.7122555 | C53 H92 O2 N1 | 1658135.266 | 1356818.368 |
| 111 | ZyE(26:3) + NH4 | 774.7122555 | C53 H92 O2 N1 | 1658135.266 | 1356818.368 |
| 112 | MGDG(18:3/18:3) + H | 775.5354765 | C45 H75 O10 | 1658135.266 | 1356818.368 |
| 113 | MGDG(16:0/20:5) + H | 777.5511265 | C45 H77 O10 | 1.23E+07 | 1397050.829 |
| 114 | PC(16:1/20:5) + H | 778.5381335 | C44 H77 O8 N1 P1 | 1160671.162 | 1409504.853 |
| 115 | TG(16:1/14:0/15:1) + NH4 | 778.6919155 | C48 H92 O6 N1 | 2859743.403 | 1409504.853 |
| 116 | PC(16:1/20:4) + H | 780.5537835 | C44 H79 O8 N1 P1 | 6388353.447 | 1421139.691 |
| 117 | CerG1(d18:2/22:1) + H | 780.6347955 | C46 H86 O8 N1 | 3996861.474 | 1428550.812 |
| 118 | TG(16:0/13:0/16:1) + NH4 | 780.7075655 | C48 H94 O6 N1 | 4104926.614 | 1428550.812 |
| 119 | PC(16:0/20:4) + H | 782.5694335 | C44 H81 O8 N1 P1 | 2293306.68 | 1443289.679 |
| 120 | TG(16:0/14:0/15:0) + NH4 | 782.7232155 | C48 H96 O6 N1 | 4.93E+06 | 1.45E+06 |
| 121 | PC(16:0/20:3) + H | 784.5850835 | C44 H83 O8 N1 P1 | 1687489.65 | 1457777.891 |
| 122 | PC(18:0/18:2) + H | 786.6007335 | C44 H85 O8 N1 P1 | 1826384.028 | 1568242.71 |
| 123 | SM(d16:0/24:1) + H | 787.6687525 | C45 H92 O6 N2 P1 | 1 | 1574194.876 |
| 124 | PC(18:0/18:1) + H | 788.6163835 | C44 H87 O8 N1 P1 | 201033.513 | 1578140.397 |
| 125 | TG(16:0e/13:0/16:0) + K | 789.6732845 | C48 H94 O5 K1 | 4905987.584 | 1586487.641 |
| 126 | TG(16:1/12:0/18:1) + NH4 | 792.7075655 | C49 H94 O6 N1 | 793977.438 | 1624200.908 |
| 127 | TG(16:0/14:0/16:1) + NH4 | 794.7232155 | C49 H96 O6 N1 | 2.56E+07 | 1712458.663 |
| 128 | Co(Q9) + H | 795.6285865 | C54 H83 O4 | 4091215.849 | 1723000.308 |
| 129 | TG(16:0/14:0/16:0) + NH4 | 796.7388655 | C49 H98 O6 N1 | 2545856.286 | 1757197.789 |
| 130 | MGDG(18:3/20:6) + H | 797.5198265 | C47 H73 O10 | 3828334.683 | 1796758.817 |
| 131 | PC(16:0/21:3) + H | 798.6007335 | C45 H85 O8 N1 P1 | 3193628.707 | 1832224.876 |
| 132 | MGDG(18:2/20:6) + H | 799.5354765 | C47 H75 O10 | 3193628.707 | 1832224.876 |
| 133 | PE(22:0/18:2) + H | 800.6163835 | C45 H87 O8 N1 P1 | 627830.742 | 1844821.277 |
| 134 | PC(16:0e/22:2) + H | 800.6527685 | C46 H91 O7 N1 P1 | 451258.13 | 1866334.475 |
| 135 | CerGl(d22:0/18:1 + O) + H | 800.6610105 | C46 H90 O9 N1 | 1.25E+07 | 1885698.509 |
| 136 | MGDG(18:2/20:5) + H | 801.5511265 | C47 H77 O10 | 3218234.483 | 1975336.948 |
| 137 | MGDG(18:1/20:4) + H | 805.5824265 | C47 H81 O10 | 3218234.483 | 1975336.948 |
| 138 | PC(16:0/22:6) + H | 806.5694335 | C46 H81 O8 N1 P1 | 3225480.406 | 1975336.948 |
| 139 | TG(16:0/15:1/16:1) + NH4 | 806.7232155 | C50 H96 O6 N1 | 3218234.483 | 1975890.277 |
| 140 | CerG1(d18:2/24:1) + H | 808.6660955 | C48 H90 O8 N1 | 1515567.592 | 2036335.679 |
| 141 | TG(16:0/15:0/16:1) + NH4 | 808.7388655 | C50 H98 O6 N1 | 5722635.222 | 2042016.725 |
| 142 | PC(18:0/20:4) + H | 810.6007335 | C46 H85 O8 N1 P1 | 5215144.093 | 2070037.151 |
| 143 | TG(16:0/15:0/16:0) + NH4 | 810.7545155 | C50 H100 O6 N1 | 5215144.093 | 2070037.151 |
| 144 | SM(d16:0/26:3) + H | 811.6687525 | C47 H92 O6 N2 P1 | 3638255.96 | 2169861.389 |
| 145 | PE(16:0/22:1) + K | 812.5566165 | C43 H84 O8 N1 P1 K1 | 3171629.347 | 2240390.664 |
| 146 | PC(20:1/18:2) + H | 812.6163835 | C46 H87 O8 N1 P1 | 1.24E+07 | 2248084.433 |
| 147 | SM(d16:0/26:2) + H | 813.6844025 | C47 H94 P6 N2 P1 | 3124941.275 | 2255746.981 |
| 148 | PG(16:0/22:5) + NH4 | 814.5592635 | C44 H81 O10 N1 P1 | 3124941.275 | 2255746.981 |
| 149 | PC(20:0p/19:1) + H | 814.6684185 | C47 H93 O7 N1 P1 | 3124941.275 | 2255746.981 |
| 150 | SM(d16:0/26:1) + H | 815.7000525 | C47 H96 O6 N2 P1 | 3.07E+07 | 2266806.368 |

TABLE 1-continued

Lipids in HJT decoctosome and PGY decoctosome.

| No. | Lipid in ionic form | Molecular weight | Molecular formula | HJT decoctosome | PGY decoctosome |
|---|---|---|---|---|---|
| 151 | CerGl(d22:1/18:0 + 2O) + H | 816.6559255 | C46 H90 O10 N1 | 7701671.44 | 2294410.726 |
| 152 | TG(16:1/14:0/18:2) + NH4 | 818.7232155 | C51 H96 O6 N1 | 94806.519 | 2337992.129 |
| 153 | TG(16:0/14:0/18:2) + NH4 | 820.7388655 | C51 H98 O6 N1 | 7.68E+07 | 2437867.716 |
| 154 | TG(16:0/14:0/18:1) + NH4 | 822.7545155 | C51 H100 O6 N1 | 6539612.263 | 2476000.263 |
| 155 | TG(16:0/16:0/16:0) + NH4 | 824.7701655 | C51 H102 O6 N1 | 67055.821 | 2510367.052 |
| 156 | TG(18:4/16:0/16:0) + H | 827.7123165 | C53 H95 O6 | 7602971.241 | 2515441.944 |
| 157 | PE(24:0/18:2) + H | 828.6476835 | C47 H91 O8 N1 P1 | 1079205046.046 | 2537702.771 |
| 158 | CerGl(d24:0/18:1 + O) + H | 828.6923105 | C48 H94 O9 N1 | 8497622.232 | 2555017.725 |
| 159 | TG(16:0/16:0/18:3) + H | 829.7279665 | C53 H97 O6 | 8845982.298 | 2555017.725 |
| 160 | TG(16:1/15:0/18:2) + NH4 | 832.7388655 | C52 H98 O6 N1 | 8.15E+07 | 2555864.359 |
| 161 | TG(16:0/16:1/17:1) + NH4 | 834.7545155 | C52 H100 O6 N1 | 1665504.949 | 2583546.213 |
| 162 | PI(16:0/18:2) + H | 835.5331095 | C43 H80 O13 N0 P1 | 7836794.71 | 2660458.252 |
| 163 | TG(16:0/15:0/18:1) + NH4 | 836.7701655 | C52 H102 O6 N1 | 7836794.71 | 2660458.252 |
| 164 | TG(16:0/16:0/17:0) + NH4 | 838.7858155 | C52 H104 O6 N1 | 1 | 2667039.687 |
| 165 | TG(14:0/18:2/18:3) + NH4 | 842.7232155 | C53 H96 O6 N1 | 7457712.048 | 2698263.487 |
| 166 | TG(16:0/16:0/18:2) + NH4 | 848.7701655 | C53 H102 O6 N1 | 3117177.732 | 2939662.058 |
| 167 | TG(14:0/18:2/20:5) + H | 849.6966665 | C55 H93 O6 | 2882001.001 | 3019434.864 |
| 168 | TG(16:0/16:0/18:1) + NH4 | 850.7858155 | C53 H104 O6 N1 | 1.64E+07 | 3.07E+06 |
| 169 | TG(16:0/18:3/18:3) + H | 851.7123165 | C55 H95 O6 | 4.38E+07 | 3076611.31 |
| 170 | TG(16:0/17:0/17:0) + NH4 | 852.8014655 | C53 H106 O6 N1 | 3702976.213 | 3186374.052 |
| 171 | TG(16:0/16:0/20:5) + H | 853.7279665 | C55 H97 O6 | 3278567.909 | 3259422.694 |
| 172 | TG(16:0/18:1/18:3) + H | 855.7436165 | C55 H99 O6 | 1448986.196 | 3265491.034 |
| 173 | TG(15:0/18:2/18:3) + NH4 | 856.7388655 | C54 H98 O6 N1 | 2962279.683 | 3272286.838 |
| 174 | TG(18:0/18:3/18:3) + H | 857.7592665 | C55 H101 O6 | 7702748.834 | 3358029.901 |
| 175 | TG(15:0/18:2/18:2) + NH4 | 858.7545155 | C54 H100 O6 N1 | 7702748.834 | 3358029.901 |
| 176 | TG(16:0/17:1/18:2) + NH4 | 860.7701655 | C54 H102 O6 N1 | 5491186.88 | 3384766.298 |
| 177 | TG(16:0/17:1/18:1) + NH4 | 862.7858155 | C54 H104 O6 N1 | 2.14E+07 | 3470218.27 |
| 178 | Co(Q10) + H | 863.6911865 | C59 H91 O4 | 4268929.475 | 3556931.782 |
| 179 | TG(16:0/17:0/18:1) + NH4 | 864.8014655 | C54 H106 O6 N1 | 5758516.782 | 3583143.66 |
| 180 | TG(18:0/16:0/17:0) + NH4 | 866.8171155 | C54 H108 O6 N1 | 9174698.596 | 3652349.072 |
| 181 | TG(10:0p/22:6/22:6) + NH4 | 868.6813505 | C57 H90 O5 N1 | 9174698.596 | 3652349.072 |
| 182 | TG(18:4/18:3/18:3) + H | 871.6810165 | C57 H91 O6 | 4572289.266 | 3715286.618 |
| 183 | TG(8:0/16:0/21:4) + (CH3CH2)3NH | 872.7575895 | C54 H100 O6 N2 | 2.29E+07 | 3756416.138 |
| 184 | TG(18:3/18:3/18:3) + H | 873.6966665 | C57 H93 O6 | 6310376.314 | 3793593.876 |
| 185 | TG(18:3/18:2/18:3) + H | 875.7123165 | C57 H95 O6 | 5914201.082 | 4071221.369 |
| 186 | TG(16:0/18:1/18:1) + NH4 | 876.8014655 | C55 H106 O6 N1 | 5914201.082 | 4071221.385 |
| 187 | TG(16:0/18:2/20:5) + H | 877.7279665 | C57 H97 O6 | 1.90E+07 | 4148774.509 |
| 188 | TG(18:0/16:0/18:1) + NH4 | 878.8171155 | C55 H108 O6 N1 | 1.90E+07 | 4148774.509 |
| 189 | TG(16:0/18:1/20:5) + H | 879.7436165 | C57 H99 O6 | 7534392.644 | 4230984.901 |
| 190 | TG(18:0/16:0/18:0) + NH4 | 880.8327655 | C55 H110 O6 N1 | 5.34E+07 | 4475225.248 |
| 191 | TG(16:0/18:2/20:4) + H | 881.7592665 | C57 H101 O6 | 5.54E+07 | 4475225.248 |
| 192 | TG(17:0/18:3/18:3) + NH4 | 882.7545155 | C56 H100 O6 N1 | 5052602.769 | 4478342.531 |
| 193 | TG(18:0/16:0/20:4) + H | 883.7749165 | C57 H103 O6 | 5784527.473 | 4660990.822 |
| 194 | TG(17:0/18:2/18:3) + NH4 | 884.7701655 | C56 H102 O6 N1 | 4482756.516 | 4672785.705 |
| 195 | TG(17:0/18:2/18:2) + NH4 | 886.7858155 | C56 H104 O6 N1 | 7454754.499 | 4726088.259 |
| 196 | TG(17:0/18:1/18:2) + NH4 | 888.8014655 | C56 H106 O6 N1 | 1265262.193 | 4764847.927 |
| 197 | TG(17:0/18:1/18:1) + NH4 | 890.8171155 | C56 H108 O6 N1 | 140126.277 | 5149855.933 |
| 198 | TG(16:0/16:1/21:0) + NH4 | 892.8327655 | C56 H110 O6 N1 | 4962844.564 | 5149855.933 |
| 199 | TG(6:0/18:3/23:4) + (CH3CH2)3NH | 894.7419395 | C56 H98 O6 N2 | 9291077.065 | 5156650.083 |
| 200 | TG(15:0/14:0/24:0) + NH4 | 894.8484155 | C56 H112 O6 N1 | 492454.422 | 5207985.888 |
| 201 | TG(18:4/18:3/20:5) + H | 895.6810165 | C59 H91 O6 | 6089561.802 | 5245553.541 |
| 202 | TG(6:0/18:2/23:4) + (CH3CH2)3NH | 896.7575895 | C56 H100 O6 N2 | 1582567.8 | 5259759.322 |
| 203 | TG(18:3/18:3/20:5) + H | 897.6966665 | C59 H93 O6 | 1.17E+07 | 5350123.549 |
| 204 | TG(6:0/18:2/23:3) + (CH3CH2)3NH | 898.7732395 | C56 H102 O6 N2 | 1630296.575 | 5439965.387 |
| 205 | TG(18:3/18:2/20:5) + H | 899.7123165 | C59 H95 O6 | 1.62E+07 | 5651893.831 |
| 206 | TG(16:2/13:0/18:2) + (CH3CH2)3NH | 900.7888895 | C56 H104 O6 N2 | 1 | 5727851.112 |
| 207 | TG(20:5/18:2/18:2) + H | 901.7279665 | C59 H97 O6 | 6701516.595 | 5875239.363 |
| 208 | TG(8:0/18:1/21:2) + (CH3CH2)3NH | 902.8045395 | C56 H106 O6 N2 | 6874401.285 | 5875239.363 |
| 209 | TG(16:0/18:1/20:2) + NH4 | 902.8171155 | C57 H108 O6 N1 | 6874401.285 | 5875239.363 |
| 210 | TG(18:1/18:2/20:5) + H | 903.7436165 | C59 H99 O6 | 6574610.08 | 6317164.375 |
| 211 | TG(18:0/18:1/18:1) + NH4 | 904.8327655 | C57 H110 O6 N1 | 8673046.78 | 6499861.567 |
| 212 | TG(18:1/18:2/20:4) + H | 905.7592665 | C59 H101 O6 | 5155615.948 | 6.69E+06 |
| 213 | TG(18:0/18:0/18:1) + NH4 | 906.8484155 | C57 H112 O6 N1 | 1.58E+07 | 6849883.536 |
| 214 | TG(18:1/18:1/20:4) + H | 907.7749165 | C59 H103 O6 | 4559240.845 | 7196188.345 |
| 215 | TG(18:0/16:0/20:0) + NH4 | 908.8640655 | C57 H114 O6 N1 | 2.28E+07 | 7217491.252 |
| 216 | TG(18:0/18:1/20:4) + H | 909.7905665 | C59 H105 O6 | 8855056.976 | 7419109.87 |
| 217 | PG(28:1/18:3) + H | 911.6735645 | C52 H96 O10 N0 P1 | 2.68E+06 | 7.44E+06 |
| 218 | PG(28:0/18:2) + H | 915.7048645 | C52 H100 O10 N0 P1 | 2.25E+07 | 7479487.582 |
| 219 | TG(18:1/18:1/19:1) + NH4 | 916.8327655 | C58 H110 O6 N1 | 7716514.673 | 7825778.605 |
| 220 | TG(16:0/18:1/21:1) + NH4 | 918.8484155 | C58 H112 O6 N1 | 5743432.404 | 7968577.636 |
| 221 | TG(16:0/16:1/23:0) + NH4 | 920.8640655 | C58 H114 O6 N1 | 1.21E+07 | 8956738.021 |
| 222 | TG(10:0/15:1/24:6) + (CH3CH2)3NH | 922.7732395 | C58 H102 O6 N2 | 343736.931 | 9258523.996 |
| 223 | TG(16:0/15:0/24:0) + NH4 | 922.8797155 | C58 H116 O6 N1 | 2.50E+07 | 9441741.193 |
| 224 | TG(20:0/18:2/18:2) + NH4 | 928.8327655 | C59 H110 O6 N1 | 1.93E+07 | 1.06E+07 |
| 225 | TG(20:0/18:1/18:2) + NH4 | 930.8484155 | C59 H112 O6 N1 | 2.23E+07 | 1.07E+07 |

TABLE 1-continued

Lipids in HJT decoctosome and PGY decoctosome.

| No. | Lipid in ionic form | Molecular weight | Molecular formula | HJT decoctosome | PGY decoctosome |
|---|---|---|---|---|---|
| 226 | TG(16:0/18:1/22:1) + NH4 | 932.8640655 | C59 H114 O6 N1 | 2.74E+07 | 1.12E+07 |
| 227 | TG(16:0/18:1/22:0) + NH4 | 934.8797155 | C59 H116 O6 N1 | 200369.136 | 1.20E+07 |
| 228 | TG(16:0/16:0/24:0) + NH4 | 936.8953655 | C59 H118 O6 N1 | 649574.619 | 1.21E+07 |
| 229 | TG(21:0/18:2/18:2) + NH4 | 942.8484155 | C60 H112 O6 N1 | 1.25E+07 | 1.25E+07 |
| 230 | TG(16:0/18:3/23:0) + NH4 | 944.8640655 | C60 H114 O6 N1 | 6207969.868 | 1.25E+07 |
| 231 | TG(16:0/18:2/23:0) + NH4 | 946.8797155 | C60 H116 O6 N1 | 1.81E+08 | 1.28E+07 |
| 232 | TG(15:0/18:1/24:0) + NH4 | 948.8953655 | C60 H118 O6 N1 | 2.66E+07 | 1.34E+07 |
| 233 | TG(25:0/15:0/17:0) + NH4 | 950.9110155 | C60 H120 O6 N1 | 2092609.791 | 1.38E+07 |
| 234 | TG(22:0/18:2/18:3) + NH4 | 954.8484155 | C61 H112 O6 N1 | 5.40E+07 | 1.39E+07 |
| 235 | TG(22:0/18:2/18:2) + NH4 | 956.8640655 | C61 H114 O6 N1 | 5.40E+07 | 1.39E+07 |
| 236 | TG(16:0/18:3/24:0) + NH4 | 958.8797155 | C61 H116 O6 N1 | 1.08E+07 | 1.40E+07 |
| 237 | TG(16:0/18:1/24:1) + NH4 | 960.8953655 | C61 H118 O6 N1 | 1.36E+08 | 1.43E+07 |
| 238 | TG(16:0/18:1/24:0) + NH4 | 962.9110155 | C61 H120 O6 N1 | 1.41E+07 | 1.51E+07 |
| 239 | TG(20:0/16:0/22:0) + NH4 | 964.9266655 | C61 H122 O6 N1 | 4.22E+07 | 1.55E+07 |
| 240 | TG(23:0/18:2/18:3) + NH4 | 968.8640655 | C62 H114 O6 N1 | 4357343.609 | 1.69E+07 |
| 241 | TG(23:0/18:2/18:2) + NH4 | 970.8797155 | C62 H116 O6 N1 | 3.47E+07 | 1.71E+07 |
| 242 | TG(18:1/18:2/23:0) + NH4 | 972.8953655 | C62 H118 O6 N1 | 321103.904 | 1.72E+07 |
| 243 | TG(25:0/16:0/18:2) + NH4 | 974.9110155 | C62 H120 O6 N1 | 1.17E+07 | 1.78E+07 |
| 244 | TG(27:0/14:0/18:1) + NH4 | 976.9266655 | C62 H122 O6 N1 | 1.14E+08 | 2.07E+07 |
| 245 | TG(18:4/21:4/22:5) + NH4 | 980.7701655 | C64 H102 O6 N1 | 4.89E+07 | 2.24E+07 |
| 246 | TG(24:0/18:3/18:3) + NH4 | 980.8640655 | C63 H114 O6 N1 | 7.09E+07 | 2.25E+07 |
| 247 | TG(24:0/18:2/18:3) + NH4 | 982.8797155 | C63 H116 O6 N1 | 2002411.796 | 2.26E+07 |
| 248 | TG(18:1/18:3/24:0) + NH4 | 984.8953655 | C63 H118 O6 N1 | 2.41E+08 | 2.27E+07 |
| 249 | TG(18:0/18:3/24:0) + NH4 | 986.9110155 | C63 H120 O6 N1 | 3.58E+07 | 2.29E+07 |
| 250 | TG(18:1/18:1/24:0) + NH4 | 988.9266655 | C63 H122 O6 N1 | 3.20E+07 | 2.35E+07 |
| 251 | TG(26:0/16:0/18:1) + NH4 | 990.9423155 | C63 H124 O6 N1 | 4.21E+08 | 2.54E+07 |
| 252 | TG(20:0/20:0/20:0) + NH4 | 992.9579655 | C63 H126 O6 N1 | 5.91E+07 | 2.77E+07 |
| 253 | TG(25:0/18:2/18:2) + NH4 | 998.9110155 | C64 H120 O6 N1 | 6.62E+07 | 2.86E+07 |
| 254 | TG(30:1/15:0/16:1) + NH4 | 1002.942315 | C64 H124 O6 N1 | 2.76E+07 | 2.94E+07 |
| 255 | TG(26:0/18:3/18:3) + NH4 | 1010.911015 | C65 H120 O6 N1 | 3.49E+07 | 2.95E+07 |
| 256 | TG(26:0/18:2/18:2) + NH4 | 1012.926665 | C65 H122 O6 N1 | 5158621.809 | 3.08E+07 |
| 257 | TG(26:0/18:1/18:2) + NH4 | 1014.942315 | C65 H124 O6 N1 | 4.95E+07 | 3.26E+07 |
| 258 | TG(20:0/18:2/24:0) + NH4 | 1016.957965 | C65 H126 O6 N1 | 4.98E+07 | 3.29E+07 |
| 259 | TG(30:0/16:0/16:1) + NH4 | 1018.973615 | C65 H128 O6 N1 | 1.62E+08 | 3.71E+07 |
| 260 | TG(16:0/22:0/24:0) + NH4 | 1020.989265 | C65 H130 O6 N1 | 2.55E+08 | 3.80E+07 |
| 261 | TG(32:1/15:0/16:0) + NH4 | 1032.989265 | C66 H130 O6 N1 | 1.20E+08 | 3.85E+07 |
| 262 | TG(22:0/18:2/24:0) + NH4 | 1044.989265 | C67 H130 O6 N1 | 1.15E+08 | 3.92E+07 |
| 263 | TG(26:1/15:0/24:1) + NH4 | 1059.004915 | C68 H132 O6 N1 | 1.15E+08 | 3.92E+07 |
| 264 | TG(24:0/18:2/24:0) + NH4 | 1073.020565 | C69 H134 O6 N1 | 1.57E+07 | 4.03E+07 |
| 265 | TG(18:1/24:0/24:0) + NH4 | 1075.036215 | C69 H136 O6 N1 | 1.20E+08 | 4.06E+07 |
| 266 | TG(26:0/18:2/24:0) + NH4 | 1101.051865 | C71 H138 O6 N1 | 3.66E+07 | 4.31E+07 |
| 267 | TG(36:1/16:0/18:2) + NH4 | 1127.067515 | C73 H140 O6 N1 | 7.03E+07 | 4.40E+07 |
| 268 | TG(20:0/24:2/24:2) + (CH3CH2)3NH | 1195.117539 | C77 H146 O6 N2 | 4.44E+07 | 4.61E+07 |
| 269 | LPA(16:0) − H | 409.2360665 | C19 H38 O7 N0 P1 | 2232476.522 | 4.86E+07 |
| 270 | LPE(16:0) − H | 452.2782655 | C21 H43 O7 N1 P1 | 2232476.522 | 4.86E+07 |
| 271 | LPE(17:1) − H | 464.2782655 | C22 H43 O7 N1 P1 | 6187754.425 | 4.94E+07 |
| 272 | LPE(18:1) − H | 478.2939155 | C23 H45 O7 N1 P1 | 1.87E+08 | 4.95E+07 |
| 273 | LdMePE(16:0) − H | 480.3095655 | C23 H47 P7 N1 P1 | 1.26E+08 | 5.28E+07 |
| 274 | PAF(14:0e) + HCOO | 540.3306955 | C25 H51 P9 N1 P1 | 6.74E+07 | 5.37E+07 |
| 275 | PAF(16:1p) + HCOO | 564.3306955 | C27 H51 P9 N1 P1 | 7.11E+07 | 5.50E+07 |
| 276 | PAF(16:0p) + HCOO | 566.3463455 | C27 H53 O9 N1 P1 | 6.73E+07 | 5.77E+07 |
| 277 | PAF(16:0e) + HCOO | 568.3619955 | C27 H55 O9 N1 P1 | 5.93E+07 | 6.84E+07 |
| 278 | PMe(15:0/18:3) − H | 669.4500815 | C37 H66 O8 N0 P1 | 2.33E+07 | 7.01E+07 |
| 279 | PMe(15:0/18:2) − H | 671.4657315 | C37 H68 O8 N0 P1 | 5.36E+07 | 7.48E+07 |
| 280 | PEt(16:1/16:1) − H | 671.4657315 | C37 H68 O8 N0 P1 | 5.36E+07 | 7.48E+07 |
| 281 | PEt(16:0/16:1) − H | 673.4813815 | C37 H70 O8 N0 P1 | 1.24E+08 | 7.71E+07 |
| 282 | dMePE(16:1/14:0) − H | 688.4922805 | C37 H71 O8 N1 P1 | 2.49E+08 | 8.08E+07 |
| 283 | dMePE(16:0/14:0) − H | 690.5079305 | C37 H73 O8 N1 P1 | 2.49E+08 | 8.08E+07 |
| 284 | PEt(16:2/18:2) − H | 695.4657315 | C39 H68 O8 N0 P1 | 5.58E+07 | 8.57E+07 |
| 285 | PEt(16:0/18:2) − H | 699.4970315 | C39 H72 O8 N0 P1 | 2.39E+07 | 8.62E+07 |
| 286 | dMePE(17:1/14:0) − H | 702.5079305 | C38 H73 O8 N1 P1 | 3.00E+08 | 9.06E+07 |
| 287 | dMePE(16:1/16:1) − H | 714.5079305 | C39 H73 O8 N1 P1 | 1.81E+08 | 9.14E+07 |
| 288 | dMePE(18:1/14:0) − H | 716.5235805 | C39 H75 O8 N1 P1 | 5.29E+07 | 1.10E+08 |
| 289 | dMePE(19:1/14:0) − H | 730.5392305 | C40 H77 O8 N1 P1 | 1.26E+07 | 2.69E+08 |
| 290 | dMePE(16:2/18:2) − H | 738.5079305 | C41 H73 O8 N1 P1 | 2.72E+08 | 2.80E+08 |
| 291 | MGDG(16:0/18:2) + HCOO | 799.5577035 | C44 H79 O12 | 5203598.126 | 2.98E+08 |
| 292 | PAF(32:2) + HCOO | 802.5603605 | C43 H81 O10 N1 P1 | 1.78E+08 | 3.87E+08 |
| 293 | PAF(32:1) + HCOO | 804.5760105 | C43 H83 O10 N1 P1 | 2.01E+08 | 6.03E+08 |
| 294 | PAF(34:6) + HCOO | 822.5290605 | C45 H77 O10 N1 P1 | 6.00E+08 | 1.23E+09 |
| 295 | MGDG(18:2/18:2) + HCOO | 823.5577035 | C46 H79 O12 | 7.59E+08 | 1.52E+09 |
| 296 | DGDG(16:0/16:0) − H | 891.6050485 | C47 H87 O15 | 7.05E+08 | 2.27E+09 |

TABLE 2

List of non-functional small molecules in HJT decoctosome.

| No. | Compound ID | Name | Description | Molecular formula | score | m/e | Retention time(min) |
|---|---|---|---|---|---|---|---|
| 1 | HMDB60017 | Pyrogallol-2-O-glucuronide | Pyrogallol-2-O-glucuronide | C12H14O9 | 44.4 | 285.06 | 4.02 |
| 2 | HMDB41511 | Glycerol 2-(9Z,12Z-octadecadienoate) 1-hexadecanoate 3-O-[alpha-D-galactopyranosyl-(1->6)-beta-D-galactopyranoside] | Glycerol 2-(9Z,12Z-octadecadienoate) 1-hexadecanoate 3-O-[alpha-D-galactopyranosyl-(1->6)-beta-D-galactopyranoside] | C49H88O15 | 56.5 | 939.60 | 11.20 |
| 3 | HMDB41266 | Quercetin 3-(6''-caffeoylsophorotrioside) | Quercetin 3-(6''-caffeoylsophorotrioside) | C42H46O25 | 44.4 | 951.23 | 3.16 |
| 4 | HMDB40769 | Dioxinoacrimarine A | Dioxinoacrimarine A | C29H23NO8 | 55 | 531.17 | 2.82 |
| 5 | HMDB40701 | 9-Hydroxy-7-megastigmen-3-one glucoside | 9-Hydroxy-7-megastigmen-3-one glucoside | C19H32O7 | 40.5 | 395.20 | 4.21 |
| 6 | HMDB40358 | (R)-Bitalin A | (R)-Bitalin A | C13H14O3 | 52.1 | 219.10 | 2.82 |
| 7 | HMDB39301 | Epiafzelechin 3-O-gallate-(4beta->6)-epigallocatechin 3-O-gallate | Epiafzelechin 3-O-gallate-(4beta->6)-epigallocatechin 3-O-gallate | C44H34O20 | 51.5 | 883.17 | 1.29 |
| 8 | HMDB39286 | 1-O-Galloylfructose | 1-O-Galloylfructose | C13H16O10 | 42.1 | 315.07 | 4.75 |
| 9 | HMDB38057 | Dehydrophytosphingosine | Dehydrophytosphingosine | C18H37NO3 | 49.8 | 316.28 | 6.57 |
| 10 | HMDB37543 | (Halogen)-(Z)-2-(5-Tetradecenyl)-cyclobutanone | (Halogen)-(Z)-2-(5-Tetradecenyl)-cyclobutanone | C18H32O | 43.7 | 282.28 | 10.29 |
| 11 | HMDB37519 | 2-(5,8-Tetradecadienyl)-cyclobutanone | 2-(5,8-Tetradecadienyl)-cyclobutanone | C18H30O | 42.4 | 280.26 | 9.75 |
| 12 | HMDB37476 | Neocarthamin | Neocarthamin | C21H22O11 | 52.3 | 433.11 | 3.33 |
| 13 | HMDB33538 | Fragransol B | Fragransol B | C19H22O5 | 52.5 | 331.15 | 2.82 |
| 14 | HMDB32960 | 1-Octen-3-yl primeveroside | 1-Octen-3-yl primeveroside | C19H34O10 | 46.8 | 440.25 | 1.95 |
| 15 | HMDB32677 | Soyacerebroside I | Soyacerebroside I | C40H75NO9 | 55.3 | 696.54 | 12.51 |
| 16 | HMDB32147 | Geranylcitronellol | Geranylcitronellol | C20H36O | 39.5 | 310.31 | 11.01 |
| 17 | HMDB31068 | Isopalmitic acid | Isopalmitic acid | C16H32O2 | 43.2 | 274.27 | 5.83 |
| 18 | HMDB30964 | Linolenelaidic acid | Linolenelaidic acid | C18H30O2 | 51.3 | 296.26 | 8.46 |
| 19 | HMDB29766 | (3S,7E,9R)-4,7-Megastigmadiene-3,9-diol 9-[apiosyl-(1->6)-glucoside] | (3S,7E,9R)-4,7-Megastigmadiene-3,9-diol 9-[apiosyl-(1->6)-glucoside] | C24H40O11 | 53.2 | 522.29 | 1.45 |
| 20 | HMDB29711 | Maritimetin | Maritimetin | C15H10O6 | 51.2 | 287.05 | 3.33 |
| 21 | HMDB29348 | Neryl arabinofuranosyl-glucoside | Neryl arabinofuranosyl-glucoside | C21H36O10 | 53 | 466.26 | 3.68 |
| 22 | HMDB13897 | 4-ene-Valproic acid | 4-ene-Valproic acid | C8H14O2 | 42.4 | 125.10 | 1.17 |
| 23 | HMDB11507 | lysophosphatidyl ethanolamine (18:2(9Z, 12Z)/0:0) | LysoPE(18:2(9Z, 12Z)/0:0) | C23H44NO7P | 50.8 | 478.29 | 7.89 |
| 24 | HMDB11127 | 1,2-Di-(9Z,12Z,15Z-octadecatrienoyl)-3-(Galactosyl-alpha-1-6-Galactosyl-beta-1)-glycerol | 1,2-Di-(9Z,12Z,15Z-octadecatrienoyl)-3-(Galactosyl-alpha-1-6-Galactosyl-beta-1)-glycerol | C51H84O15 | 43.3 | 959.57 | 11.39 |
| 25 | HMDB10386 | lysophosphatidyl choline (18:2(9Z, 12Z) | LysoPC(18:2(9Z,12Z)) | C26H50NO7P | 55.7 | 520.34 | 8.08 |
| 26 | HMDB00413 | 3-Hydroxydodecanedioic acid | 3-Hydroxydodecanedioic acid | C12H22O5 | 49 | 269.14 | 7.14 |
| 27 | HMDB00269 | Sphinganine | Sphinganine | C18H39NO2 | 41 | 302.30 | 6.95 |

TABLE 3

List of functional small molecules in HJT decoctosome.

| No. | Compound ID | Name | English name | Molecular formula | score | m/e | Retention time(min) | Description of function |
|---|---|---|---|---|---|---|---|---|
| 1 | HMDB10366 | Hyaluronan | Hyaluronan | C28H44N2O23 | 52.7 | 799.22023 | 3.3343 | Anti-fibrosis; anti-inflammatory |
| 2 | HMDB05801 | Kaempferol | Kaempferol | C15H10O6 | 54.4 | 287.05458 | 4.565633333 | Anti-fibrosis; anti-tumor; anti-bacterial, etc. |
| 3 | HMDB10382 | lysophosphatidyl choline(16:0) | LysoPC(16:0) | C24H50NO7P | 45.3 | 496.33797 | 8.649783333 | Anti-fibrosis |
| 4 | HMDB13648 | Palmitoleoyl Ethanolamide | Palmitoleoyl Ethanolamide | C18H35NO2 | 43.5 | 320.255 | 9.00865 | Anti-inflammatory; analgesic |
| 5 | HMDB12166 | 4alpha-Carboxy-5alpha-cholesta-8-en-3beta-ol | 4alpha-Carboxy-5alpha-cholesta-8-en-3beta-ol | C28H46O3 | 43.9 | 431.35036 | 13.47345 | Anti-inflammatory |
| 6 | HMDB15168 | Cerulenin | Cerulenin | C12H17NO3 | 45.9 | 241.15454 | 1.018633333 | antifungal; anti-tumor |
| 7 | HMDB40586 | Vitamin D5 | Vitamin D5 | C29H48O | 41.2 | 395.36602 | 10.4718 | Decreasing vagus activity |
| 8 | HMDB61062 | 7-hydroxygranisetron | 7-hydroxygranisetron | C18H24N4O2 | 48.4 | 346.22 | 7.14 | Anti-tumor |
| 9 | HMDB33214 | Schottenol | Schottenol | C29H50O | 48.1 | 397.38218 | 12.70096667 | Regulate cholesterol metabolism |

TABLE 4

List of non-functional small molecules in PGY decoctosome.

| No. | Compound ID | Name | Description | Molecular formula | Score | m/e | Retention time (min) |
|---|---|---|---|---|---|---|---|
| 1 | HMDB13248 | Monoethylhexylphthalic acid | Monoethylhexylphthalic acid | C16H22O4 | 39.9 | 301.14 | 0.76 |
| 2 | HMDB09725 | Phosphatidylethanolamine (24:0/20:1(11Z)) | PE(24:0/20:1(11Z)) | C49H96NO8P | 42 | 880.68 | 11.88 |
| 3 | HMDB10689 | Phosphatidylglycerol (18:3(9Z,12Z,15Z)/22:6(4Z,7Z,10Z,13Z,16Z,19Z)) | PG(18:3(9Z,12Z,15Z)/22:6(4Z,7Z,10Z,13Z,16Z,19Z)) | C46H73O10P | 40 | 817.50 | 11.49 |
| 4 | HMDB32843 | AS 1-5 | AS 1-5 | C40H77NO9 | 47.1 | 738.54 | 12.84 |
| 5 | HMDB37840 | N-(1-Deoxy-1-fructosyl)leucine | N-(1-Deoxy-1-fructosyl)leucine | C12H23NO7 | 48.1 | 294.15 | 0.91 |
| 6 | HMDB35402 | Culinariside | Culinariside | C45H87NO10 | 39.6 | 824.62 | 11.69 |
| 7 | HMDB94265 | Diglyceride (21:0/i-13:0/0:0) | DG(21:0/i-13:0/0:0) | C37H72O5 | 46 | 619.52 | 12.65 |
| 8 | HMDB55993 | Diglyceride (15:0/0:0/22:ln9) | DG(15:0/0:0/22:ln9) | C40H76O5 | 49 | 654.60 | 13.03 |
| 9 | HMDB36855 | | Cincassiol B | C20H32O8 | 48.7 | 423.20 | 8.02 |
| 10 | HMDB41511 | Glycerol 2-(9Z,12Z-octadecadienoate)1-hexadecanoate 3-O-[alpha-D-galactopyranosyl-(1->6)-beta-D-galactopyranoside] | Glycerol 2-(9Z,12Z-octadecadienoate)1-hexadecanoate 3-O-[alpha-D-galactopyranosyl-(1->6)-beta-D-galactopyranoside] | C49H88O15 | 52.8 | 939.59 | 13.61 |
| 11 | HMDB37846 | N-(1-Deoxy-1-fructosyl)-phenylalanine | N-(1-Deoxy-1-fructosyl)-phenylalanine | C15H21NO7 | 40.6 | 328.14 | 1.07 |
| 12 | HMDB35970 | (3beta,17alpha,23S)-17,23-Epoxy-3,29-dihydroxy-27-norlanosta-7,9(11)-diene-15,24-dione | (3beta,17alpha,23S)-17,23-Epoxy-3,29-dihydroxy-27-norlanosta-7,9(11)-diene-15,24-dione | C29H42O5 | 38.5 | 941.61 | 11.30 |
| 13 | HMDB11384 | Phosphatidylethanolamine (P-18:0/20:3(8Z,11Z,14Z)) | PE(P-18:0/20:3(8Z,11Z,14Z)) | C43H80NO7P | 45.3 | 776.56 | 13.41 |

TABLE 4-continued

List of non-functional small molecules in PGY decoctosome.

| No. | Compound ID | Name | Description | Molecular formula | Score | m/e | Retention time (min) |
|---|---|---|---|---|---|---|---|
| 14 | HMDB37344 | 3'',4''-Diacetylcosmosiin | 3'',4''-Diacetylcosmosiin | C25H24O12 | 45.8 | 499.12 | 1.42 |
| 15 | HMDB11127 | 1,2-Di-(9Z,12Z,15Z-octadecatrienoyl)-3-(Galactosyl-alpha-1-6-Galactosyl-beta-1)-glycerol | 1,2-Di-(9Z,12Z,15Z-octadecatrienoyl)-3-(Galactosyl-alpha-1-6-Galactosyl-beta-1)-glycerol | C51H84O15 | 41.4 | 959.56 | 11.49 |
| 16 | HMDB00614 | Phosphatidylserine (16:0/16:0) | PS(16:0/16:0) | C38H74NO10P | 41.1 | 753.54 | 13.80 |
| 17 | HMDB36333 | 4'-Hydroxyacetophenone 4''-[4-hydroxy-3,5-dimethoxybenzoyl-(->5)-apiosyl-(1->2)-glucoside] | 4'-Hydroxyacetophenone 4''-[4-hydroxy-3,5-dimethoxybenzoyl-(->5)-apiosyl-(1->2)-glucoside] | C28H34O15 | 50.7 | 628.22 | 1.24 |
| 18 | HMDB04816 | Formamide pyrimidine-adenine | FAPy-adenine | C5H7N5O | 40.8 | 136.06 | 0.91 |
| 19 | HMDB33621 | Araliacerebroside | Araliacerebroside | C40H77NO10 | 49.2 | 732.56 | 11.69 |
| 20 | HMDB37396 | xi-10-Hydroxyoctadecanoic acid | xi-10-Hydroxyoctadecanoic acid | C18H36O3 | 41.7 | 318.30 | 5.92 |
| 21 | HMDB35469 | N-(2R-Hydroxydocosanoyl)-2S-amino-1,3S,4R-octadecanetriol | N-(2R-Hydroxydocosanoyl)-2S-amino-1,3S,4R-octadecanetriol | C40H81NO5 | 42.5 | 678.60 | 11.69 |
| 22 | HMDB31658 | L-2-Amino-5-hydroxypentanoic acid | L-2-Amino-5-hydroxypentanoic acid | C5H11NO3 | 41.3 | 116.07 | 0.91 |
| 23 | HMDB32794 | AS 1-1 | AS 1-1 | C38H71NO9 | 44.9 | 708.51 | 13.61 |
| 24 | HMDB29276 | Cis-Caffeoyl tartaric acid | Cis-Caffeoyl tartaric acid | C13H12O9 | 49.5 | 295.04 | 1.42 |
| 25 | HMDB35212 | Sonchuiono side C | Sonchuiono side C | C19H30O8 | 42.8 | 409.18 | 7.44 |
| 26 | HMDB38732 | alpha-Ionol O-[arabinosyl-(1->6)-glucoside] | alpha-Ionol O-[arabinosyl-(1->6)-glucoside] | C24H40O10 | 53.6 | 511.25 | 8.22 |
| 27 | HMDB41140 | Prenyl cis-caffeate | Prenyl cis-caffeate | C14H16O4 | 48.7 | 266.14 | 1.07 |
| 28 | HMDB08765 | Phosphatidylcholine (24:0/18:3(9Z,12Z,15Z)) | PC(24:0/18:3(9Z,12Z,15Z)) | C50H94NO8P | 42 | 850.67 | 11.30 |
| 29 | HMDB28725 | Asparaginyl-Arginine | Asparaginyl-Arginine | C10H20N6O4 | 43.3 | 311.14 | 6.69 |
| 30 | HMDB02823 | Docosatrienoic acid | Docosatrienoic acid | C22H38O2 | 41.1 | 352.32 | 10.15 |
| 31 | HMDB34159 | Acetyl tributyl citrate | Acetyl tributyl citrate | C20H34O8 | 52.6 | 425.21 | 8.22 |
| 32 | HMDB28802 | Glutaminyl-Lysine | Glutaminyl-Lysine | C11H22N4O4 | 44.5 | 292.20 | 7.07 |
| 33 | HMDB00269 | Sphinganine | Sphinganine | C18H39NO2 | 46.8 | 284.29 | 11.11 |
| 34 | HMDB29782 | 6-Epi-7-isocucurbic acid glucoside | 6-Epi-7-isocucurbic acid glucoside | C18H30O8 | 45.9 | 357.19 | 7.44 |
| 35 | HMDB35159 | Paullinic acid | Paullinic acid | C20H38O2 | 48.2 | 328.32 | 10.92 |

TABLE 5

List of functional small molecules in PGY decoctosome.

| No. | Compound ID | Name | English name | Molecular formula | score | m/e | Retention time (min) | Description of function |
|---|---|---|---|---|---|---|---|---|
| 1 | HMDB00734 | Indoleacrylic acid | Indoleacrylic acid | C11H9NO2 | 44.6 | 205.10 | 1.06608333 | Anti-inflammation |
| 2 | HMDB28959 | Lysyl-Proline | Lysyl-Proline | C11H21N3O3 | 40.2 | 226.15 | 1.42 | Alleviate inflammation and renal fibrosis |
| 3 | HMDB36846 | Icariside B8 | Icariside B8 | C19H32O8 | 55.1 | 411.20 | 7.44408333 | Anti-inflammation |
| 4 | HMDB35988 | Ganoderic acid F | Ganoderic acid F | C32H42O9 | 44.8 | 593.27 | 10.7289167 | Anti-inflammation |
| 5 | HMDB02375 | Chicoric acid | Chicoric acid | C22H18O12 | 40.4 | 492.11 | 1.42343333 | Stimulate phagocytosis |

TABLE 5-continued

List of functional small molecules in PGY decoctosome.

| No. | Compound ID | Name | English name | Molecular formula | score | m/e | Retention time (min) | Description of function |
|---|---|---|---|---|---|---|---|---|
| 6 | HMDB35990 | Cerebroside B | Cerebroside B | C41H77NO9 | 39.4 | 750.54 | 12.8375833 | Inhibit mononuclear cell migration and Cartilage degradation |
| 7 | HMDB60681 | 4-Hydroxy-2,6-dimethylaniline | 4-Hydroxy-2,6-dimethylaniline | C8H11NO | 50.5 | 120.08 | 1.06608333 | Relieve itching, heat, and pain caused by inflammation of the skin; antiarrhythmic |
| 8 | HMDB00050 | Adenosine | Adenosine | C10H13N5O4 | 45.2 | 268.10 | 0.90858333 | Dilate blood vessels, arrhythmia drugs of type V |
| 9 | HMDB02117 | Oleamide | Oleamide | C18H35NO | 50.9 | 282.28 | 10.53575 | Relieve emotion and sleep disorders |
| 10 | HMDB10715 | 2-Phenylacetamide | 2-Phenylacetamide | C8H9NO | 42.3 | 118.06 | 1.06608333 | Antiarrhythmic |
| 11 | HMDB61104 | 7-hydroxymethotrexate | 7-hydroxymethotrexate | C20H22N8O6 | 41.8 | 453.16 | 7.2539 | Folic acid antagonist; anti-tumor; treat autoimmune diseases |
| 12 | HMDB03431 | L-Histidinol | L-Histidinol | C6H11N3O | 40.79 | 124.0 | 11.49425 | Enhance effects of anti-tumor drugs |

TABLE 6

List of proteins in HJT decoctosome.

| No. | Protein ID No. | Protein name | English name | Score | Density |
|---|---|---|---|---|---|
| 1 | P42739 | Polyubiquitin | Polyubiquitin | 18.922 | 3810200 |
| 2 | P69310 | Ubiquitin-60S ribosomal protein L40-2 | Ubiquitin-60S ribosomal protein L40-2 | 13.257 | 2414600 |
| 3 | Q39752 | Calmodulin-5 | Calmodulin-5 | 8.8684 | 3206100 |
| 4 | P08477 | Glyceraldehyde-3-phosphate dehydrogenase GAPC2, cytosolic | Glyceraldehyde-3-phosphate dehydrogenase GAPC2, cytosolic | 6.7177 | 2599300 |
| 5 | Q271K6 | Phragmoplast orienting kinesin | Phragmoplast orienting kinesin | 6.7093 | 19854000 |
| 6 | K4LMW2 | Sesquiterpene synthase 2 | Sesquiterpene synthase 2 | 6.4161 | 2251300 |
| 7 | O81028 | Pentatricopeptide repeat-containing protein At2g26790, mitochondrial | Pentatricopeptide repeat-containing protein At2g26790, mitochondrial | 6.1664 | 2385500 |
| 8 | Q10D00 | ATP-dependent RNA helicase SUV3, mitochondrial; | ATP-dependent RNA helicase SUV3, mitochondrial; | 5.9266 | 1658900 |
| 9 | Q9LQ32 | Glucuronoxylan 4-O-methyltransferase 3 | Glucuronoxylan 4-O-methyltransferase 3 | 5.9167 | 70158000 |
| 10 | Q6R2K1 | Protein STRUBBELIG-RECEPTOR FAMILY 5 | Protein STRUBBELIG-RECEPTOR FAMILY 5 | 5.9167 | 41164000 |
| 11 | Q8W4H7 | Elongation factor 1-alpha 2 | Elongation factor 1-alpha 2 | 5.9167 | 20457000 |
| 12 | Q9SCJ9 | Ubiquitin carboxyl-terminal hydrolase 26 | Ubiquitin carboxyl-terminal hydrolase 26 | 5.9167 | 16483000 |
| 13 | Q05753 | Ankyrin repeat domain-containing protein, chloroplastic | Ankyrin repeat domain-containing protein, chloroplastic | 5.9167 | 15696000 |
| 14 | Q67J19 | Probable BRI1 kinase inhibitor 1 | Probable BRI1 kinase inhibitor 1 | 5.9167 | 12764000 |
| 15 | P26563 | Aspartate aminotransferase P2, mitochondrial | Aspartate aminotransferase P2, mitochondrial | 5.9167 | 9863500 |

TABLE 6-continued

List of proteins in HJT decoctosome.

| No. | Protein ID No. | Protein name | English name | Score | Density |
|---|---|---|---|---|---|
| 16 | P04672 | Nodulin-44 | Nodulin-44 | 5.9167 | 9466800 |
| 17 | Q9SMO9 | V-type proton ATPase catalytic subunit A | V-type proton ATPase catalytic subunit A | 5.9167 | 8766600 |
| 18 | Q8RWG2 | Protein high chlorophyll fluorescent 107 | Protein high chlorophyll fluorescent 107 | 5.9167 | 8229500 |
| 19 | Q9FYH1 | Histone acetyltransferase HAC2 | Histone acetyltransferase HAC2 | 5.9167 | 7007400 |
| 20 | P02857 | Legumin A | Legumin A | 5.9167 | 5423500 |
| 21 | F415D5 | WAT1-related protein At1g70260 | WAT1-related protein At1g70260 | 5.9167 | 5284100 |
| 22 | Q9SY74 | Zinc finger CCCH domain-containing protein 5 | Zinc finger CCCH domain-containing protein 5 | 5.9167 | 5050900 |
| 23 | P00585 | Granule-bound starch synthase 1, chloroplastic/amyloplastic | Granule-bound starch synthase 1, chloroplastic/amyloplastic | 5.9167 | 4542000 |
| 24 | O22197 | Probable E3 ubiquitin-protein ligase RHC1A | Probable E3 ubiquitin-protein ligase RHC1A | 5.9167 | 3564800 |
| 25 | O22056 | RNA polymerase sigma factor sigB | RNA polymerase sigma factor sigB | 5.9167 | 3414300 |
| 26 | O22300 | Homeobox protein knotted-1-like LET12 | Homeobox protein knotted-1-like LET12 | 5.9167 | 3027700 |
| 27 | Q0JCU7 | Zeaxanthin epoxidase, chloroplastic | Zeaxanthin epoxidase, chloroplastic | 5.9167 | 2818100 |
| 28 | P31582 | Ras-related protein RABF2A | Ras-related protein RABF2A | 5.9167 | 2650700 |
| 29 | Q940K0 | Probable disease resistance protein At1g61180 | Probable disease resistance protein At1g61180 | 5.9167 | 2376800 |
| 30 | Q40237 | Major pollen allergen Lol p 5b | Major pollen allergen Lol p5 b | 5.9167 | 2061200 |
| 31 | Q00864 | Light-independent protochlorophyllide reductase subunit B | Light-independent protochlorophyllide reductase subunit B | 5.9167 | 2028700 |
| 32 | Q2R2Z0 | Glutamyl-tRNA(Gln) amidotransferase subunit B | Glutamyl-tRNA(Gln) amidotransferase subunit B | 5.9167 | 1639300 |
| 33 | O65282 | 20 kDa chaperonin, chloroplastic | 20 kDa chaperonin, chloroplastic | 5.9167 | 1363600 |
| 34 | Q56W64-2 | Probable isoaspartyl peptidase/L-asparaginase 3 | Probable isoaspartyl peptidase/L-asparaginase 3 | 5.9167 | 1299600 |
| 35 | A7Y3C4 | Photosystem II D2 protein | Photosystem II D2 protein | 5.9167 | 405460 |
| 36 | Q8VZ79 | Protein INVOLVED IN DE NOVO 2 | Protein INVOLVED IN DE NOVO 2 | 5.9167 | 322920 |
| 37 | P52705 | (S)-hydroxynitrile lyase | (S)-hydroxynitrile lyase | 5.9167 | 209640 |
| 38 | O80467 | Spermidine sinapoyl CoA acyltransferase | Spermidine sinapoyl CoA acyltransferase | 5.9167 | 167870 |

TABLE 7

List of proteins in PGY decoctosome.

| No. | Protein ID | Protein name | Sample name | Score | Density |
|---|---|---|---|---|---|
| 1 | P86055 | Peroxidase 2 | Peroxidase 2 | 224.9 | 37332000 |
| 2 | Q8RX86-2 | Alpha-galactosidase 2 | Alpha-galactosidase 2 | 194.44 | 7066200 |
| 3 | P86067 | Peroxidase 10 | Peroxidase 10 | 107.25 | 46486000 |
| 4 | A0A0B4JDK1 | Non-specific lipid-transfer protein | Non-specific lipid-transfer protein | 72.406 | 206080000 |
| 5 | P27322 | Heat shock 70 kDa protein 3 | Heat shock 70 kDa protein 3 | 69.029 | 72537000 |
| 6 | P49693 | 60S ribosomal protein L19-3 | 60S ribosomal protein L19-3 | 58.835 | 6670300 |
| 7 | Q40677 | Probable fructose-bisphosphate aldolase 1, chloroplastic | Probable fructose-bisphosphate aldolase 1, chloroplastic | 54.273 | 37424000 |
| 8 | B3EWQ2 | Antimicrobial peptide 2 | Antimicrobial peptide 2 | 53.733 | 17372000 |
| 9 | P26320 | Oxygen-evolving enhancer protein 1 | Oxygen-evolving enhancer protein 1 | 48.621 | 101720000 |
| 10 | Q41246 | 14-3-3-like protein GF14 omicron | 14-3-3-like protein GF14 omicron | 42.923 | 29295000 |
| 11 | P00073 | Ubiquitin-NEDD8-like protein RUB2 | Ubiquitin-NEDD8-like protein RUB2 | 37.614 | 621770000 |
| 12 | Q39752 | Calmodulin-5 | Calmodulin-5 | 37.051 | 60273000 |

TABLE 7-continued

List of proteins in PGY decoctosome.

| No. | Protein ID | Protein name | Sample name | Score | Density |
|---|---|---|---|---|---|
| 13 | P28450 | Ribulose bisphosphate carboxylase large chain | Ribulose bisphosphate carboxylase large chain | 28.505 | 51941000 |
| 14 | Q9ZT00 | Ribulose bisphosphate carboxylase/oxygenase activase | Ribulose bisphosphate carboxylase/oxygenase activase | 26.205 | 37659000 |
| 15 | P27879 | 18.1 kDa class I heat shock protein | 18.1 kDa class I heat shock protein | 24.306 | 101640000 |
| 16 | P26300 | Enolase | Enolase | 22.081 | 28302000 |
| 17 | P46523 | Chaperone protein ClpC1, chloroplastic | Chaperone protein ClpC1, chloroplastic | 20.657 | 9179000 |
| 18 | O49065 | Root allergen protein | Root allergen protein | 18.921 | 190000000 |
| 19 | P27337 | Peroxidase 1 | Peroxidase 1 | 16.936 | 22889000 |
| 20 | P49249 | Probable aldo-keto reductase 5 | Probable aldo-keto reductase 5 | 16.249 | 3262800 |
| 21 | Q43831 | Chaperonin 60 subunit beta 2, chloroplastic | Chaperonin 60 subunit beta 2, chloroplastic | 15.476 | 32546000 |
| 22 | P85088 | ATP synthase subunit beta | ATP synthase subunit beta | 14.837 | 9836400 |
| 23 | P36688 | 50S ribosomal protein L12 | 50S ribosomal protein L12 | 14.819 | 167360000 |
| 24 | O04996 | Superoxide dismutase [Cu-Zn] | Superoxide dismutase [Cu-Zn] | 14.344 | 324980000 |
| 25 | P46257 | Fructose-bisphosphate aldolase | Fructose-bisphosphate aldolase | 13.778 | 72863000 |
| 26 | P08477 | Glyceraldehyde-3-phosphate dehydrogenase GAPC2, cytosolic | Glyceraldehyde-3-phosphate dehydrogenase GAPC2, cytosolic | 13.706 | 30987000 |
| 27 | P30170 | Actin-12 | Actin-12 | 12.918 | 77830000 |
| 28 | O49080 | Oxygen-evolving enhancer protein 2 | Oxygen-evolving enhancer protein 2 | 12.461 | 18880000 |
| 29 | Q43215 | Histone H2B.7 | Histone H2B.7 | 12.287 | 65959000 |
| 30 | Q9XEK6 | 40S ribosomal protein S14-1 | 40S ribosomal protein S14-1 | 11.553 | 141790000 |
| 31 | B3A0N2 | Non-specific lipid-transfer protein | Non-specific lipid-transfer protein | 11.477 | 63259000 |
| 32 | Q8L4N1-2 | Universal stress protein PHOS34 | Universal stress protein PHOS34 | 10.193 | 13338000 |
| 33 | Q9LEJ0 | Enolase 1 | Enolase 1 | 9.3352 | 5224700 |
| 34 | Q9ASR1 | Elongation factor 2 | Elongation factor 2 | 8.6402 | 15693000 |
| 35 | P48493 | Triosephosphate isomerase | Triosephosphate isomerase | 8.6026 | 54557000 |
| 36 | P85915 | Elongation factor 1-alpha 2 | Elongation factor 1-alpha 2 | 8.2353 | 19138000 |
| 37 | Q8GVE8 | Phosphoenolpyruvate carboxylase 4 | Phosphoenolpyruvate carboxylase 4 | 8.1239 | 17825000 |
| 38 | Q38872 | Calcium-dependent protein kinase 6 | Calcium-dependent protein kinase 6 | 7.4954 | 70644000 |
| 39 | Q08080 | Heat shock 70 kDa protein 6, chloroplastic | Heat shock 70 kDa protein 6, chloroplastic | 7.3833 | 48170000 |
| 40 | Q41649 | Peptidyl-prolyl cis-trans isomerase FKBP15-1 | Peptidyl-prolyl cis-trans isomerase FKBP15-1 | 7.3335 | 8230800 |
| 41 | P83218 | Pectinesterase/pectinesterase inhibitor 3 | Pectinesterase/pectinesterase inhibitor 3 | 7.1315 | 215680000 |
| 42 | Q9FLG1 | Beta-D-xylosidase 4 | Beta-D-xylosidase 4 | 7.0715 | 19208000 |
| 43 | P47921 | Nucleoside diphosphate kinase | Nucleoside diphosphate kinase | 6.9705 | 11757000 |
| 44 | P83373 | Malate dehydrogenase 1, mitochondrial | Malate dehydrogenase 1, mitochondrial | 6.8677 | 9450300 |
| 45 | Q9SWF5 | Adenosylhomocysteinase 2 | Adenosylhomocysteinase 2 | 6.822 | 19916000 |
| 46 | F4IN32 | MATH domain and coiled-coil domain-containing protein At2g42460 | MATH domain and coiled-coil domain-containing protein At2g42460 | 6.8169 | 3016800 |
| 47 | Q9FJD6 | Putative respiratory burst oxidase homolog protein H | Putative respiratory burst oxidase homolog protein H | 6.8116 | 8143800 |
| 48 | P02520 | Class I heat shock protein | Class I heat shock protein | 6.6857 | 34589000 |
| 49 | P86066 | Peroxidase 9 | Peroxidase 9 | 6.6696 | 6907400 |
| 50 | O50003 | 60S ribosomal protein L12-2 | 60S ribosomal protein L12-2 | 6.6548 | 15793000 |
| 51 | Q8M9Y8 | 50S ribosomal protein L20 | 50S ribosomal protein L20 | 6.5835 | 4242500 |
| 52 | P85962 | 60S acidic ribosomal protein P2 | 60S acidic ribosomal protein P2 | 6.5112 | 4430800 |
| 53 | O04350 | Tubulin-folding cofactor A | Tubulin-folding cofactor A | 6.503 | 6355900 |
| 54 | Q2R482 | DNA replication licensing factor MCM2 | DNA replication licensing factor MCM2 | 6.4837 | 493670000 |

TABLE 7-continued

List of proteins in PGY decoctosome.

| No. | Protein ID | Protein name | Sample name | Score | Density |
|---|---|---|---|---|---|
| 55 | Q8GYD9 | Probable RNA helicase SDE3 | Probable RNA helicase SDE3 | 6.4036 | 10678000 |
| 56 | Q9FEF8-2 | Probable mediator of RNA polymerase II transcription subunit 36b | Probable mediator of RNA polymerase II transcription subunit 36b | 6.3693 | 49624000 |
| 57 | P83442 | Late embryogenesis abundant protein Dc3 | Late embryogenesis abundant protein Dc3 | 6.3587 | 17038000 |
| 58 | Q9SML8 | Malate dehydrogenase, cytoplasmic 1 | Malate dehydrogenase, cytoplasmic 1 | 6.3468 | 4554300 |
| 59 | Q7DMN9 | Calmodulin-5/6/7/8 | Calmodulin-5/6/7/8 | 6.306 | 31812000 |
| 60 | Q42662 | 5-methyltetrahydropteroyltriglutamate--homocysteine methyltransferase | 5-methyltetrahydropteroyltriglutamate--homocysteine methyltransferase | 6.2899 | 3134700 |
| 61 | Q9ZU90 | F-box protein SKIP28 | F-box protein SKIP28 | 6.2367 | 42902000 |
| 62 | Q9SLN1 | Filament-like plant protein 7 | Filament-like plant protein 7 | 6.2279 | 3639900 |
| 63 | F4JUI9 | Kinesin-like protein | Kinesin-like protein | 6.1026 | 172810000 |
| 64 | P15252 | Rubber elongation factor protein | Rubber elongation factor protein | 6.0825 | 9877400 |
| 65 | B9HCR2 | Methylthioribose-1-phosphate isomerase | Methylthioribose-1-phosphate isomerase | 6.0763 | 6670100 |
| 66 | Q39615 | Photo system I reaction center subunit II-2, chloroplastic | Photosystem I reaction center subunit II-2, chloroplastic | 6.0636 | 12355000 |
| 67 | Q7XYS3 | Allene oxide synthase 2 | Allene oxide synthase 2 | 6.0586 | 7798500 |
| 68 | Q8VY00 | Pre-mRNA-splicing factor ATP-dependent RNA helicase DEAH1 | Pre-mRNA-splicing factor ATP-dependent RNA helicase DEAH1 | 6.0386 | 1458700 |
| 69 | P27456 | Glutathione reductase, chloroplastic | Glutathione reductase, chloroplastic | 6.0181 | 3722600 |
| 70 | Q8W171 | Peptidyl-prolyl cis-trans isomerase 1 | Peptidyl-prolyl cis-trans isomerase 1 | 6.0126 | 3996200 |
| 71 | Q9LJX4-2 | Pumilio homolog 5 | Pumilio homolog 5 | 5.9912 | 13389000 |
| 72 | Q00383 | Protein TIC 214 | Protein TIC 214 | 5.9887 | 17037000 |
| 73 | Q8LEU3 | Chlorophyll(ide) b reductase NOL, chloroplastic | Chlorophyll(ide) b reductase NOL, chloroplastic | 5.9849 | 15552000 |
| 74 | Q39528 | Agglutinin-1 | Agglutinin-1 | 5.9834 | 8563200 |
| 75 | F4JQZ3 | Rho GTPase-activating protein REN1 | Rho GTPase-activating protein REN1 | 5.9802 | 45841000 |
| 76 | Q39291 | V-type proton ATPase catalytic subunit A | V-type proton ATPase catalytic subunit A | 5.9751 | 13904000 |
| 77 | Q9ZV88 | BES1/BZR1 homolog protein 4 | BES1/BZR1 homolog protein 4 | 5.9713 | 8200900 |
| 78 | Q9MB95 | 1-aminocyclopropane-1-carboxylate synthase 1 | 1-aminocyclopropane-1-carboxylate synthase 1 | 5.9712 | 11179000 |
| 79 | Q8W4F0 | Protein DA1-related 1 | Protein DA1-related 1 | 5.951 | 17844000 |
| 80 | A6MMS5 | Maturase K | Maturase K | 5.9461 | 15716000 |
| 81 | Q0JHF8 | Fructose-1,6-bisphosphatase | Fructose-1,6-bisphosphatase | 5.9436 | 5507400 |
| 82 | Q99070 | Glycine-rich RNA-binding protein 2 | Glycine-rich RNA-binding protein 2 | 5.9435 | 110970000 |
| 83 | Q5JLS2 | CBL-interacting protein kinase 12 | CBL-interacting protein kinase 12 | 5.9368 | 4959100 |
| 84 | F4IGL2 | Kinesin-like protein | Kinesin-like protein | 5.9359 | 8858700 |
| 85 | P35687 | 40S ribosomal protein S21 | 40S ribosomal protein S21 | 5.9336 | 22222000 |
| 86 | Q0DUI1 | Probable serine acetyltransferase 3 | Probable serine acetyltransferase 3 | 5.9311 | 5516400 |
| 87 | Q9ZWC8 | Serine/threonine-protein kinase BRI1-like 1 | Serine/threonine-protein kinase BRI1-like 1 | 5.9226 | 4741100 |
| 88 | P26413 | Heat shock 70 kDa protein | Heat shock 70 kDa protein | 5.9225 | 5500600 |
| 89 | Q9LM66 | Xylem cysteine proteinase 2 | Xylem cysteine proteinase 2 | 5.9057 | 8304600 |
| 90 | Q8VZY6 | Polycomb group protein FIE2 | Polycomb group protein FIE2 | 5.9054 | 3038900 |
| 91 | Q9FPS9 | Ubiquitin carboxyl-terminal hydrolase 15 | Ubiquitin carboxyl-terminal hydrolase 15 | 5.9045 | 7895400 |
| 92 | Q9FEC4 | Trans-splicing factor Raa3 | Trans-splicing factor Raa3 | 5.8962 | 28562000 |

TABLE 7-continued

List of proteins in PGY decoctosome.

| No. | Protein ID | Protein name | Sample name | Score | Density |
|---|---|---|---|---|---|
| 93 | Q75W17 | Furcatin hydrolase | Furcatin hydrolase | 5.8778 | 3844900 |
| 94 | Q8LG77 | Isocitrate dehydrogenase [NAD] catalytic subunit 6, mitochondrial | Isocitrate dehydrogenase [NAD] catalytic subunit 6, mitochondrial | 5.8737 | 5903800 |
| 95 | Q43153 | Bifunctional L-3-cyanoalanine synthase/cysteine synthase | Bifunctional L-3-cyanoalanine synthase/cysteine synthase | 5.8735 | 8302400 |
| 96 | O80673 | CDPK-related kinase 1 | CDPK-related kinase 1 | 5.8663 | 3386400 |
| 97 | Q07510 | 3-oxoacyl-[acyl-carrier-protein] synthase III | 3-oxoacyl-[acyl-carrier-protein] synthase III | 5.8656 | 12050000 |
| 98 | Q6KAIO | Polyribonucleotide nucleotidyltransferase 2 | Polyribonucleotide nucleotidyltransferase 2 | 5.8626 | 5509000 |
| 99 | Q0D317 | WUSCHEL-related homeobox 12 | WUSCHEL-related homeobox 12 | 5.8621 | 6510400 |
| 100 | P18905 | Elongation factor Tu | Elongation factor Tu | 5.8615 | 3084900 |
| 101 | Q6WNRO | Isoflavone 2'-hydroxylase | Isoflavone 2'-hydroxylase | 5.8569 | 26449000 |
| 102 | P85905 | Translationally-controlled tumor protein homolog | Translationally-controlled tumor protein homolog | 5.8548 | 19728000 |
| 103 | Q0J9V3 | Kinesin-like protein KIN-14H | Kinesin-like protein KIN-14H | 5.8546 | 3860700 |
| 104 | Q9C5Q8 | Small RNA 2-O-methyltransferase | Small RNA 2-O-methyltransferase | 5.8542 | 18023000 |
| 105 | Q00081 | Glucose-1-phosphate adenylyltransferase large subunit 1 | Glucose-1-phosphate adenylyltransferase large subunit 1 | 5.8513 | 12444000 |
| 106 | Q9FJK7 | Cyclin-C1-2 | Cyclin-C1-2 | 5.8513 | 53998000 |
| 107 | Q0WT24 | Protein SENSITIVE TO PROTON RHIZOTOXICITY 2 | Protein SENSITIVE TO PROTON RHIZOTOXICITY 2 | 5.8488 | 5961500 |
| 108 | P12466 | Ribulose bisphosphate carboxylase large chain | Ribulose bisphosphate carboxylase large chain | 5.8477 | 5198800 |
| 109 | Q859K3 | Zinc finger protein VAR3, chloroplastic | Zinc finger protein VAR3, chloroplastic | 5.8469 | 5129100 |
| 110 | Q8LG10 | GATA transcription factor 15 | GATA transcription factor 15 | 5.8463 | 8793300 |
| 111 | F4IDW9 | Protein PARTING DANCERS | Protein PARTING DANCERS | 5.8442 | 3152300 |
| 112 | Q9ZPY2-2 | Laccase-6 | Laccase-6 | 5.8436 | 12149000 |
| 113 | Q9SBB2 | Protein ABC transporter 1 | Protein ABC transporter 1 | 5.8407 | 5570200 |
| 114 | P09753 | Uncharacterized 38.5 kDa protein in psbA intron 1 | Uncharacterized 38.5 kDa protein in psbA intron 1 | 5.8387 | 21558000 |
| 115 | A4GNA8 | Phosphatidylserine decarboxylase proenzyme 3 | Phosphatidylserine decarboxylase proenzyme 3 | 5.8376 | 6961500 |
| 116 | AIXGTO | Protein Ycf2 | Protein Ycf2 | 5.8374 | 6466300 |
| 117 | Q9LEL5 | 3'-hydroxy-N-methyl-(S)-coclaurine 4'-O-methyltransferase | 3'-hydroxy-N-methyl-(S)-coclaurine 4'-O-methyltransferase | 5.8359 | 4223300 |
| 118 | Q8WHZ0 | 30S ribosomal protein S11 | 30S ribosomal protein S11 | 5.833 | 13403000 |
| 119 | Q9ZUB9 | Putative F-box protein At1g23770 | Putative F-box protein At1g23770 | 5.8316 | 4699200 |
| 120 | Q42831 | Non-symbiotic hemoglobin | Non-symbiotic hemoglobin | 5.8313 | 21708000 |
| 121 | Q8LPS6 | Pentatricopeptide repeat-containing protein At1g02150 | Pentatricopeptide repeat-containing protein At1g02150 | 5.831 | 1790000 |
| 122 | O64597 | Putative F-box protein At1g70390 | Putative F-box protein At1g70390 | 5.8308 | 5481900 |
| 123 | Q93ZG9 | Peptidyl-prolyl cis-trans isomerase FKBP53 | Peptidyl-prolyl cis-trans isomerase FKBP53 | 5.8305 | 1454100 |
| 124 | P42777 | G-box-binding factor 4 | G-box-binding factor 4 | 5.8304 | 5305500 |
| 125 | Q9LF41 | Probable ubiquitin conjugation factor E4 | Probable ubiquitin conjugation factor E4 | 5.8298 | 4992200 |
| 126 | P36183 | Endoplasmin homolog | Endoplasmin homolog | 5.8297 | 13029000 |
| 127 | O49696 | Aluminum-activated malate transporter 12 | Aluminum-activated malate transporter 12 | 5.8294 | 5467900 |

TABLE 7-continued

List of proteins in PGY decoctosome.

| No. | Protein ID | Protein name | Sample name | Score | Density |
|---|---|---|---|---|---|
| 128 | Q9SFD8 | Nuclear transcription factor Y subunit B-9 | Nuclear transcription factor Y subunit B-9 | 5.8291 | 2838000 |
| 129 | Q6ZFZ4 | Calpain-type cysteine protease ADL1 | Calpain-type cysteine protease ADL1 | 5.829 | 5255300 |
| 130 | Q9LYT5 | Probable pectinesterase/pectinesterase inhibitor 35 | Probable pectinesterase/pectinesterase inhibitor 35 | 5.829 | 3104900 |
| 131 | Q7XAMO | Spindle and kinetochore-associated protein 1 homolog | Spindle and kinetochore-associated protein 1 homolog | 5.8289 | 4385400 |
| 132 | Q6YXR4 | Photosystem I assembly protein Ycf4 | Photosystem I assembly protein Ycf4 | 5.8288 | 2716300 |
| 133 | Q9SYM4 | Alpha,alpha-trehalose-phosphate synthase [UDP-forming] 1 | Alpha,alpha-trehalose-phosphate synthase [UDP-forming] 1 | 5.8279 | 3427200 |
| 134 | Q1PET6 | Probable isoprenylcysteine alpha-carbonyl methylesterase ICMEL2 | Probable isoprenylcysteine alpha-carbonyl methylesterase ICMEL2 | 5.8278 | 12092000 |
| 135 | Q9LKG7 | UTP--glucose-1-phosphate uridylyltransferase | UTP--glucose-1-phosphate uridylyltransferase | 5.8278 | 18078000 |
| 136 | Q6NPP4 | Calmodulin-binding transcription activator 2 | Calmodulin-binding transcription activator 2 | 5.8277 | 3782600 |
| 137 | Q9CAM8 | Pentatricopeptide repeat-containing protein At1g63150 | Pentatricopeptide repeat-containing protein At1g63150 | 5.8277 | 16708000 |
| 138 | O04204 | 60S acidic ribosomal protein P0-1 | 60S acidic ribosomal protein P0-1 | 5.8274 | 19674000 |
| 139 | QOWRJ2 | 3-dehydrosphinganine reductase TSC10A | 3-dehydrosphinganine reductase TSC10A | 5.8266 | 3549600 |
| 140 | Q6AUV1 | Xanthine dehydrogenase | Xanthine dehydrogenase | 5.8262 | 1690900 |

TABLE 8

List of small RNA sequences in HJT decoctosome.

| Column 1 | Sequence | Decoction | Decoctosome | Control | 0 h | 60 h |
|---|---|---|---|---|---|---|
| HJT-sRNA-18 | TTGGGTGCGAGAGGTCCC (SEQ ID NO: 40) | 1113 | 535 | 866 | 1135 | 1108 |
| HJT-sRNA-19 | CTTTGTCGCTTCGATTCGT (SEQ ID NO: 41) | 380 | 157 | 0 | 49 | 41 |
| HJT-sRNA-20 | GAAGTCCTCGTGTTGCACCCC (SEQ ID NO: 42) | 7539 | 6007 | 1 | 42 | 33 |
| HJT-sRNA-21 | AGTCCTCGTGTTGCACCCCT (SEQ ID NO: 43) | 17747 | 13298 | 1 | 37 | 28 |
| HJT-sRNA-22 | CTCGGCCTTTTGGCTAAG (SEQ ID NO: 44) | 657 | 199 | 10 | 28 | 30 |
| HJT-sRNA-23 | ACGACTCTCGGCAACGGA (SEQ ID NO: 45) | 14450 | 8944 | 7 | 27 | 21 |
| HJT-sRNA-24 | CGACTCTCGGCAACGGATA (SEQ ID NO: 46) | 16051 | 7604 | 7 | 23 | 20 |
| HJT-sRNA-25 | CATAACGACTCTCGGCAA (SEQ ID NO: 47) | 841 | 467 | 0 | 20 | 7 |

TABLE 8-continued

List of small RNA sequences in HJT decoctosome.

| Column 1 | Sequence | Decoction | Decoctosome | Control | 0 h | 60 h |
|---|---|---:|---:|---:|---:|---:|
| HJT-sRNA-26 | CTCGGCAACGGATATCTCG (SEQ ID NO: 48) | 9252 | 5581 | 4 | 15 | 18 |
| HJT-sRNA-27 | CCTATGTCGCTTCGATTCG (SEQ ID NO: 49) | 417139 | 215505 | 0 | 9 | 16 |
| HJT-sRNA-28 | CTATGTCGCTTCGATTCGT (SEQ ID NO: 50) | 422659 | 208523 | 0 | 9 | 15 |
| HJT-sRNA-29 | CTCTCGGCAACGGATATCT (SEQ ID NO: 51) | 9174 | 4957 | 5 | 14 | 17 |
| HJT-sRNA-30 | CGGATATCTCGGCTCTCG (SEQ ID NO: 52) | 20596 | 6860 | 2 | 7 | 16 |
| HJT-sRNA-31 | GGTGCGAGAGGTCCCGAGT (SEQ ID NO: 53) | 429 | 216 | 14 | 17 | 29 |
| HJT-sRNA-32 | ACGGATATCTCGGCTCTC (SEQ ID NO: 54) | 8662 | 4222 | 2 | 10 | 12 |
| HJT-sRNA-33 | CTGGTTGATCCTGCCAGTAGT (SEQ ID NO: 55) | 452 | 480 | 8 | 17 | 16 |
| HJT-sRNA-34 | CGACCCCAGGTCAGGCGGG (SEQ ID NO: 56) | 44210 | 13924 | 2 | 12 | 9 |
| HJT-sRNA-35 | CGGCAACGGATATCTCGGCT (SEQ ID NO: 57) | 3915 | 3718 | 2 | 7 | 14 |
| HJT-sRNA-36 | GCGACCCCAGGTCAGGCGG (SEQ ID NO: 58) | 39609 | 12687 | 2 | 12 | 8 |
| HJT-sRNA-37 | GACTCTCGGCAACGGATATC (SEQ ID NO: 59) | 3876 | 2756 | 4 | 11 | 13 |
| HJT-sRNA-38 | TACCCGGCCGTCGGGCA (SEQ ID NO: 60) | 4637 | 1841 | 0 | 11 | 5 |
| HJT-sRNA-39 | TCTCGGCTCTCGCATCGA (SEQ ID NO: 61) | 10898 | 4833 | 0 | 7 | 8 |
| HJT-sRNA-40 | GGGGATGTAGCTCAGATG (SEQ ID NO: 62) | 58885 | 27774 | 0 | 9 | 5 |
| HJT-sRNA-41 | TTCCCACAGACGGCGCCA (SEQ ID NO: 63) | 1144 | 2106 | 0 | 6 | 8 |
| HJT-sRNA-42 | ATTGTGAAGCAGAATTCA (SEQ ID NO: 64) | 1149 | 270 | 200 | 232 | 181 |
| HJT-sRNA-43 | CCAAGTGTTGGATTGTTCA (SEQ ID NO: 65) | 6126 | 2240 | 1 | 7 | 8 |
| HJT-sRNA-44 | GGTCATCGCGCTTGGTTGA (SEQ ID NO: 66) | 18171 | 9379 | 3 | 9 | 9 |

TABLE 8-continued

List of small RNA sequences in HJT decoctosome.

| Column 1 | Sequence | Decoction | Decoctosome | Control | 0 h | 60 h |
| --- | --- | --- | --- | --- | --- | --- |
| HJT-sRNA-45 | TGCCGGCCGGGGGACGGA (SEQ ID NO: 67) | 26430 | 10501 | 0 | 7 | 5 |
| HJT-sRNA-46 | GTTAAGCGTGCTTGGGCGA (SEQ ID NO: 68) | 10017 | 5458 | 0 | 5 | 7 |
| HJT-sRNA-47 | ACTCGACGGATCGCACGGC (SEQ ID NO: 69) | 14872 | 12327 | 0 | 6 | 5 |
| HJT-sRNA-48 | CTGGTCGATGGAACAATGT (SEQ ID NO: 70) | 3808 | 2992 | 0 | 5 | 6 |
| HJT-sRNA-49 | TGCTTTTTGATCCTTCGATG (SEQ ID NO: 71) | 9523 | 2830 | 0 | 5 | 5 |
| HJT-sRNA-50 | TTGGGTGCGAGAGGTCCCGGGT (SEQ ID NO: 72) | 1113 | 535 | 866 | 1135 | 1108 |
| HJT-sRNA-51 | CCTGGGAAGTCCTCGTGTTGCACCCCT (SEQ ID NO: 73) | 7539 | 6007 | 1 | 42 | 33 |
| HJT-sRNA-52 | TTCTCGGCCTTTTGGCTAAGA (SEQ ID NO: 74) | 657 | 199 | 10 | 28 | 30 |
| HJT-sRNA-53 | CATAACGACTCTCGGCAACGGATA (SEQ ID NO: 75) | 14450 | 8944 | 7 | 27 | 21 |
| HJT-sRNA-54 | ATTGTGAAGCAGAATTCACC (SEQ ID NO: 76) | 99 | 39 | 193 | 215 | 170 |
| HJT-sRNA-55 | TGCACCGGATCCCATCAGA (SEQ ID NO: 77) | 2971 | 2051 | 0 | 8 | 5 |
| HJT-sRNA-56 | CCTTAACGAGGATCCATT (SEQ ID NO: 78) | 3331 | 630 | 2 | 5 | 6 |
| HJT-sRNA-57 | ATTGGTCATCGCGCTTGG (SEQ ID NO: 79) | 12495 | 5966 | 3 | 5 | 7 |
| HJT-sRNA-58 | CACGGACCAAGGAGTCTG (SEQ ID NO: 80) | 1071 | 637 | 4 | 6 | 7 |
| HJT-sRNA-59 | TTAGGGTTCGATTCCGGA (SEQ ID NO: 81) | 15336 | 2974 | 6 | 10 | 5 |

TABLE 9

List of small RNA sequences in PGY decoctosome.

| Column 1 | Sequence | TZ | Decoctosome | Ctrl | 0 h | 55 h |
| --- | --- | --- | --- | --- | --- | --- |
| PGY-sRNA-33 | CCCGAGAGAGGGGCCCGT (SEQ ID NO: 82) | 147 | 95 | 784 | 1259 | 45148 |

TABLE 9-continued

List of small RNA sequences in PGY decoctosome.

| Column 1 | Sequence | TZ | Decoctosome | Ctrl | 0 h | 55 h |
|---|---|---|---|---|---|---|
| PGY-sRNA-34 | GGGGTGCGAGAGGTCCCG (SEQ ID NO: 83) | 411 | 80 | 2942 | 4643 | 25291 |
| PGY-sRNA-35 | TGGGGTGCGAGAGGTCCC (SEQ ID NO: 84) | 405 | 78 | 2687 | 4281 | 23813 |
| PGY-sRNA-36 | TTGGGGTGCGAGAGGTCC (SEQ ID NO: 85) | 411 | 95 | 2538 | 3885 | 21700 |
| PGY-sRNA-37 | TGGGTGCGAGAGGTCCCG (SEQ ID NO: 86) | 677 | 268 | 899 | 1671 | 11667 |
| PGY-sRNA-38 | TTGGGTGCGAGAGGTCCC (SEQ ID NO: 40) | 687 | 269 | 866 | 1600 | 11472 |
| PGY-sRNA-39 | GGGTTGCGAGAGGTCCCG (SEQ ID NO: 87) | 136 | 53 | 1001 | 1661 | 8788 |
| PGY-sRNA-40 | TTGGGTTGCGAGAGGTCC (SEQ ID NO: 88) | 144 | 51 | 860 | 1398 | 7574 |
| PGY-sRNA-41 | TTGGTTGCGAGAGGTCCC (SEQ ID NO: 89) | 191 | 52 | 246 | 443 | 3125 |
| PGY-sRNA-42 | TCTGAACTCTGAACTCCAGTCA (SEQ ID NO: 90) | 1238 | 18306 | 1 | 13 | 377 |
| PGY-sRNA-43 | GGTGCGAGAGGTCCCGAG (SEQ ID NO: 91) | 276 | 317 | 14 | 25 | 161 |
| PGY-sRNA-44 | GTGCGAGAGGTCCCGAGT (SEQ ID NO: 92) | 337 | 517 | 14 | 24 | 145 |
| PGY-sRNA-45 | CAAGGAAGGCAGCAGGCG (SEQ ID NO: 93) | 1200 | 1957 | 338 | 356 | 409 |
| PGY-sRNA-46 | GCGACCCCAGGTCAGGCG (SEQ ID NO: 94) | 79325 | 88783 | 3 | 15 | 5 |
| PGY-sRNA-47 | AGGCTGGGTGTGGAAGTG (SEQ ID NO: 95) | 146 | 644 | 1 | 7 | 9 |
| PGY-sRNA-48 | TCGTGTCGTGAGATGTTG (SEQ ID NO: 96) | 620 | 1862 | 1 | 6 | 8 |
| PGY-sRNA-49 | CGCCCCGAGAGAGGGGCCCGTG (SEQ ID NO: 97) | 147 | 95 | 784 | 1259 | 45148 |
| PGY-sRNA-50 | TTGGGGTGCGAGAGGTCCCGGGT (SEQ ID NO: 98) | 411 | 80 | 2942 | 4643 | 25291 |
| PGY-sRNA-51 | TTGGGTGCGAGAGGTCCCGGGT (SEQ ID NO: 72) | 677 | 268 | 899 | 1671 | 11667 |
| PGY-sRNA-52 | TTGGTTGCGAGAGGTCCCGGGT (SEQ ID NO: 99) | 191 | 52 | 246 | 443 | 3125 |

TABLE 9-continued

List of small RNA sequences in PGY decoctosome.

| Column 1 | Sequence | TZ | Decoctosome | Ctrl 0 h | 55 h |
|---|---|---|---|---|---|
| PGY-sRNA-53 | ATCCAAGGAAGGCAGCAGGCG (SEQ ID NO: 100) | 1200 | 1957 | 338 356 | 409 |
| PGY-sRNA-54 | CAGAGTTCTACAGTCCGA (SEQ ID NO: 21) | 8227 | 122940 | 967 1051 | 3115 |

The technical solutions of the present application can significantly improve the high-efficiency targeted delivery of nucleic acids, and overcome the shortcomings in the prior art nucleic acid liposome, including low encapsulation rate, poor safety, poor stability, complicated manufacture process, heterogeneity in product, low reproducibility, and the targeting to be improved.

TABLE 10

List of synthetic lipids

| No. | Manufacturer | Catalogue # | Abbreviation | Working Concentration (mg/mL) |
|---|---|---|---|---|
| 1 | Avanti | 110882 | DG(18:0/18:0/0:0) | 5 |
| 2 | Avanti | 110883 | DG(18:0/16:0/0:0) | 5 |
| 3 | Avanti | 800816C | DG(16:0/16:0/0:0) | 10 |
| 4 | Avanti | 860627P | C18 Dihydroceramide (d18:0/18:0) | 10 |
| 6 | Avanti | 110613 | TG(18:1/18:1/18:1) | 1 |
| 8 | Avanti | 850756C | PE(16:0/18:2) | 10 |
| 9 | Avanti | 110521 | TG(16:0/16:0/18:1) | 5 |
| 10 | Avanti | 111000 | TG(16:0/16:0/16:0) | 10 |
| 11 | Avanti | 850468 | PC(18:0/18:2) | 10 |
| 12 | Avanti | 850458C | PC(16:0/18:2) | 10 |
| 13 | Avanti | 111002 | TG(18:2/18:2/18:2) | 10 |
| 14 | Avanti | 860634P | C16 Dihydroceramide (d18:0/16:0) | 5 |
| 15 | Sigma | P8577 | TG(16:0/18:1/18:2) | 1 |
| 16 | Nu-chek | T-160 | TG(18:0/18:0/18:0) | 1 |
| 17 | Matreya | 1326 | So(d16:0) | 1 |
| 18 | Sigma | D1782 | TG(16:0/18:1/18:1) | 5 |
| 19 | Larodan | 32-1656-7 | DG(16:0/18:2) | 5 |
| 20 | Larodan | 34-1603-7 | TG(16:0/16:0/18:2) | 5 |
| 21 | Larodan | 34-1862-7 | TG(16:0/18:2/18:2) | 5 |
| 22 | Larodan | 34-3003-7 | TG(18:0/16:0/18:1) | 5 |
| 23 | Larodan | 34-1822-7 | TG(18:0/18:1/18:1) | 5 |
| 24 | Larodan | 34-3007-7 | TG(18:0/18:1/18:2) | 5 |
| 25 | Larodan | 34-1827-7 | TG(18:1/18:1/18:2) | 5 |
| 26 | Larodan | 34-1828-7 | TG(18:1/18:1/18:3) | 5 |
| 27 | Larodan | 34-1866-7 | TG(18:1/18:2/18:2) | 5 |
| 28 | Larodan | 34-1855-7 | TG(18:3/18:2/18:2) | 5 |
| 29 | Larodan | 10-1840-4 | FA(18:4) | 5 |
| 30 | Avanti | 110748 | Sphinganine (d18:0) | 5 |
| 31 | Avanti | 110749 | Sphinganine (d20:0) | 1 |
| 32 | Avanti | 110520 | TG(18:0/16:0/16:0) | 5 |
| 33 | Larodan | 34-1810-7 | TG(18:0/16:0/18:0) | 10 |
| 34 | Larodan | 31-1820-7 | MG(18:2p) | 10 |
| 35 | nu-chek | D-251 | DG(18:2/18:2) | 10 |
| 36 | Larodan | 38-1802-0 | LPC(18:2) | 10 |
| 37 | avanti | 791251 | LPC(18:3) | 10 |
| 38 | avanti | 791016 | PE(16:0/16:1) | 10 |
| 39 | avanti | 792077C | 16:1-18:1 PE | 10 |
| 40 | avanti | 792078C | 16:0-22:1 PE | 10 |
| 41 | avanti | 792079P | Sphinganine(d22:0) | 10 |
| 42 | Larodan | 31-2220 | MG(22:2) | 10 |
| 43 | Larodan | 32-1658 | DG(16:0/18:3) | 10 |
| 44 | Larodan | 34-1289 | TG(18:1/18:1/20:4) | 10 |
| 45 | Larodan | 34-1870 | DG(18:3/18:2) | 10 |
| 46 | Larodan | 32-1871 | DG(20:5/18:2) | 10 |
| 47 | Larodan | 34-1880 | TG(18:3/18:2/18:3) | 10 |
| 48 | Larodan | 34-2230 | TG(18:1/22:1/22:1) | 10 |
| 49 | Larodan | 34-3031 | TG(16:0/16:1/18:1) | 10 |
| 50 | Larodan | 34-3032 | TG(16:0/18:1/18:3) | 10 |
| 51 | Larodan | 34-3033 | TG(16:0/18:1/20:4) | 10 |
| 52 | Larodan | 34-3034 | TG(18:3/18:2/20:5) | 10 |
| 53 | Avanti | 792143 | Cer(d16:0/16:0) | 10 |
| 54 | Avanti | 792144 | Cer(d20:0/18:0) | 10 |
| 55 | Avanti | 792145 | Cer(d22:0/18:0) | 10 |
| 56 | Avanti | 792146 | TG(16:0/18:2/18:3) | 10 |
| 57 | Avanti | 792147 | TG(18:1/18:2/18:3) | 10 |
| 58 | Avanti | 792150 | PEt(16:1/16:1) | 10 |
| 59 | Avanti | 792151 | dMePE(16:1/14:0) | 10 |
| 60 | Avanti | 792152 | dMePE(16:1/16:1) | 10 |
| 61 | Avanti | 792153 | dMePE(18:1/14:0) | 10 |
| 62 | Avanti | 792154 | dMePE(16:1/18:1) | 10 |
| 63 | Avanti | 792156 | PC(18:0/18:3(6Z,9Z,12Z)) | 10 |
| 64 | Avanti | 792155 | PE(15:0/24:1(15Z)) | 10 |
| 65 | Avanti | 792157 | PC(20:0/14:1(9Z)) | 10 |
| 66 | Avanti | 792160 | TG(18:0/18:2/18:3) | 10 |
| 67 | Avanti | 792148 | TG(18:1/18:2/20:5) | 10 |
| 68 | Avanti | 792149 | TG(20:5/18:2/18:2) | 10 |
| 69 | Avanti | 792158 | PC(18:1(11Z)-16:1(9Z)) | 10 |
| 70 | Larodan | 32-1830-7 | DG(18:3/18:3) | 25 |
| 71 | Larodan | 37-1620-7 | PE(16:0/16:0) | 25 |

TABLE 11

Description of lipids 1-32.

| No. | Abbreviation | IUPAC name | Structure |
|---|---|---|---|
| 1 | DG(18:0/18:0/0:0) | (2S)-1-hydroxy-3-(octadecanoyloxy)propan-2-yl octadecanoate | 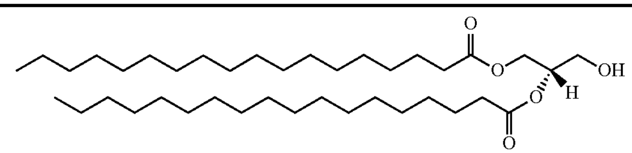 |
| 2 | DG(18:0/16:0/0:0) | (2S)-2-(hexadecanoyloxy)-3-hydroxypropyl octadecanoate | 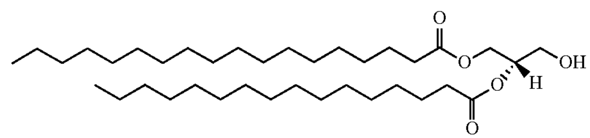 [SMILES: CCCCCCCCCCCCCCCCCC(=O)OC[C@H](CO)OC(=O)CCCCCCCCCCCCCCC] |
| 3 | DG(16:0/16:0/0:0) | (2S)-1-(hexadecanoyloxy)-3-hydroxypropan-2-yl hexadecanoate | 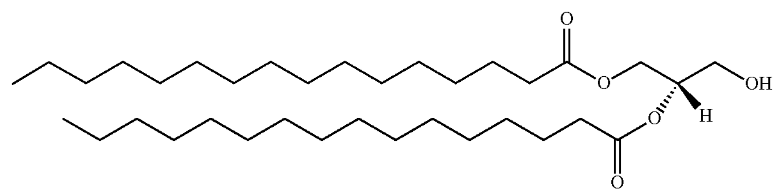 [SMILES: CCCCCCCCCCCCCCCC(=O)OC[C@H](CO)OC(=O)CCCCCCCCCCCCCCC] |
| 4 | C18 Dihydroceramide (d18:0/18:0) | N-[(2S,3R)-1,3-dihydroxyoctadecan-2-yl]octadecanamide | 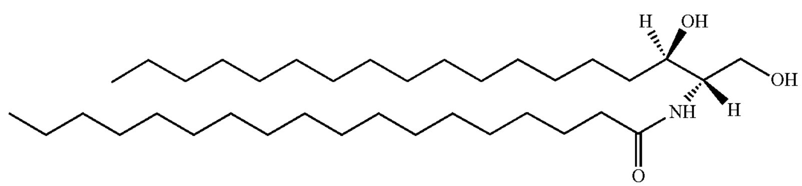 [SMILES: CCCCCCCCCCCCCCCCCC(=O)N[C@@H](CO)[C@H](O)CCCCCCCCCCCCCCC] |
| 6 | TG(18:1/18:1/18:1) | 1,3-bis[(9Z)-octadec-9-enoyloxy]propan-2-yl (9Z)-octadec-9-enoate | 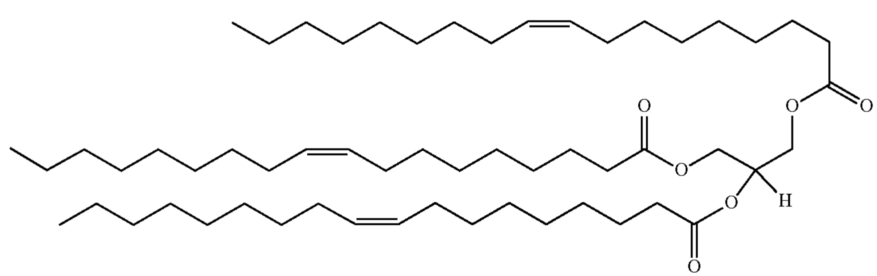 [SMILES: CCCCCCCC/C=C\CCCCCCCC(=O)OCC(COC(=O)CCCCCCC/C=C\CCCCCCCC)OC(=O)CCCCCCC/C=C\CCCCCCCC] |

TABLE 11-continued

Description of lipids 1-32.

| No. | Abbreviation | IUPAC name | Structure |
|---|---|---|---|
| 8 | PE(16:0/18:2) | (2-aminoethoxy)[(2R)-3-(hexadecanoyloxy)-2-[(9Z,12Z)-octadeca-9,12-dienoyloxy]propoxy]phosphinic acid | 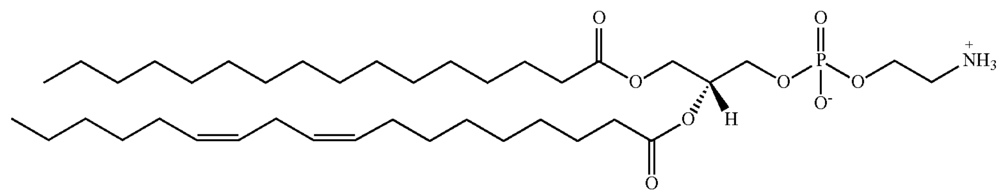 [SMILES: CCCCC/C=C\C/C=C\CCCCCCCC(=O)O[C@H](COC(=O)CCCCCCCCCCCCCCC)COP(=O)([O-])OCCN] |
| 9 | TG(16:0/16:0/18:1) | (2R)-2,3-bis(hexadecanoyloxy)propyl (9Z)-octadec-9-enoate | 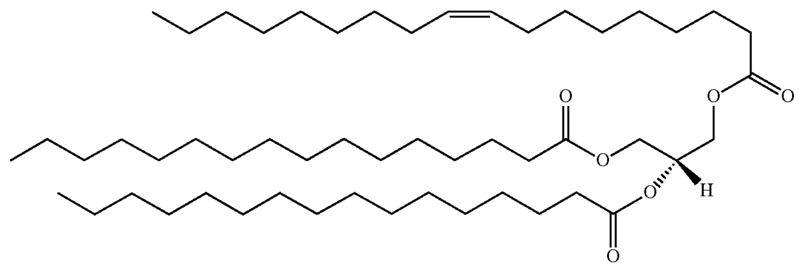 [SMILES: CCCCCCCC/C=C\CCCCCCCC(=O)OC[C@@H](COC(=O)CCCCCCCCCCCCCCC)OC(=O)CCCCCCCCCCCCCCC] |
| 10 | TG(16:0/16:0/16:0) | 1,3-bis(hexadecanoyloxy)propan-2-yl hexadecanoate | 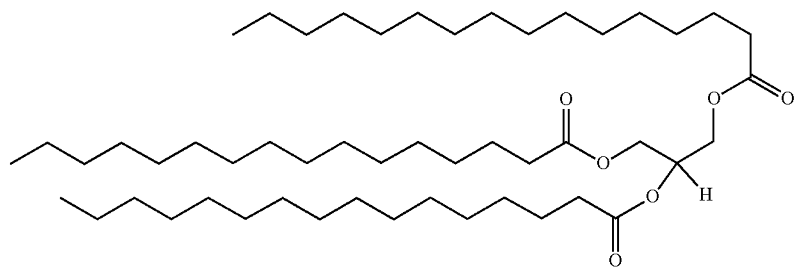 [SMILES: CCCCCCCCCCCCCCCC(=O)OCC(COC(=O)CCCCCCCCCCCCCCC)OC(=O)CCCCCCCCCCCCCCC] |
| 11 | PC(18:0/18:2) | trimethyl(2-{[(2R)-2-[(9Z,12Z)-octadeca-9,12-dienoyloxy]-3-(octadecanoyloxy)propyl phosphonato]oxy}ethyl)azanium | 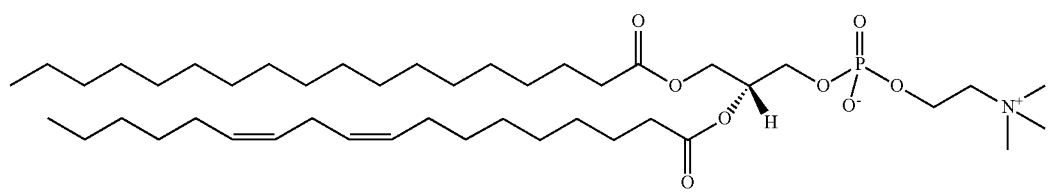 [SMILES: CCCCC/C=C\C/C=C\CCCCCCCC(=O)O[C@H](COC(=O)CCCCCCCCCCCCCCCCC)COP(=O)([O-])OCC[N+](C)(C)C] |

TABLE 11-continued
Description of lipids 1-32.
| No. | Abbreviation | IUPAC name | Structure |
|---|---|---|---|
| 12 | PC(16:0/18:2) | (2-{[(2R)-3-(hexadecanoyloxy)-2-[(9Z,12Z)-octadeca-9,12-dienoyloxy]propyl phosphonato]oxy}ethyl)trimethyl-azanium | 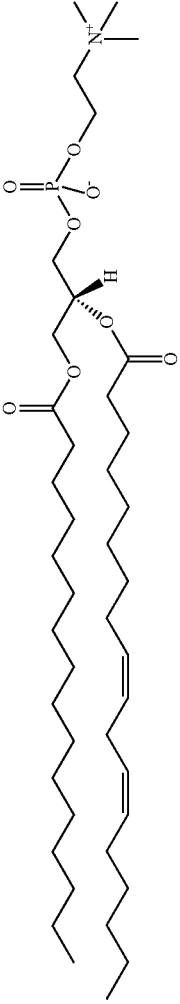 |
| 13 | TG(18:2/18:2/18:2) | 1,3-bis[(9Z,12Z)-octadeca-9,12-dienoyloxy]propan-2-yl (9Z,12Z)-octadeca-9,12-dienoate | 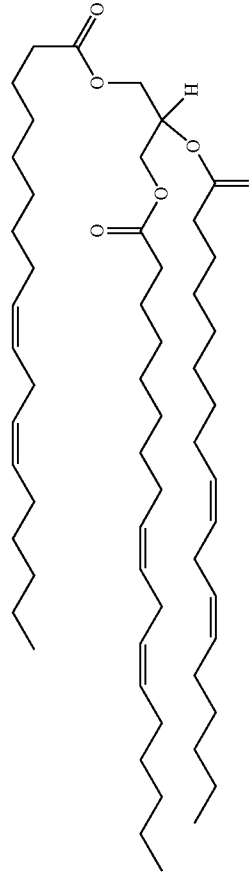 |
| 14 | C16 Dihydroceramide (d18:0/16:0) | N-[(2S,3R)-1,3-dihydroxy-octadecan-2-yl]hexadecanamide | 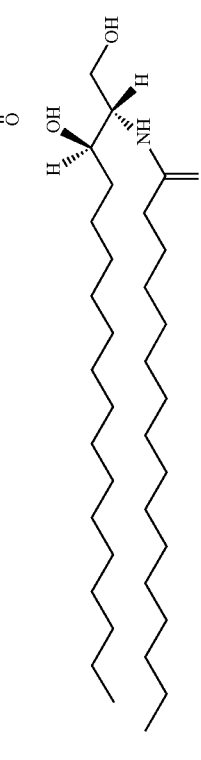 |

TABLE 11-continued
Description of lipids 1-32.
| No. | Abbreviation | IUPAC name | Structure |
|---|---|---|---|
| 15 | TG(16:0/18:1/18:2) | 1-Palmitoyl-2-oleoyl-3-linoleoyl-rac-glycerol | 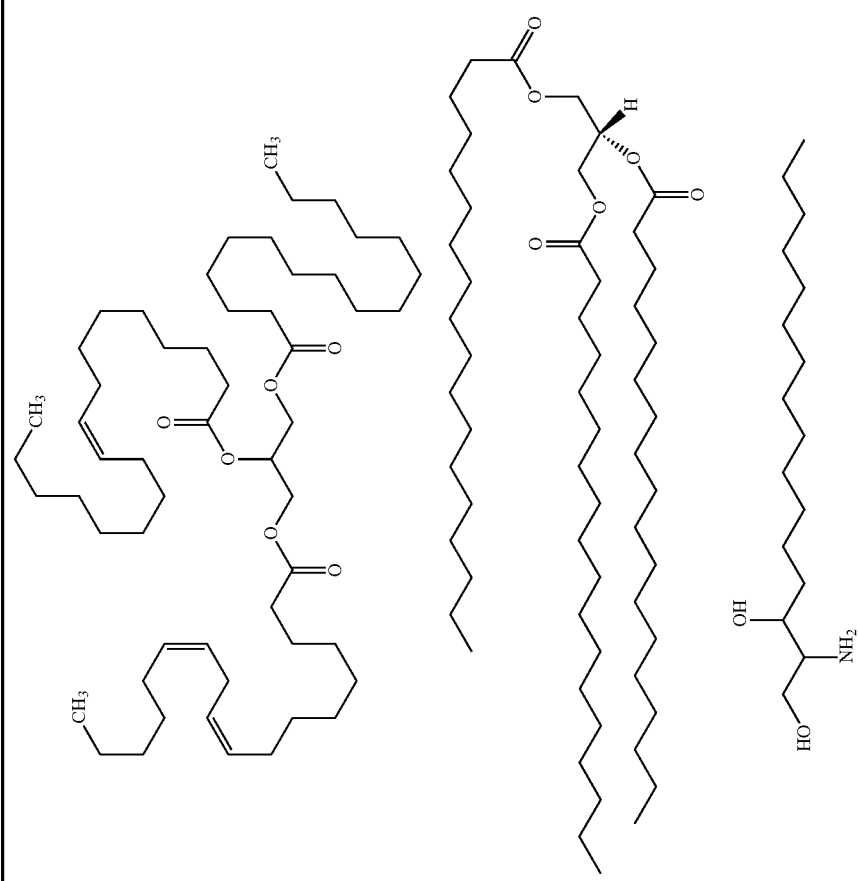 |
| 16 | TG(18:0/18:0/18:0) | 1,3-bis(octadecanoyloxy)propan-2-yl octadecanoate | 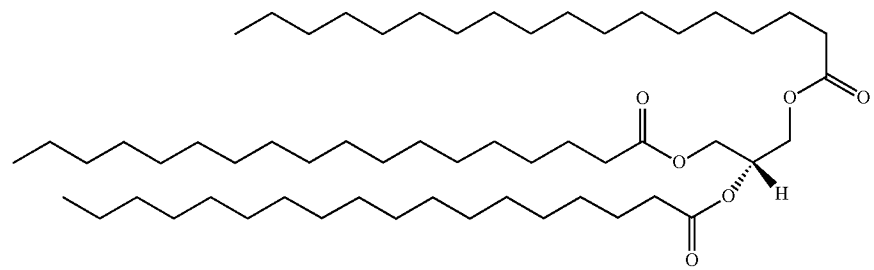 |
| 17 | So(d16:0) | D,L-2-Amino-hexadecane-1,3-diol | 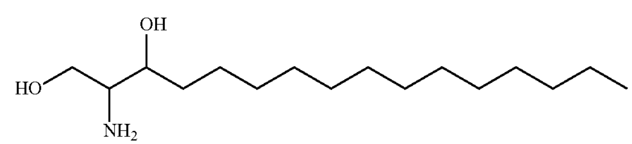 [SMILES: CCCCCCCCCCCCCC(O)C(N)CO] |

TABLE 11-continued

Description of lipids 1-32.

| No. | Abbreviation | IUPAC name | Structure |
|---|---|---|---|
| 18 | TG(16:0/18:1/18:1) | 1,2-Di(cis-9-octadecenoyl)-3-hexadecanoyl-rac-glycerol | 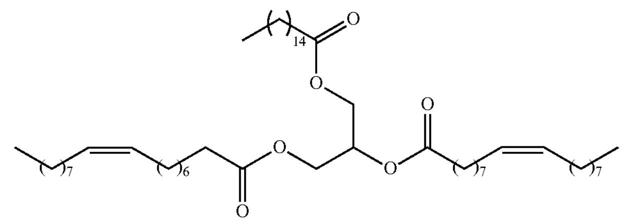 |
| 19 | DG(16:0/18:2) | 1-Palmitoyl-3-Linoleoyl-sn-glycerol | 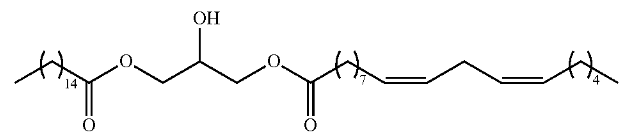 |
| 20 | TG(16:0/16:0/18:2) | 1,2-Palmitoyl-3-Linoleoyl-sn-glycerol | 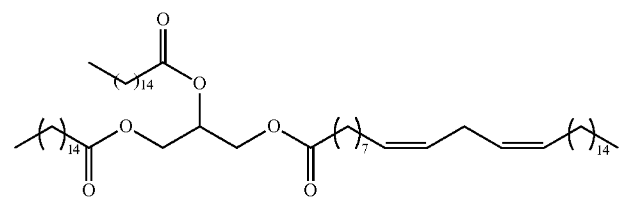 |
| 21 | TG(16:0/18:2/18:2) | 1,2-Linoleoyl-3-Palmitoyl-sn-glycerol | 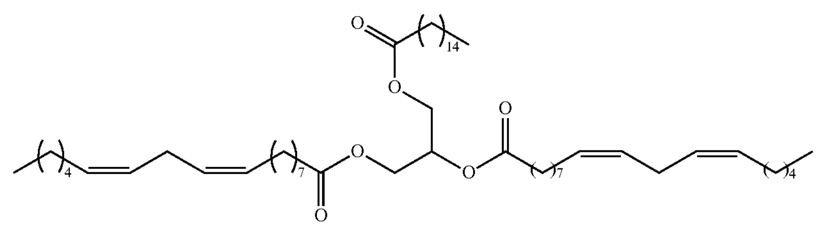 |
| 22 | TG(18:0/16:0/18:1) | 1-Stearoyl-2-Palmitoyl-3-Oleoyl-sn-glycerol | 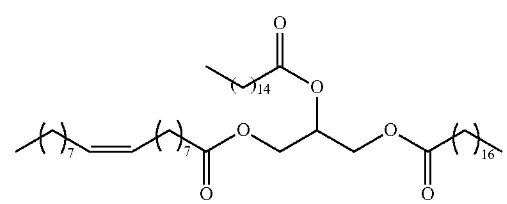 |

TABLE 11-continued
Description of lipids 1-32.
| No. | Abbreviation | IUPAC name | Structure |
|---|---|---|---|
| 23 | TG(18:0/18:1/18:1) | 1,2-olein-3-stearin | 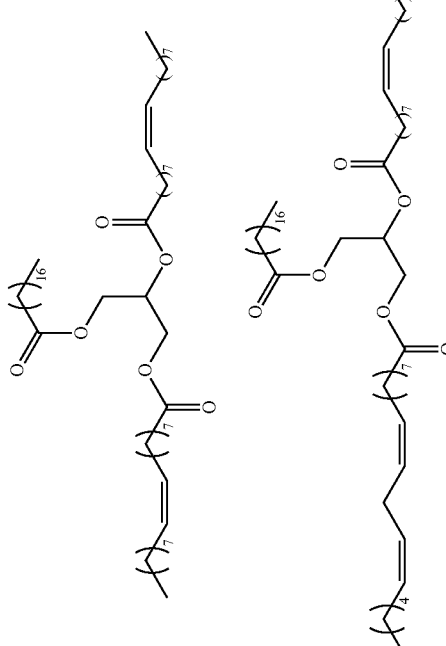 |
| 24 | TG(18:0/18:1/18:2) | 1-Stearoyl-2-Oleoyl-3-Linoleoyl-sn-glycerol | 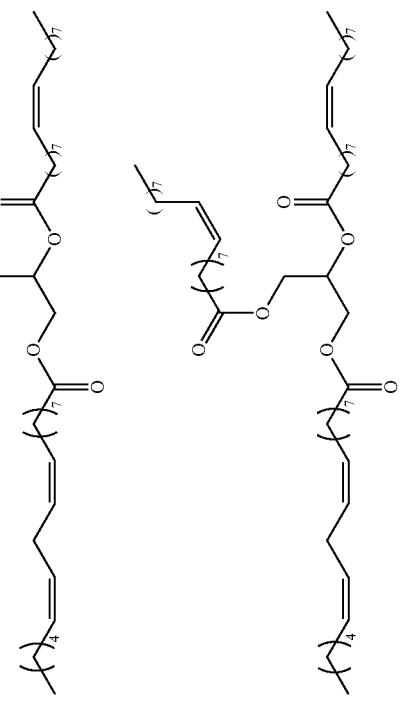 |
| 25 | TG(18:1/18:1/18:2) | 1,2-Oleoyl-3-Linoleoyl-sn-glycerol | 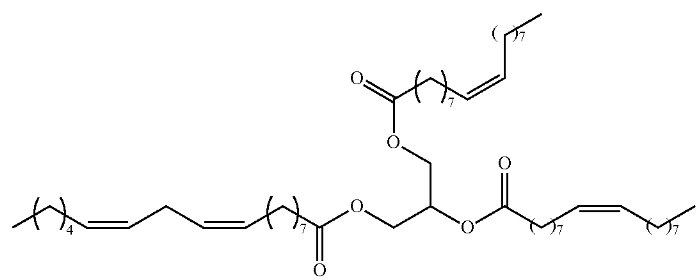 |

TABLE 11-continued

Description of lipids 1-32.

| No. | Abbreviation | IUPAC name | Structure |
|---|---|---|---|
| 26 | TG(18:1/ 18:1/18:3) | 1,2-Oleoyl-3-Linolenoyl-sn-glycerol | 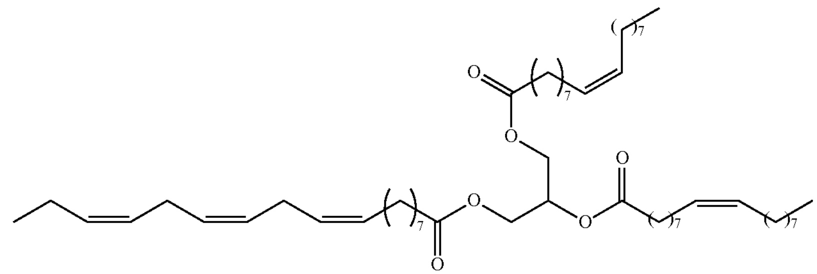 |
| 27 | TG(18:1/ 18:2/18:2) | 1,2-Linoleoyl-3-Oleoyl-sn-glycerol | 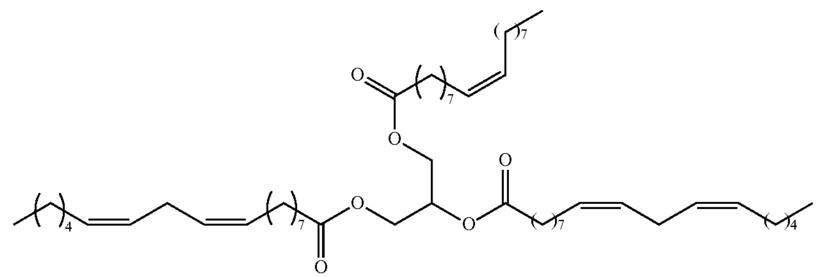 |
| 28 | TG(18:3/ 18:2/18:2) | 1,2-Linoleoyl-3-Linolenoyl-sn-glycerol | 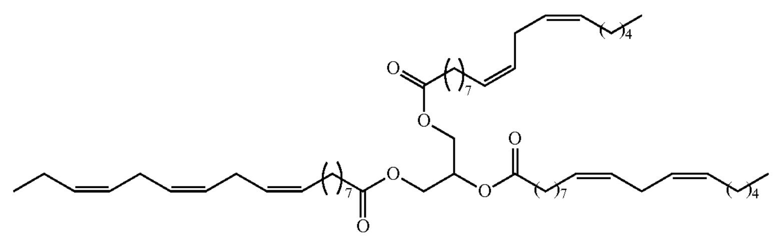 |
| 29 | FA(18:4) | 6c,9c,12c,15c-Octadecatetraenoic Acid | 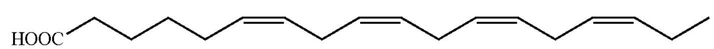 [SMILES: CC/C=C\C/C=C\C/C=C\C/C=C\CCCCC(=O)O] |

TABLE 11-continued

Description of lipids 1-32.

| No. | Abbreviation | IUPAC name | Structure |
|---|---|---|---|
| 30 | Sphinganine (d18:0) | (2S,3R)-2-aminooctadecane-1,3-diol | 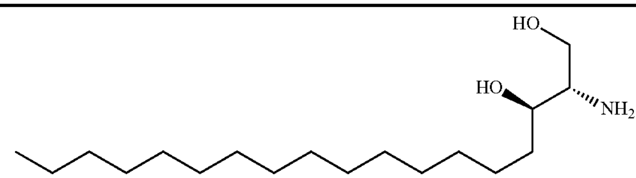 |
| 31 | Sphinganine (d20:0) | (2S,3R)-2-amino-1,3-eicosanediol | 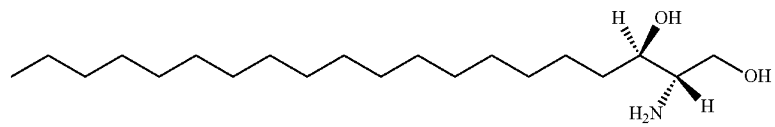 [SMILES: CCCCCCCCCCCCCCCCC[C@@H](O)[C@@H](N)CO] |
| 32 | TG(18:0/16:0/16:0) | (2R)-2,3-bis(hexadecanoyloxy)propyl octadecanoate | 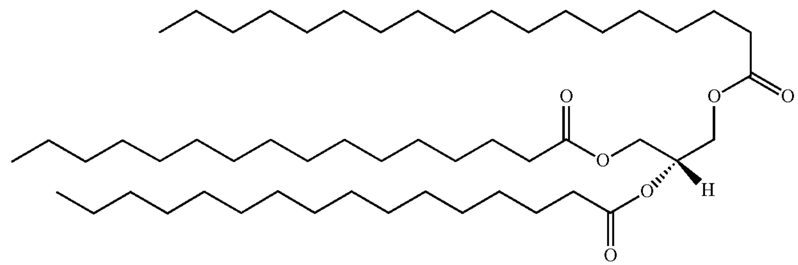 [SMILES: CCCCCCCCCCCCCCCCCC(=O)OC[C@@H](COC(=O)CCCCCCCCCCCCCCC)OC(=O)CCCCCCCCCCCCCCC] |

TABLE 12

Description of lipids 33-71.

| No. | Abbreviation | IUPAC Name | Structure |
|-----|--------------|------------|-----------|
| 33 | TG(18:0/16:0/18:0) | 1,3-Stearin-2-Palmitin 1,3-Octadecanoyl-2-Palmitoyl-glycerol | 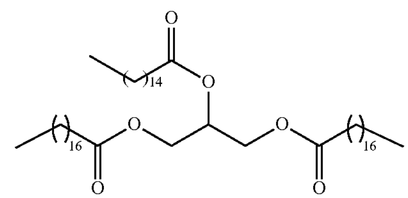 |
| 34 | MG(18:2p) | (9Z,12Z)-Octadeca-9,12-dienoic acid, monoester with glycerol 9,12-Octadecadienoic acid (9Z,12Z)-, monoester with 1,2,3-propanetriol 9,12-Octadecadienoic acid, (Z,Z)-, monoester with 1,2,3-propanetriol | |
| 35 | DG(18:2/18:2) | (2S)-1-hydroxy-3-[(9Z,12Z)-octadeca-9,12-dienoyloxy]propan-2-yl (9Z,12Z)-octadeca-9,12-dienoate, | 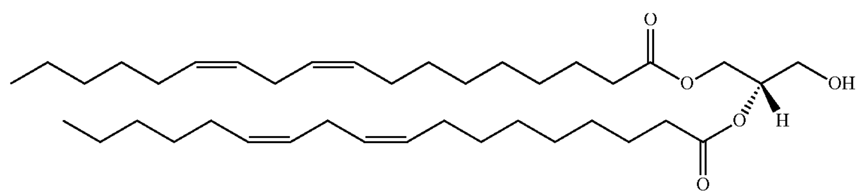 [SMILES: CCCCC/C=C\C/C=C\CCCCCCCC(=O)OC[C@H](CO)OC(=O)CCCCCCC/C=C\C/C=C\CCCCC] |
| 36 | LPC(18:2) | 1-Linoleoyl-2-Hydroxy-sn-Glycero-3-Phosphatidylcholine | 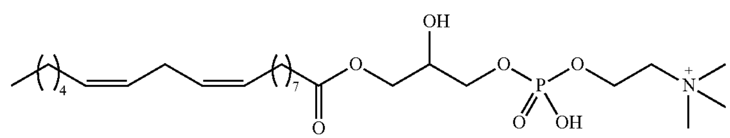 |
| 37 | LPC(18:3) | (2-{[(2R)-2-hydroxy-3-[(9Z,12Z,15Z)-octadeca-9,12,15-trienoyloxy]propyl phosphonato]oxy}ethyl)trimethylazanium | 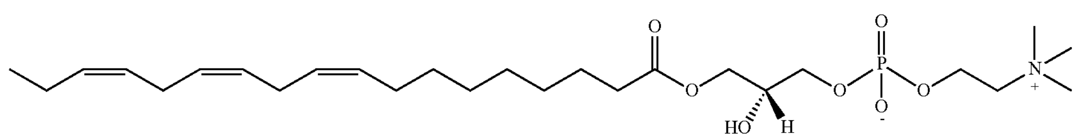 |

TABLE 12-continued

Description of lipids 33-71.

| No. | Abbreviation | IUPAC Name | Structure |
|---|---|---|---|
| 38 | PE(16:0/16:1) | (2-aminoethoxy)[(2R)-2-[(9Z)-hexadec-9-enoyloxy]-3-(hexadecanoyloxy)propoxy]phosphinic acid | 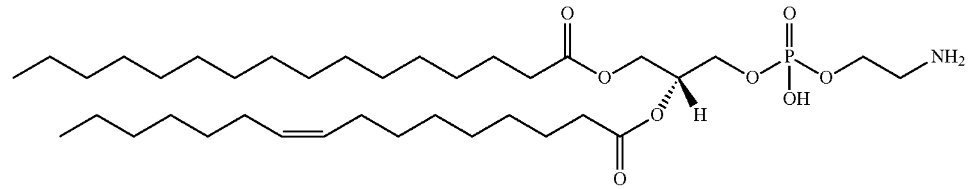 [SMILES: CCCCCC/C=C\CCCCCCCC(=O)O[C@H](COC(=O)CCCCCCCCCCCCCCC)COP(=O)(O)OCCN] |
| 39 | 16:1-18:1PE | (2-aminoethoxy)[(2R)-3-[(9Z)-hexadec-9-enoyloxy]-2-[(11Z)-octadec-11-enoyloxy]propoxy]phosphinic acid | 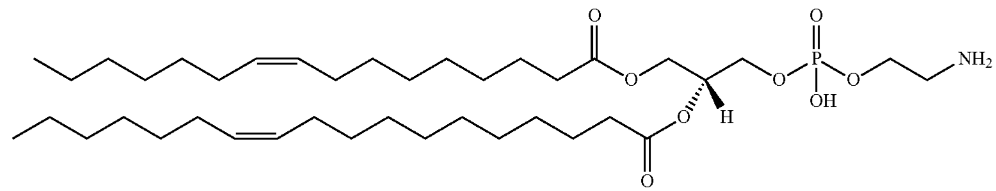 [SMILES: CCCCCC/C=C\CCCCCCCCCC(=O)O[C@H](COC(=O)CCCCCCC/C=C\CCCCCC)COP(=O)(O)OCCN] |
| 40 | 16:0-22:1 PE | (2-aminoethoxy)[(2R)-2-[(13Z)-docos-13-enoyloxy]-3-(hexadecanoyloxy)propoxy]phosphinic acid | 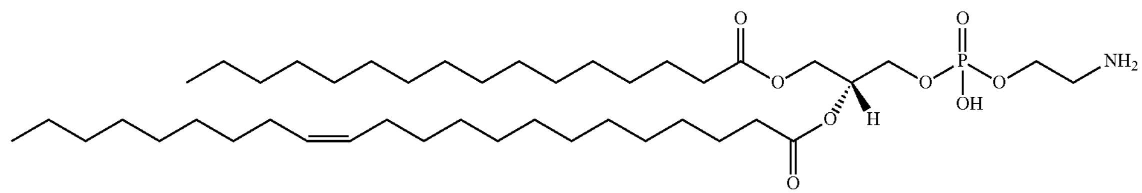 [SMILES: CCCCCCCC/C=C\CCCCCCCCCCCC(=O)O[C@H](COC(=O)CCCCCCCCCCCCCCC)COP(=O)(O)OCCN] |
| 41 | Sphinganine(d22:0) | | 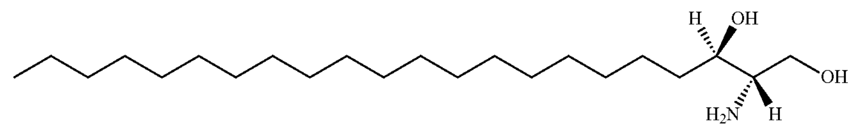 [SMILES: CCCCCCCCCCCCCCCCCCC[C@@H](O)[C@@H](N)CO] |
| 42 | MG(22:2) | Monodocosadienoin | 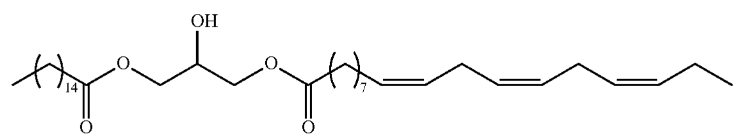 |
| 43 | DG(16:0/18:3) | 1-Palmitin-3-Linolenin | 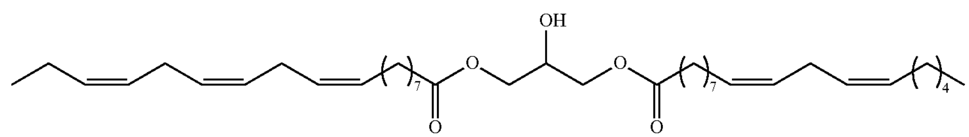 |

TABLE 12-continued

Description of lipids 33-71.

| No. | Abbreviation | IUPAC Name | Structure |
|---|---|---|---|
| 44 | TG(18:1/18:1/20:4) | 1,2-Olein-3-Arachidonin (5Z,8Z,11Z,14Z) | 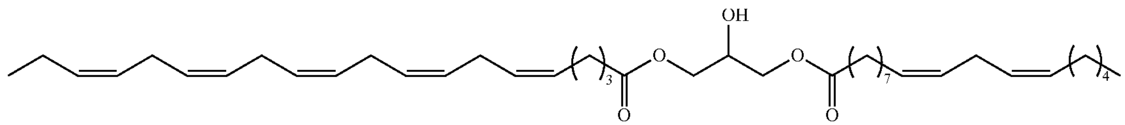 |
| 45 | DG(18:3/18:2) | 1-Linolein-3-Linolenin | 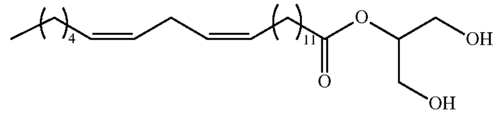 |
| 46 | DG(20:5/18:2) | 1-EPA-3-Linolein | 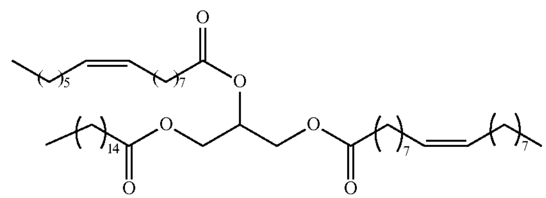 |
| 47 | TG(18:3/18:2/18:3) | 1,3-Linolenin-2-Linolein | 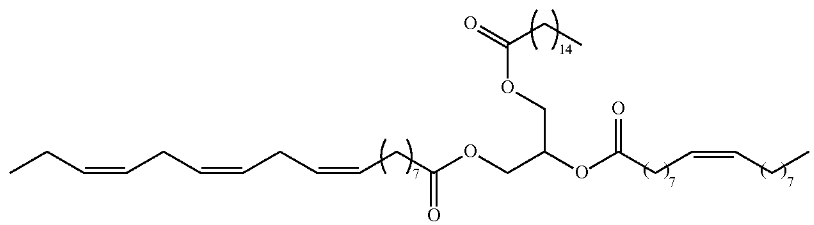 |

TABLE 12-continued

Description of lipids 33-71.

| No. | Abbreviation | IUPAC Name | Structure |
|---|---|---|---|
| 48 | TG(18:1/22:1/22:1) | 1,2-Erucin(13Z)-3-Olein | 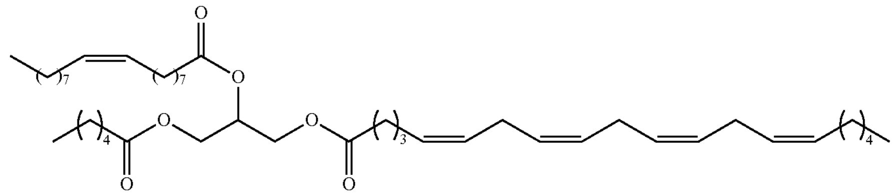 |
| 49 | TG(16:0/16:1/18:1) | 1-Palmitin-2-Palmitolein-3-Olein | 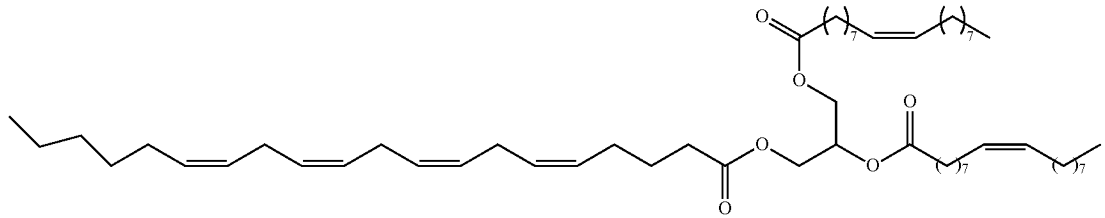 |
| 50 | TG(16:0/18:1/18:3) | 1-Palmitin-2-Olein-3-Linolenin | 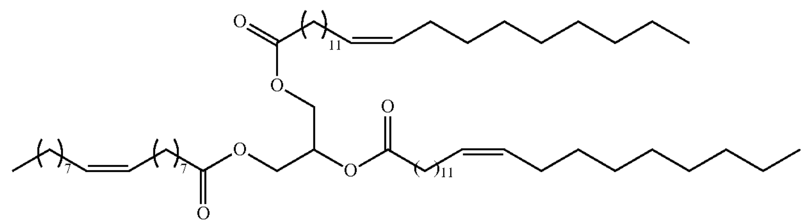 |
| 51 | TG(16:0/18:1/20:4) | 1-Palmitin-2-Olein-3-Arachidonin (5Z,8Z,11Z,14Z) | 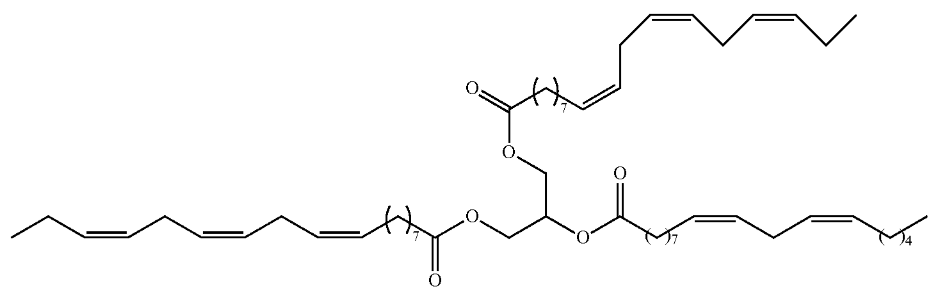 |

TABLE 12-continued

Description of lipids 33-71.

| No. | Abbreviation | IUPAC Name | Structure |
|---|---|---|---|
| 52 | TG(18:3/18:2/20:5) | 1-Linolenin-2-Linolein-3-EPA | 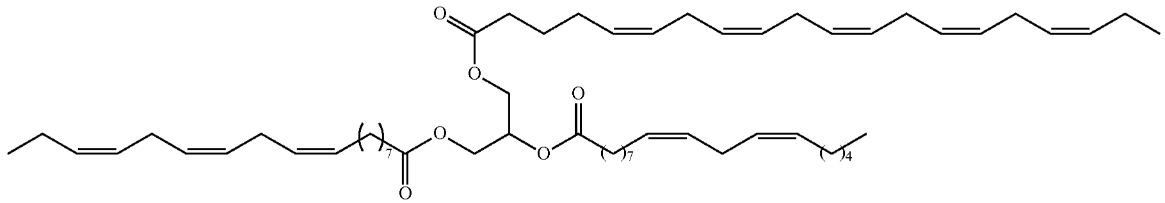 |
| 53 | Cer(d16:0/16:0) | C16 dihydroceramide (d16:0/16:0) | 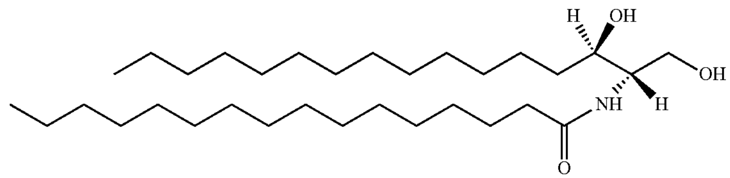 [SMILES: CCCCCCCCCCCCCCCC(=O)N[C@@H](CO)[C@H](O)CCCCCCCCCCCCC] |
| 54 | Cer(d20:0/18:0) | C18 dihydroceramide (d20:0/18:0) | 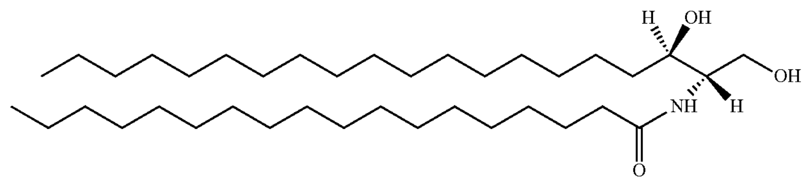 [SMILES: CCCCCCCCCCCCCCCCCC(=O)N[C@@H](CO)[C@H](O)CCCCCCCCCCCCCCCCC] |
| 55 | Cer(d22:0/18:0) | C18 dihydroceramide (d22:0/18:0) | 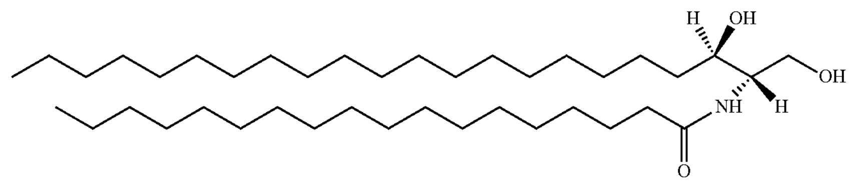 [SMILES: CCCCCCCCCCCCCCCCCCC[C@@H](O)[C@H](CO)NC(=O)CCCCCCCCCCCCCCCCC] |

TABLE 12-continued
Description of lipids 33-71.
| No. | Abbreviation | IUPAC Name | Structure |
|---|---|---|---|
| 56 | TG(16:0/18:2/18:3) | Triglyceride (16:0/18:2/18:3) | 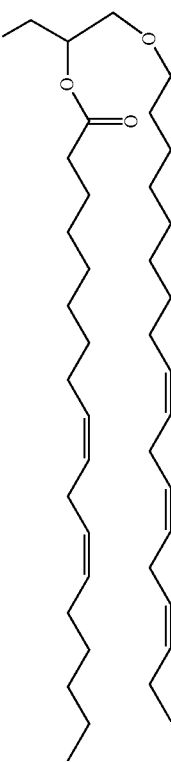 |
| 57 | TG(18:1/18:2/18:3) | Triglyceride (18:1/18:2/18:3) | 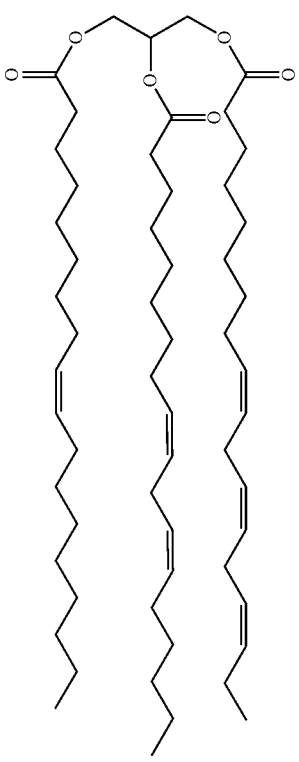 |
| 58 | PEt(16:1/16:1) | 1,2-dipalmitoleoyl-sn-glycero-3-phosphoethanol | 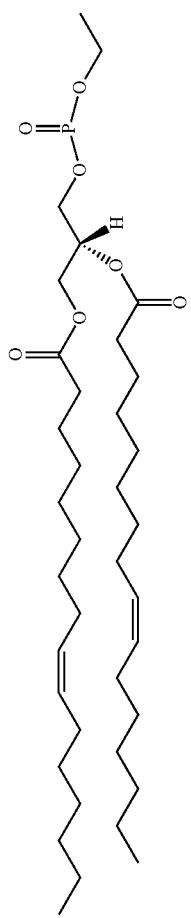 |
| 59 | dMePE(16:1/14:0) | 1-palmitoleoyl-2-myristoyl-sn-glycero-3-phosphoethanolamine-N,N-dimethyl | 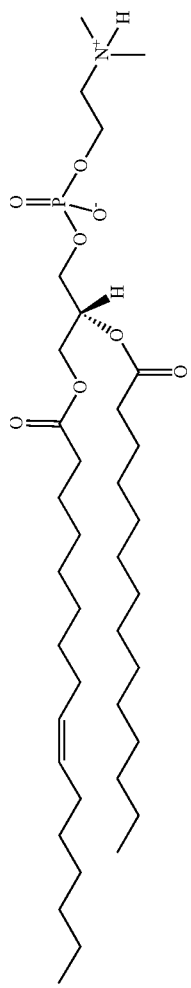 |

TABLE 12-continued

Description of lipids 33-71.

| No. | Abbreviation | IUPAC Name | Structure |
|---|---|---|---|
| 60 | dMePE(16:1/16:1) | 1,2-dipalmitoleoyl-sn-glycero-3-phosphoethanolamine-N,N-dimethyl | 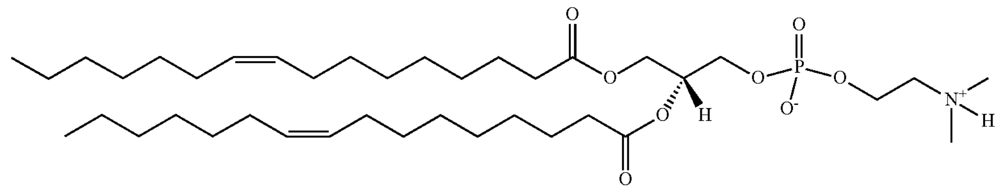 [SMILES: CCCCCC/C=C\CCCCCCCC(=O)OC[C@H](COP(=O)([O-])OCC[NH+](C)C)OC(=O)CCCCCCC/C=C\CCCCCC] |
| 61 | dMePE(18:1/14:0) | 1-oleoyl-2-myristoyl-sn-glycero-3-phosphoethanolamine-N,N-dimethyl | 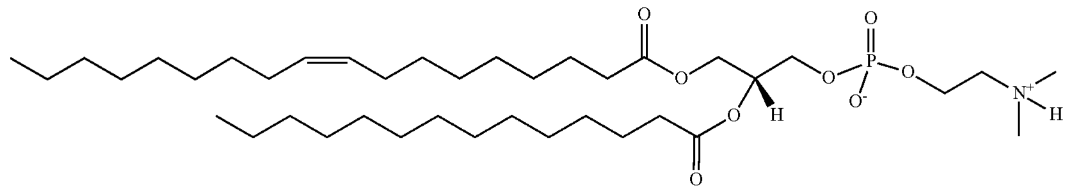 [SMILES: CCCCCCCC/C=C\CCCCCCCC(=O)OC[C@H](COP(=O)([O-])OCC[NH+](C)C)OC(=O)CCCCCCCCCCCCC] |
| 62 | dMePE(16:1/18:1) | 1-palmitoleoyl-2-oleoyl-sn-glycero-3-phosphoethanolamine-N,N-dimethyl | 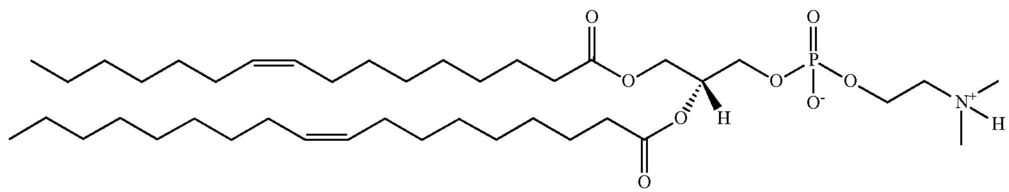 [SMILES: CCCCCC/C=C\CCCCCCCC(=O)OC[C@H](COP(=O)([O-])OCC[NH+](C)C)OC(=O)CCCCCCC/C=C\CCCCCCCC] |
| 63 | PC(18:0/18:3(6Z,9Z,12Z)) | 1-stearoyl-2-linolenoyl(gamma)-sn-glycero-3-phosphocholine | 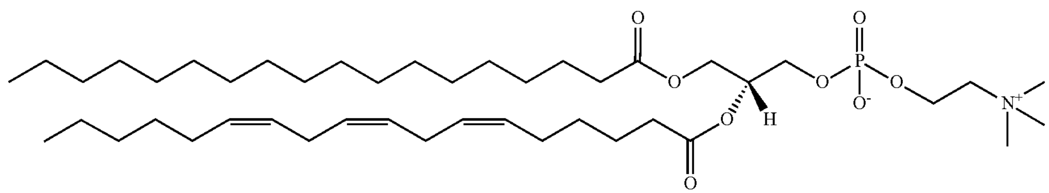 [SMILES: CCCCC/C=C\C/C=C\C/C=C\CCCCC(=O)O[C@H](COC(=O)CCCCCCCCCCCCCCCCC)COP(=O)([O-])OCC[N+](C)(C)C] |
| 64 | PE(15:0/24:1(15Z)) | 1-pentadecanoyl-2-nervonoyl-sn-glycero-3-phosphoethanolamine | 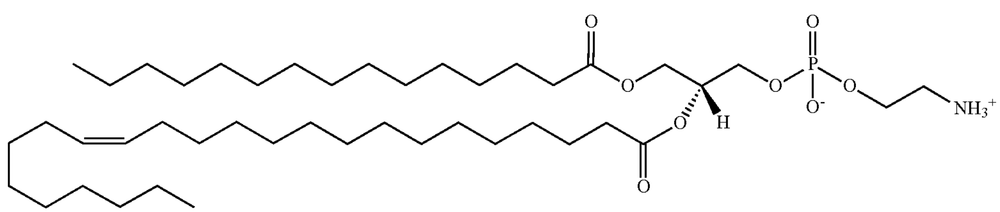 [SMILES: CCCCCCCC/C=C\CCCCCCCCCCCCCC(=O)O[C@H](COC(=O)CCCCCCCCCCCCCC)COP(=O)([O-])OCC[NH3+]] |

TABLE 12-continued

Description of lipids 33-71.

| No. | Abbreviation | IUPAC Name | Structure |
|---|---|---|---|
| 65 | PC(20:0/14:1(9Z)) | 1-eicosanoyl-2-myristoleoyl-sn-glycero-3-phosphocholine | 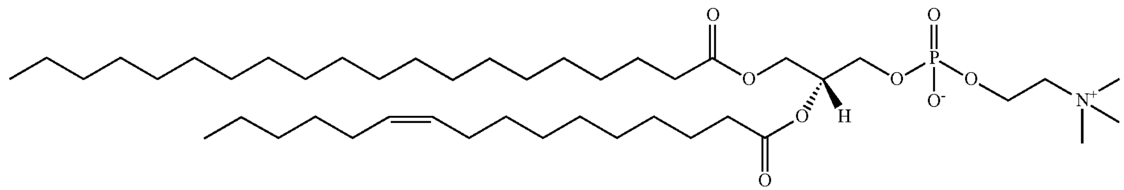 [SMILES: CCCCC/C=C\CCCCCCCCC(=O)O[C@H](COC(=O)CCCCCCCCCCCCCCCCCCC)COP(=O)([O-])OCC[N+](C)(C)C] |
| 66 | TG(18:0/18:2/18:3) | Triglyceride (18:0/18:2/18:3) | 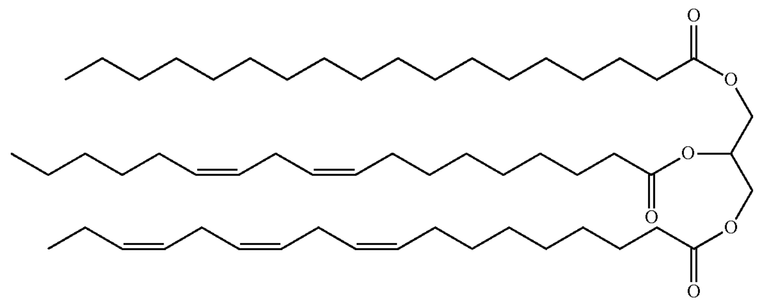 [SMILES: CC/C=C\C/C=C\C/C=C\CCCCCCCC(=O)OCC(COC(=O)CCCCCCCCCCCCCCCCC)OC(=O)CCCCCCC/C=C\C/C=C\CCCCC] |
| 67 | TG(18:1/18:2/20:5) | Triglyceride (18:1/18:2/20:5) | 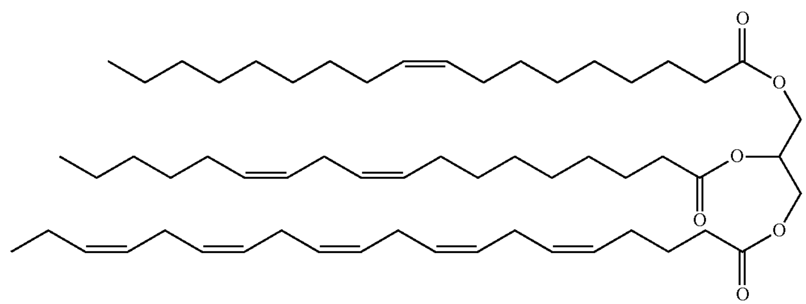 [SMILES: CC/C=C\C/C=C\C/C=C\C/C=C\C/C=C\CCCC(=O)OCC(COC(=O)CCCCCCC/C=C\CCCCCCCC)OC(=O)CCCCCCC/C=C\C/C=C\CCCCC] |

TABLE 12-continued

Description of lipids 33-71.

| No. | Abbreviation | IUPAC Name | Structure |
|---|---|---|---|
| 68 | TG(20:5/18:2/18:2) | Triglyceride (20:5/18:2/18:2) | 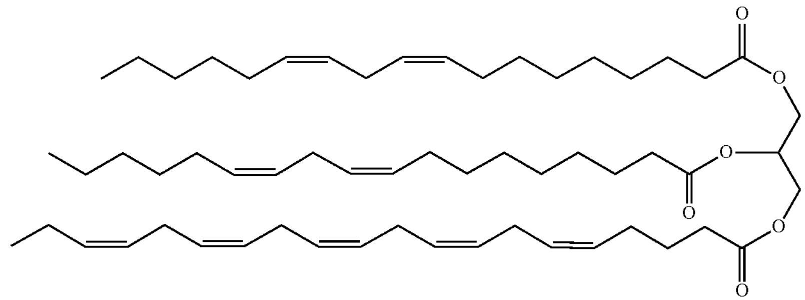 [SMILES: CC/C=C\C/C=C\C/C=C\C/C=C\C/C=C\CCCC(=O)OCC(COC(=O)CCCCCCC/C=C\C/C=C\CCCCC)OC(=O)CCCCCCC/C=C\C/C=C\CCCCC] |
| 69 | PC(18:1(11Z)-16:1(9Z)) | 1-vaccenoyl-2-palmitoleoyl-sn-glycero-3-phosphocholine | 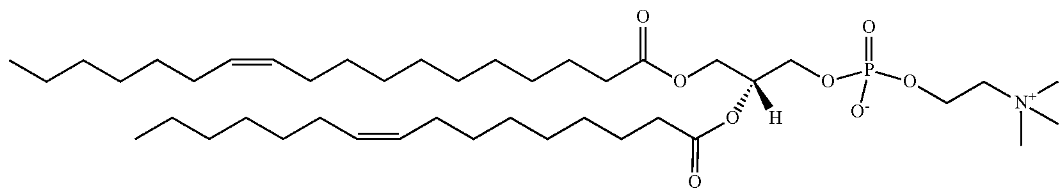 [SMILES: CCCCCC/C=C\CCCCCCCCCC(=O)OC[C@H](COP(=O)([O-])OCC[N+](C)(C)C)OC(=O)CCCCCCC/C=C\CCCCCC] |
| 70 | DG(18:3/18:3) | Dilinolenin | 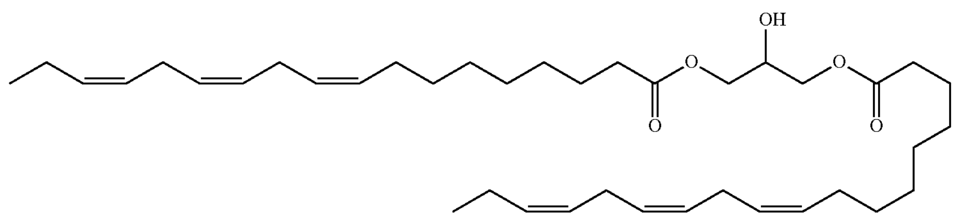 [SMILES: CC/C=C\C/C=C\C/C=C\CCCCCCCC(=O)OCC(O)COC(=O)CCCCCCC/C=C\C/C=C\C/C=C\CC] |
| 71 | PE(16:0/16:0) | 1,2-Dipalmitoyl-sn-Glycero-3-Phosphatidyl-ethanolamine | 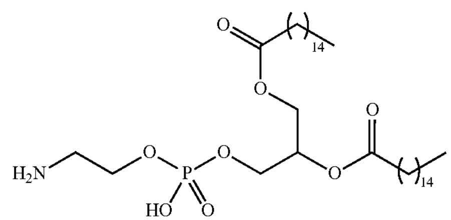 |

Definition of Terms

Decoctosome: a nanoparticulate substance derived from the plant decoction, having a thermally stable, exosome-like membrane structure and composed of lipids, proteins, nucleic acids, compounds and the like. In the present application, the decoctosome can also be referred to as an active composition with a membrane structure, preferably an active combination prepared by the method of the foregoing embodiments 10-13.

Bencaosome: Artificially prepared nano-particulate substance with membrane structure. The membrane structure includes one or more lipid components, which are characterized by being derived from chemical synthesis or chemical separation and purification, and include but not limited to the lipids shown in Table 1 or Table 10 or lipids having 70% or more similarity with those shown in Table 1 or Table 10 (the lipid similarity is defined by the following method: having the same parent structure), and has an impurity content less than 5%. The lipids are mixed with any one or more of the following: one or more nucleic acids, one or more compounds, and one or more macromolecules. Bencaosome is a nano-particulate substance with a membrane structure prepared by heating lipids and other substances including one or more nucleic acids, one or more compounds, and/or one or more macromolecules. In this application, bencaosome can also be referred to as an active composition with a membrane structure, preferably an active composition prepared by the method of the foregoing embodiments 1-2, 5-9 or 20-28.

The one or more lipid components can be synthesized or purified, including but not limited to the lipids shown in Table 1 or Table 10; the one or more nucleic acid components can be synthesized or purified, including but not limited to the RNA shown in Table 8, 9 or 13; the one or more compounds can be synthesized or purified, including but not limited to the compounds shown in Table 2 to Table 5; the one or more macromolecular components can be synthesized or purified, including but not limited to the proteins shown in Table 6 or Table 7.

The term "reverse evaporation method" as described herein refers to adding an aqueous solution of nucleic acids/macromolecules/compounds to a solution of lipid in organic solvent, ultrasonicating, evaporating to remove the organic solvent, and then hydrating to obtain a mixture of lipid and nucleic acids/macromolecules/compounds.

The term "boiling method" (also refers to "heating method") as described herein refers to adding a solution of lipid in an organic solvent to an aqueous solution of nucleic acids/macromolecules/compounds and boiling at about 90° C. for 15 minutes to obtain a mixture of lipid and nucleic acids/macromolecules/compounds. The method is not limited to heating in water bath, and other means for raising temperature or heating known in the art can also be used.

The reverse evaporation method and boiling method are carried out under controlled temperature and mixing conditions. Suitable processing time and temperature can be readily determined by a person skilled in the art. For example, the temperature for reverse evaporation method preferably ranges from about 25° C. to about 70° C., more preferably from about 30° C. to about 65° C., and more preferably from about 40° C. to about 60° C., especially about 55° C. The temperature for boiling method preferably ranges from about 0° C. to about 100° C., more preferably from about 50° C. to about 100° C., and more preferably from about 70° C. to about 90° C., especially preferably from about 80° C. to 90° C.

The nucleic acid as described herein includes synthetic and purified DNA and RNA, preferably RNA, more preferably small RNA, for example, the small RNA having a length of 14-32 bp, 16-28 bp, 18-24 bp, and particularly, a length of 14, 15, 16, 17, 18, 19, 20, 21, 22, 23, 24, 25, 26, 27, 28, 29, 30, 31, 32 bp.

The inventor has surprisingly found that various lipids can form lipid-nucleic acids/macromolecules/compounds mixtures that effectively promote cellular absorption and entry of nucleic acid, which has the potential to increase the efficiency of clinical delivery of the nucleic acid drug. Further studies have shown that the lipid nucleic acid mixture of the present application promotes the efficiency of nucleic acid absorption and entry into cells in different cell lines, but differences were observed in different cell lines, which provides the possibility of targeted drug delivery. Moreover, such lipid nucleic acid mixtures show no sequence selectivity in nucleic acid delivery, and could deliver nucleic acid fragments having different sequences and sizes corresponding to small RNA (e.g. about 20 bp). In addition, confocal laser-scanning microscopy confirmed that the lipid nucleic acid mixture formed by artificially synthetic lipids can effectively promote the entry of exogenous nucleic acids into cytoplasm. The inventor has unexpectedly discovered that lipid nucleic acid mixtures prepared by boiling method or reverse evaporation method can facilitate entry of nucleic acids, such as RNA, into blood circulation and target tissues via non-invasive routes (e.g. via digestive tract, respiratory tract and topical administration). The inventor has also surprisingly discovered that lipids of the present application are capable of promoting entry of nucleic acids, such as RNA, into cells and modulating (e.g., inhibiting) the expression of their target sequences, while not exhibiting such modulating effects on non-target sequences, suggesting a target-specific modulating effect, which can be used as a mean for the delivery of nucleic acid drug.

Lipid compounds of the present application are selected from the group consisting of lysolecithin, ceramide, diglyceride, phosphatidylethanolamine, phosphatidylcholine, triglyceride, monogalactosyl diglycerides, sphingosine, phosphatidyl ethanol, monoacylglycerol, fatty acid, platelet activating factor, or dimethyl phosphatidyl ethanolamine. In one embodiment, the lipid is non-natural, e.g. synthetic, or manufactured from fermentation.

Synthesized or purified lipids can be used to deliver nucleic acids/macromolecules/compounds into a target cell. The lipid can be used to deliver nucleic acids/macromolecules/compounds into a subject in need thereof and into its blood circulation and/or a target site/cell.

Synthesized or purified lipid can be selected from phosphatidylcholine, e.g., 1-stearoyl-2-oleoyl-sn-glycerol-3-phosphocholine (PC(18:0/18:2), i.e., lipid No. 11 in Table 1), and 1-palmitoyl-2-oleoyl-sn-glycerol-3-phosphocholine (PC(16:0/18:2), i.e., lipid No. 12 in Table 1). These two phosphocholines (PCs) are capable of efficiently encapsulating nucleic acids or promoting entry of nucleic acids into cells. The lipid may be lipid No. 41 in Table 1, i.e. sphinganine (d22:0), which is capable of efficiently encapsulating nucleic acids or promoting entry of nucleic acids into cells.

The present application provides compositions comprising lipids and nucleic acids, macromolecules, compounds provided herein, preferably the nucleic acid is small RNA.

The composition can be prepared for administration via non-invasive routes (e.g., topical administration) and/or injection, e.g., administration via digestive tract, respiratory tract, and/or injection, e.g., oral administration, inhalation and/or injection. In some instances, invasive routes are preferably used (e.g., injection, including intramuscular, subcutaneous, intravenous, intraarterial, intraperitoneal, and injection into a target tissue). In other instances, non-invasive routes are preferably used.

In the compositions, at least part of or all of the lipids and nucleic acids can be prepared into the form of lipid nucleic acid mixture. Various methods for preparing the lipid nucleic acid mixtures have been widely disclosed, and the suitable methods for preparing the lipid nucleic acid mixture can be selected according to actual needs.

The present application provides kits comprising the lipids and nucleic acids described herein, wherein the lipids and the nucleic acids are each independently provided in a first container and a second container. The first container and the second container may be the same or different. In some embodiments, at least part of or all of the lipids and the nucleic acids are prepared into lipid nucleic acid mixtures immediately prior to use.

The present application provides methods of delivering a nucleic acid, macromolecule, and compound into a target tissue/cell, wherein the nucleic acid, macromolecule, compound are provided in a form of a pharmaceutical composition or the kit as described herein.

The present application provides methods of in vivo delivering a nucleic acid, macromolecule, compound into a subject in need thereof, wherein the nucleic acid is provided in a form of a pharmaceutical composition or the kit as described herein, for example, in vivo delivering the nucleic acid into blood circulation or a target tissue/cell of the subject, e.g., wherein the lipid and the nucleic acid are administrated via non-invasive routes (e.g., topical administration) and/or injection, e.g., via digestive tract, respiratory tract and/or injection, e.g., by oral administration, inhalation and/or injection.

The present application provides methods of preventing and/or treating a disease/disorder that can be prevented and/or treated with decoctosome and bencaosome, comprising providing the pharmaceutical composition or the kit described herein to a subject in need thereof, for example wherein the lipid and the nucleic acid are administered via non-invasive routes (e.g., topical administration) and/or by injection, e.g., via digestive tract, respiratory tract and/or injection, e.g., by oral administration, inhalation and/or injection. Surprisingly, the administration via non-invasive routes (e.g., via digestive tract, respiratory tract, including oral administration, gavage, inhalation and the like) can significantly promote the entry and efficacy of nucleic acids.

The present application provides methods for the manufacture of the pharmaceutical composition or the kit, and use of the pharmaceutical composition and/or the kit in the methods described in the above aspects. Besides, also provides lipids, pharmaceutical compositions and/or kits for use in the various methods described above.

The nucleic acid can be a small RNA, for example, the small RNA may have a length of 14-32 bp, 16-28 bp, 18-24 bp, in particular, a length of 14, 15, 16, 17, 18, 19, 20, 21, 22, 23, 24, 25, 26, 27, 28, 29, 30, 31, 32 bp. In addition, the small RNA may be single-stranded, e.g., having a stem-loop structure, or double-stranded. For example, the nucleic acid may be HJT-sRNA-m7 having a sequence of ugagguagua gguugugugg uuguaagc.

The compositions or the kits or the compounds of the present application can be used for treating a disease, such as cancer, e.g., gastric cancer, lung cancer, colorectal cancer, liver cancer, pancreatic cancer, cervical cancer, breast cancer, leukemia, multiple myeloma; such as inflammation, such as pneumonia, myocarditis, acute and chronic gastritis, acute and chronic enteritis, acute and chronic hepatitis, acute and chronic nephritis, dermatitis, encephalitis, Lymphitis, conjunctivitis, keratitis, iridocyclitis, otitis media, allergic rhinitis, asthma, pulmonary fibrosis, chronic obstructive pulmonary disease, allergic dermatitis, sickle cell disease, multiple sclerosis, systemic lupus erythematosus, lupus nephritis; and fibrosis etc.

The compositions or the kits or the compounds of the present application can be used for treatment in vitro or in vivo, for example, to inhibit the growth of NCI-N87 cell (gastric cancer cell), MRC-5 cell (lung fibroblast) and A549 cell (lung cancer cell).

In various embodiments of the present application, the lipid nucleic acid mixture can be obtained by a variety of methods, e.g., reverse evaporation method or boiling method. In the reverse evaporation method, an aqueous solution of nucleic acid is added to a solution of lipid in an organic solvent, ultrasonicated, evaporated to remove the organic solvent, and then hydrated to obtain a lipid nucleic acid mixture. The boiling method described in the present application refers to adding a solution of lipid in an organic solvent to an aqueous solution of nucleic acid and boiling at about 100° C. for 30 minutes to obtain a lipid nucleic acid mixture. The reverse evaporation method and the boiling method are carried out under controlled temperature and mixing conditions. Suitable processing times and temperatures can be readily determined by a person skilled in the art. For example, the temperature of reverse evaporation method can range preferably from about 25° C. to about 70° C., more preferably from about 30° C. to about 65° C., more preferably from about 40° C. to about 60° C., especially preferably about 55° C. The temperature of the boiling method (also referred to as heating) can range preferably from about 25° C. to about 100° C., more preferably from about 50° C. to about 100° C., more preferably from about 70° C. to about 90° C., especially preferably about 90° C.

Exemplary embodiments of the present application include, but are not limited to, the following:

Embodiment 1. A method for preparing a bencaosome, comprising the steps of:
(3) mixing one or more lipid components with any one or more of the following: one or more nucleic acids, one or more compounds and/or one or more macromolecules;
preferably, the one or more lipid components are synthesized or purified, such as include lipids selected from those shown in Table 1 or Table 10;
(4) treating the obtained mixture by heating,
wherein the heating temperature is preferably from about 0° C. to about 100° C., more preferably from about 50° C. to about 100° C., and more preferably from about 70° C. to about 90° C., in particular preferably from about 80° C. to about 90° C., preferably 90° C.;
preferably, the time for heating is about 0 minute to about 24 hours, about 5 minutes to about 20 hours, about 10 minutes to about 16 hours, about 30 minutes to about 12 hours, about 1 hour to about 8 hours, or about 0.5 hour to about 4 hours, preferably 5 minutes to 30 minutes;
preferably, the mixing is performed by adding a solution of the lipid components in an organic solvent into an aqueous solution of the nucleic acid, macromolecule and/or compound;
preferably, the organic solvent includes alcohols, ethers, and benzenes, preferably chloroform, ethyl ether, methanol, or ethanol;

preferably, the aqueous solution is selected from the group consisting of aqueous buffers, saline solutions, aqueous solutions of organic solvents and water;

preferably, wherein the bencaosome is a nano-particulate substance with a membrane structure, preferably a nanoparticulate substance with a double layered membrane structure;

preferably, wherein the bencaosome is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 2. The method of embodiment 1, wherein the lipid is Sphinganine (d22:0), and/or the small RNA is PGY-sRNA-6 or HJT-sRNA-m7, wherein preferably, the Sphinganine (d22:0) is used as 10 mg/ml chloroform solution, lipid: sRNA=0.1-20 μg:0.1 nmol;

wherein preferably, the bencaosome has a Zeta potential of less than 60 mV, less than 50 mV, less than 0, −80 to −20, or −60 to −20, and has an average particle size of 50-1000, 90-300 or 100-200 nm.

Embodiment 3. The bencaosome prepared by the method of embodiment 1 or 2, preferably used in one or more of the following:

(9) lowering the expression of fibronectin and/or alpha-SMA, preferably the protein expression of fibronectin in MRC-5 cells fibrosis model induced by TGF-beta1;

(10) reducing hydroxyproline, preferably the hydroxyproline in pulmonary fibrosis model, preferably the hydroxyproline in pulmonary fibrosis model of mice;

(11) preventing or treating fibrosis, preferably pulmonary fibrosis, preferably in the fibrosis model of MRC-5 cells induced by TGF-beta1 or the fibrosis model of mice induced by Bleomycin;

(12) lowering IL-1beta, IL-6 and/or TNF-alpha, preferably the IL-1beta, IL-6 and/or TNF-alpha in A549 cells model induced by poly(I:C);

(13) lowering the level of IL-1alpha, IL-1b, IL-2, IL-3, IL-4, IL-5, IL-6, IL-9, IL-10, IL-12 p40, IL-12 p70, IL-13, IL-17A, GM-CSF, IFN-gamma or MCP-1beta, preferably the level of plasma, preferable in an inflammation model of mouse;

(14) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and

(15) enabling small RNA to enter cells efficiently; and/or

(16) lowering the expression of RELA genes;

preferably, the bencaosome lowers the expression of fibrosis-associated protein fibronectin and alpha-SMA, and/or lowers the expression of IL-1beta, IL-6 and/or TNF-alpha, preferably the expression level of IL-1beta, IL-6 and/or TNF-alpha in A549 cells model induced by poly(I:C).

Embodiment 4. Use of the bencaosome of embodiment 3 in one or more of the following, or use of the bencaosome of embodiment 3 in manufacture of medicament for use in one or more of the following, or methods for using the bencaosome of embodiment 3 in one or more of the following:

(9) lowering the expression of fibronectin and/or alpha-SMA, preferably the protein expression of fibronectin in MRC-5 cells fibrosis model induced by TGF-beta1;

(10) reducing hydroxyproline, preferably the hydroxyproline in pulmonary fibrosis model, preferably the hydroxyproline in pulmonary fibrosis model of mice;

(11) preventing or treating fibrosis, preferably pulmonary fibrosis, preferably in the fibrosis model of MRC-5 cells induced by TGF-beta1 or the fibrosis model of mice induced by Bleomycin;

(12) lowering IL-1beta, IL-6 and/or TNF-alpha, preferably the IL-1beta, IL-6 and/or TNF-alpha in A549 cells model induced by poly(I:C);

(13) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;

(14) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and

(15) enabling small RNA to enter cells efficiently; and/or

(16) lowering the expression of RELA genes;

preferably, the bencaosome lowers the expression of fibrosis-associated protein fibronectin and alpha-SMA, and/or lowers the expression of IL-1beta, IL-6 and/or TNF-alpha, preferably the expression level of IL-1beta, IL-6 and/or TNF-alpha in A549 cells model induced by poly(I:C);

preferably, wherein the medicament is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 5. A method of facilitating nucleic acid delivery comprising heating or warming up nucleic acid and one or more lipids in Table 1 or Table 10, preferably Sphinganine (d22:0), the temperature for heating or warming up is preferably from about 4° C. to about 100° C., from about 25° C. to about 100° C., more preferably from about 50° C. to about 100° C., more preferably from about 95° C. to about 100° C., particularly preferably from about 80° C. to about 100° C., i.e. 4° C., 37° C., 60° C., 80° C. or 100° C., wherein preferably, the nucleic acid is a small nucleic acid, preferably is single or double stranded, preferably the small nucleic acid has a length of 14-32 bp, 16-28 bp or 18-24 bp, preferably any one or more small RNA in Tables 8, 9 and 13, preferably PGY-sRNA-6 or HJT-sRNA-m7; preferably, the nucleic acid delivery is by oral administration; preferably, the nucleic acid is used for treating a disease, such as inflammation-associated diseases and cancer, for example gastric cancer or lung cancer, preferably used for anti-inflammation and anti-fibrosis, preferably for reducing inflammation-associated factors IL-1beta, IL-6 and/or TNF-alpha, cytokine storm IL-1alpha, IL-1beta, IL-2, IL-3, IL-4, IL-5, IL-9, IL-10, IL-12 p40, IL-12 p70, IL-13, IL-17A, GM-CSF, IFN-gamma, RANTES or MCP-1beta, and lowering the expression of fibrosis-associated protein fibronectin and α-SMA.

Embodiment 6. The method of embodiment 5, further comprising further mixing one or compounds, one or more nucleic acids, and/or one or more macromolecules; wherein the nucleic acids include DNA and RNA, preferably RNA, more preferably small RNA;

preferably mixing one or more compounds shown in Table 2 to Table 5, one or more small RNA shown in Table 8 and/or Table 9 and/or Table 13, one or more DNA and/or one or more macromolecules shown in Table 6 or Table 7.

Embodiment 7. The method of any one of embodiments 1-6, wherein the more lipids are the lipids comprising the lipid combination selected from the following: a lipid combination of No. 8: No. 41-6:1; a lipid combination of No. 38: No. 41=6:1; a lipid combination of No. 39: No. 41=6:1; a lipid combination of No. 40: No. 41=6:1; a lipid combination of No. 38: No. 12: No. 41: No. 29=1:2:1:1; a lipid combination of No. 40: No. 12: No. 41=2:4:3; a lipid combination of No. 12: No. 41=1:6; a lipid combination of No. 12: No. 41=1:1; a lipid combination of No. 12: No. 41=6:1; a lipid combination of No. 40: No. 12: No. 41=2:2:2; a lipid combination of No. 4: No. 12: No. 41=1:1:1; DG combination of No. 1: No. 2: No. 3: No. 19: No. 35=1:1:1:1:1; TG combination of No. 6: No. 9: No. 10: No. 13: No. 15: No. 16: No. 18: No. 20: No. 21: No. 22: No. 23: No. 24: No. 25: No. 26: No. 27: No. 28: No. 32: No. 33=1:1:1:1:1: 1:1:1:1:1:1:1:1:1:1:1:1; LPC combination of No. 36: No. 37=1:1; PC combination of No. 11: No. 12=1:1; PE combination of No. 8: No. 38=1:1; Cer combination of No. 4: No. 14=1:1; So combination of No. 17: No. 30: No. 31=1: 1:1; an equal volume combination of No. 1-36 without No. 5, No. 7; an equal volume combination of No. 1-36 without No. 5, No. 7, No. 34; an equal volume combination of No. 1-36 without No. 5, No. 7, No. 1, No. 2, No. 3, No. 19, No. 35; an equal volume combination of No. 1-36 No. 5, No. 7, No. 6, No. 9, No. 10, No. 13, No. 15, No. 16, No. 18, No. 20, No. 21, No. 22, No. 23, No. 24, No. 25, No. 26, No. 27, No. 28, No. 32, No. 33; an equal volume combination of No. 1-36 without No. 5, No. 7, No. 36, No. 37; an equal volume combination of No. 1-36 without No. 5, No. 7, No. 11, No. 12; an equal volume combination of No. 1-36 without No. 5, No. 7, No. 8 in; an equal volume combination of No. 1-36 without No. 5, No. 7, No. 4, No. 14; an equal volume combination of No. 1-36 without No. 5, No. 7, No. 29; a lipid combination of No. 1: No. 34=2:1; a lipid combination of No. 1: said DG composition=2:1; a lipid combination of No. 1: said TG composition=2:1; a lipid combination of No. 1: said LPC composition=2:1; a lipid combination of No. 1: No. 8=2:1; a lipid combination of No. 1: No. 12=2:1; a lipid combination of No. 1: said Cer composition=2:1; a lipid combination of No. 1: said So composition=2:1; a lipid combination of No. 1: No. 29=2:1; a lipid combination of No. 1: No. 8: No. 12=1:1:1; a lipid combination of No. 8: No. 34=2:1; a lipid combination of No. 8: said DG composition=2:1; a lipid combination of No. 8: said TG composition=2:1; a lipid combination of No. 8: said LPC composition=2:1; a lipid combination of No. 8: No. 37=4:1; a lipid combination of No. 8: No. 12-2:1; a lipid combination of No. 8: said Cer composition=2:1; a lipid combination of No. 8: said So composition=2:1; a lipid combination of No. 8: No. 31=6:1; a lipid combination of No. 8: No. 29=2:1; a lipid combination of No. 12: No. 34=2:1; a lipid combination of No. 12: said DG composition=2:1; a lipid combination of No. 12: said TG composition=2:1; a lipid combination of No. 12: said LPC composition=2:1; a lipid combination of No. 12: No. 8=2:1; a lipid combination of No. 12: said Cer composition=2:1; a lipid combination of No. 12: said So composition=2:1; a lipid combination of No. 12: No. 29=2:1; a lipid combination of No. 12: No. 8: No. 1&2=2:1:1; a lipid combination of No. 12: No. 8: No. 15=2:1:1; a lipid combination of No. 12: No. 8: No. 36&37=2:1:1; a lipid combination of No. 12: No. 8: No. 11=2:1:1; a lipid combination of No. 12: No. 8: No. 12=2: 1:1; a lipid combination of No. 12: No. 8: No. 4=2:1:1; a lipid combination of No. 12: No. 8: No. 31-2:1:1; a lipid combination of No. 12: No. 8: No. 29=2:1:1; a lipid combination of No. 12: No. 8: No. 34-3:2:1; a lipid combination of No. 12: No. 8: No. 34-4:2:3; a lipid combination of No. 12: No. 8: No. 2=4:2:3; a lipid combination of No. 12: No. 8: No. 2=16:8:3; a lipid combination of No. 12: No. 8: No. 32=4:2:3; a lipid combination of No. 12: No. 8: No. 37=4: 2:3; a lipid combination of No. 12: No. 8: No. 11=4:2:3; a lipid combination of No. 12: No. 8: No. 38=4:2:3; a lipid combination of No. 12: No. 8: No. 4-4:2:3; a lipid combination of No. 12: No. 8: No. 31=4:2:3; a lipid combination of No. 12: No. 8: No. 29=4:2:3; a lipid combination of No. 12: No. 8: No. 29: No. 31=2:1:1:1; a lipid combination of No. 12: No. 8: No. 29: No. 31: No. 34=4:2:2:2:5; a lipid combination of No. 12: No. 8: No. 29: No. 31: No. 2=4:2: 2:2:5; a lipid combination of No. 12: No. 8: No. 29: No. 31: No. 32=4:2:2:2:5; a lipid combination of No. 12: No. 8: No. 29: No. 31: No. 11=4:2:2:2:5; a lipid combination of No. 12: No. 8: No. 29: No. 31: No. 37=4:2:2:2:5; a lipid combination of No. 12: No. 8: No. 29: No. 31: No. 38=4:2:2:2:5; a lipid combination of No. 12: No. 8: No. 29: No. 31: No. 4=4:2: 2:2:5; a lipid combination of No. 12: No. 8: No. 29: No. 31: No. 4: No. 1: No. 16=2:1:1:3:2:2:3; a lipid combination of No. 1: No. 8: No. 12: No. 1&2=2:2:2:3; a lipid combination of No. 1: No. 8: No. 12: No. 15=2:2:2:3; a lipid combination of No. 1: No. 8: No. 12: No. 36&37=2:2:2:3; a lipid combination of No. 1: No. 8: No. 12: No. 12=2:2:2:3; a lipid combination of No. 1: No. 8: No. 12: No. 4=2:2:2:3; a lipid combination of No. 1: No. 8: No. 12: No. 31=2:2:2:3; a lipid combination of No. 1: No. 8: No. 12: No. 29=2:2:2:3; a lipid combination of No. 8: No. 34: No. 1&2=2:1:1; a lipid combination of No. 8: No. 34: No. 15=2:1:1; a lipid combination of No. 8: No. 34: No. 36&37=2:1:1; a lipid combination of No. 8: No. 34: No. 12=2:1:1; a lipid combination of No. 8: No. 34: No. 4=2:1:1; a lipid combination of No. 8: No. 34: No. 31=2:1:1; a lipid combination of No. 8: No. 34: No. 29=2:1:1; a lipid combination of No. 8: No. 31: No. 34=12:3:5; a lipid combination of No. 8: No. 31: No. 2=12:3:5; a lipid combination of No. 8: No. 31: No. 37=12: 3:5; a lipid combination of No. 8: No. 31: No. 11=12:3:5; a lipid combination of No. 8: No. 31: No. 12=12:3:5; a lipid combination of No. 8: No. 31: No. 4=12:3:5; a lipid combination of No. 8: No. 31: No. 29=12:3:5; a lipid combination of No. 8: No. 31: No. 32=12:3:5; a lipid combination of No. 8: No. 4: No. 34=12:3:5; a lipid combination of No. 8: No. 4: No. 2=12:3:5; a lipid combination of No. 8: No. 4: No. 37=12:3:5; a lipid combination of No. 8: No. 4: No. 12=12:3:5; a lipid combination of No. 8: No. 4: No. 31=12:3:5; a lipid combination of No. 8: No. 4: No. 29=12:3:5; a lipid combination of No. 8: No. 4: No. 32=12:3:5; a lipid combination of No. 38: No. 34=2:1; a lipid combination of No. 38: No. 1=2:1; a lipid combination of No. 38: No. 2=2:1; a lipid combination of No. 38: No. 1&2=2:1; a lipid combination of No. 38: No. 15=2:1; a lipid combination of No. 38: No. 32=2:1; a lipid combination of No. 38: No. 37=2:1; a lipid combination of No. 38: No. 37=4:1; a lipid combination of No. 38: No. 11=2:1; a lipid combination of No. 38: No. 12-2:1; a lipid combination of No. 38: No. 11&12=2:1; a lipid combination of No. 38: No. 12=4:1; a lipid combination of No. 38: No. 8=2:1; a lipid combination of No. 38: No. 4=2:1; a lipid combination of No. 38: So (30)=2:1; a lipid combination of No. 38: No. 31=2:1; a lipid combination of No. 38: No. 29=2:1; a lipid combination of No. 1: No. 38: No. 12: No. 34=2:2:2:3; a lipid combination of No. 1: No. 38: No. 12: No. 15=2:2:2:3; a lipid combination of No. 1: No. 38: No. 12: No. 37=2:2:2:3; a lipid combination of No. 1: No. 38: No. 12: No. 8=2:2:2:3; a lipid combination of No. 1: No. 38: No. 12: No. 4=2:2:2:3; a lipid combination of No. 1: No. 38: No. 12: No. 31=2:2:2:3; a lipid combination of No. 1: No. 38: No. 12: No. 29=2:2:2:3; a lipid combination of No. 38: No. 34: No. 1=2:1:3; a lipid combination of No. 38: No. 34: No. 15=2:1:3; a lipid combination of No. 38: No. 34: No. 37=2:1:3; a lipid combination of No. 38: No. 34: No. 12=2:1:3; a lipid combination of No. 38: No. 34: No. 8=2:1:3; a lipid combination of No. 38: No. 34: No. 4=2:1:3; a lipid combination of No. 38: No. 34: No. 31=2:1:3; a lipid combination of No. 38: No. 34: No. 29=2:1:3; a lipid combination of No. 38: No. 12: No. 1=2:1:3; a lipid combination of No. 38: No. 12: No. 2=4:1:3; a lipid combination of No. 38: No. 12: No. 15=2:1:3; a lipid combination of No. 38: No. 12: No. 37=2:1:3; a lipid combination of No. 38: No. 12: No. 8=2:1:3; a lipid combination of No. 38: No. 12: No. 4=2:1:3; a lipid combination of No. 38: No. 12: No. 31=2:1:3; a lipid combination of No. 38: No. 12: No. 29=2:1:3; a lipid combination of No. 38: No. 12: No. 1: No. 15: No. 34=22:22:22:33:36; a lipid combination of No. 38: No. 12: No. 1: No. 15: No. 37=22:22:22:33:36; a lipid combination of No. 38: No. 12: No. 1: No. 15: No. 4=22:22:22:33:36; a lipid combination of No. 38: No. 12: No. 1: No. 15: No. 31=22:22:22:33:36; a lipid combination of No. 38: No. 12: No. 1: No. 15: No. 29-22:22:22:33:36; a lipid combination of No. 38: No. 34: No. 37: No. 1=44:22:33:36; a lipid combination of No. 38: No. 34: No. 37: No. 15=44:22:33:36; a lipid combination of No. 38: No. 34: No. 37: No. 12=44:22:33:36; a lipid combination of No. 38: No. 34: No. 37: No. 4=44:22:33:36; a lipid combination of No. 38: No. 34: No. 37: No. 31=44:22:33:36; a lipid combination of No. 38: No. 12: No. 4: No. 34=44:22:33:36; a lipid combination of No. 38: No. 12: No. 4: No. 1=44:22:33:36; a lipid combination of No. 38: No. 12: No. 4: No. 15=44:22:33:36; a lipid combination of No. 38: No. 12: No. 4: No. 37=44:22:33:36; a lipid combination of No. 38: No. 12: No. 4: No. 37=8:2:5:3; a lipid combination of No. 38: No. 12: No. 4: No. 31=44:22:33:36; a lipid combination of No. 38: No. 12: No. 4: No. 29=44:22:33:36; a lipid combination of No. 38: No. 12: No. 4: No. 29: No. 34=88:44:66:72:135; a lipid combination of No. 38: No. 12: No. 4: No. 29: No. 1=88:44:66:72:135; a lipid combination of No. 38: No. 12: No. 4: No. 29: No. 15=88:44:66:72:135; a lipid combination of No. 38: No. 12: No. 4: No. 29: No. 37=88:44:66:72:135; a lipid combination of No. 38: No. 12: No. 4: No. 29: No. 31=88:44:66:72:135; a lipid combination of No. 38: No. 12: No. 4: No. 2=20:10:15:9; a lipid combination of No. 38: No. 12: No. 4: No. 6=20:10:15:9; a lipid combination of No. 38: No. 12: No. 4: No. 17=20:10:15:9; a lipid combination of No. 38: No. 12: No. 4: No. 29=20:10:15:9; a lipid combination of No. 38: No. 12: No. 4: No. 34=20:10:15:9; a lipid combination of No. 38: No. 12: No. 4: No. 37=20:10:15:9; a lipid combination of No. 38: No. 12: No. 31: No. 34=2:1:3:3; a lipid combination of No. 38: No. 12: No. 31: No. 1=2:1:3:3; a lipid combination of No. 38: No. 12: No. 31: No. 15=2:1:3:3; a lipid combination of No. 38: No. 12: No. 31: No. 37=2:1:3:3; a lipid combination of No. 38: No. 12: No. 31: No. 4=2:1:3:3; a lipid combination of No. 38: No. 12: No. 31: No. 29=2:1:3:3; a lipid combination of No. 38: No. 34: No. 37: No. 31: No. 1=88:44:66:72:135; a lipid combination of No. 38: No. 34: No. 37: No. 31: No. 15=88:44:66:72:135; a lipid combination of No. 38: No. 34: No. 37: No. 31: No. 12=88:44:66:72:135; a lipid combination of No. 38: No. 34: No. 37: No. 31: No. 4=88:44:66:72:135; a lipid combination of No. 38: No. 34: No. 37: No. 31: No. 29=88:44:66:72:135; a lipid combination of No. 38: No. 37: No. 34=4:2:3; a lipid combination of No. 38: No. 37: No. 1=4:2:3; a lipid combination of No. 38: No. 37: No. 2=4:2:3; a lipid combination of No. 38: No. 37: No. 1&2=4:2:3; a lipid combination of No. 38: No. 37: No. 2=32:8:5; a lipid combination of No. 38: No. 37: No. 32=32:8:5; a lipid combination of No. 38: No. 37: No. 15-4:2:3; a lipid combination of No. 38: No. 37: No. 32=4:2:3; a lipid combination of No. 38: No. 37: No. 8=4:2:3; a lipid combination of No. 38: No. 37: No. 11=4:2:3; a lipid combination of No. 38: No. 37: No. 12=4:2:3; a lipid combination of No. 38: No. 37: No. 11&12=4:2:3; a lipid combination of No. 38: No. 37: No. 12=4:1:1; a lipid combination of No. 38: No. 37: No. 4=4:2:3; a lipid combination of No. 38: No. 37: No. 30=4:2:3; a lipid combination of No. 38: No. 37: No. 31=4:2:3; a lipid combination of No. 38: No. 37: No. 29=4:2:3; a lipid combination of No. 8: No. 37: No. 32=4:1:2; a lipid combination of No. 8: No. 37: No. 2=4:1:2; a lipid combination of No. 38: No. 37: No. 15: No. 34=64:16:10:45; a lipid combination of No. 38: No. 37: No. 15: No. 1=64:16:10:45; a lipid combination of No. 38: No. 37: No. 15: No. 12=64:16:10:45; a lipid combination of No. 38: No. 37: No. 15: No. 4=64:16:10:45; a lipid combination of No. 38: No. 37: No. 15: No. 31=64:16:10:45; a lipid combination of No. 38: No. 37: No. 15: No. 29=64:16:10:45; a lipid combination of No. 38: No. 2: No. 37=4:2:3; a lipid combination of No. 38: No. 2: No. 31=4:2:3; a lipid combination of No. 38: No. 2: No. 29-4:2:3; a lipid combination of No. 38: No. 2: No. 34=4:2:3; a lipid combination of No. 38: No. 2: No. 32=4:2:3; a lipid combination of No. 38: No. 2: No. 12=4:2:3; a lipid combination of No. 38: No. 2: No. 12=4:5:1; a lipid combination of No. 38: No. 2: No. 4=4:2:3; lipids No. 1&2, No. 11&12 and No. 36&37 represent lipids No. 1 and No. 2 in any ratio, lipids No. 11 and No. 12 in any ratio, lipids No. 36 and No. 37 in any ratio, respectively.

Embodiment 8. A method of promoting the formation of bencaosome from nucleic acid and lipid, comprising heating a mixture of nucleic acid and lipid to promote the insertion of nucleic acid into the lipid membrane and promoting the stability of the lipid-nucleic acid complex, as determined by critical micelle concentration;

wherein the nucleic acid inserts into the lipid layer or is encapsulated by the lipid layer to form the bencaosome, which is a nanoparticulate substance with a membrane structure, preferably a nanoparticulate substance with a double membrane structure;

wherein the heating temperature is preferably from about 0° C. to about 100° C., more preferably from about 50° C. to about 100° C., and more preferably from about 80° C. to about 100° C., particularly preferably from about 80° C. to about 90° C., preferably 90° C.;

preferably, the time for heating is about 0 minute to about 24 hours, about 5 minutes to about 20 hours, about 10 minutes to about 16 hours, about 15 minutes to about 12 hours, about 1 hour to about 8 hours, or about 2 hours to about 4 hours, preferably 15 minutes;

preferably, the lipid is one or more lipids in Table 1 or Table 10, preferably Sphinganine (d22:0), or the lipid combination of embodiment 7; preferably, the nucleic acid is small RNA, preferably one or more small RNA shown in Tables 8, 9 and 13, preferably PGY-sRNA-6 or HJT-sRNA-m7.

Embodiment 9. A method for lipid delivery of proteins to cells, comprising heating the proteins and lipids, wherein the heating temperature is preferably from about 0° C. to about 100° C., more preferably from about 50° C. to about 100° C., and more preferably from about 80° C. to about 100° C., particularly preferably from about 80° C. to about 90° C., preferably 90° C.;

preferably, the time for heating is about 0 minute to about 24 hours, about 5 minutes to about 20 hours, about 10 minutes to about 16 hours, about 15 minutes to about 12 hours, about 1 hour to about 8 hours, or about 2 hours to about 4 hours, preferably 6 hours;

or the method for lipid delivery of proteins to cells comprises mixing a protein solution with a solution of lipid in an organic solvent, preferably at v/v=1/5; removing the organic solvent, preferably by evaporation; and hydrating with an aqueous reagent;

or conduct the preparation by a boiling method comprising adding a solution of lipid in an organic solvent to a protein solution, and warming up after mixing;

preferably, the lipid is one or more lipids in Table 1 or Table 10, preferably sphinganine (d22:0) or PE(16:0/16:0) or PE(16:0/22:1).

Embodiment 10. A method for preparing a decoctosome from plants, comprising the steps of:

(4) preparing an extract of the plants using a solvent, preferably an aqueous solvent, wherein preferably, the extract of the plants is prepared by decocting the plants soaked in the solvent;

wherein preferably, the decocting includes decocting with intense heating for 15-45 min, preferably 20-30 min, preferably 30 min, followed by decocting with gentle heating for 5-30 min, preferably 5-20 min, preferably 10 min;

wherein preferably, the temperature of the intense heating is above 90° C., preferably 90° C.-2000° C., 90° C.-1500° C., 90° C.-1000° C., 90° C.-500° C., 90° C.-300° C., 90° C.-250° C. or 90° C.-200° C.;

preferably, the temperature of the gentle heating is above 50° C., preferably 50° C.-2000° C., 50° C.-1500° C., 50° C.-1000° C., 50° C.-500° C., 50° C.-300° C., 50° C.-250° C., 50° C.- 200° C., 50° C.-100° C., 50° C.-80° C., 50° C.-70° C. or 50° C.-60° C.;

preferably, the aqueous solvent is selected from the group consisting of aqueous buffers, saline solutions, aqueous solutions of organic solvents and water;

(5) differential centrifuging the extract at an appropriate temperature, preferably 0-10° C., 4° C., preferably at 800-5000 g, preferably 1000-4000 g, preferably 2000-3000 g, preferably at 2000 g for 20-40 min, preferably 30 min; taking the supernatant, and then centrifuging the supernatant at 6000 g-15000 g, preferably 7000 g-12000 g, preferably 8000 g-11000 g, preferably at 10000 g for 20-40 min, preferably 30 min; taking the supernatant, and then centrifuging the supernatant at 100000-200000, preferably at 200000 g for 60-120 min, preferably 90 min; taking the precipitates, which are the solid form of the decoctosome; and (6) optionally, resuspending the precipitates with an aqueous solution, preferably an aqueous buffer, preferably PBS buffer, more preferably PBS buffer at pH7-9, preferably pH7.4 to provide the decoctosome, which is a nanoparticulate substance with a membrane structure, preferably a nano-particulate substance with a double layered membrane structure, the aqueous solution is selected from the group consisting of aqueous buffers, saline solutions, aqueous solutions of organic solvents and water.

Embodiment 11. The method of embodiment 10, wherein the decoctosome has an average particle size of 30-1,000 nm, preferably 80-300 nm, and a potential absolute value of 20-100 mV.

Embodiment 12. The method of embodiment 10 or 11, wherein the plant is selected from the group consisting of *Taraxacum mongolicum*, *Rhodiola*, *Andrographis paniculata*, Cabbage and Woody etc.

Embodiment 13. The method of any one of embodiments 10-12, wherein for *Taraxacum mongolicum*, the decoctosome has a peak value for the average particle size of 30-300 nm, preferably 150-200 nm, and a Zeta potential of −39±3 mV; for *Rhodiola*, the decoctosome has an average particle size of 50-300 nm, preferably 150-210 nm, and a Zeta potential of −37±2 mV;

the *Taraxacum mongolicum* decoctosome has a potential absolute value of 20-100 mV, and the *Rhodiola* decoctosome has a potential absolute value of 20-100 mV.

Embodiment 14. The decoctosome prepared by the method of any one of embodiments 10-13, wherein the decoctosome is in the form of solid or liquid or colloid, and the decoctosome comprises a nanoparticulate substance with a membrane structure, preferably a nanoparticulate substance with a double layered membrane structure.

Embodiment 15. The decoctosome of embodiment 14, comprising one or more lipid components shown in Table 1 or 10, one or more compounds, one or more DNAs, one or more macromolecules and/or one or more RNAs;

preferably, the decoctsome comprises one or more lipid components shown in Table 1 or Table 10, one or more compounds shown in Table 2 or 4, one or more compounds shown in Table 3 or 5, one or more macromolecules shown in Table 6 or 7, and/or one or more small RNAs shown in Table 8, 9 or 13.

Embodiment 16. The decoctosome of embodiment 14 or 15, which is a composition used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 17. The decoctosome of any one of embodiments 14-16, used in one or more of the following:

(1) lowering the expression of fibronectin and/or alpha-SMA, preferably the protein expression of fibronectin in MRC-5 cells fibrosis model induced by TGF-beta1;

(2) reducing hydroxyproline, preferably the hydroxyproline in pulmonary fibrosis model, preferably the hydroxyproline in pulmonary fibrosis model of mice;

(3) preventing or treating fibrosis, preferably pulmonary fibrosis;

(4) lowering IL-1beta, IL-6 and/or TNF-alpha, preferably the IL-1beta, IL-6 and/or TNF-alpha in A549 cells model induced by poly(I:C);

(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1 beta, preferably the level of plasma, preferable in an inflammation model of mouse;

(6) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and/or (7) lowering the expression of RELA genes.

Embodiment 18. Use of the decoctosome of any one of embodiments 14-16 in the manufacture of medicament for use in one or more of the following:

(8) lowering the expression of fibronectin and/or alpha-SMA, preferably the protein expression of fibronectin in MRC-5 cells fibrosis model induced by TGF-beta1;

(9) reducing hydroxyproline, preferably the hydroxyproline in pulmonary fibrosis model, preferably the hydroxyproline in pulmonary fibrosis model of mice;

(10) preventing or treating fibrosis, preferably pulmonary fibrosis;

(11) lowering IL-1beta, IL-6 and/or TNF-alpha, preferably the IL-1beta, IL-6 and/or TNF-alpha in A549 cells model induced by poly(I:C);

(12) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;

(13) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and/or

(14) lowering the expression of RELA genes;

wherein the medicament is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 19. Method for the following purposes including the use of the decoctosome in any one of embodiments 14-16:

(1) lowering the expression of fibronectin and/or alpha-SMA, preferably the protein expression of fibronectin in MRC-5 cells fibrosis model induced by TGF-beta1;

(2) reducing hydroxyproline, preferably the hydroxyproline in pulmonary fibrosis model, preferably the hydroxyproline in pulmonary fibrosis model of mice;

(3) preventing or treating fibrosis, preferably pulmonary fibrosis;

(4) lowering IL-1beta, IL-6 and/or TNF-alpha, preferably the IL-1beta, IL-6 and/or TNF-alpha in A549 cells model induced by poly(I:C);

(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;

(6) treating IL-1beta, IL-6 and/or TNF-alpha-associated diseases, or for anti-inflammation, and/or (7) lowering the expression of RELA genes.

Embodiment 20. The methods of embodiments 1, 2 or 5, wherein the nucleic acid is synthesized or purified and is selected from RNA and DNA, such as selected from single stranded or double stranded or partially double-stranded RNA and DNA.

Embodiment 21. The method of embodiment 20, wherein the RNA is selected from the group consisting of messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, transfer-messenger RNA (tmRNA), telomerase RNA and antisense RNA, preferably small RNA, preferably one or more small RNAs shown in Table 8, 9 or 13.

Embodiment 22. The method of embodiment 20, wherein the DNA is selected from the group consisting of complementary DNA (cDNA), chloroplast DNA, multicopy single-stranded DNA (msDNA), mitochondrial DNA (mtDNA) and ribosomal DNA (rDNA).

Embodiment 23. The method of embodiment 1, 2 or 6, wherein the macromolecule is synthesized or purified and is selected from proteins or polysaccharide drugs, and/or one or more macromolecules shown in Table 6 or 7.

Embodiment 24. The method of embodiment 23, wherein the protein is selected from the group consisting of antibody, β-lactoglobulin, albumin, erythropoietin (EPO), interferon, colony stimulating factor, tissue plasminogen activator and various labeled proteins, such as green fluorescent protein, red fluorescent protein, phycoerythrin, etc.

Embodiment 25. The method of embodiment 24, wherein the antibody is selected from IgG, IgA, IgM, IgD or IgE antibodies.

Examples

The following examples are merely illustrative of the invention disclosed herein, and are not to be construed as limiting the scope of the appended claims.

TABLE 13

Part of small RNAs and their sequences used in the examples

| SEQ ID No | siRNA | Sequence | Length |
|---|---|---|---|
| 1 | sly-miR168b-5p | TCGCTTGGTGCAGGTCGGGAC | 21 |
| 2 | Pab-miR3711 | GGCCCTCCTTCTAGCGCCA | 19 |
| 3 | CXL-sRNA-17 | CAGAGTCGCGCAGCGGAA | 18 |
| 4 | PGY-sRNA-6 | GTTCAGAGTTCTACAGTCCGA | 21 |
| 5 | PGY-sRNA-18 | CGGGGCTACGCCTGTCTGAGCGTCGC | 26 |
| 6 | HJT-sRNA-m7 | TGAGGTAGTAGGTTGTGTGGTTGTAAGC | 28 |
| 7 | HJT-sRNA-3 | CAGCCAAGGATGACTTGCCGG | 21 |
| 8 | HJT-sRNA-a2 | TAGCACCATCCGAAATCGGTA | 21 |
| 9 | HJT-sRNA-h3 | TGGGGCTACGCCTGTCTGAGCGTCGCT | 27 |
| 10 | si-XRN2 | GAGUACAGAUGAUCAUGUUGAGTACAGATGATCATGTT | 19 |
| 11 | si-Ssu72 | GACUCACGUGAAGCUUCCAGACTCACGTGAAGCTTCCA | 19 |
| 12 | si-CPSF4 | GAGUCAUCUGUGUGAAUUAGAGTCATCTGTGTGAATTA | 19 |
| 13 | si-LAMP1 | CAAUGCGAGCUCCAAAGAA | 19 |
| 14 | si-LAMP2 | GCGGUCUUAUGCAUUGGAA | 19 |
| 15 | si-NFκB | AGUACCCUGAAGCUAUAUUUU | 21 |
| 16 | si-TNFα | CACAACCAACUAGUGGUGCUU | 21 |
| 17 | PGY-sRNA-23 | CCCTCCGCGGCCAGCTTCT | 19 |
| 18 | PGY-sRNA-26 | TCCGGAATGATTGGGCGTAAAGCGT | 25 |
| 19 | PGY-sRNA-32 | CCGGCCCCGAACCCGTCGGC | 20 |
| 20 | PGY-sRNA-1 | GCGACCCCAGGTCAGGCGGGA | 21 |
| 21 | PGY-sRNA-2 | CAGAGTTCTACAGTCCGA | 18 |
| 22 | PGY-sRNA-3 | AGAGTTCTACAGTCCGACGAT | 21 |
| 23 | PGY-sRNA-4 | CAGAGTTCTACAGTCCGACGAT | 22 |
| 24 | PGY-sRNA-5 | GTTCAGAGTTCTACAGTC | 18 |
| 25 | PGY-sRNA-6 | GTTCAGAGTTCTACAGTCCGA | 21 |
| 26 | PGY-sRNA-7 | GTTCTACAGTCCGACGATC | 19 |
| 27 | PGY-sRNA-8 | CAGAGTTCTACAGTCCGACGATC | 23 |
| 28 | PGY-sRNA-9 | GACCGCATAGCGCAGTGGA | 19 |
| 29 | PGY-sRNA-10 | CGGTGGCCATGGAAGTCGG | 19 |
| 30 | PGY-sRNA-11 | TCTGAACTCTGAACTCCAGTCAC | 23 |
| 31 | PGY-sRNA-12 | CGCCTGTCTGAGCGTCGCT | 19 |
| 32 | PGY-sRNA-13 | GGCTTTGGTCTAGGGGTATGATTCT | 25 |
| 33 | PGY-sRNA-14 | ACGCCTGTCTGAGCGTCGCT | 20 |
| 34 | PGY-sRNA-15 | GCTACGCCTGTCTGAGCGTCGCT | 23 |
| 35 | PGY-sRNA-16 | GGGCTACGCCTGTCTGAGCGTCGCT | 25 |
| 36 | PGY-sRNA-17 | GGGGCTACGCCTGTCTGAGCGTCGCT | 26 |
| 37 | PGY-sRNA-18 | CGGGGCTACGCCTGTCTGAGCGTCGC | 26 |
| 38 | PGY-sRNA-19 | CGGGGCTACGCCTGTCTGAGCGTCGCT | 27 |
| 39 | PGY-sRNA-20 | CCGGGGCTACGCCTGTCTGAGCGT | 24 |

Note:
Double-stranded sRNA is indicated by the "si-" prefix.

Note: Double-stranded sRNA is indicated by the "si-" prefix.

TABLE 14

Partial antibodies used in examples

| Primary antibody name | Company | Catalog No. | Primary antibody dilution ratio | Secondary antibody |
|---|---|---|---|---|
| Fibronectin | Sigma Aldrich | F7387 | 1:2000 | M |
| α-SMA | Abcam | ab7817 | 1:1000 | M |
| GAPDH | Protein Tech | 60004-1-lg | 1:5000 | M |
| LAMP1 | Santa Cruze | sc-20011 | 1:1000 | M |
| LAMP2 | Santa Cruze | sc-18822 | 1:1000 | M |
| XRN2 | Santa Cruze | sc-365258 | 1:2000 | M |
| CPSF4 | Protein Tech | 15023-1-AP | 1:1000 | R |
| Ssu72 | CST | 12816s | 1:1000 | R |
| NF-κB | CST | 4764S | 1:2000 | R |
| β-Actin | Sigma Aldrich | A5441 | 1:5000 | M |
| NF-κB p65 | CST | #6956 | 1:1000 | R |

First Part of the Experiments

Example 1

1. Preparation of Decoction of Herbal Medicine and the Extraction of Decoctosome.
1.1 Preparation of Decoction of Herbal Medicine
  1) 200 g herbal medicine decoction pieces (*Rhodiola crenulata, Taraxacum mongolicum*, purchased from Beijing Tongrentang pharmacy) was added into 1000 mL ddH$_2$O and soaked for 30 min.
  2) The mixture was decocted in a decoction pot with intense heating for 30 min, and with gentle heating for 10 min.
  3) After decocting, the decoction of *Rhodiola crenulata* was about 250 ml, and the decoction of *Taraxacum mongolicum* was about 360 ml.
1.2 Preparation of Decoctosome
  1) 200 g decoction pieces (*Rhodiola crenulata, Taraxacum mongolicum*, purchased from Beijing Tongrentang pharmacy) was added into 1000 mL ddH$_2$O and soaked for 30 min.
  2) The mixture was decocted in a decoction pot with intense heating for 30 min, and with gentle heating for 10 min.

3) After decocting, the decoction of *Rhodiola crenulata* was about 250 ml, and the decoction of *Taraxacum mongolicum* was about 360 ml.
4) The obtained decoction was differential centrifuged at 4° C. (centrifuged at 2,000 g for 30 min to get the supernatant, at 10,000 g for 30 min to get the supernatant, and at 200,000 g for 90 min, and discarded the supernatant) to get the precipitates.
5) The obtained precipitates were resuspended in double-distilled water, from which an appropriate amount was taken into the EP tube and vacuum dried for about 5 hours, thereby obtaining the precipitates of the decoctosome, which were weighed and quantified.

The preparation methods of the decoction and decoctosome precipitates of other herbal medicines were the same as the methods described in Sections 1.1 and 1.2. For a schematic diagram of the preparation process of the decoctosome, see FIG. 1.

2. Features of the Decoctosome of Herbal Medicine
2.1 Morphology of the Decoctosome of Herbal Medicine Observed by Transmission Electron Microscope The precipitates obtained in Section 1.2 were resuspended in double-distilled water to obtain decoctosome solution.
2) The morphology of the decoctosome was observed by transmission scanning electron microscope.

2.2 Determination of Particle Size and Zeta Potential of Decoctosome of Herbal Medicine
1) The precipitates obtained in Section 1.2 were resuspended in pH7.4 PBS buffer to obtain decoctosome solution.
2) Particle size and Zeta potential of the decoctosome were determined by dynamic light scattering technology (DLS), Instrument Zetasizer Nano ZS90 (Malvern Instrument, UK), and the data were analyzed.

The electron microscope observation results of the decoctosomes of *Rhodiola crenulata* and *Taraxacum mongolicum* are shown in FIG. 2 and FIG. 3, respectively. See FIG. 4 and FIG. 5 for the particle size distribution and Zeta potential of *Rhodiola crenulata* and *Taraxacum mongolicum* decoctosomes, respectively.

3. Analysis for Components of Decoctosome of Herbal Medicines.
3.1 Proteomics Analysis of Decoctosome of Herbal Medicine
3.1.1 Reagents and Materials Milli-Q water, Non-powder gloves, Face mask, Hat, 10 µl and 200 µl tips (eppendorf), Acetonitrile (Fisher A/0626/17), Methanol (Fisher), Sodium thiosulfate pentahydrate (Sigma), Potassium ferricyanide (Sigma), Dithiothreitol (PlusOne), Iodoacetamide (Sigma), Trypsin (Promega V5280), Trypsin resolve solution (Promega V530), Ammonium bicarbonate (Sigma A6141), Zip Tip (Millipore), FA Formic acid (Sigma), 0.2 ml and 0.5 ml EP tubes (eppendorf), 50 ml EP, 15 ml EP (Corning).

3.1.2 Main Equipments:
Q Exactive mass spectrometer (Thermo fisher), vacuum dryer, water bath, 10u and 200u pipettes, waste tank, ice making and ice filling equipment, 200u tube rack, scissors, plastic box that can hold 200u tube rack, 200 µl tube centrifugal machine.

3.1.3 Experimental Steps:
1) Protein Extraction:
A. An appropriate amount of sample was weighed and was added 5 times volume of pre-cooled 10% TCA-acetone, shaken and mixed, and settled at −20° C. for 2 hours or overnight.
B. The mixture was centrifuged at 12000 g and 4° C. for 10 min, and the precipitates were collected.
C. An appropriate volume of pre-cooled acetone was added to the precipitates, shaked and mixed, and centrifuged at 12000 g, 4° C. for 15 min. The precipitates were collected. Repeated this step twice to remove other impurities completely.
D. The precipitates were dried at room temperature, dissolved in 1 ml sample dissolving solution (9M urea, 4% CHAPS, 1% IPG Buffer, 1% DTT) and completely dissolved the proteins to be used for follow-up experiments.

2) Enzyme Digestion:
Trypsin at a concentration of 15 ng/µL was diluted with 25 mmol/L $NH_4HCO_3$. Trypsin solution was added in an amount of 7-10 µL/tube, and incubated in the refrigerator at 4° C. for 40 min. After taking the tube out, each tube was supplemented with 5-10 µL of 25 mmol/L $NH_4HCO_3$ solution, sealed and placed in a 37° C. water bath for enzyme digestion for 16h.

3) Peptide Fragment Extraction:
Extraction solution (5% TFA-50% ACN-45% water) was added at 100 µL/tube. The tube was placed in 37° C. water bath for 1 hour, ultrasound for 5 minutes, centrifuged for 5 minutes. The extraction solution was transferred to another new EP tube, and the extraction was repeated once. The extracts were combined and dried by vacuum centrifugation.

4) Mass Spectrometry Measurement
A. Peptide fragments were dissolved by sample dissolving solution (0.1% formic acid, 2% acetonitrile), shaken and vortexed completely, centrifuged at 13200 rpm, 4° C. for 10 min. The supernatant was transferred into sample tube to perform mass spectrometry measurement.
B. Chromatography column information:
300 um i.d.×5 mm, filled with Acclaim PepMap RSLC C18, 5 µm, 100 Å, nano Viper
Acclaim PepMap 75 um×150 mm, C18, 3 um, 100A
Mobile phase A: 0.1% formic acid;
Mobile phase B: 0.1% formic acid, 80% ACN;
Flow rate: 300 nL/min;
Analysis time for each component: 40 min;

| Time | Phase B |
|---|---|
| 0 | 5% |
| 5 | 5% |
| 25 | 50% |
| 30 | 90% |
| 35 | 90% |
| 45 | 5% |

C. The separated peptide fragments were directly tested online, and the specific parameters were as follows:
Primary mass spectrometry parameters:
Resolution: 70,000
AGC target: 3e6
Maximum IT: 40 ms
Scan range: 350 to 1800 m/z
Secondary mass spectrometry parameters:
Resolution: 17,500
AGC target: 1e5
Maximum IT: 60 ms
TopN: 20
NCE/stepped NCE: 27

4) Database Search

Initial mass spectrometry documents were processed and converted by MM File Conversion software to get the MGF format file. MAXQUANT was used to search in uniprot-Viridiplantae database with the search parameters as follows:
- a) Fixed modifications: Carbamidomethyl (C)
- b) Variable modifications: Oxidation (M)
- c) Enzyme: Trypsin
- d) Maximum Missed Cleavages: 2
- e) Peptide Mass Tolerance: 20 ppm
- f) Fragment Mass Tolerance: 0.6 Da
- g) Mass values of peptide fragment/fragment ion: Monoisotopic
- h) Significance threshold: 0.05

3.1.4 Description of Results

Accession (ID No. of proteins in uniprot database), Description (annotation of proteins), Exp. q-value (q-value, the smaller the better), Sum PEP Score (protein score, the higher the score, the better), Coverage (coverage of identified amino acids of the peptide fragments in the total amino acids of the protein), #Peptides (the number of peptide fragments of the identified protein), #PSMs (the total number of all peptide fragments in the identified corresponding protein), #Unique Peptides (the number of unique peptide fragments in the identified corresponding protein), #Protein Groups (the number of proteins corresponding to the identified peptide fragments), #Aas (theoretical amino acid number of identified corresponding protein), MW [kDa] (theoretical molecular weight of identified corresponding protein), calc. pI (theoretical isoelectric point of identified corresponding protein), score: protein score; intensity: protein relative intensity.

Sequence (amino acid sequence of the peptide fragment), #Proteins (the number of proteins corresponding to the peptide fragments), #PSMs (the number of times the peptide fragment was identified), Master Protein Accessions (ID of proteins corresponding to peptide fragments), Theo. MH+ [Da] (theoretical molecular weight of peptide fragment).

See Table 6 and Table 7 and FIGS. 19 and 20 for the proteomics analysis results.

3.2 Metabolomics Analysis of Compounds in Decoctosome of Herbal Medicines

1) The Conditions for Liquid Chromatography

Samples were separated by Waters H-class type Ultra Performance Liquid Chromatography (UPLC). The analysis conditions were as follows: chromatographic column: waters HSS C18 (3.0×100 mm, 1.7 μm), column temperature: 50° C.; mobile phase A is 0.1% formic acid in water, mobile phase is acetonitrile; analysis gradient: 0-1 min, 2% B; 1-3 min, 2% B-15% B; 3-6 min, 15% B-50% B; 6-9 min, 50-95% B; 9-9.1 min, 95-100% B-2% B; 9.1-12 min, 100% B; flow rate was 0.5 ml/min; volume of injection was 5 μl.

2) The Conditions for Mass Spectrum (MS)

UPLC-MS tandem LTQ-Orbitrap velos (Thermo Fisher Scientific, SanJose, CA, USA) mass spectrum using electronspray ion source in positive ion mode; sheath gas was nitrogen and auxiliary gas, the flow rate was 45 arbitrary and 10 arbitrary units, respectively; MS scan range was 100-1000 m/z; spray voltage was set to 4.2 KV; capillary temperature was 350° C. The data was acquired by high resolution Fourier Transform mode (FT), with primary resolution of 60000 and secondary resolution of 15000. The secondary data was acquired in data-dependent analysis mode; dynamic exclusion time was 15s; HCD was selected as the fragmentation method with related parameters set as follows: isolation width: 3 Da; collision energy: 20%, 40% and 60% depending on different metabolites; activation time: 30 ms.

3) Results Analysis:

The original data acquired by UPLC-LTQ was processed by commercial omics analysis software progenesis QI (Version 2.0, Nonlinear Dynamics, UK) of Waters Company. The processing included peak alignment, peak identification, peak calibration, and three-dimensional matrix output including spectral peak index variables composed of retention time and accurate m/e, sample names and peak intensities/areas. Variables having the coefficient of variation (CV) less than 30% were screened from the acquired data based on the CV of quality control samples, and were subjected to subsequent multivariate statistical analysis. Variable matrix was first imported into SIMCA-P software 14.0 (Umetrics AB, Umea, Sweden) for PCA analysis, and the intergroup changes were visualized. Intergroup difference variables were screened using VIP value acquired by OPLS-DA model. The variable with VIP value greater than 1.5 was considered as significant intergroup difference variable, and could be used as a potential marker candidate. The metabolic pathway analysis was conducted on the identified difference variables to analyze the metabolic pathway closely correlated with disease process.

The analysis results for small molecules in decoctosome of *Rhodiola* and *Taraxacum mongolicum* are shown in Tables 2-5 and FIGS. 17-18.

3.3 High-Throughput Sequencing and Analysis of Small RNA in the Decoctosome of Herbal Medicines 1) The precipitates of the decoctosome of the herbal medicines obtained during the extraction process were cleaved with Trizol (Sigma) to extract RNA;
2) The sequencing was performed by Beijing BerryGenomics Biotechnology Co., Ltd using the Illumina HiSeq2500 platform, 50SE;
3) Using Fastx_toolkit software (v0.0.13), the adaptors of the sequencing reads were removed and small RNA sequences with a length greater than or equal to 18 nt were retained (by calling the command "fastx_clipper"), and the low-quality sequences were removed (by calling the command "fastq_quality_filter", set the parameters −q10, −p100));
4) Length distribution statistics on small RNA sequences was performed;
5) De-redundancy processing on small RNA sequences was performed and duplicate reads were removed;
6) A library of small RNA sequences in herbal medicine soup and decoctosome was built (by calling the command "bowtie-build") using bowtie software (http://bowtie-bio.sourceforge.net/index.shtml), and the small RNA sequences that can match both the herbal medicine soup and the decoctosome in the human blood after administrating the herbal medicines ((herbal medicines (10 g, about 100 ml) decoction was administered orally and continuously for three days) was screened (by calling the command "bowtie");
7) For herbal medicines with known genomes such as *Rhodiola*, it was necessary to use bowtie software to match the small RNA sequences above to the genomes of herbal medicines to obtain the matched sequences;
8) Small RNAs having a number of reads greater than 5 in the herbal medicine soup and decoctosome and a number of reads in human blood after administrating the herbal medicines that was higher than that before administrating the herbal medicines were screened from the small RNAs obtained above;

9) For the above small RNA sequences with inclusion relationships, the shortest small RNA sequence and the sequence having the highest number of reads in human blood after administrating herbal medicines (10 g, about 100 ml) were selected.

See Tables 8-9 and FIGS. 21-22 for the analysis results of small RNAs in *Rhodiola* and *Taraxacum mongolicum* decoctosomes.

3.4 Lipid Mass Spectrometry Method:

Lipid Extraction and High Performance Liquid Chromatography-Tandem Secondary Mass Spectrometry Technology The lipids in *Rhodiola* and *Taraxacum mongolicum* decoctosomes were extracted by Bligh&Dyer method (Bligh and Dyer, 1959). High performance liquid chromatography-tandem analysis was completed by Shanghai Minxin Information Technology Co., Ltd. Chromatographic conditions: column temperature was 45° C.; flow rate was 0.4 mL/min; binary gradient elution, 70% mobile phase A 2 min; linear increased to 100% mobile phase B for at least 20 min; 100% B 2 min; 70% A 5 min; volume of injection was 4 μl. Negative ion mode mass conditions: source spray voltage was 3.0 kV; heating capillary temperature 300° C.; flow rate of sheath gas was 45Arb; flow rate of auxiliary gas was 15Arb; scavenging flow rate was 1Arb; s-lens RF level was 30%; scanning range was m/z 200-1,500. Positive ion mode mass conditions: source spray voltage was 2.5 kV; heating capillary temperature was 350° C.; flow rate of sheath gas was 45Arb; flow rate of auxiliary gas was 10Arb; scavenging flow rate was 1Arb; s-lens RF level was 60%; scanning range was m/z 200-1,500.

LC-MS data was initially analyzed by Thermo SIEVE 2.1 Qualitative analysis software (Thermo Fisher Scientific, USA). Then, the data of each sample were normalized to the total area, and all data including peak value number [based on retention time and mass-to-charge ratio (m/z)], sample name, and normalized peak intensity were imported into SIMCA-P+13.0 (Umetrics, Sweden) to process and analyze again.

4. Functional Verification Experiment in Cell Models for Decoction of Herbal Medicines and Decoctosome 4.1 Culture of MRC-5 Cells and A549 Cells Human embryo lung fibroblast cell line MRC-5, human lung adenocarcinoma cell line A549 used in the experiments were purchased from Cell Culture Center in Peking Union Medical College. Cells were cultured in 37° C., 5% $CO_2$ incubator, wherein MRC-5 cells were cultured in EME medium (Gibco); A549 cells were cultured in Ham's F-12 medium (HyClone). Each medium contained 10% fetal bovine serum and a certain percentage of antibiotics (Penicillin 100U/ml & Streptomycin 100 mg/ml).

4.2 Changes in the Protein Expression Levels of Fibronectin in MRC-5 Cells Fibrosis Model Induced by TGF-β1 for *Rhodiola* (HJT) Decoction and HJT Decoctosome, as Determined by Western Blot 4.2.1 Experiment Groups for Decoction were as Follows:
1) Naive group: untreated MRC-5 cells. This group acted as a blank control group.
2) TGF-β1 stimulation group: MRC-5 cells were treated with 3 ng/mL transforming growth factor TGF-β1 (Pepro Tech) for 72 hours. This group acted as a positive control group.
3) Decoction experiment group: MRC-5 cells were treated with 3 ng/mL transforming growth factor TGF-1 (Pepro Tech) for 72 hours, added 300 μg/ml decoction of control plant Woody (MX, the preparation method for decoction of woody was the same as that for decoction of *Rhodiola*) or HJT (300 μg decoction was added per ml of culture medium, the decoction was quantified by the amount of precipitates after the liquid was drained) 24 hours in advance.

4.2.2 Experiment Groups for Decoctsome were as Follows:
1) Naive group: untreated MRC-5 cells. This group acted as a blank control group
2) TGF-β1 stimulation group: MRC-5 cells were treated with 3 ng/ml transforming growth factor TGF-β1 (Pepro Tech) for 72 hours. This group acted as a positive control group.
3) Decoctosome experiment group: MRC-5 cells were treated with 3 ng/ml transforming growth factor TGF-β1 (Pepro Tech) for 72 hours, added 50 μg/ml decoctosome of control plant MX or HJT (50 μg decoctosome was added per ml of culture medium, the decoction was quantified by the amount of precipitates after the liquid was drained) 24 hours in advance.

4.2.3 Collection of Protein Samples and Concentration Measurement by BCA Method:
1) Collection of protein samples of MRC-5 cells which were stimulated by TGF-β1 for 72 hours and intervened 24 hours in advance and protein concentration measurement by BCA method:
A. The medium and 12-well plate cells ($10^6$) were discarded. Each well was added 1 mL PBS buffer to wash, and was added 100 μL of pre-cooled strong RIPA lysis solution (recipe of which was shown below). The cells was scraped with a pipette and transferred into a centrifuge tube and lysed on ice for 20 minutes:

| Component | Dosage (200 ml) | Molecular weight | Final concentration |
| --- | --- | --- | --- |
| NaCl | 1.75 g | 58.44 | 150 mM |
| Tris | 1.2114 g | 121.14 | 50 mM |
| NP-40 | 2 ml | | 1% |
| Sodium Deoxycholate | 1 g | 414.55 | 0.5% |
| SDS | 0.2 g | 288.38 | 0.1% |

B. Centrifugation was conducted at 4° C., 12,000 rpm, for 10 min. The supernatant was transferred into new centrifuge tube;
C. BCA reagents A and B (TIANGEN, #PA115) (50:1, v/v) were mixed sufficiently to prepare BCA working solution;
D. 25 μL of freshly prepared BSA standard solution and sample to be tested were taken and added to a 96-well plate, respectively. 200 μL of BCA working solution was added to each well and mixed thoroughly. Incubation was conducted at 37° C. for 30 min;
E. The absorbance at 562 nm was measured with an ultraviolet spectrophotometer (Synergy 4 multifunctional microplate reader), and the protein concentration in the sample was calculated according to the standard curve;
F. The sample concentration was adjusted with RIPA lysis solution and Loading Buffer (10% SDS 20 ml, sucrose 5 g, bromophenol blue 0.2 g, beta-mercaptoethanol 5 ml) to make the concentration of each sample consistent (consistent with the lowest concentration);
G. Conducted denaturation treatment at 95° C. for 10 min.

4.2.4 Western Blot Measurement
A. Gel preparation: separation gel (lower layer gel) at a concentration of 10% and concentrated gel (upper layer gel) at a concentration of 5% were used, 15-hole comb was used to make lanes, and the amount of sample protein in each lane was equal;

B. Protein electrophoresis: the electrophoresis buffer was added, and the electrophoresis starting voltage was 80V. When the bromophenol blue dye reached the separation gel, the voltage was increased to 120V and the electrophoresis continued until the bromophenol blue dye reached the bottom of the separation gel or all of it swam out of the gel;

C. Wet transfer: assembly was done following the order of transfer splint (negative electrode)-sponge-filter paper-gel-PVDF film-filter paper-sponge-transfer splint (positive electrode). After installation, the entire transfer device was placed in 4° C. cold room. The constant current was 300 mA, and the film was transferred for 120 min;

D. Blocking: after transferring the film, it was placed in 3% BSA blocking solution and blocked for 1 hour at room temperature;

E. Primary antibody incubation: the sealed PVDF film was transferred to the hybridization bag. 3% BSA blocking solution containing the corresponding primary antibody (the information of which was as follows) was added. The air bubbles in the bag were driven out, and incubation was conducted at 4° C. overnight after sealing;

Fibronectin antibody (sigma F7387)
GAPDH antibody (protein tech 60004-1)

F. Washing the film: the PVDF film was taken out and washed 3 times with TBST, 10 min each time.

G. Secondary antibody incubation: TBST was discarded and 3% BSA blocking solution (secondary antibody dilution ratio 1:5000) containing goat anti-rabbit or goat anti-mouse secondary antibody (purchased from Hangzhou Lianke Biotechnology Co., Ltd.) with horseradish peroxidase (HRP) was added. Incubation was conducted at room temperature for 1 hour;

H. Washing the film: the film was washed 3 times with TBST, 10 min each time.

I. Development: Western color-substrate solution (1:1, V/V, Merck Millipore, ECL chemiluminescence color-substrate solution purchased from Millipore) was prepared, and evenly dropped onto one side of the membrane-bound proteins. The film was carefully wrapped with plastic wrap and was observed after the colors were developed;

J. Analysis: Image J software was used for analysis.

4.3 the mRNA Expression Level of IL-1β/IL-6/TNF-α for PGY Decoction and PGY Decoctosome in the Inflammation Model of Poly(I:C) Stimulated A549 Cells as Determined by Real-Time Fluorescent Quantitative PCR (RT-qPCR)

4.3.1 Experiment Groups for Decoction were as Follows:
1) Naive group: untreated A549 cells. This group acts as a blank control group.
2) Poly(I:C) stimulation group: A549 cells were treated with 1 μg/mL double stranded RNA virus mimics poly(I:C) (P1530, Sigma-Aldrich) for 6 hours. This group acted as a positive control group.
3) Decoction experiment group: A549 cells were added control plants cabbage (JXC) or *Taraxacum mongolicum* decoction (10 μg/ml, 30 μg/ml, 100 μg/ml) in advance and co-incubated for 24 hours, followed by treatment with 1 μg/mL double stranded RNA virus mimics poly(I:C) for 6 hours.

4.3.2 Experiment Groups for Decoctsome were as Follows:
1) Naive group: untreated A549 cells. This group acts as a blank control group
2) Poly(I:C) stimulation group: A549 cells were treated with 1 μg/mL double stranded RNA virus mimics poly(I:C) (P1530, Sigma-Aldrich) for 6 hours. This group acts as a positive control group.
3) Decoctosome experiment group: A549 cells were treated with 1 μg/mL double stranded RNA virus mimics poly(I:C) (P1530, Sigma-Aldrich) for 6 hours, added control plants cabbage (JXC) or *Taraxacum mongolicum* (PGY) decoctosome (the preparation method of which was the same as that of *Rhodiola* decoctosome) 2 μg/ml, 6 μg/ml, 20 μg/ml 24 hours in advance.

4.3.3 Extraction of total RNA in cells
A. Cells were cultured in a 12-well plate (about $1 \times 10^6$ cells/well). After discarding the culture medium, 1 mL TRIzol lysis solution was added to each well. The plate was placed on ice first. After all samples were added TRIzol, the samples were left at room temperature for 5 minutes to be fully lysed.
B. Centrifugation was conducted at 4° C., 12000 rpm for 5 min. The precipitates were discarded and TRIzol was transferred into new centrifuge tubes;
C. Chloroform was added at 200 μL chloroform/mL TRIzol. After sufficient shaking and uniform mixing, the mixture was placed at room temperature for 5 min;
D. Centrifugations was conducted at 4° C., 12000 rpm for 15 min;
E. The upper water phase was pipetted into another centrifuge tube, to which was added isopropanol at 0.5 mL isopropanol/mL TRIzol and mixed well. The mixture was placed at room temperature for 5-10 min;
F. Centrifugations was conducted at 4° C., 12000 rpm for 15 min. The supernatant was discarded, and RNA deposited at the bottom of the tube;
G. The centrifuge tube was added 1 mL 75% ethanol and gently shaken to suspend the sediment;
H. 4° C., 12000 rpm centrifuged for 10 min, discarded supernatant, added 1 mL 75% ethanol, gently shook the centrifuge tube to suspend the sediment;
I. Centrifugations was conducted at 4° C., 12000 rpm for 10 min. The supernatant was discarded. The RNA samples were dried at room temperature and dissolved with 50 μL RNase-free water. O.D value was measured to quantify RNA concentration.

4.3.4 Reverse Transcription of Total RNA to cDNA
Reverse Transcription Kit (High-Capacity cDNA Reverse Transcription Kits, Applied Biosystems, cat. No. 4368813) was used to reverse transcribe RNA into cDNA. The reverse transcription system was as follows: total RNA extracted above (150 ng/μl) 10 μL, 10×RT buffer 2.0 μL, 25×dNTP Mix (100 mM) 0.8 μL, RT random primer 2.0 μL, MultiScribe™ reverse transcriptase 1.0 μL, RNase inhibitor 1.0 μL (Invitrogen), nuclease-free H₂O 3.2 μL. After short spin, the sample was loaded into a PCR reactor to react, and the reaction conditions were as follows: (1) 25° C., 10 min; (2) 37° C., 120 min; (3) 85° C., 5 min; (4) 4° C., terminating the reaction. 20 μl RNase-free ddH₂O was added to make up the final volume to 40 μl after the reaction.

4.3.5 Quantitative PCR Amplification Reaction
The qPCR reaction system had a total volume of 10 μl, containing: 5 μL 2×SYBR Green Master Mix, 0.5 μL forward primer (10 μM), 0.5 μL reverse primer (10 μM), 1 μL cDNA obtained by reverse transcription, 3 μL RNase-free ddH₂O. LightCycler 480 fluorescence quantitative PCR instrument was used, and the PCR reaction conditions were: 95° C. for 5 min for pre-denaturation, followed by PCR amplification cycle: (1) 95° C., 10 s; (2) 55° C., 10 s; (3) 72°

C., 20 s; a total of 40 cycles; 40° C. for 10 s in the end to cool down. Both the forward and reverse primers of the amplification reaction were designed and synthesized by Beijing Tsingke Biotechnology Co., Ltd. Primer sequence (reference gene UBC forward primer: CTGGAA-GATGGTCGTACCCTG (SEQ ID NO: 101), reference gene UBC reverse primer: GGTCTTGCCAGTGAGTGTCT (SEQ ID NO: 102); target gene IL-1ß forward primer: CTCGCCAGTGAAATGATGGCT (SEQ ID NO: 103); target gene IL-1ß reverse primer: GTCGGAGAT-TCGTAGCTGGAT (SEQ ID NO: 104); target gene IL-6 forward primer: GGTACATCCTCGACGGCATCT (SEQ ID NO: 105); target gene IL-6 reverse primer: GTGCCTCTTTGCTGCTTTCAC (SEQ ID NO: 106); target gene TNF-α forward primer: CTGCCCCAATCCCTT-TATT (SEQ ID NO: 107); target gene TNF-α reverse primer: CCCAATTCTCTTTTTGAGCC (SEQ ID NO: 108)).

4.3.6 the Calculation of Relative Expression Level of mRNA

2-ΔCt method (gene relative expression level=2−(Ct target gene−Ct reference gene)) was used to calculate the relative entry level (single stranded or double stranded RNA).

4.4 the Target Gene of PGY-sRNA-6 Verified by Double Fluorescent Reporter Gene

HEK293T cells were trypsinized and added to a 48-well plate to culture for about 24 hours, then PGY-sRNA-6 and NC negative control (single-stranded NC sequence UUGUACUACACAAAAGUACUG (SEQ ID NO: 109)) were transiently transfected with the transfection reagent Lipofectamine RNAiMAX, with the final concentration of 100 nM. After 24 hours, transfection reagent Lipofectamine 2000 was used to transfect 300 ng wild-type psiCHECK2-3'-UTR (purchased from Promega, #C8201) and mutant psiCHECK2-3'-mUTR plasmid (biosynthesis, see FIG. 32 for the mutant sequence) per well. After 48 hours of transfection, cell samples were collected to detect the expression level according to the steps of the dual luciferase reporter gene detection kit (Promega, #E1960).

4.5 the Protein Expression Levels of IL-6 for *Taraxacum mongolicum* Decoction and Decoctosome in the Inflammation Model of Poly(I:C) Stimulated A549 Cells as Determined by Enzyme Linked Immunosorbent Assay (ELISA)

4.5.1 Experiment Groups for Decoction were as Follows:
1) Naive group: untreated A549 cells. The supernatant of medium was collected for use in ELISA test for protein content. This group acted as a blank control group.
2) Poly(I:C) stimulation group: A549 cells were treated with 1 μg/mL double stranded RNA virus mimics poly(I:C) (P1530, Sigma-Aldrich) for 6 hours. The supernatant of medium was collected for use in ELISA test for protein content. This group acted as a positive control group.
3) Decoction experiment group: A549 cells were added control plants cabbage (JXC) or *Taraxacum mongolicum* (PGY) decoction (10 μg/ml, 30 μg/ml, 100 μg/ml) in advance and co-incubated for 24 hours, followed by treatment with 1 μg/mL double stranded RNA virus mimics poly(I:C) for 6 hours. The supernatant of medium was collected for use in ELISA test for protein content.

According to FIG. 9D, 100 μg/ml decoction can reduce the expression of interleukin-6 in A549 cells induced by poly(I:C) stimulation.

4.5.2 Experiment Groups for Decoctsome were as Follows:
1) Naive group: untreated A549 cells. This group acted as a blank control group
2) Poly(I:C) stimulation group: A549 cells were treated with 1 μg/mL double stranded RNA virus mimics poly(I:C) (P1530, Sigma-Aldrich) for 6 hours. The supernatant of medium was collected for use in ELISA test for protein content. This group acted as a positive control group.
3) Decoctosome experiment group: A549 cells were added control plants cabbage (JXC) or *Taraxacum mongolicum* (PGY) decoctsome (2 μg/ml, 6 μg/ml, 20 μg/ml) in advance and co-incubated for 24 hours, followed by treatment with 1 μg/mL double stranded RNA virus mimics poly(I:C) for 6 hours. The supernatant of medium was collected for use in ELISA test for protein content.

According to FIG. 9E, 20 μg/ml decoctosome can reduce the expression of interleukin-6 in A549 cells caused by poly(I:C) stimulation, the effectiveness is significantly higher than the same dose of decoction 4.6 Extraction of RNA from *Rhodiola* Decoctosome and Detection of Small RNA in Decoctosome by Agarose Gel Electrophoresis
1) Decoctosome was extracted by decocting 200 g *Rhodiola* decoction pieces followed by differential centrifugation;
2) Decoctosome precipitates were added 6 ml TRIZol (sigma-Aldrich) to be fully lysed, and RNA of decoctosome was extracted;
3) The extracted RNA was evenly divided into 4 parts which were treated as follows: without treatment, added 5 μl DNase I, added 5 μl RNase A, added 5 μl DNase I and RNase A, and digested overnight in a 37° C. water bath;
4) Agarose gel electrophoresis: gel electrophoresis was carried out using 1% agarose gel under 90 volts for 20 minutes. After completion, UV lamp was used for observation.

According to FIG. 9F, there were small RNAs of about 25 bp in *Rhodiola* decoctosome.

4.7 Extraction of RNA from *Taraxacum mongolicum* Decoctosome and Determination of Small RNA in Decoctosome by Agarose Gel Electrophoresis
1) Decoctosome was extracted by decocting 200 g *Taraxacum mongolicum* decoction pieces followed by differential centrifugation;
2) Decoctosome precipitates were added 6 ml TRIZol (sigma-Aldrich) to be fully lysed, and RNA of decoctosome was extracted;
3) The extracted RNA was evenly divided into 4 parts which were treated as follows: without treatment, added 5 μl DNase I, added 5 μl RNase A, added 5 μl DNase I and RNase A, and digested overnight in a 37° C. water bath;
4) Agarose gel electrophoresis: gel electrophoresis was carried out using 1% agarose gel under 90 volts for 20 minutes. After completion, UV lamp was used for observation.

According to FIG. 9G, there were small RNAs of about 25 bp in *Taraxacum mongolicum* decoctosome.

5. Functional Verification Experiment in Animal Model for Decoctosome of Herbal Medicine 5.1 Experimental Animal The 6-8 week old male C57BL/6J mice used in the experiment were purchased from Beijing Charles River and raised under sterile conditions in the Animal Experiment Center of Peking Union Medical College. All animal experiment procedures follow the guidelines of government and animal care and use committee.

5.1.1 Bleomycin-Induced Pulmonary Fibrosis in Mice

In the model group, bleomycin (Beijing Hisun Pfizer Pharmaceutical Co., Ltd.) was injected by instillation into the trachea at a dose of 2.5 U/kg to build the model, while the control group was only injected with saline by intratracheal instillation. The mice were sacrificed on the 21st day, and the left and right lungs were collected for testing.

5.1.2 Mouse Acute Lung Injury Model

Under sterile conditions, poly(I:C) was dissolved in PBS to prepare a stock solution with a concentration of 10 mg/mL. According to the dose of 500 μg poly(I:C) per mouse, the stock solution was divided into aliquots at 50 μL per tube. An acute lung injury model was created by intratracheal instillation, and the mice were sacrificed 9 hours later, and blood and alveolar lavage fluid were collected for testing.

5.2 Function of HJT Decoctosome in Bleomycin-Induced Fibrosis Model in Mice 5.2.1 the Animal Experiment Groups were as Follows:
1) Control group: this group was only injected with saline by intratracheal instillation, and served as saline control group.
2) Bleomycin group: bleomycin was injected by instillation into the trachea at a dose of 2.5 U/kg to build the model. After 21 days, the left and right lungs were collected for testing. This group served as a positive control group.
3) Woody decoctosome experiment group: bleomycin was injected by instillation into the trachea at a dose of 2.5 U/kg to build the model. The woody decoction-derived decoctosome was administered by gavage for three consecutive days in advance at a dose of 40 g woody decoction source decoctosome (500 μL) per mouse. After 21 days, the left and right lungs were collected for testing.
4) *Rhodiola* decoctosome experiment group: bleomycin was injected by instillation into the trachea at a dose of 2.5 U/kg to build the model. The *Rhodiola* decoction-derived decoctosome was administered by gavage for three consecutive days in advance at a dose of 40 g *Rhodiola* decoction source decoctosome (500 μL) per mouse. After 21 days, the left and right lungs were collected for testing.

5.2.2 Determination of Hydroxyproline Content in Animal Lung Tissue

The hydroxyproline assay kit (#MAK008, Sigma Aldrich) was used to determine the collagen content of mouse lungs. The mouse right lung tissue was vacuum dried, weighed and hydrolyzed with 6M hydrochloric acid at 120° C. for 3 hours, and the hydroxyproline content was determined according to the kit instructions. Hydroxyproline content was expressed as "μg/right lung", unless otherwise specified 5.2.3 Pathological Examination of Animal Lung Tissue
1) Experimental Steps of Embedding Sections into Tissue Paraffin
   A. Material taking: Fresh tissues were fixed in 4% paraformaldehyde for more than 24 hours. The tissues were taken out of the fixative solution and placed in a fume hood to trim the target site tissue with a scalpel. Put the trimmed tissues and the corresponding label in the dehydration box.
   B. Dehydrating: The dehydration box was put into the hanging basket and dehydrated with gradient alcohol in the dehydrator. 75% alcohol 4h-85% alcohol 2h-90% alcohol 2h-95% alcohol 1h-anhydrous ethanol I 30 min-anhydrous ethanol II 30 min-alcohol benzene 5-10 min-xylene I 5-10 min-xylene II 5-10 min-wax I 1h-wax II 1h-wax III 1h.
   C. Embedding: The wax-soaked tissue was embedded in the embedding machine. First the melted wax was put into the embedding frame, and before the wax solidified, the tissue was taken out of the dehydration box and put into the embedding frame according to the requirements of the embedding surface and was attached the corresponding label. The tissue of cooled on a −20° C. freezing table, and after the wax solidified the wax block was removed from the embedding frame and trimmed.
   D. Sectioning: Put the trimmed wax block on a paraffin microtome for sectioning into a thickness of 4 μm. The slices were floated on the 40° C. warm water of spreader to flatten the tissues. The tissues were picked out with glass slides, and baked in a 60° C. oven. After the water was gone and the wax melted, the sections were taken out and stored at room temperature for later use.
2) Experimental Steps of HE Staining
   A. Dewaxing the paraffin sections to water: the sections were sequentially put into xylene I 20 min-xylene II 20 min-anhydrous ethanol I 10 min-anhydrous ethanol II 10 min-95% alcohol 5 min-90% alcohol 5 min-80% alcohol 5 min-70% alcohol 5 min-washed with distilled water.
   B. Hematoxylin staining of cell nuclei: the sections were put into Harris hematoxylin to stain for 3-8 min, washed with tap water, differentiated with 1% hydrochloric acid alcohol for a few seconds, rinsed with tap water, turned blue with 0.6% ammonia, and rinsed with running water. If the cytoplasm was blue, the differentiation time can be prolonged.
   C. Eosin stained cytoplasm: the sections were put into eosin stain solution and stained for 1-3 min without wash with water.
   D. Dehydration and covering of sections: the sections were sequentially put in 95% alcohol I 5 min-95% alcohol II 5 min-anhydrous ethanol I 5 min-anhydrous ethanol II 5 min-xylene I 5 min-xylene II 5 min to dehydrate to transparent. The sections were taken out from xylene and dried, and were covered with neutral gum
   E. Microscopic examination, image acquisition and analysis.
   F. Staining results: cell nuclei was blue, cytoplasm was red.

5.2.4 Masson Staining Detection of Animal Lung Tissue
1) Dewaxing the paraffin sections to water: the sections were put into xylene I 20 min-xylene II 20 min-anhydrous ethanol I 10 min-anhydrous ethanol II 10 min-95% alcohol 5 min-90% alcohol 5 min-80% alcohol 5 min-70% alcohol 5 min-washed with distilled water.
2) Hematoxylin staining of cell nuclei: Weigert's iron hematoxylin in the masson staining kit was used to stain for 5 min. The sections were washed with tap water, differentiated with 1% hydrochloric acid alcohol for a few seconds, rinsed with tap water, rinsed with running water for a few minutes to return to blue.
3) Ponceau staining: Ponceau acid magenta solution in the masson staining kit was used to stain for 5-10 min. The sections were rinsed quickly with distilled water.

4) Phosphomolybdic acid treatment: the phosphomolybdic acid aqueous solution in the masson staining kit was used for treating for about 3-5 min.
5) Aniline blue staining: the aniline blue solution in the masson staining kit was directly used to counterstained for 5 min without washing with water.
6) Differentiation: 1% acetic acid was used for treating for 1 min.
7) Dehydration and covering sections: the sections were sequentially put in 95% alcohol I 5 min-95% alcohol II 5 min-anhydrous ethanol I 5 min-anhydrous ethanol II 5 min-xylene I 5 min-xylene II 5 min, dehydrated to transparent, and taken out from xylene and dried, then covered with neutral gum
8) Microscopic examination, image acquisition and analysis.

Staining results: collagen fibers, mucus, and cartilage were blue; muscle fibers, cellulose, and red blood cells were red; cell nuclei was blue-black.

5.3 Function of PGY Decoctosome in Poly(I:C)-Induced Inflammation Model in Mice 5.3.1 the Animal Experiment Groups were as Follows:
1) Control group: this group was only infused with saline by intratracheal instillation, and served as a saline control group.
2) Poly(I:C) group: 500 μg poly(I:C) was injected by instillation into the trachea to build the model. After 9 h, the alveolar lavage fluid and whole blood samples of mice were collected. This group served as a positive control group.
3) Cabbage (JXC) decoctosome experiment group: the cabbage decoction-derived decoctosome was constantly administered by gavage 72h, 48h, 24 h, 3h in advance at a dose of 10 mg cabbage decoctosome (500 μL) per mouse. 500 μg poly(I:C) was injected by instillation into the trachea to stimulate and build the inflammation model. 3h after model building, 10 mg cabbage decoctosome (500 μL) was administered by gavage. After 9h of intratracheal instillation of 500 μg poly(I:C), the alveolar lavage fluid and whole blood samples of mice were collected.
4) *Taraxacum mongolicum* decoctosome experiment group: poly(I:C) was injected by instillation into the trachea at a dose of 2.5 U/kg to build the model. 10 mg (500 μL) of the *Taraxacum mongolicum* decoction-derived decoctosome was administered by gavage for three consecutive days in advance. 500 μg poly(I:C) was injected by instillation into the trachea to build the model. 3h after model building, 10 mg cabbage decoctosome (500 μL) was administered by gavage. 9h after model building, the alveolar lavage fluid and whole blood samples of mice were collected.

5.3.2 the Expression of Cytokines in Mouse Plasma Determined by Bioplex Mouse 23 Cytokine Kit
1) Sample treatment: The whole blood of mice was collected in an EDTA-2K anticoagulation tube, and the plasma was collected by centrifugation at 2000 rpm, 4° C. for 10 min. The plasma continued to be centrifuged at 12000 rpm, 4° C. for 10 min, the precipitates were discarded, and the upper plasma was used for measurement.
2) Bioplex experimental method: The cytokine expression in mouse alveolar lavage fluid and plasma was measured using Bioplex Mouse 23 Cytokine Detection Kit (Cat #M60009RDPD) according to the instructions. 2 replicate holes were set for the standard to improve the accuracy of the test results.

5.4 Statistical Analysis

The data were expressed as mean±SEM. All experimental data had been verified by two or more independent repeated experiments. The data showed normal distribution and there was no significant difference between groups. The parameter difference between the experimental group and the control group was evaluated by unpaired t test. The measurement data of hydroxyproline content and mouse cytokine expression content were statistically analyzed by GraphPad Prism5.0 software, and the results of Masson staining were statistically analyzed by Image Pro PLUS software. The mouse cytokine expression content was normalized with poly(I:C) group, and the statistics of Masson staining results were normalized with saline group. $P<0.05$ was considered statistically significant.

6. Preparation of Bencaosome and Function Verification Thereof 6.1 Preparation Process of Bencaosome 6.1.1 Experiment Materials Lipid Sphinganine (d22:0) (AVANTI, #792079P) was purchased from Avanti Polar Lipids company in US, and stored in chloroform at the concentration of 10 mg/ml. HJT-sRNA-m7 was purchased from Guangzhou Ruibo Biotechnology Co., Ltd., PGY-sRNA-6 was purchased from Suzhou Gemma Gene Co., Ltd., and the stored concentration was 20 μMol.

6.1.2 Preparation Method
A. The small RNA was diluted with RNase-removed water to a 100 μL system according to the required dose.
B. The corresponding amount of lipid stock solution was added to the diluted small RNA solution with a ratio of small RNA to lipid of 0.1 nmol-20 μg, 0.2 nmol-25 μg, 0.4 nmol-200 μg. The solution was mixed thoroughly to make the components fully dispersed.
C. The dispersion system was heated in a water bath at 90° C. for 15 minutes to obtain a homogeneous system of herbal medicine.

6.2 Functional Process Verification in Cell Models for Bencaosome 6.2.1 the Culture of MRC-5 Cells, A549 Cells and 293T Cells Human embryo lung fibroblast cell line MRC-5, human lung adenocarcinoma cell line A549, human embryonic kidney cell line HEK293T used in experiments were purchased from Cell Culture Center in Peking Union Medical College. Cells were cultured in 37° C., 5% $CO_2$ incubator, wherein MRC-5 cells were cultured in EME medium (Gibco), and A549 and HEK-293T cells were cultured in Ham's F-12 medium (HyClone) and DMEM (Gibco). All mediums contained 10% fetal bovine serum and a certain percentage of antibiotics (Penicillin 100U/ml& Streptomycin 100 mg/ml). The cells were cultured to the logarithmic growth phase, and then plated into 12-well plates respectively with a cell density of $6\times10^{5/1}$ ml medium/well. The cells were incubated overnight at 37° C., and subsequent experiments were conducted after the cells adhered to the wall.

6.2.2 the Expression of the Nucleic Acid Delivered by Bencaosome in the Cell Model Determined by Real-Time Fluorescent Quantitative PCR (RT-qPCR)

6.2.2.1 Experiment Groups for Bencaosome were as Follows:
1) Naive control group: untreated cells. This group acted as a blank control group.

2) Free uptake group: HJT-sRNA-m7 or PGY-sRNA-6 solution was added directly (final concentration was 100 nM). This group acted as a negative control group;

3) Bencaosome treatment group: the mixture of lipid prepared in step 2 with HJT-sRNA-m7 or PGY-sRNA-6 was added to cells and mixed well. The final concentration of HJT-sRNA-m7 or PGY-sRNA-6 was 100 nM.

6.2.2.2 Measurement of Expression of Nucleic Acid Delivered by Bencaosome

After co-incubating with cells for 12-24h, the cells were washed with PBS twice and collected with TRIzol lysis solution (Sigma). The total RNA was extracted. RT-qPCR (SYBR Green dye method) was used to measure the abundance of HJT-sRNA-m7 or PGY-sRNA-6 entering the cells with the specific steps as follows:

A. Extraction of total RNA in cells:
1) Cells were added Trizol and placed on ice. After all samples were added Trizol, they were left at room temperature for 5 minutes to be fully lysed.
2) Centrifugation was conducted at 12000 rpm for 5 min. The precipitates were discarded and Trizol was transferred into new centrifuge tubes;
3) Chloroform was added at 200 μL chloroform/mL Trizol. The mixture was fully shaken and mixed, followed by placing at room temperature for 5 min;
4) Centrifugation was conducted at 4° C., 12000 rpm for 15 min;
5) The upper water phase was pipetted into another centrifuge tube, and isopropanol was added at 0.5 mL isopropanol/mL Trizol, mixed well, and placed at room temperature for 5-10 min;
6) Centrifugation was conducted at 4° C., 12000 rpm for 15 min, supernatant was discarded, and RNA deposited to the bottom of the tube;
7) 1 mL 75% ethanol was added. The centrifuge tube was gently shaken to suspend the precipitates;
8) 4° C., 12000 rpm centrifuged for 10 min, discarded supernatant, added 1 mL 75% ethanol, gently shook the centrifuge tube to suspend the precipitates;
9) Centrifugation was conducted at 4° C., 12000 rpm for 10 min. The supernatant was discarded. The RNA samples were dried at room temperature and dissolved by 50 μL RNase-free water. RNA concentration was quantified by measuring O.D value.

B. The total RNA was reverse transcribed to cDNA: Reverse Transcription Kit (High-Capacity cDNA Reverse Transcription Kits, Applied Biosystems, cat. No. 4368813) was used to reverse transcribe sRNA into cDNA by stem-loop method. The reverse transcription system was as follows: RNA template (150 ng/μl) 10 μl, 10×RT buffer, 2.0 μl, 25×dNTP Mix (100 mM) 0.8 μl, U6 RT stem-loop primer 2.0 μl, HJT-sRNA-RT-m7 stem-loop primer 2.0 μl (or PGY-sRNA-6 RT stem-loop primer 2.0 μL), MultiScribe™ reverse transcriptase 1.0 μl, RNase inhibitor 1.0 μl, nuclease-free H₂O 1.2 μl. After short spin, the sample was loaded into a PCR reactor to react, and the reaction conditions were as follows: (1) 25° C., 10 min; (2) 37° C., 120 min; (3) 85° C., 5 min; (4) 4° C., terminating the reaction. 20 μl RNase-free ddH₂O was added to make up the final volume to 40 μl after the reaction. The stem-loop primer used in the reverse transcription process was synthesized by Beijing Tsingke Biotechnology Co., Ltd. (U6 RT primer: GTCGTATCCA- GTGCA- GGGTCCGAGGTATTCGCACTGGATACGACA- AAAATA TG (SEQ ID NO: 110); HJT-sRNA-m7 RT stem-loop primer: GTCGTATCCAGTGCACGC-TCCGAGGTATTCGCACTGGATACGACGCTTACAA (SEQ ID NO: 111)). PGY-sRNA-6 RT primer: GTCGTATCCAGTGCACGCTCCGAGGTAT-TCGCACTGGATACGACTCGGAC (SEQ ID NO: 112).

C. Quantitative PCR amplification reaction: the qPCR reaction system has a total volume of 10 μl, containing: 5 μL 2×SYBR Green Master Mix, 0.5 μl forward primer (10 μM), 0.5 μl reverse primer (10 μM), 1 μl cDNA obtained by reverse transcription, 3 μl RNase-free dH2O. LightCycler 480 fluorescence quantitative PCR instrument was used, and the PCR reaction conditions were: 95° C. for 5 min for pre-denaturation, followed by PCR amplification cycle: (1) 95° C., 10 s; (2) 55° C., 10 s; (3) 72° C., 20 s; a total of 40 cycles; 40° C. for 10 s in the end to cool down. Both the forward and reverse primers of the amplification reaction were designed and synthesized by Beijing Tsingke Biotechnology Co., Ltd. (U6 forward primer: GCGCGTCGTGAAGCGTTC (SEQ ID NO: 113), U6 reverse primer: GTGCAGGGTCCGAGGT (SEQ ID NO: 114), HJT-sRNA-m7 forward primer: TCGCGCT-GAGGTAGTAGGTT (SEQ ID NO: 115), HJT-sRNA-m7 reverse primer: GTGCACGCTCCGAGGT (SEQ ID NO: 116)). PGY-SRNA-6 primer: GTCGTA-TCCAGTGCACGCTCCGAGGTATTCGCACTGGA-TACGACTCGGAC (SEQ ID NO: 112).

E. The relative entry level calculated by 2-ΔCt method.

6.2.3 the Expression Level of mRNA Determined by the Real-Time Fluorescent Quantitative PCR (RT-qPCR)

6.2.3.2 Experiment Groups were as Follows:

1) Naive group: untreated cells. This group acted as a blank control group.
2) Poly(I:C) treatment group: A549 cells were treated by 1 μg/mL double stranded RNA virus mimics poly(I:C) for 6 hours. This group acted as a positive stimulation group.
3) So(d22:0)-NC group: A549 cells were added So(d22:0)-NC bencaosome solution (final concentration was 400 nM) in advance and co-incubated for 24h, followed by treatment with 1 μg/mL double stranded RNA virus mimics poly(I:C) for 6 hours. This group acted as a negative control group;
4) So(d22:0)-PGY-sRNA-6 bencaosome treatment group: A549 cells were added So(d22:0)-PGY-sRNA-6 bencaosome prepared in step 2, in which final concentration of nucleic acid was 400 nM, and co-incubated for 24h, followed by treatment with 1 μg/mL double stranded RNA virus mimics poly(I:C) for 6 hours.

6.2.2.3 Cells were Lysed with TRIzol Lysis Solution. The Total RNA was Extracted, and mRNA Expression Level of Corresponding Genes was Measured by RT-qPCR (SYBR-Green Dye Method), in which the Specific Steps were as Follows:

1) Extraction of total RNA in cells:
After Trizol was added into cells, the cells were placed on ice first. After all samples were added Trizol, the samples were left at room temperature for 5 minutes to be fully lysed;
Centrifugation was conducted at 12000 rpm for 5 min. The precipitates were discarded and Trizol was transferred into new centrifuge tubes;

Chloroform was added at 200 μL chloroform/mL Trizol. After sufficient shaking and uniform mixing, the mixture was placed at room temperature for 5 min;

Centrifugation was conducted at 4° C., 12000 rpm for 15 min;

The upper water phase was pipetted into another centrifuge tube, to which was added isopropanol at 0.5 mL isopropanol/mL Trizol and mixed well. The mixture was placed at room temperature for 5-10 min;

Centrifugation was conducted at 4° C., 12000 rpm for 15 min. The supernatant was discarded, and RNA deposited at the bottom of the tube;

The centrifuge tube was added 1 mL 75% ethanol and gently shaken to suspend the precipitates;

Centrifugation was conducted at 4° C., 12000 rpm for 10 min. The supernatant was discarded. The centrifuge tube was added 1 mL 75% ethanol and gently shaken to suspend the precipitates;

Centrifugation was conducted at 4° C., 12000 rpm for 10 min. The supernatant was discarded. The RNA samples were dried at room temperature and dissolved with 50 μL RNase-free water. O.D value was measured to quantify RNA concentration.

2) The total RNA was reverse transcribed to cDNA: Reverse Transcription Kit (High Capacity cDNA Reverse Transcription Kits, Applied Biosystems, cat. No. 4368813) was used to reverse transcribe the total RNA into cDNA. The reverse transcription system was as follows: RNA template (150 ng/μl) 10 μl, 10×RT buffer, 2.0 μl, 25×dNTP Mix (100 mM) 0.8 μl, random primer (included in the kit) 2.0 μl, MultiScribe™ reverse transcriptase 1.0 μl, RNase inhibitor 1.0 μl, nuclease-free H$_2$O 3.2 μl. After short spin, the samples was loaded into a PCR reactor to react, and the reaction conditions were as follows: (1) 25° C., 10 min; (2) 37° C., 120 min; (3) 85° C., 5 min; (4) 4° C., terminating the reaction. 20 μl RNase-free ddH$_2$O was added to make up the final volume to 40 μl after the reaction.

3) Quantitative PCR amplification reaction: the qPCR reaction system has a total volume of 10 μl, containing: 5 μL 2×SYBR Green Master Mix, 0.5 μl forward primer (10 μM), 0.5 μl reverse primer (10 μM), 1 μl cDNA obtained by reverse transcription, 3 μl RNase-free dH2O. LightCycler 480 fluorescence quantitative PCR instrument was used, and the PCR reaction conditions were: 95° C. for 5 min for pre-denaturation, followed by PCR amplification cycle: (1) 95° C., 10 s; (2) 55° C., 10 s; (3) 72° C., 20 s; a total of 40 cycles; 40° C. for 10 s in the end to cool down. Both the forward and reverse primers of the amplification reaction were designed and synthesized by Beijing Tsingke Biotechnology Co., Ltd. The primer sequence was same as that in section 4.3.5.

4) The relative expression level was calculated by 2-ΔCt method.

6.2.4 Protein Expression Level Detected by Western Blot 6.2.4.1 Experiment Groups were as Follows:

1) Naive group: untreated cells. This group acted as a blank control group.
2) TGF-β1 treatment group: MRC-5 cells were stimulated by 3 ng/mL transforming growth factor TGF-β1 and collected after 72 hours of treatment. This group acted as the positive stimulation group.
3) So(d22:0)-NC group: MRC-5 cells were added So(d22:0)-NC bencaosome solution (final concentration was 400 nM) and co-incubated for 24 hours, followed by stimulation with 3 ng/mL transforming growth factor TGF-β1 and collection after 72 hours of treatment. This group served as a negative control group;
4) So(d22:0)-HJT-sRNA-m7 bencaosome treatment group: MRC-5 cells were added prepared So(d22:0)-HJT-sRNA-m7 bencaosome (final concentration was 400 nM) and co-incubated for 24 hours, followed by stimulation with 3 ng/mL transforming growth factor TGF-β1 and collection after 72 hours of treatment.

6.2.4.2 after 24h Co-Incubation with Cells, MRC-5 Cells were Stimulated with 3 ng/mL Transforming Growth Factor TGF-β1 for 72 Hours and Lysed with Strong RIPA Lysis Solution. Lysis Solution was Collected to Detect the Protein Expression Level of Corresponding Genes by Western Blot.

6.2.5 the Expression Levels of Inflammatory Cytokines as Determined by Enzyme Linked Immunosorbent Assay (ELISA)

6.2.5.1 Experiment Groups were as Follows:

1) Naive group: untreated A549 cells supernatant. This group acted as a blank control group.
2) Poly(I:C) treatment group: cell supernatant obtained by treating A549 cells with 1 μg/mL double stranded RNA virus mimics poly(I:C) for 6 hours. This group acted as a positive stimulation group.
3) So(d22:0)-NC group: A549 cells were added So(d22:0)-NC bencaosome solution (final concentration is 400 nM) and co-incubated for 24 hours, followed by treatment with 1 μg/mL double stranded RNA virus mimics poly(I:C) for 6 hours. The cell supernatant was collected. This group acted as a negative control group;
4) So(d22:0)-PGY-sRNA-6 bencaosome treatment group: A549 cells were added prepared So(d22:0)-PGY-sRNA-6 bencaosome with the final concentration of nucleic acid of 400 nM and co-incubated for 24 hours, followed by treatment with 1 μg/mL double stranded RNA virus mimics poly(I:C) for 6 hours. The cell supernatant was collected.

6.2.5.2 The cell supernatant was centrifuged at 4° C., 12,000 rpm for 5 min, then transferred to a new 1.5 mL EP tube, and was added 100xx cocktail. ELISA was used to detect the expression level of inflammatory cytokines. The specific steps were as follows:

Coating: Self-coated ELISA plate (kit: IL-1 #DY201-05, IL-6 #DY206-05, TNF-α #DY210-05, which includes Detection Antibody and Related Genes Avidin-HRP of corresponding genes) from R&D company was used. Capture Antibody (IL-1, IL-6, TNF-α) was diluted with PBS (according to the dilution ratio in the instructions) and coated overnight at room temperature for about 16-18h;

Patent washing: The coated ELISA plate was taken out, with the Capture Antibody solution discarded and remaining liquid patted to dry with the filter paper. Then 300 μL of the prepared washing solution (PBS+ 0.1% tween 20) was added for washing, each time 1 min (using ELISA plate shaker). Each time the washing solution was discarded and the remaining liquid was patted to dry with the filter paper (below is the same). The washing was conducted 4 times;

Blocking: After washing, 300 μL blocking solution (PBS+ 1% BSA) was added and incubation was conducted at room temperature for 1h;

Preparation: The corresponding standards (IL-1, IL-6, TNF-α) were prepared within 1 hour, diluted according to the concentration gradient of ½ after preparing the highest concentration according to the instructions, and diluted 7 times. The eighth tube was added diluent and taken as the blank tube;

Plate washing: The plate was washed 4 times with washing solution after incubating for 1 hour;

Sample adding: The prepared standards were added to the left and right rows of the ELISA plate, and samples were added to other wells. The incubation was conducted at room temperature for 2 hours;

Adding primary antibody: The plate was washed 4 times with washing solution, added 100 μL Detection Antibody, sealed and incubated at room temperature for 2h;

Adding secondary antibody: The plate was washed 4 times with washing solution, added 100 μL Avidin-HRP, sealed and incubated at room temperature for 20 min;

Adding substrate: The plate was washed 4 times with washing solution, added 100 μL TMB Substrate Solution in the dark, and then immediately put into a drawer in the dark for about 10~20 min. After the color turned blue, 100 μL termination solution was added to terminate the reaction, and the color changed from blue to yellow;

The absorbance was measured within 30 minutes, the detection wavelength is 450 nm, and the reference wavelength is 570 nm.

6.3 Functional Process Verification for Bencaosome in Animal Model 6.3.1 Experiment Steps:

1) Preparation of bencaosome: Bencaosome was prepared by boiling method, 400 μL NC mimic (provided by Guangzhou Ruibo Biotechnology Co., Ltd.) or HJT-sRNA-m7 (10 nmol) double-stranded RNA DEPC-treated aqueous solution was respectively added 10 μL sphinganine (d22:0) lipid, mixed well and heated at 90° C. for 30 min.

2) 6-8 week old male C57 mice were administered RNA by gavage, the bencaosome solution system of lipid with NC or HJT-sRNA-m7 was administered with an intragastric needle, 400 μL/mouse, the groups were as follows:

1) Saline control group: untreated mice which were administered with saline only.

2) Bleomycin group: bleomycin was injected by instillation into the trachea at a dose of 2.5 U/kg to build the model. After 21 days, the left and right lungs were collected for testing. This group served as a positive control group.

3) Lipid Sphinganine-NC group: bleomycin was injected by instillation into the trachea at a dose of 2.5 U/kg to build the model. The bencaosome composed of lipid Sphinganine-NC (0.1 mg:5 nmol) was administered by gavage for three consecutive days in advance. After bleomycin was injected by instillation into the trachea to build the model, the same dose of bencaosome composed of lipid Sphinganine-NC was administered on Days 7-14 days. After 21 days, the left and right lungs were collected for testing.

4) Lipid Sphinganine-HJT-sRNA-m7 group: bleomycin was injected by instillation into the trachea at a dose of 2.5 U/kg to build the model. The bencaosome composed of lipid Sphinganine-HJT-sRNA-m7 (0.1 mg:5 nmol) was administered for three consecutive days in advance. After bleomycin was injected by instillation into the trachea to build the model, the same dose of bencaosome composed of lipid Sphinganine-HJT-sRNA-m7 was administered on Days 7-14. After 21 days, the left and right lungs were collected for testing.

6.3.2 Determination of Hydroxyproline Content in Animal Lung Tissue

The hydroxyproline assay kit (#MAK008, Sigma Aldrich) was used to determine the collagen content of mouse lungs. The mouse right lung tissue was vacuum dried, weighed and hydrolyzed with 6M hydrochloric acid at 120° C. for 3 hours, and the hydroxyproline content was determined according to the kit instructions. Hydroxyproline content was expressed as "μg/right lung", unless otherwise specified.

6.3.3 Pathological Examination of Animal Lung Tissue
See 5.2.3.

6.3.4 Masson Staining Detection of Animal Lung Tissue
See 5.2.4.

Example 2. Detection of Characteristics of Decoctosome of Herbal Medicine

Based on the schematic diagram for the preparation of decoctosome of herbal medicine in FIG. 1, the decoctions of two herbal medicines of *Rhodiola* (HJT) and *Taraxacum mongolicum* (PGY) were prepared according to the specific steps in Example 1, and then the precipitates of two herbal medicines, HJT and PGY, were obtained by differential centrifugation. The decoctosome precipitates were dissolved in double distilled water and their characteristics were detected after quantification. The results of transmission electron microscope are shown in FIG. 2 and FIG. 3. Both HJT decoctosome and PGY decoctosome were exosome-like nanoparticles having the outermost double-layer membrane and inhomogeneous diameter. However, the diameter of most of the decoctosomes fell between 100 nm and 200 nm.

To further observe the characteristic of decoctosome, we measured the particle size and Zeta potential of decoctosome. FIG. 4 and FIG. 5 showed that the average particle size peak of HJT decoctosome was 197.6 nm, the average particle size peak of PGY decoctosome was 153.2 nm. The particle size was uniformly distributed and showed normal distribution. Zeta potential results showed that the potential absolute value of HJT decoctosome and PGY decoctosome were greater than 30 mV, and the system was relatively stable.

Example 3. Functional Verification of Decoctosome of Herbal Medicine in Cell Model After quantifying the HJT decoction and the HJT decoctosome extracted from the decoction, the decoction with the concentration of 300 μg/ml and the decoctosome with the concentration of 50 μg/ml were selected to verify their functions in fibrosis model of MRC-5 cells induced by TGF-β1. The results were shown in FIG. 6 and FIG. 7. Both HJT decoction and HJT decoctosome could effectively reduce the expression of fibrin fibronectin in MRC-5 cells induced by TGF-β1, compared with decoction and decoctosome of control woody (MX) with the same concentration and prepared by same method.

After quantifying the PGY decoction and the PGY decoctosome extracted from the decoction, the decoction with the concentration of 10 μg/ml, 30 μg/ml, and 100 μg/ml and the decoctosome with the concentration of 2 μg/ml, 6 μg/ml, and 20 μg/ml were selected to verify their functions in inflammation model of A549 cells stimulated by poly(I:C). The results were shown in FIG. 8A-C and FIG. 9A-E, both PGY decoction and PGY decoctosome could effectively reduce the relative expression of mRNA of IL-1β, IL-6, TNF-α in inflammation model of A549 cells stimulated by poly(I:C), compared with decoction and decoctosome of control cabbage (JXC) with the same concentration and prepared by same method.

The above results were completed in cell models. The decoction and decoctosome of two herbal medicines HJT and PGY had anti-fibrosis and anti-inflammatory functions, respectively. The effective concentration of the decoction was significantly higher than that of the decoctosome, proving that the decoctosome may be a form of a mixture of herbal medicines that primarily function.

Example 4. Functional Verification of Decoctosome of Herbal Medicines in Animal Model After quantifying the HJT decoctosome extracted from decoction, decoction-derived HJT decoctosome prepared by decocting *Rhodiola* as prepared above (previously prepared with 200 g) was selected to verify the anti-fibrosis function in the bleomycin-induced mouse fibrosis model. Animal experiments groups were as follows:
1) Control group: this group was injected with saline by intratracheal instillation, and served as a saline control group.
2) Bleomycin group: bleomycin was injected by instillation into the trachea at a dose of 2.5 U/kg to build the model. After 21 days, the left and right lungs were collected for testing. This group served as a positive control group.
3) Woody decoctosome control group: bleomycin was injected by instillation into the trachea at a dose of 2.5 U/kg to build the model. The woody decoction-derived decoctosome was administered by gavage for three consecutive days in advance at a dose of 40 g woody decoction-derived decoctosome (500 µL) per mouse. After 21 days, the left and right lungs were collected for testing.
4) *Rhodiola* decoctosome control group: bleomycin was injected by instillation into the trachea at a dose of 2.5 U/kg to build the model. The *Rhodiola* decoction-derive decoctosome was administered by gavage for three consecutive days in advance at a dose of 40 g *Rhodiola* decoction-derived decoctosome (500 µL) per mouse. After 21 days, the left and right lungs were collected for testing.

The results were shown in FIGS. 10-13. Compared with the control MX decoctosome prepared by the same method at the same dose, the HJT decoctosome could effectively reduce the level of hydroxyproline in mouse lung in bleomycin-induced mouse fibrosis model (FIG. 10), effectively reduced the pulmonary fibrosis in the fibrosis model of mice induced by bleomycin (FIG. 11 and FIG. 12), and effectively reduced the pathological changes in the lungs of mice in the bleomycin-induced mouse fibrosis model (FIG. 13).

After quantifying PGY decoctosome extracted from decoction, inflammation model of A549 cells stimulated by poly(I:C) were selected when the dose of PGY decoctosome was 10 mg/mouse to verify its function. The animal experiment groups were as follows:
1) Control group: this group was only infused with saline by intratracheal instillation, served as a saline control group.
2) Poly(I:C) group: 500 µg poly(I:C) was injected by instillation into the trachea to build the model. After 9 h, the alveolar lavage fluid and whole blood samples of mice were collected. This group served as a positive control group.
3) Cabbage (JXC) decoctosome control group: the cabbage decoction derived decoctosome was administered by gavage for 72h, 48h, 24 h, 3h in advance at a dose of 10 mg cabbage decoctosome (500 µL) per mouse. 500 µg poly(I:C) was injected by instillation into the trachea to stimulate and build the inflammation model. After 3h of model building, 10 mg cabbage decoctosome (500 µL) was administered by gavage. 9h after intratracheal instillation of 500 µg poly(I:C), the alveolar lavage fluid and whole blood samples of mice were collected.
4) *Taraxacum mongolicum* decoctosome control group: the *Taraxacum mongolicum* decoction derived decoctosome 10 mg (500 µL) was administered by gavage for three consecutive days in advance. 500 µg poly(I:C) was injected by instillation into the trachea to build the model. 3h after model building, 10 mg *Taraxacum mongolicum* decoctosome (500 µL) was administered by gavage. 9h after model building, the alveolar lavage fluid and whole blood samples of mice were collected.

The results were shown in FIG. 14A-B. Compared with the control JXC decoctosome prepared by the same method at same dose, PGY decoctosome could effectively reduce the expression of all kinds of cytokines in mice plasma in mice inflammation model induced by poly(I:C).

The above results were completed in animal models. The decoctosome of two herbal medicines HJT and PGY had anti-fibrosis and anti-inflammatory functions, respectively. Based on the function verification of decoctosome in cell model in Example 3, it is proved that the decoctosome may be an important component for herbal medicine to function.

Example 5. Identification of Each Component in Decoctosome of Herbal Medicines

Since the decoctosome of herbal medicines plays an important role in its medicinal value, it is important to study the composition of the decoctosome. Taking the HJT and PGY herbal medicines as examples, first we used HPLC-MS/MS to identify the lipid components of these two decoctosomes, and a total of 25 kinds of lipid components were identified, as shown in FIG. 15 (Identification of lipids in *Rhodiola* decoctosome), FIG. 16 (Identification of lipids in *Rhodiola* decoctosome). The contents of TG, Cer, DG, PE and PC accounted for the main part of the lipids in the decoctosome.

By analyzing the compound components in HJT decoctosome and PGY decoctosome, FIG. 17 showed that 36 kinds of compounds were identified in HJT decoctosome. FIG. 18 showed that 47 kinds of compounds were identified in PGY decoctosome.

By analyzing protein components, FIG. 19 showed that 38 kinds of proteins were identified in HJT decoctosome. Similarly, FIG. 20 showed that 140 kinds of proteins were identified in PGY decoctosome. Upon simple classification of these proteins, the identified protein components in decoctosome were mainly related to metabolism, signal transduction, ubiquitination and transcription, and translation.

By extracting the RNA in the precipitates of the decoctosome, the small RNA sequencing was performed. As shown in FIG. 21 and FIG. 22, the length of the small RNA in the HJT decoctosome and the PGY decoctosome was mainly distributed between 18 nt to 25 nt. Table 8-9 showed the main information of the small RNA sequence in HJT decoctosome and PGY decoctosome. 80,573 small RNAs were identified in HJT decoctosome, and 614,545 small RNAs were identified in PGY decoctosome.

In summary, the components in the decoctosome include lipids, compounds, proteins and small RNAs.

Example 6. Preparation and Function Identification of Bencaosome

We defined bencaosome as artificially prepared nanoparticulate substances with thermally stable exosome-like membrane structure, composed of one or more synthetic lipids and substances including but not limited to synthetic or extracted lipids, artificially expressed or modified proteins, artificially synthesized or purified nucleic acids (including DNA, RNA, including small RNA), artificially synthesized or purified compounds and the like. As shown in FIG. 23, bencaosome is a substance formed by artificially combining two or more active ingredients, such as lipids, compounds, small RNAs, and proteins followed by heat treatment.

Figure 27:
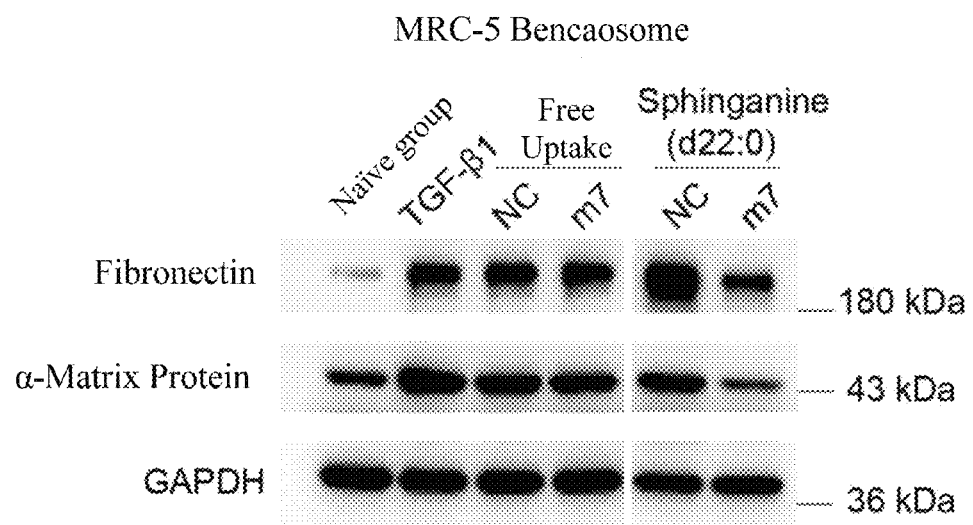

Our research proved that the small RNA in *Rhodiola* decoction, i.e., HJT-sRNA-m7, had effective anti-fibrosis effect in both fibrosis model of MRC-5 cells induced by TGF-β1 and mice fibrosis model induced by bleomycin (Du. et al., 2017). We mixed a certain proportion of lipid Sphinganine with HJT-sRNA-m7, and heated and boiled to form the bencaosome of Sphinganine-HJT-sRNA-m7. As shown in FIG. 24-FIG. 26, RT-PCR was used to detect the relative expression level of HJT-sRNA-m7 in MRC-5 cells, flow cytometry was used to detect the entry of HJT-sRNA-m7 in MRC-5 cells and the cell confocal experiment was used to detect the entry and distribution of Cy5-labeled HJT-sRNA-m7 in A549 cells, all of which proved that the bencaosome of Sphinganine-HJT-sRNA-m7 could make HJT-sRNA-m7 effectively enter cells. FIG. 27 showed that Sphinganine-HJT-sRNA-m7 had an anti-fibrosis effect in the fibrosis model of MRC-5 cells induced by TGF-β1. Sphinganine-HJT-sRNA-m7 could effectively reduce the expression of fibrosis-related protein fibronectin and α-SMA.

We synthesized and screened the top 20 small RNAs (PGY-sRNA-1~20) with the highest kurtosis in PGY decoction to verify their anti-inflammatory function. FIG. 28 showed that in the inflammation model of poly(I:C)-induced A549, PGY-sRNA-6 was the most effective in reducing the expression of IL-1β, IL-6 and TNF-α in A549 cells. PGY-sRNA-6 was verified in poly(I:C) stimulated A549 cells and PUMC cell inflammation models, FIG. 29A-C and FIG. 30A-C showed that PGY-sRNA-6 could effectively reduce the relative expression of IL-1β, IL-6 and TNF-α mRNA in A549 cells and PBMC cells stimulated by poly(I:C). Bioinformatics analysis and dual-fluorescence reporter gene detection methods were also used, and FIG. 31 and FIG. 32 showed that RELA (p65, Gene ID: 5970) was the direct target gene of PGY-sRNA-6. As shown in FIG. 33, upon bioinformatics analysis, PGY-sRNA-6 existed in both PGY decoction and PGY decoctosome, and the latter contained higher kurtosis. We mixed a certain proportion of lipid Sphinganine with PGY-sRNA-6, which was heated and boiled to form the bencaosome of Sphinganine-PGY-sRNA-6. As shown in FIG. 34-FIG. 36, RT-PCR was used to detect the relative expression level of PGY-sRNA-6 in A549 cells, flow cytometry was used to detect the entry of PGY-sRNA-6 in A549 cells and the cell confocal experiment was used to detect the entry and distribution of Cy5-labeled PGY-sRNA-6 in A549 cells, all of which proved that the bencaosome of Sphinganine-PGY-sRNA-6 can make PGY-sRNA-6 effectively enter cells. FIG. 37A-C showed that Sphinganine-PGY-sRNA-6 had an anti-inflammatory effect in the inflammation model of A549 cells stimulated by poly(I:C). Sphinganine-PGY-sRNA-6 could effectively reduce the relative expression of IL-1β, IL-6 and TNF-α mRNA in cells. FIG. 38 showed that Sphinganine-PGY-sRNA-6 effectively reduced the expression of 3'UTR of PGY-sRNA-6 target gene RELA in HEK 293T cells.

The bencaosome formed by combining lipid Sphinganine with two functional small RNAs, HJT-sRNA-m7 or PGY-sRNA-6, had effective anti-fibrosis and anti-inflammatory effects in cell models of fibrosis and inflammation. The bencaosome of Sphinganine-HJT-sRNA-m7 was shown in FIGS. 39-41. Sphinganine-HJT-sRNA-m7 could effectively reduce the changes in mouse lung cases in a bleomycin-induced fibrosis model of mice (FIG. 39), effectively reduced fibrosis of mouse lung in a mice fibrosis model induced by bleomycin (FIG. 40 and FIG. 41).

Example 7: The Bencaosome Formed by Combining Sphinganine-PGY-sRNA-6 had an Effective Anti-Inflammatory Effect in the Inflammation Model of Mice 1) Preparation of bencaosome: Boiling and heating method was used. 500 μL aqueous solution of NC mimic or PGY-sRNA-6 (5 nmol) single-stranded RNA treated with DEPC was respectively added 10 μL sphinganine (d22:0) lipid, mixed well and heated at 90° C. for 15 min.
2) The bencaosome solution systems of lipid and NC or PGY-sRNA-6 was administered to 6-8 week old male C57 mice with an intragastric needle at 500 μL/mouse. Groups were as follows:
1) Naive group: untreated mice.
2) Poly(I:C) group: 500 μg poly(I:C) was injected by instillation into the trachea to stimulate to build the model. 9h after stimulation, mice plasma was collected to detect cytokine. This group served as a positive control group.
3) Lipid Sphinganine-NC group: After the bencaosome composed of lipid Sphinganine (d22:0)-NC was administered 48h, 24 h, 3h in advance, 500 μg poly(I:C) was injected by instillation into the trachea to stimulate to build a model. 3h after stimulation, lipid Sphinganine (d22:0)-NC bencaosome was administered again. 9h after stimulation, mice plasma was collected to detect cytokine.
4) Lipid Sphinganine-PGY-sRNA-6 group: After the bencaosome composed of lipid Sphinganine (d22:0)-HJT-sRNA-m7 was administered 48h, 24 h, 3h in advance, 500 μg poly(I:C) was injected by instillation into the trachea to stimulate to build a model. 3h after stimulation, lipid Sphinganine (d22:0)-PGY-sRNA-6 bencaosome was administered again. 9h after stimulation, mice plasma was collected to detect cytokine. The reagent kit BIO-Plex Pro™ Mouse Cytokines Standard 23-Plex, Group I kit (#60009RDPD, BIO-RAD) was used to determine the expression levels of mouse plasma cytokines. Whole blood was taken into an EDTA-2K anticoagulation tube, and centrifuged at 4° C. 2000 g for 10 minutes. The upper plasma was taken and centrifuged at 4° C. 12000 g for 10 minutes. The supernatant was taken for cytokine detection.

The results were shown in FIG. 42A-G. Bencaosome effectively reduced the levels of cytokines shown in the figure.

Example 8: Different Ways to Detect the Physical and Chemical Properties of Bencaosome 1. Critical Micelle Concentration (CMC) Detection:
  6 μM 1,6-diphenyl-1,3,5-hexatriene (DPH) solution was prepared using 0.25% tetrahydrofuran: 99.75% water (v/v). 50 μL DPH solution was added to 50 μL experimental group solution in each well of a black 96-well plate. After the plate was incubated at room temperature for 1 hour in the dark, DPH fluorescence was detected. The excitation wavelength was 350 nm and the emission wavelength was 420 nm.
  2. sRNA group: 50 μL DPH solution was added to 50 μL sRNA solution in each well of a black 96-well plate. After the plate was incubated at room temperature for 1 hour in the dark, DPH fluorescence was detected.
  3. Sphinganine (So, d22:0) group: 50 μL DPH solution was added to 50 μL So(d22:0) solution in each well of a black 96-well plate. After the plate was incubated at room temperature for 1 hour in the dark, DPH fluorescence was detected.
  4. Bencaosome group: 50 μL DPH solution was added to 50 μL bencaosome solution in each well of a black 96-well plate. After the plate was incubated at room temperature for 1 hour in the dark, DPH fluorescence was detected.
  A. So(d22:0)-HJT-sRNA-m7 (200 nM) bencaosome group of heating method: 50 μL DPH solution was added to 50 μL So(d22:0)-HJT-sRNA-m7 (200 nM) bencaosome solution prepared by heating method in each well of a black 96-well plate. After the plate was incubated at room temperature for 1 hour in the dark, DPH fluorescence was detected.
  B. So(d22:0)-HJT-sRNA-m7 (600 nM) bencaosome group of heating method: 50 μL DPH solution was added to 50 μL So(d22:0)-HJT-sRNA-m7 (600 nM) bencaosome solution prepared by heating method in each well of a black 96-well plate. After the plate was incubated at room temperature for 1 hour in the dark, DPH fluorescence was detected.
  C. Unheated So(d22:0)-HJT-sRNA-m7 (200 nM) bencaosome group: 50 μL DPH solution was added to 50 μL So(d22:0)-HJT-sRNA-m7 (200 nM) bencaosome solution prepared by directly mixing in each well of a black 96-well plate. After the plate was incubated at room temperature for 1 hour in the dark, DPH fluorescence was detected.
  D. Unheated So(d22:0)-HJT-sRNA-m7 (600 nM) bencaosome group: 50 μL DPH solution was added to 50 μL So(d22:0)-HJT-sRNA-m7 (600 nM) bencaosome solution prepared by directly mixing in each well of a black 96-well plate. After the plate was incubated at room temperature for 1 hour in the dark, DPH fluorescence was detected.

As shown in FIG. 43-44, the small and medium RNAs of bencaosome may exist in the form of being embedded in lipid membranes. Heating can promote the stability of the process of inserting small and medium RNAs of bencaosome into lipid membranes.

2. The Results of the Geometric Distribution and Zeta Potential of Bencaosome Determined by Static Light Scattering Method
Detection of Particle Size and Zeta Potential of Bencaosome
  1) Preparation of bencaosome: To 100 microliters of RNA solution (2 μM, 4 μM, 6 μM) was added 30 μg lipid respectively, mixed well and heated in a water bath at 90° C. for 15 minutes, then diluted to 1 ml with ddH$_2$O during measurement.
  2) Particle size measurement: 1 ml of the system was transferred to a cuvette and measured with a Zetasizer Nano ZS90 (Malvern Instrument, UK) instrument. The measuring temperature was 25° C. . . .
  3) Zeta potential measurement: Zetasizer Nano ZS90 (Malvern Instrument, UK) instrument was used. The measuring temperature was 25° C.

3. Particle Size Distribution, Zeta Potential Measurement and Transmission Electron Microscope Morphological Observation of Bencaosome
  Preparation of bencaosome: To 100 microliters of water or RNA solution (6 μM) was added 30 μg lipid respectively, mixed well and heated in a water bath at 90° C. for 15 minutes, then diluted to 1 ml with ddH$_2$O during measurement.
  1) Particle size measurement: 1 ml of the system was transferred to a cuvette and measured with a Zetasizer Nano ZS90 (Malvern Instrument, UK) instrument. Measuring temperature was 25 degrees.
  2) Zeta potential detection: 1 ml of the system was transferred to a cuvette and measured with a Zetasizer Nano ZS90 (Malvern Instrument, UK) instrument. Measuring temperature was 25 degrees.
  3) Transmission electron microscope observation: a drop of bencaosome solution was dripped on a 200-mesh copper mesh, and the excess liquid was absorbed with filter paper. 2% phosphotungstic acid (w/w, pH 7.0) was dripped for negative dyeing for 2 minutes, excess liquid was absorbed with filter paper and dried at room temperature for 1 hour. JEOL JEM-1400 PLUS transmission electron microscope was used to observe. Observation condition voltage was 80 kV.

The geometric distribution of bencaosome was shown in FIG. 45, the Zeta potential results were shown in FIG. 46, and the particle size distribution was shown in FIG. 47A-47D. The particle size distribution of the bencaosome was about 100 nanometers, the static light scattering intensity was 50-120kcps, the zeta potential was less than 60 mV, and the absolute value was greater than 20 mV.

Example 9: The Protein Delivery Efficiency and Positioning of Bencaosome

1. Efficiency of Lipid 40 PE(16:0/22:1) to Deliver Protein Determined by Flow Cytometry
  Experimental materials: A549 cells (purchased from the Cell Center of the Chinese Academy of Medical Sciences), green fluorescent protein (internally constructed plasmid expression, 200 nM), lipid 40 PE(16:0/22:1) (10 mg/mL), Accuri® C6 instrument (Purchased from American BD Company)
  Experimental method: The bencaosome was prepared by reverse evaporation of ether. 0.2 nmol green fluorescent protein dissolved in 20 μl water was added to 100 μl ether solutions containing 0 μg, 1 μg, 3 μg lipid respectively. After fully mixing, sonication was conducted for 3 min. After evaporation at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were digested with trypsin for three minutes. The trypsin was removed, and then the samples were washed with PBS and blown off. Accuri® C6 instrument was used to measure.
  According to FIG. 149A-D, the efficiency of green fluorescent protein free entry into A549 cells was 3.6%, the efficiency of 10 μg/mL lipid 40 to deliver green fluorescent protein into A549 cells was 7.2%, and the efficiency of 30 μg/mL lipid 41 to deliver green fluorescent protein into A549 cells was 9.1%, which was higher. Lipid 40 could deliver protein into A549 cells 2. Efficiency of Lipid 41 Sphinganine (d22:0) to Deliver Protein Determined by Flow Cytometry Experimental materials: A549 cells (purchased from the Cell Center of the Chinese Academy of Medical Sciences), green fluorescent protein (internally constructed plasmid expression, 200 nM), lipid 41 sphinganine (d22:0) (10 mg/mL), Accuri® C6 instrument (Purchased from American BD Company).

Experimental method: The bencaosome was prepared by reverse evaporation method. 0.2 nmol green fluorescent protein dissolved in 20 μl water was added to 100 μl ether solutions containing 0 μg, 1 μg, 3 μg lipid respectively. After fully mixing, sonication was conducted for 3 min. After evaporation at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were digested with trypsin for three minutes. The trypsin was removed, and then the samples were washed with PBS and blown off. Accuri® C6 instrument was used to measure.

According to FIG. 150A-D, the efficiency of green fluorescent protein free entry into A549 cells was 3.6%, the efficiency of 10 μg/mL lipid 41 to deliver green fluorescent protein into A549 cells was 23.4%, and the efficiency of 30 μg/mL lipid 41 to deliver green fluorescent protein into A549 cells was 26.6%, which was higher. Lipid 41 could deliver protein into A549 cells efficiently.

3. Efficiency of Lipid 41 Sphinganine (d22:0) to Deliver Protein Determined by Flow Cytometry Experimental materials: A549 cells (purchased from the Cell Center of the Chinese Academy of Medical Sciences), green fluorescent protein (internally constructed plasmid expression, 200 nM), lipid 41 sphinganine (d22:0) (10 mg/mL), Accuri® C6 instrument (Purchased from American BD Company)

Experimental method: The bencaosome was prepared by heating method. 0.2 nmol green fluorescent protein dissolved in 100 μl water was added to 0 μL, 1 μL, 3 μL of lipid respectively. After fully mixing, the bencaosome solution was obtained by heating at 90° C. for 15 min. Then the bencaosome was added to A549 cells and co-incubated for 6 hours. The samples were collected and tested. After washing three times with PBS, the samples were digested with trypsin for three minutes, the trypsin was removed, and then the samples were washed with PBS and blown off. Accuri® C6 instrument was used to measure.

According to FIG. 150E-H, the efficiency of green fluorescent protein free entry into A549 cells was 3.6%, the efficiency of 10 μg/mL lipid 41 to deliver green fluorescent protein into A549 cells was 5.5%, and the efficiency of 30 μg/mL lipid 41 to deliver green fluorescent protein into A549 cells was 9.5%, which was higher. Lipid 41 could deliver protein into A549 cells efficiently.

4. Efficiency of Lipid 71 PE(16:0/16:0) to Deliver Protein Determined by Flow Cytometry Experimental materials: A549 cells (purchased from the Cell Center of the Chinese Academy of Medical Sciences), green fluorescent protein (internally constructed plasmid expression, 200 nM), lipid 71 PE(16:0/16:0) (10 mg/mL), Accuri® C6 instrument (Purchased from American BD Company)

Experimental method: The bencaosome was prepared by reverse evaporation method. 0.2 nmol green fluorescent protein dissolved in 20 μl water was added 100 μl ether solutions containing 0 μg, 1 μg, 3 μg lipid respectively. After fully mixing, sonication was conducted for 3 min. After evaporated at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were digested with trypsin for three minutes, the trypsin was removed, and the samples were washed with PBS and blown off. Accuri® C6 instrument was used to measure.

According to FIG. 151A-D, the efficiency of green fluorescent protein free entry into A549 cells was 3.6%, the efficiency of 10 μg/mL lipid 71 to deliver green fluorescent protein into A549 cells was 7.1%, and the efficiency of 30 μg/mL lipid 41 to deliver green fluorescent protein into A549 cells was 9.1%, which was higher. Lipid 71 could deliver protein into A549 cells efficiently.

5. Localization of Protein Delivered by Lipid 40 PE(16:0/22:1) in Cells Observed by Confocal Fluorescence Microscope Experimental materials: A549 cells (purchased from the Cell Center of the Chinese Academy of Medical Sciences), green fluorescent protein (internally constructed plasmid expression), lipid 40 PE(16:0/22:1) (10 mg/mL), Zeiss LSM780 (purchased from Germany Zeiss Company), Alexa Fluor® 488 phalloidin (purchased from Invitrogen, USA), DAPI (purchased from Invitrogen, USA), paraformaldehyde (purchased from Sigma Company, USA)

Experimental method: The bencaosome was prepared by reverse evaporation method. 0.2 nmol green fluorescent protein dissolved in 20 μl water was added to 100 μl ether solutions containing 0 μg, 0.25 μg, 0.75 μg lipid respectively. After fully mixing, sonication was conducted for 3 min. After evaporated at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were fixed with 4% paraformaldehyde. After washing three times with PBS, the samples were stained with Alexa Fluor® 488 phalloidin for 30 min. After washing three times with PBS, the samples were stained with Dapi for 5 min, then washed with PBS and sealed for observation.

According to FIG. 152, under confocal microscope, the entry of green fluorescent protein could be clearly observed, and lipid 40 could effectively deliver protein into A549 cells.

6. Localization of Protein Delivered by Lipid 41 Sphinganine (d22:0) in Cells Observed by Confocal Fluorescence Microscope Experimental materials: A549 cells (purchased from the Cell Center of the Chinese Academy of Medical Sciences), green fluorescent protein (internally constructed plasmid expression), lipid 41 sphinganine (d22:0), Zeiss LSM780 (purchased from Germany Zeiss Company), Alexa Fluor® 488 phalloidin (purchased from Invitrogen, USA), DAPI (purchased from Invitrogen, USA), paraformaldehyde (purchased from Sigma Company, USA)

Experimental method: The bencaosome was prepared by reverse evaporation method. 0.2 nmol green fluorescent protein dissolved in 20 μl water was added to 100 μl ether solutions containing 0 μg, 0.25 μg, 0.75 μg lipid respectively. After fully mixing, sonication was conducted for 3 min. After evaporated at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were fixed with 4% paraformaldehyde. After washing three times with PBS, the samples were stained with Alexa Fluor® 488 phalloidin for 30 min. After washing three times with PBS, the samples were stained with Dapi for 5 min, then washed with PBS and sealed for observation.

According to FIG. 153, under confocal microscope, the entry of green fluorescent protein could be clearly observed, and lipid 41 could effectively deliver protein into A549 cells.

7. Localization of Protein Delivered by Lipid 71 PE(16:0/16:0) in Cells Observed by Confocal Fluorescence Microscope Experimental materials: A549 cells (purchased from the Cell Center of the Chinese Academy of Medical Sciences), green fluorescent protein (internally constructed plasmid expression), lipid 71 PE(16:0/16:0), Zeiss LSM780 (purchased from Germany Zeiss Company), Alexa Fluor® 488 phalloidin (purchased from Invitrogen, USA), DAPI (purchased from Invitrogen, USA), paraformaldehyde (purchased from Sigma Company, USA)

Experimental method: The bencaosome was prepared by reverse evaporation method. 0.2 nmol green fluorescent protein dissolved in 20 μl water was added to 100 μl ether solutions containing 0 μg, 0.25 μg, 0.75 μg lipid respectively. After fully mixing, sonication was conducted for 3 min. After evaporated at 60° C. to remove organic solvent, the bencaosome solution was obtained by hydrating with 100 μL opti-MEM. Then the bencaosome was added to A549 cells and co-incubated for 6 hours. The samples were collected and tested. After washing three times with PBS, the samples were fixed with 4% paraformaldehyde. After washing three times with PBS, the samples were stained with Alexa Fluor® 488 phalloidin for 30 min. After washing three times with PBS, the samples were stained with Dapi for 5 min, then washed with PBS and sealed for observation.

According to FIG. 154, under confocal microscope, the entry of green fluorescent protein could be clearly observed, and lipid 71 could effectively deliver protein into A549 cells.

Second Part of the Experiment

Method

1. Extraction of Lipids from Herbal Medicine 1.1 Decoction Preparation of Herbal Medicine
1) 100 g decoction pieces (*Rhodiola crenulata, Taraxacum mongolicum, Lonicera japonica* and *Andrographis paniculata*, purchased from Beijing Tongrentang pharmacy) were added to 1000 mL ddH$_2$O and soaked for 30 min.
2) The mixture was decocted in a decoction pot for 15 min with intense heating, and for 20 min with gentle heating.
3) 400 mL of the heated medicine soup was added to a rotary evaporator, and was concentrated to 100 mL at 60° C., 60 rpm, 30 min.

1.2 Lipid Extraction
1) To the 160 mL decoction based on the above 1.1 (concentrated by rotary evaporator) was added 600 mL of chloroform-methanol mixture (chloroform:methanol=1:2, v/v) to make chloroform:methanol:water=1:2:0.8, and stirred for 10-15 min to mix.
2) 200 mL chloroform was add to the Erlenmeyer flask and stirred for 10 min to mix.
3) 200 ml ddH$_2$O was added to the Erlenmeyer flask to make chloroform:methanol:water=2:2:1.8, stirred for 10 min to mix.
4) The liquid of upper layer and the insoluble substances of intermediate layer was removed, and the chloroform layer of lower layer was taken out and stored at −40° C.

1.3 HPLC-MS/MS Identification of Lipid Components

Instrument Setup

1) Chromatographic Setup:
Instrument: Ultimate 3000; column: Kinetex C18 (100× 2.1 mm, 1.9 μm); column temperature: 45° C.; mobile phase A: acetonitrile:water (v/v, 60:40), the solution containing 10 mmol/L ammonium formate, mobile phase B: acetonitrile:isopropanol (10:90, v/v), the solution containing 10 mmol/L ammonium formate and 0.1% formic acid. Flow rate: 0.4 mL/min; injection volume: 4 μl.

2) Mass Spectrometry Parameters:
a) Positive mode: Heater Temp 300° C., Sheath Gas Flow rate, 45 arb, Aux Gas Flow Rate, 15 arb, Sweep Gas Flow Rate, 1 arb, spray volt age, 3.0 KV, Capillary Temp, 350° C., S-Lens RF Level, 30%. Scan ranges: 200-1500.
b) Negative mode: Heater Temp 300° C., Sheath Gas Flow rate, 45 arb, Aux Gas Flow Rate, 15 arb, Sweep Gas Flow Rate, 1 arb, spray voltage, 2.5 KV, Capillary Temp, 350° C., S-Lens RF Level, 60%. Scan ranges: 200-1500.

1.4 Identification of the Lipids Derived from Herbal Medicine

The lipid components were identified by HPLC-MS/MS, and a total of 138 lipid components derived from herbal medicine were identified, among which 125 were identified in positive mode and 13 in negative mode. The following experiments was performed on the compounds 1-69 shown in Table 10. It should be noted that the lipids tested below were all commercially purchased or commercially synthesized, and used as described in Table 10.

2. Manufacture of Lipid Nucleic Acid Mixture 2.1 Reverse Evaporation Method:
100 μl lipid in diethyl ether solution was prepared, and grouped according to the lipid numbers shown in Table 1 (the lipid concentrations are shown in the table below). To the lipid solution was added 20 μl nucleic acid solution (HJT sRNA or siRNA) at the volume ratio of 5:1, and sonicated for after 3 min. The diethyl ether was removed by evaporation at 55° C., and then 100 μl DEPC water was added for hydration to give nucleic acid lipid mixture.

TABLE 15

| FIG. | Single lipid or lipid combination | | Concentration/ (mg/mL) |
|---|---|---|---|
| 83 | 8 + 12 = 1:2 | No. 8 | 0.0833 |
| | | No. 12 | 0.1667 |
| 103 | 38 + 12 + 37 = 4:1:1 | No. 38 | 0.2 |
| | | No. 12 | 0.05 |
| | | No. 37 | 0.05 |
| 108/109/111/114 | No. 41 | No. 41 | 0.25 |
| 119 | 40 + 12 + 41 = 2:4:3 | No. 40 | 0.0667 |
| | | No. 12 | 0.1333 |
| | | No. 41 | 0.1 |
| 120 left | 12 + 41 = 1:6 | No. 12 | 0.0428 |
| | | No. 41 | 0.2571 |
| 120 right | 12 + 41 = 1:1 | No. 12 | 0.15 |
| | | No. 41 | 0.15 |
| 121 left | 12 + 41 = 6:1 | No. 12 | 0.2571 |
| | | No. 41 | 0.0428 |
| 121 right | 4 + 12 + 41 = 1:1:1 | No. 4 | 0.1 |
| | | No. 12 | 0.1 |
| | | No. 41 | 0.1 |
| 122 | 4 + 12 + 41 = 1:1:1 | No. 4 | 0.1 |
| | | No. 12 | 0.1 |
| | | No. 41 | 0.1 |

TABLE 15-continued

| FIG. | Single lipid or lipid combination | | Concentration/ (mg/mL) |
|---|---|---|---|
| 125 | No. 38 | No. 38 | 0.25 |
| 131/132/134 | No. 40 | No. 40 | 0.25 |
| 136/137 | No. 39 | No. 39 | 0.25 |
| 138 | No. 60 | No. 60 | 0.25 |
| 139 | No. 62 | No. 62 | 0.25 |

2.2 Boiling Method:

100 μL of the nucleic acid solution (HJT sRNA or siRNA) was added to 2-5 μL of the lipid solution (the concentration was shown in Table 1), mixed, and heated at 80-100° C. for 15-30 min to give nucleic acid lipid mixture.

3. In Vitro Delivery Experiment of Lipid Nucleic Acid Mixture 3.1 Real-Time Quantitative PCR (RT-qPCR) Detection of Intracellular Expression of Nucleic Acids Delivered by Lipid.

3.1.1 MRC-5 cell (pulmonary embryonic fibroblast), A549 cell (human lung adenocarcinoma cell), Caco-2 cell (human colon adenocarcinoma cell) (purchased from the Cell Resource Center of the Institute of Basic Medical Sciences, Chinese Academy of Medical Sciences) were cultured to logarithmic growth phase, then plated into 12-well plates at a cell density of $6 \times 10^{5/1}$ mL medium/well; MRC-5 and Caco-2 cells were cultured in Eagle's MEM medium (MEM, Gibco); A549 cells were cultured in Ham's F-12 medium (HyClone); followed by incubation overnight at 37° C., and the follow-up experiments were performed after the cells were attached to the walls.

3.1.2 Experimental groups were as follows:
1) Naive group: it referred to untreated cells, and this group served as a blank control group.
2) RNAimax treatment group: 2 μl Lipofectamine™MRNAimax transfection reagent (full name of Lipofectamine RNAiMAX, Invitrogen, Thermo Fisher Scientific) and HJT-sRNA-m7 solution were diluted in 100 μl opti-MEM medium (purchased from Invitrogen, Thermo Fisher Scientific) respectively and then the two were mixed, allowed to stand for 15 min, added into cells and then mixed. The final concentration of HJT-sRNA-m7 was 100 nM; this group served as a positive control group.
3) Free uptake group: HJT-sRNA-m7 solution was directly added (the final concentration was 100 nM), and the group served as a negative control group.
4) Lipid nucleic acid mixture: the mixture of lipid and HJT-sRNA-m7 prepared from the step 2 were added into cells and mixed, and the final concentration of HJT-sRNA-m7 was 100 nM.

3.1.3 After co-incubation with cells for 12-24 hours, the cells were washed twice with PBS. The cells were harvested with TRIzol lysis buffer (purchased from Sigma-Aldrich), and total RNA was extracted. The abundance of HJT-sRNA-m7 that entered the cells was detected by RT-qPCR; the protocols were as follows:

1) Extraction of total cellular RNA:
   A. To the cells cultured in a 12-well plate (about $1 \times 10^6$ cells/well) was added 1 mL TRIzol lysis buffer in each well, and then placed on ice. After to all the samples was added TRIzol, they were allowed to stand at room temperature for 5 min to allow them fully lysed.
   B. Centrifuge at 4° C., 12,000 rpm for 5 min, discard the pellet and transfer TRIzol to a fresh centrifuge tube;
   C. Add chloroform at a ratio of 200 μL chloroform/mL TRIzol, shake well, mix and allow to stand for 5 min at room temperature;
   D. Centrifuge at 4° C., 12,000 rpm for 15 min;
   E. Pipette the upper aqueous phase into another centrifuge tube, add isopropanol at a ratio of 0.5 mL isopropanol/mL TRIzol and allow to stand at room temperature for 5-10 min;
   F. Centrifuge at 4° C., 12,000 rpm for 15 min, discard the supernatant, and allow the RNA to precipitate to the bottom of the tube;
   G. Add 1 mL 75% ethanol, gently shake the tube to suspend the precipitate;
   H. Centrifuge at 4° C., 12,000 rpm for 10 min, discard the supernatant, add 1 mL 75% ethanol, gently shake the centrifuge tube to suspend the precipitate;
   I. Centrifuge at 4° C., 12,000 rpm for 10 min, discard the supernatant, dry at room temperature, dissolve the RNA sample with 50 μL RNase-free $H_2O$, and quantify the RNA concentration by the measurement of OD value.

2) Total RNA was reverse transcribed to cDNA: Reverse Transcription Kit (High-Capacity cDNA Reverse Transcription Kits, Applied Biosystems, cat. no. 4368813) was used to reverse transcribe sRNA to cDNA by stem-loop method (see, e.g. Real-time quantification of microRNAs by stem-loop RT-PCR, Nucleic Acids Res. 2005 Nov. 27; 33 (20): e179, incorporated by reference herein). The reverse transcription system was as follows: template RNA (150 ng/μL) 10 μL, 10×RT buffer 2.0 μL, 25× dNTP Mix (100 mM) 0.8 μL, U6 RT stem-loop primer 2.0 μL, HJT-sRNA-m7 RT stem-Loop primer 2.0 μL, MultiScribe™ reverse transcriptase 1.0 μL, RNase inhibitor 1.0 μL, nuclease-free $H_2O$ 1.2 μL, loaded into a PCR reactor after brief centrifugation. The reaction conditions were as follows: (1) 25° C., 10 min; (2) 37° C., 120 min; (3) 85° C., 5 min; (4) 4° C., termination of reaction. 20 μl RNase-free dd$H_2O$ was added to make up the final volume to 40 μl after the reaction. The stem-loop primer used in the reverse transcription process was synthesized by Beijing Tsingke Biotechnology Co., Ltd. (U6 RT primer, because the quantification of small RNA by RT-qPCR reaction can only be relative, so U6 was used as a standard reference gene for calculating relative expression level): GTCGTATCCAGTGCAGGGTCCGAGGTATTCGCACTGGATACGACAAAAATATG (SEQ ID NO: 110); HJT-sRNA-m7 RT stem-loop primer: GTCGTATCCAGTGCACGCTCCGAGGTATTCGCACTGGATACGACGCTTACAA (SEQ ID NO: 111)).

3) Quantitative PCR amplification reaction: the qPCR reaction system had a total volume of 10 μl, containing: 5 μL 2×SYBR Green Master Mix, 0.5 μl forward primer (10 μM), 0.5 μl reverse primer (10 μM), 1 μl. cDNA by reverse transcription, 3 μl RNase-free d$H_2O$. LightCycler 480 fluorescence quantitative PCR instrument was used, and the PCR reaction conditions were: 95° C., pre-denaturation for 5 min, followed by PCR amplification cycle: (1) 95° C., 10 s; (2) 55° C., 10 s; (3) 72° C., 20 s; a total of 40 cycles; 40° C. for 10 s in the end to cool down. Both the forward and reverse primers of the amplification reaction were designed and synthesized by Beijing Tsingke Biotechnology Co., Ltd. (U6 forward primer: GCGCGTCGTGAAGCGTTC (SEQ ID NO: 113), U6 reverse primer:

GTGCAGGGTCCGAGGT (SEQ ID NO: 114), HJT-sRNA-m7 forward primer: TCGCGCTGAGGTAGTAGGTT (SEQ ID NO: 115), HJT-sRNA-m7 reverse primer: GTGCACGCTCCGAGGT (SEQ ID NO: 116)).

4) 2-ΔCt method (relative gene expression level=2-(Ct target gene-Ct internal reference gene)) was used to calculate the relative amount of entry (single or double stranded RNA).

3.2 Real-Time Quantitative PCR (RT-qPCR) Detection of mRNA Expression Levels 3.2.1 THP-1 cell (human monocyte) was cultured to logarithmic growth phase, then plated into 12-well plates at a cell density of $6\times10^{5/1}$ mL medium/well; THP-1 cells were cultured in RPMI-1640 medium (HyClone); the cells were incubated overnight at 37° C., and the follow-up experiments were performed after the cells were attached to the walls.

3.2.2 Experimental groups were as follows:
1) naive group: referred to untreated THP-1 cells, and this group served as a blank control group.
2) RNAiMAX treatment group: 2 μl Lipofectamine-™MRNAimax transfection reagent (Invitrogen, Thermo Fisher Scientific) and nucleic acid solution (TNFα siRNA) were diluted in 100 μl opti-MEM medium (Invitrogen, Thermo Fisher Scientific) respectively and then the two were mixed, allowed to stand for 15 min, added into cells, and then mixed. The final concentration of nucleic acid was 400 nM; this group served as a positive control group.
3) Free uptake group: nucleic acid solution (TNFα siRNA) was directly added (the final concentration was 400 nM), the group served as a negative control group.
4) Lipid nucleic acid mixture: the mixture of lipid and nucleic acid prepared from the step 2 were added into cells and mixed, and the final concentration of nucleic acid was to 400 nM.

3.2.3 After 24 hours of treatment, the cells were stimulated with 1 μg/mL *E. coli* LPS (Lipopolysaccharide, LPS, *Escherichia coli* 0111: B4, L4391, Sigma-Aldrich), and harvested using TRIzol lysis buffer after 9 hours to extract total RNA. The mRNA expression level of TNF-α (the target genes of the subsequent examples varied case by case and were indicated in the Figures) was determined by RT-qPCR (SYBR Green dye method), and the protocols were as follows:
1) Extraction of the total RNA from cells: the procedures were the same as the method of extracting total RNA in Section 3.1.3.
2) Total RNA was reverse transcribed to cDNA: Reverse Transcription Kit (High-Capacity cDNA Reverse Transcription Kits, Applied Biosystems, cat. no. 4368813) was used to reverse transcribe the total RNA to cDNA. The reverse transcription system was as follows: template RNA (150 ng/μL) 10 μL, 10×RT buffer 2.0 μL, 25×dNTP Mix (100 mM) 0.8 μL, random primers 2.0 μL, MultiScribe™ reverse transcriptase 1.0 μL, RNase inhibitor 1.0 μL, nuclease-free H₂O 3.2 μL, loaded into a PCR reactor after brief centrifugation. The reaction conditions were as follows: (1) 25° C., 10 min; (2) 37° C., 120 min; (3) 85° C., 5 min; (4) 4° C., termination of reaction. 20 μl RNase-free dd H₂O was added to make up the final volume to 40 μl after the reaction.
3) Quantitative PCR amplification reaction: the total volume of qPCR reaction system was 10 μl, containing: 5 μL 2×SYBR Green Master Mix, 0.5 μl forward primer (10 μM), 0.5 μl reverse primer (10 μM), 1 μl cDNA by reverse transcription, 3 μl RNase-free dH2O. LightCycler 480 fluorescence quantitative PCR instrument was used, the PCR reaction conditions were: 95° C., pre-denaturation for 5 min, followed by PCR amplification cycle: (1) 95° C., 10 s; (2) 55° C., 10 s; (3) 72° C., 20 s; a total of 40 cycles; 40° C. for 10 s in the end to cool down. Both the forward and reverse primers of the amplification reaction were designed and synthesized by Beijing Qingke Biotechnology Co., Ltd. The primer sequences were as follows: forward primer for internal reference gene UBC: CTGGAAGATGGTCGTACCCTG (SEQ ID NO: 101), reverse primer for internal reference gene UBC: GGTCTTGCCAGTGAGTGTCT (SEQ ID NO: 102); forward primer for target gene TNF-α: CTGCCCCAATCCCTTTATT (SEQ ID NO: 107): reverse primer for target gene TNF-α: CCCAATTCTCTTTTTGAGCC (SEQ ID NO: 108).

4) The relative expression level was calculated 2-ΔCt method as described above.

3.3 Western Blot Detection of Protein Expression Levels 3.3.1 MRC-5 cell (pulmonary embryonic fibroblast), and A549 cell (human lung adenocarcinoma cell) were cultured to logarithmic growth phase, and then plated into 12-well plates at a cell density of $6\times10^{5/1}$ mL medium/well; MRC-5 cells were cultured in Eagle's MEM medium (MEM, Gibco); A549 cells were cultured in Ham's F-12 medium (HyClone); followed by incubation overnight at 37° C., and the follow-up experiments were performed after the cells were attached to the walls.

3.3.2 Experimental groups were as follows:
1) Naive group: it referred to the untreated cells, and this group served as a blank control group.
2) RNAiMAX treatment group: 2 μl Lipofectamine-™MRNAimax transfection reagent (Invitrogen, Thermo Fisher Scientific) and nucleic acid solution were diluted in 100 μl opti-MEM medium (Invitrogen, Thermo Fisher Scientific) respectively and then the two were mixed, allowed to stand for 15 min, added into cells, and then mixed. The final concentration of nucleic acid was 400 nM; this group served as a positive control group.
3) Free uptake group: the nucleic acid solution was directly added (the final concentration was 400 nM), and the group served as a negative control group.
4) Lipid nucleic acid mixture: the mixture of lipid and nucleic acid prepared from the step 2 were added into cells and mixed, and the final concentration of nucleic acid was 400 nM.

3.3.3 After 24 hours of treatment, the cells were stimulated with the stimulant (1 μg/mL poly(I:C) (P1530, Sigma-Aldrich) as double-stranded RNA viruses mimetics) or 3 ng/mL transforming growth factor TGFβ1 (Pepro Tech)). The cells were harvested using strong RIPA lysis buffer, and after incubation for some time, Western blot was used to detect the protein expression level of the related genes (the types of the related gene varied case by case and were indicated in the corresponding Figures) (the protein expression level of REL-A was detected 24 hours after the A549 cells were stimulated by poly(I:C) with β-actin as the internal reference protein; the protein expression levels of fibronectin and α-SMA were detected 72 hours after MRC-5 cells were stimulated with TGF-1 with GAPDH as the internal reference protein; the protein expression of the corresponding knockdown genes was detected in the siRNA delivery assay with β-actin as the internal reference protein). The protocols were as follows:

1) Collection of protein samples and determination of the concentration by BCA method.
H. Discard the medium, add 1 mL PBS buffer into each well of the 12-well plate to wash the cells once, add 100 µL precooled strong RIPA lysis buffer into each cell, scrap off the cells with a pipette tip and transfer to a centrifuge tube, place and keep on ice for 20 min for lysis;
I. Centrifuge at 4° C., 12,000 rpm for 10 min, transfer the supernatant to a french centrifuge tube;
J. Mix BCA reagent A and B (50:1, v/v) thoroughly to prepare a BCA working solution;
K. Add 25 µL of the freshly prepared BSA standard solution and the samples to be tested to a 96-well plate, add 200 µL BCA working solution to each well and mix well; incubate at 37° C. for 30 min;
L. Measure the absorbance at 562 nm using an ultraviolet spectrophotometer (Synergy 4 multi-function microplate reader), and calculate the protein concentration in the samples according to the standard curve;
M. Adjust the concentration of the samples with RIPA lysis buffer and loading buffer so that the concentration of each sample was the same;
N. Denaturation at 95° C. for 10 min.
2) Western blot
E. Gel preparation: a resolving gel (lower layer gel) with a concentration of 10% and stacking gel (upper layer gel) with a concentration of 5% were used. The lanes were made with a 15-well comb, and equal amounts of protein were loaded in each lane;
F. Protein electrophoresis: add electrophoresis buffer and use an initial voltage of 80V for electrophoresis; when the bromophenol blue dye reach the resolving gel, increase the voltage to 120V and continue electrophoresis until the bromophenol blue dye reach the bottom or completely out of the resolving gel;
G. Wet transfer: make the assembly in the following order: transfer pad (anode)-sponge-filter paper-gel-PVDF membrane-filter paper-sponge-transfer pad (cathode); install the assembly and put the whole transfer device at 4° C. cold chamber; set constant current at 300 mA for a 120 min transfer;
H. Blocking: place the membrane in a 3% BSA blocking solution after the transfer and block at room temperature for 1 hour;
I. Primary antibody incubation: transfer the blocked PVDF membrane to the hybridization bag, add 3% BSA blocking solution containing the corresponding primary antibody (the primary antibody informations were as follows), remove the bubbles in the bag, and incubate overnight at 4° C.
J. Membrane wash: take out the PVDF membrane and wash the membrane 3 times with TBST for 10 min each time;
K. Secondary antibody incubation: discard TBST, add 3% BSA blocking solution containing goat anti-rabbit or goat anti-mouse secondary antibody with horseradish peroxidase (HRP) (purchased from Hangzhou Lianke Biotechnology Co., Ltd.) (dilution ratio of secondary antibody was 1:5000), incubate for 1 hour at room temperature;
L. Membrane wash: wash the membrane 3 times with TBST for 10 min each time;
M. Developing: prepare Western developing solution (1:1, V/V, Merck Millipore, ECL chemiluminescence developing solution purchased from Millipore), and add the prepared developing solution evenly to the side the membrane that is bound to the proteins; carefully wrap the film with plastic wrap and observe after developing;
N. Analysis: analysis was performed using Image J software.

4. In Vivo Delivery Experiments of Lipid Nucleic Acid Mixture 4.1 Experimental Steps:
1) Preparation of lipid nucleic acid mixture: boiling method was used. To 400 µL HJT-sRNA-m7 (5 nmol) single-stranded RNA in DEPC-treated solution was added 9 µL or 18 µL lipid combinations (lipid PE (No. 38) & LPC (No. 37) & TG (No. 32), 4:2:3, V/V/V) respectively, mixed and heated at 100° C. for 30 min.
2) Intragastric administration of RNA in 6-8 weeks old male C57BL/6J wild type mice: HJT-sRNA-m7 aqueous solution or the mixture solution of lipid and HJT-sRNA-m7 were administered using a gavage needle, 400 µL/animal (HJT)-sRNA-m7, 5 nmol/animal). The groups were as follows:
A. Control group (naive group): mice that did not receive any treatment;
B. Negative control group (lipid group): intragastric administration of 9 µL lipid combinations (lipid PE (No. 38) & LPC (No. 37) & TG (No. 32), 4:2:3, V/V/V);
C. Free uptake group: direct intragastric administration of HJT-sRNA-m7 single-stranded RNA solution;
D. Lipid and nucleic acid mixture group: intragastric administration of the mixture of lipid combination and HJT-sRNA-m7 single-stranded RNA.
3) Sample collection: 3 hours after intragastric administration, the mouse whole lung was lysed with 3 mL TRIzol, homogenized and frozen at −80° C.
4) Total RNA extraction:
A. Add 3.0 mL TRIzol lysis buffer to mouse lung tissue, grind with a homogenizer, centrifuge at 12,000 rpm, 4° C., for 10 min, remove the tissue precipitate that failed to homogenize;
B. Add chloroform at a ratio of 200 µl/mL TRIzol, shake well to mix, and keep at room temperature for 15 min.
C. centrifuge at 12,000 rpm, 4° C., for 15 min, pipette the upper aqueous phase to another centrifuge tube;
D. Repeat the above step, add equal amount of chloroform to the upper aqueous phase, mix well, and keep for 10 min at room temperature;
E. 12,000 rpm, 4° C., centrifuge for 15 min;
F. Draw the upper aqueous phase to a fresh EP tube, add isopropanol a ratio of 0.5 ml/mL TRIzol, mix and keep at room temperature for 5-10 min;
G. 12,000 rpm, 4° C., centrifuge for 15 min, discard the supernatant;
H. Add 1 mL 75% ethanol, gently shake the centrifuge tube, and suspend the precipitate;
I. 12,000 rpm, 4° C., centrifuge for 10 min, discard the supernatant as much as possible;
J. Dry at room temperature for 5-10 min and dissolve the RNA sample with 50 µl DEPC-treated H$_2$O.
5) Detection of the abundance of HJT-sRNA-m7 by RT-qPCR (SYBR Green universal dye method).

Unless otherwise indicated, the single stranded HJT-sRNA-m7 solution refers to single-stranded HJT-sRNA-m7 in DEPC-treated aqueous solution. The double-stranded HJT-sRNA-m7 solution refers to a double-stranded HJT-sRNA-m7 in DEPC-treated aqueous solution.

Example 1-1: Delivery of Single-Stranded Nucleic Acids into MRC-5 Cell by Different Types of Lipid Combination 1. Experimental Groups:
   1) Naive group: untreated MRC-5 cell;
   2) RNAiMAX treatment group: 2 μl RNAiMAX transfection reagent and single-stranded HJT-sRNA-m7 in DEPC-treated aqueous solution were diluted in 100 μl opti-MEM medium, respectively, and then the two were mixed, allowed to stand for 15 min, added into cells, and then mixed. The final concentration of single-stranded HJT-sRNA-m7 was 200 nM;
   3) Free uptake group: single-stranded HJT-sRNA-m7 solution was directly added (the final concentration was 200 nM);
   4) Lipid nucleic acid mixture: mixtures of 3 μL single lipid or lipid combination and HJT-sRNA-m7 single-stranded nucleic acid solution treated by boiling method were added to the cells and mixed. The final concentration of RNA was 200 nM.
2. Experimental Procedures
   1) Boiling method conditions: to 100 μL single-stranded HJT-sRNA-m7 solution was added 3 μL single lipid or lipid combination in chloroform solution (lipid No. 1/2/4/9/14/18/19/20/21/22/23/24/25/26/27/28/29/30/32 in chloroform solution having a concentration of 5 mg/mL, lipid No. Mar. 8, 2010/11/12/13/33/34/35/36 in chloroform solution having a concentration of 10 mg/mL, lipid No. Jun. 15, 2016/17/31 in chloroform solution having a concentration of 1 mg/mL), and heated at 100° C. for 30 min;
   a) Lipid combination:
   b) MG (monoglyceride): 3 μL lipid No. 34;
   c) DG (diglyceride): 3 μL mixture of equal volume of lipids No. 1/2/3/19/35 in chloroform solution;
   d) TG (triglyceride): 3 μL mixture of equal volume of lipids No. 6/9/10/13/15/16/18/20/21/22/23/24/25/26/27/28/32/33 in chloroform solution;
   e) LPC (Lysophosphatidylcholine): 3 μL mixture of equal volume of lipids No. 36/37 in chloroform solution;
   f) PC (phosphatidylcholine): 3 μL mixture of equal volume of lipids No. 11/12 in chloroform solution;
   g) PE (phosphatidylethanolamine): 3 μL mixture of equal volume of lipids No. 8/38 in chloroform solution;
   h) Cer (Ceramides): 3 μL mixture of equal volume of lipids No. 4/14 in chloroform solution;
   i) So (Sphingoshine): 3 μL mixture of equal volume of lipids No. 17/30/31 in chloroform solution;
   j) FA (fatty acid): 3 μL lipid No. 29;
   k) Mixture: 3 μL mixture of equal volume of lipids No. 1-36 (without No. 5/7) in chloroform solution;
   l) Mixture 1:3 μL mixture of equal volume of lipids No. 1-36 (without No. 5/7/34) in chloroform solution;
   m) Mixture 2:3 μL mixture of equal volume of lipids No. 1-36 (without No. 5/7/1/2/3/19/35) in chloroform solution;
   n) Mixture 3:3 μL mixture of equal volume of lipids No. 1-36 (without No. 5/7/6/9/10/13/15/16/18/20/21/22/23/24/25/26/27/28/32/33) in chloroform solution;
   0) Mixture 4:3 μL mixture of equal volume of lipids No. 1-36 (without No. 5/7/36/37) in chloroform solution;
   p) Mixture 5:3 μL mixture of equal volume of lipids No. 1-36 (without No. 5/7/11/12) in chloroform solution;
   q) Mixture 6:3 μL mixture of equal volume of lipids No. 1-36 (without No. 5/7/8) in chloroform solution;
   r) Mixture 7:3 μL mixture of equal volume of lipids No. 1-36 (without No. 5/7/4/14) in chloroform solution;
   s) Mixture 8:3 μL mixture of equal volume of lipids No. 1-36 (without No. 5/7/29) in chloroform solution;
   2) Experimental conditions: the final concentration of HJT-sRNA-m7 was 200 nM. 12 hours after being added to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipid". The experiments were all performed in triplicates.

Conclusions: The results showed that the above lipid combinations were all effective in delivering nucleic acids into cells as compared to the free uptake group (see FIG. 48), having the potential of improving the efficiency of the delivery of nucleic acid drug in clinical settings. Nucleic acids that were mediated by the mixture 2, mixture 3, mixture 5, mixture 7, mixture 8 entered into MRC-5 cells in higher amounts.

Example 1-2: Delivery of Single-Stranded Nucleic Acids into MRC-5 Cell and Caco-2 Cell by Lipid Combination 1. Experimental Groups:
   Cells to be tested were MRC-5 cell and Caco-2 cell.
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and the two were mixed, allowed to stand for 15 min, added into cells, and then mixed. The final concentration of single-stranded HJT-sRNA-m7 was 200 nM;
   3) Free uptake group: single-stranded HJT-sRNA-m7 solution was directly added (the final concentration was 200 nM);
   4) Treatment group with single lipid and nucleic acid: a mixture of 3 μL single lipid (No. 1 or 8 or 12) and the HJT-sRNA-m7 single-stranded nucleic acid solution that was treated by boiling method was added to the cells and mixed, and the final concentration of RNA was 200 nM;
   5) Treatment group with lipid combination mixture and nucleic acid mixture: a mixture of 3 μL lipid combination (No. Jan. 8, 2012 mixed in equal volumes) and HJT-sRNA-m7 single-stranded nucleic acid solution treated by boiling method was added to the cells and mixed, and the final concentration of RNA was 200 nM;
   6) Treatment group with lipid combination and nucleic acid mixture: a mixture of 3 μL lipid combination (a mixture of 2 μL single lipid No. 1 or No. 8 or No. 12 and 1 μL of the following types of lipids (MG, DG, TG, LPC, Cer, So, or FA)) and HJT-sRNA-m7 single-stranded nucleic acid solution that were treated by boiling method was added to the cells and mixed, and the final concentration of RNA was 200 nM. In FIGS. 49A and 49B, the treatment groups were collectively represented as No. 1 2 μL+mix 1 μL, No. 8 2 μL+mix 1 μL, and No. 12 2 μL+mix 1 μL, wherein, within the horizontal line, MG represented 2 μL single lipid of No. 1 or No. 8 or No. 12+1 μL MG, DG represented 2 μL single lipid of No. 1 or No. 8 or No. 12+1 μL DG, TG represented 2 μL single lipid of No. 1 or No. 8 or No.

12+1 μL TG, LPC represented 2 μL single lipid of No. 1 or No. 8 or No. 12+1 μL LPC, Cer represented 2 μL single lipid of No. 1 or No. 8 or No. 12+1 UL Cer, So represented 2 μL single lipid of No. 1 or No. 8 or No. 12+1 μL So, FA represented 2 μL single lipid of No. 1 or No. 8 or No. 12+1 μL FA.

2. Experimental Procedures

1) Conditions of the boiling method: to 100 μL single-stranded HJT-sRNA-m7 solution was added 3 μL single lipid (lipid No. 1 in chloroform solution having a concentration of 5 mg/mL, lipids No. 8/12 in chloroform solution having a concentration of 10 mg/mL) or lipid combination, and heated at 100° C. for 30 min;

MG (monoglyceride): 2 μL lipid No. 34;

DG (diglyceride): 2 μL mixture of equal volume of lipids No. 1/2/3/19/35 in chloroform solution;

TG (triglyceride): 2 μL mixture of equal volume of lipids No. 6/9/10/13/15/16/18/20/21/22/23/24/25/26/27/28/32/33 in chloroform solution;

LPC (Lysophosphatidylcholine): 2 μL mixture of equal volume of lipids No. 36/37 in chloroform solution;

Cer (Ceramides): 2 μL mixture of equal volume of lipids No. 4/14 in chloroform solution;

So (Sphingoshine): 2 μL mixture of equal volume of lipids No. 17/30/31 in chloroform solution;

FA (fatty acid): 2 μL lipid No. 29;

2) Experimental conditions: the final concentration of HJT-sRNA-m7 was 200 nM. 24 hours after being added to the cells, the amount of HJT-sRNA-m7 that entered into the cells was detected by RT-qPCR method (SYBR Green Universal dye method). For the protocols, see "Real-time quantitative PCR detection of intracellular expression of nucleic acids delivered by lipid". All experiments were performed in triplicates.

Conclusion: The results showed that for MRC-5 cells, the mixture (No. 1/8/12 mixed in equal volume), No. 1 2 μL+No. 8 1 μL, No. 1 2 μL+No. 12 1 μL, No. 1 2 μL+MG 1 μL, No. 8 2 μL+MG 1 μL, No. 12 2 μL+No. 8 1 μL, and No. 12 2 μL+So 1 μL, delivered nucleic acid more efficiently.

For Caco-2 cells, the mixtures (No. 1/8/12 in equal volume), No. 1 2 μL+No. 8 1 μL, No. 1 2 μL+No. 12 1 μL, No. 1 2 μL+MG 1 μL, No. 8 2 μL+MG 1 μL, No. 12 2 μL+No. 8 1 μL, No. 12 2 μL+LPC 1 μL and No. 12 2 μL+So 1 μL, delivered nucleic acid more efficiently.

Example 1-3: Delivery of Single-Stranded Nucleic Acid into Cell by Lipid Combination Cell types: A549, MRC-5 and Caco-2 cells.

1. Experimental Groups:

1) Naive group: untreated cell;

2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;

3) Free uptake group: single-stranded HJT-sRNA-m7 solution was directly added (the final concentration was 100 nM);

4) Treatment group by single lipid and nucleic acid: a mixture of 3 μL single lipid (No. 8 or No. 12) and the HJT-sRNA-m7 single-stranded nucleic acid solution that was treated by boiling method was added to the cells and mixed, and the final concentration of RNA was 100 nM;

5) Treatment group by lipid combination PC (No. 12) & PE (No. 8) and nucleic acid mixture: a mixture of 2.25 μL lipid combination (PC (No. 12) & PE (No. 8), 2:1, V/V) and the HJT-sRNA-m7 single-stranded nucleic acid solution that was treated by boiling method was added to the cells and mixed, and the final concentration of RNA was 100 nM;

6) Treatment group by lipid combination and nucleic acid mixture: a mixture of 3 μL lipid combination (mixture of 2.25 μL lipid combination PC (No. 12) & PE (No. 8) and 0.75 μL of the following types of lipid, DG, TG, LPC, PC, Cer, So or FA) and the HJT-sRNA-m7 single-stranded nucleic acid solution that were treated by boiling method was added to the cells and mixed, and the final concentration of RNA was 100 nM. In FIG. 50, the mixture treatment group corresponds to the treatment groups within the horizontal line above "2.25 μL+0.75 μL".

2. Experimental Procedures

1) Boiling method conditions: to 100 μL single-stranded HJT-sRNA-m7 solution was added single lipid (lipids No. 8/12 in chloroform solution having a concentration of 10 mg/mL) or lipid combination, and heated at 100° C. for 30 min;

DG (diglyceride): 0.75 μL mixture of equal volume of lipids No. 1/2 in chloroform solution;

TG (triglyceride): 0.75 μL lipid No. 15 in chloroform solution;

LPC (Lysophosphatidylcholine): 0.75 μL mixture of equal volume of lipids No. 36/37 in chloroform solution;

PC (Lysophosphatidylcholine): 0.75 μL lipid No. 12 in chloroform solution;

Cer (Ceramides): 0.75 μL lipid No. 4 in chloroform solution;

So (Sphingoshine): 0.75 μL lipid No. 31 in chloroform solution;

FA (fatty acid): 0.75 μL lipid No. 29;

2) Experimental conditions: the final concentration of HJT-sRNA-m7 was 100 nM. 24 hours after being added to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipids and lipid combinations were effective in delivering nucleic acids into cells as compared to the free uptake group (see FIG. 50), having the potential of improving the efficiency of the delivery of nucleic acid drug in clinical settings.

For A549, MRC-5 and Caco-2 cells, 2.25 μL PC (No. 12) & PE (No. 8)+0.75 μL DG (mixture of equal volume of lipids No. 1/2 in chloroform solutions) achieved the best efficiency of delivery.

Example 1-4: Delivery of Single-Stranded Nucleic Acid into Cells by Lipid Combination Cell types: A549, MRC-5 and Caco-2 cells.

1. Experimental Groups:

1) Naive group: untreated cell;

2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
3) Free uptake group: single-stranded HJT-sRNA-m7 solution was directly added (the final concentration was 100 nM);
4) Treatment group of single lipid and nucleic acid: a mixture of 3 μL single lipid (No. 8 or No. 12) and the HJT-sRNA-m7 single-stranded nucleic acid solution that was treated by boiling method was added to the cells and mixed, and the final concentration of RNA was 100 nM;
5) Treatment group of lipid combination DG (No. 1) & PE (No. 8) & PC (No. 12) and nucleic acid mixture: a mixture of 3 μL lipid combination (DG (No. 1) & PE (No. 8) & PC (No. 12), 1:1:1, V/V/V) and the HJT-sRNA-m7 single-stranded nucleic acid solution that was treated by boiling method was added to the cells and mixed, and the final concentration of RNA was 100 nM;
6) Treatment group of lipid combination and nucleic acid mixture: a mixture of 3 μL lipid combination (mixture of 2 μL lipid combination DG (No. 1) & PE (No. 8) & PC (No. 12) and 1 μL of the following types of lipids, DG, TG, LPC, PC, Cer, So or FA) and the HJT-sRNA-m7 single-stranded nucleic acid solution that was treated by boiling method was added to the cells and mixed, and the final concentration of RNA was 100 nM. In FIG. 51, the mixture treatment groups correspond to the treatment groups within the horizontal line above 2 μL lipid combination DG (No. 1) & PE (No. 8) & PC (No. 12))+1 μL.

2. Experimental Procedures
1) Boiling method conditions: to 100 μL single-stranded HJT-sRNA-m7 solution was added 3 μL single lipid (lipid No. 1 in chloroform solution having a concentration of 5 mg/mL, lipids No. 8/12 in chloroform solution having a concentration of 10 mg/mL) or lipid combination, and heated at 100° C. for 30 min;
DG (diglyceride): 1 μL mixture of equal volume of lipids No. 1/2 in chloroform solution;
TG (triglyceride): 1 μL lipid No. 15 in chloroform solution;
LPC (Lysophosphatidylcholine): 1 μL mixture of equal volume of lipids No. 36/37 in chloroform solution;
PC (Lysophosphatidylcholine): 1 μL lipid No. 12 in chloroform solution;
Cer (Ceramides): 1 μL lipid No. 4 in chloroform solution;
So (Sphingoshine): 1 μL lipid No. 31 in chloroform solution;
FA (fatty acid): 1 μL lipid No. 29;
2) Experimental conditions: the final concentration of HJT-sRNA-m7 was 100 nM. 24 hours after being added to the cells, the amount of HJT-sRNA-m7 was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells as compared to the free uptake group (see FIG. 51), having the potential of improving the efficiency of the delivery of nucleic acid drug in clinical settings.

For A549, MRC-5 and Caco-2 cells, 2 μL DG (No. 1) & PE (No. 8) & PC (No. 12)+1 μL TG (No. 15) achieved the best efficiency of delivery.

Example 1-5: Delivery of Single-Stranded Nucleic Acid into Cell by Lipid Combination Cell types: A549, MRC-5 and Caco-2 cells.
1. Experimental Groups:
1) Naive group: untreated cell;
2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
3) Free uptake group: single-stranded HJT-sRNA-m7 solution was directly added (the final concentration was 100 nM);
4) Treatment group of single lipid and nucleic acid: a mixture of 3 μL single lipid of No. 8 and the HJT-sRNA-m7 single-stranded nucleic acid solution that was treated by boiling method was added to the cells and mixed, and the final concentration of RNA was 100 nM;
5) Treatment group of lipid combination PE (No. 8) & MG (No. 34) and nucleic acid mixture: a mixture of 2.25 μL lipid combination (PE (No. 8) & MG (No. 34), 2:1, V/V) and the HJT-sRNA-m7 single-stranded nucleic acid solution that was treated by boiling method was added to the cells and mixed, and the final concentration of RNA was 100 nM;
6) Treatment group of lipid combination and nucleic acid mixture: a mixture of 3 μL lipid combination (mixture of 2.25 μL lipid combination PE (No. 8) & MG (No. 34) and 0.75 μL of the following types of lipid, DG, TG, LPC, PC, Cer, So or FA) and the HJT-sRNA-m7 single-stranded nucleic acid solution that was treated by boiling method was added to the cells and mixed, and the final concentration of RNA was 100 nM. In FIG. 52, the mixture treatment group corresponds to the treatment groups within the horizontal line above "2.25 μL [lipid combination PE (No. 8) & MG (No. 34)]+0.75 μL".

2. Experimental Procedures
1) Boiling method conditions: to 100 μL single-stranded HJT-sRNA-m7 solution was added single lipid (lipid No. 8 in chloroform solution having a concentration of 10 mg/mL) or lipid combination, and heated at 100° C. for 30 min;
DG (diglyceride): 0.75 μL mixture of equal volume of lipids No. 1/2 in chloroform solution;
TG (triglyceride): 0.75 μL lipid No. 15 in chloroform solution;
LPC (Lysophosphatidylcholine): 0.75 μL mixture of equal volume of lipids No. 36/37 in chloroform solution;
PC (Lysophosphatidylcholine): 0.75 μL lipid No. 12 in chloroform solution;
Cer (Ceramides): 0.75 μL lipid No. 4 in chloroform solution;
So (Sphingoshine): 0.75 μL lipid No. 31 in chloroform solution;
FA (fatty acid): 0.75 μL lipid No. 29;
2) Experimental conditions: the final concentration of HJT-sRNA-m7 was 100 nM. 24 hours after being added to the cells, the amount of HJT-sRNA-m7 that entered in to cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipid and lipid combinations were effective in delivering nucleic acids into cells as compared to the free uptake group (see FIG. 52), having the potential of improving the efficiency of the delivery of nucleic acid drug in clinical settings.

For A549, MRC-5 and Caco-2 cells, 2.25 µL PE (No. 8) & MG (No. 34)+0.75 UL So (No. 31) achieved the best efficiency of delivery.

Example 1-6: Delivery of Single-Stranded Nucleic Acid into A549 Cells by Lipid Combination 1. Experimental Groups:
   1) Naive group: untreated A549 cell;
   2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of single lipid and nucleic acid: a mixture of 3 µL single lipid No. 38 and the HJT-sRNA-m7 single-stranded nucleic acid solution that was treated by boiling method was added to the cell, and mixed, and the final concentration of RNA was 100 nM;
   5) Treatment group of lipid combination and nucleic acid mixture: a mixture of 3 µL lipid combination (mixture of 2 µL single lipid No. 38 and 1 µL of the following types of lipid, MG, DG, TG, LPC, PC, PE, Cer, So or FA) and the HJT-sRNA-m7 single-stranded nucleic acid solution that was treated by boiling method was added to the cells and mixed, and the final concentration of RNA was 100 nM;

2. Experimental Procedures
   1) Boiling method conditions: to 100 µL single-stranded HJT-sRNA-m7 solution was added 3 µL single lipid (lipid No. 38 in chloroform solution having a concentration of 10 mg/mL) or lipid combination, and heated at 100° C. for 30 min;
   MG (monoglyceride): 1 µL lipid No. 34;
   DG (diglyceride): 1 µL lipid No. 1 in chloroform solution;
   TG (triglyceride): 1 µL lipid No. 15 in chloroform solution;
   LPC (Lysophosphatidylcholine): 1 µL lipid No. 37 in chloroform solution;
   PC (Lysophosphatidylcholine): 1 µL lipid No. 12 in chloroform solution;
   PE (phosphatidylethanolamine): 1 µL lipid No. 8 in chloroform solution;
   Cer (Ceramides): 1 µL lipid No. 4 in chloroform solution;
   So (Sphingoshine): 1 µL lipid No. 31 in chloroform solution;
   FA (fatty acid): 1 µL lipid No. 29 in chloroform solution;
   2) Experimental conditions: the final concentration of HJT-sRNA-m7 was 100 nM. 24 hours after being added to the cell, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that for A549 cells, the above 2 µL single lipid No. 38 and 1 µL LPC (No. 37), TG (No. 15), PC (No. 12), DG (No. 1) were effective in delivering nucleic acids into cells as compared to the free uptake group (see FIG. 53).

Example 1-7: Delivery of Single-Stranded Nucleic Acid into A549 Cells by Lipid Combination 1. Experimental Groups:
   1) Naive group: untreated A549 cell;
   2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination DG (No. 1) & PE (No. 38) & PC (No. 12) and nucleic acid mixture: a mixture of 3 µL lipid combination (DG (No. 1) & PE (No. 38) & PC (No. 12), 1:1:1, V/V/V) and the HJT-sRNA-m7 single-stranded nucleic acid solution that was treated by boiling method was added to the cells and mixed, and the final concentration of RNA was 100 nM;
   5) Treatment group of lipid combination and nucleic acid mixture: a mixture of 3 µL lipid combination (mixture of 2 µL lipid combination DG (No. 1) & PE (No. 38) & PC (No. 12) and 1 µL of the following types of lipid, MG, TG, LPC, PE, Cer, So or FA) and the HJT-sRNA-m7 single-stranded nucleic acid solution that was treated by boiling method was added to the cells and mixed, and the final concentration of RNA was 100 nM.

2. Experimental Procedures
   1) Boiling method conditions: to 100 µL single-stranded HJT-sRNA-m7 solution was added 3 µL lipid combination, and heated at 100° C. for 30 min;
   MG (monoglyceride): 1 µL lipid No. 34;
   TG (triglyceride): 1 µL lipid No. 15 in chloroform solution;
   LPC (Lysophosphatidylcholine): 1 µL lipid No. 37 in chloroform solution;
   PE (phosphatidylethanolamine): 1 µL lipid No. 8 in chloroform solution;
   Cer (Ceramides): 1 µL lipid No. 4 in chloroform solution;
   So (Sphingoshine): 1 µL lipid No. 31 in chloroform solution;
   FA (fatty acid): 1 µL lipid No. 29 in chloroform solution;
   2) Experimental conditions: the final concentration of HJT-sRNA-m7 was 100 nM. 24 hours after being added to the cells, the amount of HJT-sRNA-m7 was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above 2 µL lipid combination DG (No. 1) & PE (No. 38) & PC (No. 12) and 1 µL TG (No. 15), Cer (No. 4), So (No. 31), FA (No. 29), LPC (No. 37), PE (No. 8) were all effective in delivering nucleic acids into A549 cells as compared to the free uptake group (see FIG. 54), having the potential of improving the efficiency of the delivery of nucleic acid drug in clinical settings.

Example 1-8: Delivery of Single-Stranded Nucleic Acid into A549 Cells by Lipid Combination 1. Experimental Groups:
    1) Naive group: untreated A549 cell;
    2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
    3) Free uptake group: single-stranded HJT-sRNA-m7 solution was directly added (the final concentration was 100 nM);
    4) Treatment group of lipid combination PE (No. 38) & MG (No. 34) and nucleic acid mixture: a mixture of 3 µL lipid combination (PE (No. 38) & MG (No. 34), 2:1, V/V) and the HJT-sRNA-m7 single-stranded nucleic acid solution that was treated by boiling method was added to the cells and mixed, and the final concentration of RNA was 100 nM;
    5) Treatment group of lipid combination and nucleic acid mixture: a mixture of 3 µL lipid combination (mixture of 2 µL lipid combination PE (No. 38) & MG (No. 34) and 1 µL of the following types of lipid, DG, TG, LPC, PC, PE, Cer, So or FA) and the HJT-sRNA-m7 single-stranded nucleic acid solution that was treated by boiling method was added to the cells and mixed, and the final concentration of RNA was 100 nM;
2. Experimental Procedures
    1) Boiling method conditions: to 100 µL single-stranded HJT-sRNA-m7 solution was added 3 µL lipid combination, and heated at 100° C. for 30 min;
    DG (diglyceride): 1 µL lipid No. 1 in chloroform solution;
    TG (triglyceride): 1 µL lipid No. 15 in chloroform solution;
    LPC (Lysophosphatidylcholine): 1 µL lipid No. 37 in chloroform solution;
    PC (phosphatidylcholine): 1 µL lipid No. 12 in chloroform solution;
    PE (phosphatidylethanolamine): 1 µL lipid No. 8 in chloroform solution;
    Cer (Ceramides): 1 µL lipid No. 4 in chloroform solution;
    So (Sphingoshine): 1 µL lipid No. 31 in chloroform solution;
    FA (fatty acid): 1 µL lipid No. 29 in chloroform solution;
    2) Experimental conditions: the final concentration of HJT-sRNA-m7 was 100 nM. 24 hours after being added to the cells, the amount of HJT-sRNA-m7 was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were all effective in delivering nucleic acids into cells (see FIG. 55), having the potential of improving the efficiency of the delivery of nucleic acid drug in clinical settings, wherein 2 µL lipid combination PE (No. 38) & MG (No. 34) and 1 µL LPC (No. 37) achieved the best delivery effect.

Example 1-9: Delivery of Single-Stranded Nucleic Acid into A549 Cells by Lipid Combination 1. Experimental Groups:
    1) Naive group: untreated cell;
    2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
    3) Free uptake group: single-stranded HJT-sRNA-m7 solution was directly added (the final concentration was 100 nM);
    4) Treatment group of lipid combination PE (No. 38) & PC (No. 12) and nucleic acid mixture: a mixture of 3 µL lipid combination (PE (No. 38) & PC (No. 12), 2:1, V/V) and the HJT-sRNA-m7 single-stranded nucleic acid solution that was treated by boiling method was added to the cells, and mixed, and the final concentration of RNA was 100 nM;
    5) Treatment group of lipid combination and nucleic acid mixture: a mixture of 3 µL lipid combination (mixture of 2 µL lipid combination PE (No. 38) & PC (No. 12) and 1 µL of the following types of lipid, MG, DG, TG, LPC, PE, Cer, So or FA) and the HJT-sRNA-m7 single-stranded nucleic acid solution that was treated by boiling method was added to the cells, and mixed, and the final concentration of RNA was 100 nM;
2. Experimental Procedures
    1) Boiling method conditions: to 100 µL single-stranded HJT-sRNA-m7 solution was added 3 µL lipid combination, and heated at 100° C. for 30 min;
    MG (monoglyceride): 1 µL lipid No. 34;
    DG (diglyceride): 1 µL lipid No. 1 in chloroform solution;
    TG (triglyceride): 1 µL lipid No. 15 in chloroform solution;
    LPC (Lysophosphatidylcholine): 1 µL lipid No. 37 in chloroform solution;
    PE (phosphatidylethanolamine): 1 µL lipid No. 8 in chloroform solution;
    Cer (Ceramides): 1 µL lipid No. 4 in chloroform solution;
    So (Sphingoshine): 1 µL lipid No. 31 in chloroform solution;
    FA (fatty acid): 1 µL lipid No. 29;
    2) Experimental conditions: the final concentration of HJT-sRNA-m7 was 100 nM, 24 hours after being added to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 56), having the potential of improving the efficiency of the delivery of nucleic acid drug in clinical settings, wherein 2 µL lipid combination PE (No. 38) & PC (No. 12) and 1 UL Cer (No. 4) achieved the best effect.

Example 1-10: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination PE (No. 38) & PC (No. 12) & DG (No. 1) & TG (No. 15) and nucleic acid mixture: a mixture of 3 μL lipid combination (PE (No. 38) & PC (No. 12) & DG (No. 1) & TG (No. 15), 2:2:2:3, V/V/V/V) and the HJT-sRNA-m7 single-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2.2 μL lipid combination PE (No. 38) & PC (No. 12) & DG (No. 1) & TG (No. 15) and 0.8 μL of the following types of lipid, MG, LPC, Cer, So or FA) and the HJT-sRNA-m7 single-stranded nucleic acid solution that was treated by boiling method was added to the cells, and mixed, and the final concentration of RNA was 100 nM.
2. Experimental Procedures
   1) Boiling method conditions: to 100 μL single-stranded HJT-sRNA-m7 solution was added 3 μL lipid combination, and heated at 100° C. for 30 min;
   MG (monoglyceride): 0.8 μL lipid No. 34;
   LPC (Lysophosphatidylcholine): 0.8 μL lipid No. 37 in chloroform solution;
   Cer (Ceramides): 0.8 μL lipid No. 4 in chloroform solution;
   So (Sphingoshine): 0.8 μL lipid No. 31 in chloroform solution;
   FA (fatty acid): 0.8 μL lipid No. 29;
   2) Experimental conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 57), wherein 2.2 L lipid combination PE (No. 38) & PC (No. 12) & DG (No. 1) & TG (No. 15), 2.2 μL lipid combination PE (No. 38) & PC (No. 12) & DG (No. 1) & TG (No. 15) and 0.8 μL LPC (No. 37) or So (No. 31) achieved relative better efficiency of delivery.

Example 1-11: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination PE (No. 38) & MG (No. 34) & LPC (No. 37) and nucleic acid mixture: a mixture of 3 μL lipid combination (PE (No. 38) & MG (No. 34) & LPC (No. 37), 4:2:3, V/V/V) and the HJT-sRNA-m7 single-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2.2 μL lipid combination PE (No. 38) & MG (No. 34) & LPC (No. 37) and 0.8 μL of the following types of lipid, DG, TG, PC, Cer, or So) and the HJT-sRNA-m7 single-stranded nucleic acid solution that was treated by boiling method was added to the cells, and mixed, and the final concentration of RNA was 100 nM;
2. Experimental Procedures
   1) Boiling method conditions: to 100 μL single-stranded HJT-sRNA-m7 solution was added 3 μL lipid combination, and heated at 100° C. for 30 min;
   DG (diglyceride): 0.8 μL lipid No. 1 in chloroform solution;
   TG (triglyceride): 0.8 μL lipid No. 15 in chloroform solution;
   PC (phosphatidylcholine): 0.8 μL lipid No. 12 in chloroform solution;
   Cer (Ceramides): 0.8 μL lipid No. 4 in chloroform solution;
   So (Sphingoshine): 0.8 μL lipid No. 31 in chloroform solution;
   2) Experimental conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 58), having the potential of improving the efficiency of the delivery of nucleic acid drug in clinical settings.

Example 1-12: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;

3) Free uptake group: single-stranded HJT-sRNA-m7 solution was directly added (the final concentration was 100 nM);
4) Treatment group of lipid combination PE (No. 38) & PC (No. 12) & Cer (No. 4) and nucleic acid mixture: a mixture of 3 µL lipid combination (PE (No. 38) & PC (No. 12) & Cer (No. 4), 4:2:3, V/V/V) and the HJT-sRNA-m7 single-stranded nucleic acid solution that was treated by boiling method was added to the cells, and mixed, and the final concentration of RNA was 100 nM;
5) Treatment group of lipid combination and nucleic acid mixture: a mixture of 3 µL lipid combination (mixture of 2.2 µL lipid combination PE (No. 38) & PC (No. 12) & Cer (No. 4) and 0.8 µL of the following types of lipid, MG, DG, TG, LPC, So or FA) and the HJT-sRNA-m7 single-stranded nucleic acid solution that was treated by boiling method was added to the cells, and mixed, and the final concentration of RNA was 100 nM.

2. Experimental Procedures
1) Boiling method conditions: to 100 µL single-stranded HJT-sRNA-m7 solution was added 3 µL lipid combination, and heated at 100° C. for 30 min;
MG (monoglyceride): 0.8 µL lipid No. 34;
DG (diglyceride): 0.8 µL lipid No. 1 in chloroform solution;
TG (triglyceride): 0.8 µL lipid No. 15 in chloroform solution;
LPC (lysophosphatidylcholine): 0.8 µL lipid No. 37 in chloroform solution;
So (Sphingoshine): 0.8 µL lipid No. 31 in chloroform solution;
FA (fatty acid): 0.8 µL lipid No. 29 in chloroform solution;
2) Experimental conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 59), wherein 2.2 µL lipid combination PE (No. 38) & PC (No. 12) & Cer (No. 4) and 0.8 µL FA (No. 29) achieved the best efficiency of delivery.

Example 1-13: Delivery of Single-Stranded Nucleic Acid into A549 Cells by Lipid Combination 1. Experimental Groups:
1) Naive group: untreated cell;
2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
3) Free uptake group: single-stranded HJT-sRNA-m7 solution was directly added (the final concentration was 100 nM);
4) Treatment group of lipid combination PE (No. 38) & PC (No. 12) & Cer (No. 4) & FA (No. 29) and nucleic acid mixture: a mixture of 3 µL lipid combination (PE (No. 38) & PC (No. 12) & Cer (No. 4) & FA (No. 29), 44:22:33:36, V/V/V/V) and the HJT-sRNA-m7 single-stranded nucleic acid solution that was treated by boiling method was added to the cells, and mixed, and the final concentration of RNA was 100 nM;
5) Treatment group of lipid combination and nucleic acid mixture: a mixture of 3 µL lipid combination (mixture of PE (No. 38) & PC (No. 12) & Cer (No. 4) & FA (No. 29) and 1 µL of the following types of lipid) and the HJT-sRNA-m7 single-stranded nucleic acid solution that was treated by boiling method was added to the cells, and mixed, and the final concentration of RNA was 100 nM.

2. Experimental Procedures
1) Boiling method conditions: to 100 µL single-stranded HJT-sRNA-m7 solution was added 3 µL lipid combination, and heated at 100° C. for 30 min;
MG (monoglyceride): 1 µL lipid No. 34;
DG (diglyceride): 1 µL lipid No. 1 in chloroform solution;
TG (triglyceride): 1 µL lipid No. 15 in chloroform solution;
LPC (lysophosphatidylcholine): 1 µL lipid No. 37 in chloroform solution;
So (Sphingoshine): 1 µL lipid No. 31 in chloroform solution;
2) Experimental conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 60), having the potential of improving the efficiency of the delivery of nucleic acid drug in clinical settings.

Example 1-14: Delivery of Single-Stranded Nucleic Acid into A549 Cells by Lipid Combination 1. Experimental Groups:
1) Naive group: untreated cell;
2) RNAiMAX treatment group: 2 µl RNAiMAX transfection reagent and single-stranded HJT-sRNA-m7 solution were diluted in 100 µl opti-MEM medium, respectively, and then the two were mixed, allowed to stand for 15 min, added into cells, and then mixed. The final concentration of single-stranded HJT-sRNA-m7 was 100 nM;
3) Free uptake group: single-stranded HJT-sRNA-m7 solution was directly added (the final concentration was 100 nM);
4) Treatment group of lipid combination PE (No. 38) & PC (No. 12) & So (No. 31) and nucleic acid mixture: a mixture of 3 µL lipid combination (PE (No. 38) & PC (No. 12) & So (No. 31), 2:1:3, V/V/V) and the HJT-sRNA-m7 single-stranded nucleic acid solution that was treated by boiling method was added to the cells, and mixed, and the final concentration of RNA was 100 nM;
5) Treatment group of lipid combination and nucleic acid mixture: a mixture of 3 µL lipid combination (mixture of 2 µL PE (No. 38) & PC (No. 12) & So (No. 31) and 1 µL of the following types of lipid, MG, DG, TG, LPC, Cer or FA) and the HJT-sRNA-m7 single-stranded nucleic acid solution that was treated by boiling method was added to the cells, and mixed, and the final concentration of RNA was 100 nM.

2. Experimental Procedures
   1) Boiling method conditions: to 100 μL Single-stranded HJT-sRNA-m7 solution was added 3 μL lipid combination, and heated at 100° C. for 30 min;
   DG (diglyceride): 1 μL lipid No. 1 in chloroform solution;
   TG (triglyceride): 1 μL lipid No. 15 in chloroform solution;
   PC (phosphatidylcholine): 1 μL lipid No. 12 in chloroform solution;
   Cer (Ceramides): 1 μL lipid No. 4 in chloroform solution;
   FA (fatty acid): 1 μL lipid No. 29 in chloroform solution;
   2) Experimental conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 61), wherein 2 μL lipid combination PE (No. 38) & PC (No. 12) & So (No. 31) and 1 μL FA (No. 29) achieved the best delivery effect.

Example 1-15: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination PE (No. 38) & MG (No. 34) & LPC (No. 37) & So (No. 31) and nucleic acid mixture: a mixture of 3 μL lipid combination (PE (No. 38) & MG (No. 34) & LPC (No. 37) & So (No. 31), 44:22:33:36, V/V/V/V) and the HJT-sRNA-m7 single-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL PE (No. 38) & MG (No. 34) & LPC (No. 37) & So (No. 31) and 1 μL of the following types of lipid, DG, TG, PC, Cer or FA) and the HJT-sRNA-m7 single-stranded nucleic acid solution that was treated by boiling method was added to the cells, and mixed, and the final concentration of RNA was 100 nM.

2. Experimental Procedures
   1) Boiling method conditions: to 100 μL single-stranded HJT-sRNA-m7 solution was added 3 μL lipid combination, and heated at 100° C. for 30 min;
   DG (diglyceride): 1 μL lipid No. 1 in chloroform solution;
   TG (triglyceride): 1 μL lipid No. 15 in chloroform solution;
   PC (phosphatidylcholine): 1 μL lipid No. 12 in chloroform solution;
   Cer (Ceramides): 1 μL lipid No. 4 in chloroform solution;
   FA (fatty acid): 1 μL lipid No. 29 in chloroform solution;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that as compared to the free uptake group, the addition of 1 μL DG (No. 1), TG (No. 15), PC (No. 12), Cer (No. 4) or FA (No. 29) to 2 μLPE (No. 38) & MG (No. 34) & LPC (No. 37) & So (No. 31), could efficiently deliver nucleic acids into cells (see FIG. 62), having the potential of improving the efficiency of the delivery of nucleic acid drug in clinical settings. The addition of 1 μL PC (No. 12) achieved the best efficiency in nucleic acid delivery and could enhance the efficiency of delivery.

Example 1-16: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination PE (No. 38) & LPC (No. 37) and nucleic acid mixture: a mixture of 3 μL lipid combination (PE (No. 38) & LPC (No. 37), 2:1, V/V) and the HJT-sRNA-m7 single-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL PE (No. 38) & LPC (No. 37) and 1 μL of the following types of lipid, MG, DG, TG, PC, Cer, So or FA) and the HJT-sRNA-m7 single-stranded nucleic acid solution that was treated by boiling method was added to the cells, and mixed, and the final concentration of RNA was 100 nM;

2. Experimental Procedures
   1) Boiling method conditions: to 100 μL single-stranded HJT-sRNA-m7 solution was added 3 μL lipid combination, and heated at 100° C. for 30 min;
   MG (monoglyceride): 1 μL lipid No. 34;
   DG (diglyceride): 1 μL lipid No. 1 in chloroform solution;
   TG (triglyceride): 1 μL lipid No. 15 in chloroform solution;
   PC (phosphatidylcholine): 1 μL lipid No. 12 in chloroform solution;
   Cer (Ceramides): 1 μL lipid No. 4 in chloroform solution;
   So (Sphingoshine): 1 μL lipid No. 31 in chloroform solution;
   FA (fatty acid): 1 μL lipid No. 29 in chloroform solution;

2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that as compared to the free uptake group, the above lipid combinations were effective in delivering nucleic acids into cells (see FIG. 63), having the potential of improving the efficiency of the delivery of nucleic acid drug in clinical settings. The addition of 1 μL TG (No. 15) to 2 μL lipid combination PE (No. 38) & LPC (No. 37) achieved the best effect in nucleic acid delivery.

Example 1-17: Delivery of Single-Stranded Nucleic Acid into A549 Cells by Lipid Combination 1. Experimental Groups:
   1) Naive group: untreated cell;
   2) RNAiMAX treatment group: 2 μl RNAiMAX transfection reagent and single-stranded HJT-sRNA-m7 solution were diluted in 100 μl opti-MEM medium, respectively, and then the two were mixed, allowed to stand for 15 min, added into cells, and then mixed. The final concentration of single-stranded HJT-sRNA-m7 was 100 nM;
   3) Free uptake group: single-stranded HJT-sRNA-m7 solution was directly added (the final concentration was 100 nM);
   4) Treatment group of lipid combination PE (No. 38) & LPC (No. 37) & TG (No. 15) and nucleic acid mixture: a mixture of 3 μL lipid combination (PE (No. 38) & LPC (No. 37) & TG (No. 15), 32:8:5, V/V/V) and the HJT-sRNA-m7 single-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL PE (No. 38) & LPC (No. 37) & TG (No. 15) and 1 μL of the following types of lipid, MG, DG, PC, Cer, So or FA) and the HJT-sRNA-m7 single-stranded nucleic acid solution that was treated by boiling method was added to the cells, and mixed, and the final concentration of RNA was 100 nM;
2. Experimental Procedures
   1) Boiling method conditions: to 100 μL single-stranded HJT-sRNA-m7 solution was added 3 μL lipid combination, and heated at 100° C. for 30 min;
   MG (monoglyceride): 1 μL lipid No. 34;
   DG (diglyceride): 1 μL lipid No. 1 in chloroform solution;
   PC (phosphatidylcholine): 1 μL lipid No. 12 in chloroform solution;
   Cer (Ceramides): 1 μL lipid No. 4 in chloroform solution;
   So (Sphingoshine): 1 μL lipid No. 31 in chloroform solution;
   FA (fatty acid): 1 μL lipid No. 29 in chloroform solution;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 64), having the potential of improving the efficiency of the delivery of nucleic acid drug in clinical settings. The lipid combination PE (No. 38) & LPC (No. 37) & TG (No. 15) efficiently delivered nucleic acids into cells. Further addition of other types of lipid to the lipid combination PE (No. 38) & LPC (No. 37) & TG (No. 15) did not enhance this effect.

Example 2-1: Delivery of Double-Stranded Nucleic Acid into MRC-5 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) Treatment group of single lipid and nucleic acid: a mixture of 3 μL single lipid No. 38 and the HJT-sRNA-m7 double-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL single lipid No. 38 and 1 μL lipid No. 8, 1, 2, 11, 12, 34, 37, 4, 30, 31, 29, 32, 1+2 (mixed in equal volume) or 11+12 (mixed in equal volume) in chloroform solution) and the HJT-sRNA-m7 double-stranded nucleic acid solution that was treated by boiling method was added to the cells, and mixed, and the final concentration of RNA was 100 nM;
2. Experimental Procedures
   1) Boiling method conditions: to 100 μL double-stranded HJT-sRNA-m7 solution was added 3 μL single lipid (lipid No. 38 in chloroform solution having a concentration of 10 mg/mL) or lipid combination, and heated at 100° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipids and lipid combinations were effective in delivering nucleic acids into cells (see FIG. 65), having the potential of improving the efficiency of the delivery of nucleic acid drug in clinical settings. The single lipid No. 38 effectively delivered nucleic acids into MRC-5 cells, showing an effect close to the transfection reagent RNAiMAX. The addition of other lipids to it did not further enhance the effect.

Example 2-2: Delivery of Double-Stranded Nucleic Acid into MRC-5 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM
   3) Free uptake group: double-stranded HJT-sRNA-m7 solution was directly added (the final concentration was 100 nM);
   4) Treatment group of lipid combination (No. 38 & No. 37, 2:1, V/V) and nucleic acid: a mixture of 3 μL lipid combination and the HJT-sRNA-m7 double-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL lipid combination No. 38 & No. 37 and 1 μL lipid No. 8, 1, 2, 11, 12, 34, 37, 4, 30, 31, 29, 32, 1+2 (mixed in equal volume) or 11+12 (mixed in equal volume) in chloroform solution) and the HJT-sRNA-m7 double-stranded nucleic acid solution that was treated by boiling method was added to the cells, and mixed, and the final concentration of RNA was 100 nM;
2. Experimental Procedures
   1) Boiling method conditions: to 100 μL double-stranded HJT-sRNA-m7 solution was added to 3 μL lipid combination, and heated at 100° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipids and lipid combinations were effective in delivering nucleic acids into cells (see FIG. 66), having the potential of improving the efficiency of the delivery of nucleic acid drug in clinical settings. Lipid No. 38 & No. 37 mixture efficiently delivered nucleic acids into MRC-5 cells. To addition of 1 μL lipids, except No. 11 and 34, to 2 μL No. 38 & No. 37 mixture could enhance this effect. In addition, unexpectedly, the addition of 1 μL lipid No. 32 to 2 μL No. 38 & No 37 mixture achieved the best effect, even better than the effect of RNAiMAX.

Example 2-3: Delivery of Double-Stranded Nucleic Acid into A549 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) Treatment group of lipid combination (PE (No. 38) & PC (No. 12) & Cer (No. 4)) and nucleic acid: a mixture of 3 μL lipid combination (PE (No. 38) & PC (No. 12) & Cer (No. 4), 4:2:3, V/V/V) and the HJT-sRNA-m7 double-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2.5 μL PE (No. 38) & PC (No. 12) & Cer (No. 4) and 0.5 μL lipids (DG (No. 2), TG (No. 6), So (No. 17), FA (No. 29), MG (No. 34) and LPC (No. 37)) and the HJT-sRNA-m7 double-stranded nucleic acid solution that was treated by boiling method was added to the cells, and mixed, and the final concentration of RNA was 100 nM;
2. Experimental Procedures
   1) Boiling method conditions: to 100 μL HJT-sRNA-m7 double-stranded solution was added 3 μL lipid combination, and heated at 100° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipids and lipid combinations were effective in delivering nucleic acids into cells (see FIG. 67), having the potential of improving the efficiency of the delivery of nucleic acid drug in clinical settings. The addition of ⅕ LPC (No. 37) to PE (No. 38) & PC (No. 12) & Cer (No. 4) mixture could significantly enhance the effect in delivery of the nucleic acid. In addition, the addition of DG (No. 2) and TG (No. 16) could also further enhance the effect in delivery.

Example 2-4: Delivery of Double-Stranded Nucleic Acid into A549 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) Treatment group of lipid combination (PE (No. 38) & DG (No. 2)) and nucleic acid: a mixture of 3 μL lipid combination (PE (No. 38) & DG (No. 2), 2:1, V/V) and the HJT-sRNA-m7 double-stranded nucleic acid solution that was treated by boiling method was added to the cells, and mixed, and the final concentration of RNA was 100 nM;
   5) Treatment group of lipid combination and nucleic acid mixture: a mixture of 3 μL lipid combination (mixture of 2 μL PE (No. 38) & DG (No. 2) mixture and 1 μL other lipid of No. 37, 31, 29, 34, 12 or 4) and the HJT-sRNA-m7 double-stranded nucleic acid solution that was treated by boiling method was added to the cells, and mixed, and the final concentration of RNA was 100 nM;

2. Experimental Procedures
   1) Boiling method conditions: to 100 μL double-stranded HJT-sRNA-m7 solution was added 3 μL lipid combination, and heated at 100° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method (SYBR Green Universal dye method). For the protocols, see "Real-time quantitative PCR detection of intracellular expression of nucleic acids delivered by lipids". All experiments were performed in triplicates.

Conclusions: The results indicated that the above single lipids and lipid combinations were effective in delivering nucleic acids into cells (see FIG. 68), having the potential of improving the efficiency of the delivery of nucleic acid drug in clinical settings. Lipid combination (2 μL PE (No. 38) & DG (No. 2) mixture) could effectively deliver the double stranded nucleic acid into the A549 cells. As compared with this lipid combination, the lipid combination of 2 μL PE (No. 38) & DG (No. 2) and No. 37, 31, 12 or 4 mixed at a ratio of 2:1 could enhance the efficiency of delivery.

Example 2-5: Delivery of Double-Stranded Nucleic Acid into A549 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination (PE (No. 38) & LPC (No. 37), 4:1, V/V) and the HJT-sRNA-m7 double-stranded nucleic acid solution that was treated by boiling method was added to the cells, and mixed, and the final concentration of RNA was 100 nM;
2. Experimental Procedures
   1) Boiling method conditions: to 100 μL double-stranded HJT-sRNA-m7 solution was added 3 μL lipid combination, and heated at 70° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 69), having the potential of improving the efficiency of the delivery of nucleic acid drug in clinical settings, with an effect close to the transfection reagent RNAiMAX.

Example 2-6: Delivery of Double-Stranded Nucleic Acid into A549 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination (PE (No. 38) & PC (No. 12), 4:1, V/V) and the HJT-sRNA-m7 double-stranded nucleic acid solution that was treated by boiling method was added to the cells, and mixed, and the final concentration of RNA was 100 nM;
2. Experimental Procedures
   1) Boiling method conditions: to 100 μL double-stranded HJT-sRNA-m7 solution was added 3 μL lipid combination, and heated at 70° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 70), having the potential of improving the efficiency of the delivery of nucleic acid drug in clinical settings. The effect is better than or the same as that of RNAiMAX.

Example 2-7: Delivery of Double-Stranded Nucleic Acid into A549 Cells by Lipid Combination 1. Experimental Groups:
   1) Naive group: untreated cell;
   2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination (PE (No. 38) & PC (No. 12) & DG (No. 2), 4:1:5, V/V/V) and the double-stranded HJT-sRNA-m7 nucleic acid solution that was treated by boiling method was added to the cells, and mixed, and the final concentration of RNA was 100 nM;
2. Experimental Procedures
   1) Boiling method conditions: to 100 μL double-stranded HJT-sRNA-m7 solution was added 2 μL lipid combination, and heated at 80° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 71), having the potential of improving the efficiency of the delivery of nucleic acid drug in clinical settings. Lipid combination (PE (No. 38) & PC (No. 12) & DG (No. 2), 4:1:5, V/V/V) showed better effect in the delivery of double-stranded nucleic acid into A549 cells than RNAiMAX.

Example 2-8: Delivery of Double-Stranded Nucleic Acid into A549 Cells by Lipid Combination 1. Experimental Groups:
    1) Naive group: untreated cell;
    2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
    3) Free uptake group: double-stranded HJT-sRNA-m7 solution was directly added (the final concentration was 100 nM);
    4) A mixture of lipid combination (PE (No. 38) & LPC (No. 37) & DG (No. 2), 32:8:5, V/V/V) and the HJT-sRNA-m7 double-stranded nucleic acid solution that was treated by boiling method was added to the cells, and mixed, and the final concentration of RNA was 100 nM;
2. Experimental Procedures
    1) Boiling method conditions: to 100 µL double-stranded HJT-sRNA-m7 solution was added 2 µL lipid combination, and heated at 80° C. for 30 min;
    2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 72), having the potential of improving the efficiency of the delivery of nucleic acid drug in clinical settings. The effect was similar to that of RNAiMAX.

Example 2-9: Delivery of Double-Stranded Nucleic Acid into A549 Cells by Lipid Combination 1. Experimental Groups:
    1) Naive group: untreated cell;
    2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
    3) Free uptake group: double-stranded HJT-sRNA-m7 solution was directly added (the final concentration was 100 nM);
    4) A mixture of lipid combination (PE (No. 8) & PC (No. 12), 1:2, V/V) and the HJT-sRNA-m7 double-stranded nucleic acid solution that was treated by boiling method was added to the cells, and mixed, and the final concentration of RNA was 100 nM;
2. Experimental Procedures
    1) Boiling method conditions: to 100 µL double-stranded HJT-sRNA-m7 solution was added to 2 µL lipid combination, and heated at 80° C. for 30 min;
    2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 73), having the potential of improving the efficiency of the delivery of nucleic acid drug in clinical settings. Lipid combination (PE (No. 8) & PC (No. 12), 1:2, V/V) showed better effect in the delivery of double-stranded nucleic acid into A549 cells than RNAiMAX.

Example 2-10: Delivery of Double-Stranded Nucleic Acid into A549 Cells by Lipid Combination 1. Experimental Groups:
    1) Naive group: untreated cell;
    2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
    3) Free uptake group: double-stranded HJT-sRNA-m7 solution was directly added (the final concentration was 100 nM);
    4) A mixture of lipid combination (PE (No. 8) & LPC (No. 37), 4:1, V/V) and the HJT-sRNA-m7 double-stranded nucleic acid solution that was treated by boiling method was added to the cells, and mixed, and the final concentration of RNA was 100 nM;
2. Experimental Procedures
    1) Boiling method conditions: to 100 µL double-stranded HJT-sRNA-m7 solution was added 2 µL lipid combination, and heated at 80° C. for 30 min;
    2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 74), having the potential of improving the efficiency of the delivery of nucleic acid drug in clinical settings.

Example 2-11: Delivery of Double-Stranded Nucleic Acid into MRC-5 Cells by Lipid Combination 1. Experimental Groups:
   1) Naive group: untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of Lipid combination (PE (No. 8) & PC (No. 12), 1:2, V/V) and the HJT-sRNA-m7 double-stranded nucleic acid solution that was treated by boiling method was added to the cells, and mixed, and the final concentration of RNA was 100 nM;
   5) Treatment group of lipid combination and double-stranded HJT-sRNA-m7 mixture: a mixture of 3 µL lipid combination (mixture of 2 µL PE (No. 8) & PC (No. 12) and 1 µL other type of lipids (MG (No. 34), DG (No. 2), TG (No. 32), LPC (No. 37), PC (No. 11), PE (No. 38), Cer (No. 4), So (No. 31) or FA (No. 29))) and the double-stranded HJT-sRNA-m7 nucleic acid solution that was treated by boiling method was added to the cells, and mixed, and the final concentration of RNA was 100 nM;
2. Experimental Procedures
   1) Boiling method conditions: to 100 µL double-stranded HJT-sRNA-m7 solution was added to 3 µL lipid combination, and heated at 80° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 75), having the potential of improving the efficiency of the delivery of nucleic acid drug in clinical settings. PE (No. 8) & PC (No. 12) could effectively deliver nucleic acids into cells with significantly better effect than RNAiMAX. Compared to PE (No. 8) & PC (No. 12), a mixture of PE (No. 8) & PC (No. 12) and Cer (No. 4) or PE (No. 38) at a ratio of 2:1 could enhance this effect.

Example 2-12: Delivery of Double-Stranded Nucleic Acid into MRC-5 Cells by Lipid Combination 1. Experimental Groups:
   1) Naive group: untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination (PE (No. 8) & PC (No. 12) &DG (No. 2), 8:16:3, V/V/V) and the HJT-sRNA-m7 double-stranded nucleic acid solution that was treated by boiling method was added to the cells, and mixed, and the final concentration of RNA was 100 nM;
   5). Experimental procedures
   1) Boiling method conditions: to 100 µL double-stranded HJT-sRNA-m7 solution was added 2 µL lipid combination, and heated at 80° C. for 30 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that as compared with the free uptake group and RNAiMAX group, the lipid combination (PE (No. 8) & PC (No. 12) &DG (No. 2), 8:16:3, V/V/V) showed better effect in delivery than RNAiMAX (see FIG. 76), having the potential of improving the efficiency of the delivery of nucleic acid drug in clinical settings.

Example 2-13: Delivery of Double-Stranded Nucleic Acid into MRC-5 Cells by Lipid Combination 1. Experimental Groups:
   1) Naive group: untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination and the HJT-sRNA-m7 double-stranded nucleic acid solution that was treated by boiling method was added to the cells, and mixed, and the final concentration of RNA was 100 nM;
   Mixture 1: PE (No. 8): LPC (No. 37): TG (No. 32)=4:1:2
   Mixture 2: PE (No. 8): LPC (No. 37): DG (No. 2)=4:1:2
   Mixture 3: PE (No. 8): PC (No. 12): So (No. 31): FA (No. 29)=1:2:1:1
   5). Experimental procedures
   1) Boiling method conditions: to 100 µL double-stranded HJT-sRNA-m7 solution was added 2.5 µL lipid combination, and heated at 90° C. for 15 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 77), having the potential of improving the efficiency of the delivery of nucleic acid drug in clinical settings. As compared with RNAiMAX group, mixture 1: PE (No. 8): LPC (No. 37): TG (No. 32)-4:1:2, and mixture 2: PE (No. 8): LPC (No. 37): DG (No. 2)=4:1:2 showed comparable effect in delivery, whereas mixture 3: PE (No. 8): PC (No. 12): So (No. 31): FA (No. 29)-1:2:1:1 showed better effect.

Example 2-14: Delivery of Double-Stranded Nucleic Acid into MRC-5 Cells by Lipid Combination 1. Experimental Groups:
   1) Naive group: referred to untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) Treatment group of lipid combination mixture and double-stranded HJT-sRNA-m7 mixture: a mixture of 3 µL lipid combination (PE (No. 8): PC (No. 12): So (No. 31): FA (No. 29)=1:2:1:1) and the HJT-sRNA-m7 double-stranded nucleic acid solution that was treated by boiling method was added to the cells, and mixed, and the final concentration of RNA was 100 nM;
   5) Treatment group of lipid combination and double-stranded HJT-sRNA-m7 mixture: a mixture of 3 µL lipid combination (mixture of 2 µL lipid combination mix and 1 µL other type of lipid shown in FIG. 78, i.e. lipids No. 34, 2, 32, 11, 37, 38 or4) and the HJT-sRNA-m7 double-stranded nucleic acid solution that was treated by boiling method was added to the cells, and mixed, and the final concentration of RNA was 100 nM;

2. Experimental Procedures
   1) Boiling method conditions: to 100 µL double-stranded HJT-sRNA-m7 solution was added 3 µL lipid combination, and heated at 90° C. for 15 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective in delivering nucleic acids into cells (see FIG. 78), having the potential of improving the efficiency of the delivery of nucleic acid drug in clinical settings. The mixture (PE (No. 8): PC (No. 12): So (No. 31): FA (No. 29)=1:2:1:1) showed better effect in delivery than RNAiMAX. Compared to mixture (PE (No. 8): PC (No. 12): So (No. 31): FA (No. 29)=1:2:1:1), the addition of mixture PE (No. 8): PC (No. 12): So (No. 31): FA (No. 29)=1:2:1:1) to lipids No. 2, 38 or 4 at a ratio of 2:1 could enhance the delivery effect.

Example 2-15: Delivery of Double-Stranded Nucleic Acid into MRC-5 Cells by Lipid Combination 1. Experimental Groups:
   1) Naive group: untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) A mixture of lipid combination (PE (No. 8) & So (No. 31), 6:1, V/V) and the HJT-sRNA-m7 double-stranded nucleic acid solution that was treated by boiling method was added to the cells, and mixed, and the final concentration of RNA was 100 nM;
   5). Experimental procedures
   1) Boiling method conditions: to 100 µL double-stranded HJT-sRNA-m7 solution was added 2 µL lipid combination, and heated at 90° C. for 15 min;
   2) Experiment conditions: the final concentration of HJT-sRNA-m7 was 100 nM, 24 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the lipid combination (PE (No. 8) & So (No. 31), 6:1, V/V) showed better effect in delivery than RNAiMAX (see FIG. 79), having the potential of improving the efficiency of the delivery of nucleic acid drug in clinical settings.

Example 2-16: Delivery of Double-Stranded Nucleic Acid into MRC-5 Cells by Lipid Combination 1. Experimental Groups:
   1) Naive group: untreated cell;
   2) RNAiMAX treatment group: 2 µl RNAiMAX transfection reagent and double-stranded HJT-sRNA-m7 solution were diluted in 100 µl opti-MEM medium, respectively, and then the two were mixed, allowed to stand for 15 min, added into cells, and then mixed. The final concentration of double-stranded HJT-sRNA-m7 was 100 nM;
   3) Free uptake group: double-stranded HJT-sRNA-m7 solution was directly added (the final concentration was 100 nM);
   4) Treatment group of lipid combination (PE (No. 8) & So (No. 31), 4:1, V/V) and the HJT-sRNA-m7 mixture: a mixture of 2 µL the lipid combination and the HIT-sRNA-m7 double-stranded nucleic acid solution that was treated by boiling method was added to the cells, and mixed, and the final concentration of RNA was 100 nM;
   5) Treatment group of lipid combination and double-stranded HJT-sRNA-m7 mixture: a mixture of lipid combination (a mixture of PE (No. 8) & So (No. 31), 4:1, V/V) and other types of lipid (MG (No. 34), DG (No. 2), LPC (No. 37), PC (No. 12), PC (No. 11), Cer (No. 4), FA (No. 29) or TG (No. 32), 12:3:5, V/V, FIG. 80) and the HJT-sRNA-m7 double-stranded nucleic acid solution that was treated by boiling method was added to the cells, and mixed, and the final concentration of RNA was 100 nM;

2. Experimental Procedures
1) Boiling method conditions: to 100 μL double-stranded HJT-sRNA-m7 solution was added 2 μL lipid combination, and heated at 90° C. for 15 min;
2) Experiment conditions: the final concentration of HJT-sRNA-m7 was 100 nM, 12 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective for delivering nucleic acids into cells (see FIG. 80), having the potential of improving the efficiency of the delivery of nucleic acid drug in clinical settings. PE (No. 8): So (No. 31) (4:1, V/V) could effectively deliver nucleic acids into cells with an effect close to RNAiMAX. Compared to PE (No. 8): So (No. 31), the mixture of PE (No. 8): So (No. 31) and MG (No. 34), DG (No. 2), PC (No. 12), PC (No. 11), or TG (No. 32) at a ratio of 12:3:5 could enhance the effect in delivery of nucleic acid, and PE (No. 8): So (No. 31): PC (No. 11) showed the best effect, significantly better than RNAiMAX.

Example 2-17: Delivery of Double-Stranded Nucleic Acid into MRC-5 Cells by Lipid Combination 1. Experimental Groups:
1) Naive group: untreated cell;
2) RNAiMAX treatment group: 2 μl RNAiMAX transfection reagent and double-stranded HJT-sRNA-m7 solution were diluted in 100 μl opti-MEM medium, respectively, and then the two were mixed, allowed to stand for 15 min, added into cells, and then mixed. The final concentration of double-stranded HJT-sRNA-m7 was 100 nM;
3) Free uptake group: double-stranded HJT-sRNA-m7 solution was directly added (the final concentration was 100 nM);
4) Treatment group of lipid combination (PE (No. 8): Cer (No. 4), 4:1, V/V) and the HJT-sRNA-m7 mixture: a mixture of 2 μL lipid combination and the HJT-sRNA-m7 double-stranded nucleic acid solution that was treated by boiling method was added to the cells, and mixed, and the final concentration of RNA was 100 nM;
5) Treatment group of lipid combination and double-stranded HJT-sRNA-m7 mixture: a mixture of lipid combination (mixture of PE (No. 8): Cer (No. 4) and other types of lipids MG (No. 34), DG (No. 2), LPC (No. 37), PC (No. 12), PC (No. 31), FA (No. 29) or TG (No. 32), 12:3:5, V/V, FIG. 81) and the double-stranded HJT-sRNA-m7 nucleic acid solution that was treated by boiling method was added to the cells, and mixed, and the final concentration of RNA was 100 nM;
2. Experimental Procedures
1) Boiling method conditions: to 100 μL double-stranded HJT-sRNA-m7 solution was added 2 μL lipid combination, and heated at 90° C. for 15 min;
2) Experiment conditions: the final concentration of HJT-sRNA-m7 was 100 nM, 12 hours after the addition to the cells, the amount of HJT-sRNA-m7 that entered the cells was detected by RT-qPCR method. For the protocols, see "Real-time quantitative PCR detection of intracellular expression of nucleic acids delivered by lipids". All experiments were performed in triplicates.

Conclusions: The results indicated that the above lipid combinations were effective for delivering nucleic acids into cells (see FIG. 81), having the potential of improving the efficiency of the delivery of nucleic acid drug in clinical settings. Lipid combination PE (No. 8): Cer (No. 4) could effectively deliver nucleic acids into cells with an effect close to RNAiMAX. Compared to PE (No. 8): So (No. 31), the mixture of PE (No. 8): So (No. 31) and DG (No. 2), FA (No. 29) or TG (No. 32) at a ratio of 12:3:5 could enhance the effect in delivery of nucleic acid, and FA (No. 29) could significantly improve the effect (significantly better than RNAiMAX) of PE (No. 8): So (No. 31) in delivery.

Example 3: Lipid Combination Promotes Nucleic Acid Entry into the Lung Through Digestive Tract The lipid combination was as follow:
Lipids PE (No. 38) & LPC (No. 37) & TG (No. 32), 4:2:3, V/V/V
1. Preparation of Lipid Nucleic Acid Mixture:
Method: boiling method
To 400 μL of HJT-sRNA-m7 (5 nmol) single-stranded RNA in DEPC-treated aqueous solution was added 9 μL or 18 μL lipid combination (lipid PE (No. 38) & LPC (No. 37) & TG (No. 32), 4:2:3, V/V/V), mixed and heated at 100° C. for 30 min.
2. Delivery Experiment of Nucleic Acid Via Digestive Tract
RNA was administered via gavage to 6-8 weeks old male C57 mice: HJT-sRNA-m7 in aqueous solution or a mixture solution of lipid and HJT-sRNA-m7 was administered via gavage needle, 400 μL/animal (HJT-sRNA-m7, 5 nmol/animal). Groups were as follows:
(1) Control group (naive group): mice that did not receive any treatment;
(2) Negative control group (lipid group): administration of 9 μL lipid combinations (lipid PE (No. 38) & LPC (No. 37) & TG (No. 32), 4:2:3, V/V/V) via gavage;
(3) Free uptake group: direct administration of single-stranded HJT-sRNA-m7 RNA via gavage;
(4) Lipid and nucleic acid mixture group: administration of a mixture of lipid combination and single-stranded HJT-sRNA-m7 RNA via gavage.
3 hours after administration via gavage, the mouse whole lung was lysed with 3 mL TRIzol, the total RNA was extracted and the abundance of HJT-sRNA-m7 was detected by RT-qPCR.

Conclusion: As shown in FIG. 82, 9 μL or 18 μL lipid combination (lipid PE (No. 38) & LPC (No. 37) & TG (No. 32), 4:2:3, V/V/V) significantly promoted the entry of small fragments of nucleic acids into lung tissue (* indicating a P value of less than 0.05) as compared to the free uptake group. With this (non-invasive) administration via gavage, the lipid combination (lipid PE (No. 38) & LPC (No. 37) & TG (No. 32), 4:2:3, V/V/V) could promote small fragments of nucleic acids entering the lung tissue, which could be used as a means of nucleic acid drug delivery.

Example 4: Function Experiments of Delivery of Double-Stranded Nucleic Acid into Cells Mediated by Lipid Mixture 1. No. 8 (PE): No. 12 (PC) (v:v=1:2) Lipid Mixture Mediated the Entry of Nucleic Acids into Cells to Function
Experimental method: Western blot, see above "Western blot detection of protein expression level".

1) No. 8 (PE): No. 12 (PC) (v:v=1:2) lipid mixture mediated anti-fibrotic double-stranded HJT-sRNA-m7 entry into MRC-5 cells.

As shown in FIG. 83, by boiling method and reverse evaporation method, No. 8 (PE): No. 12 (PC) (V:V=1:2) lipid mixture could effectively deliver nucleic acid into cells to function.

Naive group: untreated MRC-5 cells, i.e., a blank control group;

TGF β G1 group: MRC-5 cells were stimulated with TGF β 1 protein (final concentration of 3 ng/mL), and the samples were collected after 72 hours.

NC group: the mixture of lipid combination of No. 8 (PE): No. 12 (PC) (V:V=1:2) and double-stranded NC mimics was added to the MRC-5 cells and mixed well, and the final concentration of nucleic acid was 200 nM. After 24 hours, the cells were stimulated with TGFβ1 protein (final concentration of 3 ng/mL), and samples were collected 72 hours after the stimulation with TGFβ1.

M7 group: the mixture of lipid combination of No. 8 (PE): No. 12 (PC) (V:V=1:2) with double-stranded HJT-sRNA-m7 was added to the MRC-5 cells and mixed, and the final concentration of nucleic acid was 200 nM. After 24 hours, the cells were stimulated with TGFβ1 protein (final concentration of 3 ng/ml), and samples were collected after 72 hours.

2) No. 8 (PE): No. 12 (PC) (v:v=1:2) lipid mixture mediated siRNA entry into A549 cells.

As shown in FIGS. 84 and 85, by the boiling method, lipid No. 8 (PE): No. 12 (PC) (v:v=1:2) lipid mixture could effectively deliver nucleic acid into cells to knockdown protein expression.

The naive group in FIG. 84: untreated cells, i.e., a blank control group;

si-NC: the mixture of lipid combination of No. 8 (PE): No. 12 (PC) (v:v=1:2) and si-NC (synthesized by Guangzhou Ribobio Co., Ltd., unknown sequences) was added to A549 cells and mixed, and the final concentration was 400 nM; the cells were harvested after 48 hours, and lysed by RIPA strong lysis buffer to collect protein samples.

si-CPSF30: the mixture of lipid combination of No. 8 (PE): No. 12 (PC) (v:v=1:2) and si-CPSF30 was added to A549 cells and mixed, and the final concentration was 400 nM; the cells were harvested after 48 hours, and lysed by RIPA strong lysis buffer to collect protein samples.

si-LAMP1: the mixture of lipid combination of No. 8 (PE): No. 12 (PC) (v:v=1:2) and si-LAMP1 was added to A549 cells and mixed, the final concentration was 400 nM; the cells were harvested after 48 hours, and lysed by RIPA strong lysis buffer to collect protein samples.

si-LAMP2: the mixture of lipid combination of No. 8 (PE): No. 12 (PC) (v:v=1:2) and si-LAMP2 was added to A549 cells and mixed, and the final concentration was 400 nM; the cells were harvested after 48 hours, and lysed by RIPA strong lysis buffer to collect protein samples.

Free uptake group as shown in FIG. 85: the nucleic acid solution was added directly.

Lipo 2000 group: 2 μL Lipofectamine™ 2000 transfection reagent (Invitrogen, Thermo Fisher Scientific) and si-NF-κB solution were diluted in 100 μL opti-MEM medium, respectively, and the two were mixed, allowed to stay for 15 min, added to the cells and mixed, and the final concentration of nucleic acid solution was 400 nM; after 24 hours, the cells were stimulated with polyI:C (the concentration was 1 μg/mL), and the protein samples were collected after 6 hours.

No. 8 (PE): No. 12 (PC) (1:2): No. 8 (PE): No. 12 (PC) (1:2) was mixed with the si-NF-κB solution by heating method, then added to the cells, and the final concentration of the nucleic acid solution was 400 nM; after 24 hours, the cells were stimulated with polyI:C (the concentration was 1 μg/mL), and the protein samples were collected after 6 hours.

See Table 2 for the types and sequences of the above nucleic acids.

3) No. 8 (PE): No. 12 (PC) (v:v=1:2) lipid mixture mediated siRNA entry into THP-1 cells.

As shown in FIG. 86, by boiling method, No. 8 (PE): No. 12 (PC) (v:v=1:2) lipid mixture could effectively deliver nucleic acid into cells to function.

Naive group: untreated cells, i.e., a blank control group;

LPS group: no siRNA, but only LPS was added for stimulation, and the final concentration was 1 μg/mL. The RNA samples and cell supernatants were harvested after 9 hours;

si-NC group: the mixture of lipid combination of No. 8 (PE): No. 12 (PC) (v:v=1:2) and si-NC was added to THP-1 cells and mixed, and the final concentration was 400 nM; LPS was added after 24 hours at a final concentration of 1 μg/mL for stimulation, and the TRIzol lysate of the cells were collected 9 hours after the stimulation, and the supernatants were collected for ELISA detection.

si-TNFα group: the mixture of lipid combination of No. 8 (PE): No. 12 (PC) (v:v=1:2) and si-TNFα was added to THP-1 cells and mixed, and the final concentration was 400 nM; LPS was added after 24 hours at a final concentration of 1 μg/mL for stimulation, the TRIzol lysate of the cells were collected 9 hours after the stimulation, and the supernatants were collected for ELISA detection.

2. No. 8 (PE): No. 12 (PC): No. 2 (DG) (v:v:v=2:4:3) Lipid Mixture Mediated Entry of nucleic acids into cells to function.

1) No. 8 (PE): No. 12 (PC): No. 2 (DG) (v:v:v=2:4:3) lipid mixture mediated anti-fibrotic HJT-sRNA-m7 entry into MRC-5 cells.

As shown in FIG. 87, by boiling method, No. 8 (PE): No. 12 (PC): No. 2 (DG) (v:v:v=2:4:3) lipid mixture could effectively deliver anti-fibrotic HJT-sRNA-m7 into MRC-5 cells to reduce fibronectin protein expression.

2) No. 8 (PE): No. 12 (PC): No. 2 (DG) (v:v:v=2:4:3) lipid mixture mediated XRN2 siRNA entry into A549 cells to inhibit gene expression.

As shown in FIG. 88, by boiling method, the addition of No. 2 (DG) to the mixture of No. 8 (PE): No. 12 (PC): No. 20 (DG), V:V:V=2:4:3 could effectively deliver nucleic acid into the cells to function.

Naive group: untreated A549 cells;

NC siRNA group: the mixture of lipid mixture of No. 8 (PE): No. 12 (PC): No. 2 (DG) (v:v:v=2:4:3) and si-NC that was prepared by boiling method was added to the cells and mixed, and the final concentration of the nucleic acid was 400 nM;

XRN2 siRNA group: the mixture of lipid mixture of No. 8 (PE): No. 12 (PC): No. 2 (DG) (v:v:v=2:4:3) and XRN2 siRNA that was prepared by boiling method was added to the cells and mixed, and the final concentration of the nucleic acid was 400 nM.

3. No. 8 (PE): No. 12 (PC): No. 4 (Cer) (v:v:v=1:2:1) Lipid Mixture Mediated Entry of Nucleic Acids into Cells to Function.

1) No. 8 (PE): No. 12 (PC): No. 4 (Cer) (v:v:v=1:2:1) lipid mixture mediated anti-fibrotic HJT-sRNA-m7 entry into MRC-5 cells (boiling method).

As shown in FIG. 89, by boiling method, the addition of No. 4 (Cer) to the lipid mixture of No. 8 (PE), No. 12 (PC) (V:V=1:2), v:v:v=1:2:1, could effectively deliver anti-fibrotic HJT-sRNA-m7 into MRC-5 cells to reduce fibronectin protein expression.

Naive group: untreated cells;

TGF-β1 group: TGF-1 protein was added at a final concentration of 3 ng/mL for stimulation, and the samples were collected after 72 hours.

NC group: lipid combination of No. 38 (PE): No. 37 (LPC): No. 32 (TG) (V:V:V=32:8:5) was used to deliver NC mimics. After 24 hours, TGF-β1 TGFb1 protein (final concentration of 3 ng/mL) was added for stimulation, and the samples were collected after 72 hours.

m7 group: the mixture of lipid combination of No. 8 (PE): No. 12 (PC): No. 4 (Cer) (V:V:V=1:2:1) with double-stranded HJT-sRNA-m7 was added to the MRC-5 cells and mixed, and the final concentration of nucleic acid was 400 nM. After 24 hours, TGF-β1 protein (final concentration of 3 ng/mL) was added for stimulation, and the samples were collected after 72 hours.

2) No. 8 (PE): No. 12 (PC): No. 4 (Cer) (v:v:v=1:2:1) lipid mixture mediated NF-κB siRNA entry into A549 cells to inhibit gene expression (boiling method).

As shown in FIG. 90, the addition of No. 4 (Cer) to a lipid mixture of No. 8 (PE), No. 12 (PC) (V:V=1:2), v:v:v=1:2:1, could effectively deliver nucleic acids into cells to function.

Naive group: untreated cells;

si-NC group: the mixture of lipid mixture of No. 8 (PE): No. 12 (PC): No. 4 (Cer) (v:v:v=1:2:1) and si-NC siNC was added to cells and mixed, and the final concentration of the nucleic acid was 400 nM;

si-NF-κB group: the mixture of lipid mixture of No. 8 (PE): No. 12 (PC): No. 4 (Cer) (v:v:v=1:2:1) and NF-κB siRNA was added to cells and mixed, the final concentration of the nucleic acid was 400 nM;

4. No. 8 (PE): No. 12 (PC): No. PC(11) (v:v:v=1:2:1) Lipid Mixture Mediated Entry of Nucleic Acids into Cells to Function.

1) No. 8 (PE): No. 12 (PC): No. PC(11) (v:v:v=1:2:1) lipid mixture mediated XRN2 siRNA entry into A549 cells to inhibit gene expression.

As shown in FIG. 91, the addition of No. 11 (PC) to the mixture of No. 8 (PE), No. 12 (PC) (V:V=1:2), V:V:V=1:2:1, could effectively deliver nucleic acid into the cells to function.

Naive group: untreated cells;

si-NC siNC group: the mixture of lipid mixture of No. 8 (PE): No. 12 (PC): No. PC (11) (v:v:v=1:2:1) and si-NC was added to the cells and mixed, and the final concentration of the nucleic acid was 400 nM;

si-XRN2 group: the mixture of lipid mixture of No. 8 (PE): No. 12 (PC): No. PC (11) (v:v:v=1:2:1) and XRN2 siRNA was added to the cells and mixed, and the final concentration of the nucleic acid was 400 nM.

5. No. 8 (PE): No. 12 (PC): No. LPC(37) (v:v:v=1:2:1) Lipid Mixture Mediated Entry of Nucleic Acids into Cells to Function.

1) No. 8 (PE): No. 12 (PC): No. LPC(37) (v:v:v=1:2:1) lipid mixture mediated XRN2 siRNA entry into A549 cells to inhibit gene expression.

As shown in FIG. 92, based on the addition of No. 37 (LPC) to the lipid mixture of No. 8 (PE), No. 12 (PC) (V:V=1:2), V:V:V=1:2:1, could effectively deliver nucleic acid into the cells to function.

Naive group: untreated cells;

si-NC group: the mixture of lipid mixture of No. 8 (PE): No. 12 (PC): No. LPC(37) (v:v:v=1:2:1) and si-NC was added to the cells and mixed, and the final concentration of the nucleic acid was 400 nM;

si-XRN2 group: the mixture of lipid mixture of No. 8 (PE): No. 12 (PC): No. LPC (37) (v:v:v=1:2:1) and XRN2 siRNA was added to the cells and mixed, and the final concentration of the nucleic acid was 400 nM.

6. No. 8 (PE): No. 12 (PC): No. MG (34) (v:v:v=2:3:1) Lipid Mixture Mediated Entry of Nucleic Acids into Cells to Function.

1) No. 8 (PE): No. 12 (PC): No. MG (34) (v:v:v=2:3:1) lipid mixture mediated CPSF4 siRNA entry into A549 cells to inhibit gene expression.

Naive group: untreated cells;

si-NC siNC group: the mixture of lipid mixture of No. 8 (PE): No. 12 (PC): No. MG (34) (v:v:v=2:3:1) and si-NCsiNC was added to the cells and mixed, and the final concentration of the nucleic acid was 400 nM;

si-CPSF4 group: the mixture of lipid mixture of No. 8 (PE): No. 12 (PC): No. MG (34) (v:v:v=2:3:1) and CPSF4 siRNA was added to the cells and mixed, and the final concentration of the nucleic acid was 400 nM.

As shown in FIG. 93, No. 8 (PE): No. 12 (PC): No. MG (34) (v:v:v=2:3:1) lipid mixture could effectively deliver nucleic acid into the cells to function.

7. No. 38 (PE): No. 37 (LPC): No. 32 (TG) (v:v:v=32:8:5) Lipid Mixture Mediated Entry of Nucleic Acids into Cells to Function.

1) No. 38 (PE): No. 37 (LPC): No. 32 (TG) (v:v:v=32:8:5) lipid mixture mediated anti-fibrotic HJT-sRNA-m7 entry into MRC-5 cells (boiling method).

As shown in FIG. 94, the m7 band was lighter compared to control. The effect of M7 was not sufficient to restore cells to unstimulated levels.

Naive group: untreated cells, i.e., a blank control group;

TGF-β1 group: cells were stimulated with TGF-β1 protein (final concentration of 3 ng/mL), and the samples were collected after 72 hours.

NC group: lipid combination of No. 38 (PE): No. 37 (LPC): No. 32 (TG) (V:V:V=32:8:5) was used to deliver NC mimics. After 24 hours, the cells were stimulated with TGF-β1 protein (final concentration of 3 ng/mL), and the samples were collected after 72 hours.

M7 group: the mixture of lipid combination of No. 38 (PE): No. 37 (LPC): No. 32 (TG) (V:V:V=32:8:5) with double-stranded HJT-sRNA-m7 was added to the MRC-5 cells and mixed, and the final concentration of nucleic acid was 400 nM. After 24 hours, the cells were stimulated with TGF-1 protein (final concentration of 3 ng/ml), and the samples were collected after 72 hours.

2) No. 38 (PE): No. 37 (LPC): No. 32 (TG) (V:V:V=32:8:5) lipid mixture mediated XRN2 siRNA entry into A549 cells to inhibit gene expression.

As shown in FIG. 95, No. 38 (PE): No. 37 (LPC): No. 32 (TG) (V:V:V=32:8:5) lipid mixture could effectively deliver nucleic acid entering the cells to function.
- si-NC group: the mixture of lipid mixture of No. 38 (PE): No. 37 (LPC): No. 32 (TG) (V:V:V=32:8:5) and si-NC was added to the cells and mixed, and the final concentration of the nucleic acid was 400 nM;
- si-XRN2 group: the mixture of the lipid mixture of No. 38 (PE): No. 37 (LPC): No. 32 (TG) (V:V:V=32:8:5) and XRN2 siRNA was added to the cells and mixed, and the final concentration of the nucleic acid was 400 nM.

8. No. 1 (DG): No. 8 (PE): No. 12 (PC): No. 4 (Cer): No. 31 (so): No. 29 (FA): No. 16 (TG) (v:v:v:v:v:v:v=2:1:2:2:3:1:3) Lipid Mixture Mediated Entry of Nucleic Acids into Cells to Function.

1) As shown in FIG. 96, No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) lipid mixture mediated anti-fibrotic HJT-sRNA-m7 entry into MRC-5 cells (boiling method).
- Naive group: untreated cells, i.e., a blank control group;
- TGF-β1 group: cells were stimulated with TGF-β1 protein (final concentration of 3 ng/mL), and the samples were collected after 72 hours.
- NC group: lipid combination of No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) was used to was used to deliver NC mimics. After 24 hours, TGF-β1 protein (final concentration of 3 ng/mL) was added for stimulation, and the samples were collected after 72 hours.
- M7 group: the mixture of lipid combination of No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) with single-stranded HJT-sRNA-m7 was added to the MRC-5 cells, and mixed, and the final concentration of nucleic acid was 400 nM. After 24 hours, TGF-β1 protein (final concentration of 3 ng/mL) was added for stimulation, and the samples were collected after 72 hours.

2) As shown in FIG. 97, No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) lipid mixture mediated XRN2 siRNA entry into A549 cells to inhibit gene expression (boiling method).

No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) lipid mixture could effectively deliver nucleic acid entering the cells to function.
- si-NC group: the mixture of lipid mixture of No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) and si-NC was added to the cells and mixed, and the final concentration of the nucleic acid was 400 nM;
- si-XRN2 group: the mixture of lipid mixture of No. 1 (DG): No. 8 (PE): No. 12 (PC): No. 4 (Cer): No. 31 (So): No. 29 (FA): No. 16 (TG) (v:v:v:v:v:v:v=2:1:2:2:3:1:3) and XRN2 siRNA was added to the cells and mixed, and the final concentration of the nucleic acid was 400 nM.

No. 8 (PE): No. 12 (PC): No. 31 (So): No. 29 (FA): No. 4 (Cer) (v:v:v:v:v=2:4:2:2:5) lipid mixture mediated entry of nucleic acids into cells to function.

1) As shown in FIG. 98, No. 8 (PE): No. 12 (PC): No. 31 (So): No. 29 (FA): No. 4 (Cer) (v:v:v:v:v=2:4:2:2:5) lipid mixture mediated anti-fibrotic HJT-sRNA, HJT-SRNA-3, HJT-sRNA-a2, HJT-sRNA-h3, HJT-sRNA-m7 entry into MRC-5 cells (boiling method).
- Naive group: untreated cells, i.e., a blank control group;
- TGF-β1 group: cells were stimulated with TGF-β1 protein (final concentration of 3 ng/mL), and the samples were collected after 72 hours.
- NC group: lipid combination of No. 8 (PE): No. 12 (PC): No. 31 (So): No. 29 (FA): No. 4 (Cer) (v:v:v:v:v=2:4:2:2:5) was used to deliver NC mimics. After 24 hours, the cells were stimulated with TGF-β1 protein (final concentration of 3 ng/mL), and the samples were collected after 72 hours.
- M7 group: the mixture of lipid combination of No. 8 (PE): No. 12 (PC): No. 31 (So): No. 29 (FA): No. 4 (Cer) (v:v:v:v:v=2:4:2:2:5) with HJT-sRNA-m7 single-stranded was added to the MRC-5 cells, mixed, and the final concentration of nucleic acid was 400 nM. After 24 hours, the cells were stimulated with TGF-β1 protein (final concentration of 3 ng/mL), and the samples were collected after 72 hours.

2) As shown in FIG. 99, No. 8 (PE): No. 12 (PC): No. 31 (So): No. 29 (FA): No. 4 (Cer) (v:v:v:v:v=2:4:2:2:5) lipid mixture mediated XRN2 siRNA entry into A549 cells to inhibit gene expression (boiling method).

No. 8 (PE): No. 12 (PC): No. 31 (So): No. 29 (FA): No. 4 (Cer) (v:v:v:v:v=2:4:2:2:5) lipid mixture could effectively deliver nucleic acid into the cells to function.
- si-NC group: the mixture of lipid mixture of No. 8 (PE): No. 12 (PC): No. 31 (So): No. 29 (FA): No. 4 (Cer) (v:v:v:v:v=2:4:2:2:5) and si-NC was added to the cells and mixed, and the final concentration of the nucleic acid was 400 nM;
- si-XRN2 group: the mixture of lipid mixture of No. 8 (PE): No. 12 (PC): No. 31 (So): No. 29 (FA): No. 4 (Cer) (v:v:v:v:v=2:4:2:2:5) and XRN2 siRNA was added to the cells and mixed, and the final concentration of the nucleic acid was 400 nM.

10. No. 38 (PE): No. 37 (LPC) (v:v=4:1) Lipid Mixture Mediated Entry of Nucleic Acids into Cells to Function.

1) As shown in FIG. 100, No. 38 (PE): No. 37 (LPC) (v:v=4:1) lipid mixture mediated anti-fibrotic HJT-sRNA, HJT-sRNA-3, HJT-sRNA-a2, HJT-sRNA-h3, HJT-sRNA-m7 entry into MRC-5 cells (boiling method).
- Naive group: untreated cells, i.e., a blank control group;
- TGF-β1 group: cells were stimulated with TGF-β1 protein (final concentration of 3 ng/mL), and the samples were collected after 72 hours.
- NC group: lipid combination of No. 38 (PE): No. 37 (LPC) (v:v=4:1) was used to was used to deliver NC mimics. After 24 hours, the cells were stimulated with TGF-β1 protein (final concentration of 3 ng/mL), and the samples were collected after 72 hours.
- M7 group: the mixture of lipid combination of No. 38 (PE): No. 37 (LPC) (v:v=4:1) with HJT-sRNA-3, HJT-sRNA-a2, HJT-sRNA-h3, HJT-sRNA-m7 was added to the MRC-5 cells, and mixed, and the final concentration of nucleic acid was 400 nM. After 24 hours, the cells were stimulated with TGF-β1 protein (final concentration of 3 ng/mL), and the samples were collected after 72 hours.

Figure 101:
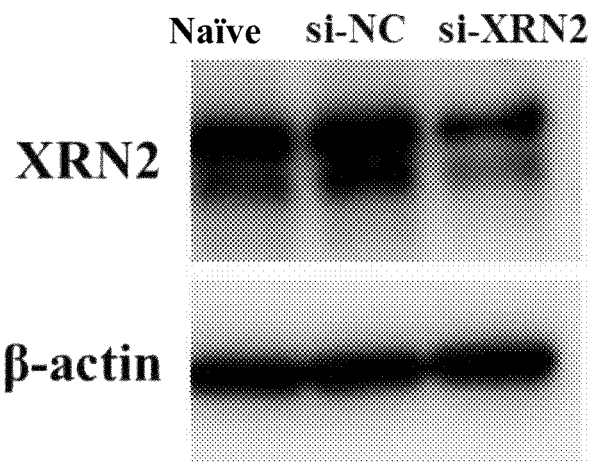

2) As shown in FIG. 101, No. 38 (PE): No. 37 (LPC) (v:v=4:1) lipid mixture mediated XRN2 siRNA entry into A549 cells to inhibit gene expression (boiling method).

No. 38 (PE): No. 37 (LPC) (v:v=4:1) lipid mixture could effectively deliver nucleic acid entering the cells to function.

si-NC group: the mixture of lipid mixture of No. 38 (PE): No. 37 (LPC) (v:v=4:1) and si-NC was added to the cells and mixed, and the final concentration of the nucleic acid was 400 nM;

si-XRN2 group: the mixture of lipid mixture of No. 38 (PE): No. 37 (LPC) (v:v=4:1) and XRN2 siRNA was added to the cells and mixed, and the final concentration of the nucleic acid was 400 nM.

11. No. 38 (PE): No. 12 (PC): No. 2 (DG) (v:v:v=4:1:3) Lipid Mixture Mediated Entry of Nucleic Acids into Cells to Function.

Figure 102:
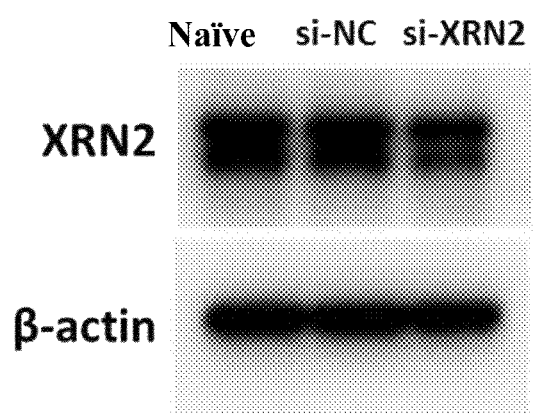

As shown in FIG. 102, No. 38 (PE): No. 12 (PC): No. 2 (DG) (v:v:v=4:1:3) lipid mixture mediated XRN2 siRNA entry into A549 cells to inhibit gene expression.

The lipid mixture of No. 38 (PE), in place of No. 8 (PE), with No. 12 (PC), No. 2 (DG) (v:v:v=4:1:3) could effectively deliver nucleic acid entering the cells to function.

si-NC group: the mixture of lipid mixture of No. 38 (PE): No. 12 (PC): No. 2 (DG) (v:v:v=4:1:3) and si-NC was added to the cells and mixed, and the final concentration of the nucleic acid was 400 nM;

si-XRN2 group: the mixture of lipid mixture of No. 38 (PE): No. 12 (PC): No. 2 (DG) (v:v:v=4:1:3) and XRN2 siRNA was added to the cells and mixed, and the final concentration of the nucleic acid was 400 nM.

12. No. 38 (PE): No. 37 (LPC): No. 12 (PC) (v:v:v=4:1:1) Lipid Mixture Mediated Entry of Nucleic Acids into Cells to Function.

Figure 103:
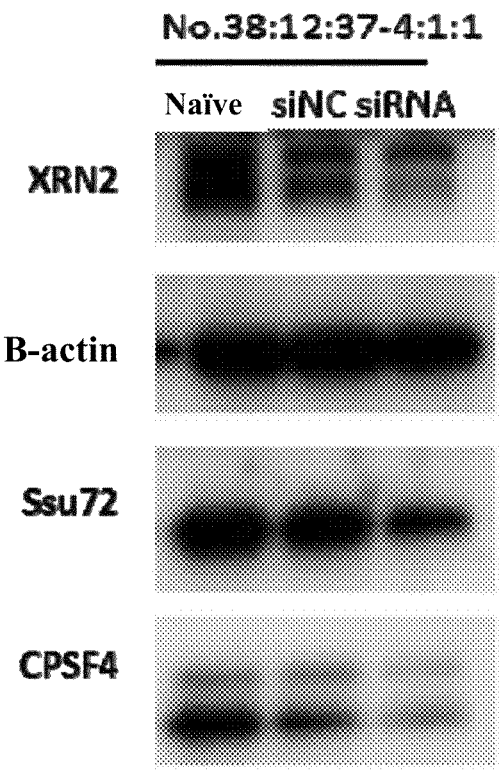

As shown in FIG. 103, No. 38 (PE): No. 37 (LPC): No. 12 (PC) (v:v:v=4:1:1) lipid mixture mediated XRN2 siRNA entry into A549 cells to inhibit gene expression (reverse evaporation method).

The addition of No. 12 (PC) (v:v:v=4:1:1) to the lipid mixture of No. 38 (PE): No. 37 (LPC) (v:v=4:1), could effectively deliver nucleic acid into cells to inhibit gene expression.

si-NC group: the mixture of lipid mixture of No. 38 (PE): No. 37 (LPC): No. 12 (PC) (v:v:v=4:1:1) and si-NC was added to the cells and mixed, and the final concentration of the nucleic acid was 400 nM;

si-RNA group: the mixture of lipid mixture of No. 38 (PE): No. 37 (LPC): No. 12 (PC) (v:v:v=4:1:1) and XRN2 siRNA, β-actin siRNA, Ssu 72 siRNA or CPSF4 siRNA was added to the cells and mixed, and the final concentration of the nucleic acid was 400 nM.

13. No. 4 (Cer): No. 12 (PC): No. 38 (PE): No. 37 (LPC) (v:v:v:v=5:2:8:3) Lipid Mixture Mediated Entry of Nucleic Acids into Cells to Function.

Figure 104:
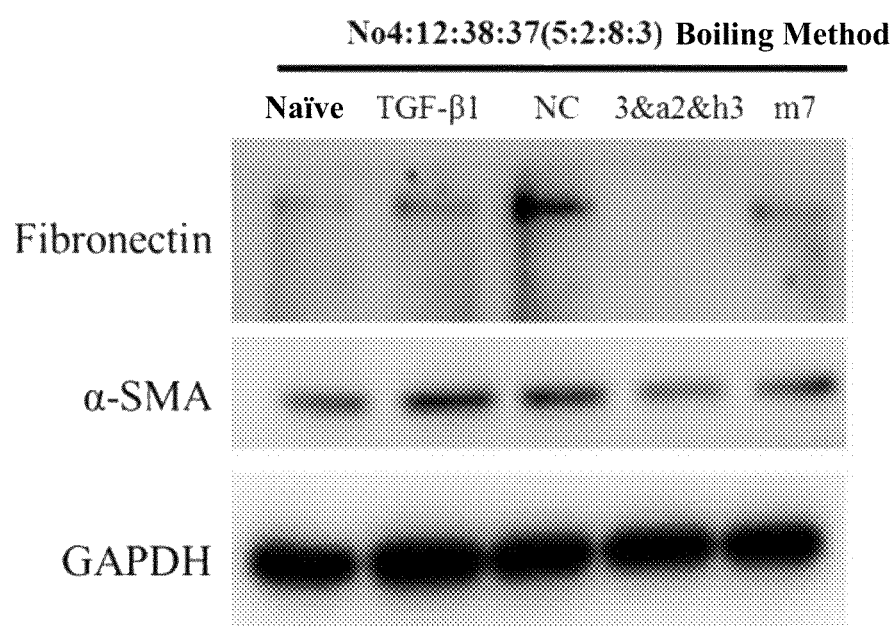

1) As shown in FIG. 104, the addition of No. 4 (Cer) to the lipid mixture of No. 38 (PE), No. 37 (LPC), No. 12 (PC) led to the lipid mixture of No. 4 (Cer): No. 12 (PC): No. 38 (PE): No. 37 (LPC) (v:v:v:v=5:2:8:3), which mediated anti-fibrotic HJT-sRNA, HJT-sRNA-3, HJT-sRNA-a2, HJT-sRNA-h3, HJT-sRNA-m7 double-stranded RNA entry into MRC-5 cells to reduce fibronectin expression levels (boiling method).

Naive group: untreated cells, i.e., a blank control group;
TGF-β1 group: cells were stimulated with TGF-β1 protein (final concentration of 3 ng/mL), and the samples were collected after 72 hours.
NC group: lipid combination of No. 4 (Cer): No. 12 (PC): No. 38 (PE): No. 37 (LPC) (v:v:v:v=5:2:8:3) was used to deliver NC mimics, after 24 hours, TGF-β1 protein (final concentration of 3 ng/ml) was added for stimulation, and the samples were collected after 72 hours.

HJT-3 & a2 & h3 group: the mixture of lipid mixture of No. 4 (Cer): No. 12 (PC): No. 38 (PE): No. 37 (LPC) (v:v:v:v=5:2:8:3) with HJT-sRNA-3, HJT-sRNA-a2, HJT-sRNA-h3 and HJT-sRNA-m7 double-strand, was added to the cells, and mixed and the final concentration of nucleic acid was 400 nM.

m7 group: the mixture of lipid combination of No. 4 (Cer): No. 12 (PC): No. 38 (PE): No. 37 (LPC) (v:v:v:v=5:2:8:3) with HJT-sRNA-m7 was added to the cells, and mixed, and the final concentration of nucleic acid was 400 nM.

Figure 105:
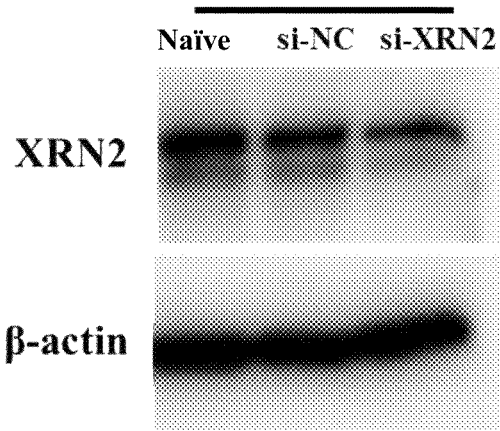

2) As shown in FIG. 105, No. 4 (Cer): No. 12 (PC): No. 38 (PE): No. 37 (LPC) (v:v:v:v=5:2:8:3) lipid mixture mediated XRN2 siRNA entry into cells to inhibit gene expression.

si-NC group: the mixture of lipid mixture of No. 4 (Cer): No. 12 (PC): No. 38 (PE): No. 37 (LPC) (v:v:v:v=5:2:8:3) and si-NC was added to the cells and mixed, and the final concentration of the nucleic acid was 400 nM;

si-XRN2 group: the mixture of lipid mixture of No. 4 (Cer): No. 12 (PC): No. 38 (PE): No. 37 (LPC) (v:v:v:v=5:2:8:3) and XRN2 siRNA was added to the cells and mixed, and the final concentration of the nucleic acid was 400 nM.

14. No. 38 (PE): No. 2 (DG): No. 31 (so) (v:v:v=4:2:3) Lipid Mixture Mediated Entry of Nucleic Acids into Cells to Function.

Figure 106:
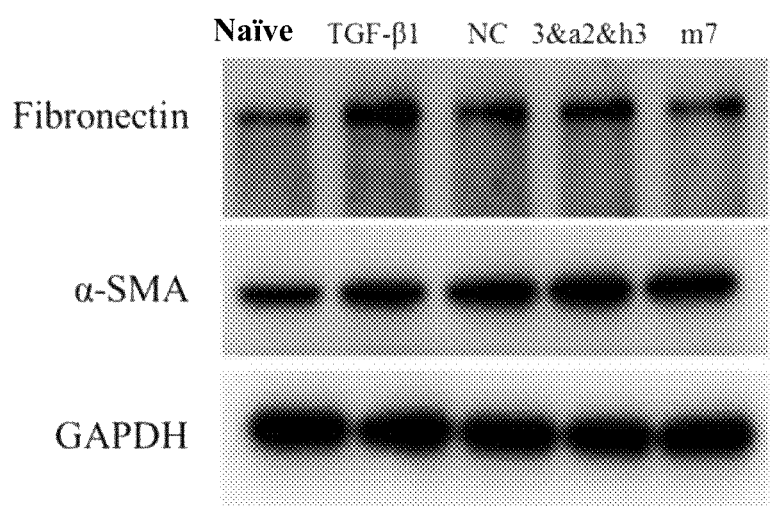

1) As shown in FIG. 106, No. 38 (PE): No. 2 (DG): No. 31 (So) (v:v:v=4:2:3) lipid mixture mediated anti-fibrotic HJT-sRNA, HJT-sRNA-3, HJT-sRNA-a2, HJT-sRNA-h3, HJT-sRNA-m7 double-stranded RNA entry into MRC-5 cells to reduce fibronectin expression levels (boiling method).

Naive group: untreated cells, i.e., a blank control group;
TGF-β1 group: cells were stimulated with TGF-1 protein (final concentration of 3 ng/mL), and the samples were collected after 72 hours.
NC group: lipid combination of No. 38 (PE): No. 2 (DG): No. 31 (So) (v:v:v=4:2:3) was used to deliver NC mimics. After 24 hours, TGF-β1 protein (final concentration of 3 ng/ml) was added for stimulation, and the samples were collected after 72 hours.

HJT-3 & a2 & h3 group: the mixture of lipid mixture of No. 38 (PE): No. 37 (LPC) (v:v:v=4:1) with HJT-sRNA-3, HJT-sRNA-a2 and HJT-sRNA-h3, was added to the cells, and mixed and the final concentration of nucleic acid was 400 nM.

M7 group: the mixture of lipid combination of No. 38 (PE): No. 37 (LPC) (v:v=4:1) with HJT-sRNA-m7 was added to the cells, and mixed, and the final concentration of nucleic acid was 400 nM.

Figure 107:
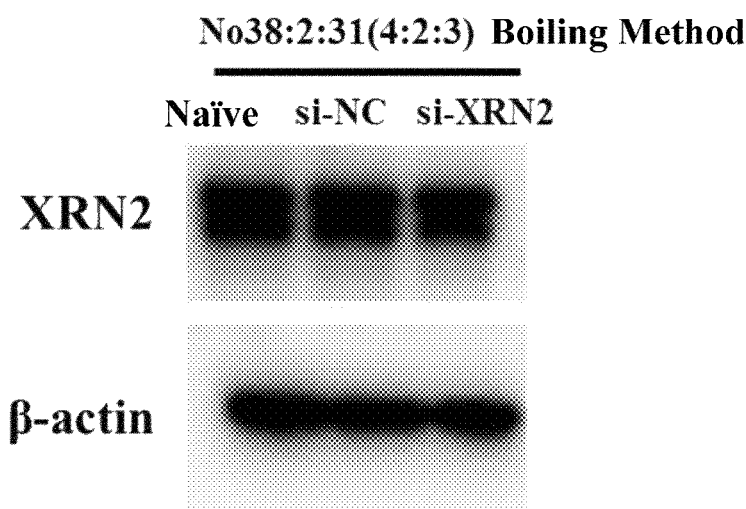

2) As shown in FIG. 107, No. 38 (PE): No. 2 (DG): No. 31 (So) (v:v:v=4:2:3) lipid mixture mediated XRN2 siRNA entry into A549 cells to inhibit gene expression (boiling method).

No. 38 (PE): No. 2 (DG): No. 31 (So) (v:v:v=4:2:3) lipid mixture effectively delivered XRN2 siRNA into A549 cells to function.

si-NC group: the mixture of lipid mixture of No. 38 (PE): No. 2 (DG): No. 31 (So) (v:v:v=4:2:3) and si-NC was added to the cells and mixed, and the final concentration of the nucleic acid was 400 nM;

si-XRN2 group: the mixture of lipid mixture of No. 38 (PE): No. 2 (DG): No. 31 (So) (v:v:v=4:2:3) and XRN2 siRNA was added to the cells and mixed, and the final concentration of the nucleic acid was 400 nM.

Example 5: Validation of the Effects of Lipid No. 41 and its Composition

I. Single Lipids Delivered Nucleic Acids (Double-Stranded RNA and Single-Stranded RNA) into Cells by Different Preparation Methods (Reverse Evaporation and Boiling Method)
Lipid No. 41. Sphinganine (d22:0)

dsRNA by RNAiMAX, and the samples were collected for detection after 6 hours; (4) No. 41 group: lipid No. 41 prepared by different methods (boiling method or reverse evaporation method) delivered double-stranded RNA into A549 cells, and samples were collected for detection after 6 hours.

Figure 111:
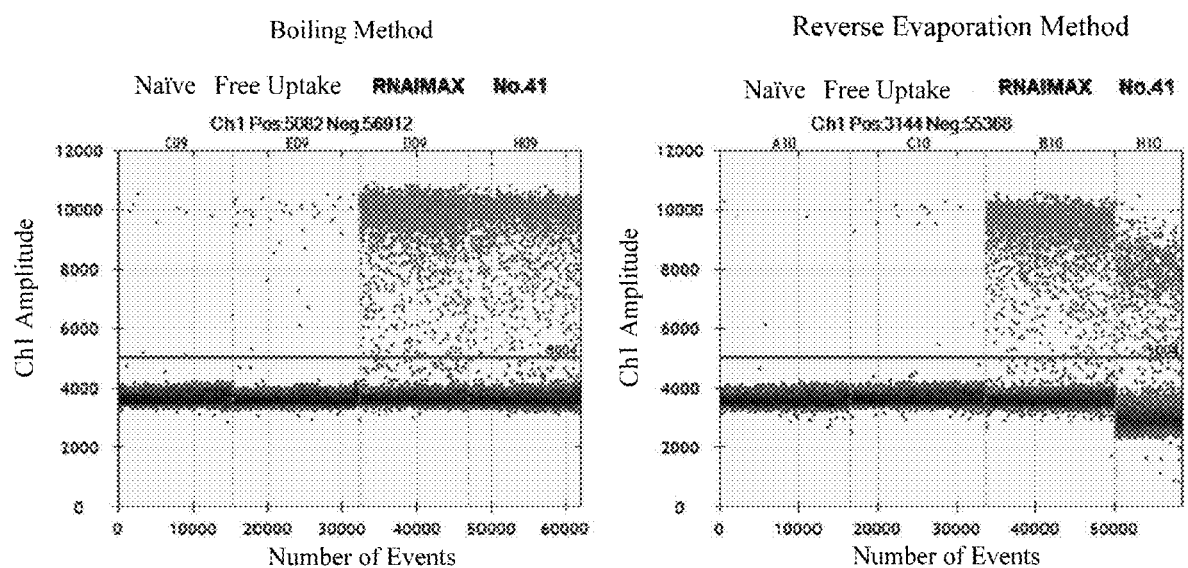

Experimental results and analysis: as shown in FIG. 111, by both the boiling method and reverse evaporation method, lipid No. 41 could effectively deliver HJT-sRNA-m7 dsRNA into A549 cells, and the boiling method had better effects than reverse evaporation method.

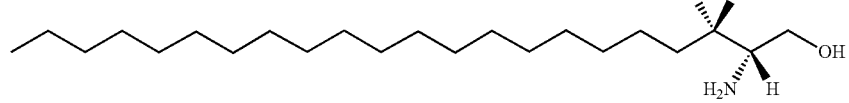

1. Quantitative Real-Time PCR (Real-Time PCR) Detection of the Efficiency of Nucleic Acid Delivery by Lipid.

As shown in FIG. 108, lipid No. 41 prepared by different methods (boiling or reverse evaporation method) delivered HJT-sRNA-m7 double-stranded RNA into A549 cells. For A549 cells, in the case of the boiling method, the delivery effect of lipid No. 41 was about twice that of RNAiMAX, and in the case of the reverse evaporation method, the delivery effect of lipid No. 41 was also significantly higher than that of RNAiMAX.

As shown in FIG. 109, lipid No. 41 prepared by different methods (boiling or reverse evaporation method) delivered HJT-sRNA-m7 double-stranded RNA into MRC-5 cells. For MRC-5 cells, in the case of the boiling method, lipid No. 41 delivered double-stranded RNA into MRC-5 cells, and in the case of the reverse evaporation method, the delivery effect of lipid No. 41 was significantly higher than that of RNAiMAX.

As shown in FIG. 110, lipid No. 41 delivered HJT-sRNA-m7 single-stranded RNA into A549 and MRC-5 cells by the boiling method.

2. Digital PCR (ddPCR) Detection of the Efficiency of Nucleic Acid Delivery by Lipid 2.1 Experimental materials: A549 cells were purchased from the Cell Center of the Institute of Basic Medical Sciences, Chinese Academy of Medical Sciences, TRIzol lysis buffer was purchased from Sigma, High capacity cRNA Reverse Transcription Kit was purchased from ABI, USA, and the digital PCR related reagents were purchased from Bio-Rad USA.

2.3 Experimental method: the total cellular RNA was collected and extracted by TRIzol lysis buffer according to the above methods, and reverse transcribed to cDNA using High capacity cRNA Reverse Transcription Kit, and the cDNA from different groups was subject to digital PCR reaction. Referring to the QX200 Droplet Reader and QuantaSoft Software manual for the protocols, the results were analyzed using QuantaSoft software. The groups were as follows: (1) naive group: A549 cells without treatment; (2) free uptake group: the cells were directly incubated with HJT-sRNA-m7 dsRNA for 6 hours; (3) RNAiMAX group: A549 cells were transfected with the HJT-sRNA-m7

3. Flow Cytometry Detection of the Efficiency of Nucleic Acid Delivery by Lipid

Experimental materials: A549 cells (purchased from the Cell Center of the Chinese Academy of Medical Sciences), FAM-sRNA (purchased from Ribobio Biotechnology Co., Ltd.), lipid No. 41, Accuri® C6 instrument (purchased from BD, USA).

Experimental methods: PGY-sRNA-6-FAM was dissolved in 100 µl water, mixed with 4 µl lipid, and prepared by boiling method. Then the mixture was dropped into A549 cells, and after 6 hours of co-incubation, the samples were collected for detection as follows: firstly wash three times with PBS, then digest with trypsin for 3 minutes and remove trypsin, wash with PBS again and then blow down the cells. The detection was performed using Accuri® C6 instrument.

Figure 112:
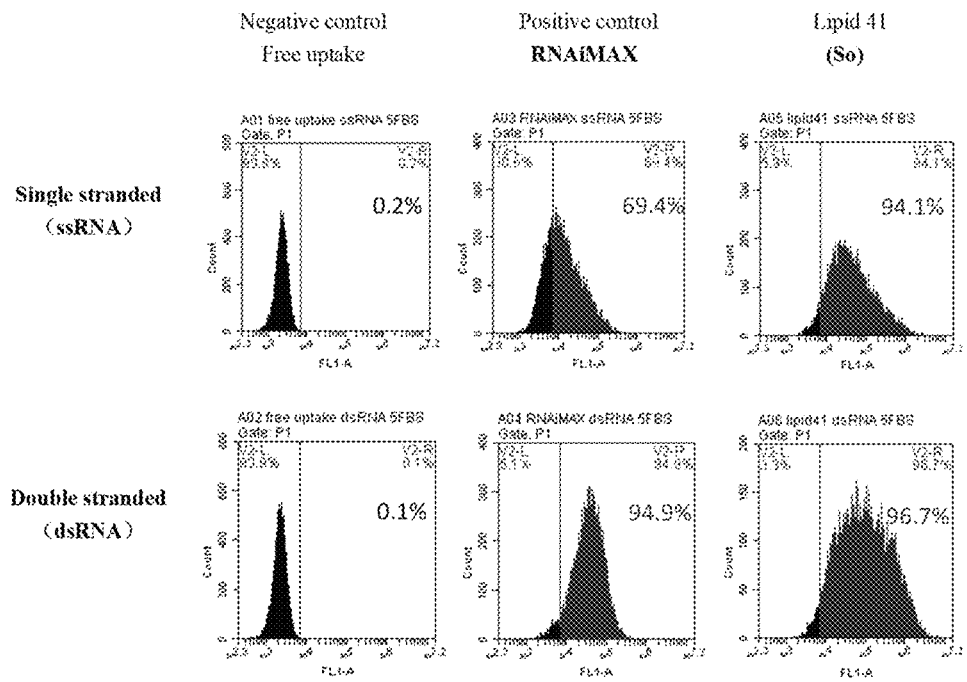

Experimental results as shown in FIG. 112: lipid No. 41 had an efficiency of 94.1% in delivering PGY-sRNA-6 single-stranded RNA, which was higher than 69.4% of the positive control RNAiMAX. And lipid No. 41 had an efficiency of 96.7% in delivering PGY-sRNA-6 double-stranded RNA, which was also higher than 94.9% of the positive control RNAiMAX. Lipids 41 could efficiently deliver single-stranded and double-stranded nucleic acids into A549 cells.

4. Observation of the Localization of the Nucleic Acid Delivered by Lipid in Cells by Confocal Fluorescence Microscopy Experimental materials: A549 cells (purchased from the Cell Center of the Chinese Academy of Medical Sciences), PGY-sRNA-6-Cy3 (purchased from Ribobio Biotechnology Co., Ltd.), lipid No. 41, Zeiss LSM780 (purchased from Zeiss, Germany), Alexa Fluor® 488 phalloidin (purchased from Invitrogen, USA), DAPI (purchased from Invitrogen, USA), paraformaldehyde (purchased from sigma, USA).

Experimental methods: PGY-sRNA-6-FAM was dissolved in 100 µl water, mixed with 4 µl lipid, and prepared by the boiling method. Then the mixture was dropped into A549 cells, and after 6 hours of co-incubation, the samples were washed three times with PBS, fixed with 4% paraformaldehyde, washed three times with PBS, stained with Alexa Fluor® 488 phalloidin for 30 min, washed 3 times with PBS, and stained with DAPI for 5 min, washed with PBS, and then sealed.

Figure 113:
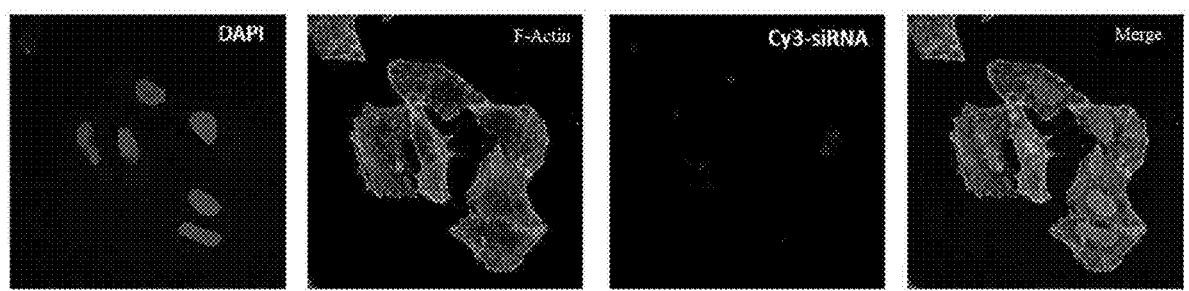

Experimental results as shown in FIG. 113: the entry of red PGY-sRNA-6-Cy3 could be obviously observed under the confocal microscopy. Lipid No. 41 could effectively deliver double-stranded nucleic acid into A549 cells.

5. Western Blot Detection of the Efficiency of Nucleic Acid Delivery by Lipid

Figure 114:
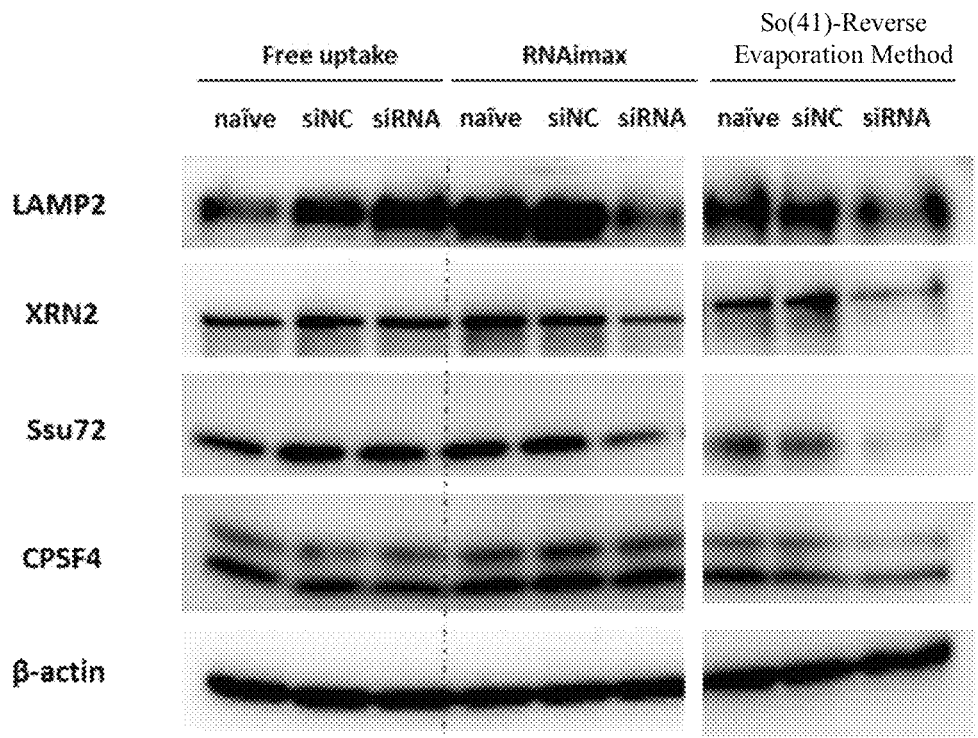

As shown in FIG. 114, single lipid No. 41 mediated sRNAi entry into MRC-5A549 cells to knockdown protein expression (by reverse evaporation method). At protein level, the protein knockdown effect mediated by the single lipid No. 41 was significantly higher than the inhibitory effect of HJT-sRNA-m7 mediated by RNAiMAX.

Figure 115:
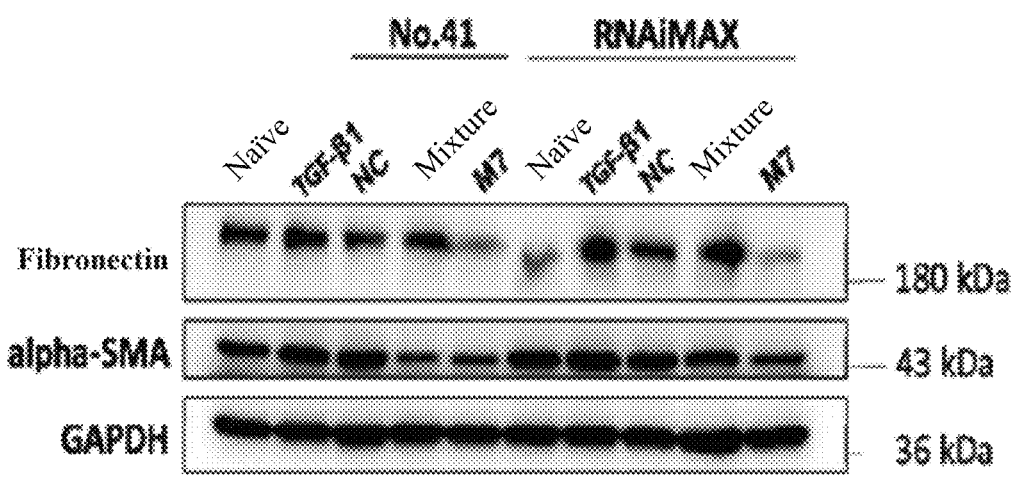

Naive group: untreated MRC-5A549 cells.

siNC group: the mixture of single lipid No. 41 and siNC was added to the cells and mixed, and the final concentration of the nucleic acid was 400 nM;

siRNA group: the mixture of single lipid No. 41 and LAMP2, XPN2, Ssu72, CPSF4 or β-actin siRNA was added to the cells, mixed, and the final concentration of the nucleic acid was 400 nM;

Free uptake group: the test substance was directly added;

RNAiMAX group: 2 μl RNAiMAX transfection reagent and nucleic acid solution were diluted with 100 μl opti-MEM medium, respectively, and the two were mixed, allowed to stay for 15 min, added to the cells, and then mixed, and the final concentration of nucleic acid was 400 nM;

So (41) group (reverse evaporation method): the mixture of lipid No. 41 and the nucleic acid was added to the cells and mixed, and the final concentration of the nucleic acid was 400 nM;

As shown in FIG. 115, single lipid No. 41 mediated anti-fibrotic HJT-sRNA-m7 double-strand entry into MRC-5 cells (reverse evaporation method). At protein level, single lipid No. 41 mediated HJT-sRNA-m7 inhibition was higher than RNAiMAX mediated HJT-sRNA-m7 inhibition.

TGF β 1 group: TGF-β 1 protein (final concentration was 3 ng/mL) was added for stimulation, and the samples were collected after 72 hours;

NC group: single lipid No. 41 delivered NC mimics. After 24 hours, the cells were stimulated with TGF-β1 TGFb1 protein (final concentration was 3 ng/ml), and the samples were collected after 72 hours;

HJT-3 & a2 & $H_3$ group: the mixture of single lipid No. 41 and HJT-sRNA-3, HJT-sRNA-a2 and HJT-sRNA-h3 were added to the cells and mixed, and the final concentration of the nucleic acid was 400 nM;

m7 group: the mixture of single lipid No. 41 and HJT-sRNA-m7 was added to the cells and mixed, and the final concentration of the nucleic acid was 400 nM;

6. Summary of In Vivo Results of Lipid No. 41

[Experimental method] 6-8 weeks old mice, 22-24 g, were raised in SPF room of the Animal Center of the Institute of Basic Medical Sciences of Chinese Academy of Medical Sciences. The mice were fasted for 12 hours before intragastric administration. The mice were randomly divided into 3 groups: (1) control group, 400 μl DEPC-treated water, intragastric administration; (2) free uptake group, small RNA (PGY-sRNA-26, PGY-sRNA-32 and PGY-sRNA-23), each small RNA 1 nmol/animal, dissolved in 400 μl DEPC-treated water, intragastric administration; (3) lipid No. 41 group: a mixture of small RNA (PGY-sRNA-26 and PGY-sRNA-32) and lipid No. 41 prepared by heating method was intragastrically administered, each small RNA 1 nmol/animal, lipid No. 41 10 μl/animal, dissolved in 400 μl DEPC-treated water. All tissue and organ samples were collected after 6 hours of intragastric administration. All small RNAs were single-stranded RNA modified by 3p-terminal 2-O-methylation.

[Experimental Results]

As shown in FIG. 140, lipid No. 41 could promote the entry of small RNA into the blood, protecting it from degradation in the blood.

As shown in FIG. 141, lipid No. 41 could promote the entry of small RNA into the stomach cells, protecting it from degradation in the stomach.

As shown in FIG. 142, lipid No. 41 could promote the entry of small RNA into small intestinal cells, protecting it from degradation in the small intestine.

As shown in FIG. 143, lipid No. 41 could promote the entry of small RNA into the liver, protecting it from degradation in the liver.

7. Effect of Lipid Combination Containing Lipid No. 41 on Nucleic Acid Delivery

1) Effect of Lipid Combination 1 (No. 8+No. 41=6:1) and Lipid Combination 2 (No. 38+No. 41=6:1) on Nucleic Acid Delivery.

Figure 116:
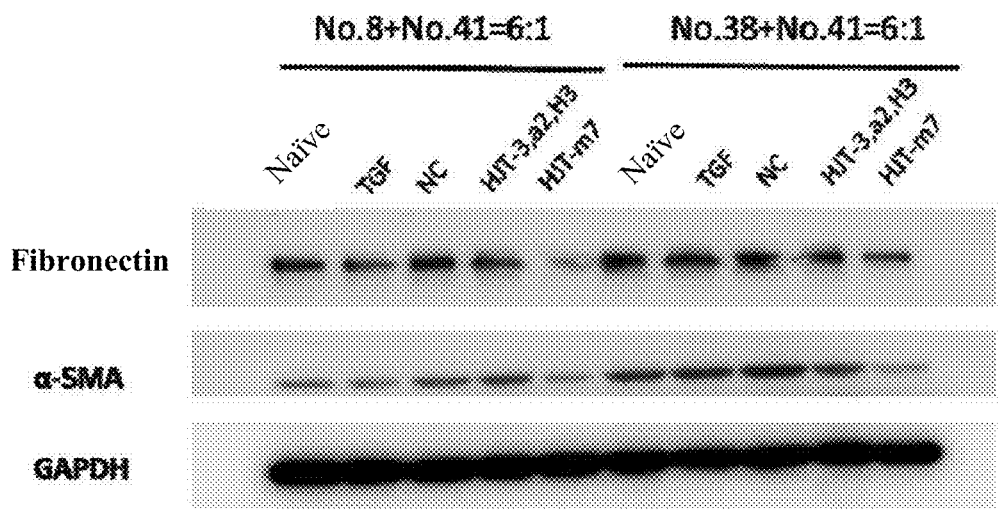

As shown in FIG. 116, lipid combination 1 (No. 8+No. 41=6:1) and lipid combination 2 (No. 38+No. 41=6:1) mediated anti-fibrotic HJT-3 & a2 & $H_3$, HJT-sRNA-m7 entry into MRC-5 cells (heating method), and mediated a significant inhibitory effect of the HJT-sRNA-m7 at protein level.

TGF: TGF-β1 protein (final concentration was 3 ng/mL) was added for stimulation, and the samples were collected after 72 hours;

NC group: single lipid No. 41 was used to deliver NC mimics. After 24 hours, TGF-β1 TGF-b 1 protein (final concentration was 3 ng/mL) was added for stimulation, and the samples were collected after 72 hours;

HJT-3 & a2 & $H_3$ group: the mixture of the lipid mixture with HJT-sRNA-3, HJT-sRNA-a2 and HJT-sRNA-h3 was added to the cells and mixed, and the final concentration of the nucleic acid was 400 nM;

HJT-m7: the mixture of the lipid mixture and HJT-sRNA-m7 was added to the cells and mixed, and the final concentration of the nucleic acid was 400 nM;

2) Effects of Lipid Combination 3 (No. 39+No. 41=6:1) and Lipid Combination 4 (No. 40+No. 41=6:1) on Nucleic Acid Delivery.

Figure 117:
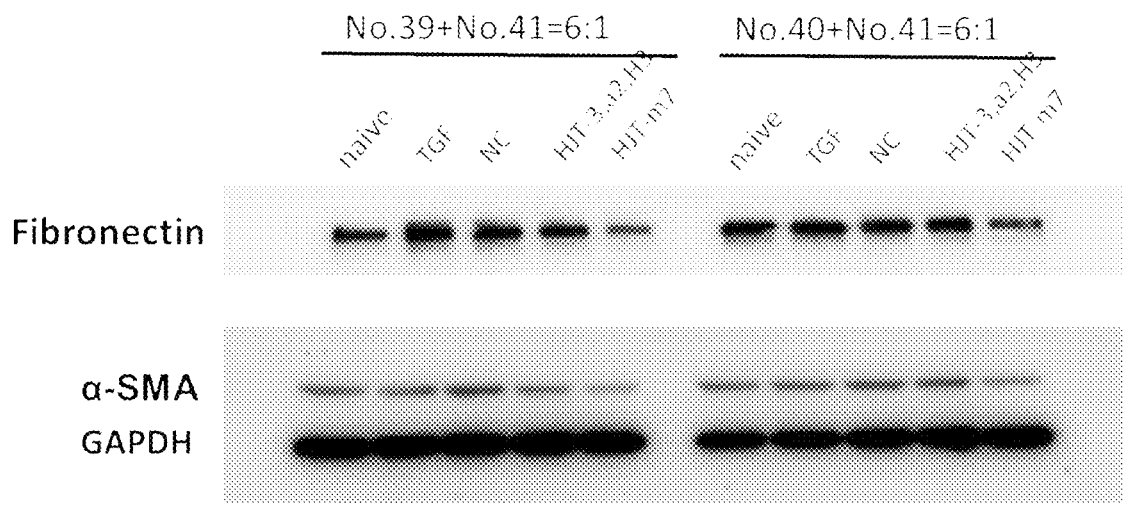

As shown in FIG. 117, lipid combination 3 (No. 39+No. 41=6:1) and lipid combination 4 (No. 40+No. 41=6:1) mediated anti-fibrotic HJT-3 & a2 & $H_3$, HJT-sRNA-m7 entering into MRC-5 cells (heating method), and mediated a significant inhibitory effect of HJT-sRNA-m7 at protein the level.

TGF: TGF-1 protein (final concentration was 3 ng/mL) was added for stimulation, and the samples were collected after 72 hours;

NC group: lipid mix was used to deliver NC mimics. After 24 hours, the TGF-β1 protein (final concentration was 3 ng/mL) was added for stimulation, and the samples were collected after 72 hours;

HJT-3 & a2 & $H_3$ group: the mixture of the lipid mixture with HJT-sRNA-3, HJT-sRNA-a2 and HJT-sRNA-$H_3$ was added to the cells and mixed, and the final concentration of the nucleic acid was 400 nM;

HJT-m7: the mixture of the lipid mixture and HJT-sRNA-m7 was added to the cells and mixed, and the final concentration of the nucleic acid was 400 nM;

3) Effect of Lipid Combination 5 (No. 38+12+41+29=1:2:1:1) on Nucleic Acid Delivery.

Figure 118:
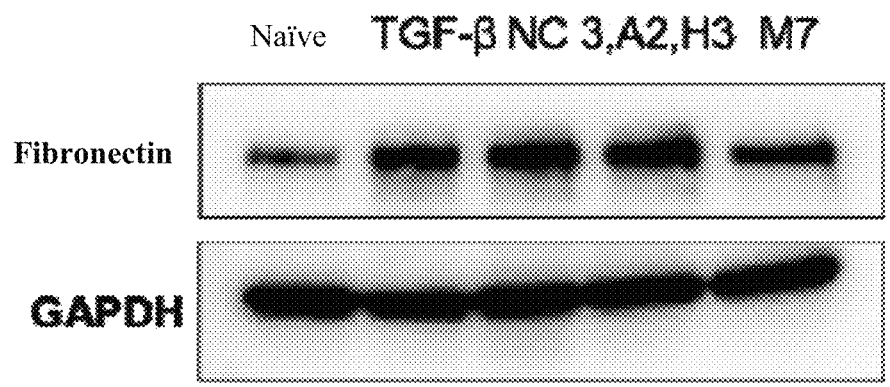

As shown in FIG. 118, lipid combination 5 (No. 38+12+41+29=1:2:1:1) mediated anti-fibrotic HJT-3 & a2 & $H_3$ and HJT-sRNA-m7 entering into MRC-5 cells (heating method), and mediated a significant inhibitory effect of HJT-sRNA-m7 at the protein level.

TGF: TGF-β1 protein (final concentration was 3 ng/mL) was added for stimulation, and samples were collected after 72 hours;

NC group: lipid mixture was used to deliver NC mimics. After 24 hours TGF-β1 protein (final concentration was 3 ng/mL) was added for stimulation, and the samples were collected after 72 hours;

HJT-3 & a2 & $H_3$ group: the mixture of the lipid mixture with HJT-sRNA-3, HJT-sRNA-a2 and HJT-sRNA-$H_3$ mixture was added to the cells and mixed, and the final concentration of the nucleic acid was 400 nM;

HJT-m7: a mixture of the lipid mixture and HJT-sRNA-m7 was added to the cells and mixed, and the final concentration of the nucleic acid was 400 nM;

4) Effect of Lipid Combination 6 (No. 40 (PE)+No. 12 (PC)+No. 41(so)=2:4:3) on Nucleic Acid Delivery.

As shown in FIG. 119, lipid combination 6 (No. 40 (PE)+No. 12 (PC)+No. 41 (So)=2:4:3) mediated anti-fibrotic HJT-3 & a2 & $H_3$, HJT-sRNA-m7 entering into MRC-5 cells (boiling and reverse evaporation method), and mediated a significant inhibitory effect of the HJT-3 & a2 & $H_3$, HJT-sRNA-m7 at the protein level.

TGF: TGF-β1 protein (final concentration was 3 ng/mL) was added for stimulation, and samples were collected after 72 hours;

3'—NC group: lipid mixture was used to deliver NC mimics, and after 24 hours TGF-β1 TGFb1 protein (final concentration was 3 ng/mL) was added for stimulation, and samples were collected after 72 hours;

3'-3 & a2 & $H_3$ group: the mixture of lipid mixture with HJT-sRNA-3, HJT-sRNA-a2, HJT-sRNA-$H_3$ was added to the cells and mixed, and the final concentration of the nucleic acid was 400 nM;

3'-m7: a mixture of lipid mixture and HJT-sRNA-m7 was added to the cells, mixed, and the final concentration of the nucleic acid was 400 nM;

Right Figure: lipid-RNA mixture was prepared by reverse evaporation. Lipid combination 6 (No. 40 (PE)+No. 12 (PC)+No. 41(So)=2:4:3) could effectively deliver XRN2, Ssu72, CPSF4 siRNA into A549 Cells, which significantly reduce expression levels at the protein level.

siNC: the mixture of lipid mixture and siNC was added to the cells and mixed, and the final concentration of the nucleic acid was 400 nM;

siRNA: the mixture of lipid mixture and XRN2, Ssu72, CPSF4 siRNA were added to the cells, mixed, and the final concentration of the nucleic acid was 400 nM;

5) Effect of Lipid Combination 7 (No. 12 (PC)+No. 41(so)= 1:6) and Lipid Combination 8 (No. 12 (PC)+No. 41(so)=1:1) on Nucleic Acid Delivery.

As shown in FIG. 120, by the reverse evaporation method, lipid combination 7 (No. 12 (PC)+No. 41(So)=1:6) and lipid combination 8 (No. 12 (PC)+No. 41(So)=1:1) could effectively deliver Ssu72, CPSF4 siRNA into A549 Cells, which significantly reduced the expression levels at the protein level.

siNC: the mixture of lipid mixture and siNC was added to the cells and mixed, and the final concentration of the nucleic acid was 400 nM;

siRNA: the mixture of lipid mixture and XRN2, Ssu72, CPSF4 siRNA was added to the cells, mixed, and the final concentration of the nucleic acid was 400 nM;

6) Effect of Lipid Combination 9 (No. 12 (PC)+No. 41 (so)=6:1) and Lipid Combination 10 (No. 40 (PE)+No. 12 (PC)+No. 41(so)=2:2:2) on Nucleic Acid Delivery.

As shown in FIG. 121, by the reverse evaporation method, lipid combination 9 (No. 12 (PC)+No. 41 (So)=6:1) and lipid combination 10 (No. 40 (PE)+No. 12 (PC)+No. 41 (So)=2:2:2) could effectively deliver XRN2, Ssu72, CPSF4 siRNA into A549 Cells, which significantly reduced the expression levels at the protein level.

siNC: the mixture of lipid mixture and siNC was added to the cells and mixed, and the final concentration of the nucleic acid was 400 nM;

siRNA: the mixture of lipid mixture and XRN2, Ssu72, CPSF4 siRNA was added to the cells, mixed, and the final concentration of the nucleic acid was 400 nM;

7) Effect of Lipid Combination 11 (No. 4 (Cer)+No. 12 (PC)+No. 41(so)=1:1:1) on Nucleic Acid Delivery.

Figure 122:
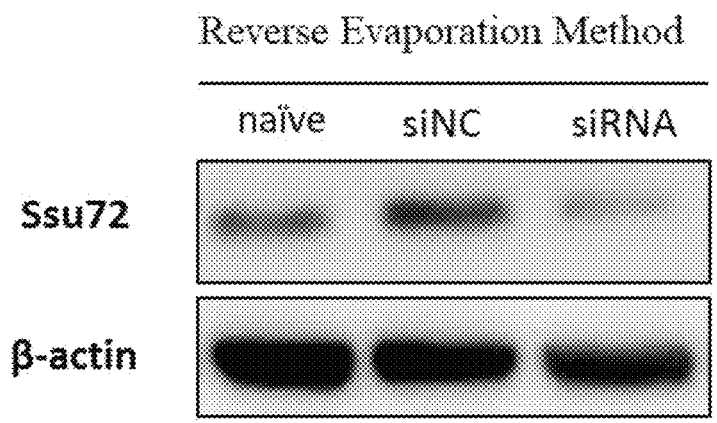

As shown in FIG. 122, by the reverse evaporation method, lipid combination 11 (No. 4 (Cer)+No. 12 (PC)+No. 41(So)= 1:1:1) could effectively deliver Ssu72 siRNA into A549 Cells, which significantly reduced the expression levels at protein level.

siNC: the mixture of lipid mixture and siNC was added to the cells and mixed, and the final concentration of the nucleic acid was 400 nM;

siSsu72: the mixture of lipid mixture and Ssu72 siRNA was added to the cells, mixed, and the final concentration of the nucleic acid was 400 nM;

Example 6: Validation of the effect of lipid No. 38 and its combination

Lipid No. 38 PE(16:0/16:1)

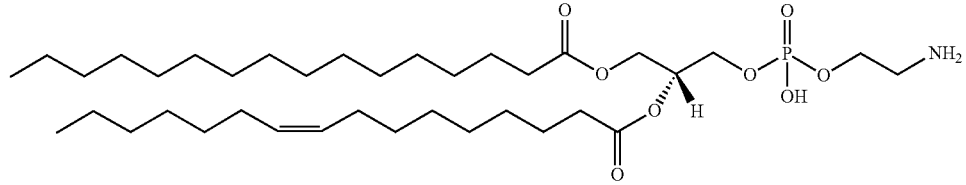 [SMILES: CCCCCC/C=C\CCCCCCCC(=O)O[C@H](COC(=O)CCCCCCCCCCCCCCC)COP(=O)(O)OCCN]

1. Quantitative Real-Time PCR (Real-Time PCR) Detection of the Efficiency of the Nucleic Acid Delivery by Lipid (1) Lipid No. 38 by Boiling Method Delivered Double-Stranded RNA into A549 and MRC-5 Cells.

Figure 123:
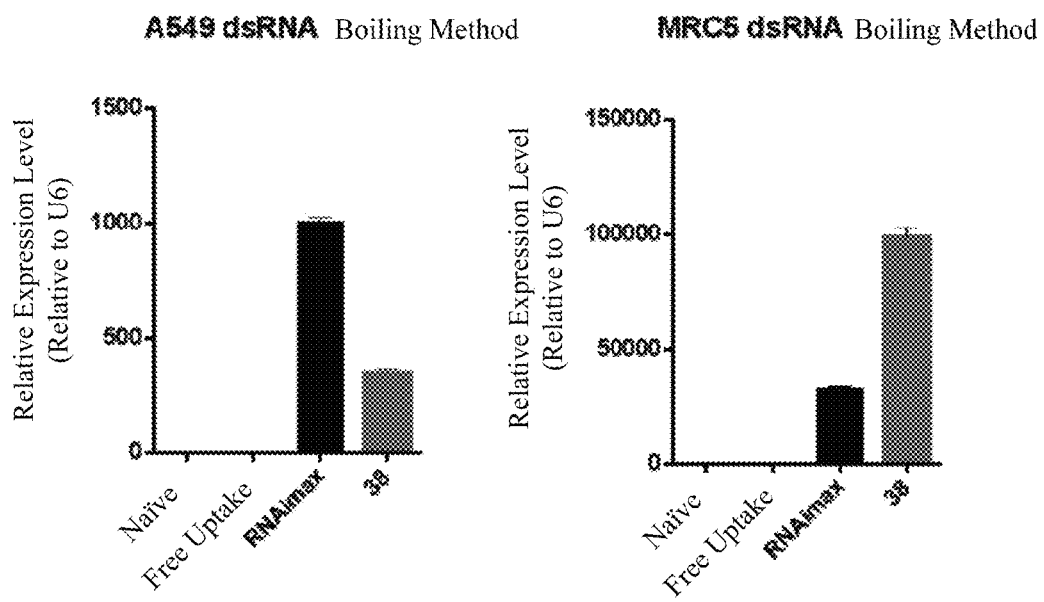

As shown in FIG. 123, lipid No. 38 by heating method delivered double-stranded RNA into A549 and MRC-5 cells. For MRC-5 cells, in the case of the heating method, the delivery effect of lipid No. 38 on double-stranded RNA was about twice that of RNAiMAX.

1) Naive group: untreated A549 cells;

2) Free uptake group: HJT-sRNA-m7 dsRNA was directly incubated with cells for 12 hours; the final concentration of nucleic acid was 100 nM;

3) RNAiMAX group: 2 μL RNAiMAX transfection reagent and double-stranded HJT-sRNA-m7 solution were diluted in 100 μL opti-MEM medium respectively, and then the two were mixed, allowed to stay for 15 min, added into the cells, and then mixed. The final concentration of HJT-sRNA-m7 double-strand was 100 nM;

4) Treatment group of lipid and nucleic acid: a mixture of 2.5 μL single lipid No. 38 and HJT-sRNA-m7 double-stranded nucleic acid solution was prepared by boiling method or reverse evaporation method, and then added to A549 cells. The final concentration of RNA was 100 nM. After 12 hours, the sample was collected to detect the amount of entry.

(2) Lipid No. 38 by Boiling Method Delivered HJT-sRNA-m7 Single-Stranded RNA into A549 and MRC-5 Cells.

As shown in FIG. 124, lipid No. 38 by heating method delivered HJT-sRNA-m7 single-stranded RNA into A549 and MRC-5 cells, where the efficiency of delivery was much higher than that of RNAiMAX.

1) Naive group: untreated A549 cells;
2) Free uptake group: HJT-sRNA-m7 single stranded RNA was directly incubated with cells for 12 hours; the final concentration of nucleic acid was 100 nM;
3) RNAiMAX group: 2 μL RNAiMAX transfection reagent and single-stranded HJT-sRNA-m7 solution were diluted in 100 μL opti-MEM medium respectively, and then the two were mixed, allowed to stay for 15 min, added into the cells, and then mixed, and the final concentration of single-stranded HJT-sRNA-m7 was 100 nM;
4) Treatment group of lipid and nucleic acid: a mixture of 2.5 μL single lipid No. 64 and HJT-sRNA-m7 double-stranded nucleic acid solution was prepared by boiling method or reverse evaporation method, and added to A549 cells, the final concentration of RNA was 100 nM. After 12 hours, the sample was collected to detect the amount of entry.

2. Digital PCR (ddPCR) Detection of the Efficiency of Nucleic Acid Delivery by Lipid 2.1 Experimental materials: A549 cells were purchased from the Cell Center of the Institute of Basic Medical Sciences, Chinese Academy of Medical Sciences, TRIzol lysis buffer was purchased from Sigma, High capacity cRNA Reverse Transcription Kit was purchased from ABI, USA, and digital PCR related reagents were purchased from Bio-Rad.

2.2 Experimental method: total RNA was collected and extracted by TRIzol lysis buffer according to the above method, and reverse transcribed to cDNA using High capacity cRNA Reverse Transcription Kit, and the cDNA from different groups was subjected to digital PCR reaction. Refer to the QX200 Droplet Reader and QuantaSoft Software manual for the protocols; the results were analyzed using QuantaSoft software.

Figure 125:
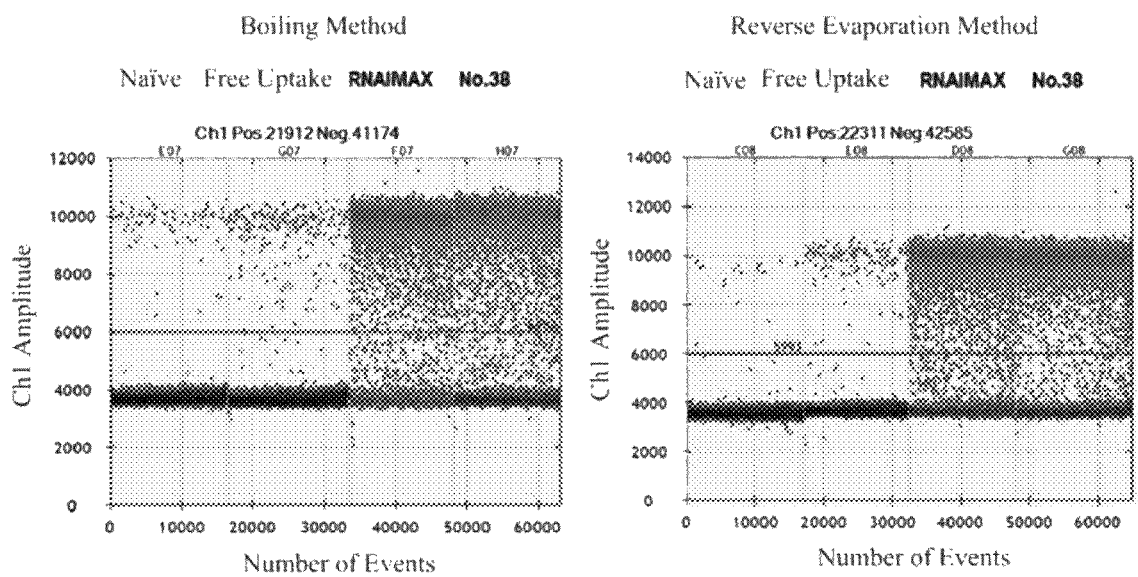

(1) Naive group: A549 cells without any treatment;
(2) Free uptake group: the cells were directly co-incubated with HJT-sRNA-m7 dsRNA for 6 hours;
(3) RNAiMAX group: the HJT-sRNA-m7 dsRNA was transfected into A549 cells by RNAiMAX, and the samples were collected for detection after 6 hours;
(4) No. 38 group: lipid No. 38 delivered double-stranded RNA into A549 cells by different preparation methods (boiling or evaporation method), and the samples were collected for detection after 6 hours;

Experimental results and analysis: As shown in FIG. 125, in the boiling or reverse evaporation method, lipid No. 38 could effectively deliver HJT-sRNA-m7 dsRNA into A549 cells.

3. Flow Cytometry Detection of the Efficiency of Nucleic Acid Delivery by Lipid

Experimental materials: A549 cells (purchased from the Cell Center of the Chinese Academy of Medical Sciences), FAM-sRNA (purchased from Ribobio Biotechnology Co., Ltd.), lipid No. 38, Accuri® C6 instrument (purchased from BD, USA).

Experimental Method: PGY-sRNA-6-FAM was dissolved in 100 μl water, and mixed with 4 μl lipid, and prepared into lipid-sRNA mixture by boiling method. Then, the mixture was dropped into A549 cells, and after 6 hours of co-incubation, the samples were collected and washed three times with PBS, then digested with trypsin into single cells, washed with re-suspended with PBS and then blown down for Accuri® C6 instrument detection.

Figure 126:
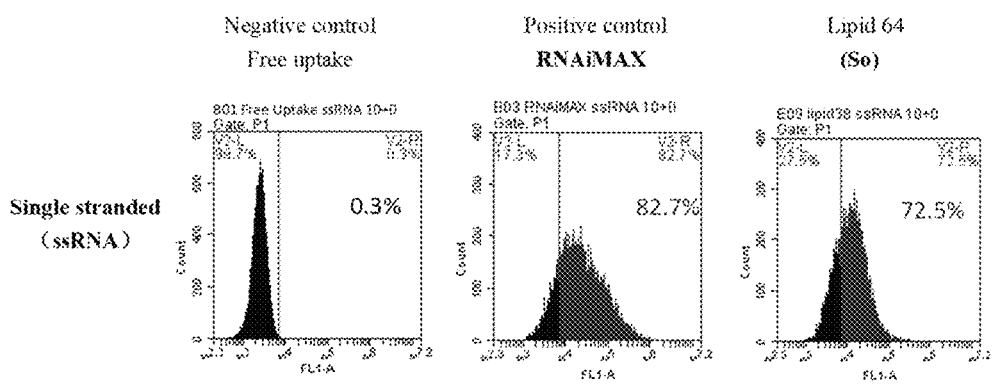

Experimental results (shown in FIG. 126): lipid No. 38 delivered PGY-sRNA-6 single-stranded RNA at an efficiency of 72.5%, which was close to that of the positive control RNAiMAX.

4. Confocal Fluorescence Microscopy to Observe the Location of the Nucleic Acid Delivered by Lipids in Cells Experimental materials: A549 cells (purchased from the Cell Center of the Chinese Academy of Medical Sciences), PGY-sRNA-6-Cy3 (purchased from Ribobio Biotechnology Co., Ltd.), lipid No. 38, Zeiss LSM780 (purchased from Zeiss, Germany), Alexa Fluor® 488 phalloidin (purchased from Invitrogen, USA), DAPI (purchased from Invitrogen, USA), paraformaldehyde (purchased from sigma, USA).

Experimental method: PGY-sRNA-6-FAM was dissolved in 100 μl water, and mixed with 4 μl lipid, and prepared by boiling method. Then, the mixture was dropped into A549 cells, and after 6 hours of co-incubation, the samples were washed three times with PBS, fixed with 4% paraformaldehyde, washed three times with PBS, stained with Alexa Fluor® 488 phalloidin for 30 min, washed 3 times with PBS, and stained with DAPI for 5 min, PBS washed, and then sealed.

Figure 127:
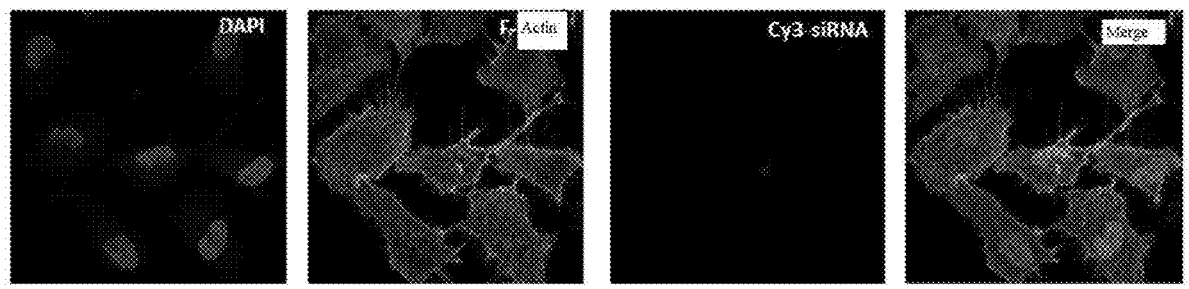

Experimental results (shown in FIG. 127): the entry of red PGY-sRNA-6-Cy3 could be obviously observed under the confocal microscopy. Lipid No. 38-sRNA mixture prepared by boiling method could effectively deliver double-stranded nucleic acid into A549 cells.

Example 7: Validation of the effect of lipid No. 64 and its composition

Lipid No. 64 PE(15:0/24:1 (15Z))

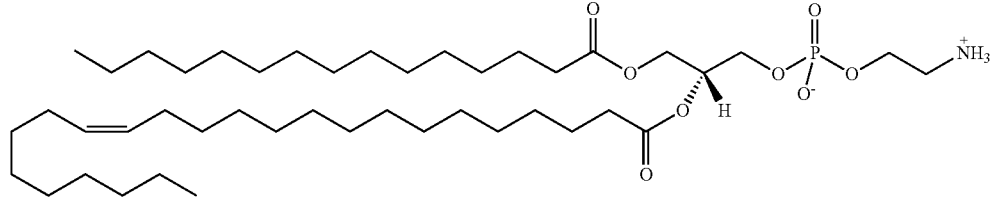 [SMILES: CCCCCCCC/C=C\CCCCCCCCCCCCCC(=O)O[C@H](COC(=O)CCCCCCCCCCCCCC)COP(=O)([O-])OCCN]

1. Quantitative Real-Time PCR (Real-Time PCR) Detection of the Efficiency of the Nucleic Acid Delivery by Lipid (1) Lipid No. 64 Prepared by Different Methods (Boiling or Reverse Evaporation Method) Delivered HJT-sRNA-m7 Double-Stranded RNA into A549 Cells.

Figure 128:
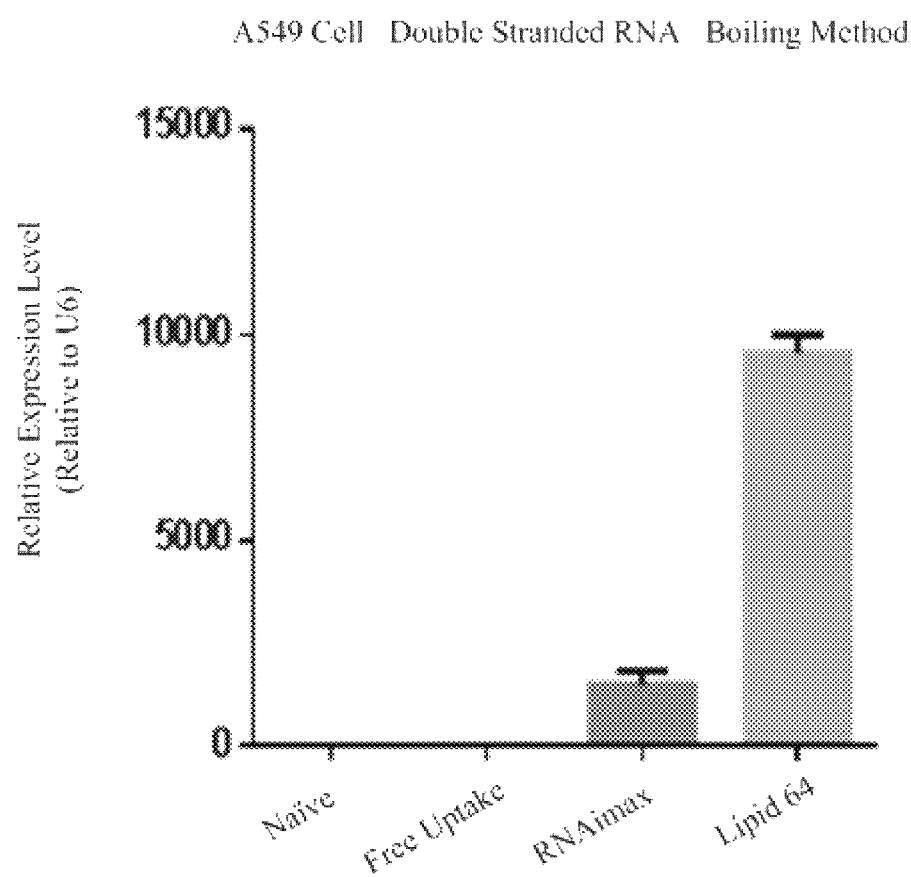

As shown in FIG. 128, lipid No. 64 delivered HJT-sRNA-m7 double-stranded RNA into A549 cells by different preparation methods (boiling or reverse evaporation method). For A549 cells, in the case of the boiling method, the delivery effect of lipid No. 64 was about 3 times that of RNAiMAX.

1) Naive group: untreated A549 cells;
2) Free uptake group: HJT-sRNA-m7 dsRNA was directly incubated with cells for 12 hours; the final concentration of nucleic acid was 100 nM;
3) RNAiMAX group: 2 µL RNAiMAX transfection reagent and double-stranded HJT-sRNA-m7 solution were diluted in 100 µL opti-MEM medium respectively, mixed, and allowed to stay for 15 min, added into the cells and mixed, and the final concentration of HJT-sRNA-m7 double-strand was 100 nM;
4) Treatment group of lipid and nucleic acid: a mixture of 2.5 µL single lipid No. 64 and HJT-sRNA-m7 double-stranded nucleic acid solution was prepared by boiling method or reverse evaporation method and added to A549 cells, the final concentration of RNA was 100 nM. After 12 hours, the sample was collected to detect the amount of entry.

2. Flow Cytometry Detection of the Efficiency of Nucleic Acid Delivery by Lipid

Experimental materials: A549 cells (purchased from the Cell Center of the Chinese Academy of Medical Sciences), FAM-sRNA (purchased from Ribobio Biotechnology Co., Ltd.), lipid No. 64, Accuri® C6 instrument (purchased from BD, USA).

Experimental Method: FAM-sRNA was dissolved in 100 µl water, and mixed with 4 µl lipid, prepared by boiling method. Then, the lipid-sRNA mixture was dropped into A549 cells, and after 6 hours of co-incubation, the samples were collected and washed three times with PBS, then digested into single cells with trypsin, re-suspended with PBS and then used Accuri® C6 instrument to detect relative entry amount.

Figure 129:
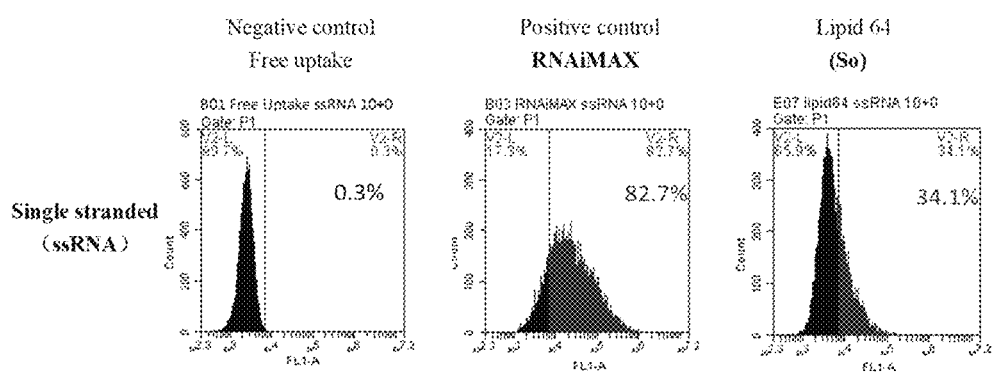

Experimental results (shown in FIG. 129): lipid No. 64 deliverED PGY-sRNA-6 single-stranded RNA with an efficiency of about a half (½) of efficiency the positive control RNAiMAX.

3. Confocal Fluorescence Microscopy to Observe the Location of the Nucleic Acid Delivered by Lipids in Cells Experimental materials: A549 cells (purchased from the Cell Center of the Chinese Academy of Medical Sciences), PGY-sRNA-6-Cy3 (purchased from Ribobio Biotechnology Co., Ltd.), lipid No. 64, Zeiss LSM780 (purchased from Zeiss, Germany), Alexa Fluor® 488 phalloidin (purchased from Invitrogen, USA), DAPI (purchased from Invitrogen, USA), paraformaldehyde (purchased from sigma, USA).

Experimental method: PGY-sRNA-6-FAM was dissolved in 100 µl water, and mixed with 4 µl lipid, and prepared by boiling method. Then, the mixture was dropped into A549 cells, and after 6 hours of co-incubation, the samples were washed three times with PBS, fixed with 4% paraformaldehyde, washed three times with PBS, stained with Alexa Fluor® 488 phalloidin for 30 min, washed 3 times with PBS, and stained with DAPI for 5 min, PBS washed, and then sealed.

Figure 130:
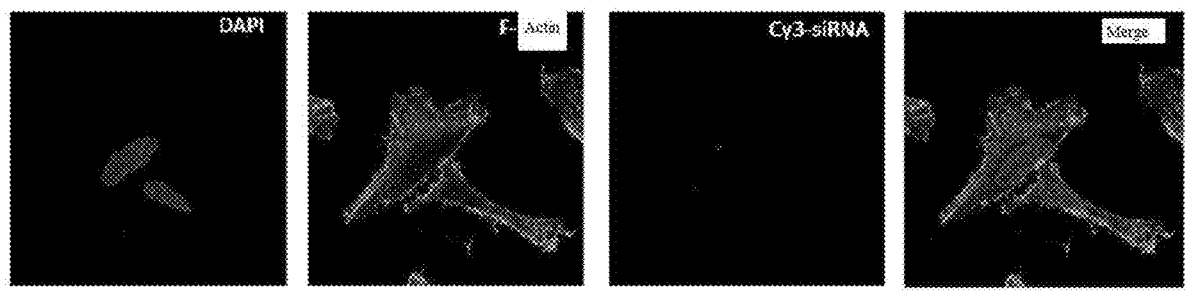

Experimental results (shown in FIG. 130): the entry of red PGY-sRNA-6-Cy3 could be obviously observed under the confocal microscopy. Lipid No. 64 could effectively deliver single-stranded RNA into A549 cells.

Example 8: Validation of the Effect of Lipid No. 40 and its Composition

Lipid No. 40 PE(16:0/22:1)

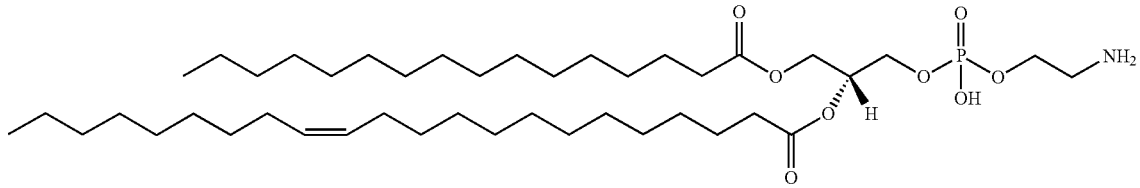 [SMILES: CCCCCCCC/C=C\CCCCCCCCCCCC(=O)O[C@H](COC(=O)CCCCCCCCCCCCCCC)COP(=O)(O)OCCN]

1. Quantitative Real-Time PCR (Real-Time PCR) Detection of the Efficiency of the Nucleic Acid Delivery by Lipid (1) Lipid No. 40 Prepared by Different Methods (Boiling or Reverse Evaporation Method) Delivered Double-Stranded RNA into A549 Cells.

Figure 131:
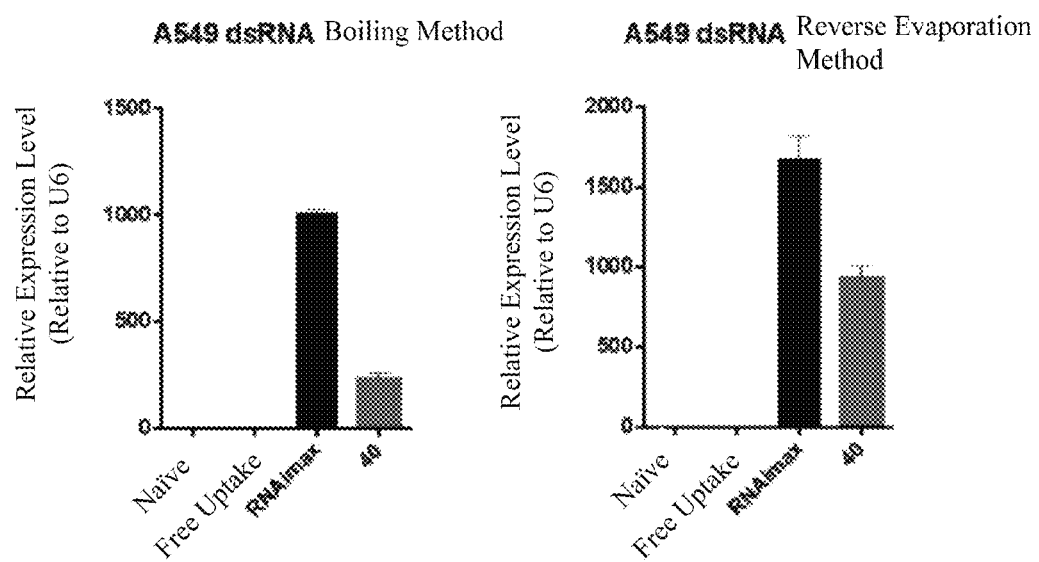

As shown in FIG. 131, lipid No. 40 by prepared by different methods (boiling or reverse evaporation method) delivered double-stranded RNA into A549 cells. For A549 cells, in the case of the reverse evaporation method, delivery effect of lipid No. 40 was about a half (½) of that of RNAiMAX.

1) Naive group: untreated A549 cells;
2) Free uptake group: HJT-sRNA-m7 dsRNA was directly incubated with cells for 12 hours; the final concentration of nucleic acid was 100 nM;
3) RNAiMAX group: 2 μL RNAiMAX transfection reagent and double-stranded HJT-sRNA-m7 solution were diluted in 100 μL opti-MEM medium respectively, and then the two were mixed, allowed to stay for 15 min, added into the cells, mixed, and the final concentration of HJT-sRNA-m7 double-strand was 100 nM;
4) Treatment group of lipid and nucleic acid: a mixture of 2.5 μL single lipid No. 40 and HJT-sRNA-m7 double-stranded nucleic acid solution was prepared by boiling method or reverse evaporation method, and added to A549 cells. The final concentration of RNA was 100 nM. After 12 hours, the sample was collected to detect the amount of entry.

2. Digital PCR (ddPCR) Detection of the Efficiency of Nucleic Acid Delivery by Lipid 2.1 Experimental materials: A549 cells were purchased from the Cell Center of the Institute of Basic Medical Sciences, Chinese Academy of Medical Sciences, TRIzol lysis buffer was purchased from Sigma, TaqMan™ MicroRNA Reverse Transcription KitHigh was purchased from Thermo Fisher Technology, and digital PCR related reagents were purchased from Bio-Rad.

2.2 Experimental method: Total RNA was collected and extracted by TRIzol lysis buffer according to the above method, and reverse transcribed to cDNA using TaqMan™ MicroRNA Reverse Transcription KitHigh, and the cDNA from different groups was subjected to digital PCR reaction. Refer to the QX200 Droplet Reader and QuantaSoft Software manual for the protocols; the results were analyzed using QuantaSoft software.

Figure 132:
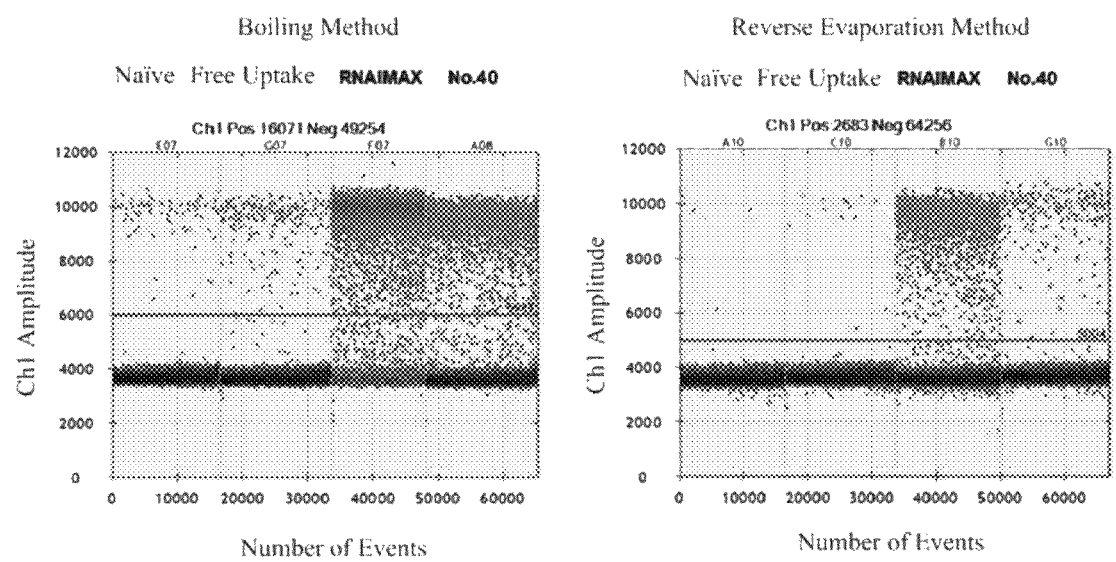

(1) Naive group: A549 cells without any treatment
(2) Free uptake group: the cells were directly co-incubated with HJT-sRNA-m7 dsRNA for 6 hours;
(3) RNAiMAX group: the HJT-sRNA-m7 dsRNA was transfected into A549 cells by RNAiMAX, and the samples were collected for detection after 6 hours;
(4) No. 40 group: lipid No. 40 prepared by different methods (boiling or evaporation method) delivered double-stranded RNA into A549 cells, and the samples were collected for detection after 6 hours;

Experimental results and analysis: As shown in FIG. 132, in the boiling or reverse evaporation method, lipid No. 40 could effectively deliver HJT-sRNA-m7 dsRNA into A549 cells.

3. Confocal Fluorescence Microscopy to Observe the Location of the Nucleic Acid Delivered by Lipids in Cells Experimental materials: A549 cells (purchased from the Cell Center of the Chinese Academy of Medical Sciences), PGY-sRNA-6-Cy3 (purchased from Ribobio Biotechnology Co., Ltd.), lipid No. 40, Zeiss LSM780 (purchased from Zeiss, Germany), Alexa Fluor® 488 phalloidin (purchased from Invitrogen, USA), DAPI (purchased from Invitrogen, USA), paraformaldehyde (purchased from sigma, USA).

Experimental method: PGY-sRNA-6-FAM was dissolved in 100 μl water, and mixed with 4 μl lipid, and prepared by boiling method. Then, the mixture was dropped into A549 cells, and after 6 hours of co-incubation, the samples were washed three times with PBS, fixed with 4% paraformaldehyde, washed three times with PBS, stained with Alexa Fluor® 488 phalloidin for 30 min, washed 3 times with PBS, and stained with DAPI for 5 min, PBS washed, and then sealed.

Figure 133:
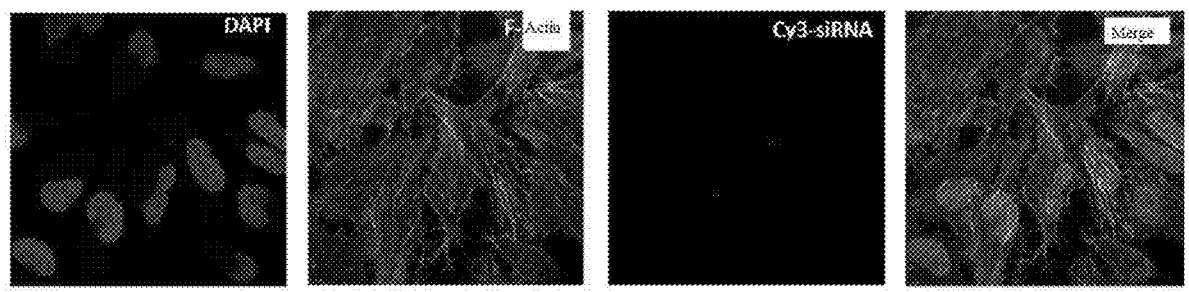

Experimental results (shown in FIG. 133): the entry of red PGY-sRNA-6-Cy3 could be obviously observed under the confocal microscopy. Lipid No. 40 could effectively deliver single-stranded RNA into A549 cells.

Figure 134:
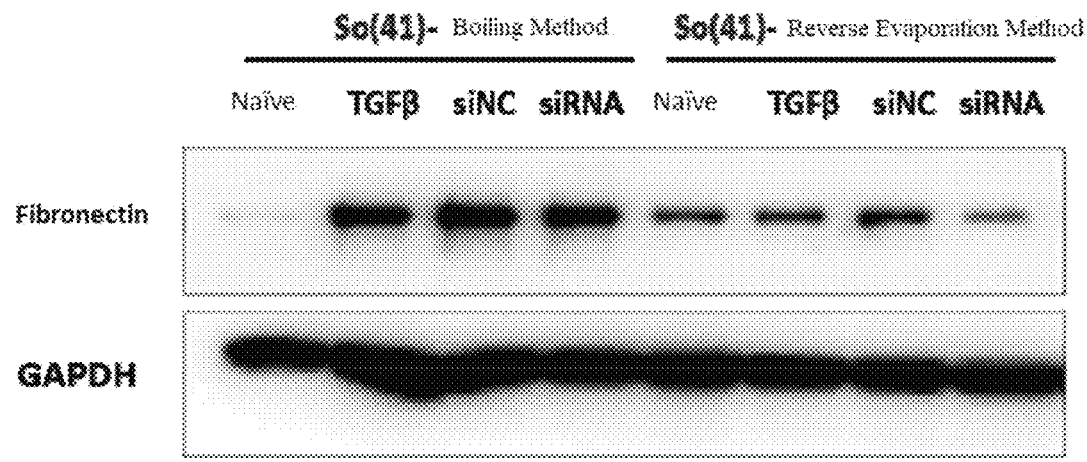

4. Western Blotting Detection of the Efficiency of Nucleic Acid Delivery by Lipid As shown in FIG. 134, phosphatidylethanolamine single lipid No. 40 mediated anti-fibrotic double-stranded RNA HJT-sRNA-m7 entry into MRC-5 cells to down-regulate fibronectin protein expression.

TGF: TGF-β1 protein (final concentration was 3 ng/mL) was added for stimulation, and the samples were collected after 72 hours;
3'—NC group: lipid mixture was used to deliver NC mimics and after 24 hours, the cells were stimulated with TGF-β 1 protein (final concentration was 3 ng/ml), and the samples were collected after 72 hours;
3'-m7 group: a mixture of lipid mixture and HJT-sRNA-m7 double-stranded nucleic acid solution was added to the cells and mixed, and the final concentration of the nucleic acid was 400 nM;

Example 8: Validation of the Effect of Lipid No. 37

Lipid No. 37 LPC(18:3)

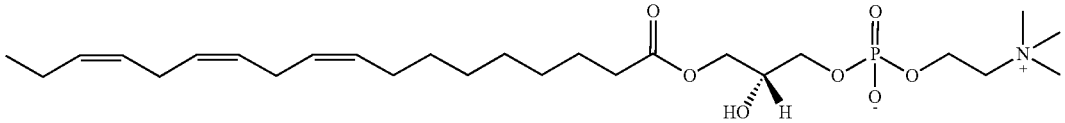

1. Quantitative Real-Time PCR (Real-Time PCR) Detection of the Efficiency of the Nucleic Acid Delivery by Lipid
(1) Lipid No. 37 Delivered Single-Stranded RNA into A549 and MRC-5 Cells by Boiling Method.

As shown in FIG. 135, single-stranded RNA was delivered to A549 and MRC5 cells by boiling method.
1) Naive group: untreated A549 cells;
2) Free uptake group: HJT-sRNA-m7 dsRNA was directly incubated with cells for 3 hours; the final concentration of nucleic acid was 100 nM;
3) RNAiMAX group: 2 μL RNAiMAX transfection reagent and single-stranded HJT-sRNA-m7 solution were diluted in 100 μL opti-MEM medium respectively, mixed, and allowed to stay for 15 min, added into the cells, mixed, and the final concentration of HJT-sRNA-m7 single-strand was 100 nM;
4) Treatment group of lipid and nucleic acid: a mixture of 2.5 μL single lipid No. 39 and HJT-sRNA-m7 single-stranded nucleic acid solution was prepared by boiling method or reverse evaporation method and added to A549 cells, the final concentration of RNA was 100 nM. After 3 hours, the sample was collected to detect the amount of entry.

Example 9: Validation of the Effect of Lipid No. 39

Lipid No. 39 PE(16:1-18:1)

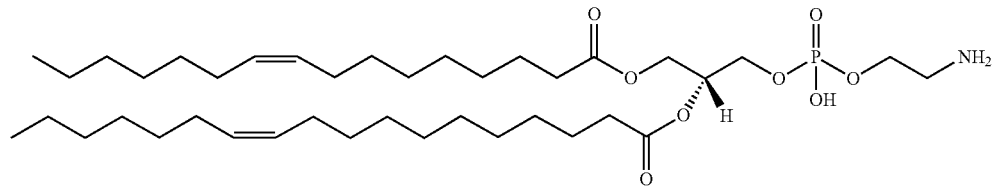 [SMILES: CCCCCC/C=C\CCCCCCCCCC(=O)O[C@H](COC(=O)CCCCCCC/C=C\CCCCCC)COP(=O)(O)OCCN]

1. Quantitative Real-Time PCR (Real-Time PCR) Detection of the Efficiency of the Nucleic Acid Delivery by Lipid As shown in FIG. 136, Lipid No. 39 prepared by different methods (boiling or reverse evaporation method) delivered double-stranded RNA into A549 cells
1) Naive group: untreated A549 cells;
2) Free uptake group: HJT-sRNA-m7 dsRNA was directly incubated with cells for 6 hours; the final concentration of nucleic acid was 100 nM;
3) RNAiMAX group: 2 μL RNAiMAX transfection reagent and double-stranded HJT-sRNA-m7 solution were diluted in 100 μL opti-MEM medium respectively, mixed, and allowed to stay for 15 min, added into the cells and mixed, and the final concentration of HJT-sRNA-m7 double-strand was 100 nM;
4) Treatment group of lipid and nucleic acid: a mixture of 2.5 μL single lipid No. 39 and HJT-sRNA-m7 double-stranded nucleic acid solution was prepared by boiling method or reverse evaporation method and added to A549 cells, the final concentration of RNA was 100 nM. After 12 hours, the sample was collected to detect the amount of entry.

2. Digital PCR (ddPCR) Detection of the Efficiency of Nucleic Acid Delivery by Lipid 2.1 Experimental materials: A549 cells were purchased from the Cell Center of the Institute of Basic Medical Sciences, Chinese Academy of Medical Sciences, TRIzol lysis buffer was purchased from Sigma, High capacity cRNA Reverse Transcription Kit was purchased from ABI, USA, and digital PCR related reagents were purchased from Bio-Rad.

2.2 Experimental method: Total RNA was collected and extracted by TRIzol lysis buffer according to the above method, and reversed to cDNA using High capacity CRNA Reverse Transcription Kit, and the cDNA from different groups was subjected to digital PCR reaction. Refer to the QX200 Droplet Reader and QuantaSoft Software manual for the protocols; the results were analyzed using QuantaSoft software.
(1) Naive group: A549 cells without any treatment;
(2) Free uptake group: the cells were directly co-incubated with HJT-sRNA-m7 dsRNA for 6 hours; 12 hours;
(3) RNAiMAX group: the HJT-sRNA-m7 dsRNA was transfected into A549 cells by RNAiMAX, and the samples were collected for detection after 6 hours, 12 hours;
(4) No. 39 group: lipid No. 39 delivered double-stranded RNA into A549 cells by reverse evaporation method, and the samples were collected for detection after 6 hours, 12 hours;

As shown in FIG. 137, by the reverse evaporation method, lipid No. 39 could effectively deliver HJT-sRNA-m7 dsRNA into A549 cells.

Example 10: Validation of the Effect of Lipid No. 60 and No. 62

Lipid No. 60 dMePE (16:1/16:1)

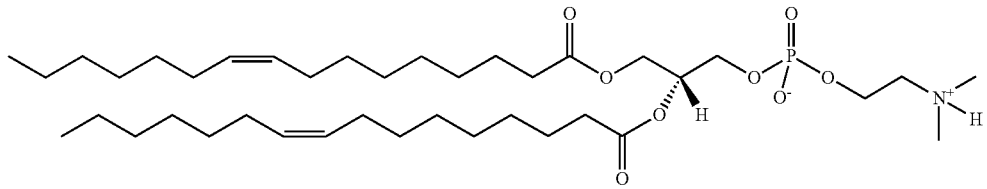 [SMILES: CCCCCC/C=C\CCCCCCCC(=O)OC[C@H](COP(=O)([O-])OCC[NH+](C)C)OC(=O)CCCCCCC/C=C\CCCCCC]

1. Quantitative Real-Time PCR (Real-Time PCR) Detection of the Efficiency of the Nucleic Acid Delivery by Lipid As shown in FIG. 138, Lipid No. 60 prepared by different methods (boiling or reverse evaporation method) delivered double-stranded RNA into A549 cells
7) Naive group: untreated A549 cells;
8) Free uptake group: HJT-sRNA-m7 dsRNA was directly incubated with cells for 6 hours; the final concentration of nucleic acid was 100 nM;
RNAiMAX group: 2 μL RNAiMAX transfection reagent and double-stranded HJT-sRNA-m7 solution were diluted in 100 μL opti-MEM medium respectively, and then the two were mixed, allowed to stay for 15 min, added into the cells, and then mixed, the the final concentration of double-stranded HJT-sRNA-m7 was 100 nM;
4) Lipid and nucleic acid: a mixture of 2.5 μL single lipid No. 60 and HJT-sRNA-m7 double-stranded nucleic acid solution was prepared by boiling method or reverse evaporation method and added to cells, the final concentration of RNA was 100 nM. After 12 hours, the sample was collected to detect the amount of entry.

Lipid No. 62 dMePE(16:77:1)

1. Quantitative Real-Time PCR (Real-Time PCR) Detection of the Efficiency of the Nucleic Acid Delivery by Lipid As shown in FIG. 139, Lipid No. 62 prepared by different methods (boiling or reverse evaporation method) delivered double-stranded RNA into A549 cells
 1) Naive group: untreated A549 cells;
 2) Free uptake group: HJT-sRNA-m7 dsRNA was directly incubated with cells for 6 hours; the final concentration of nucleic acid was 100 nM;
 3) RNAiMAX group: 2 μL RNAiMAX transfection reagent and double-stranded HJT-sRNA-m7 solution were diluted in 100 μL opti-MEM medium respectively, and then the two were mixed, allowed to stay for 15 min, added into the cells, and then mixed, and the final concentration of HJT-sRNA-m7 double-strand was 100 nM;
 4) Treatment group of lipid and nucleic acid: a mixture of 2.5 μL single lipid No. 62 and HJT-sRNA-m7 double-stranded nucleic acid solution was prepared by boiling method or reverse evaporation method and added to cells, and the final concentration of RNA was 100 nM. After 12 hours, the sample was collected to detect the amount of entry.

In Vivo Delivery Experiment of Lipid Nucleic Acid Mixture
 1. Experimental animals: C57 mice, male, approximately 6 weeks old.
 2. Manufacture of lipid mixture: the preparation was conducted on the basis of a dose of 10 μl lipid-1 nmol sRNA per mouse as follows: dissolve 1 nmol of each sRNA in 500 μl DEPC water, add 10 μl of the corresponding lipid, pipette to mix thoroughly, and then naturally cool down after water bath for 15 min at 90° C., and administer via gavage.
 3. sRNA: PGY-sRNA-26, PGY-sRNA-32
 4. Experimental groups:
 1) Naive group: intragastric administration of 500 μl saline;
 2) RNAiMAX treatment group: 10 μl RNAiMAX-1 nmol sRNA was mixed thoroughly and intragastrically administered to each mouse. This group served as a positive control group. RNAiMAX was purchased from Invitrogen.
 3) Free uptake group: sRNA solution (1 nmol/animal, 500 μL) was directly added, and the group served as a negative control;
 4) Treatment group of lipid nucleic acid mixture: the lipid-sRNA mixture prepared in the step 2 was intragastrically administrated.
 5. Detection of the relative amount of entry:
 1) Tissue sampling and extraction of RNA: 6 hours after gavage in mice, take 500 μl of blood from the eyeball, add 1.5 ml Trizol Reagent LS to thoroughly mix and lyse, add 3 ml Trizol Reagent (purchased from Invitrogen) to the tissue samples and homogenize until complete lysis. Tissues sampled: live/stomach/small intestine.
 2) Reverse transcription of sRNA to cDNA: Reverse Transcription Kit (High-Capacity cDNA Reverse Transcription Kits, Applied Biosystems, cat. no. 4368813), was used to reverse transcribe the total RNA to cDNA, and the reverse system was as follows: template RNA (150 ng/μL) 10 μL, 10×RT buffer, 2.0 μL, 25×dNTP Mix (100 mM) 0.8 μL, random primers 2.0 μL, the MultiScribe™ reverse Transcriptase 1.0 μL, RNase inhibitor 1.0 L, nuclease-free H₂O 3.2 μL. After a brief centrifugation, the reaction was loaded in a PCR reactor. The reaction conditions were as follows: (1) 25° C., 10 min; (2) 37° C., 120 min; (3) 85° C., 5 min; (4) 4° C., termination of the reaction. After the reaction, 20 μL RNase-free ddH₂O was added to make up the final volume to 40 μL.
 3) Quantitative PCR amplification reactions: the qPCR reaction system had a total volume of 10 μl, containing: 5 μl 2×SYBR Green Master Mix, 0.5 μl forward primer (10 μM), 0.5 μL reverse primer, 1 μl cDNA by reverse transcription, 3 μl RNase-free dH2O. LightCycler 480 fluorescence quantitative PCR instrument was used, and the PCR reaction conditions were: 95° C., 5 min for pre-denaturation, followed by the PCR amplification cycle: (1) 95° C., 10 s; (2) 55° C., 10 s; (3) 72° C., 20 s; a total of 40 cycles; 40° C. for 10 s in the end to cool down. The forward primer and reverse primer of the amplification reaction was designed and synthesized by Beijing Qing Ke New Industrial Biotechnology Co., Ltd. (U6 F primer: GCGCGTCGTGAAGCGTTC (SEQ ID NO: 113), U6 R primer: GTGCAGGGTCCGAGGT (SEQ ID NO: 114)).
 3) The relative expression amount was calculated by the 2-ΔCt method.

Example 11-1: Delivery of Single-Stranded Nucleic Acids by Single Lipid No. 41 In Vivo 1. Experimental animals: C57 mice, male, approximately 6 weeks old.
 1) Naive group: intragastric administration of 500 μl saline;
 2) RNAiMAX treatment group: 10 μl RNAiMAX-1 nmol sRNA was mixed and intragastrically administered to each mouse. This group served as a positive control group. RNAiMAX was purchased from Invitrogen.
 3) Free uptake group: single-stranded sRNA mixture solution (1 nmol each) was directly added (1 nmol each);
 4) Treatment group of POPC and nucleic acid: a mixture of 10 μL of POPC with single-stranded sRNA mixture solution (1 nmol) was treated by heating method and then given to mice by intragastric administration.
 5) Treatment group of single lipid and nucleic acid mixture: a mixture of 10 μL of single lipid (No. 41) with single-stranded sRNA mixture solution (PGY-sRNA-23, PGY-sRNA-26 and PGY-sRNA-32, 1 nmol each) was treated by heating method and then given to mice by intragastric administration.
2. 12 hours after intragastric administration, the blood was taken from the eyeball, and various tissues (liver/stomach/small intestine) was sampled. TRIzol was used for full lysis and the RNA was extracted to detect the amount of entry.

Conclusion:

As shown in FIG. 140, single PE (No. 41) could effectively deliver sRNA single-stranded nucleic acid into the mouse blood via oral administration to protect sRNA from degradation, and the delivery effect was better than POPC and Lipofectamine RNAiMAX.

As shown in FIG. 141, single PE (No. 41) could effectively deliver sRNA single-stranded nucleic acid into the mouse stomach via oral administration to protect sRNA from degradation.

As shown in FIG. 142, single PE (No. 41) could effectively deliver sRNA single-stranded nucleic acid into the mouse small intestine via oral administration to protect sRNA from degradation.

As shown in FIG. 143, single PE (No. 41) could effectively deliver sRNA single-stranded nucleic acid into the mouse liver via oral administration to protect sRNA from degradation.

Example 11-2: Delivery of Single-Stranded Nucleic Acids by Single Lipid No. 38 In Vivo 1. Experimental animals: C57 mice, male, approximately 6 weeks old.
1) Naive group: intragastric administration of 500 µl saline;
2) RNAiMAX treatment group: 10 µl RNAiMAX-1 nmol sRNA was mixed and intragastrically administered to each mouse. This group served as a positive control group. RNAiMAX was purchased from Invitrogen.
3) Free uptake group: single-stranded sRNA mixture solution (1 nmol each) was directly added (each 1 nmol);
4) Treatment group of POPC and nucleic acid: a mixture of 10 µL POPC and single-stranded PGY-sRNA-32 sRNA (each 1 nmol) mixture solution that was treated by heating method was given to mice by gavage.
5) Treatment group of single lipid and nucleic acid mixture: a mixture of a 10 µL single lipid (No. 38) and single-stranded sRNA (PGY-sRNA-32) mixture solution (each 1 nmol) that was treated by heating method was given to mice by gavage.
2. 12 hours after gavage, the blood was taken from the eyeball and lysed by TRIzol to extract RNA for the detection of the amount of entry.

Conclusion:

As shown in FIG. 144, single PE (No. 38) could effectively deliver sRNA single-stranded nucleic acid into mouse blood via oral administration, and the delivery effect was better than POPC and Lipofectamine RNAiMAX.

Example 11-3: Delivery of Single-Stranded Nucleic Acids by Single Lipid No. 40 In Vivo 1. Experimental animals: C57 mice, male, approximately 6 weeks old.
1) Naive group: intragastric administration of 500 µl saline;
2) RNAiMAX treatment group: 10 µl RNAiMAX-1 nmol sRNA was mixed and intragastrically administered to each mouse. This group served as a positive control group. RNAiMAX was purchased from Invitrogen.
3) Free uptake group: single-stranded sRNA mixture solution was directly added (each 1 nmol);
4) Treatment group of POPC and nucleic acid: a mixture of 10 µL POPC and single-stranded sRNA (each 1 nmol) mixture solution that was treated by heating method was given to mice by gavage.
5) Treatment group of single lipid and nucleic acid mixture: a mixture of a 10 µL single lipid (No. 40) and single-stranded sRNA (PGY-sRNA-32 and PGY-sRNA-26, 1 nmol each) mixture solution that was treated by heating method was given to mice by gavage.
2. 12 hours after gavage, the blood was taken from the eyeball and lysed by TRIzol to extract RNA for the detection of the amount of entry.

Conclusion:

As shown in FIG. 145, single PE (No. 40) could effectively deliver sRNA single-stranded nucleic acid into mouse blood via oral administration, and the delivery effect was better than POPC and Lipofectamine RNAiMAX.

Example 11-4: Delivery of Single-Stranded Nucleic Acids by Single Lipid No. 64 In Vivo 1. Experimental animals: C57 mice, male, approximately 6 weeks old.
1) Naive group: intragastric administration of 500 µl saline;
2) RNAiMAX treatment group: 10 µl RNAiMAX-1 nmol sRNA was mixed and intragastrically administered to each mouse. This group served as a positive control group. RNAiMAX was purchased from Invitrogen.
3) Free uptake group: single-stranded sRNA mixture solution was directly added (each 1 nmol);
4) Treatment group of POPC and nucleic acid: a mixture of 10 µL POPC and single-stranded sRNA (each 1 nmol) mixture solution that was treated by heating method was given to mice by gavage.
5) Treatment group of single lipid and nucleic acid mixture: a mixture of a 10 µL single lipid (No. 64) and single-stranded sRNA (PGY-sRNA-32, 1 nmol each) mixture solution that was treated by heating method was given to mice by gavage.
2. 12 hours after gavage, the blood was taken from the eyeball and lysed by TRIzol to extract RNA for the detection of the amount of entry.

Conclusion:

As shown in FIG. 146, single PE (No. 64) could effectively deliver sRNA single-stranded nucleic acid into mouse blood via oral administration, and the delivery effect was better than POPC and Lipofectamine RNAiMAX.

Example 11-5: Delivery of Single-Stranded Nucleic Acids by Single Lipid No. 71 In Vivo 1. Experimental animals: C57 mice, male, approximately 6 weeks old.
1) Naive group: intragastric administration of 500 µl saline;
2) RNAiMAX treatment group: 10 µl RNAiMAX-1 nmol sRNA was mixed and intragastrically administered to each mouse. This group served as a positive control group. RNAiMAX was purchased from Invitrogen.
3) Free uptake group: single-stranded sRNA mixture solution was directly added (each 1 nmol);
4) Treatment group of POPC and nucleic acid: a mixture of 10 µL POPC and single-stranded sRNA (each 1 nmol) mixture solution that was treated by heating method was given to mice by gavage.
5) Treatment group of single lipid and nucleic acid mixture: a mixture of a 10 µL single lipid (No. 71) and single-stranded sRNA mixture (PGY-sRNA-32, 1 nmol each) solution that was treated by heating method was given to mice by gavage.
2. 12 hours after gavage, the blood was taken from the eyeball and lysed by TRIzol to extract RNA for the detection of the amount of entry.

Conclusion:

As shown in FIG. 147, single PE (No. 71) could effectively deliver sRNA single-stranded nucleic acid into mouse blood via oral administration, and the delivery effect was better than POPC and Lipofectamine RNAiMAX.

Example 12: Lipids Effectively Deliver Single-Stranded Nucleic Acids into MRC-5 Cell at Different Temperature Gradients 1. Experimental Groups:
   1) Naive group: untreated cells;
   2) RNAiMAX treatment group: 2 μL RNAiMAX transfection reagent and single-stranded HJT-sRNA-m7 solution were diluted in 100 μL opti-MEM medium respectively, and then the two were mixed, allowed to stay for 15 min, added into the cells, and then mixed, and the final concentration of single-stranded HJT-sRNA-m7 was 100 nM;
   3) Treatment group of single lipid and nucleic acid mixture: mixtures of 2.5 L single lipid (No. 38) and HJT-sRNA-m7 double-stranded nucleic acid solution that were treated by boiling method at different temperatures was added to the cells and then mixed, and the final concentration of RNA was 100 nM.
   4° C.: to 100 μL single-stranded HJT-sRNA-m7 solution was added 2.5 μL single lipid and placed at 4° C. for 15 min; 6 hours after the addition of the cells, the expression level of HJT-sRNA-m7 in cells was detected by RT-qPCR.
   37° C.: to 100 μL single-stranded HJT-sRNA-m7 solution was added 2.5 μL single lipid and placed at 37° C. for 15 min. 6 hours after the addition of the cells, the expression level of HJT-sRNA-m7 in cells was detected by RT-qPCR.
   60° C.: to 100 μL single-stranded HJT-sRNA-m7 solution was added 2.5 μL single lipid and heated at 50° C. for 15 min. 6 hours after the addition of the cells, the expression level of HJT-sRNA-m7 in cells was detected by RT-qPCR.
   80° C.: to 100 μL single-stranded HJT-sRNA-m7 solution was added 2.5 μL single lipid and heated at 80° C. for 15 min. 6 hours after the addition of the cells, the expression level of HJT-sRNA-m7 in cells was detected by RT-qPCR.
   100° C.: to 100 μL HJT-sRNA-m7 single-stranded solution was added 2.5 μL single lipid and heated at 100° C. for 15 min. 6 hours after the addition of the cells, the expression level of HJT-sRNA-m7 in cells was detected by RT-qPCR.

Conclusion:
As shown in FIG. 148, results showed that the lipids by the boiling method at different temperate conditions could effectively deliver nucleic acids into cells (statistically significant, $p<0.01$), having the potential of improving the efficiency of the delivery of nucleic acid drug in clinical settings.

EMBODIMENTS

Embodiment 1. Bencaosome: Artificially prepared nanoparticulate substance with membrane structure. The membrane structure comprises one or more lipid components, which are characterized by being derived from chemical synthesis or chemical separation and purification, and include but not limited to the lipids shown in Table 1 or Table 10 or lipids having 70% or more similarity with those shown in Table 1 or Table 10 (the lipid similarity is defined by the following method: having the same parent structure), and has an impurity content less than 5%. The lipids are mixed with any one or more of the following: one or more nucleic acids, one or more compounds, and one or more macromolecules. Bencaosome is a nano-particulate substance with a membrane structure prepared by heating lipids and other substances including one or more nucleic acids, one or more compounds, and/or one or more macromolecules. In this application, bencaosome can also be referred to as an active composition with a membrane structure, preferably an active composition prepared by the method of the foregoing embodiments 1-2, 5-9 or 20-28. The one or more lipid components can be synthesized or purified, including but not limited to the lipids shown in Table 1 or Table 10; the one or more nucleic acid components can be synthesized or purified, including but not limited to the RNA shown in Table 8, 9 or 13; the one or more compounds can be synthesized or purified, including but not limited to the compounds shown in Table 2 to Table 5; the one or more macromolecular components can be synthesized or purified, including but not limited to the proteins shown in Table 6 or Table 7. The method for preparing a bencaosome includes the steps of:

(1) mixing one or more lipid components with any one or more of the following: one or more nucleic acids, one or more compounds and/or one or more macromolecules;

preferably, the one or more lipid components are synthesized or purified, such as lipids selected from those shown in Table 1 or Table 10;

(2) treating the obtained mixture by heating, wherein the heating temperature is preferably from about 0° C. to about 100° C., more preferably from about 50° C. to about 100° C., and more preferably from about 70° C. to about 90° C., in particular preferably from about 80° C. to about 90° C., preferably 90° C.;

preferably, the time for heating is about 0 minute to about 24 hours, about 5 minutes to about 20 hours, about 10 minutes to about 16 hours, about 30 minutes to about 12 hours, about 1 hour to about 8 hours, or about 0.5 hour to about 4 hours, preferably 5 minutes to 15 minutes;

preferably, the mixing is performed by adding a solution of the lipid components in an organic solvent into an aqueous solution of the nucleic acid/macromolecule/compound;

preferably, the organic solvent includes alcohols, ethers, and benzenes, preferably chloroform, ethyl ether, methanol, or ethanol;

preferably, the aqueous solution is selected from the group consisting of aqueous buffers, saline solutions, aqueous solutions of organic solvents and water;

preferably, the bencaosome is a nano-particulate substance with a membrane structure, preferably a nanoparticulate substance with a double layered membrane structure;

preferably, the bencaosome is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 2. The method of Embodiment 1, wherein the lipid is Sphinganine (d22:0), and/or the small RNA is PGY-sRNA-6 or HJT-sRNA-m7, wherein preferably, the Sphinganine (d22:0) is used as 10 mg/ml chloroform solution, lipid: sRNA=0.1-20 μg:0.1 nmol;

wherein preferably, the bencaosome has a Zeta potential of less than 60 mV, less than 50 mV, less than 0, −80 to −20, or −60 to −20, and has an average particle size of 50-1000, 90-300 or 100-200 nm.

Embodiment 3. The bencaosome prepared by the method of Embodiment 1 or 2, used in one or more of the following:

(1) lowering the expression of fibronectin and/or alpha-SMA, preferably the protein expression of fibronectin in MRC-5 cells fibrosis model induced by TGF-beta1;

(2) reducing hydroxyproline, preferably the hydroxyproline in pulmonary fibrosis model, preferably the hydroxyproline in pulmonary fibrosis model of mice;

(3) preventing or treating fibrosis, preferably pulmonary fibrosis, preferably in the fibrosis model of MRC-5 cells induced by TGF-beta1 or the fibrosis model of mice induced by Bleomycin;

(4) lowering IL-1beta, IL-6 and/or TNF-alpha, preferably the IL-1beta, IL-6 and/or TNF-alpha in A549 cells model induced by poly(I:C);

(5) lowering the level of IL-1alpha, IL-1b, IL-2, IL-3, IL-4, IL-5, IL-6, IL-9, IL-10, IL-12 p40, IL-12 p70, IL-13, IL-17A, GM-CSF, IFN-gamma or MCP-1beta, preferably the level of plasma, preferable in an inflammation model of mouse;

(6) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and (7) enabling small RNA to enter cells efficiently; and/or (8) lowering the expression of RELA genes;

preferably, the bencaosome lowers the expression of fibrosis-associated protein fibronectin and alpha-SMA, and/or lowers the expression of IL-1beta, IL-6 and/or TNF-alpha, preferably the expression level of IL-1beta, IL-6 and/or TNF-alpha in A549 cells model induced by poly(I:C).

Embodiment 4. Use of the bencaosome of Embodiment 3 in one or more of the following, or use of the bencaosome of Embodiment 3 in manufacture of medicament for use in one or more of the following, or methods for using the bencaosome of Embodiment 3 in one or more of the following:

(1) lowering the expression of fibronectin and/or alpha-SMA, preferably the protein expression of fibronectin in MRC-5 cells fibrosis model induced by TGF-beta1;

(2) reducing hydroxyproline, preferably the hydroxyproline in pulmonary fibrosis model, preferably the hydroxyproline in pulmonary fibrosis model of mice;

(3) preventing or treating fibrosis, preferably pulmonary fibrosis, preferably in the fibrosis model of MRC-5 cells induced by TGF-beta1 or the fibrosis model of mice induced by Bleomycin;

(4) lowering IL-1beta, IL-6 and/or TNF-alpha, preferably the IL-1beta, IL-6 and/or TNF-alpha in A549 cells model induced by poly(I:C);

(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;

(6) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and (7) enabling small RNA to enter cells efficiently; and/or (8) lowering the expression of RELA genes;

preferably, the bencaosome lowers the expression of fibrosis-associated protein fibronectin and alpha-SMA, and/or lowers the expression of IL-1beta, IL-6 and/or TNF-alpha, preferably the expression level of IL-1beta, IL-6 and/or TNF-alpha in A549 cells model induced by poly(I:C);

preferably, the medicament is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 5. A method of facilitating nucleic acid delivery comprising heating or warming up nucleic acid and one or more lipids in Table 1 or Table 10, preferably Sphinganine (d22:0), the temperature for heating or warming up is preferably from about 4° C. to about 100° C., from about 25° C. to about 100° C., more preferably from about 50° C. to about 100° C., more preferably from about 95° C. to about 100° C., particularly preferably from about 80° C. to about 100° C., i.e. 4° C., 37° C., 60° C., 80° C. or 100° C., wherein preferably, the nucleic acid is a small nucleic acid, preferably is single or double stranded, preferably the small nucleic acid has a length of 14-32 bp, 16-28 bp or 18-24 bp, preferably any one or more small RNA in Tables 8, 9 and 13, preferably PGY-sRNA-6 or HJT-sRNA-m7; preferably, the nucleic acid delivery is by oral administration; preferably, the nucleic acid is used for treating a disease, such as inflammation-associated diseases and cancer, for example gastric cancer or lung cancer, preferably used for anti-inflammation and anti-fibrosis, preferably for reducing inflammation-associated factors IL-1beta, IL-6 and/or TNF-alpha, cytokine storm IL-1alpha, IL-1beta, IL-2, IL-3, IL-4, IL-5, IL-9, IL-10, IL-12 p40, IL-12 p70, IL-13, IL-17A, GM-CSF, IFN-gamma, RANTES or MCP-1beta, and lowering the expression of fibrosis-associated protein fibronectin and α-SMA.

Embodiment 6. The method of Embodiment 5, further comprising further mixing one or compounds, one or more nucleic acids, and/or one or more macromolecules; wherein the nucleic acids include DNA and RNA, preferably RNA, more preferably small RNA;

preferably mixing one or more compounds shown in Table 2-Table 5, one or more small RNA shown in Table 8 and/or Table 9 and/or Table 13, one or more DNA and/or one or more macromolecules shown in Table 6 or 7;

or, the method of Embodiment 5, further comprising further mixing one or more compounds, one or more DNAs, and/or one or more macromolecules;

preferably mixing one or more compounds shown in Table 2 or 4, one or more compounds shown in Table 3 or 5, one or more DNA and/or one or more macromolecules shown in Table 6 or 7.

Embodiment 7. The method of any one of Embodiment 1-6, wherein the more lipids are the lipids comprising the lipid combination selected from the following: a lipid combination of No. 8: No. 41=6:1; a lipid combination of No. 38: No. 41=6:1; a lipid combination of No. 39: No. 41=6:1; a lipid combination of No. 40: No. 41=6:1; a lipid combination of No. 38: No. 12: No. 41: No. 29=1:2:1:1; a lipid combination of No. 40: No. 12: No. 41=2:4:3; a lipid combination of No. 12: No. 41=1:6; a lipid combination of No. 12: No. 41=1:1; a lipid combination of No. 12: No. 41-6:1; a lipid combination of No. 40: No. 12: No. 41=2:2:2; a lipid combination of No. 4: No. 12: No. 41=1:1:1; DG combination of No. 1: No. 2: No. 3: No. 19: No. 35=1:1:1:1:1; TG combination of No. 6: No. 9: No. 10: No. 13: No. 15: No. 16: No. 18: No. 20: No. 21: No. 22: No. 23: No. 24: No. 25: No. 26: No. 27: No. 28: No. 32: No. 33=1:1:1:1:1:1:1:1:1:1:1:1:1:1:1:1:1; LPC combination of No. 36: No. 37=1:1; PC combination of No. 11: No. 12=1:1; PE combination of No. 8: No. 38=1:1; Cer combination of No. 4: No. 14=1:1; So combination of No. 17: No. 30: No. 31=1:1:1; an equal volume combination of No. 1-36 without No. 5, No. 7; an equal volume combination of No. 1-36 without No. 5, No. 7, No. 34; an equal volume combination of No. 1-36 without No. 5, No. 7, No. 1, No. 2, No. 3, No. 19, No. 35; an equal volume combination of No. 1-36 No. 5, No. 7, No. 6, No. 9, No. 10, No. 13, No. 15, No. 16, No. 18, No. 20, No. 21, No. 22, No. 23, No. 24, No. 25, No. 26, No. 27, No. 28, No. 32, No. 33; an equal volume combination of No. 1-36 without No. 5, No. 7, No. 36, No. 37; an equal volume combination of No. 1-36 without No. 5, No. 7, No. 11, No. 12; an equal volume combination of No. 1-36 without No. 5, No. 7, No. 8 in; an equal volume combination of No. 1-36 without No. 5, No. 7, No. 4, No. 14; an equal volume combination of No. 1-36 without No. 5, No. 7, No. 29; a lipid combination of No. 1: No. 34=2:1; a lipid combination of No. 1: said DG composition=2:1; a lipid combination of No. 1: said TG composition=2:1; a lipid combination of No. 1: said LPC composition=2:1; a lipid combination of No. 1: No. 8=2:1; a lipid combination of No. 1: No. 12=2:1; a lipid combination of No. 1: said Cer composition=2:1; a lipid combination of No. 1: said So composition=2:1; a lipid combination of No. 1: No. 29=2:1; a lipid combination of No. 1: No. 8: No. 12=1:1:1; a lipid combination of No. 8: No. 34-2:1; a lipid combination of No. 8: said DG composition=2:1; a lipid combination of No. 8: said TG composition=2:1; a lipid combination of No. 8: said LPC composition=2:1; a lipid combination of No. 8: No. 37=4:1; a lipid combination of No. 8: No. 12-2:1; a lipid combination of No. 8: said Cer composition=2:1; a lipid combination of No. 8: said So composition=2:1; a lipid combination of No. 8: No. 31=6:1; a lipid combination of No. 8: No. 29=2:1; a lipid combination of No. 12: No. 34=2:1; a lipid combination of No. 12: said DG composition=2:1; a lipid combination of No. 12: said TG composition=2:1; a lipid combination of No. 12: said LPC composition=2:1; a lipid combination of No. 12: No. 8=2:1; a lipid combination of No. 12: said Cer composition=2:1; a lipid combination of No. 12: said So composition=2:1; a lipid combination of No. 12: No. 29=2:1; a lipid combination of No. 12: No. 8: No. 1&2-2:1:1; a lipid combination of No. 12: No. 8: No. 15=2:1:1; a lipid combination of No. 12: No. 8: No. 36&37=2:1:1; a lipid combination of No. 12: No. 8: No. 11=2:1:1; a lipid combination of No. 12: No. 8: No. 12=2:1:1; a lipid combination of No. 12: No. 8: No. 4=2:1:1; a lipid combination of No. 12: No. 8: No. 31=2:1:1; a lipid combination of No. 12: No. 8: No. 29=2:1:1; a lipid combination of No. 12: No. 8: No. 34-3:2:1; a lipid combination of No. 12: No. 8: No. 34=4:2:3; a lipid combination of No. 12: No. 8: No. 2=4:2:3; a lipid combination of No. 12: No. 8: No. 2=16:8:3; a lipid combination of No. 12: No. 8: No. 32=4:2:3; a lipid combination of No. 12: No. 8: No. 37=4:2:3; a lipid combination of No. 12: No. 8: No. 11=4:2:3; a lipid combination of No. 12: No. 8: No. 38=4:2:3; a lipid combination of No. 12: No. 8: No. 4=4:2:3; a lipid combination of No. 12: No. 8: No. 31=4:2:3; a lipid combination of No. 12: No. 8: No. 29=4:2:3; a lipid combination of No. 12: No. 8: No. 29: No. 31=2:1:1:1; a lipid combination of No. 12: No. 8: No. 29: No. 31: No. 34-4:2:2:2:5; a lipid combination of No. 12: No. 8: No. 29: No. 31: No. 2=4:2:2:2:5; a lipid combination of No. 12: No. 8: No. 29: No. 31: No. 32=4:2:2:2:5; a lipid combination of No. 12: No. 8: No. 29: No. 31: No. 11=4:2:2:2:5; a lipid combination of No. 12: No. 8: No. 29: No. 31: No. 37=4:2:2:2:5; a lipid combination of No. 12: No. 8: No. 29: No. 31: No. 38=4:2:2:2:5; a lipid combination of No. 12: No. 8: No. 29: No. 31: No. 4-4:2:2:2:5; a lipid combination of No. 12: No. 8: No. 29: No. 31: No. 4: No. 1: No. 16=2:1:1:3:2:2:3; a lipid combination of No. 1: No. 8: No. 12: No. 1&2=2:2:2:3; a lipid combination of No. 1: No. 8: No. 12: No. 15=2:2:2:3; a lipid combination of No. 1: No. 8: No. 12: No. 36&37=2:2:2:3; a lipid combination of No. 1: No. 8: No. 12: No. 12=2:2:2:3; a lipid combination of No. 1: No. 8: No. 12: No. 4=2:2:2:3; a lipid combination of No. 1: No. 8: No. 12: No. 31=2:2:2:3; a lipid combination of No. 1: No. 8: No. 12: No. 29=2:2:2:3; a lipid combination of No. 8: No. 34: No. 1&2=2:1:1; a lipid combination of No. 8: No. 34: No. 15=2:1:1; a lipid combination of No. 8: No. 34: No. 36&37=2:1:1; a lipid combination of No. 8: No. 34: No. 12-2:1:1; a lipid combination of No. 8: No. 34: No. 4=2:1:1; a lipid combination of No. 8: No. 34: No. 31=2:1:1; a lipid combination of No. 8: No. 34: No. 29=2:1:1; a lipid combination of No. 8: No. 31: No. 34-12:3:5; a lipid combination of No. 8: No. 31: No. 2=12:3:5; a lipid combination of No. 8: No. 31: No. 37=12:3:5; a lipid combination of No. 8: No. 31: No. 11=12:3:5; a lipid combination of No. 8: No. 31: No. 12=12:3:5; a lipid combination of No. 8: No. 31: No. 4=12:3:5; a lipid combination of No. 8: No. 31: No. 29=12:3:5; a lipid combination of No. 8: No. 31: No. 32=12:3:5; a lipid combination of No. 8: No. 4: No. 34=12:3:5; a lipid combination of No. 8: No. 4: No. 2=12:3:5; a lipid combination of No. 8: No. 4: No. 37=12:3:5; a lipid combination of No. 8: No. 4: No. 12=12:3:5; a lipid combination of No. 8: No. 4: No. 31=12:3:5; a lipid combination of No. 8: No. 4: No. 29=12:3:5; a lipid combination of No. 8: No. 4: No. 32=12:3:5; a lipid combination of No. 38: No. 34=2:1; a lipid combination of No. 38: No. 1=2:1; a lipid combination of No. 38: No. 2=2:1; a lipid combination of No. 38: No. 1&2=2:1; a lipid combination of No. 38: No. 15=2:1; a lipid combination of No. 38: No. 32=2:1; a lipid combination of No. 38: No. 37=2:1; a lipid combination of No. 38: No. 37=4:1; a lipid combination of No. 38: No. 11=2:1; a lipid combination of No. 38: No. 12=2:1; a lipid combination of No. 38: No. 11&12=2:1; a lipid combination of No. 38: No. 12=4:1; a lipid combination of No. 38: No. 8=2:1; a lipid combination of No. 38: No. 4=2:1; a lipid combination of No. 38: So (30)=2:1; a lipid combination of No. 38: No. 31=2:1; a lipid combination of No. 38: No. 29=2:1; a lipid combination of No. 1: No. 38: No. 12: No. 34=2:2:2:3; a lipid combination of No. 1: No. 38: No. 12: No. 15=2:2:2:3; a lipid combination of No. 1: No. 38: No. 12: No. 37=2:2:2:3; a lipid combination of No. 1: No. 38: No. 12: No. 8=2:2:2:3; a lipid combination of No. 1: No. 38: No. 12: No. 4-2:2:2:3; a lipid combination of No. 1: No. 38: No. 12: No. 31=2:2:2:3; a lipid combination of No. 1: No. 38: No. 12: No. 29=2:2:2:3; a lipid combination of No. 38: No. 34: No. 1=2:1:3; a lipid combination of No. 38: No. 34: No. 15=2:1:3; a lipid combination of No. 38: No. 34: No. 37=2:1:3; a lipid combination of No. 38: No. 34: No. 12=2:1:3; a lipid combination of No. 38: No. 34: No. 8=2:1:3; a lipid combination of No. 38: No. 34: No. 4=2:1:3; a lipid combination of No. 38: No. 34: No. 31=2:1:3; a lipid combination of No. 38: No. 34: No. 29=2:1:3; a lipid combination of No. 38: No. 12: No. 1=2:1:3; a lipid combination of No. 38: No. 12: No. 2=4:1:3; a lipid combination of No. 38: No. 12: No. 15=2:1:3; a lipid combination of No. 38: No. 12: No. 37=2:1:3; a lipid combination of No. 38: No. 12: No. 8=2:1:3; a lipid combination of No. 38: No. 12: No. 4=2:1:3; a lipid combination of No. 38: No. 12: No. 31=2:1:3; a lipid combination of No. 38: No. 12: No. 29=2:1:3; a lipid combination of No. 38: No. 12: No. 1: No. 15: No. 34=22:22:22:33:36; a lipid combination of No. 38: No. 12: No. 1: No. 15: No. 37=22:22:22:33:36; a lipid combination of No. 38: No. 12: No. 1: No. 15: No. 4=22:22:22:33:36; a lipid combination of No. 38: No. 12: No. 1: No. 15: No. 31=22:22:22:33:36; a lipid combination of No. 38: No. 12: No. 1: No. 15: No. 29=22:22:22:33:36; a lipid combination of No. 38: No. 34: No. 37: No. 1=44:22:33:36; a lipid combination of No. 38: No. 34: No. 37: No. 15=44:22:33:36; a lipid combination of No. 38: No. 34: No. 37: No. 12=44:22:33:36; a lipid combination of No. 38: No. 34: No. 37: No. 4=44:22:33:36; a lipid combination of No. 38: No. 34: No. 37: No. 31=44:22:33:36; a lipid combination of No. 38: No. 12: No. 4: No. 34=44:22:33:36; a lipid combination of No. 38: No. 12: No. 4: No. 1=44:22:33:36; a lipid combination of No. 38: No. 12: No. 4: No. 15=44:22:33:36; a lipid combination of No. 38: No. 12: No. 4: No. 37=44:22:33:36; a lipid combination of No. 38: No. 12: No. 4: No. 37=8:2:5:3; a lipid combination of No. 38: No. 12: No. 4: No. 31=44:22:33:36; a lipid combination of No. 38: No. 12: No. 4: No. 29=44:22:33:36; a lipid combination of No. 38: No. 12: No. 4: No. 29: No. 34=88:44:66:72:135; a lipid combination of No. 38: No. 12: No. 4: No. 29: No. 1=88:44:66:72:135; a lipid combination of No. 38: No. 12: No. 4: No. 29: No. 15=88:44:66:72:135; a lipid combination of No. 38: No. 12: No. 4: No. 29: No. 37=88:44:66:72:135; a lipid combination of No. 38: No. 12: No. 4: No. 29: No. 31=88:44:66:72:135; a lipid combination of No. 38: No. 12: No. 4: No. 2=20:10:15:9; a lipid combination of No. 38: No. 12: No. 4: No. 6=20:10:15:9; a lipid combination of No. 38: No. 12: No. 4: No. 17=20:10:15:9; a lipid combination of No. 38: No. 12: No. 4: No. 29-20:10:15:9; a lipid combination of No. 38: No. 12: No. 4: No. 34=20:10:15:9; a lipid combination of No. 38: No. 12: No. 4: No. 37=20:10:15:9; a lipid combination of No. 38: No. 12: No. 31: No. 34=2:1:3:3; a lipid combination of No. 38: No. 12: No. 31: No. 1=2:1:3:3; a lipid combination of No. 38: No. 12: No. 31: No. 15=2:1:3:3; a lipid combination of No. 38: No. 12: No. 31: No. 37=2:1:3:3; a lipid combination of No. 38: No. 12: No. 31: No. 4=2:1:3:3; a lipid combination of No. 38: No. 12: No. 31: No. 29=2:1:3:3; a lipid combination of No. 38: No. 34: No. 37: No. 31: No. 1=88:44:66:72:135; a lipid combination of No. 38: No. 34: No. 37: No. 31: No. 15-88:44:66:72:135; a lipid combination of No. 38: No. 34: No. 37: No. 31: No. 12=88:44:66:72:135; a lipid combination of No. 38: No. 34: No. 37: No. 31: No. 4=88:44:66:72:135; a lipid combination of No. 38: No. 34: No. 37: No. 31: No. 29=88:44:66:72:135; a lipid combination of No. 38: No. 37: No. 34-4:2:3; a lipid combination of No. 38: No. 37: No. 1=4:2:3; a lipid combination of No. 38: No. 37: No. 2=4:2:3; a lipid combination of No. 38: No. 37: No. 1&2=4:2:3; a lipid combination of No. 38: No. 37: No. 2=32:8:5; a lipid combination of No. 38: No. 37: No. 32=32:8:5; a lipid combination of No. 38: No. 37: No. 15=4:2:3; a lipid combination of No. 38: No. 37: No. 32=4:2:3; a lipid combination of No. 38: No. 37: No. 8=4:2:3; a lipid combination of No. 38: No. 37: No. 11=4:2:3; a lipid combination of No. 38: No. 37: No. 12=4:2:3; a lipid combination of No. 38: No. 37: No. 11&12=4:2:3; a lipid combination of No. 38: No. 37: No. 12=4:1:1; a lipid combination of No. 38: No. 37: No. 4=4:2:3; a lipid combination of No. 38: No. 37: No. 30=4:2:3; a lipid combination of No. 38: No. 37: No. 31=4:2:3; a lipid combination of No. 38: No. 37: No. 29=4:2:3; a lipid combination of No. 8: No. 37: No. 32=4:1:2; a lipid combination of No. 8: No. 37: No. 2=4:1:2; a lipid combination of No. 38: No. 37: No. 15: No. 34=64:16:10:45; a lipid combination of No. 38: No. 37: No. 15: No. 1=64:16:10:45; a lipid combination of No. 38: No. 37: No. 15: No. 12=64:16:10:45; a lipid combination of No. 38: No. 37: No. 15: No. 4-64:16:10:45; a lipid combination of No. 38: No. 37: No. 15: No. 31=64:16:10:45; a lipid combination of No. 38: No. 37: No. 15: No. 29=64:16:10:45; a lipid combination of No. 38: No. 2: No. 37=4:2:3; a lipid combination of No. 38: No. 2: No. 31=4:2:3; a lipid combination of No. 38: No. 2: No. 29=4:2:3; a lipid combination of No. 38: No. 2: No. 34=4:2:3; a lipid combination of No. 38: No. 2: No. 32=4:2:3; a lipid combination of No. 38: No. 2: No. 12=4:2:3; a lipid combination of No. 38: No. 2: No. 12=4:5:1; a lipid combination of No. 38: No. 2: No. 4=4:2:3; lipids No. 1&2, No. 11&12 and No. 36&37 represent lipids No. 1 and No. 2 in any ratio, lipids No. 11 and No. 12 in any ratio, lipids No. 36 and No. 37 in any ratio, respectively.

Embodiment 8. A method of promoting the formation of bencaosome from nucleic acid and lipid, comprising heating a mixture of nucleic acid and lipid to promote the insertion of nucleic acid into the lipid membrane and promoting the stability of the lipid-nucleic acid complex, as determined by critical micelle concentration;
   wherein the nucleic acid inserts into the lipid layer or is encapsulated by the lipid layer to form the bencaosome, which is a nanoparticulate substance with a membrane structure, preferably a nanoparticulate substance with a double membrane structure;
   wherein the heating temperature is preferably from about 0° C. to about 100° C., more preferably from about 50° C. to about 100° C., and more preferably from about 80° C. to about 100° C., particularly preferably from about 80° C. to about 90° C., preferably 90° C.;
   preferably, the time for heating is about 0 minute to about 24 hours, about 5 minutes to about 20 hours, about 10 minutes to about 16 hours, about 15 minutes to about 12 hours, about 1 hour to about 8 hours, or about 2 hours to about 4 hours, preferably 15 minutes;

preferably, the lipid is one or more lipids in Table 1 or Table 10, preferably Sphinganine (d22:0), or the lipid combination of claim 7; preferably, the nucleic acid is small RNA, preferably one or more small RNA shown in Tables 8, 9 and 13, preferably PGY-sRNA-6 or HJT-sRNA-m7.

Embodiment 9. A method of lipid delivery of proteins to cells, comprising heating the proteins and lipids, wherein the heating temperature is preferably from about 0° C. to about 100° C., more preferably from about 50° C. to about 100° C., and more preferably from about 80° C. to about 100° C., particularly preferably from about 80° C. to about 90° C., preferably 90° C.;

preferably, the time for heating is about 0 minute to about 24 hours, about 5 minutes to about 20 hours, about 10 minutes to about 16 hours, about 15 minutes to about 12 hours, about 1 hour to about 8 hours, or about 2 hours to about 4 hours, preferably 6 hours;

or the method for lipid delivery of proteins to cells comprises mixing a protein solution with a solution of lipid in an organic solvent (v/v=1/5), removing the organic solvent by evaporation, and hydrating with an aqueous reagent; or the preparation is conducted by a boiling method comprising adding a solution of lipid in an organic solvent to a protein solution, and warming up after mixing;

or the method for lipid delivery of proteins to cells comprises mixing the proteins with a solution of lipid in an organic solvent, removing the organic solvent, and hydrating with an aqueous reagent;

preferably, the lipid is one or more lipids in Table 1 or Table 10, preferably sphinganine (d22:0) or PE(16:0/16:0) or PE(16:0/22:1).

Embodiment 10. Decoctosome: a nanoparticulate substance derived from the plant decoction, having a thermally stable, exosome-like membrane structure and composed of lipids, proteins, nucleic acids, compounds and the like. In the present application, the decoctosome can also be referred to as an active composition with a membrane structure, preferably an active combination prepared by the method of the foregoing embodiments 10-13.

Embodiment 11. Method for preparing a decoctosome from plants comprises the steps of:
(1) preparing an extract of the plants using a solvent, preferably an aqueous solvent,
wherein preferably, the extract of the plants is prepared by decocting the plants soaked in the solvent;
wherein preferably, the decocting includes decocting with intense heating for 15-45 min, preferably 20-30 min, preferably 30 min, followed by decocting with gentle heating for 5-30 min, preferably 5-20 min, preferably 10 min;
wherein preferably, the temperature of the intense heating is above 90° C., preferably 90° C.-2000° C., 90° C.-1500° C., 90° C.-1000° C., 90° C.-500° C., 90° C.-300° C., 90° C.-250° C. or 90° C.-200° C.;
preferably, the temperature of the gentle heating is above 50° C., preferably 50° C.-2000° C., 50° C.-1500° C., 50° C.-1000° C., 50° C.-500° C., 50° C.-300° C., 50° C.-250° C., 50° C.- 200° C., 50° C.-100° C., 50° C.-80° C., 50° C.-70° C. or 50° C.-60° C.;
preferably, the aqueous solvent is selected from the group consisting of aqueous buffers, saline solutions, aqueous solutions of organic solvents and water;

(2) differential centrifuging the extract at an appropriate temperature, preferably 0-10° C., 4° C., preferably at 800-5000 g, preferably 1000-4000 g, preferably 2000-3000 g, preferably at 2000 g for 20-40 min, preferably 30 min; taking the supernatant, and then centrifuging the supernatant at 6000 g-15000 g, preferably 7000 g-12000 g, preferably 8000 g-11000 g, preferably at 10000 g for 20-40 min, preferably 30 min; taking the supernatant, and then centrifuging the supernatant at 100000-200000, preferably at 200000 g for 60-120 min, preferably 90 min; taking the precipitates, which are the solid form of the decoctosome; and (3) optionally, resuspending the precipitates with an aqueous solution, preferably an aqueous buffer, preferably PBS buffer, more preferably PBS buffer at pH7-9, preferably pH7.4 to provide the decoctosome, which is a nanoparticulate substance with a membrane structure, preferably a nano-particulate substance with a double layered membrane structure, the aqueous solution is selected from the group consisting of aqueous buffers, saline solutions, aqueous solutions of organic solvents and water.

Embodiment 12. The method of Embodiment 11, wherein the decoctosome has an average particle size of 30-1,000 nm, preferably 80-300 nm, and a potential absolute value of 20-100 mV.

Embodiment 13. The method of Embodiment 11 or 12, wherein the said plant is selected from the group consisting of *Taraxacum mongolicum, Rhodiola, Andrographis paniculata*, Cabbage and Woody etc.

Embodiment 14. The method of any one of Embodiments 11-13, wherein for *Taraxacum mongolicum*, the decoctosome has a peak value for the average particle size of 30-300 nm, preferably 150-200 nm, and a Zeta potential of −39+3 mV; for *Rhodiola*, the decoctosome has an average particle size of 50-300 nm, preferably 150-210 nm, and a Zeta potential of −37+2 mV;

the *Taraxacum mongolicum* decoctosome has a potential absolute value of 20-100 mV, and the *Rhodiola* decoctosome has a potential absolute value of 20-100 mV.

Embodiment 15. The decoctosome prepared by the method of any one in Embodiments 11-14, wherein the decoctosome is in the form of solid or liquid or colloid, and the decoctosome comprises a nanoparticulate substance with a membrane structure, preferably a nanoparticulate substance with a double layered membrane structure.

Embodiment 16. The decoctosome of Embodiments 15, comprising one or more lipid components shown in Table 1 or 10, one or more compounds, one or more DNAs, one or more macromolecules and/or one or more RNAs;

preferably, the decoctsome comprises one or more lipid components shown in Table 1 or Table 10, one or more compounds shown in Table 2 or 4, one or more compounds shown in Table 3 or 5, one or more macromolecules shown in Table 6 or 7, and/or one or more small RNAs shown in Table 8, 9 or 13.

Embodiment 17. The decoctosome of Embodiment 15 or 16, which is a composition used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 18. The decoctosome of any one of Embodiments 15-17, used in one or more of the following:
(1) lowering the expression of fibronectin and/or alpha-SMA, preferably the protein expression of fibronectin in MRC-5 cells fibrosis model induced by TGF-beta1;
(2) reducing hydroxyproline, preferably the hydroxyproline in pulmonary fibrosis model, preferably the hydroxyproline in pulmonary fibrosis model of mice;
(3) preventing or treating fibrosis, preferably pulmonary fibrosis;
(4) lowering IL-1beta, IL-6 and/or TNF-alpha, preferably the IL-1beta, IL-6 and/or TNF-alpha in A549 cells model induced by poly(I:C);
(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;
(6) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and/or
(7) lowering the expression of RELA genes.

Embodiment 19. Use of the decoctosome of any one of Embodiments 15-17 in the manufacture of medicament for use in one or more of the following:
(1) lowering the expression of fibronectin and/or alpha-SMA, preferably the protein expression of fibronectin in MRC-5 cells fibrosis model induced by TGF-beta1;
(2) reducing hydroxyproline, preferably the hydroxyproline in pulmonary fibrosis model, preferably the hydroxyproline in pulmonary fibrosis model of mice;
(3) preventing or treating fibrosis, preferably pulmonary fibrosis;
(4) lowering IL-1beta, IL-6 and/or TNF-alpha, preferably the IL-1beta, IL-6 and/or TNF-alpha in A549 cells model induced by poly(I:C);
(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;
(6) treating IL-1beta, IL-6 and/or TNF-alpha-associated diseases, or for anti-inflammation, preferably for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and/or
(7) lowering the expression of RELA genes;
wherein the medicament is used for oral and intravenous administration, such as bolus injection or continuous infusion for a period of time, via subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes such as intranasal, typically intravenous or subcutaneous administration.

Embodiment 20. Method for the following purposes, including the use of the decoctosome in any one of Embodiments 15-17:
(1) lowering the expression of fibronectin and/or alpha-SMA, preferably the protein expression of fibronectin in MRC-5 cells fibrosis model induced by TGF-beta1;
(2) reducing hydroxyproline, preferably the hydroxyproline in pulmonary fibrosis model, preferably the hydroxyproline in pulmonary fibrosis model of mice;
(3) preventing or treating fibrosis, preferably pulmonary fibrosis;
(4) lowering IL-1beta, IL-6 and/or TNF-alpha, preferably the IL-1beta, IL-6 and/or TNF-alpha in A549 cells model induced by poly(I:C);
(5) lowering the level of IL-1alpha, IL-1beta, IL-2, IL-3, IL-4, IL-5, IL-9, IL-10, IL-12 p40, IL-12 p70, IL-13, IL-17A, GM-CSF, IFN-gamma or MCP-1beta, preferably the level of plasma, preferable in an inflammation model of mouse;
(6) treating IL-1beta, IL-6 and/or TNF-alpha-associated diseases, or for anti-inflammation, and/or
(7) lowering the expression of RELA genes.

The invention claimed is:

1. A method for preparing a bencaosome, comprising the steps of:
   (1) mixing Sphinganine (d22:0) with one or more small RNAs;
   wherein the Sphinganine (d22:0) is synthesized or purified;
   wherein the one or more small RNAs have a length of 14-32 bp;
   (2) treating the mixture obtained from step (1) by heating,
   wherein the heating temperature is from about 80° C. to about 100° C.;
   wherein the time for heating is about 15 minutes to about 30 minutes;
   wherein the mixing is performed by adding a solution of the Sphinganine (d22:0) in an organic solvent into an aqueous solution of the small RNA;
   wherein the bencaosome is a nano-particulate substance with a membrane structure.

2. The method of claim 1, wherein the small RNA is PGY-sRNA-6 or HJT-sRNA-m7, and
   the Sphinganine (d22:0): the small RNA=0.1-20 μg:0.1 nmol;
   wherein the bencaosome has a Zeta potential of less than 60 mV, less than 50 mV, less than 0, −80 to −20, or −60 to −20, and has an average particle size of 50-1000, 90-300 or 100-200 nm.

3. The method of claim 1, wherein the one or more small RNAs are as set forth in SEQ ID NOs: 1-100.

4. The method of claim 1, wherein the small RNA is selected from single stranded or double stranded or partially double-stranded RNA.

5. The method of claim 1, wherein the bencaosome is used in one or more of the following:
   (1) lowering the expression of fibronectin and/or alpha-SMA, or lowering the protein expression of fibronectin in MRC-5 cells fibrosis model induced by TGF-beta1;
   (2) reducing hydroxyproline, or the hydroxyproline in pulmonary fibrosis model, or the hydroxyproline in pulmonary fibrosis model of mice;
   (3) preventing or treating fibrosis, or pulmonary fibrosis, or in the fibrosis model of MRC-5 cells induced by TGF-beta1 or the fibrosis model of mice induced by Bleomycin;
   (4) lowering IL-1beta, IL-6 and/or TNF-alpha, or the IL-1beta, IL-6 and/or TNF-alpha in A549 cells model induced by poly(I:C);
   (5) lowering the level of IL-1alpha, IL-1b, IL-2, IL-3, IL-4, IL-5, IL-6, IL-9, IL-10, IL-12 p40, IL-12 p70, IL-13, IL-17A, GM-CSF, IFN-gamma or MCP-1beta;
   (6) treating IL-1beta, IL-6 and/or TNF-alpha-associated diseases, or for anti-inflammation, or for the treatment of pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergy rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout; and
   (7) enabling small RNA to enter cells efficiently; and/or
   (8) lowering the expression of RELA genes.

6. The method of claim 5, wherein the bencaosome is used for oral administration, intravenous administration, subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration via inhalation routes.

* * * * *

UNITED STATES PATENT AND TRADEMARK OFFICE
CERTIFICATE OF CORRECTION

PATENT NO. : 12,280,114 B2  
APPLICATION NO. : 17/042924  
DATED : April 22, 2025  
INVENTOR(S) : Chengyu Jiang et al.

Page 1 of 1

It is certified that error appears in the above-identified patent and that said Letters Patent is hereby corrected as shown below:

On the Title Page

On left Column, Lines 14-15, item (73) Assignee shall read as:  
Assignee: BEIJING BAISHIHEKANG PHARMACEUTICAL TECHNOLOGY (BSJPHARMA) CO., LTD, Beijing (CN)

Signed and Sealed this  
Sixteenth Day of September, 2025

Coke Morgan Stewart  
*Acting Director of the United States Patent and Trademark Office*

SEQUENCE LISTING

<160> NUMBER OF SEQ ID NOS: 116

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcgcttggtg caggtcggga c          21

<210> SEQ ID NO 2

```
<211> LENGTH: 19
<212> TYPE: DNA
<213> ORGANISM: Artificial Sequence
<220> FEATURE:
<223> OTHER INFORMATION: Synthetic

<400> SEQUENCE: 2
ggccctcctt ctagcgcca                                              19

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
cagagtcgcg cagcggaa                                               18

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gttcagagtt ctacagtccg a                                           21

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
cggggctacg cctgtctgag cgtcgc                                      26

<210> SEQ ID NO 6
<211> LENGTH: 28
<212> TYPE: DNA
<213> ORGANISM: Artificial Sequence
<220> FEATURE:
<223> OTHER INFORMATION: Synthetic

<400> SEQUENCE: 6
tgaggtagta ggttgtgtgg ttgtaagc                                    28

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
cagccaagga tgacttgccg g                                           21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
```
tagcaccatc cgaaatcggt a                                                        21

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
tggggctacg cctgtctgag cgtcgct                                                  27

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
gaguacagau gaucauguug agtacagatg atcatgtt                                      38

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
gacucacgug aagcuuccag actcacgtga agcttcca                                      38

<210> SEQ ID NO 12
<211> LENGTH: 38
<212> TYPE: DNA
<213> ORGANISM: Artificial Sequence
<220> FEATURE:
<223> OTHER INFORMATION: Synthetic

<400> SEQUENCE: 12
gagucaucug ugugaauuag agtcatctgt gtgaatta                                      38

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
caaugcgagc uccaaagaa                                                           19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
gcggucuuau gcauuggaa                                                           19

<210> SEQ ID NO 15
<211> LENGTH: 21
<212> TYPE: RNA

```
<213> ORGANISM: Artificial Sequence
<220> FEATURE:
<223> OTHER INFORMATION: Synthetic

<400> SEQUENCE: 15
aguacccuga agcuauauuu u                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetic

<400> SEQUENCE: 16
cacaaccaac uaguggugcu u                                              21

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17
ccctccgcgg ccagcttct                                                 19

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
tccggaatga ttgggcgtaa agcgt                                          25

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ccggccccga acccgtcggc                                                20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
gcgaccccag gtcaggcggg a                                              21

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
cagagttcta cagtccga                                                  18
```

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
agagttctac agtccgacga t                                             21

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
cagagttcta cagtccgacg at                                            22

<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24
gttcagagtt ctacagtc                                                 18

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gttcagagtt ctacagtccg a                                             21

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
gttctacagt ccgacgatc                                                19

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
cagagttcta cagtccgacg atc                                           23

<210> SEQ ID NO 28
<211> LENGTH: 19
<212> TYPE: DNA
<213> ORGANISM: Artificial Sequence
<220> FEATURE:

<223> OTHER INFORMATION: Synthetic

<400> SEQUENCE: 28
gaccgcatag cgcagtgga                                              19

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
cggtggccat ggaagtcgg                                              19

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
tctgaactct gaactccagt cac                                         23

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
cgcctgtctg agcgtcgct                                              19

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
ggctttggtc tagggtatg attct                                        25

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
acgcctgtct gagcgtcgct                                             20

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
gctacgcctg tctgagcgtc gct                                         23

```
<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35
gggctacgcc tgtctgagcg tcgct                                   25

<210> SEQ ID NO 36
<211> LENGTH: 26
<212> TYPE: DNA
<213> ORGANISM: Artificial Sequence
<220> FEATURE:
<223> OTHER INFORMATION: Synthetic

<400> SEQUENCE: 36
ggggctacgc ctgtctgagc gtcgct                                  26

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
cggggctacg cctgtctgag cgtcgc                                  26

<210> SEQ ID NO 38
<211> LENGTH: 27
<212> TYPE: DNA
<213> ORGANISM: Artificial Sequence
<220> FEATURE:
<223> OTHER INFORMATION: Synthetic

<400> SEQUENCE: 38
cggggctacg cctgtctgag cgtcgct                                 27

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
ccggggctac gcctgtctga gcgt                                    24

<210> SEQ ID NO 40
<211> LENGTH: 18
<212> TYPE: DNA
<213> ORGANISM: Artificial Sequence
<220> FEATURE:
<223> OTHER INFORMATION: Synthetic

<400> SEQUENCE: 40
ttgggtgcga gaggtccc                                           18

<210> SEQ ID NO 41
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 41
ctttgtcgct tcgattcgt                                          19

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
gaagtcctcg tgttgcaccc c                                       21

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
agtcctcgtg ttgcacccct                                         20

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
ctcggccttt tggctaag                                           18

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
acgactctcg gcaacgga                                           18

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
cgactctcgg caacggata                                          19

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
cataacgact ctcggcaa                                           18

<210> SEQ ID NO 48
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 48
ctcggcaacg gatatctcg                                                19

<210> SEQ ID NO 49
<211> LENGTH: 19
<212> TYPE: DNA
<213> ORGANISM: Artificial Sequence
<220> FEATURE:
<223> OTHER INFORMATION: Synthetic

<400> SEQUENCE: 49
cctatgtcgc ttcgattcg                                                19

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
ctatgtcgct tcgattcgt                                                19

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
ctctcggcaa cggatatct                                                19

<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
cggatatctc ggctctcg                                                 18

<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
ggtgcgagag gtcccgagt                                                19

<210> SEQ ID NO 54
<211> LENGTH: 18
<212> TYPE: DNA
<213> ORGANISM: Artificial Sequence
<220> FEATURE:
<223> OTHER INFORMATION: Synthetic

<400> SEQUENCE: 54
```
acggatatct cggctctc                                                      18

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
ctggttgatc ctgccagtag t                                                  21

<210> SEQ ID NO 56
<211> LENGTH: 19
<212> TYPE: DNA
<213> ORGANISM: Artificial Sequence
<220> FEATURE:
<223> OTHER INFORMATION: Synthetic

<400> SEQUENCE: 56
cgaccccagg tcaggcggg                                                     19

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cggcaacgga tatctcggct                                                    20

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
gcgaccccag gtcaggcgg                                                     19

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gactctcggc aacggatatc                                                    20

<210> SEQ ID NO 60
<211> LENGTH: 18
<212> TYPE: DNA
<213> ORGANISM: Artificial Sequence
<220> FEATURE:
<223> OTHER INFORMATION: Synthetic

<400> SEQUENCE: 60
tacccggccg tcggggca                                                      18

<210> SEQ ID NO 61
<211> LENGTH: 18
<212> TYPE: DNA
<213> ORGANISM: Artificial Sequence

```
<220> FEATURE:
<223> OTHER INFORMATION: Synthetic

<400> SEQUENCE: 61
tctcggctct cgcatcga                                                18

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
ggggatgtag ctcagatg                                                18

<210> SEQ ID NO 63
<211> LENGTH: 18
<212> TYPE: DNA
<213> ORGANISM: Artificial Sequence
<220> FEATURE:
<223> OTHER INFORMATION: Synthetic

<400> SEQUENCE: 63
ttcccacaga cggcgcca                                                18

<210> SEQ ID NO 64
<211> LENGTH: 18
<212> TYPE: DNA
<213> ORGANISM: Artificial Sequence
<220> FEATURE:
<223> OTHER INFORMATION: Synthetic

<400> SEQUENCE: 64
attgtgaagc agaattca                                                18

<210> SEQ ID NO 65
<211> LENGTH: 19
<212> TYPE: DNA
<213> ORGANISM: Artificial Sequence
<220> FEATURE:
<223> OTHER INFORMATION: Synthetic

<400> SEQUENCE: 65
ccaagtgttg gattgttca                                               19

<210> SEQ ID NO 66
<211> LENGTH: 19
<212> TYPE: DNA
<213> ORGANISM: Artificial Sequence
<220> FEATURE:
<223> OTHER INFORMATION: Synthetic

<400> SEQUENCE: 66
ggtcatcgcg cttggttga                                               19

<210> SEQ ID NO 67
<211> LENGTH: 18
<212> TYPE: DNA
<213> ORGANISM: Artificial Sequence
<220> FEATURE:
<223> OTHER INFORMATION: Synthetic

<400> SEQUENCE: 67
tgccggccgg gggacgga                                                18
```

```
<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
gttaagcgtg cttgggcga                                                     19

<210> SEQ ID NO 69
<211> LENGTH: 19
<212> TYPE: DNA
<213> ORGANISM: Artificial Sequence
<220> FEATURE:
<223> OTHER INFORMATION: Synthetic

<400> SEQUENCE: 69
actcgacgga tcgcacggc                                                     19

<210> SEQ ID NO 70
<211> LENGTH: 19
<212> TYPE: DNA
<213> ORGANISM: Artificial Sequence
<220> FEATURE:
<223> OTHER INFORMATION: Synthetic

<400> SEQUENCE: 70
ctggtcgatg gaacaatgt                                                     19

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71 tgcttttga tccttcgatg                                                     20

<210> SEQ ID NO 72
<211> LENGTH: 22
<212> TYPE: DNA
<213> ORGANISM: Artificial Sequence
<220> FEATURE:
<223> OTHER INFORMATION: Synthetic

<400> SEQUENCE: 72
ttgggtgcga gaggtcccgg gt                                                 22

<210> SEQ ID NO 73
<211> LENGTH: 27
<212> TYPE: DNA
<213> ORGANISM: Artificial Sequence
<220> FEATURE:
<223> OTHER INFORMATION: Synthetic

<400> SEQUENCE: 73
cctgggaagt cctcgtgttg cacccct                                            27

<210> SEQ ID NO 74
<211> LENGTH: 21
<212> TYPE: DNA
<213> ORGANISM: Artificial Sequence
<220> FEATURE:
<223> OTHER INFORMATION: Synthetic
```

<400> SEQUENCE: 74
ttctcggcct tttggctaag a                                              21

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
cataacgact ctcggcaacg gata                                           24

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
attgtgaagc agaattcacc                                                20

<210> SEQ ID NO 77
<211> LENGTH: 19
<212> TYPE: DNA
<213> ORGANISM: Artificial Sequence
<220> FEATURE:
<223> OTHER INFORMATION: Synthetic

<400> SEQUENCE: 77
tgcaccggat cccatcaga                                                 19

<210> SEQ ID NO 78
<211> LENGTH: 18
<212> TYPE: DNA
<213> ORGANISM: Artificial Sequence
<220> FEATURE:
<223> OTHER INFORMATION: Synthetic

<400> SEQUENCE: 78
ccttaacgag gatccatt                                                  18

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79
attggtcatc gcgcttgg                                                  18

<210> SEQ ID NO 80
<211> LENGTH: 18
<212> TYPE: DNA
<213> ORGANISM: Artificial Sequence
<220> FEATURE:
<223> OTHER INFORMATION: Synthetic

<400> SEQUENCE: 80
cacggaccaa ggagtctg                                                  18

<210> SEQ ID NO 81

-continued

```
<211> LENGTH: 18
<212> TYPE: DNA
<213> ORGANISM: Artificial Sequence
<220> FEATURE:
<223> OTHER INFORMATION: Synthetic

<400> SEQUENCE: 81
ttagggttcg attccgga                                              18

<210> SEQ ID NO 82
<211> LENGTH: 18
<212> TYPE: DNA
<213> ORGANISM: Artificial Sequence
<220> FEATURE:
<223> OTHER INFORMATION: Synthetic

<400> SEQUENCE: 82
cccgagagag gggcccgt                                              18

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
ggggtgcgag aggtcccg                                              18

<210> SEQ ID NO 84
<211> LENGTH: 18
<212> TYPE: DNA
<213> ORGANISM: Artificial Sequence
<220> FEATURE:
<223> OTHER INFORMATION: Synthetic

<400> SEQUENCE: 84
tggggtgcga gaggtccc                                              18

<210> SEQ ID NO 85
<211> LENGTH: 18
<212> TYPE: DNA
<213> ORGANISM: Artificial Sequence
<220> FEATURE:
<223> OTHER INFORMATION: Synthetic

<400> SEQUENCE: 85
ttggggtgcg agaggtcc                                              18

<210> SEQ ID NO 86
<211> LENGTH: 18
<212> TYPE: DNA
<213> ORGANISM: Artificial Sequence
<220> FEATURE:
<223> OTHER INFORMATION: Synthetic

<400> SEQUENCE: 86
tgggtgcgag aggtcccg                                              18

<210> SEQ ID NO 87
<211> LENGTH: 18
<212> TYPE: DNA
<213> ORGANISM: Artificial Sequence
<220> FEATURE:
<223> OTHER INFORMATION: Synthetic

<400> SEQUENCE: 87
```

```
gggttgcgag aggtcccg                                              18

<210> SEQ ID NO 88
<211> LENGTH: 18
<212> TYPE: DNA
<213> ORGANISM: Artificial Sequence
<220> FEATURE:
<223> OTHER INFORMATION: Synthetic

<400> SEQUENCE: 88
ttgggttgcg agaggtcc                                              18

<210> SEQ ID NO 89
<211> LENGTH: 18
<212> TYPE: DNA
<213> ORGANISM: Artificial Sequence
<220> FEATURE:
<223> OTHER INFORMATION: Synthetic

<400> SEQUENCE: 89
ttggttgcga gaggtccc                                              18

<210> SEQ ID NO 90
<211> LENGTH: 22
<212> TYPE: DNA
<213> ORGANISM: Artificial Sequence
<220> FEATURE:
<223> OTHER INFORMATION: Synthetic

<400> SEQUENCE: 90
tctgaactct gaactccagt ca                                         22

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
ggtgcgagag gtcccgag                                              18

<210> SEQ ID NO 92
<211> LENGTH: 18
<212> TYPE: DNA
<213> ORGANISM: Artificial Sequence
<220> FEATURE:
<223> OTHER INFORMATION: Synthetic

<400> SEQUENCE: 92
gtgcgagagg tcccgagt                                              18

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93
caaggaaggc agcaggcg                                              18

<210> SEQ ID NO 94
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 94
gcgaccccag gtcaggcg                                                       18

<210> SEQ ID NO 95
<211> LENGTH: 18
<212> TYPE: DNA
<213> ORGANISM: Artificial Sequence
<220> FEATURE:
<223> OTHER INFORMATION: Synthetic

<400> SEQUENCE: 95
aggctgggtg tggaagtg                                                       18

<210> SEQ ID NO 96
<211> LENGTH: 18
<212> TYPE: DNA
<213> ORGANISM: Artificial Sequence
<220> FEATURE:
<223> OTHER INFORMATION: Synthetic

<400> SEQUENCE: 96
tcgtgtcgtg agatgttg                                                       18

<210> SEQ ID NO 97
<211> LENGTH: 22
<212> TYPE: DNA
<213> ORGANISM: Artificial Sequence
<220> FEATURE:
<223> OTHER INFORMATION: Synthetic

<400> SEQUENCE: 97
cgccccgaga gagggcccg tg                                                   22

<210> SEQ ID NO 98
<211> LENGTH: 23
<212> TYPE: DNA
<213> ORGANISM: Artificial Sequence
<220> FEATURE:
<223> OTHER INFORMATION: Synthetic

<400> SEQUENCE: 98
ttggggtgcg agaggtcccg ggt                                                 23

<210> SEQ ID NO 99
<211> LENGTH: 22
<212> TYPE: DNA
<213> ORGANISM: Artificial Sequence
<220> FEATURE:
<223> OTHER INFORMATION: Synthetic

<400> SEQUENCE: 99
ttggttgcga gaggtcccgg gt                                                  22

<210> SEQ ID NO 100
<211> LENGTH: 21
<212> TYPE: DNA
<213> ORGANISM: Artificial Sequence
<220> FEATURE:
<223> OTHER INFORMATION: Synthetic

<400> SEQUENCE: 100
atccaaggaa ggcagcaggc g                                                   21
```

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
ctggaagatg gtcgtaccct g                                    21

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
ggtcttgcca gtgagtgtct                                      20

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
ctcgccagtg aaatgatggc t                                    21

<210> SEQ ID NO 104
<211> LENGTH: 21
<212> TYPE: DNA
<213> ORGANISM: Artificial Sequence
<220> FEATURE:
<223> OTHER INFORMATION: Synthetic

<400> SEQUENCE: 104
gtcggagatt cgtagctgga t                                    21

<210> SEQ ID NO 105
<211> LENGTH: 21
<212> TYPE: DNA
<213> ORGANISM: Artificial Sequence
<220> FEATURE:
<223> OTHER INFORMATION: Synthetic

<400> SEQUENCE: 105
ggtacatcct cgacggcatc t                                    21

<210> SEQ ID NO 106
<211> LENGTH: 21
<212> TYPE: DNA
<213> ORGANISM: Artificial Sequence
<220> FEATURE:
<223> OTHER INFORMATION: Synthetic

<400> SEQUENCE: 106
gtgcctcttt gctgctttca c                                    21

<210> SEQ ID NO 107
<211> LENGTH: 19
<212> TYPE: DNA
<213> ORGANISM: Artificial Sequence
<220> FEATURE:

<223> OTHER INFORMATION: Synthetic

<400> SEQUENCE: 107
ctgccccaat ccctttatt                                                  19

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
cccaattctc tttttgagcc                                                 20

<210> SEQ ID NO 109
<211> LENGTH: 21
<212> TYPE: RNA
<213> ORGANISM: Artificial Sequence
<220> FEATURE:
<223> OTHER INFORMATION: Synthetic

<400> SEQUENCE: 109
uuguacuaca caaaaguacu g                                               21

<210> SEQ ID NO 110
<211> LENGTH: 53
<212> TYPE: DNA
<213> ORGANISM: Artificial Sequence
<220> FEATURE:
<223> OTHER INFORMATION: Synthetic

<400> SEQUENCE: 110
gtcgtatcca gtgcagggtc cgaggtattc gcactggata cgacaaaaat atg           53

<210> SEQ ID NO 111
<211> LENGTH: 52
<212> TYPE: DNA
<213> ORGANISM: Artificial Sequence
<220> FEATURE:
<223> OTHER INFORMATION: Synthetic

<400> SEQUENCE: 111
gtcgtatcca gtgcacgctc cgaggtattc gcactggata cgacgcttac aa            52

<210> SEQ ID NO 112
<211> LENGTH: 50
<212> TYPE: DNA
<213> ORGANISM: Artificial Sequence
<220> FEATURE:
<223> OTHER INFORMATION: Synthetic

<400> SEQUENCE: 112
gtcgtatcca gtgcacgctc cgaggtattc gcactggata cgactcggac              50

<210> SEQ ID NO 113
<211> LENGTH: 18
<212> TYPE: DNA
<213> ORGANISM: Artificial Sequence
<220> FEATURE:
<223> OTHER INFORMATION: Synthetic

<400> SEQUENCE: 113
gcgcgtcgtg aagcgttc                                                   18

```
<210> SEQ ID NO 114
<211> LENGTH: 16
<212> TYPE: DNA
<213> ORGANISM: Artificial Sequence
<220> FEATURE:
<223> OTHER INFORMATION: Synthetic

<400> SEQUENCE: 114
gtgcagggtc cgaggt                                                      16

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
tcgcgctgag gtagtaggtt                                                  20

<210> SEQ ID NO 116
<211> LENGTH: 16
<212> TYPE: DNA
<213> ORGANISM: Artificial Sequence
<220> FEATURE:
<223> OTHER INFORMATION: Synthetic

<400> SEQUENCE: 116
gtgcacgctc cgaggt                                                      16
```